United States Patent
Hudkins et al.

(10) Patent No.: US 12,264,149 B2
(45) Date of Patent: *Apr. 1, 2025

(54) INDAZOLE COMPOUNDS AS KINASE INHIBITORS

(71) Applicant: TYRA BIOSCIENCES, INC., Carlsbad, CA (US)

(72) Inventors: Robert L. Hudkins, Virginia Beach, VA (US); Daniel C. Bensen, Carlsbad, CA (US)

(73) Assignee: TYRA BIOSCIENCES, INC., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/259,422

(22) PCT Filed: Dec. 30, 2021

(86) PCT No.: PCT/US2021/065679
§ 371 (c)(1),
(2) Date: Jun. 27, 2023

(87) PCT Pub. No.: WO2022/147246
PCT Pub. Date: Jul. 7, 2022

(65) Prior Publication Data
US 2024/0109865 A1    Apr. 4, 2024

Related U.S. Application Data

(60) Provisional application No. 63/216,879, filed on Jun. 30, 2021, provisional application No. 63/132,031, filed on Dec. 30, 2020.

(51) Int. Cl.
| | | |
|---|---|---|
| *C07D 401/14* | (2006.01) | |
| *A61P 35/00* | (2006.01) | |
| *C07D 417/14* | (2006.01) | |
| *C07D 471/10* | (2006.01) | |
| *C07D 487/10* | (2006.01) | |
| *C07D 495/10* | (2006.01) | |

(52) U.S. Cl.
CPC ............ *C07D 401/14* (2013.01); *A61P 35/00* (2018.01); *C07D 417/14* (2013.01); *C07D 471/10* (2013.01); *C07D 487/10* (2013.01); *C07D 495/10* (2013.01)

(58) Field of Classification Search
CPC ................ C07D 401/14; C07D 417/10; C07D 471/10; C07D 487/10; C07D 495/10; A61P 35/00
USPC ........................................................ 514/333
See application file for complete search history.

(56) References Cited

U.S. PATENT DOCUMENTS

| | | |
|---|---|---|
| 4,775,612 A | 10/1988 | Abe et al. |
| 4,940,703 A | 7/1990 | Baker et al. |
| 5,041,453 A | 8/1991 | Huang et al. |
| 6,063,930 A | 5/2000 | Dinsmore et al. |
| 6,746,729 B1 | 6/2004 | Cherkaoui et al. |
| 6,953,857 B2 | 10/2005 | Nazare et al. |
| 6,995,144 B2 | 2/2006 | Ozaki et al. |
| 7,067,665 B2 | 6/2006 | Nazare et al. |
| 7,186,716 B2 | 3/2007 | Wei et al. |
| 7,244,739 B2 | 7/2007 | Cheng et al. |
| 7,265,108 B2 | 9/2007 | Ozaki et al. |
| 7,635,698 B2 | 12/2009 | Rosse et al. |
| 7,781,442 B2 | 8/2010 | Cheng et al. |
| 7,799,808 B2 | 9/2010 | Cheng et al. |
| 7,880,002 B2 | 2/2011 | Carson et al. |
| 7,915,274 B2 | 3/2011 | Ozaki et al. |
| 8,017,629 B2 | 9/2011 | Cheng et al. |
| 8,119,680 B2 | 2/2012 | Cheng et al. |
| 8,168,788 B2 | 5/2012 | Carson et al. |
| 8,324,231 B2 | 12/2012 | Koltun et al. |
| 8,338,458 B2 | 12/2012 | Meinke et al. |
| 8,399,455 B2 | 3/2013 | Rosse et al. |
| 8,455,516 B2 | 6/2013 | Gochin et al. |
| 8,642,587 B2 | 2/2014 | Lange et al. |
| 8,648,197 B2 | 2/2014 | Carson et al. |
| 8,759,337 B2 | 6/2014 | Asberom et al. |
| 8,809,370 B2 | 8/2014 | Goff et al. |
| 8,883,793 B2 | 11/2014 | Chen et al. |
| 8,957,073 B2 | 2/2015 | Allen et al. |
| 8,975,235 B2 | 3/2015 | Buckman et al. |
| 8,980,921 B2 | 3/2015 | Goff et al. |
| 8,987,303 B2 | 3/2015 | Goff et al. |
| 9,120,779 B2 | 9/2015 | Li et al. |
| 9,266,856 B2 | 2/2016 | Goff et al. |
| 9,340,489 B2 | 5/2016 | Atzrodt et al. |
| 9,464,065 B2 | 10/2016 | Schultz et al. |
| 9,550,000 B2 | 1/2017 | Robinson et al. |
| 9,663,496 B2 | 5/2017 | Irving et al. |
| 9,718,803 B2 | 8/2017 | Allen et al. |
| 10,045,979 B2 | 8/2018 | Long et al. |

(Continued)

FOREIGN PATENT DOCUMENTS

| | | |
|---|---|---|
| CA | 2753313 A1 | 8/2010 |
| CN | 103420906 A | 12/2013 |

(Continued)

OTHER PUBLICATIONS

International Patent Application No. PCT/US2021/065679; Int'l Preliminary Report on Patentability; dated Jul. 13, 2023; 8 pages.
International Patent Application No. PCT/US2021/065679; Int'l Search Report and the Written Opinion; dated May 3, 2022; 15 pages.
Shirahashi Hiromitsu et al: "The discovery of novel 3-aryl-indazole derivatives as peripherally restricted pan-Trk inhibitors for the treatment of pain", Bioorganic & Medicinal Chemistry Letters, Elsevier, Amsterdam, NL, vol. 29, No. 16, Jun. 17, 2019 (Jun. 17, 2019), pp. 2320-2326, XP085759046.

*Primary Examiner* — Kahsay Habte
(74) *Attorney, Agent, or Firm* — BakerHostetler

(57) ABSTRACT

Disclosed herein are compounds and methods of treating diseases and/or conditions associated with FGFR inhibition.

21 Claims, No Drawings

(56) References Cited

U.S. PATENT DOCUMENTS

| | | |
|---|---|---|
| 10,100,042 B2 | 10/2018 | Chen et al. |
| 10,166,237 B2 | 1/2019 | Schultz et al. |
| 10,180,626 B2 | 1/2019 | Fujiwara et al. |
| 10,208,017 B2 | 2/2019 | Hommes et al. |
| 10,377,742 B2 | 8/2019 | Goff et al. |
| 10,463,661 B2 | 11/2019 | Long et al. |
| 10,519,133 B2 | 12/2019 | Chen et al. |
| 10,550,326 B2 | 2/2020 | Wittek et al. |
| 10,562,883 B2 | 2/2020 | Hommes et al. |
| 10,781,218 B2 | 9/2020 | Wu et al. |
| 10,941,134 B2 | 3/2021 | Goff et al. |
| 11,040,976 B2 | 6/2021 | Maianti et al. |
| 11,124,628 B2 | 9/2021 | Zhang et al. |
| 2004/0127538 A1 | 7/2004 | Oinuma et al. |
| 2004/0167224 A1 | 8/2004 | Ozaki et al. |
| 2007/0135485 A1 | 6/2007 | Gillig et al. |
| 2012/0040977 A1 | 2/2012 | Li et al. |
| 2013/0059834 A1 | 3/2013 | Chen et al. |
| 2013/0131034 A1 | 5/2013 | Follmann et al. |
| 2013/0310379 A1 | 11/2013 | Albrecht et al. |
| 2014/0213538 A1 | 7/2014 | Buckman et al. |
| 2015/0087673 A1 | 3/2015 | Hitoshi et al. |
| 2016/0289196 A1 | 10/2016 | Choi et al. |
| 2017/0369780 A1 | 12/2017 | Adlem et al. |
| 2018/0222886 A1 | 8/2018 | Chen et al. |
| 2018/0305334 A1 | 10/2018 | Larsen et al. |
| 2019/0055444 A1 | 2/2019 | Fujiwara et al. |
| 2019/0177617 A1 | 6/2019 | Adlem et al. |
| 2020/0165224 A1 | 5/2020 | Li et al. |
| 2020/0247792 A1 | 8/2020 | Burris et al. |
| 2020/0392083 A1 | 12/2020 | Jiang et al. |
| 2021/0009582 A1 | 1/2021 | Vechorkin et al. |
| 2021/0106588 A1 | 4/2021 | Vechorkin et al. |
| 2021/0187902 A1 | 6/2021 | Fujiwara et al. |
| 2021/0220408 A1 | 7/2021 | Boitano et al. |
| 2022/0079928 A1 | 3/2022 | Lou et al. |
| 2022/0259201 A1 | 8/2022 | Su et al. |
| 2022/0273665 A1 | 9/2022 | McGovern et al. |
| 2023/0097358 A1 | 3/2023 | Araujo et al. |
| 2023/0148214 A1 | 5/2023 | Garofalo et al. |
| 2023/0357269 A1 | 11/2023 | Blom et al. |

FOREIGN PATENT DOCUMENTS

| | | |
|---|---|---|
| CN | 112409331 A | 2/2021 |
| CN | 112812014 A | 5/2021 |
| EP | 1046631 A1 | 10/2000 |
| EP | 1217000 A1 | 6/2002 |
| EP | 2398474 A1 | 12/2011 |
| EP | 3333157 A1 | 6/2018 |
| JP | 62-135830 A | 6/1987 |
| JP | 62-135834 A | 6/1987 |
| JP | 62-135835 A | 6/1987 |
| JP | 62-136650 A | 6/1987 |
| JP | 62-136651 A | 6/1987 |
| JP | 62-136654 A | 6/1987 |
| JP | 2010-111624 A | 5/2010 |
| JP | 5763937 B2 | 8/2015 |
| KR | 10-2014-0144613 A | 12/2014 |
| KR | 10-2020-0069184 A | 6/2020 |
| WO | 97/36876 A1 | 10/1997 |
| WO | 99/23076 A1 | 5/1999 |
| WO | 99/23077 A1 | 5/1999 |
| WO | 01/53268 A2 | 7/2001 |
| WO | 02/00651 A2 | 1/2002 |
| WO | 2002/083648 A1 | 10/2002 |
| WO | 2003/084948 A1 | 10/2003 |
| WO | 2003/101968 A1 | 12/2003 |
| WO | 2004/110350 A2 | 12/2004 |
| WO | 2005/040157 A2 | 5/2005 |
| WO | 2005/060958 A1 | 7/2005 |
| WO | 2006/071875 A1 | 7/2006 |
| WO | 2006/071958 A1 | 7/2006 |
| WO | 2006/096564 A1 | 9/2006 |
| WO | 2007/044085 A2 | 4/2007 |
| WO | 2007/050124 A1 | 5/2007 |
| WO | 2007/058626 A1 | 5/2007 |
| WO | 2007/117465 A2 | 10/2007 |
| WO | 2008/003396 A1 | 1/2008 |
| WO | 2008/008650 A1 | 1/2008 |
| WO | 2008/100867 A2 | 8/2008 |
| WO | 2008/137105 A1 | 11/2008 |
| WO | 2010/048149 A2 | 4/2010 |
| WO | 2010/065681 A1 | 6/2010 |
| WO | 2010/075203 A1 | 7/2010 |
| WO | 2010/075273 A1 | 7/2010 |
| WO | 2010/080537 A1 | 7/2010 |
| WO | 2010/088518 A2 | 8/2010 |
| WO | 2010/092181 A1 | 8/2010 |
| WO | 2010/096777 A1 | 8/2010 |
| WO | 2011/107474 A1 | 9/2011 |
| WO | 2011/109551 A2 | 9/2011 |
| WO | 2011/143365 A1 | 11/2011 |
| WO | 2012/016217 A1 | 2/2012 |
| WO | 2012/068589 A2 | 5/2012 |
| WO | 2012/092471 A2 | 7/2012 |
| WO | 2012/129562 A2 | 9/2012 |
| WO | 2013/025733 A1 | 2/2013 |
| WO | 2013/030138 A1 | 3/2013 |
| WO | 2013/036869 A2 | 3/2013 |
| WO | 2013/178816 A1 | 12/2013 |
| WO | 2014/113485 A1 | 7/2014 |
| WO | 2015/048553 A1 | 4/2015 |
| WO | 2015/082499 A2 | 6/2015 |
| WO | 2015/103527 A1 | 7/2015 |
| WO | 2015/154169 A1 | 10/2015 |
| WO | 2015/179414 A1 | 11/2015 |
| WO | 2016/022446 A1 | 2/2016 |
| WO | 2016/172631 A2 | 10/2016 |
| WO | 2017/024968 A1 | 2/2017 |
| WO | 2017/066705 A1 | 4/2017 |
| WO | 2017/068064 A1 | 4/2017 |
| WO | 2017/161028 A1 | 9/2017 |
| WO | 2017/194665 A1 | 11/2017 |
| WO | 2018/226976 A1 | 12/2018 |
| WO | 2019/018795 A1 | 1/2019 |
| WO | 2019/034172 A1 | 2/2019 |
| WO | 2019/036562 A1 | 2/2019 |
| WO | 2019/209948 A1 | 10/2019 |
| WO | 2020/139748 A1 | 7/2020 |
| WO | 2020/147739 A1 | 7/2020 |
| WO | 2020/228756 A1 | 11/2020 |
| WO | 2021/104305 A1 | 6/2021 |
| WO | 2021/127333 A1 | 6/2021 |
| WO | 2021/138391 A1 | 7/2021 |
| WO | 2021/155253 A1 | 8/2021 |
| WO | 2021/161230 A1 | 8/2021 |
| WO | 2021/178780 A1 | 9/2021 |
| WO | 2021/183970 A1 | 9/2021 |
| WO | 2021/224320 A1 | 11/2021 |
| WO | 2022/147246 A1 | 7/2022 |
| WO | 2022/194976 A1 | 9/2022 |
| WO | 2022/198112 A1 | 9/2022 |
| WO | 2023/279041 A1 | 1/2023 |
| WO | 2023/196720 A2 | 10/2023 |
| WO | 2024/006883 A1 | 1/2024 |
| WO | 2024/006897 A1 | 1/2024 |
| WO | 2024/050396 A1 | 3/2024 |

INDAZOLE COMPOUNDS AS KINASE INHIBITORS

CROSS-REFERENCE TO RELATED APPLICATIONS

This application is the United States National Stage Application of International Patent Application No. PCT/US2021/065679, filed Dec. 30, 2021, which claims the benefit of U.S. Provisional Patent Application No. 63/132,031, filed on Dec. 30, 2020, and U.S. Provisional Patent Application No. 63/216,879, filed on Jun. 30, 2021. Each of the aforementioned applications is incorporated by reference in its entirety herein.

TECHNICAL FIELD

The disclosure pertains to indazole compounds that are useful in treating cancer, pharmaceutical compositions that include one or more such indazole compounds, and methods of using such indazole compounds in treating cancer.

BACKGROUND

Kinase inhibitors have been used to block the activity of kinases and thereby treat cancer (e.g., by inhibiting mitotic processes). These kinase inhibitors are often small molecules that target kinases to block the development, growth or spread of cancer.

However, although various inhibitors of kinases are known, there remains a need for selective inhibitors to be used for the treatment of diseases such as hyper-proliferative diseases, which offer one or more advantages over current compounds. Those advantages include: improved activity and/or efficacy; beneficial kinase selectivity profile according to the respective therapeutic need; improved side effect profile, such as fewer undesired side effects, lower intensity of side effects, or reduced (cyto)toxicity; improved targeting of mutant receptors in diseased cells; improved physicochemical properties, such as solubility/stability in water, body fluids, and/or pharmaceutical formulations; improved pharmacokinetic properties, allowing e.g. for dose reduction or an easier dosing scheme; easier drug substance manufacturing e.g. by shorter synthetic routes or easier purification.

SUMMARY

The compounds disclosed herein provide small molecule kinase inhibitors that are both efficacious and selective.

In some aspects, the disclosure is directed to compounds of formula (I)

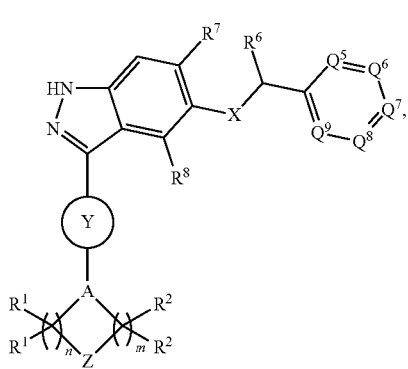

(I)

or a pharmaceutically acceptable salt thereof,
wherein n=1, 2, or 3;
m=0, 1, 2, or 3;
each $R^1$ is independently H, CN, or optionally substituted $C_1$-$C_6$alkyl;
each $R^2$ is independently H, CN, or optionally substituted $C_1$-$C_6$alkyl;
  or two $R^1$ groups attached to the same carbon atom, together with the carbon atom to which they are both attached form an optionally substituted 3-7 membered spirocycloalkyl ring or an optionally substituted 3-7 membered spiroheterocycloalkyl ring;
  or two $R^1$ groups attached to the same carbon atom, together with that carbon atom, represent a carbonyl group (C=O);
  or two $R^2$ groups attached to the same carbon atom, together with the carbon atom to which they are both attached form an optionally substituted 3-7 membered spirocycloalkyl ring or an optionally substituted 3-7 membered spiroheterocycloalkyl ring;
  or two $R^2$ groups attached to the same carbon atom, together with that carbon atom, represent a carbonyl group (C=O);
  or two $R^1$ groups attached to different carbon atoms, together with the carbon atoms to which they are attached, form a 3-7 membered cycloalkyl ring;
  or two $R^2$ groups attached to different carbon atoms, together with the carbon atoms to which they are attached, form a 3-7 membered cycloalkyl ring;
  or an $R^1$ group and an $R^2$ group are attached to form a 6-9 membered bridged bicyclic ring;
A=N or CH;
Z=$S(O)_2$; S(O); O, $NR^3$ or $CR^4R^{4'}$;
$R^3$ is H; optionally substituted $C_1$-$C_6$alkyl, 3-5 membered cycloalkyl, 3-5 membered heterocycloalkyl, —C(O)$NR^aR^b$; —C(O)$OR^c$; —C(O)$R^c$; —S(O)$_2R^c$; or —S(O)$_2NR^aR^b$;
  or $R^3$ together with an $R^1$ or an $R^2$ form an optionally substituted 3- to 7-membered heterocycloalkyl ring;
$R^a$ is H or $C_1$-$C_6$alkyl;
$R^b$ is H or $C_1$-$C_6$alkyl;
  or $R^a$ and $R^b$ together with the N atom to which they are both attached, form an optionally substituted 3 to 7 membered heterocycloalkyl ring;
$R^c$ is optionally substituted $C_1$-$C_6$alkyl, or cycloalkyl;
$R^4$ is H, —F, or optionally substituted $C_1$-$C_6$alkyl;
$R^{4'}$ is H, —F, —OH, —CN, —$NH_2$, —NH($C_1$-$C_3$alkyl), —N($C_1$-$C_3$alkyl)$_2$, —N($C_1$-$C_3$alkyl)-$SO_2$($C_1$-$C_3$alkyl), —$C_1$-$C_6$haloalkyl, optionally substituted $C_1$-$C_6$alkyl, or optionally substituted $C_1$-$C_6$alkoxyl;
  or $R^4$ and $R^{4'}$ together with the C atom to which they are both attached, form an optionally substituted 3 to 7 membered heterocycloalkyl ring or an optionally substituted 3 to 7 membered cycloalkyl ring;
  or $R^4$ and $R^{4'}$, together with the carbon atom to which they are both attached, form an oxo group;
  or $R^{4'}$ together with an $R^1$ or an $R^2$ form an optionally substituted 3- to 7-membered heterocycloalkyl ring or an optionally substituted 3- to 7-membered cycloalkyl ring;
Y is a 5- or 6-membered heteroaryl ring, or a 6-membered aryl ring;
$Q^5$, $Q^6$, $Q^7$, $Q^8$, and $Q^9$, are each independently N or $CR^5$, wherein one or two of $Q^5$, $Q^6$, $Q^7$, $Q^8$, and $Q^9$ is N and the remainder are $CR^5$;

$R^5$ is H, halogen, $C_1$-$C_3$alkyl; $C_1$-$C_3$alkoxyl, or cycloalkyl;

X=O, S, or NR wherein R is H or $C_1$-$C_3$alkyl;

$R^6$ is $C_1$-$C_6$alkyl;

$R^7$ is H, halogen, —$C_1$-$C_6$alkyl; —$C_1$-$C_6$ alkoxyl, or -cycloalkyl; and $R^8$ is H, halogen, —$C_1$-$C_6$alkyl; —$C_1$-$C_6$ alkoxyl, or -cycloalkyl.

In some embodiments, the compounds of formula (I) are those wherein n=1, 2, or 3;

m=1, 2, or 3;

each $R^1$ is independently H; or optionally substituted $C_1$-$C_6$alkyl;

each $R^2$ is independently H; or optionally substituted $C_1$-$C_6$alkyl;

or two $R^1$ groups attached to the same carbon atom, together with the carbon atom to which they are both attached form an optionally substituted 3-7 membered spirocycloalkyl ring or an optionally substituted 3-7 membered spiroheterocycloalkyl ring;

or two $R^1$ groups attached to the same carbon atom, together with that carbon atom, represent a carbonyl group (C=O);

or two $R^2$ groups attached to the same carbon atom, together with the carbon atom to which they are both attached form an optionally substituted 3-7 membered spirocycloalkyl ring or an optionally substituted 3-7 membered spiroheterocycloalkyl ring;

or two $R^2$ groups attached to the same carbon atom, together with that carbon atom, represent a carbonyl group (C=O);

or two $R^1$ groups attached to different carbon atoms, together with the carbon atoms to which they are attached, form a 3-7 membered cycloalkyl ring;

or two $R^2$ groups attached to different carbon atoms, together with the carbon atoms to which they are attached, form a 3-7 membered cycloalkyl ring;

or an $R^1$ group and an $R^2$ group are attached to form a 6-9 membered bridged bicyclic ring;

A=N or CH;

Z=S(O)$_2$; S(O); O, NR$^3$ or CR$^4$R$^{4'}$;

$R^3$ is H; optionally substituted $C_1$-$C_6$alkyl, 3-5-membered cycloalkyl, 3-5 membered heterocycloalkyl, —C(O)NR$^a$R$^b$; —C(O)OR$^c$; —C(O)R$^c$; —S(O)$_2$R$^c$; or —S(O)$_2$NR$^a$R$^b$;

$R^a$ is H or $C_1$-$C_6$alkyl;

$R^b$ is H or $C_1$-$C_6$alkyl;

or $R^a$ and $R^b$ together with the N atom to which they are both attached, form an optionally substituted 3 to 7 membered heterocycloalkyl ring;

$R^c$ is optionally substituted $C_1$-$C_6$alkyl, or cycloalkyl;

$R^4$ is H or optionally substituted $C_1$-$C_6$alkyl;

$R^{4'}$ is H, —OH, or optionally substituted $C_1$-$C_6$alkyl;

or $R^4$ and $R^{4'}$ together with the C atom to which they are both attached, form an optionally substituted 3 to 7 membered heterocycloalkyl ring;

Y is a 5- or 6-membered heteroaryl ring;

$Q^5$, $Q^6$, $Q^7$, $Q^8$, and $Q^9$, are each independently N or CR$^5$, wherein one or two of $Q^5$, $Q^6$, $Q^7$, $Q^8$, and $Q^9$ is N and the remainder are CR$^5$;

$R^5$ is H, halogen, $C_1$-$C_3$alkyl; $C_1$-$C_3$alkoxyl, or cycloalkyl;

X=O, S, or NR wherein R is H or $C_1$-$C_3$alkyl;

$R^6$ is $C_1$-$C_6$alkyl;

$R^7$ is H, halogen, —$C_1$-$C_6$alkyl; —$C_1$-$C_6$ alkoxyl, or -cycloalkyl; and $R^8$ is H, halogen, —$C_1$-$C_6$alkyl; —$C_1$-$C_6$ alkoxyl, or -cycloalkyl.

Stereoisomers of the compounds of formula (I), and the pharmaceutical salts and solvates thereof, are also described. Methods of using compounds of formula (I) are described, as well as pharmaceutical compositions including the compounds of formula (I).

DETAILED DESCRIPTION OF ILLUSTRATIVE EMBODIMENTS

The disclosure may be more fully appreciated by reference to the following description, including the following definitions and examples. Certain features of the disclosed compositions and methods which are described herein in the context of separate aspects, may also be provided in combination in a single aspect. Alternatively, various features of the disclosed compositions and methods that are, for brevity, described in the context of a single aspect, may also be provided separately or in any subcombination.

The term "optionally substituted," or "substituted" as used herein to describe a substituent defined herein, means that the substituent may, but is not required to be, substituted with one or more of: halo (i.e., —F, —Cl, —Br, —I), cyano, —OH, —$C_1$-$C_6$alkyl, $C_3$-$C_6$cycloalkyl, 3-7 membered heterocycloalkyl, —$C_3$-$C_6$spirocycloalkyl, 3-7 membered spiroheterocycloalkyl, bridged cycloalkyl, bridged heterocycloalkyl, $C_2$-$C_6$alkenyl, $C_2$-$C_6$ alkynyl, $C_1$-$C_6$haloalkyl (e.g., —CF$_3$; —CHF$_2$, —CH$_2$CF$_3$, and the like), —$C_1$-$C_6$alkoxy, —$C_1$-$C_6$ haloalkoxy (e.g., —OCF$_3$; —OCHF$_2$, —OCH$_2$CF$_3$, and the like), $C_1$-$C_6$alkylthio (e.g., —SCH$_3$; —SCH$_2$CH$_3$, and the like), $C_1$-$C_6$ alkylamino (e.g., —CH$_2$NH$_2$; —CH$_2$CH$_2$NH$_2$, and the like), —NH$_2$, —NH($C_1$-$C_6$ alkyl), —N($C_1$-$C_6$ alkyl)$_2$, —NH($C_1$-$C_6$ alkoxy), —C(O)NHC$_1$-$C_6$alkyl, —C(O)N($C_1$-$C_6$ alkyl)$_2$, —COOH, —$C_1$-$C_6$alkylCOOH, —$C_3$-$C_6$cycloalkylCOOH, —C(O)NH$_2$, —$C_1$-$C_6$alkylCONH$_2$, —$C_3$-$C_6$cycloalkylCONH$_2$, —$C_1$-$C_6$alkylCONHC$_1$-$C_6$alkyl, —$C_1$-$C_6$alkylCON($C_1$-$C_6$alkyl)$_2$, —C(O)$C_1$-$C_6$ alkyl, —C(O)O$C_1$-$C_6$ alkyl, —NHCO($C_1$-$C_6$ alkyl), —N($C_1$-$C_6$ alkyl)C(O)($C_1$-$C_6$ alkyl), —S(O)$C_1$-$C_6$ alkyl, —S(O)$_2$$C_1$-$C_6$ alkyl, oxo (i.e., =O), 6-12 membered aryl, or 5 to 12 membered heteroaryl groups. In other embodiments, "optionally substituted," or "substituted" means that the substituent may, but is not required to be, substituted with one or more of —C(O)($C_1$-$C_6$haloalkyl), —NHSO$_2$($C_1$-$C_6$alkyl), —N($C_1$-$C_6$alkyl)SO$_2$($C_1$-$C_6$alkyl), or —P(O)($C_1$-$C_6$alkyl)$_2$ (e.g., —P(O)(CH$_3$)$_2$). In some embodiments, each of the above optional substituents are themselves optionally substituted by one or two of these groups.

When a range of carbon atoms is used herein, for example, $C_1$-$C_6$, all ranges, as well as individual numbers of carbon atoms are encompassed. For example, "$C_1$-$C_3$" includes $C_1$-$C_3$, $C_1$-$C_2$, $C_2$-$C_3$, $C_1$, $C_2$, and $C_3$. Thus, for example, a "$C_1$ to $C_4$ alkyl" group refers to all alkyl groups having from 1 to 4 carbons (e.g., 1, 2, 3, or 4), that is, CH$_3$—, CH$_3$CH$_2$—, CH$_3$CH$_2$CH$_2$—, (CH$_3$)$_2$CH—, CH$_3$CH$_2$CH$_2$CH$_2$—, CH$_3$CH$_2$CH(CH$_3$)— and (CH$_3$)$_3$C—. A "$C_1$ to $C_6$ alkyl" group refers to all alkyl groups having from 1 to 6 carbons (e.g., 1, 2, 3, 4, 5, or 6).

As used herein, the term "alkyl" refers to a fully saturated aliphatic hydrocarbon group. The alkyl moiety may be branched or straight chain. Examples of branched alkyl groups include, but are not limited to, iso-propyl, sec-butyl, t-butyl and the like. Examples of straight chain alkyl groups include, but are not limited to, methyl, ethyl, n-propyl, n-butyl, n-pentyl, n-hexyl, n-heptyl and the like. The alkyl group may have 1 to 30 carbon atoms (whenever it appears herein, a numerical range such as "1 to 30" refers to each integer in the given range; e.g., "1 to 30 carbon atoms" means that the alkyl group may consist of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms, although the present definition also covers the occurrence of the term "alkyl" where no numerical range is designated). The "alkyl" group may also be a medium size alkyl having 1 to 12 carbon atoms. The "alkyl" group could also be a lower alkyl having 1 to 6 carbon atoms. An alkyl group may be substituted or unsubstituted. By way of example only, "$C_1$-$C_5$ alkyl" indicates that there are one to five carbon atoms in the alkyl chain, i.e., the alkyl chain is selected from methyl, ethyl, n-propyl, isopropyl, n-butyl, isobutyl, tert-butyl, pentyl (branched and straight-chained), etc. Typical alkyl groups include, but are in no way limited to, methyl, ethyl, propyl, isopropyl, butyl, isobutyl, tertiary butyl, pentyl and hexyl. In several embodiments, "Me" is methyl (e.g., $CH_3$).

As used herein, "alkenyl" refers to an alkyl group that contains in the straight or branched hydrocarbon chain one or more double bonds. An alkenyl group may be unsubstituted or substituted.

As used herein, "alkynyl" refers to an alkyl group that contains in the straight or branched hydrocarbon chain one or more triple bonds. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups may contain between 3 and 12 carbon atoms. For example, a $C_3$-$C_6$cycloalkyl group indicates that there three to six carbon atoms in the ring, that is, the ring is a cyclopropyl, cyclobutyl, cyclopentyl, or cyclohexyl group. A cycloalkyl group may be unsubstituted or substituted.

As used herein, the term "spirocycloalkyl ring" refers to a cycloalkyl ring that shares one carbon atom with another cyclic ring. For example, a 3-7 membered spirocycloalkyl ring indicates that there are 3, 4, 5, 6, or 7 carbon atoms in the cycloalkyl ring that shares a single carbon atom in common with another cyclic ring. By way of example, shown below are exemplary 3-7 membered spirocycloalkyl groups attached to a piperidine ring:

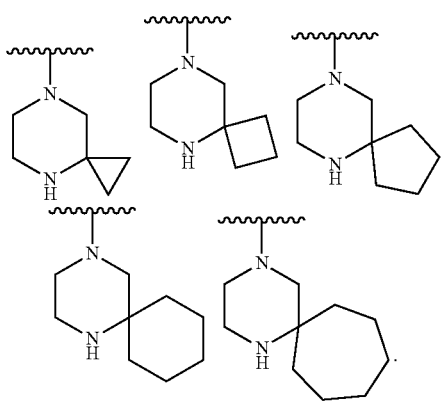

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms, that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine. Heteroaryl rings may also include bridge head nitrogen atoms. For example but not limited to: pyrazolo[1,5-a]pyridine, imidazo[1,2-a]pyridine, and pyrazolo[1,5-a]pyrimidine. A heteroaryl group may be substituted or unsubstituted.

As used herein, "heterocycloalkyl" refers to three-, four-, five-, six-, seven-, eight-, nine-, ten-, up to 18-membered monocyclic, bicyclic, and tricyclic ring system wherein carbon atoms together with from 1 to 5 heteroatoms constitute said ring system. A heterocycloalkyl may optionally contain one or more unsaturated bonds situated in such a way, however, that a fully delocalized pi-electron system does not occur throughout all the rings. The heteroatom(s) is an element other than carbon including, but not limited to, oxygen, sulfur, and nitrogen. A heterocycloalkyl may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heterocycloalkyl may be quaternized. Heterocycloalkyl groups may be unsubstituted or substituted. Examples of such "heterocycloalkyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline, 3,4-methylenedioxyphenyl).

As used herein, the term "spiroheterocycloalkyl ring" refers to a heterocycloalkyl ring that shares one carbon atom with another cyclic ring. For example, a 3-7 membered spiroheterocycloalkyl ring indicates that there are 3, 4, 5, 6, or 7 atoms in the heterocycloalkyl ring, and only one of the carbon atoms in that heterocycloalkyl ring is also a member of another cyclic ring. By way of example, shown below are exemplary 3-7 membered spiroheterocycloalkyl groups attached to a piperidine ring:

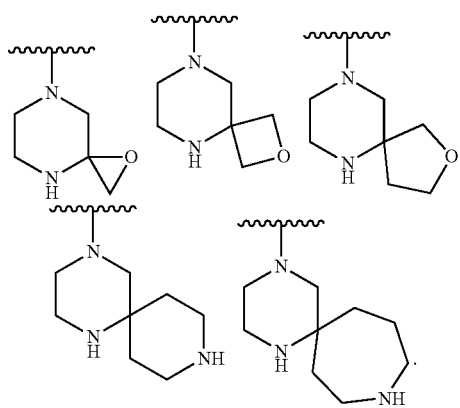

As used herein, the term "bridged bicyclic ring", refers to a ring system comprising two joined cycloalkyl or heterocycloalkyl rings that share at least three at least three atoms For example, a 6-9 membered bridged bicyclic ring indicates that there are 6, 7, 8, or 9 atoms in the bridged bicyclic ring. By way of example, shown below are exemplary 6-9 membered bridged bicyclic rings:

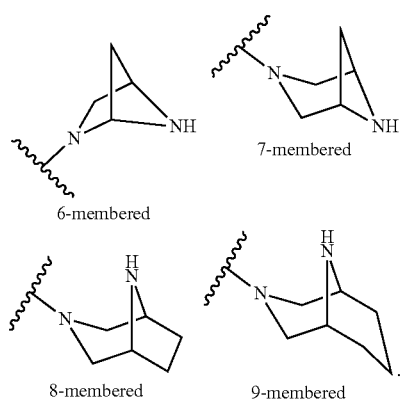

6-membered 7-membered 8-membered 9-membered

As used herein, the term "amino" refers to a —NH$_2$ group.
As used herein, the term "hydroxy" refers to a —OH group.
As used herein, the term "halogen atom" or "halogen" refers to fluorine, chlorine, bromine and iodine.
The term "pharmaceutically acceptable salt" refers to a salt of a compound that does not cause significant irritation to an organism to which it is administered and does not abrogate the biological activity and properties of the compound. In several embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, salicylic or naphthalene-sulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Other pharmaceutically acceptable salts include the trifluoroacetic acid salt.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition, it is understood that, in any compound described herein having one or more double bond(s) generating geometrical isomers that can be defined as E or Z, each double bond may independently be E or Z a mixture thereof. It is understood that, in any compound described herein having one or more chiral centers, all possible diastereomers are also envisioned. It is understood that, in any compound described herein all tautomers are envisioned. It is also understood that, in any compound described herein, all isotopes of the included atoms are envisioned. For example, any instance of hydrogen, may include hydrogen-1 (protium), hydrogen-2 (deuterium), hydrogen-3 (tritium) or other isotopes; any instance of carbon may include carbon-12, carbon-13, carbon-14, or other isotopes; any instance of oxygen may include oxygen-16, oxygen-17, oxygen-18, or other isotopes; any instance of fluorine may include one or more of fluorine-18, fluorine-19, or other isotopes; any instance of sulfur may include one or more of sulfur-32, sulfur-34, sulfur-35, sulfur-36, or other isotopes.

As used herein, the term "kinase inhibitor" means any compound, molecule or composition that inhibits or reduces the activity of a kinase. The inhibition can be achieved by, for example, blocking phosphorylation of the kinase (e.g., competing with adenosine triphosphate (ATP), a phosphorylating entity), by binding to a site outside the active site, affecting its activity by a conformational change, or by depriving kinases of access to the molecular chaperoning systems on which they depend for their cellular stability, leading to their ubiquitylation and degradation.

As used herein, "subject," "host," "patient," and "individual" are used interchangeably and shall be given its ordinary meaning and shall also refer to an organism that has FGFR proteins. This includes mammals, e.g., a human, a non-human primate, ungulates, canines, felines, equines, mice, rats, and the like. The term "mammal" includes both human and non-human mammals.

The term "sample" or "biological sample" shall be given its ordinary meaning and also encompasses a variety of sample types obtained from an organism and can be used in an imaging, a diagnostic, a prognostic, or a monitoring assay. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples.

The terms "treatment," "treating," "treat" and the like shall be given its ordinary meaning and shall also include herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein shall be given its ordinary meaning and shall also cover any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, e.g., arresting its development; and/or (c) relieving the disease symptom, e.g., causing regression of the disease or symptom.

The terms "cancer," "neoplasm," and "tumor" are used interchangeably herein, shall be given its ordinary meaning and shall also refer to cells which exhibit relatively autonomous growth, so that they exhibit an aberrant growth phenotype characterized by a significant loss of control of cell proliferation. In general, cells of interest for detection or treatment in the present application include precursors, precancerous (e.g., benign), malignant, pre-metastatic, metastatic, and non-metastatic cells. As used herein, "FGFR related cancer" denotes those cancers that involve an increased activity in a mutant FGFR kinase, for example, the continued activation of FGFR.

The term "control" refers shall be given its ordinary meaning and shall also include a sample or standard used for comparison with a sample which is being examined, processed, characterized, analyzed, etc. In several embodiments, the control is a sample obtained from a healthy patient or a non-tumor tissue sample obtained from a patient diagnosed with a tumor. In several embodiments, the control is a historical control or standard reference value or range of values. In several embodiments, the control is a comparison to a wild-type FGFR arrangement or scenario.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

In some aspects, the disclosure is directed to compounds of formula (I)

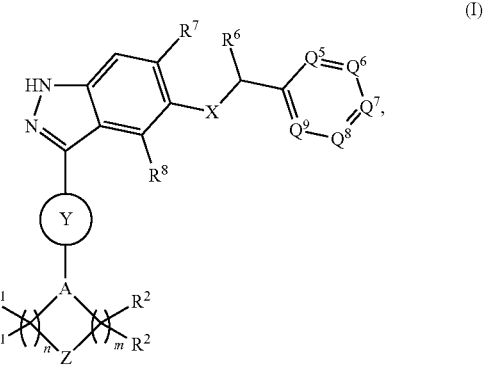

or a pharmaceutically acceptable salt thereof.

In some aspects, n in the compounds of formula (I) is 1, 2, or 3.

In some embodiments, n is 1. In other embodiments, n is 2. In other embodiments, n is 3.

In other aspects, m in the compounds of formula (I) is 0, 1, 2, or 3. In some aspects, m in the compounds of formula (I) is 0 or 1. In some aspects, m in the compounds of formula (I) is 0, 1, or 2. In some aspects, m in the compounds of formula (I) is 1 or 2. In some aspects, m in the compounds of formula (I) is 2 or 3.

In other aspects, m in the compounds of formula (I) is 1, 2, or 3.

In some embodiments, m is 1. In other embodiments, m is 2. In other embodiments, m is 3.

In some embodiments, m is 0.

In some aspects, each $R^1$ in the compounds of formula (I) is independently H, CN, or optionally substituted $C_1$-$C_6$alkyl.

In some aspects, each $R^1$ in the compounds of formula (I) is independently H or optionally substituted $C_1$-$C_6$alkyl.

In some embodiments, at least one $R^1$ in the compounds of formula (I) is H. In other embodiments, each $R^1$ in the compounds of formula (I) is H.

In some embodiments, an $R^1$ in the compounds of formula (I) is optionally substituted $C_1$-$C_6$alkyl, such as, for example, optionally substituted $C_1$-$C_6$alkyl, $C_1$-$C_5$alkyl, $C_1$-$C_4$alkyl, $C_1$-$C_3$alkyl, $C_1$-$C_2$alkyl, $C_1$alkyl, $C_2$alkyl, $C_3$alkyl, $C_4$alkyl, $C_5$alkyl, $C_6$alkyl, methyl, ethyl, n-propyl, isopropyl, n-butyl, isobutyl, sec-butyl, pentanyl, hexanyl, and the like.

In some embodiments, an $R^1$ in the compounds of formula (I) is an unsubstituted $C_1$-$C_6$alky, such as, for example, $C_1$-$C_6$alkyl, $C_1$-$C_5$alkyl, $C_1$-$C_4$alkyl, $C_1$-$C_3$alkyl, $C_1$-$C_2$alkyl, $C_1$alkyl, $C_2$alkyl, $C_3$alkyl, $C_4$alkyl, $C_5$alkyl, $C_6$alkyl, methyl, ethyl, n-propyl, isopropyl, n-butyl, isobutyl, sec-butyl, pentanyl, hexanyl, and the like.

In some embodiments, an $R^1$ in the compounds of formula (I) is —$CH_3$.

In some embodiments of the compound of formula (I), one or more $R^1$ is H and one or more $R^1$ is optionally substituted $C_1$-$C_6$alkyl.

In some embodiments of the compound of formula (I), one or more $R^1$ is a substituted $C_1$-$C_6$alkyl. In some embodiments of the compounds of formula (I), one or more $R^1$ is substituted $C_1$-$C_6$alkyl, such as, for example, —$CH_2OH$, —$CH_2N(CH_3)_2$, or —$CH_2$—CN, —$CH_2SO_2CH_3$, or —$CH_2N(CH_3)SO_2CH_3$.

In some aspects, each $R^2$ in the compounds of formula (I) is independently H, CN, or optionally substituted $C_1$-$C_6$alkyl.

In some aspects, each $R^2$ in the compounds of formula (I) is independently H or optionally substituted $C_1$-$C_6$alkyl.

In some embodiments, at least one $R^2$ in the compounds of formula (I) is H. In other embodiments, each $R^2$ in the compounds of formula (I) is H.

In some embodiments, an $R^2$ in the compounds of formula (I) is optionally substituted $C_1$-$C_6$alkyl, such as, for example, optionally substituted $C_1$-$C_6$alkyl, $C_1$-$C_5$alkyl, $C_1$-$C_4$alkyl, $C_1$-$C_3$alkyl, $C_1$-$C_2$alkyl, $C_1$alkyl, $C_2$alkyl, $C_3$alkyl, $C_4$alkyl, $C_5$alkyl, $C_6$alkyl, methyl, ethyl, n-propyl, isopropyl, n-butyl, isobutyl, sec-butyl, pentanyl, hexanyl, and the like.

In some embodiments, an $R^2$ in the compounds of formula (I) is an unsubstituted $C_1$-$C_6$alkyl, such as, for example, optionally substituted $C_1$-$C_6$alkyl, $C_1$-$C_5$alkyl, $C_1$-$C_4$alkyl, $C_1$-$C_3$alkyl, $C_1$-$C_2$alkyl, $C_1$alkyl, $C_2$alkyl, $C_3$alkyl, $C_4$alkyl, $C_5$alkyl, $C_6$alkyl, methyl, ethyl, n-propyl, isopropyl, n-butyl, isobutyl, sec-butyl, pentanyl, hexanyl, and the like.

In some embodiments, an $R^2$ in the compounds of formula (I) is —$CH_3$.

In some embodiments of the compound of formula (I), one or more $R^2$ is H and one or more $R^2$ is optionally substituted $C_1$-$C_6$alkyl.

In some embodiments of the compound of formula (I), one or more $R^2$ is a substituted $C_1$-$C_6$alkyl. In some embodiments of the compounds of formula (I), one or more $R^1$ is substituted $C_1$-$C_6$alkyl, such as, for example, —$CH_2OH$, —$CH_2N(CH_3)_2$, or —$CH_2$—CN, —$CH_2SO_2CH_3$, or —$CH_2N(CH_3)SO_2CH_3$.

In some aspects of the compounds of formula (I), two $R^1$ groups attached to the same carbon atom, together with the carbon atom to which they are both attached, form an optionally substituted 3-7 membered spirocycloalkyl ring or an optionally substituted 3-7 membered spiroheterocycloalkyl ring.

In some aspects of the compounds of formula (I), two $R^1$ groups attached to the same carbon atom, together with the carbon atom to which they are both attached, form an optionally substituted 3-7 membered spirocycloalkyl ring. In some embodiments, the 3-7 membered spirocycloalkyl ring formed by the two $R^1$ groups is an optionally substituted 3-membered spirocycloalkyl ring, an optionally substituted 4-membered spirocycloalkyl ring, an optionally substituted 5-membered spirocycloalkyl ring, an optionally substituted 6-membered spirocycloalkyl ring, an optionally substituted 7-membered spirocycloalkyl ring, an optionally substituted spirocyclopropyl ring, an optionally substituted spirocyclobutyl ring, an optionally substituted spirocyclopentyl ring, an optionally substituted spirocyclohexyl ring, or an optionally substituted spirocycloheptyl ring.

In some embodiments, the ring formed by the two $R^1$ groups is a spirocyclopropyl ring.

In some embodiments, the 3 ring formed by the two $R^1$ groups is a spirocyclobutyl ring.

In some embodiments, the ring formed by the two $R^1$ groups is a spirocyclopentyl ring.

In some embodiments, the ring formed by the two $R^1$ groups is a spirocyclohexyl ring.

In some embodiments, the ring formed by the two $R^1$ groups is a spirocycloheptyl ring.

In other aspects of the compounds of formula (I), two $R^1$ groups attached to the same carbon atom, together with the carbon atom to which they are both attached, form an optionally substituted 3-7 membered spiroheterocycloalkyl ring. In some embodiments, the 3-7 membered spiroheterocycloalkyl ring formed by the two $R^1$ groups is an optionally substituted 3-membered spiroheterocycloalkyl ring, an optionally substituted 4-membered spiroheterocycloalkyl ring, an optionally substituted 5-membered spiroheterocycloalkyl ring, an optionally substituted 6-membered spiroheterocycloalkyl ring, an optionally substituted 7-membered spiroheterocycloalkyl ring, an optionally substituted spiroaziridinyl ring, an optionally substituted spiroazetidinyl ring, an optionally substituted spiropyrrolidinyl ring, an optionally substituted spiropiperidinyl ring, an optionally substituted spiroazepanyl ring, an optionally substituted spirooxiranyl ring, an optionally substituted spirooxetanyl ring, an optionally substituted spirotetrahydrofuranyl ring, an optionally substituted spirotetrahydropyranyl ring, an optionally substituted spirooxepanyl ring, and the like.

In some aspects of the compounds of formula (I), two $R^1$ groups attached to the same carbon atom, together with that carbon atom, represent a carbonyl group (C═O).

In some aspects of the compounds of formula (I), two $R^2$ groups attached to the same carbon atom, together with the carbon atom to which they are both attached, form an optionally substituted 3-7 membered spirocycloalkyl ring or an optionally substituted 3-7 membered spiroheterocycloalkyl ring.

In some aspects of the compounds of formula (I), two $R^2$ groups attached to the same carbon atom, together with the carbon atom to which they are both attached, form an optionally substituted 3-7 membered spirocycloalkyl ring. In some embodiments, the 3-7 membered spirocycloalkyl ring formed by the two $R^2$ groups is an optionally substituted 3-membered spirocycloalkyl ring, an optionally substituted 4-membered spirocycloalkyl ring, an optionally substituted 5-membered spirocycloalkyl ring, an optionally substituted 6-membered spirocycloalkyl ring, an optionally substituted 7-membered spirocycloalkyl ring, an optionally substituted spirocyclopropyl ring, an optionally substituted spirocyclobutyl ring, an optionally substituted spirocyclopentyl ring, an optionally substituted spirocyclohexyl ring, or an optionally substituted spirocycloheptyl ring.

In some embodiments, the ring formed by the two $R^2$ groups is a spirocyclopropyl ring.

In some embodiments, the ring formed by the two $R^2$ groups is a spirocyclobutyl ring.

In some embodiments, the ring formed by the two $R^2$ groups is a spirocyclopentyl ring.

In some embodiments, the ring formed by the two $R^2$ groups is a spirocyclohexyl ring.

In some embodiments, the spirocycloalkyl ring formed by the two $R^2$ groups is a spirocycloheptyl ring.

In other aspects of the compounds of formula (I), two $R^2$ groups attached to the same carbon atom, together with the carbon atom to which they are both attached, form an optionally substituted 3-7 membered spiroheterocycloalkyl ring. In some embodiments, the 3-7 membered spiroheterocycloalkyl ring formed by the two $R^2$ groups is an optionally substituted 3-membered spiroheterocycloalkyl ring, an optionally substituted 4-membered spiroheterocycloalkyl ring, an optionally substituted 5-membered spiroheterocycloalkyl ring, an optionally substituted 6-membered spiroheterocycloalkyl ring, an optionally substituted 7-membered spiroheterocycloalkyl ring, an optionally substituted spiroaziridinyl ring, an optionally substituted spiroazetidinyl ring, an optionally substituted spiropyrrolidinyl ring, an optionally substituted spiropiperidinyl ring, an optionally substituted spiroazepanyl ring, an optionally substituted spirooxiranyl ring, an optionally substituted spirooxetanyl ring, an optionally substituted spirotetrahydrofuranyl ring, an optionally substituted spiro tetrahydropyranyl ring, an optionally substituted spiro oxepanyl ring, and the like.

In some aspects of the compounds of formula (I), two $R^2$ groups attached to the same carbon atom, together with that carbon atom, represent a carbonyl group (C=O).

In some aspects of the compound of formula (I), two $R^1$ groups attached to different carbon atoms, together with the carbon atoms to which they are attached, form an optionally substituted 3-7 membered cycloalkyl ring, such as, for example, an optionally substituted 3-7 membered cycloalkyl ring, an optionally substituted 3-6 membered cycloalkyl ring, an optionally substituted 3-5 membered cycloalkyl ring, an optionally substituted 3-4 membered cycloalkyl ring, an optionally substituted 3 membered cycloalkyl ring, an optionally substituted 4 membered cycloalkyl ring, an optionally substituted 5 membered cycloalkyl ring, an optionally substituted 6 membered cycloalkyl ring, an optionally substituted 7 membered cycloalkyl ring, an optionally substituted cyclopropyl ring, an optionally substituted cyclobutyl ring, an optionally substituted cyclopentyl ring, an optionally substituted cyclohexyl ring, or an optionally substituted cycloheptyl ring.

In some aspects of the compound of formula (I), two $R^2$ groups attached to different carbon atoms, together with the carbon atoms to which they are attached, form an optionally substituted 3-7 membered cycloalkyl ring, such as, for example, an optionally substituted 3-7 membered cycloalkyl ring, an optionally substituted 3-6 membered cycloalkyl ring, an optionally substituted 3-5 membered cycloalkyl ring, an optionally substituted 3-4 membered cycloalkyl ring, an optionally substituted 3 membered cycloalkyl ring, an optionally substituted 4 membered cycloalkyl ring, an optionally substituted 5 membered cycloalkyl ring, an optionally substituted 6 membered cycloalkyl ring, an optionally substituted 7 membered cycloalkyl ring, an optionally substituted cyclopropyl ring, an optionally substituted cyclobutyl ring, an optionally substituted cyclopentyl ring, an optionally substituted cyclohexyl ring, or an optionally substituted cycloheptyl ring.

In some aspects of the compounds of formula (I), an $R^1$ group and an $R^2$ group are attached to form a 6-9 membered bridged bicyclic ring, such as, for example, a 6-9 membered bridged bicyclic ring, a 6-8 membered bridged bicyclic ring, a 6-7 membered bridged bicyclic ring, a 6-membered bridged bicyclic ring, a 7-membered bridged bicyclic ring, a 8-membered bridged bicyclic ring, a 9-membered bridged bicyclic ring.

In some aspects, A in the compounds of formula (I) is A is N or CH.

In some embodiments of the compound of formula (I), A is N.

In some embodiments of the compound of formula (I), A is CH.

In some aspects of the disclosure, Z in the compounds of formula (I) is $S(O)_2$; S(O); O, $NR^3$ or $CR^4R^{4'}$.

In some embodiments of the compound of formula (I), Z is $S(O)_2$.

In some embodiments of the compound of formula (I), Z is S(O).

In some embodiments of the compound of formula (I), Z is O.

In some embodiments of the compound of formula (I), Z is $NR^3$.

In some embodiments of the compound of formula (I), Z is $CR^4R^{4'}$.

In some aspects of the disclosure, $R^3$ in the compounds of formula (I) is H; optionally substituted $C_1$-$C_6$alkyl, 3-5 membered cycloalkyl, 3-5 membered heterocycloalkyl, —C(O)$NR^aR^b$; —C(O)$OR^c$; —C(O)$R^c$; —S(O)$_2R^c$; or —S(O)$_2NR^aR^b$; or $R^3$ together with an $R^1$ or an $R^2$ form an optionally substituted 3- to 7-membered heterocycloalkyl ring.

In some aspects of the disclosure, $R^3$ in the compounds of formula (I) is H; optionally substituted $C_1$-$C_6$alkyl, 3-5 membered cycloalkyl, 3-5 membered heterocycloalkyl, —C(O)$NR^aR^b$; —C(O)$OR^c$; —C(O)$R^c$; —S(O)$_2R^c$; or —S(O)$_2NR^aR^b$.

In some embodiments of the compound of formula (I), $R^3$ in the compounds of formula (I) is H.

In some embodiments of the compound of formula (I), $R^3$ in the compounds of formula (I) is optionally substituted $C_1$-$C_6$alkyl, such as, for example, optionally substituted $C_1$-$C_6$alkyl, $C_1$-$C_5$alkyl, $C_1$-$C_4$alkyl, $C_1$-$C_3$alkyl, $C_1$-$C_2$alkyl, $C_1$alkyl, $C_2$alkyl, $C_3$alkyl, $C_4$alkyl, $C_5$alkyl, $C_6$alkyl, methyl, ethyl, n-propyl, isopropyl, n-butyl, isosbutyl, sec-butyl, pentanyl, hexanyl, and the like.

In some embodiments of the compound of formula (I), $R^3$ in the compounds of formula (I) is 3-5 membered cycloalkyl, such as, for example, cyclopropyl, cyclobutyl, cyclopentyl, and the like. In some embodiments of the compounds of formula (I), $R^3$ in the compounds of formula (I) is 3-5 membered substituted cycloalkyl, such as, for example, substituted cyclopropyl, cyclobutyl, cyclopentyl, and the like.

In some embodiments, $R^3$ is cyclobutyl. In some embodiments, $R^3$ is substituted cyclobutyl.

In some embodiments of the compound of formula (I), $R^3$ in the compounds of formula (I) is 3-5 membered heterocycloalkyl. In some embodiments of the compound of formula (I), $R^3$ in the compounds of formula (I) is 3-5 membered substituted heterocycloalkyl.

In some embodiments of the compound of formula (I), $R^3$ in the compounds of formula (I) is —C(O)$NR^aR^b$.

In some embodiments of the compound of formula (I), $R^3$ in the compounds of formula (I) is —C(O)$OR^c$.

In some embodiments of the compound of formula (I), $R^3$ in the compounds of formula (I) is —C(O)$R^c$.

In some embodiments of the compound of formula (I), $R^3$ in the compounds of formula (I) is —S(O)$_2R^c$.

In some embodiments of the compound of formula (I), $R^3$ in the compounds of formula (I) is —S(O)$_2NR^aR^b$.

In some aspects of the disclosure, Rain the compounds of formula (I) is H or $C_1$-$C_6$alkyl.

In some embodiments of the compound of formula (I), $R^a$ in the compounds of formula (I) is H.

In some embodiments of the compound of formula (I), $R^a$ in the compounds of formula (I) is $C_1$-$C_6$alkyl, such as, for example, $C_1$-$C_6$alkyl, $C_1$-$C_5$alkyl, $C_1$-$C_4$alkyl, $C_1$-$C_3$alkyl, $C_1$-$C_2$alkyl, $C_1$alkyl, $C_2$alkyl, $C_3$alkyl, $C_4$alkyl, $C_5$alkyl, $C_6$alkyl, methyl, ethyl, n-propyl, isopropyl, n-butyl, isosbutyl, sec-butyl, pentanyl, hexanyl, and the like.

In some aspects of the disclosure, $R^b$ in the compounds of formula (I) is H or $C_1$-$C_6$alkyl.

In some embodiments of the compound of formula (I), $R^b$ in the compounds of formula (I) is H.

In some embodiments of the compound of formula (I), $R^b$ in the compounds of formula (I) is $C_1$-$C_6$alkyl, such as, for example, $C_1$-$C_6$alkyl, $C_1$-$C_5$alkyl, $C_1$-$C_4$alkyl, $C_1$-$C_3$alkyl, $C_1$-$C_2$alkyl, $C_1$alkyl, $C_2$alkyl, $C_3$alkyl, $C_4$alkyl, $C_5$alkyl, $C_6$alkyl, methyl, ethyl, n-propyl, isopropyl, n-butyl, isosbutyl, sec-butyl, pentanyl, hexanyl, and the like.

In some aspects of the disclosure, $R^a$ and $R^b$ together with the N atom to which they are both attached, form an optionally substituted 3 to 7 membered heterocycloalkyl ring, such as, for example, an optionally substituted 3 to 7 membered heterocycloalkyl ring, an optionally substituted 3 to 6 membered heterocycloalkyl ring, an optionally substituted 3 to 5 membered heterocycloalkyl ring, an optionally substituted 3 to 4 membered heterocycloalkyl ring, an optionally substituted 3-membered heterocycloalkyl ring, an optionally substituted 4-membered heterocycloalkyl ring, an optionally substituted 5-membered heterocycloalkyl ring, an optionally substituted 6-membered heterocycloalkyl ring, an optionally substituted 7-membered heterocycloalkyl ring, an optionally substituted aziridinyl ring, an optionally substituted azetidinyl ring, an optionally substituted pyrrolidinyl ring, an optionally substituted piperidinyl ring, or an optionally substituted azepanyl ring.

In some aspects of the disclosure, $R^c$ in the compounds of formula (I) is optionally substituted $C_1$-$C_6$alkyl, or cycloalkyl.

In some embodiments of the compounds of formula (I), $R^c$ is optionally substituted $C_1$-$C_6$alkyl, such as, for example, optionally substituted $C_1$-$C_6$alkyl, $C_1$-$C_5$alkyl, $C_1$-$C_4$alkyl, $C_1$-$C_3$alkyl, $C_1$-$C_2$alkyl, $C_1$alkyl, $C_2$alkyl, $C_3$alkyl, $C_4$alkyl, $C_5$alkyl, $C_6$alkyl, methyl, ethyl, n-propyl, isopropyl, n-butyl, isobutyl, sec-butyl, pentanyl, hexanyl, and the like.

In some embodiments, $R^c$ is methyl.

In some embodiments, $R^c$ is (dimethylamino)methyl, i.e., —$CH_2N(CH_3)_2$.

In some embodiments, $R^c$ is ethyl.

In some embodiments, $R^c$ is (dimethylamino)ethyl, i.e., —$CH_2CH_2N(CH_3)_2$.

In other embodiments of the compounds of formula (I), $R^c$ is cycloalkyl, such as, for example, cyclopropyl, cyclobutyl, cyclopentyl, cyclohexyl, or cycloheptyl, and the like.

In some embodiments of the compound of formula (I), $R^3$ in the compounds of formula (I) together with an $R^1$ or an $R^2$ form an optionally substituted 3- to 7-membered heterocycloalkyl ring, such as, for example, aziridine, azetidine, pyrrolidine, a pyrazine, imidazoline, and the like. Thus, in some embodiments of compounds of formula (I), the substructure

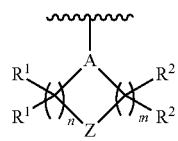

is, for example,

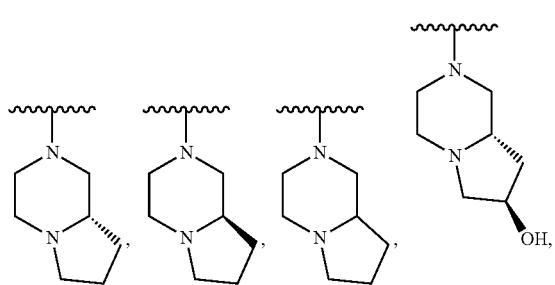

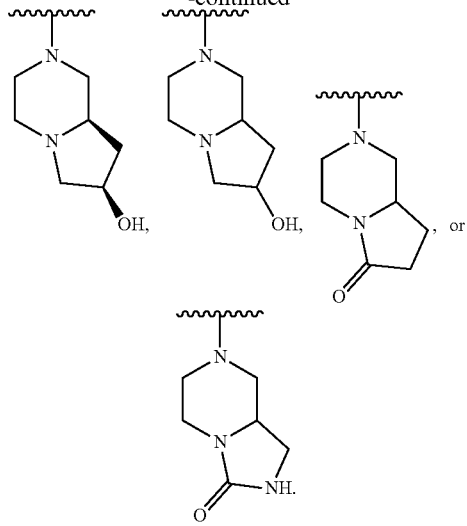

In some aspects of the disclosure, $R^4$ in the compounds of formula (I) is H, —F, or optionally substituted $C_1$-$C_6$alkyl.

In some aspects of the disclosure, $R^4$ in the compounds of formula (I) is H or optionally substituted $C_1$-$C_6$alkyl.

In some embodiments of the compounds of formula (I), is $R^4$ is H.

In some embodiments of the compounds of formula (I), is $R^4$ is optionally substituted $C_1$-$C_6$alkyl, such as, for example, optionally substituted $C_1$-$C_6$alkyl, $C_1$-$C_5$alkyl, $C_1$-$C_4$alkyl, $C_1$-$C_3$alkyl, $C_1$-$C_2$alkyl, $C_1$alkyl, $C_2$alkyl, $C_3$alkyl, $C_4$alkyl, $C_5$alkyl, $C_6$alkyl, methyl, ethyl, n-propyl, isopropyl, n-butyl, isobutyl, sec-butyl, pentanyl, hexanyl, and the like.

In some embodiments of the compounds of formula (I), is $R^4$ is unsubstituted $C_1$-$C_6$alkyl, such as, for example, $C_1$-$C_6$alkyl, $C_1$-$C_5$alkyl, $C_1$-$C_4$alkyl, $C_1$-$C_3$alkyl, $C_1$-$C_2$alkyl, $C_1$alkyl, $C_2$alkyl, $C_3$alkyl, $C_4$alkyl, $C_5$alkyl, $C_6$alkyl, methyl, ethyl, n-propyl, isopropyl, n-butyl, isobutyl, sec-butyl, pentanyl, hexanyl, and the like. In some embodiments of the compounds of formula (I), is $R^4$ is methyl (i.e., —$CH_3$).

In some embodiments of the compounds of formula (I), is $R^4$ is substituted $C_1$-$C_6$alkyl. In some embodiments of the compounds of formula (I), is $R^4$ is —$CH_2OH$.

In some embodiments of the compounds of formula (I), is $R^4$ is —F.

In some aspects of the disclosure, $R^{4'}$ in the compounds of formula (I) is H, —F, —OH, —CN, —$NH_2$, —$NH(C_1$-$C_3$alkyl), —$N(C_1$-$C_3$alkyl)$_2$, —$N(C_1$-$C_3$alkyl)-$SO_2(C_1$-$C_3$alkyl), —$C_1$-$C_6$haloalkyl, optionally substituted $C_1$-$C_6$alkyl, optionally substituted $C_1$-$C_6$alkoxyl; or $R^4$ and $R^{4'}$ together with the C atom to which they are both attached, form an optionally substituted 3 to 7 membered heterocycloalkyl ring or an optionally substituted 3 to 7 membered cycloalkyl ring; or $R^4$ and $R^{4'}$, together with the carbon atom to which they are both attached, form an oxo group; or $R^{4'}$ together with an $R^1$ or an $R^2$ form an optionally substituted 3- to 7-membered heterocycloalkyl ring or an optionally substituted 3- to 7-membered cycloalkyl ring.

In some aspects of the disclosure, $R^{4'}$ in the compounds of formula (I) is H, —OH, or optionally substituted $C_1$-$C_6$alkyl.

In some embodiments of the compounds of formula (I), is $R^{4'}$ is H.

In some embodiments of the compounds of formula (I), is $R^{4'}$ is —F.

In some embodiments of the compounds of formula (I), is $R^{4'}$ is —OH.

In some embodiments of the compounds of formula (I), is $R^{4'}$ is —CN.

In some embodiments of the compounds of formula (I), is $R^{4'}$ is —NH$_2$.

In some embodiments of the compounds of formula (I), is $R^{4'}$ is —NH($C_1$-$C_3$alkyl), such as, for example, —NH($C_1$alkyl), —NH($C_2$alkyl), —NH($C_3$alkyl), —NH(CH$_3$), —NH—CH(CH$_3$)$_2$, and the like. In some embodiments of the compounds of formula (I), is $R^{4'}$ is —NH(CH$_3$). In some embodiments of the compounds of formula (I), is $R^{4'}$ is —NH—CH(CH$_3$)$_2$.

In some embodiments of the compounds of formula (I), is $R^{4'}$ is —N($C_1$-$C_3$alkyl)$_2$, such as, for example, —N($C_1$-alkyl)$_2$, —N($C_2$alkyl)$_2$, —N($C_3$alkyl)$_2$, —N($C_1$alkyl)($C_2$alkyl), —N(CH$_3$)$_2$, and the like. In some embodiments of the compounds of formula (I), is $R^{4'}$ is —N(CH$_3$)$_2$.

In some embodiments of the compounds of formula (I), is $R^{4'}$ is —N($C_1$-$C_3$alkyl)-SO$_2$($C_1$-$C_3$alkyl), such as, for example, —N($C_1$alkyl)-SO$_2$($C_1$-$C_3$alkyl), —N($C_2$alkyl)-SO$_2$($C_1$-$C_3$alkyl), —N($C_3$alkyl)-SO$_2$($C_1$-$C_3$alkyl), —N($C_1$-$C_3$alkyl)-SO$_2$($C_1$alkyl), —N($C_1$-$C_3$alkyl)-SO$_2$($C_2$alkyl), —N($C_1$-$C_3$alkyl)-SO$_2$($C_3$alkyl), —NH—SO$_2$(CH$_3$), —N(CH$_3$)—SO$_2$(CH$_3$), and the like. In some embodiments of the compounds of formula (I), is $R^{4'}$ is —N(CH$_3$)—SO$_2$(CH$_3$).

In some embodiments of the compounds of formula (I), is $R^{4'}$ is —$C_1$-$C_6$haloalkyl, such as, for example, —$C_1$haloalkyl, —$C_2$haloalkyl, —$C_3$haloalkyl, —$C_4$haloalkyl, —$C_5$haloalkyl, —$C_6$haloalkyl, —CF$_3$, —CH$_2$CF$_3$, —CHF$_2$, —CH$_2$CHF$_2$ and the like.

In some embodiments of the compounds of formula (I), is $R^{4'}$ is optionally substituted $C_1$-$C_6$alkyl, such as, for example, optionally substituted $C_1$-$C_6$alkyl, $C_1$-$C_5$alkyl, $C_1$-$C_4$alkyl, $C_1$-$C_3$alkyl, $C_1$-$C_2$alkyl, $C_1$alkyl, $C_2$alkyl, $C_3$alkyl, $C_4$alkyl, $C_5$alkyl, $C_6$alkyl, methyl, ethyl, n-propyl, isopropyl, n-butyl, isosbutyl, sec-butyl, pentanyl, hexanyl, and the like.

In some embodiments of the compounds of formula (I), is $R^{4'}$ is unsubstituted $C_1$-$C_6$alkyl, such as, for example, $C_1$-$C_6$alkyl, $C_1$-$C_5$alkyl, $C_1$-$C_4$alkyl, $C_1$-$C_3$alkyl, $C_1$-$C_2$alkyl, $C_1$alkyl, $C_2$alkyl, $C_3$alkyl, $C_4$alkyl, $C_5$alkyl, $C_6$alkyl, methyl, ethyl, n-propyl, isopropyl, n-butyl, isosbutyl, sec-butyl, pentanyl, hexanyl, and the like. In some embodiments of the compounds of formula (I), is $R^{4'}$ is methyl (i.e., —CH$_3$).

In some embodiments of the compounds of formula (I), is $R^{4'}$ is substituted $C_1$-$C_6$alkyl, such as, for example, —CH$_2$OH, —CH$_2$N(CH$_3$)$_2$, —C(CH$_3$)$_2$—OH, —CH$_2$—CN, —CH$_2$SO$_2$CH$_3$, or —CH$_2$N(CH$_3$)SO$_2$CH$_3$.

In some embodiments of the compounds of formula (I), is $R^{4'}$ is optionally substituted $C_1$-$C_6$alkoxyl, such as, for example, optionally substituted $C_1$-$C_6$alkoxyl, $C_1$-$C_5$alkoxyl, $C_1$-$C_4$alkoxyl, $C_1$-$C_3$alkoxyl, $C_1$-$C_2$alkoxyl, $C_1$alkoxyl, $C_2$alkoxyl, $C_3$alkoxyl, $C_4$alkoxyl, $C_5$alkoxyl, $C_6$alkoxyl, methoxyl, ethoxyl, n-propoxyl, isopropoxyl, n-butoxyl, isobutoxyl, sec-butoxyl, and the like.

In some embodiments of the compounds of formula (I), is $R^{4'}$ is unsubstituted $C_1$-$C_6$alkoxyl, such as, for example, $C_1$-$C_6$alkoxyl, $C_1$-$C_5$alkoxyl, $C_1$-$C_4$alkoxyl, $C_1$-$C_3$alkoxyl, $C_1$-$C_2$alkoxyl, $C_1$alkoxyl, $C_2$alkoxyl, $C_3$alkoxyl, $C_4$alkoxyl, $C_5$alkoxyl, $C_6$alkoxyl, methoxyl, ethoxyl, n-propoxyl, isopropoxyl, n-butoxyl, isobutoxyl, sec-butoxyl, and the like. In some embodiments of the compounds of formula (I), is $R^{4'}$ is —OCH$_3$.

In some aspects of the disclosure, $R^4$ and $R^{4'}$ in the compounds of formula (I), together with the carbon atom to which they are both attached, form an optionally substituted 3 to 7 membered heterocycloalkyl ring or an optionally substituted 3 to 7 membered cycloalkyl ring, such as, for example, an optionally substituted 3 to 7 membered heterocycloalkyl ring, an optionally substituted 3 to 6 membered heterocycloalkyl ring, an optionally substituted 3 to 5 membered heterocycloalkyl ring, an optionally substituted 3 to 4 membered heterocycloalkyl ring, an optionally substituted 3-membered heterocycloalkyl ring, an optionally substituted 4-membered heterocycloalkyl ring, an optionally substituted 5-membered heterocycloalkyl ring, an optionally substituted 6-membered heterocycloalkyl ring, an optionally substituted 7-membered heterocycloalkyl ring, an optionally substituted aziridinyl ring, an optionally substituted azetidinyl ring, an optionally substituted pyrrolidinyl ring, an optionally substituted piperidinyl ring, an optionally substituted azepanyl ring, an optionally substituted oxetanyl ring, an optionally substituted tetrahydrofuranyl ring, an optionally substituted tetrahydrothiophene 1,1-dioxide, or an optionally substituted tetrahydro-2H-thiopyran 1,1-dioxide, or an optionally substituted 3 to 7 membered cycloalkyl ring, an optionally substituted 3 to 6 membered cycloalkyl ring, an optionally substituted 3 to 5 membered cycloalkyl ring, an optionally substituted 3 to 4 membered cycloalkyl ring, an optionally substituted 3-membered cycloalkyl ring, an optionally substituted 4-membered cycloalkyl ring, an optionally substituted 5-membered cycloalkyl ring, an optionally substituted 6-membered cycloalkyl ring, an optionally substituted 7-membered cycloalkyl ring, an optionally substituted cyclopropanyl ring, an optionally substituted cyclobutanyl ring, an optionally substituted cyclopentanyl ring, an optionally substituted cyclohexanyl ring, or an optionally substituted cycloheptanyl ring.

In some aspects of the disclosure, $R^4$ and $R^{4'}$ in the compounds of formula (I), together with the carbon atom to which they are both attached, form an optionally substituted 3 to 7 membered heterocycloalkyl ring, such as, for example, an optionally substituted 3 to 7 membered heterocycloalkyl ring, an optionally substituted 3 to 6 membered heterocycloalkyl ring, an optionally substituted 3 to 5 membered heterocycloalkyl ring, an optionally substituted 3 to 4 membered heterocycloalkyl ring, an optionally substituted 3-membered heterocycloalkyl ring, an optionally substituted 4-membered heterocycloalkyl ring, an optionally substituted 5-membered heterocycloalkyl ring, an optionally substituted 6-membered heterocycloalkyl ring, an optionally substituted 7-membered heterocycloalkyl ring, an optionally substituted aziridinyl ring, an optionally substituted azetidinyl ring, an optionally substituted pyrrolidinyl ring, an optionally substituted piperidinyl ring, or an optionally substituted azepanyl ring.

In embodiments of the disclosure, $R^4$ and $R^{4'}$ in the compounds of formula (I), together with the carbon atom to which they are both attached, form an optionally substituted 3 to 7 membered cycloalkyl ring, such as, for example, an optionally substituted 3 to 7 membered cycloalkyl ring, an optionally substituted 3 to 6 membered cycloalkyl ring, an optionally substituted 3 to 5 membered cycloalkyl ring, an optionally substituted 3 to 4 membered cycloalkyl ring, an optionally substituted 3-membered cycloalkyl ring, an optionally substituted 4-membered cycloalkyl ring, an optionally substituted 5-membered cycloalkyl ring, an optionally substituted 6-membered cycloalkyl ring, an optionally substituted 7-membered cycloalkyl ring, an optionally substituted cyclopropanyl ring, an optionally substituted cyclobutanyl ring, an optionally substituted cyclopentanyl ring, an optionally substituted cyclohexanyl ring, or an optionally substituted cycloheptanyl ring.

In some embodiments, $R^4$ and $R^{4'}$ in the compounds of formula (I), together with the carbon atom to which they are both attached, form optionally substituted 4-membered cycloalkyl ring or an optionally substituted 5-membered cycloalkyl ring.

In some embodiments, $R^4$ and $R^{4'}$ in the compounds of formula (I), together with the carbon atom to which they are both attached, form an optionally substituted cyclobutanyl ring or an optionally cyclopentanyl ring.

In some embodiments, $R^4$ and $R^{4'}$ in the compounds of formula (I), together with the carbon atom to which they are both attached, form a hydroxy-substituted cyclopentanyl ring, such as, for example,

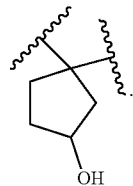 [SMILES: *C1(*)CCC(O)C1]

In other embodiments, $R^4$ and $R^{4'}$ in the compounds of formula (I), together with the carbon atom to which they are both attached, form a methoxy-substituted cyclobutanyl ring, such as, for example,

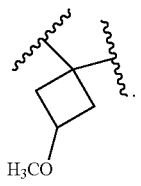

In some embodiments of formula (I), $R^{4'}$ together with an $R^1$ or an $R^2$ form an optionally substituted 3- to 7-membered heterocycloalkyl ring or an optionally substituted 3- to 7-membered cycloalkyl ring.

In some embodiments of formula (I), $R^{4'}$ together with an $R^1$ or an $R^2$ form an optionally substituted 3- to 7-membered heterocycloalkyl ring.

In other embodiments of formula (I), $R^{4'}$ together with an $R^1$ or an $R^2$ form an optionally substituted 3- to 7-membered cycloalkyl ring, such as for example, an optionally substituted 3-membered cycloalkyl ring, an optionally substituted 4-membered cycloalkyl ring, an optionally substituted 5-membered cycloalkyl ring, an optionally substituted 6-membered cycloalkyl ring, an optionally substituted fused 7-membered cycloalkyl ring, a cyclopropyl ring, and the like.

In some embodiments wherein $R^{4'}$ together with an $R^1$ or an $R^2$ form an optionally substituted cyclopropyl ring, Thus, in some embodiments of compounds of formula (I), the substructure

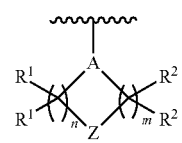

is, for example,

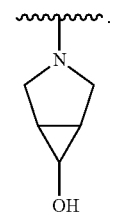

In some aspects of the disclosure, $R^4$ and $R^{4'}$ in the compounds of formula (I), together with the carbon atom to which they are both attached, form an oxo group, i.e.,

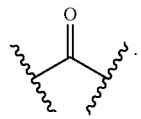

In some aspects of the disclosure, Y in the compounds of formula (I) is a 5- or 6-membered heteroaryl ring or a 6-membered aryl ring.

In some aspects of the disclosure, Y in the compounds of formula (I) is a 5- or 6-membered heteroaryl ring. In some aspects of the disclosure, Y in the compounds of formula (I) is a substituted 5- or 6-membered heteroaryl ring.

In some embodiments, Y in the compounds of formula (I) is a 5-membered heteroaryl ring, such as, for example, furan, pyrrole, thiophene, isoxazole, oxazole, pyrazole, imidazole, isothiazole, thiazole, 1,2,3-thiadiazole, 1,2,4-thiadiazole, 1,2,5-thiadiazole, 1,3,4-thiadiazole, 1,2,3,5-thiatriazole, 1,3,4-oxadiazole, 1,2,4-oxadiazole, 1,2,3-oxadiazole, 1,2,5-oxadiazole, 1,2,3,5-oxatriazole, 2H-1,2,3-triazole, 1H-1,2,4-triazole, 1H-1,2,3-triazole, 4H-1,2,4-triazole, 2H-tetrazole, 1H-tetrazole, and the like.

In some embodiments, Y in the compounds of formula (I) is a substituted 5-membered heteroaryl ring, such as, for example, substituted furan, pyrrole, thiophene, isoxazole, oxazole, pyrazole, imidazole, isothiazole, thiazole, 1,2,3-thiadiazole, 1,2,4-thiadiazole, 1,2,5-thiadiazole, 1,3,4-thiadiazole, 1,2,3,5-thiatriazole, 1,3,4-oxadiazole, 1,2,4-oxadiazole, 1,2,3-oxadiazole, 1,2,5-oxadiazole, 1,2,3,5-oxatriazole, 2H-1,2,3-triazole, 1H-1,2,4-triazole, 1H-1,2,3-triazole, 4H-1,2,4-triazole, 2H-tetrazole, 1H-tetrazole, and the like.

In some embodiments, Y in the compounds of formula (I) is a 6-membered heteroaryl ring, such as, for example, pyridine, pyridazine, pyrimidine, pyrazine, 1,2,3-triazine, 1,2,4-triazine, 1,3,5-triazine, 1,2,3,4-tetrazine, 1,2,3,5-tetrazine, 1,2,4,5-tetrazine, and the like. In some embodiments, Y in the compounds of formula (I) is a substituted 6-membered heteroaryl ring, such as, for example, substituted pyridine, pyridazine, pyrimidine, pyrazine, 1,2,3-triazine, 1,2,4-triazine, 1,3,5-triazine, 1,2,3,4-tetrazine, 1,2,3,5-tetrazine, 1,2,4,5-tetrazine, and the like.

In some embodiments of the compounds of formula (I), Y is a 6-membered aryl ring. In some embodiments, Y is a substituted 6-membered aryl ring. In some embodiments, Y is a phenyl ring. In some embodiments, Y is a substituted phenyl ring.

In some embodiments, Y is

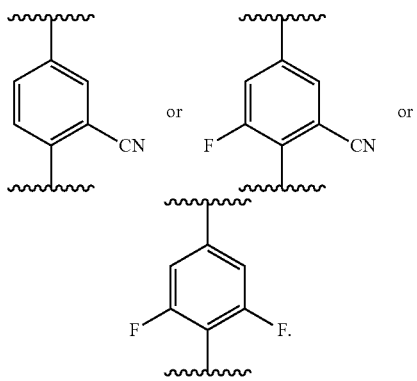

In some aspects of the disclosure, $Q^5$, $Q^6$, $Q^7$, $Q^8$, and $Q^9$ in the compounds of formula (I) are each independently N or $CR^5$, wherein one or two of $Q^5$, $Q^6$, $Q^7$, $Q^8$, and $Q^9$ is N and the remainder are each independently $CR^5$.

In some embodiments, one of $Q^5$, $Q^6$, $Q^7$, $Q^8$, or $Q^9$ is N, and the remainder are each independently $CR^5$.

In some embodiments, $Q^5$ is N and $Q^6$, $Q^7$, $Q^8$, and $Q^9$ are each independently $CR^5$.

In some embodiments, $Q^6$ is N and $Q^5$, $Q^7$, $Q^8$, and $Q^9$ are each independently $CR^5$.

In some embodiments, $Q^7$ is N and $Q^5$, $Q^6$, $Q^7$, and $Q^9$ are each independently $CR^5$.

In some embodiments, $Q^8$ is N and $Q^5$, $Q^6$, $Q^7$, and $Q^9$ are each independently $CR^5$.

In some embodiments, $Q^9$ is N and $Q^5$, $Q^6$, $Q^7$, and $Q^8$ are each independently $CR^5$.

In other embodiments, two of $Q^5$, $Q^6$, $Q^7$, $Q^8$, or $Q^9$ is N, and the remainder are each independently $CR^5$.

In some embodiments, $Q^5$ and $Q^6$ are N, and $Q^7$, $Q^8$, and $Q^9$ are each independently $CR^5$.

In some embodiments, $Q^5$ and $Q^7$ are N, and $Q^6$, $Q^8$, and $Q^9$ are each independently $CR^5$.

In some embodiments, $Q^5$ and $Q^8$ are N, and $Q^6$, $Q^7$, and $Q^9$ are each independently $CR^5$.

In some embodiments, $Q^5$ and $Q^9$ are N, and $Q^6$, $Q^7$, and $Q^8$ are each independently $CR^5$.

In some embodiments, $Q^6$ and $Q^7$ are N, and $Q^5$, $Q^8$, and $Q^9$ are each independently $CR^5$.

In some embodiments, $Q^6$ and $Q^8$ are N, and $Q^5$, $Q^7$, and $Q^9$ are each independently $CR^5$.

In some embodiments, $Q^6$ and $Q^9$ are N, and $Q^5$, $Q^7$, and $Q^8$ are each independently $CR^5$.

In some embodiments, $Q^7$ and $Q^8$ are N, and $Q^5$, $Q^6$, and $Q^9$ are each independently $CR^5$.

In some embodiments, $Q^7$ and $Q^9$ are N, and $Q^5$, $Q^6$, and $Q^8$ are each independently $CR^5$.

In some embodiments, $Q^8$ and $Q^9$ are N, and $Q^5$, $Q^6$, and $Q^7$ are each independently $CR^5$.

In some aspects of the disclosure, each $R^5$ in the compounds of formula (I), is independently H, halogen, $C_1$-$C_3$alkyl, $C_1$-$C_3$alkoxyl, or cycloalkyl. In some aspects of the disclosure, each $R^5$ in the compounds of formula (I), is independently H, halogen, substituted $C_1$-$C_3$alkyl, substituted $C_1$-$C_3$alkoxyl, or substituted cycloalkyl.

In some embodiments of the compounds of formula (I), $R^5$ is H.

In some embodiments of the compounds of formula (I), $R^5$ is halogen, such as, —F, —Cl, —Br, or —I.

In some embodiments, at least one $R^5$ is —$C_1$.

In some embodiments of the compounds of formula (I), $R^5$ is $C_1$-$C_3$alkyl, such as, for example, $C_1$-$C_3$alkyl, $C_1$-$C_2$alkyl, $C_1$alkyl, $C_2$alkyl, $C_3$alkyl, —$CH_3$, —$CH_2CH_3$, -propyl, and the like.

In some embodiments, $R^5$ is —$CH_3$.

In some embodiments of the compounds of formula (I), $R^5$ is $C_1$-$C_3$alkoxyl, such as, for example, $C_1$-$C_3$alkoxyl, $C_1$-$C_2$alkoxyl, $C_1$alkoxyl, $C_2$alkoxyl, $C_3$alkoxyl, —$OCH_3$, —$OCH_2CH_3$, -propoxyl, and the like. In some embodiments, $R^5$ is —$OCH_3$.

In some embodiments of the compounds of formula (I), $R^5$ is cycloalkyl, such as, for example, cyclopropyl, cyclobutyl, cyclopentyl, cyclohexyl, or cycloheptyl, and the like.

In some embodiments of the compounds of formula (I), two $R^5$ are halogen, and the remaining $R^5$ are H.

In other embodiments of the compounds of formula (I), two $R^5$ are —$C_1$, and the remaining $R^5$ are H.

In some embodiments of the compounds of formula (I), $Q^5$ and $Q^9$ are each independently $CR^5$ wherein each $R^5$ is halogen; $Q^6$ and $Q^8$ are each independently $CR^5$ wherein $R^5$ is H; and $Q^7$ is N.

In some embodiments of the compounds of formula (I), $Q^5$, $Q^8$, and $Q^9$ are each independently $CR^5$ wherein each $R^5$ is halogen; $Q^6$ is $CR^5$ wherein $R^5$ is H; and $Q^7$ is N.

In some embodiments of the compounds of formula (I), $Q^5$ and $Q^9$ are each independently $CR^5$ wherein each $R^5$ is —$C_1$; $Q^6$ and $Q^8$ are each independently $CR^5$ wherein $R^5$ is H; and $Q^7$ is N.

In some embodiments of the compounds of formula (I), $Q^5$ and $Q^9$ are each independently $CR^5$ wherein each $R^5$ is —$C_1$; $Q^6$ is $CR^5$ wherein $R^5$ is H; $Q^8$ is $CR^5$ wherein $R^5$ is —F; and $Q^7$ is N.

In some embodiments of the compounds of formula (I), $Q^5$ and $Q^9$ are each independently $CR^5$ wherein each $R^5$ is halogen; $Q^6$ is $CR^5$ wherein $R^5$ is H and $Q^8$ is $CR^5$ wherein $R^5$ is $C_1$-$C_3$alkyl; and $Q^7$ is N.

In some embodiments of the compounds of formula (I), $Q^5$ and $Q^9$ are each independently $CR^5$ wherein each $R^5$ is —$C_1$; $Q^6$ is $CR^5$ wherein $R^5$ is H and $Q^8$ is $CR^5$ wherein $R^5$ is —$CH_3$; and $Q^7$ is N.

In some embodiments of the compounds of formula (I), $Q^5$ and $Q^9$ are each independently $CR^5$ wherein each $R^5$ is halogen; $Q^6$ is $CR^5$ wherein $R^5$ is H and $Q^8$ is N; and $Q^7$ is $CR^5$ wherein $R^5$ is H.

In some embodiments of the compounds of formula (I), $Q^5$ and $Q^9$ are each independently $CR^5$ wherein each $R^5$ is —$C_1$; $Q^6$ is $CR^5$ wherein $R^5$ is H and $Q^8$ is N; and $Q^7$ is $CR^5$ wherein $R^5$ is H.

In some embodiments of the compounds of formula (I), $Q^5$ and $Q^9$ are each independently $CR^5$ wherein each $R^5$ is halogen; $Q^6$ is $CR^5$ wherein $R^5$ is H and $Q^8$ is N; and $Q^7$ is N.

In some embodiments of the compounds of formula (I), $Q^5$ and $Q^9$ are each independently $CR^5$ wherein each $R^5$ is —$C_1$; $Q^6$ is $CR^5$ wherein $R^5$ is H and $Q^8$ is N; and $Q^7$ is N.

In some embodiments of the compounds of formula (I), $Q^5$ and $Q^9$ are each independently $CR^5$ wherein each $R^5$ is $C_1$-$C_3$alkyl; $Q^6$ is $CR^5$ wherein $R^5$ is H and $Q^8$ is N; and $Q^7$ is N.

In some embodiments of the compounds of formula (I), $Q^5$ and $Q^9$ are each independently $CR^5$ wherein each $R^5$ is —$CH_3$; $Q^6$ is $CR^5$ wherein $R^5$ is H and $Q^8$ is N; and $Q^7$ is N.

In some aspects of the disclosure, X in the compounds of formula (I) is O, S, or NR wherein R is H or $C_1$-$C_3$alkyl.

In some embodiments of the compounds of formula (I), X is O.

In some embodiments of the compounds of formula (I), X is S.

In some embodiments of the compounds of formula (I), X is NR wherein R is H or $C_1$-$C_3$alkyl.

In some embodiments of the compounds of formula (I), X is NR wherein R is H, i.e. X is NH.

In some embodiments of the compounds of formula (I), X is NR wherein R is $C_1$-$C_3$alkyl, i.e., —N($C_1$-$C_3$alkyl)-, such as, for example, —N($C_1$-$C_3$alkyl)-, —N($C_1$-$C_2$alkyl)-, —N($C_1$alkyl)-, —N($C_2$alkyl)-, —N($C_3$alkyl)-, —N($CH_3$)—, —N($CH_2CH_3$)—, —N($CH_2CH_2CH_3$)—, and the like.

In some aspects of the disclosure, $R^6$ in the compounds of formula (I) is $C_1$-$C_6$alkyl, such as, for example, $C_1$-$C_6$alkyl, $C_1$-$C_5$alkyl, $C_1$-$C_4$alkyl, $C_1$-$C_3$alkyl, $C_1$-$C_2$alkyl, $C_1$alkyl, $C_2$alkyl, $C_3$alkyl, $C_4$alkyl, $C_5$alkyl, $C_6$alkyl, methyl, ethyl, n-propyl, isopropyl, n-butyl, isobutyl, sec-butyl, pentanyl, hexanyl, and the like.

In some embodiments of the compounds of the disclosure, $R^6$ is —$CH_3$.

In some aspects, $R^7$ in the compounds of formula (I) is H, halogen, —$C_1$-$C_6$alkyl, —$C_1$-$C_6$ alkoxyl, or -cycloalkyl.

In some embodiments, $R^7$ in the compounds of formula (I) is H.

In some embodiments, $R^7$ in the compounds of formula (I) is halogen, such as, for example, —F, —Cl, —Br, or —I.

In some embodiments, $R^7$ in the compounds of formula (I) is —F.

In other embodiments, $R^7$ in the compounds of formula (I) is —$C_1$.

In some embodiments, $R^7$ in the compounds of formula (I) is —$C_1$-$C_6$alkyl, such as, for example, substituted or unsubstituted: $C_1$-$C_6$alkyl, $C_1$-$C_5$alkyl, $C_1$-$C_4$alkyl, $C_1$-$C_3$alkyl, $C_1$-$C_2$alkyl, $C_1$alkyl, $C_2$alkyl, $C_3$alkyl, $C_4$alkyl, $C_5$alkyl, $C_6$alkyl, methyl, ethyl, n-propyl, isopropyl, n-butyl, isobutyl, sec-butyl, pentanyl, hexanyl, and the like. In some embodiments, $R^7$ is —$CH_3$.

In some embodiments, $R^7$ in the compounds of formula (I) is —$C_1$-$C_6$ alkoxyl, such as, for example, —$C_1$-$C_6$alkoxyl, —$C_1$-$C_5$alkoxyl, —$C_1$-$C_4$alkoxyl, —$C_1$-$C_3$alkoxyl, —$C_1$-$C_2$alkoxyl, —$C_1$alkoxyl, —$C_2$alkoxyl, —$C_3$alkoxyl, —$C_4$alkoxyl, —$C_5$alkoxyl, —$C_6$alkoxyl, —$OCH_3$, —$OCH_2CH_3$, -propoxyl, and the like. In some embodiments, $R^7$ is —$OCH_3$.

In some embodiments, $R^7$ in the compounds of formula (I) is -cycloalkyl, such as, for example, cyclopropyl, cyclobutyl, cyclopentyl, cyclohexyl, or cycloheptyl, and the like.

In some aspects, $R^8$ is H, halogen, —$C_1$-$C_6$alkyl, —$C_1$-$C_6$alkoxyl, or -cycloalkyl.

In some embodiments, $R^8$ in the compounds of formula (I) is H.

In some embodiments, $R^8$ in the compounds of formula (I) is halogen, such as, for example, —F, —Cl, —Br, or —I.

In some embodiments, $R^8$ in the compounds of formula (I) is —$C_1$-$C_6$alkyl, such as, for example, substituted or unsubstituted: $C_1$-$C_6$alkyl, $C_1$-$C_5$alkyl, $C_1$-$C_4$alkyl, $C_1$-$C_3$alkyl, $C_1$-$C_2$alkyl, $C_1$alkyl, $C_2$alkyl, $C_3$alkyl, $C_4$alkyl, $C_5$alkyl, $C_6$alkyl, methyl, ethyl, n-propyl, isopropyl, n-butyl, isobutyl, sec-butyl, pentanyl, hexanyl, and the like. In some embodiments, $R^8$ is —$CH_3$.

In some embodiments, $R^8$ in the compounds of formula (I) is —$C_1$-$C_6$ alkoxyl, such as, for example, —$C_1$-$C_6$alkoxyl, —$C_1$-$C_5$alkoxyl, —$C_1$-$C_4$alkoxyl, —$C_1$-$C_3$alkoxyl, —$C_1$-$C_2$alkoxyl, —$C_1$alkoxyl, —$C_2$alkoxyl, —$C_3$alkoxyl, —$C_4$alkoxyl, —$C_5$alkoxyl, —$C_6$alkoxyl, —$OCH_3$, —$OCH_2CH_3$, -propoxyl, and the like. In some embodiments, $R^8$ is —$OCH_3$.

In some embodiments, $R^8$ in the compounds of formula (I) is -cycloalkyl, such as, for example, cyclopropyl, cyclobutyl, cyclopentyl, cyclohexyl, or cycloheptyl, and the like.

In some embodiments of the compounds of formula (I), $R^7$ is —F and $R^8$ is H.

In some embodiments of the compounds of formula (I), $R^7$ is —$C_1$ and $R^8$ is H.

In some embodiments of the compounds of formula (I), $R^7$ is —$CH_3$ and $R^8$ is H.

In some embodiments of the compounds of formula (I), $R^7$ is —$OCH_3$ and $R^8$ is H.

In some embodiments of the compounds of formula (I), $R^7$ is —H and $R^8$ is —F.

In some embodiments of the compounds of formula (I), $R^7$ is —H and $R^8$ is —$C_1$.

In some embodiments of the compounds of formula (I), $R^7$ is —H and $R^8$ is —$CH_3$.

In some embodiments of the compounds of formula (I), $R^7$ is —H and $R^8$ is $OCH_3$.

In some aspects of the disclosure, the compounds of formula (I) are compounds of formula (IA):

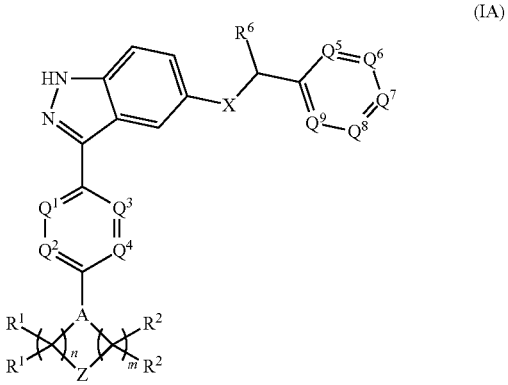

(IA)

wherein one or two of $Q^1$, $Q^2$, $Q^3$, $Q^4$ are each N and the remainder are each independently $CR^{5a}$ wherein each $R^{5a}$ is independently H, halogen, —CN, —$C_1$-$C_3$alkyl, —$C_1$-$C_3$haloalkyl, —$C_1$-$C_3$alkoxyl, —$SO_2C_1$-$C_3$alkyl, —$CH_2$—OH, —$CH_2$—N($C_1$-$C_3$alkyl)$_2$, or —$CH_2$—NH($C_1$-$C_3$alkyl), and the other variables are as set forth for formula (I).

In some aspects of the disclosure, the compounds of formula (I) are compounds of formula (IA) wherein an $R^{5a}$ may be —P(O)($C_1$-$C_6$alkyl)$_2$, such as, for example, —P(O)($CH_3$)$_2$.

In some aspects of the disclosure, the compounds of formula (I) are compounds of formula (IA) wherein each $R^{5a}$ is independently H, halogen, —CN, or $C_1$-$C_3$alkyl.

In some embodiments, one of $Q^1$, $Q^2$, $Q^3$, $Q^4$ is N and the remainder are each independently $CR^{5a}$.

In some embodiments, $Q^1$ is N and $Q^2$, $Q^3$, and $Q^4$ are each independently $CR^{5a}$.

In some embodiments, $Q^2$ is N and $Q^1$, $Q^3$, and $Q^4$ are each independently $CR^{5a}$.

In some embodiments, $Q^3$ is N and $Q^1$, $Q^2$, and $Q^4$ are each independently $CR^{5a}$.

In some embodiments, $Q^4$ is N and $Q^1$, $Q^2$, and $Q^3$ are each independently $CR^{5a}$.

In other embodiments, two of $Q^1$, $Q^2$, $Q^3$, $Q^4$ is N and the remainder are each independently $CR^{5a}$.

In some embodiments, $Q^1$ and $Q^2$ are N, and $Q^3$, and $Q^4$ are each independently $CR^{5a}$.

In some embodiments, $Q^1$ and $Q^3$ are N, and $Q^2$ and $Q^4$ are each independently $CR^{5a}$.

In some embodiments, $Q^1$ and $Q^4$ are N, and $Q^2$ and $Q^3$ are each independently $CR^{5a}$.

In some embodiments, $Q^2$ and $Q^3$ are N, and $Q^1$ and $Q^4$ are each independently $CR^{5a}$.

In some embodiments, $Q^2$ and $Q^4$ are N, and $Q^1$ and $Q^3$ are each independently $CR^{5a}$.

In some embodiments, $Q^3$ and $Q^4$ are N, and $Q^1$ and $Q^2$ are each independently $CR^{5a}$.

In some aspects of the compounds of formula (IA), each $R^{5a}$ is independently H, halogen, —CN, or $C_1$-$C_3$alkyl.

In other aspects of the compounds of formula (IA), each $R^{5a}$ is H, halogen, —CN, $C_1$-$C_3$alkyl, —$C_1$-$C_3$haloalkyl, —$C_1$-$C_3$alkoxyl, —$SO_2C_1$-$C_3$alkyl, —$CH_2$—$N(C_1$-$C_3$alkyl)$_2$, or —$CH_2$—$NH(C_1$-$C_3$alkyl).

In some embodiments of the compounds of formula (IA), $R^{5a}$ is H.

In some embodiments of the compounds of formula (IA), $R^{5a}$ is halogen, i.e., —F, —Cl, —Br, or —I.

In some embodiments of the compounds of formula (IA), at least one $R^{5a}$ is —F.

In some embodiments of the compounds of formula (IA), $R^{5a}$ is —CN.

In some embodiments of the compounds of formula (IA), $R^{5a}$ is $C_1$-$C_3$alkyl, such as, for example, $C_1$-$C_3$alkyl, $C_1$-$C_2$alkyl, $C_1$alkyl, $C_2$alkyl, $C_3$alkyl, —$CH_3$, —$CH_2CH_3$, -propyl, and the like. In some embodiments $R^{5a}$ is —$CH_3$.

In some embodiments of the compounds of formula (IA), $R^{5a}$ is $C_1$-$C_3$haloalkyl, such as, for example, $C_1$-$C_3$haloalkyl, $C_1$-$C_2$haloalkyl, $C_1$haloalkyl, $C_2$haloalkyl, $C_3$haloalkyl, —$CF_3$, —$CH_2CF_3$, and the like. In some embodiments $R^{5a}$ is —$CF_3$.

In some embodiments of the compounds of formula (IA), $R^{5a}$ is —$C_1$-$C_3$alkoxyl, such as, for example, —$C_3$alkoxyl, —$C_2$alkoxyl, or —$C_1$alkoxyl, —$OCH_2CH_3$, —$OCH_3$, and the like. In some embodiments, $R^{5a}$ is —$OCH_3$.

In some embodiments of the compounds of formula (IA), $R^{5a}$ is —$SO_2C_1$-$C_3$alkyl, such as, for example, —$SO_2C_1$alkyl, —$SO_2C_2$alkyl, —$SO_2C_3$alkyl, —$SO_2CH_2CH_3$, —$SO_2CH_3$, and the like. In some embodiments, $R^{5a}$ is —$SO_2CH_3$.

In some embodiments of the compounds of formula (IA), $R^{5a}$ is —$CH_2$—$N(C_1$-$C_3$alkyl)$_2$, such as, for example, —$CH_2$—$N(C_3$alkyl)$_2$, —$CH_2$—$N(C_2$alkyl)$_2$, —$CH_2$—$N(C_1$alkyl)$_2$, —$CH_2$—$N(C_3$alkyl)($C_1$alkyl), —$CH_2$—$N(C_2$alkyl)($C_1$alkyl), —$CH_2$—$N(C_3$alkyl)($C_2$alkyl), —$CH_2$—$N(CH_3)_2$, and the like. In some embodiments, $R^{5a}$ is —$CH_2$—$N(CH_3)_2$.

In some embodiments of the compounds of formula (IA), $R^{5a}$ is —$CH_2$—$NH(C_1$-$C_3$alkyl), such as, for example, —$CH_2$—$NH(C_3$alkyl), —$CH_2$—$NH(C_2$alkyl), —$CH_2$—$NH(C_1$alkyl), —$CH_2$—$NH(CH_3)$, and the like. In some embodiments, $R^{5a}$ is —$CH_2$—$NH(CH_3)$.

In some embodiments of the compounds of formula (IA), X is O.

In some aspects of the disclosure, the compounds of formula (IA) are compounds of formula (IA-1):

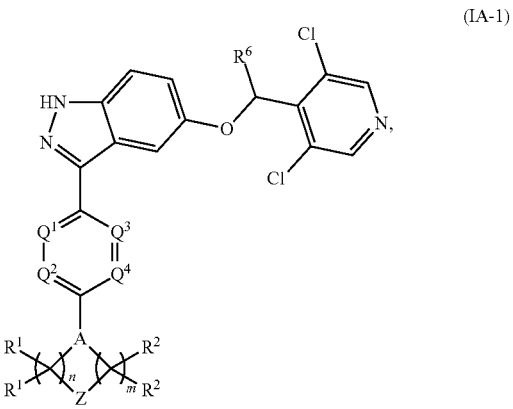

(IA-1)

wherein the variables have the values set forth above for formula (I) and (IA).

In some embodiments of the compounds of formula (IA-1), $R^6$ is —$CH_3$.

In some embodiments of the compounds of formula (IA-1), $Q^3$ is $CR^{5a}$.

In some embodiments of the compounds of formula (IA-1), at least one $R^{5a}$ is halogen.

In some embodiments of the compounds of formula (IA-1), at least one $R^{5a}$ is —F.

In some aspects of the disclosure, the compounds of formula (IA) are compounds of formula (IA-2):

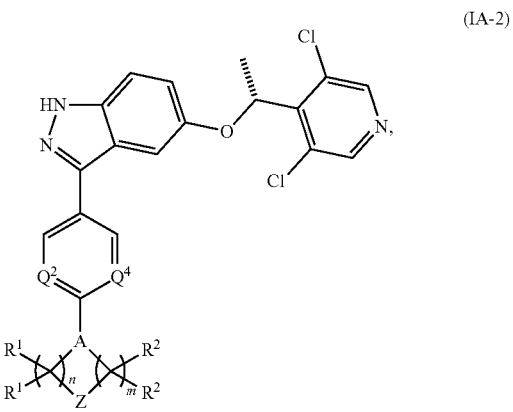

(IA-2)

wherein the variables have the values set forth above for formula (I) and (IA).

In some aspects of the compounds of formula (IA-2), n is 2 and m is 2.

In some aspects of the compounds of formula (IA-2), n is 1 and m is 1.

In some aspects of the compounds of formula (IA-2), n is 1 and m is 2.

In some aspects of the compounds of formula (IA-2), n is 3 and m is 2.

In some aspects of the disclosure, the compound of formula (IA-2) is a compound of formula (IA-3):

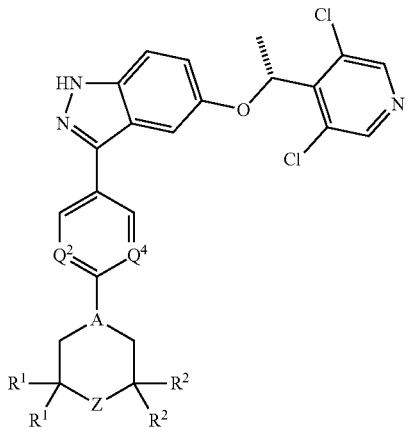

(IA-3)

wherein the variables have the values set forth above for formula (IA-2).

In some embodiments of the compounds of formula (IA-3), each $R^1$ and each $R^2$ is independently H or optionally substituted $C_1$-$C_6$alkyl.

In some embodiments of the compounds of formula (IA-3), each $R^1$ and each $R^2$ is H.

In some embodiments of the compounds of formula (IA-3), each $R^1$ and each $R^2$ is independently optionally substituted $C_1$-$C_6$alkyl, such as, for example, optionally substituted $C_1$-$C_6$alkyl, $C_1$-$C_5$alkyl, $C_1$-$C_4$alkyl, $C_1$-$C_3$alkyl, $C_1$-$C_2$alkyl, $C_1$alkyl, $C_2$alkyl, $C_3$alkyl, $C_4$alkyl, $C_5$alkyl, $C_6$alkyl, methyl, ethyl, n-propyl, isopropyl, n-butyl, isobutyl, sec-butyl, pentanyl, hexanyl, and the like.

In some embodiments of the compounds of formula (IA-3), at least one $R^1$ is H, and at least one $R^2$ is optionally substituted $C_1$-$C_6$alkyl.

In some embodiments of the compounds of formula (IA-3), at least one $R^1$ is optionally substituted $C_1$-$C_6$alkyl, and at least one $R^2$ is H.

In some embodiments of the compounds of formula (IA-3), each $R^1$ is H, and one $R^2$ is optionally substituted $C_1$-$C_6$alkyl.

In some embodiments of the compounds of formula (IA-3), one $R^1$ is optionally substituted $C_1$-$C_6$alkyl, and each $R^2$ is H.

In some embodiments of the compounds of formula (IA-3), each $R^1$ is H, and two $R^2$ groups attached to the same carbon atom, together with the carbon atom to which they are both attached, form a 3-7 membered spirocycloalkyl ring, such as, for example, a 3-membered spirocycloalkyl ring, a 4-membered spirocycloalkyl ring, a 5-membered spirocycloalkyl ring, a 6-membered spirocycloalkyl ring, a 7-membered spirocycloalkyl ring, a spirocyclopropyl ring, a spirocyclobutyl ring, a spirocyclopentyl ring, a spirocyclohexyl ring, or a spirocycloheptyl ring.

In some embodiments of the compounds of formula (IA-3), each $R^1$ is H, and two $R^2$ groups attached to the same carbon atom, together with the carbon atom to which they are both attached, form a 3-membered spirocycloalkyl ring, such as, for example, a spirocyclopropyl ring.

In some embodiments of the compounds of formula (IA-3), one $R^1$ group and one $R^2$ group are attached to form 6-9 membered bridged bicyclic ring, the other $R^1$ is H, and the other $R^2$ is H. In such embodiments, the 6-9 membered bridged bicyclic ring is a 6-membered bridged bicyclic ring, 7-membered bridged bicyclic ring, 8-membered bridged bicyclic ring, or 9-membered bridged bicyclic ring. In some embodiments, the 6-9 membered bridged bicyclic ring is a 7-membered bridged bicyclic ring.

In some embodiments of the compounds of formula (IA-3), each $R^1$ is H, and two $R^2$ groups attached to the same carbon atom, together with that carbon atom, represent a carbonyl group (C=O).

In some aspects of the disclosure, the compound of formula (IA-2) is a compound of formula (IA-4):

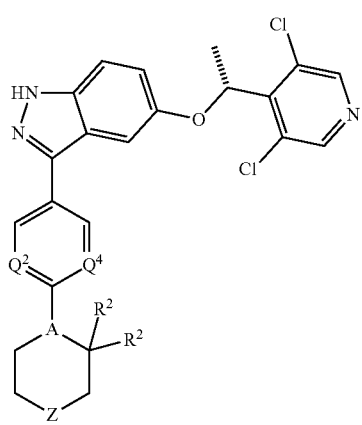

(IA-4)

wherein the variables have the values set forth above for formula (IA-2).

In some embodiments of the compounds of formula (IA-4), the two $R^2$ groups attached to the same carbon atom, together with that carbon atom, represent a carbonyl group (C=O).

In some aspects of the disclosure, the compounds of formula (IA-2) are compounds of formula (IA-5):

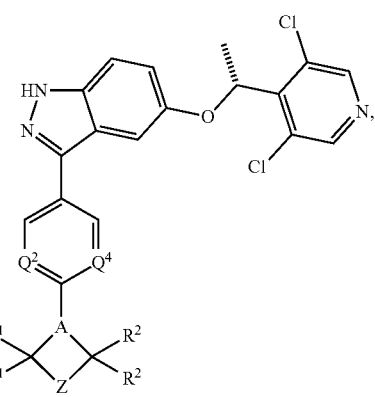

(IA-5)

wherein the variables have the values set forth above for formula (IA-2).

In some embodiments of the compounds of formula (IA-5), each $R^1$ and each $R^2$ is independently H or optionally substituted $C_1$-$C_6$alkyl, such as, for example, optionally substituted $C_1$-$C_6$alkyl, $C_1$-$C_5$alkyl, $C_1$-$C_4$alkyl, $C_1$-$C_3$alkyl, $C_1$-$C_2$alkyl, $C_1$alkyl, $C_2$alkyl, $C_3$alkyl, $C_4$alkyl, $C_5$alkyl, $C_6$alkyl, methyl, ethyl, n-propyl, isopropyl, n-butyl, isobutyl, sec-butyl, pentanyl, hexanyl, and the like.

In some embodiments of the compounds of formula (IA-5), each $R^1$ and each $R^2$ is H.

In some embodiments of the compounds of formula (IA-5), each $R^1$ is H, and two $R^2$ groups attached to the same carbon atom, together with the carbon atom to which they are both attached form a 3-7 membered spirocycloalkyl ring, such as, for example, a 3-membered spirocycloalkyl ring, a 4-membered spirocycloalkyl ring, a 5-membered spirocycloalkyl ring, a 6-membered spirocycloalkyl ring, a 7-membered spirocycloalkyl ring, a spirocyclopropyl ring, a spirocyclobutyl ring, a spirocyclopentyl ring, a spirocyclohexyl ring, or a spirocycloheptyl ring.

In some embodiments of the compounds of formula (IA-5), the 3-7 membered spirocycloalkyl ring is a 3-membered spirocycloalkyl ring.

In some embodiments of the compounds of formula (IA-5), one $R^1$ group and one $R^2$ group are attached to form 6-9 membered bridged bicyclic ring, the other $R^1$ is H, and the other $R^2$ is H. In such embodiments, the 6-9 membered bridged bicyclic ring is a 6-membered bridged bicyclic ring, 7-membered bridged bicyclic ring, 8-membered bridged bicyclic ring, or 9-membered bridged bicyclic ring. In some embodiments, the 6-9 membered bridged bicyclic ring is a 7-membered bridged bicyclic ring.

In some aspects of the disclosure, the compounds of formula (I) are compounds of formula (IA-8):

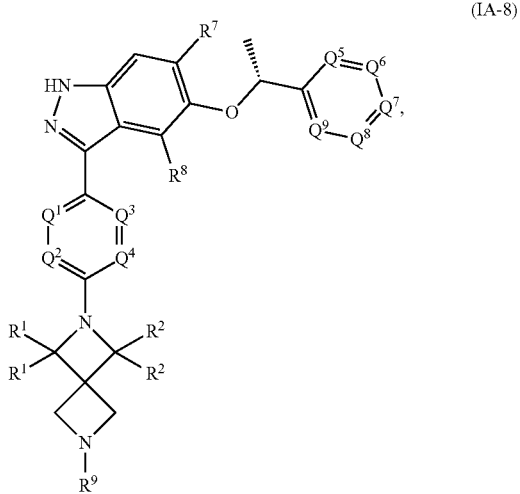

(IA-8)

wherein $R^9$ is —$C_1$-$C_6$alkyl, —$C_1$-$C_6$haloalkyl, —C(O)$C_1$-$C_6$haloalkyl, —C(O)O$C_1$-$C_6$alkyl, —C(O)$C_1$-$C_6$alkyl, —C(O)N($C_1$-$C_6$alkyl)$_2$, or —$SO_2$—$C_1$-$C_6$alkyl and the other variables have the values set forth above for formula (I).

In some embodiments of the compounds of formula (IA-8), $R^9$ is —$CH_2CF_3$, —$CH_2CHF_2$, —C(O)$CF_3$, —C(O)$OCH_3$, —C(O)$OCH_2CH_3$, —$SO_2CH_2CH_3$, —$SO_2CH(CH_3)_2$, —$CH_3$, —$CH(CH_3)_2$, —C(O)N($CH_3$)$_2$, or —$SO_2CH_3$.

In some embodiments of the compounds of formula (IA-8), $R^7$ and $R^8$ are each H.

In some embodiments of the compounds of formula (IA-8), each $R^1$ and each $R^2$ is H.

In some embodiments of the compounds of formula (IA-8), one of $Q^1$, $Q^2$, $Q^3$, $Q^4$ is N and the remainder are each independently $CR^{5a}$.

In some embodiments of the compounds of formula (IA-8), $Q^4$ is N and $Q^1$, $Q^2$, $Q^3$ are each independently $CR^{5a}$.

In other embodiments of the compounds of formula (IA-8), two of $Q^1$, $Q^2$, $Q^3$, $Q^4$ is N and the remainder are each independently $CR^{5a}$.

In other embodiments of the compounds of formula (IA-8), $Q^2$ and $Q^4$ are N, and $Q^1$ and $Q^3$ are each independently $CR^{5a}$.

In some embodiments of the compounds of formula (IA-8), one of $Q^5$, $Q^6$, $Q^7$, $Q^8$, or $Q^9$ is N, and the remainder are each independently $CR^5$.

In some embodiments of the compounds of formula (IA-8), $Q^7$ is N and $Q^5$, $Q^6$, $Q^8$, and $Q^9$ are each independently $CR^5$.

In some embodiments of the compounds of formula (IA-8), two of $Q^5$, $Q^6$, $Q^7$, $Q^8$, or $Q^9$ is N, and the remainder are each independently $CR^5$.

In some embodiments, $Q^6$ and $Q^7$ are N, and $Q^5$, $Q^8$, and $Q^9$ are each independently $CR^5$.

In some aspects of the disclosure, the compounds of formula (IA-2) are compounds of formula (IA-6):

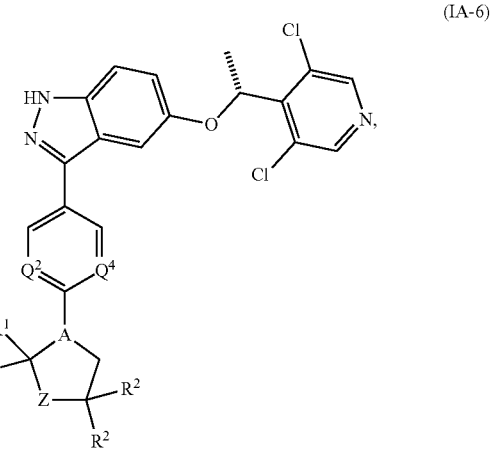

(IA-6)

wherein the variables have the values set forth above for formula (IA-2).

In some embodiments of the compounds of formula (IA-6), the two $R^1$ groups attached to the same carbon atom, together with that carbon atom, represent a carbonyl group (C=O).

In some embodiments of the compound of formula (IA-6), the two $R^2$ groups attached to the same carbon atom, together with the carbon atom to which they are both attached form an optionally substituted 3-7 membered spirocycloalkyl ring or an optionally substituted 3-7 membered spiroheterocycloalkyl ring.

In some embodiments of the compound of formula (IA-6), the two $R^2$ groups attached to the same carbon atom, together with the carbon atom to which they are both attached, form an optionally substituted 3-7 membered spiroheterocycloalkyl ring, such as, for example, an optionally substituted 3-membered spiroheterocycloalkyl ring, an optionally substituted 4-membered spiroheterocycloalkyl ring, an optionally substituted 5-membered spiroheterocycloalkyl ring, an optionally substituted 6-membered spiroheterocycloalkyl ring, an optionally substituted 7-membered spiroheterocycloalkyl ring, an optionally substituted spiroaziridinyl ring, an optionally substituted spiroazetidinyl ring, an optionally substituted spiropyrrolidinyl ring, an optionally substituted spiropiperidinyl ring, an optionally substituted spiroazepanyl ring, an optionally substituted spirooxiranyl ring, an optionally substituted spirooxetanyl ring, an optionally substituted spirotetrahydrofuranyl ring, an optionally substituted spirotetrahydropyranyl ring, an optionally substituted spirooxepanyl ring, and the like.

In some embodiments of the compound of formula (IA-6), the optionally substituted 3-7 membered spiroheterocycloalkyl ring is an optionally substituted spiroazetinyl ring, an optionally substituted spiropyrrolidinyl ring, or an optionally substituted spiropiperidinyl ring.

In some embodiments of the compound of formula (IA-6), the optionally substituted 3-7 membered spiroheterocycloalkyl ring is a spiroazetinyl ring, a spiropyrrolidinyl ring, a spiropiperidinyl ring, an N-methylspiropiperidinyl ring, or an N-(methylsulfonyl)spiropiperidinyl ring.

In some aspects of the disclosure, the compounds of formula (IA-2) are compounds of formula (IA-7):

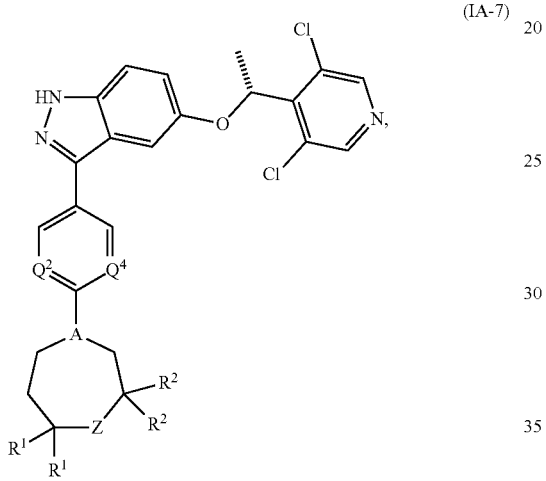

(IA-7)

wherein the variables have the values set forth above for formula (IA-2).

In some embodiments of the compounds of formula (IA-7), each $R^8$ is H.

In some embodiments of the compounds of formula (IA-7), the two $R^1$ groups attached to the same carbon atom, together with that carbon atom, represent a carbonyl group (C=O).

In some embodiments of the compounds of formula (IA-7), each $R^2$ is H.

In some embodiments of the compounds of formula (IA-7), the two $R^2$ groups attached to the same carbon atom, together with that carbon atom, represent a carbonyl group (C=O).

In some aspects of the disclosure, the compounds of formula (IA) (and subgenera IA-1, IA-2, IA-3, IA-4, IA-5, IA-6, IA-7) are those wherein $Q^2$ is N. In other aspects of the disclosure, the compounds of formula (IA) (and subgenera IA-8) are those wherein $Q^2$ is N.

In some aspects of the disclosure, the compounds of formula (IA) (and subgenera IA-1, IA-2, IA-3, IA-4, IA-5, IA-6, IA-7) are those wherein $Q^4$ is N. In other aspects of the disclosure, the compounds of formula (IA) (and subgenera IA-8) are those wherein $Q^4$ is N.

In some aspects of the disclosure, the compounds of formula (IA) are those wherein both $Q^2$ and $Q^4$ are each N.

In some aspects of the disclosure, the compounds of formula (IA) are those wherein $Q^4$ is $CR^{5a}$.

In some embodiments wherein $Q^4$ is $CR^{5a}$, $R^{5a}$ is H.

In some embodiments wherein $Q^4$ is $CR^{5a}$, $R^{5a}$ is halogen.

In some embodiments wherein $Q^4$ is $CR^{5a}$, $R^{5a}$ is —F.

In some embodiments of the compounds of formula (IA), $Q^2$ is N and $Q^4$ is $CR^{5a}$ wherein $R^{5a}$ is —F.

In some aspects of the disclosure, the compounds of formula (I) are compounds of formula (IB):

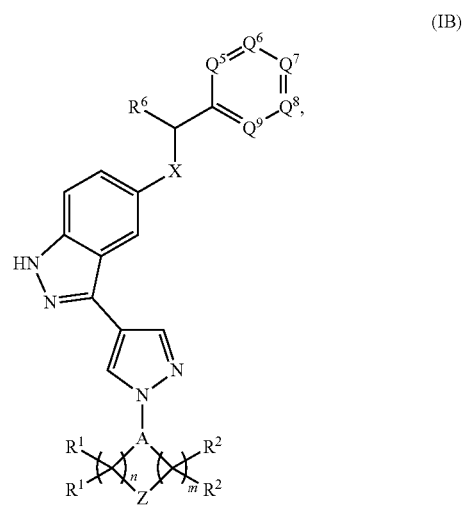

(IB)

wherein the variables have the values set forth above for formula (I).

In some aspects of the disclosure, the compounds of formula (IB) are compounds of formula (IB-1):

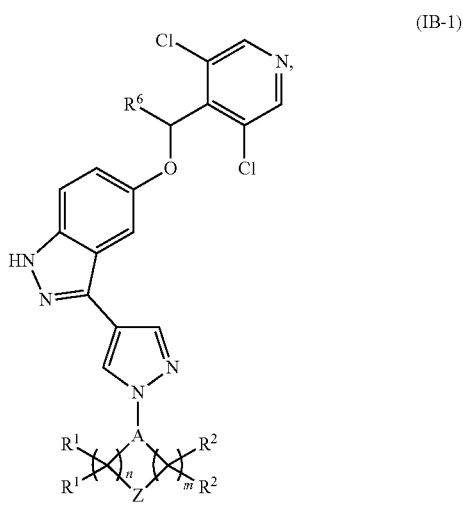

(IB-1)

wherein the variables have the values set forth above for formula (I).

In some aspects of the disclosure, the compounds of formula (IB-1) are compounds of formula (IB-2):

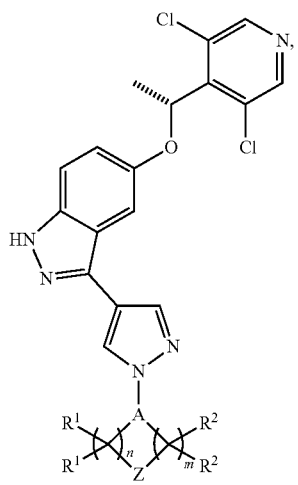

(IB-2)

wherein the variables have the values set forth above for formula (I).

In some embodiments of the compounds of formula (In), (IB-1), and (IB-2), n=2 and m=2.

In other embodiments of the compounds of formula (IB), (IB-1), and (IB-2), n=1 and m=1.

In some embodiments of the compounds of formula (In), (IB-1), and (IB-2), n=1 and m=2.

In other embodiments of the compounds of formula (IB), (IB-1), and (IB-2), n=3 and m=2.

In some embodiments of the compounds of formula (IB), (IB-1), and (IB-2), each $R^1$ is H, and each $R^2$ is H.

In some aspects, A in the compounds of formula (I) is N or CH.

In some embodiments of the compound of formula (I), A is N.

In some embodiments of the compound of formula (I), A is CH.

In some aspects, Z in the compounds of formula (I) is $S(O)_2$; $S(O)$; O; $NR^3$; or $CR^4R^{4'}$.

In some embodiments of the compound of formula (I), Z is $S(O)_2$.

In some embodiments of the compound of formula (I), Z is $S(O)$.

In some embodiments of the compound of formula (I), Z is O.

In some embodiments of the compound of formula (I), Z is $NR^3$.

In some embodiments of the compound of formula (I) wherein Z is $NR^3$, the $R^3$ is H.

In other embodiments of the compound of formula (I) wherein Z is $NR^3$, the $R^3$ is —C(O)$NR^aR^b$.

In other embodiments of the compound of formula (I) wherein Z is $NR^3$, the $R^3$ is —S(O)$_2NR^aR^b$.

In some embodiments of the compound of formula (I) wherein $R^3$ is —C(O)$NR^aR^b$ or —S(O)$_2NR^aR^b$, the $R^a$ is H and the $R^b$ is H.

In some embodiments of the compound of formula (I), $R^3$ is —C(O)$NH_2$.

In some embodiments of the compound of formula (I) wherein $R^3$ is —C(O)$NR^aR^b$ or —S(O)$_2NR^aR^b$, the $R^a$ is H and the $R^b$ is $C_1$-$C_6$alkyl, such as, for example, $C_1$-$C_6$alkyl, $C_1$-$C_5$alkyl, $C_1$-$C_4$alkyl, $C_1$-$C_3$alkyl, $C_1$-$C_2$alkyl, $C_1$alkyl, $C_2$alkyl, $C_3$alkyl, $C_4$alkyl, $C_5$alkyl, $C_6$alkyl, methyl, ethyl, n-propyl, isopropyl, n-butyl, isobutyl, sec-butyl, pentanyl, hexanyl, and the like.

In some embodiments of the compound of formula (I) wherein $R^3$ is —C(O)$NR^aR^b$ or —S(O)$_2NR^aR^b$, the $R^a$ is $C_1$-$C_6$alkyl such as, for example, $C_1$-$C_6$alkyl, $C_1$-$C_5$alkyl, $C_1$-$C_4$alkyl, $C_1$-$C_3$alkyl, $C_1$-$C_2$alkyl, $C_1$alkyl, $C_2$alkyl, $C_3$alkyl, $C_4$alkyl, $C_5$alkyl, $C_6$alkyl, methyl, ethyl, n-propyl, isopropyl, n-butyl, isobutyl, sec-butyl, pentanyl, hexanyl, and the like; and the $R^b$ is $C_1$-$C_6$alkyl, such as, for example, $C_1$-$C_6$alkyl, $C_1$-$C_5$alkyl, $C_1$-$C_4$alkyl, $C_1$-$C_3$alkyl, $C_1$-$C_2$alkyl, $C_1$alkyl, $C_2$alkyl, $C_3$alkyl, $C_4$alkyl, $C_5$alkyl, $C_6$alkyl, methyl, ethyl, n-propyl, isopropyl, n-butyl, isobutyl, sec-butyl, pentanyl, hexanyl, and the like.

In some embodiments of the compound of formula (I), $R^3$ is —C(O)N(CH$_3$)$_2$.

In some embodiments of the compound of formula (I) wherein $R^3$ is —C(O)$NR^aR^b$ or —S(O)$_2NR^aR^b$, the $R^a$ and the $R^b$, together with the N atom to which they are both attached, form an optionally substituted 3 to 7 membered heterocycloalkyl ring, such as, for example, optionally substituted 3 membered heterocycloalkyl, optionally substituted 4 membered heterocycloalkyl, optionally substituted 5 membered heterocycloalkyl, optionally substituted 6 membered heterocycloalkyl, or optionally substituted 7 membered heterocycloalkyl.

In some embodiments of the compound of formula (I), the optionally substituted 3 to 7 membered heterocycloalkyl ring is an optionally substituted piperidinyl, optionally substituted piperazinyl, or optionally substituted morpholinyl ring.

In some embodiments of the compound of formula (I), the optionally substituted 3 to 7 membered heterocycloalkyl ring is a 4-methylpiperazin-1-yl, or a morpholinyl ring.

In some embodiments of the compound of formula (I) wherein $R^3$ is —C(O)$NR^aR^b$, the $R^3$ is

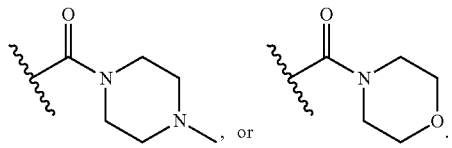

In some embodiments of the compound of formula (I) wherein $R^3$ is —S(O)$_2NR^aR^b$, the $R^3$ is

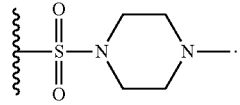 [SMILES: *S(=O)(=O)N1CCN(C)CC1]

In some embodiments of the compound of formula (I) wherein Z is $NR^3$, the $R^3$ is —C(O)$OR^c$.

In some embodiments of the compound of formula (I) wherein Z is $NR^3$, the $R^3$ is —C(O)$R^c$.

In some embodiments of the compound of formula (I) wherein Z is $NR^3$, the $R^3$ is —S(O)$_2R^c$.

In some embodiments of the compound of formula (I) wherein Z is $NR^3$, and $R^3$ is —C(O)$OR^c$, —C(O)$R^c$, or —S(O)$_2R^c$, the $R^c$ is optionally substituted $C_1$-$C_6$alkyl, or a 3-7 membered cycloalkyl.

In some embodiments of the compound of formula (I), $R^c$ is optionally substituted $C_1$-$C_6$alkyl, such as, for example, optionally substituted $C_1$-$C_6$alkyl, $C_1$-$C_5$alkyl, $C_1$-$C_4$alkyl, $C_1$-$C_3$alkyl, $C_1$-$C_2$alkyl, $C_1$alkyl, $C_2$alkyl, $C_3$alkyl, $C_4$alkyl, $C_5$alkyl, $C_6$alkyl, methyl, ethyl, n-propyl, isopropyl, n-butyl, isobutyl, sec-butyl, pentanyl, hexanyl, and the like.

In some embodiments of the compound of formula (I), $R^c$ is methyl, i.e., —$CH_3$.

In some embodiments of the compound of formula (I), $R^c$ is $(C_1-C_6alkyl)_2$N-methyl, i.e., —$CH_2N(C_1-C_6alkyl)_2$.

In some embodiments of the compound of formula (I), $R^c$ is (dimethylamino)methyl, i.e., —$CH_2N(CH_3)_2$.

In some embodiments of the compound of formula (I), $R^c$ is ethyl.

In some embodiments of the compound of formula (I), $R^c$ is $(C_1-C_6alkyl)_2$N-ethyl, i.e., —$CH_2CH_2N(C_1-C_6alkyl)_2$.

In some embodiments of the compound of formula (I), $R^c$ is (dimethylamino)ethyl, i.e., —$CH_2CH_2N(CH_3)_2$.

In some embodiments of the compound of formula (I) wherein Z is $NR^3$, and $R^3$ is —$C(O)OCH_3$, —$C(O)CH_3$, or —$S(O)_2CH_3$.

In some embodiments of the compound of formula (I) wherein Z is $NR^3$, and $R^3$ is —$C(O)OCH_3$.

In some embodiments of the compound of formula (I) wherein Z is $NR^3$, and $R^3$ is —$C(O)CH_3$.

In some embodiments of the compound of formula (I) wherein Z is $NR^3$, and $R^3$ is —$C(O)CH_2N(CH_3)_2$.

In some embodiments of the compound of formula (I) wherein Z is $NR^3$, and $R^3$ is —$C(O)CH_2CH_2N(CH_3)_2$.

In some embodiments of the compound of formula (I) wherein Z is $NR^3$, and $R^3$ is —$S(O)_2CH_3$.

In other embodiments of the compound of formula (I), $R^c$ is —$CH_2CH_3$.

In some embodiments of the compound of formula (I) wherein Z is $NR^3$, and $R^3$ is —$C(O)OCH_2CH_3$, —$C(O)CH_2CH_3$, or —$S(O)_2CH_2CH_3$.

In some embodiments of the compound of formula (I) wherein Z is $NR^3$, and $R^3$ is —$C(O)OCH_2CH_3$.

In some embodiments of the compound of formula (I) wherein Z is $NR^3$, and $R^3$ is —$C(O)CH_2CH_3$.

In some embodiments of the compound of formula (I) wherein Z is $NR^3$, and $R^3$ is —$S(O)_2CH_2CH_3$.

In some embodiments of the compound of formula (I), $R^c$ is 3-7 membered cycloalkyl, such as, for example, 3 membered cycloalkyl, 4 membered cycloalkyl, 5 membered cycloalkyl, 6 membered cycloalkyl, or 7 membered cycloalkyl.

In some embodiments of the compound of formula (I) wherein Z is $NR^3$, $R^3$ is optionally substituted $C_1-C_6$alkyl, such as, for example, $C_1-C_6$alkyl, $C_1-C_5$alkyl, $C_1-C_4$alkyl, $C_1-C_3$alkyl, $C_1-C_2$alkyl, $C_1$alkyl, $C_2$alkyl, $C_3$alkyl, $C_4$alkyl, $C_5$alkyl, $C_6$alkyl, methyl, ethyl, n-propyl, isopropyl, n-butyl, isobutyl, sec-butyl, pentanyl, hexanyl, and the like.

In some embodiments of the compound of formula (I) wherein Z is $NR^3$, and $R^3$ is optionally substituted $C_1-C_6$alkyl, the $C_1-C_6$alkyl is —$CH_3$.

In some embodiments of the compound of formula (I) wherein Z is $NR^3$, and $R^3$ is optionally substituted $C_1-C_6$alkyl, the $C_1-C_6$alkyl is —$CH_2CH_3$.

In other embodiments of the compound of formula (I) wherein Z is $NR^3$, and $R^3$ is optionally substituted $C_1-C_6$alkyl, the $C_1-C_6$alkyl is —$CH(CH_3)_2$.

In other embodiments of the compound of formula (I) wherein Z is $NR^3$, and $R^3$ is optionally substituted $C_1-C_6$alkyl, the optionally substituted $C_1-C_6$alkyl is 2-hydroxyethyl, i.e., —$CH_2CH_2OH$.

In some embodiments of the compound of formula (I) wherein Z is $NR^3$, and $R^3$ is optionally substituted $C_1-C_6$alkyl, the optionally substituted $C_1-C_6$alkyl is —$CH_2C(CH_3)_2OH$.

In some embodiments of the compound of formula (I) wherein Z is $NR^3$, the $R^3$ is a 3-5 membered cycloalkyl, such as, for example, a 3 membered cycloalkyl, a 4 membered cycloalkyl, or a 5 membered cycloalkyl.

In some embodiments of the compound of formula (I) wherein Z is $NR^3$, and the $R^3$ is a 3-5 membered cycloalkyl, the 3-5 membered cycloalkyl is cyclobutyl.

In some embodiments of the compound of formula (I) wherein Z is $NR^3$, the $R^3$ is a 3-5 membered heterocycloalkyl, such as, for example, a 3 membered heterocycloalkyl, a 4 membered heterocycloalkyl, or a 5 membered heterocycloalkyl.

In some embodiments of the compound of formula (I) wherein Z is $NR^3$, and the $R^3$ is a 3-5 membered heterocycloalkyl, the 3-5 membered heterocycloalkyl is oxetanyl,

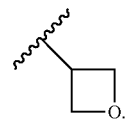

In some embodiments of the compound of formula (I), Z is $CR^4R^{4'}$.

In some embodiments of the compound of formula (I) wherein Z is $CR^4R^{4'}$, $R^4$ and $R^{4'}$ are each H.

In some embodiments of the compound of formula (I) wherein Z is $CR^4R^{4'}$, $R^4$ and $R^{4'}$ are each optionally substituted $C_1-C_6$alkyl, such as, for example, optionally substituted $C_1-C_6$alkyl, $C_1-C_5$alkyl, $C_1-C_4$alkyl, $C_1-C_3$alkyl, $C_1-C_2$alkyl, $C_1$alkyl, $C_2$alkyl, $C_3$alkyl, $C_4$alkyl, $C_5$alkyl, $C_6$alkyl, methyl, ethyl, n-propyl, isopropyl, n-butyl, isobutyl, sec-butyl, pentanyl, hexanyl, and the like.

In some embodiments of the compound of formula (I) wherein Z is $CR^4R^{4'}$, $R^4$ is H and $R^{4'}$ is OH.

In some embodiments of the compound of formula (I) wherein Z is $CR^4R^{4'}$, $R^4$ and $R^{4'}$ together with the carbon atom to which they are both attached, form an optionally substituted 3 to 7 membered heterocycloalkyl ring, such as, for example, an optionally substituted 3 membered heterocycloalkyl ring, an optionally substituted 4 membered heterocycloalkyl ring, an optionally substituted 5 membered heterocycloalkyl ring, an optionally substituted 6 membered heterocycloalkyl ring, or an optionally substituted 7 membered heterocycloalkyl ring.

In some embodiments of the compound of formula (I), the optionally substituted 3 to 7 membered heterocycloalkyl ring is an optionally substituted 4-membered heterocycloalkyl ring.

In some embodiments of the compound of formula (I), the optionally substituted 4 membered heterocycloalkyl ring is an azetidinyl ring.

In some embodiments of the compound of formula (I) wherein Z is $CR^4R^{4'}$, and $R^4$ and $R^{4'}$ together with the carbon atom to which they are both attached, form an optionally substituted azetidinyl ring, the azetidinyl ring is unsubstituted, i.e.,

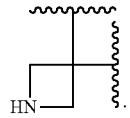

In some embodiments of the compound of formula (I) wherein Z is CR⁴R⁴', and R⁴ and R⁴' together with the carbon atom to which they are both attached, form an optionally substituted azetidinyl ring, the azetidinyl ring is

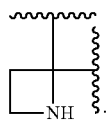

In other embodiments of the compound of formula (I) wherein Z is CR⁴R⁴' and R⁴ and R⁴' together with the carbon atom to which they are both attached form an optionally substituted azetidinyl ring, the azetidinyl ring, can be N-substituted.

In some embodiments of the compound of formula (I) wherein Z is CR⁴R⁴' and R⁴ and R⁴' together with the carbon atom to which they are both attached form an N-substituted azetidinyl ring, the N-substituent is —C₁-C₆alkyl, —C₁-C₆haloalkyl, —C(O)C₁-C₆haloalkyl, —C(O)OC₁-C₆alkyl, —C(O)C₁-C₆alkyl, —C(O)N(C₁-C₆alkyl)₂, or —SO₂—C₁-C₆alkyl.

In some embodiments of the compound of formula (I) wherein Z is CR⁴R⁴' and R⁴ and R⁴' together with the carbon atom to which they are both attached form an N-substituted azetidinyl ring, the N-substituent is —C₁-C₆alkyl, —C(O)OC₁-C₆alkyl, —C(O)C₁-C₆alkyl, —C(O)N(C₁-C₆alkyl)₂, or —SO₂—C₁-C₆alkyl.

In some embodiments of the compound of formula (I), the N-substituent is —CH₃, —CH(CH₃)₂, —C(O)N(CH₃)₂, or —SO₂CH₃, i.e.,

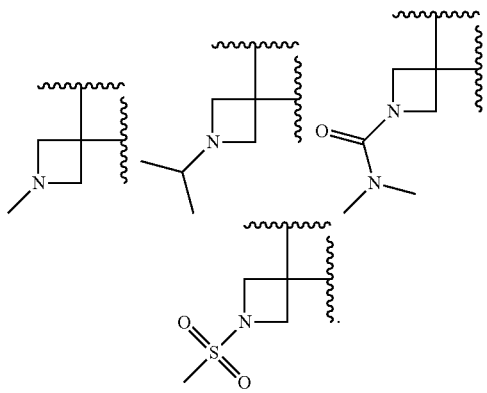

or

In other embodiments of the compound of formula (I), the N-substituent is —CH₂CF₃, —CH₂CHF₂, —C(O)CF₃, —C(O)OCH₃, —C(O)OCH₂CH₃, or —SO₂CH₂CH₃, e.g.,

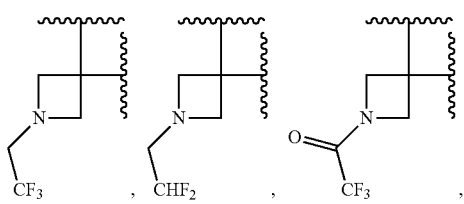

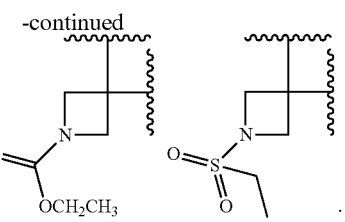

In some embodiments of the compound of formula (I) wherein Z is CR⁴R⁴' and R⁴ and R⁴' together with the carbon atom to which they are both attached form an N-substituted azetidinyl ring, the N-substituted azetidinyl ring is

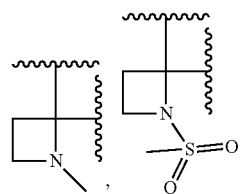

In some embodiments of the compound of formula (I) wherein Z is CR⁴R⁴' and R⁴ and R⁴' together with the carbon atom to which they are both attached form an N-substituted azetidinyl ring, the N-substituent is —C(O)OCH₂CH₃, —SO₂CH(CH₃)₂, or —SO₂CH₂CH₃.

In some embodiments of the compound of formula (I) wherein Z is CR⁴R⁴' and R⁴ and R⁴' together with the carbon atom to which they are both attached form an N-substituted azetidinyl ring, the N-substituted azetidinyl ring is

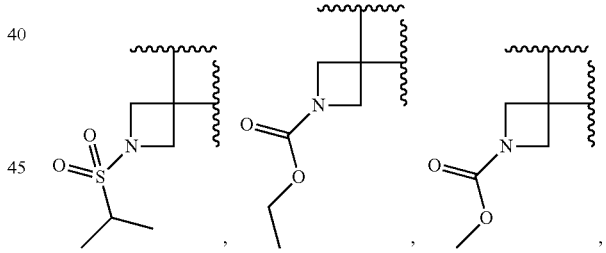

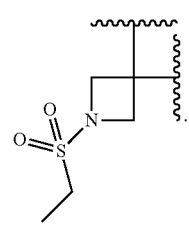

In some embodiments of the compound of formula (I) wherein Z is CR⁴R⁴', and R⁴ and R⁴' together with the carbon atom to which they are both attached, form an optionally substituted thietane 1,1-dioxide ring.

In some embodiments of the compound of formula (I), Z is:

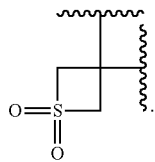

In some embodiments of the compound of formula (I) wherein Z is CR⁴R⁴', R⁴ and R⁴' together with the carbon atom to which they are both attached form an optionally substituted 4 membered heterocycloalkyl ring, the optionally substituted 4 membered heterocycloalkyl ring is a an optionally substituted oxetane ring, such as, for example,

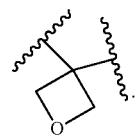 [SMILES: *C1(*)COC1]

In some embodiments of the compound of formula (I) wherein Z is CR⁴R⁴', and R⁴ and R⁴' together with the carbon atom to which they are both attached, form an optionally substituted 3 to 7 membered heterocycloalkyl ring, the optionally substituted 3 to 7 membered heterocycloalkyl ring is an optionally substituted 5-membered heterocycloalkyl ring.

In some embodiments of the compound of formula (I) wherein Z is CR⁴R⁴', and R⁴ and R⁴' together with the carbon atom to which they are both attached form an optionally substituted 5-membered heterocycloalkyl ring, the optionally substituted 5-membered heterocycloalkyl ring is an unsubstituted pyrrolidinyl ring, N-substituted pyrrolidinyl ring, unsubstituted pyrrolidinyl-2-one ring, N-substituted pyrrolidinyl-2-one ring, unsubstituted pyrrolo-2,5-dione ring, N-substituted pyrrolo-2,5-dione ring, unsubstituted imidazolidinyl-2-one ring, N-substituted imidazolidinyl-2-one ring, a tetrahydrofuranyl ring, or a tetrahydrothiophene-1,1-dioxide ring.

In some embodiments of the compound of formula (I), said N-substituent is —C₁-C₆alkyl, such as, for example, —CH₃.

In some embodiments, the N-substituent is —C₁-C₆alkyl, —C(O)OC₁-C₆alkyl, —C(O)C₁-C₆alkyl, —C(O)N(C₁-C₆alkyl)₂, or —SO₂—C₁-C₆alkyl.

In some embodiments, the N-substituent is —C(O)OC₁-C₆alkyl, such as, for example, —C(O)OCH₃, —C(O)OCH₂CH₃, —C(O)OCH(CH₃)₂, or —SO₂C₁-C₆alkyl, such as, for example, —SO₂CH₃.

In some embodiments of the compound of formula (I), Z is

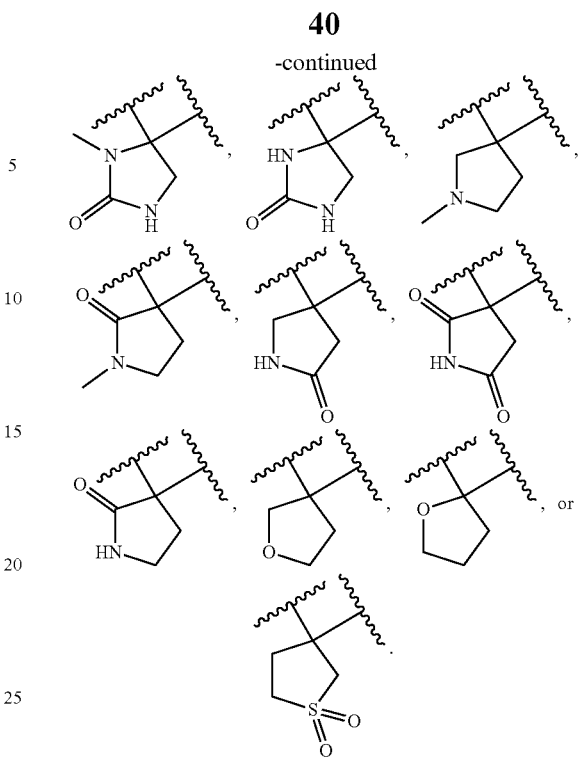

In other embodiments of the compound of formula (I), Z is

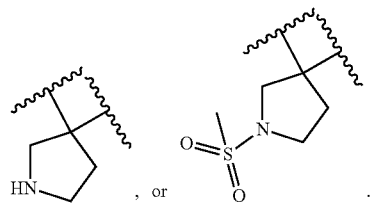 [SMILES: *C1(*)CCNC1 ; *C1(*)CCN(S(C)(=O)=O)C1]

In some embodiments of the compound of formula (I) wherein Z is CR⁴R⁴', and R⁴ and R⁴' together with the carbon atom to which they are both attached, form an optionally substituted 3 to 7 membered heterocycloalkyl ring, the optionally substituted 3 to 7 membered heterocycloalkyl ring is an optionally substituted 6-membered heterocycloalkyl ring.

In some embodiments of the compound of formula (I), the optionally substituted 6-membered heterocycloalkyl ring is an unsubstituted piperizinyl-2-one ring or an N-substituted piperizinyl-2-one ring.

In some embodiments of the compound of formula (I), the N-substituent is —CH₃.

In some embodiments of the compound of formula (I), Z is

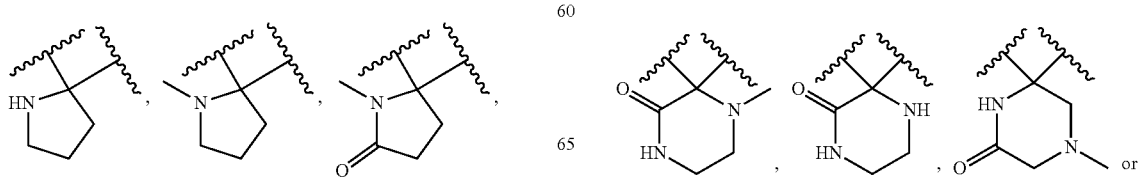

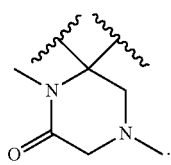

In other embodiment of the compound of formula (I) s, the optionally substituted 6-membered heterocycloalkyl ring is a substituted or unsubstituted piperidine ring, or a tetrahydro-2H-thiopyran 1,1-dioxide ring.

In some embodiments of the compound of formula (I), the piperidine ring is N-substituted with —C(O)OC$_1$-C$_6$alkyl, such as, for example, —C(O)OCH$_3$, —C(O)OCH$_2$CH$_3$, —C(O)OCH(CH$_3$)$_2$, —C$_1$-C$_6$alkyl, —C(O)C$_1$-C$_6$alkyl, or —SO$_2$C$_1$-C$_6$alkyl, such as, for example, —SO$_2$CH$_3$, —SO$_2$CH$_2$CH$_3$.

In some embodiments of the compound of formula (I), the piperidine ring is N-substituted with —C(O)OC$_1$-C$_6$alkyl, such as, for example, —C(O)OCH$_3$, —C(O)OCH$_2$CH$_3$, —C(O)OCH(CH$_3$)$_2$, —C$_1$-C$_6$alkyl, —C(O)C$_1$-C$_6$alkyl, or —SO$_2$C$_1$-C$_6$alkyl, such as, for example, —SO$_2$CH$_3$.

In some embodiments of the compound of formula (I), Z is

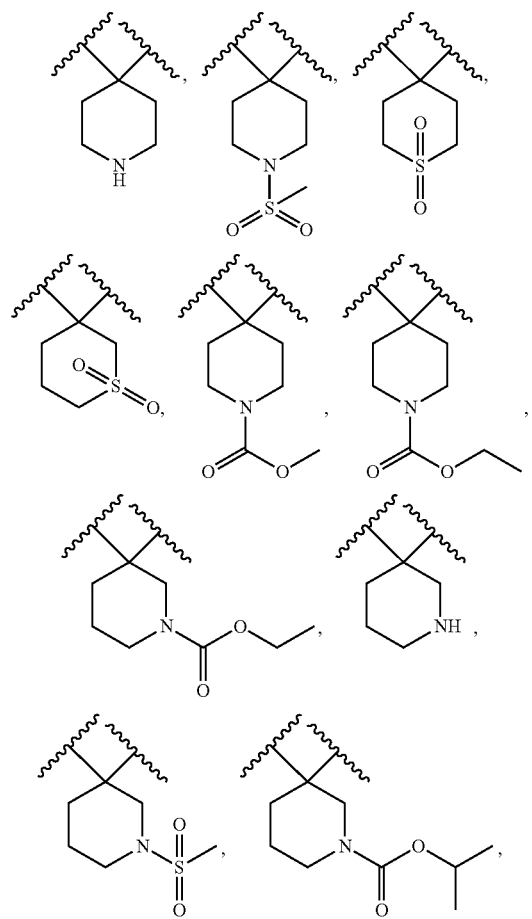

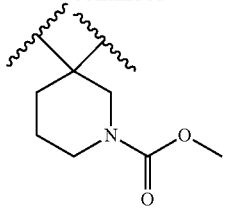

In other In some embodiments of the compound of formula (I), Z is

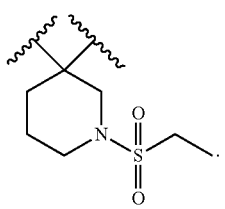 [SMILES: *C1(*)CCCN(S(=O)(=O)CC)C1]

Compounds of Formula (II)

In some aspects, the disclosure is directed to compounds of formula (II)

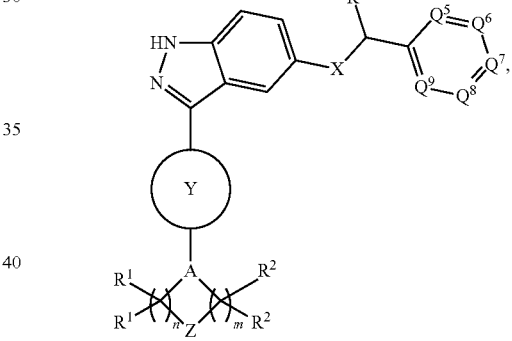

(II)

or a pharmaceutically acceptable salt thereof,
wherein n=1, 2, or 3;
m=1, 2, or 3;
each R$^1$ is independently H; or optionally substituted C$_1$-C$_6$alkyl;
each R$^2$ is independently H; or optionally substituted C$_1$-C$_6$alkyl;
or two R$^1$ groups attached to the same carbon atom, together with the carbon atom to which they are both attached form an optionally substituted 3-7 membered spirocycloalkyl ring or an optionally substituted 3-7 membered spiroheterocycloalkyl ring;
or two R$^1$ groups attached to the same carbon atom, together with that carbon atom, represent a carbonyl group (C=O);
or two R$^2$ groups attached to the same carbon atom, together with the carbon atom to which they are both attached form an optionally substituted 3-7 membered spirocycloalkyl ring or an optionally substituted 3-7 membered spiroheterocycloalkyl ring;
or two R$^2$ groups attached to the same carbon atom, together with that carbon atom, represent a carbonyl group (C=O);

or two R¹ groups attached to different carbon atoms, together with the carbon atoms to which they are attached, form a 3-7 membered cycloalkyl ring;

or two R² groups attached to different carbon atoms, together with the carbon atoms to which they are attached, form a 3-7 membered cycloalkyl ring;

or an R¹ group and an R² group are attached to form a 6-9 membered bridged bicyclic ring;

A=N or CH;

Z=S(O)$_2$; S(O); O, NR³ or CR⁴R⁴';

R³ is H; optionally substituted —C$_1$-C$_6$alkyl, 3-5-membered cycloalkyl, 3-5 membered heterocycloalkyl, —C(O)NR$^a$R$^b$; —C(O)OR$^c$; —C(O)R$^c$; —S(O)$_2$R$^c$; or —S(O)$_2$NR$^a$R$^b$;

R$^a$ is H or C$_1$-C$_6$alkyl;

R$^b$ is H or C$_1$-C$_6$alkyl;

or R$^a$ and R$^b$ together with the N atom to which they are both attached, form an optionally substituted 3 to 7 membered heterocycloalkyl ring;

R$^c$ is optionally substituted C$_1$-C$_6$alkyl, or cycloalkyl;

R⁴ is H or optionally substituted C$_1$-C$_6$alkyl;

R⁴' is H, —OH, or optionally substituted C$_1$-C$_6$alkyl;

or R⁴ and R⁴' together with the C atom to which they are both attached, form an optionally substituted 3 to 7 membered heterocycloalkyl ring;

Y is a 5- or 6-membered heteroaryl ring;

Q⁵, Q⁶, Q⁷, Q⁸, and Q⁹, are each independently CR⁵;

R⁵ is H, halogen, C$_1$-C$_3$alkyl; C$_1$-C$_3$alkoxyl, or cycloalkyl;

X=O, S, or NR wherein R is H or C$_1$-C$_3$alkyl; and

R⁶ is C$_1$-C$_6$alkyl.

In some aspects of the disclosure, the compounds of formula (II) are compounds of formula (IIA):

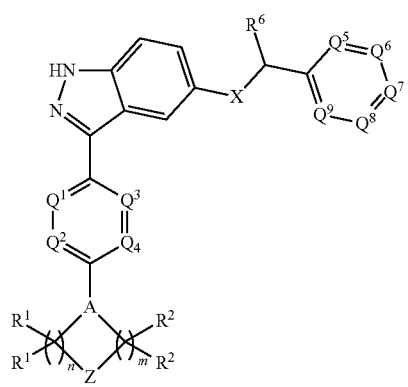

(IIA)

wherein one or two of Q¹, Q², Q³, Q⁴ are N and the remainder are CR$^{5a}$ wherein each R$^{5a}$ is independently H, halogen, or C$_1$-C$_3$alkyl, and the other variables are as set forth for formula (II).

In some aspects, the compounds of formula (II) are compounds of formula (IIB):

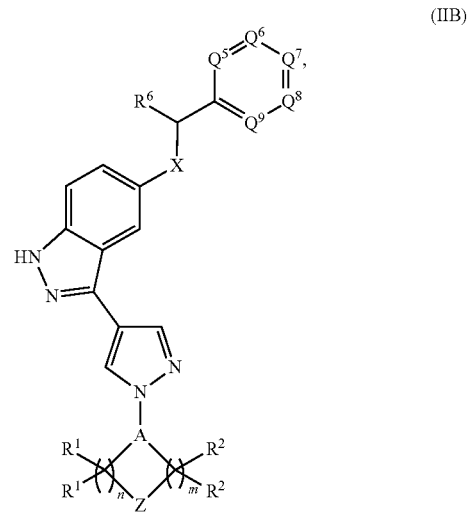

(IIB)

wherein the variables have the values set forth above for formula (II).

In some embodiments of the compounds of formula (II), Q⁶ and Q⁸ are each independently CR⁵ wherein each R⁵ is halogen, and Q⁵, Q⁷, and Q⁹ are each independently CR⁵ wherein each R⁵ is H.

In some embodiments of the compounds of formula (II), Q⁶ and Q⁸ are each independently CR⁵ wherein each R⁵ is —F, and Q⁵, Q⁷, and Q⁹ are each independently CR⁵ wherein each R⁵ is H.

In some embodiments of the compounds of formula (II), Q⁸ and Q⁹ are each independently CR⁵ wherein each R⁵ is halogen, and Q⁶, Q⁷, and Q⁸ are each independently CR⁵ wherein R⁵ is H.

In some embodiments of the compounds of formula (II), Q⁵ and Q⁹ are each independently CR⁵ wherein each R⁵ is —C$_1$, and Q⁶, Q⁷, and Q⁸ are each independently CR⁵ wherein each R⁵ is H.

In some aspects, the disclosure is directed to the following compounds, or pharmaceutically acceptable salts thereof:

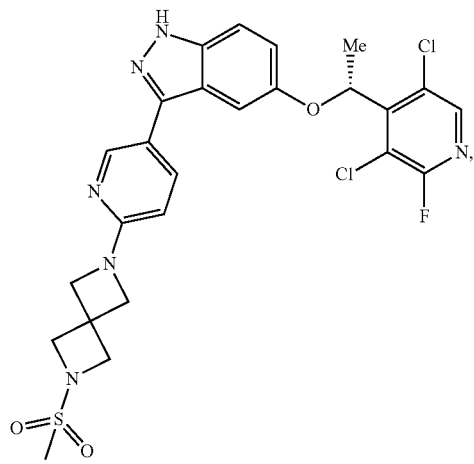

45
-continued
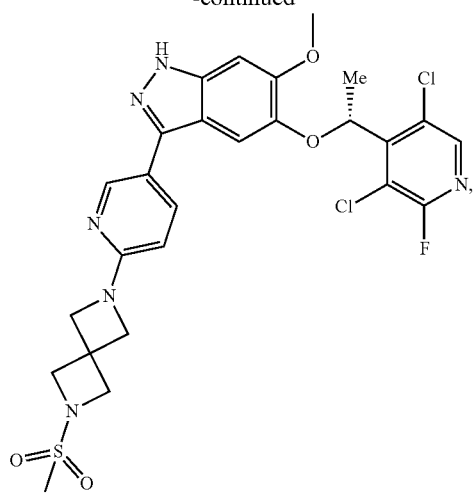
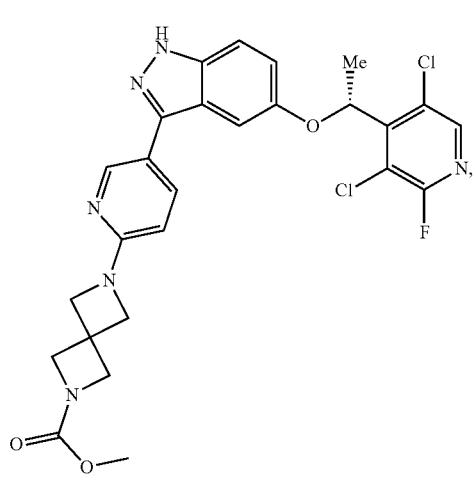
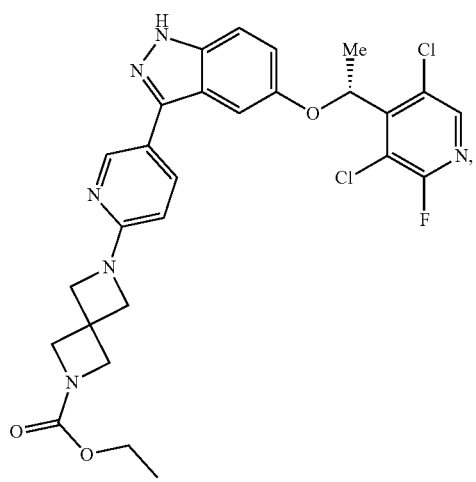
46
-continued
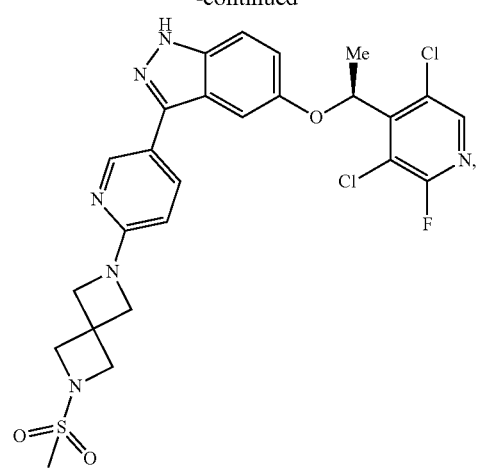
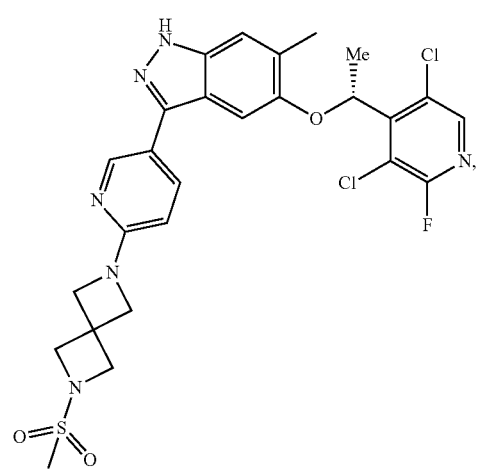
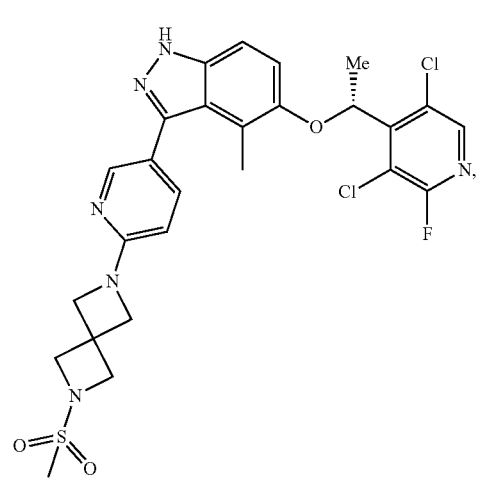

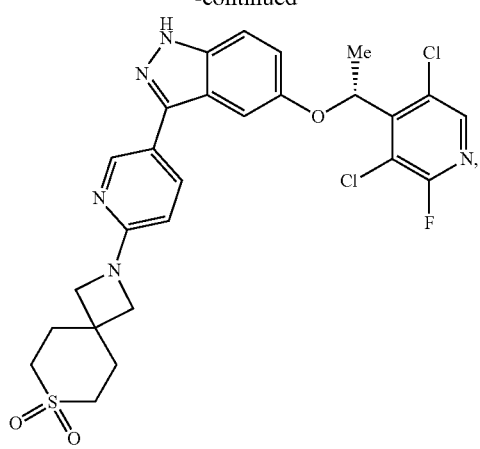
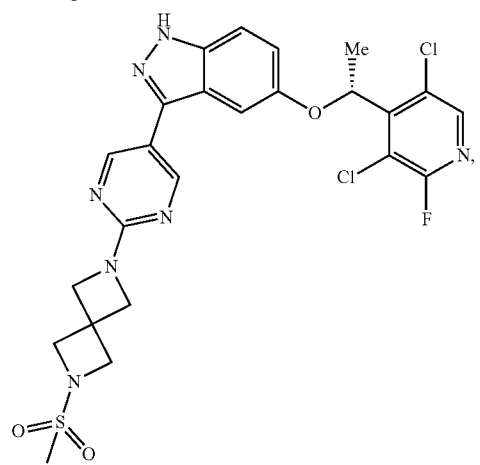
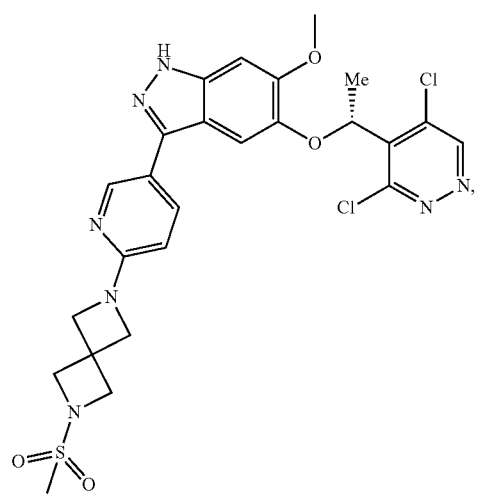
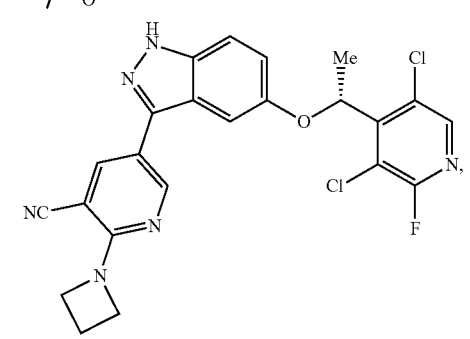
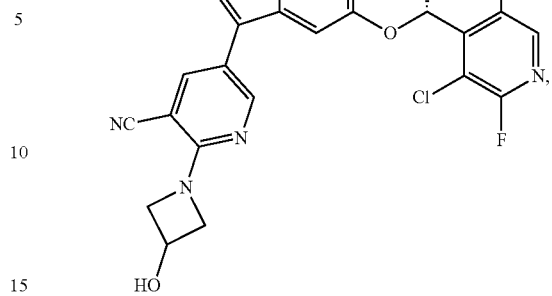
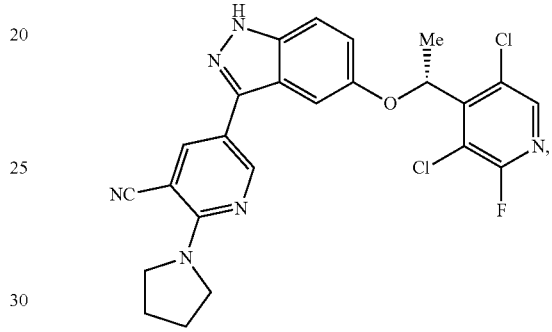
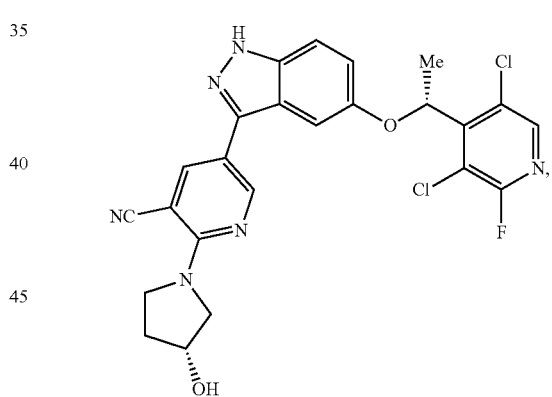
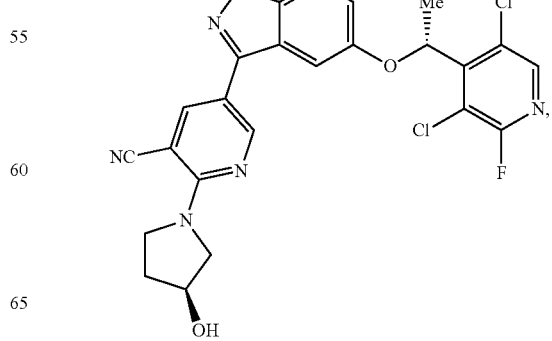

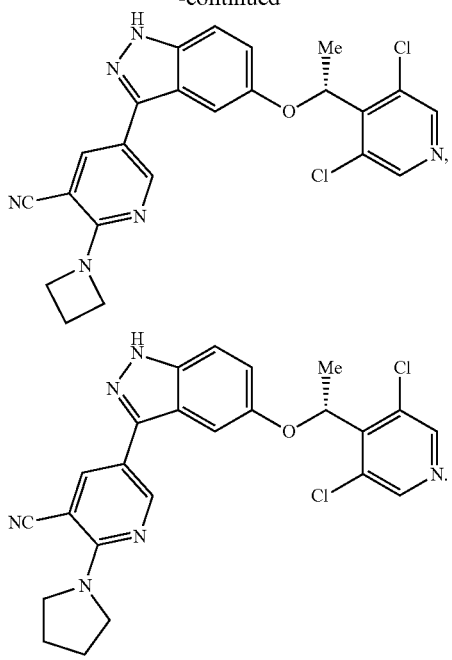

In other aspects, the disclosure is directed to the following compounds, or pharmaceutically acceptable salts thereof:

1-[5-[5-[(1R)-1-(3,5-dichloro-4-pyridyl)ethoxy]-6-methoxy-1H-indazol-3-yl]-3-methylsulfonyl-2-pyridyl]-N,3-dimethyl-azetidin-3-amine

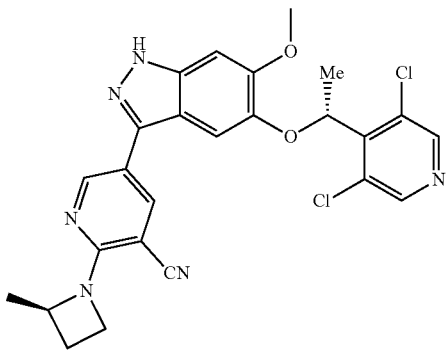 [SMILES: COc1cc2[nH]nc(-c3cnc(N4CC[C@H]4C)c(C#N)c3)c2cc1O[C@H](C)c1c(Cl)cncc1Cl]

2-(azetidin-1-yl)-5-[5-[(1R)-1-(3,5-dichloro-4-pyridyl)ethoxy]-6-methoxy-1H-indazol-3-yl]pyridine-3-carbonitrile

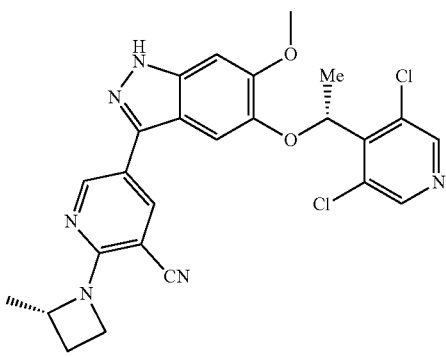 [SMILES: COc1cc2[nH]nc(-c3cnc(N4CC[C@@H]4C)c(C#N)c3)c2cc1O[C@H](C)c1c(Cl)cncc1Cl]

5-[5-[(1R)-1-(3,5-dichloro-4-pyridyl)ethoxy]-6-methoxy-1H-indazol-3-yl]-2-[(2R)-2-methylazetidin-1-yl]pyridine-3-carbonitrile 5-[5-[(1R)-1-(3,5-dichloro-4-pyridyl)ethoxy]-6-methoxy-1H-indazol-3-yl]-2-[(2S)-2-methylazetidin-1-yl]pyridine-3-carbonitrile

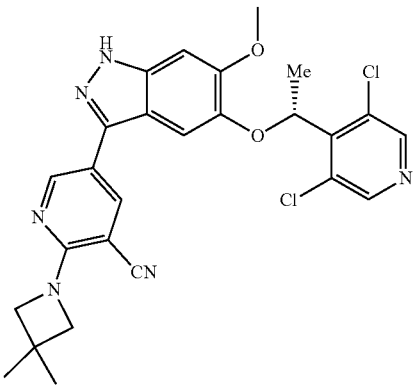 [SMILES: COc1cc2[nH]nc(-c3cnc(N4CC(C)(C)C4)c(C#N)c3)c2cc1O[C@H](C)c1c(Cl)cncc1Cl]

5-[5-[(1R)-1-(3,5-dichloro-4-pyridyl)ethoxy]-6-methoxy-1H-indazol-3-yl]-2-(3,3-dimethylazetidin-1-yl)pyridine-3-carbonitrile

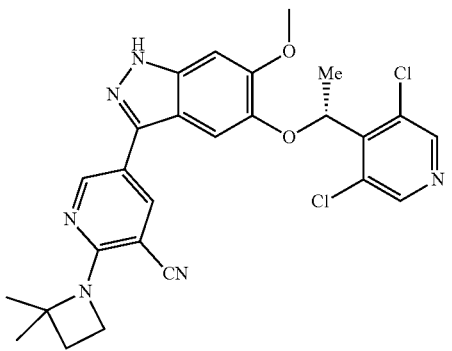 [SMILES: COc1cc2[nH]nc(-c3cnc(N4CCC4(C)C)c(C#N)c3)c2cc1O[C@H](C)c1c(Cl)cncc1Cl]

5-[5-[(1R)-1-(3,5-dichloro-4-pyridyl)ethoxy]-6-methoxy-1H-indazol-3-yl]-2-(2,2-dimethylazetidin-1-yl)pyridine-3-carbonitrile

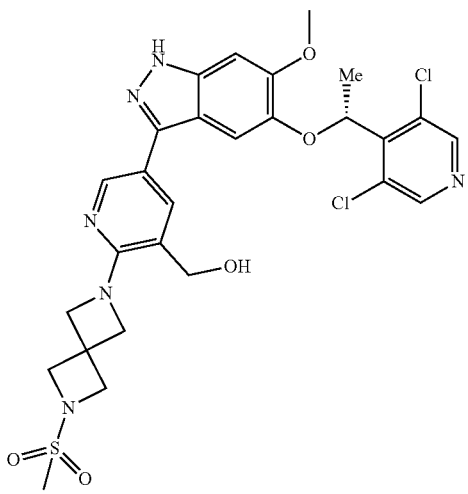 [SMILES: COc1cc2[nH]nc(-c3cnc(N4CC5(C4)CN(S(C)(=O)=O)C5)c(CO)c3)c2cc1O[C@H](C)c1c(Cl)cncc1Cl]

[5-[5-[(1R)-1-(3,5-dichloro-4-pyridyl)ethoxy]-6-methoxy-1H-indazol-3-yl]-2-(2-methylsulfonyl-2,6-diazaspiro[3.3]heptan-6-yl)-3-pyridyl]methanol

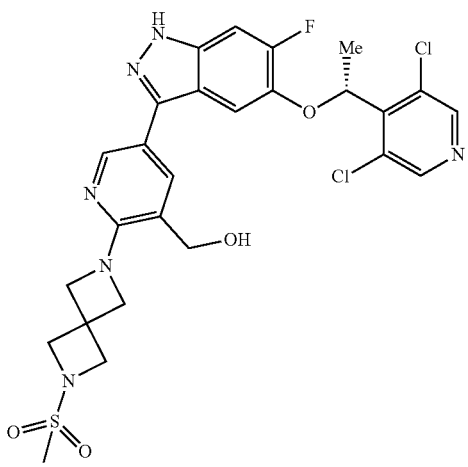

[5-[5-[(1R)-1-(3,5-dichloro-4-pyridyl)ethoxy]-6-fluoro-1H-indazol-3-yl]-2-(2-methylsulfonyl-2,6-diazaspiro[3.3]heptan-6-yl)-3-pyridyl]methanol

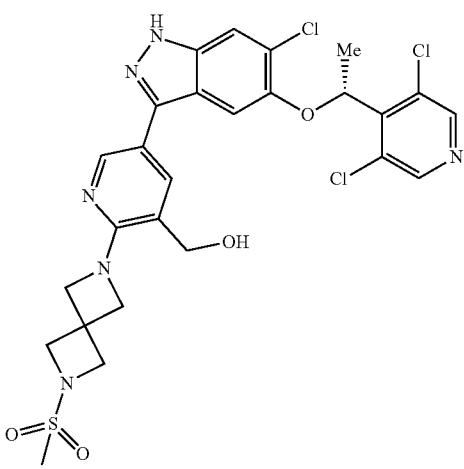 [SMILES: C[C@@H](Oc1cc2c(-c3cnc(N4CC5(C4)CN(S(C)(=O)=O)C5)c(CO)c3)n[nH]c2cc1F)c1c(Cl)cncc1Cl]

[5-[6-chloro-5-[(1R)-1-(3,5-dichloro-4-pyridyl)ethoxy]-1H-indazol-3-yl]-2-(2-methylsulfonyl-2,6-diazaspiro[3.3]heptan-6-yl)-3-pyridyl]methanol

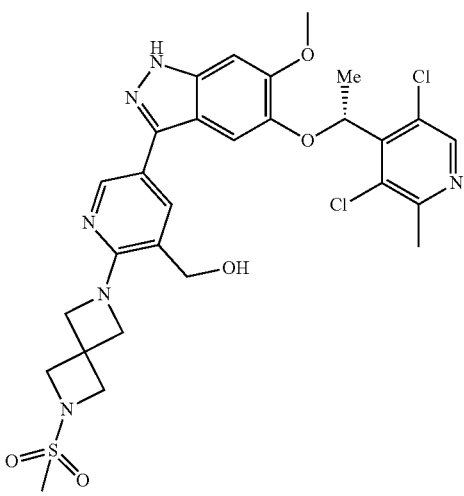 [SMILES: COc1cc2[nH]nc(-c3cnc(N4CC5(C4)CN(S(C)(=O)=O)C5)c(CO)c3)c2cc1O[C@H](C)c1c(Cl)cnc(C)c1Cl]

[5-[5-[(1R)-1-(3,5-dichloro-2-methyl-4-pyridyl)ethoxy]-6-methoxy-1H-indazol-3-yl]-2-(2-methylsulfonyl-2,6-diazaspiro[3.3]heptan-6-yl)-3-pyridyl]methanol

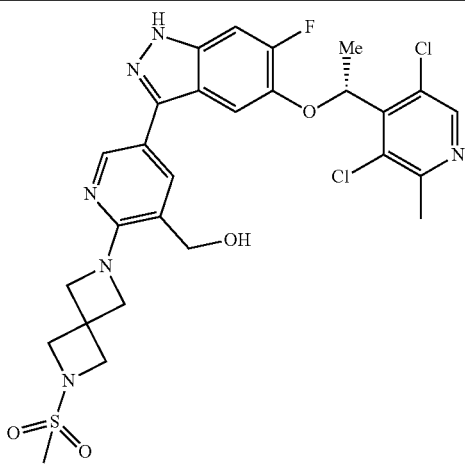

[5-[5-[(1R)-1-(3,5-dichloro-2-methyl-4-pyridyl)ethoxy]-6-fluoro-1H-indazol-3-yl]-2-(2-methylsulfonyl-2,6-diazaspiro[3.3]heptan-6-yl)-3-pyridyl]methanol

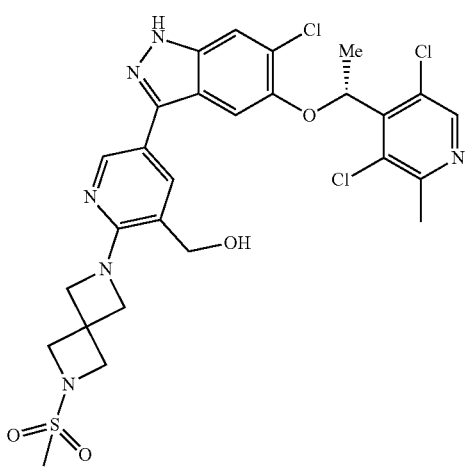 [SMILES: Cc1ncc(Cl)c([C@@H](C)Oc2cc3c(-c4cnc(N5CC6(C5)CN(S(C)(=O)=O)C6)c(CO)c4)n[nH]c3cc2Cl)c1Cl]

[5-[6-chloro-5-[(1R)-1-(3,5-dichloro-2-methyl-4-pyridyl)ethoxy]-1H-indazol-3-yl]-2-(2-methylsulfonyl-2,6-diazaspiro[3.3]heptan-6-yl)-3-pyridyl]methanol

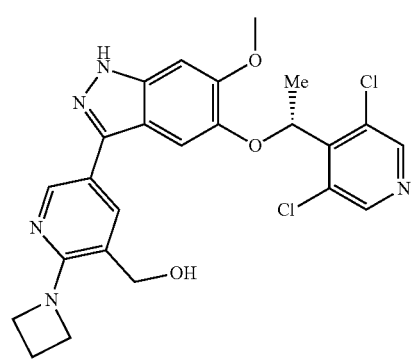 [SMILES: COc1cc2[nH]nc(-c3cnc(N4CCC4)c(CO)c3)c2cc1O[C@H](C)c1c(Cl)cncc1Cl]

[2-(azetidin-1-yl)-5-[5-[(1R)-1-(3,5-dichloro-4-pyridyl)ethoxy]-6-methoxy-1H-indazol-3-yl]-3-pyridyl]methanol

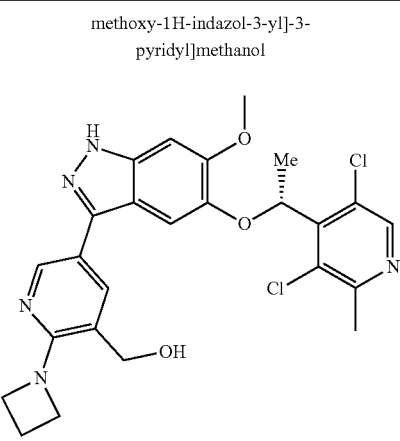

[2-(azetidin-1-yl)-5-[5-[(1R)-1-(3,5-dichloro-2-methyl-4-pyridyl)ethoxy]-6-methoxy-1H-indazol-3-yl]-3-pyridyl]methanol

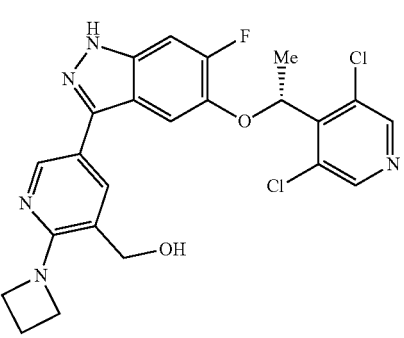 [SMILES: C[C@@H](Oc1cc2c(-c3cnc(N4CCC4)c(CO)c3)n[nH]c2cc1F)c1c(Cl)cncc1Cl]

[2-(azetidin-1-yl)-5-[5-[(1R)-1-(3,5-dichloro-4-pyridyl)ethoxy]-6-fluoro-1H-indazol-3-yl]-3-pyridyl]methanol

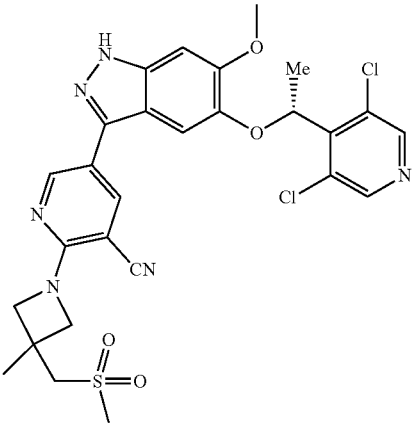 [SMILES: COc1cc2[nH]nc(-c3cnc(N4CC(C)(CS(C)(=O)=O)C4)c(C#N)c3)c2cc1O[C@H](C)c1c(Cl)cncc1Cl]

5-[5-[(1R)-1-(3,5-dichloro-4-pyridyl)ethoxy]-6-methoxy-1H-indazol-3-yl]-2-[3-methyl-1,3-(methylsulfonylmethyl)azetidin-1-yl]pyridine-3-carbonitrile

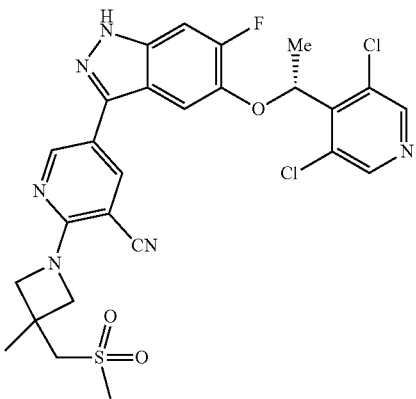 [SMILES: C[C@@H](Oc1cc2c(-c3cnc(N4CC(C)(CS(C)(=O)=O)C4)c(C#N)c3)n[nH]c2cc1F)c1c(Cl)cncc1Cl]

5-[5-[(1R)-1-(3,5-dichloro-4-pyridyl)ethoxy]-6-fluoro-1H-indazol-3-yl]-2-[3-methyl-3-(methylsulfonylmethyl)azetidin-1-yl]pyridine-3-carbonitrile

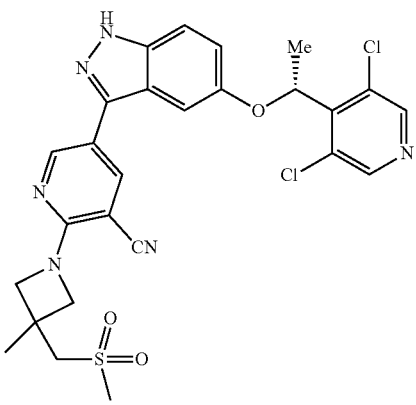 [SMILES: C[C@@H](Oc1ccc2[nH]nc(-c3cnc(N4CC(C)(CS(C)(=O)=O)C4)c(C#N)c3)c2c1)c1c(Cl)cncc1Cl]

5-[5-[(1R)-1-(3,5-dichloro-4-pyridyl)ethoxy]-1H-indazol-3-yl]-2-[3-methyl-3-(methylsulfonylmethyl)azetidin-1-yl]pyridine-3-carbonitrile

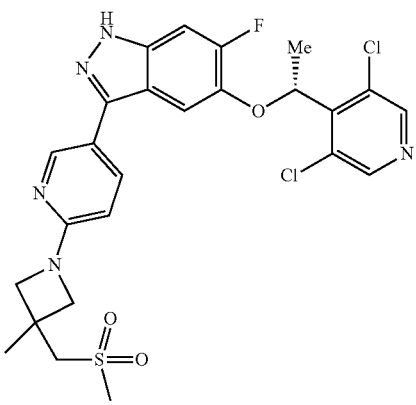

5-[(1R)-1-(3,5-dichloro-4-pyridyl)ethoxy]-6-fluoro-3-[6-[3-methyl-3-(methylsulfonylmethyl)azetidin-1-yl]-3-pyridyl]-1H-indazole

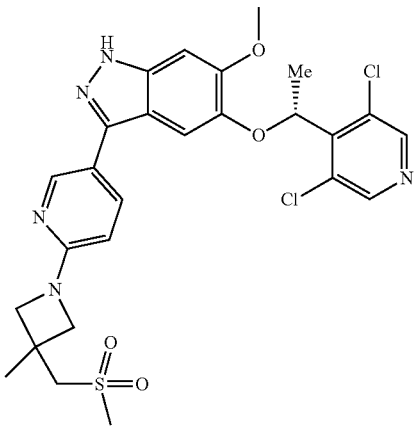 [SMILES: COc1cc2[nH]nc(-c3ccc(N4CC(C)(CS(C)(=O)=O)C4)nc3)c2cc1O[C@H](C)c1c(Cl)cncc1Cl]

5-[(1R)-1-(3,5-dichloro-4-pyridyl)ethoxy]-6-methoxy-3-[6-[3-methyl-3-(methylsulfonylmethyl)azetidin-1-yl]-3-pyridyl]-1H-indazole

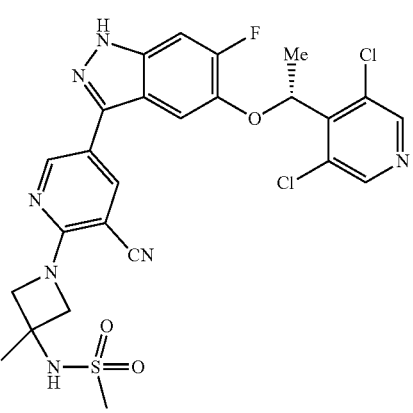 [SMILES: C[C@@H](Oc1cc2c(-c3cnc(N4CC(C)(NS(C)(=O)=O)C4)c(C#N)c3)n[nH]c2cc1F)c1c(Cl)cncc1Cl]

N-[1-[3-cyano-5-[5-[(1R)-1-(3,5-dichloro-4-pyridyl)ethoxy]-6-fluoro-1H-indazol-3-yl]-2-pyridyl]-3-methyl-azetidin-3-yl]methanesulfonamide

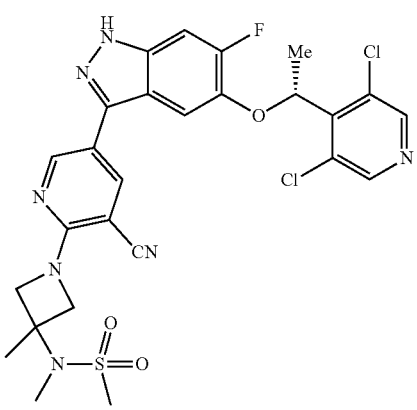 [SMILES: C[C@@H](Oc1cc2c(-c3cnc(N4CC(C)(N(C)S(C)(=O)=O)C4)c(C#N)c3)n[nH]c2cc1F)c1c(Cl)cncc1Cl]

N-[1-[3-cyano-5-[5-[(1R)-1-(3,5-dichloro-4-pyridyl)ethoxy]-6-fluoro-1H-indazol-3-yl]-2-pyridyl]-3-methyl-azetidin-3-yl]-N-methyl-methanesulfonamide

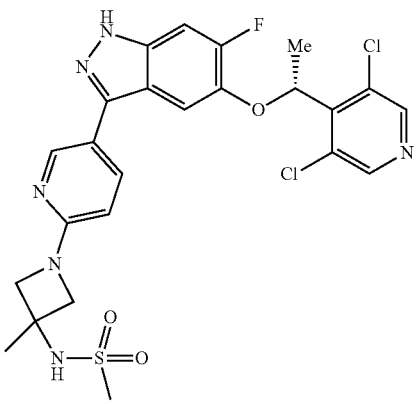 [SMILES: C[C@@H](Oc1cc2c(-c3ccc(N4CC(C)(NS(C)(=O)=O)C4)nc3)n[nH]c2cc1F)c1c(Cl)cncc1Cl]

N-[1-[5-[5-[(1R)-1-(3,5-dichloro-4-pyridyl)ethoxy]-6-fluoro-1H-indazol-3-yl]-2-pyridyl]-3-methyl-azetidin-3-yl]methanesulfonamide

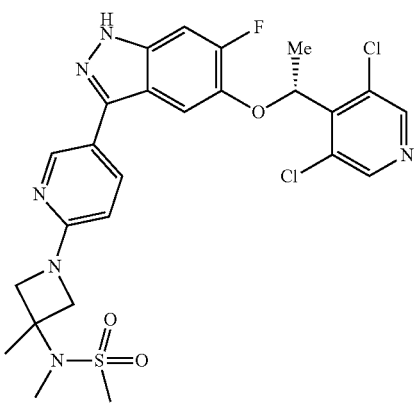 [SMILES: C[C@@H](Oc1cc2c(-c3ccc(N4CC(C)(N(C)S(C)(=O)=O)C4)nc3)n[nH]c2cc1F)c1c(Cl)cncc1Cl]

N-[1-[5-[5-[(1R)-1-(3,5-dichloro-4-pyridyl)ethoxy]-6-fluoro-1H-indazol-3-yl]-2-pyridyl]-3-methyl-azetidin-3-yl]-N-methyl-methanesulfonamide

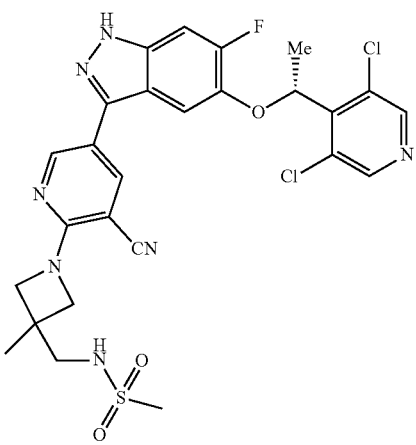 [SMILES: C[C@@H](Oc1cc2c(-c3cnc(N4CC(C)(CNS(C)(=O)=O)C4)c(C#N)c3)n[nH]c2cc1F)c1c(Cl)cncc1Cl]

N-[[1-[3-cyano-5-[5-[(1R)-1-(3,5-dichloro-4-pyridyl)ethoxy]-6-fluoro-1H-indazol-3-yl]-2-pyridyl]-3-methyl-azetidin-3-yl]methyl]methanesulfonamide

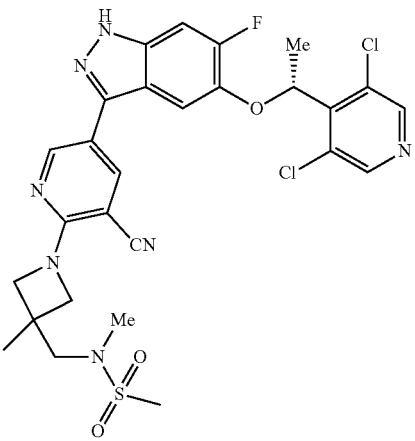 [SMILES: C[C@@H](Oc1cc2c(-c3cnc(N4CC(C)(CN(C)S(C)(=O)=O)C4)c(C#N)c3)n[nH]c2cc1F)c1c(Cl)cncc1Cl]

N-[[1-[3-cyano-5-[5-[(1R)-1-(3,5-dichloro-4-pyridyl)ethoxy]-6-fluoro-1H-indazol-3-yl]-2-pyridyl]-3-methyl-azetidin-3-yl]methyl]-N-methyl-methanesulfonamide

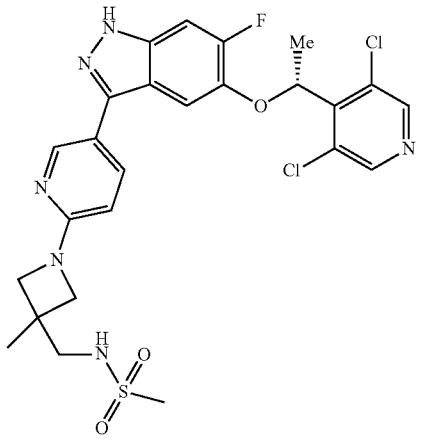 [SMILES: C[C@@H](Oc1cc2c(-c3ccc(N4CC(C)(CNS(C)(=O)=O)C4)nc3)n[nH]c2cc1F)c1c(Cl)cncc1Cl]

N-[[1-[5-[5-[(1R)-1-(3,5-dichloro-4-pyridyl)ethoxy]-6-fluoro-1H-indazol-3-yl]-2-pyridyl]-3-methyl-azetidin-3-yl]methyl]methanesulfonamide

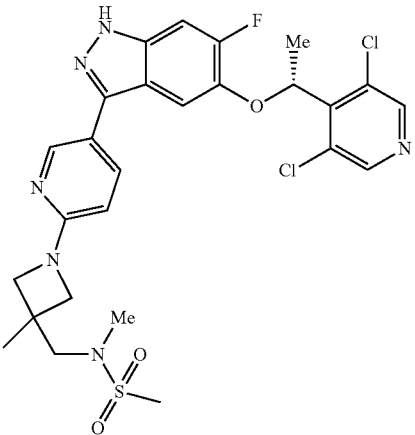 [SMILES: C[C@@H](Oc1cc2c(-c3ccc(N4CC(C)(CN(C)S(C)(=O)=O)C4)nc3)n[nH]c2cc1F)c1c(Cl)cncc1Cl]

N-[[1-[5-[5-[(1R)-1-(3,5-dichloro-4-pyridyl)ethoxy]-6-fluoro-1H-indazol-3-yl]-2-pyridyl]-3-methylazetidin-3-yl]methyl]-N-methyl-
methanesulfonamide

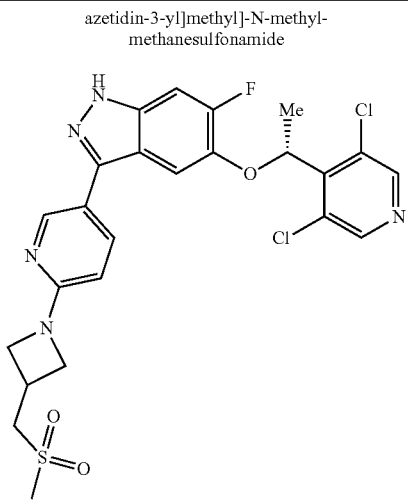

5-[(1R)-1-(3,5-dichloro-4-
pyridyl)ethoxy]-6-fluoro-3-[6-[3-
(methylsulfonylmethyl)azetidin-1-
yl]-3-pyridyl]-1H-indazole

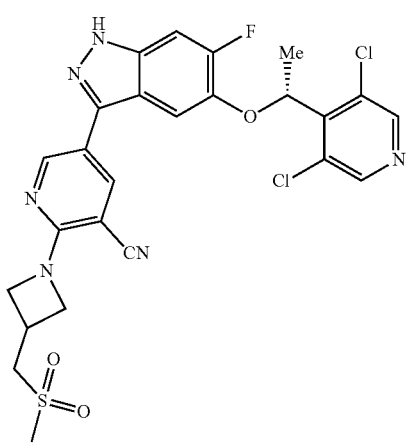 [SMILES: C[C@@H](Oc1cc2c(-c3cnc(N4CC(CS(C)(=O)=O)C4)c(C#N)c3)n[nH]c2cc1F)c1c(Cl)cncc1Cl]

5-[5-[(1R)-1-(3,5-dichloro-4-
pyridyl)ethoxy]-6-fluoro-1H-
indazol-3-yl]-2-[3-
(methylsulfonylmethyl)azetidin-1-
yl]pyridine-3-carbonitrile

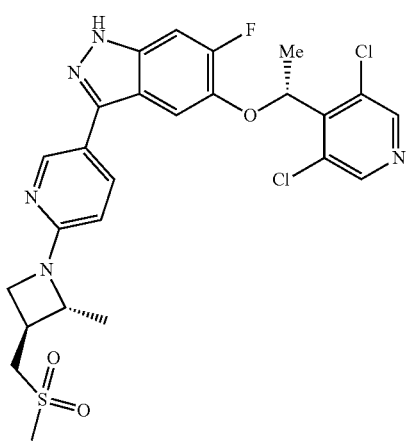 [SMILES: C[C@@H]1[C@@H](CS(C)(=O)=O)CN1c1ccc(-c2n[nH]c3cc(F)c(O[C@H](C)c4c(Cl)cncc4Cl)cc23)cn1]

5-[(1R)-1-(3,5-dichloro-4-
pyridyl)ethoxy]-6-fluoro-3-[6-

[(2R,3S)-2-methyl-3-
(methylsulfonylmethyl)azetidin-1-
yl]-3-pyridyl]-1H-indazole

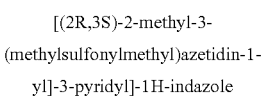

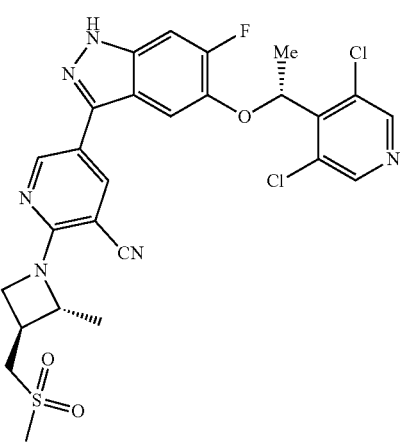 [SMILES: C[C@@H]1[C@@H](CS(C)(=O)=O)CN1c1ncc(-c2n[nH]c3cc(F)c(O[C@H](C)c4c(Cl)cncc4Cl)cc23)cc1C#N]

5-[5-[(1R)-1-(3,5-dichloro-4-
pyridyl)ethoxy]-6-fluoro-1H-
indazol-3-yl]-2-[(2R,3S)-2-methyl-
3-(methylsulfonylmethyl)azetidin-1-
yl]pyridine-3-carbonitrile

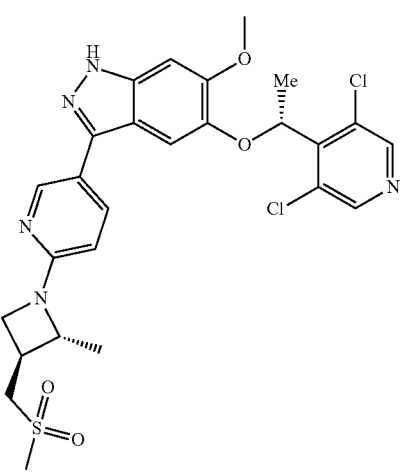 [SMILES: COc1cc2[nH]nc(-c3ccc(N4C[C@H](CS(C)(=O)=O)[C@H]4C)nc3)c2cc1O[C@H](C)c1c(Cl)cncc1Cl]

5-[(1R)-1-(3,5-dichloro-4-
pyridyl)ethoxy]-6-methoxy-3-[6-
[(2R,3S)-2-methyl-3-
(methylsulfonylmethyl)azetidin-1-
yl]-3-pyridyl]-1H-indazole -continued

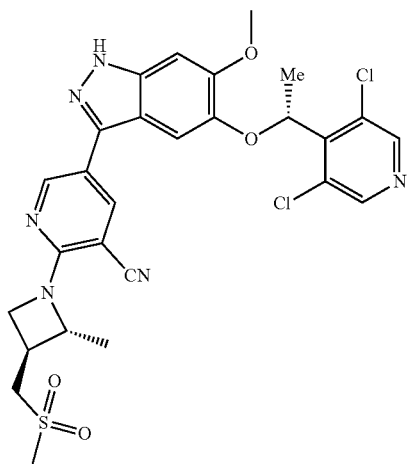 [SMILES: COc1cc2[nH]nc(-c3cnc(N4C[C@H](CS(C)(=O)=O)[C@H]4C)c(C#N)c3)c2cc1O[C@H](C)c1c(Cl)cncc1Cl]

5-[5-[(1R)-1-(3,5-dichloro-4-pyridyl)ethoxy]-6-methoxy-1H-indazol-3-yl]-2-[(2R,3S)-2-methyl-3-(methylsulfonylmethyl)azetidin-1-yl]pyridine-3-carbonitrile

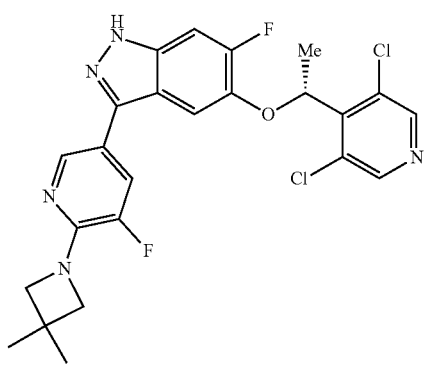 [SMILES: C[C@@H](Oc1cc2c(-c3cnc(N4CC(C)(C)C4)c(F)c3)n[nH]c2cc1F)c1c(Cl)cncc1Cl]

5-[(1R)-1-(3,5-dichloro-4-pyridyl)ethoxy]-3-[6-(3,3-dimethylazetidin-1-yl)-5-fluoro-3-pyridyl]-6-fluoro-1H-indazole

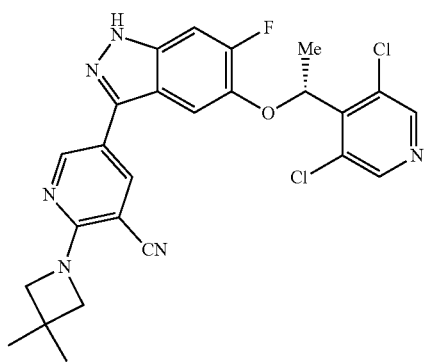 [SMILES: C[C@@H](Oc1cc2c(-c3cnc(N4CC(C)(C)C4)c(C#N)c3)n[nH]c2cc1F)c1c(Cl)cncc1Cl]

5-[5-[(1R)-1-(3,5-dichloro-4-pyridyl)ethoxy]-6-fluoro-1H-indazol-3-yl]-2-(3,3-dimethylazetidin-1-yl)pyridine-3-carbonitrile -continued

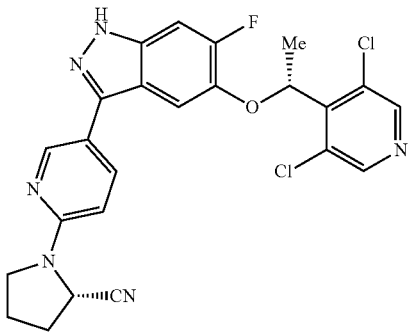 [SMILES: C[C@@H](Oc1cc2c(-c3ccc(N4CCC[C@H]4C#N)nc3)n[nH]c2cc1F)c1c(Cl)cncc1Cl]

(2S)-1-[5-[5-[(1R)-1-(3,5-dichloro-4-pyridyl)ethoxy]-6-fluoro-1H-indazol-3-yl]-2-pyridyl]pyrrolidine-2-carbonitrile

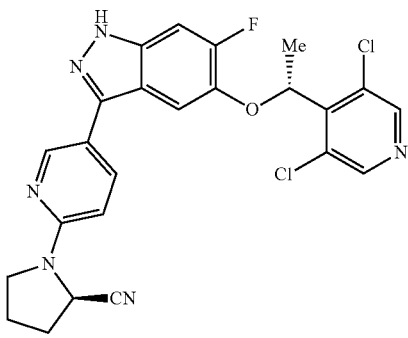 [SMILES: C[C@@H](Oc1cc2c(-c3ccc(N4CCC[C@@H]4C#N)nc3)n[nH]c2cc1F)c1c(Cl)cncc1Cl]

(2R)-1-[5-[5-[(1R)-1-(3,5-dichloro-4-pyridyl)ethoxy]-6-fluoro-1H-indazol-3-yl]-2-pyridyl]pyrrolidine-2-carbonitrile

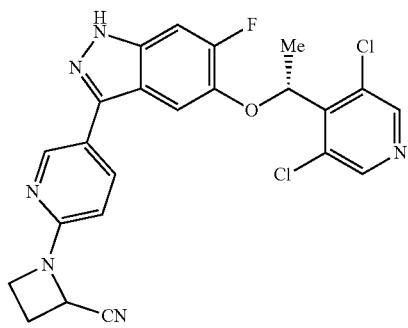 [SMILES: C[C@@H](Oc1cc2c(-c3ccc(N4CCC4C#N)nc3)n[nH]c2cc1F)c1c(Cl)cncc1Cl]

1-[5-[5-[(1R)-1-(3,5-dichloro-4-pyridyl)ethoxy]-6-fluoro-1H-indazol-3-yl]-2-pyridyl]azetidine-2-carbonitrile

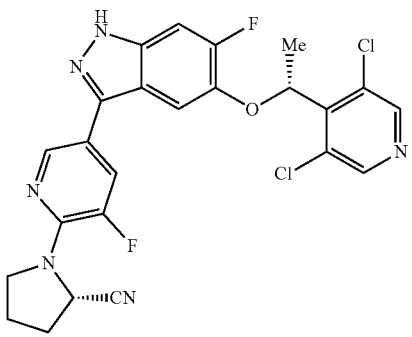 [SMILES: C[C@@H](Oc1cc2c(-c3cnc(N4CCC[C@H]4C#N)c(F)c3)n[nH]c2cc1F)c1c(Cl)cncc1Cl]

(2S)-1-[5-[5-[(1R)-1-(3,5-dichloro-
4-pyridyl)ethoxy]-6-fluoro-1H-
indazol-3-yl]-3-fluoro-2-
pyridyl]pyrrolidine-2-carbonitrile

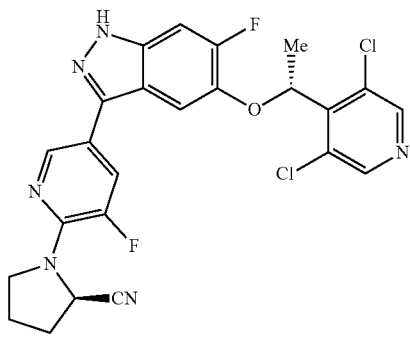 [SMILES: C[C@@H](Oc1cc2c(-c3cnc(N4CCC[C@@H]4C#N)c(F)c3)n[nH]c2cc1F)c1c(Cl)cncc1Cl]

(2R)-1-[5-[5-[(1R)-1-(3,5-dichloro-
4-pyridyl)ethoxy]-6-fluoro-1H-
indazol-3-yl]-3-fluoro-2-
pyridyl]pyrrolidine-2-carbonitrile

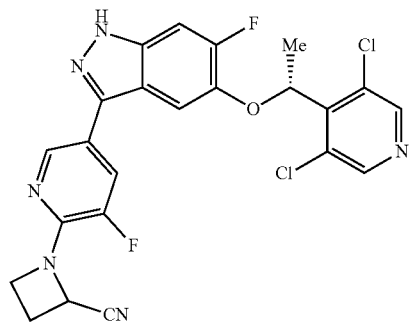

1-[5-[5-[(1R)-1-(3,5-dichloro-4-
pyridyl)ethoxy]-6-fluoro-1H-
indazol-3-yl]-3-fluoro-2-
pyridyl]azetidine-2-carbonitrile

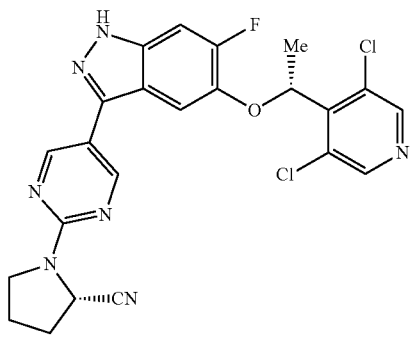 [SMILES: C[C@@H](Oc1cc2c(-c3cnc(N4CCC[C@H]4C#N)nc3)n[nH]c2cc1F)c1c(Cl)cncc1Cl]

(2S)-1-[5-[5-[(1R)-1-(3,5-dichloro-
4-pyridyl)ethoxy]-6-fluoro-1H-
indazol-3-yl]pyrimidin-2-
yl]pyrrolidine-2-carbonitrile

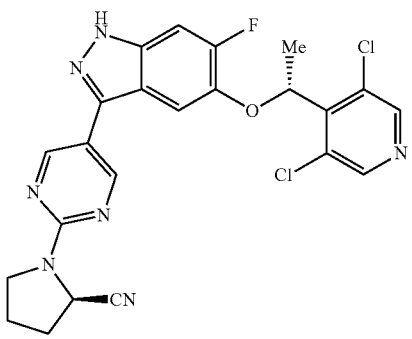 [SMILES: C[C@@H](Oc1cc2c(-c3cnc(N4CCC[C@@H]4C#N)nc3)n[nH]c2cc1F)c1c(Cl)cncc1Cl]

(2R)-1-[5-[5-[(1R)-1-(3,5-dichloro-
4-pyridyl)ethoxy]-6-fluoro-1H-
indazol-3-yl]pyrimidin-2-
yl]pyrrolidine-2-carbonitrile

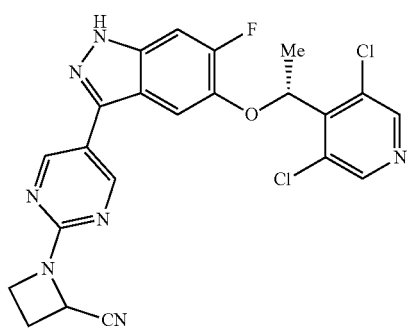 [SMILES: C[C@@H](Oc1cc2c(-c3cnc(N4CCC4C#N)nc3)n[nH]c2cc1F)c1c(Cl)cncc1Cl]

1-[5-[5-[(1R)-1-(3,5-dichloro-4-
pyridyl)ethoxy]-6-fluoro-1H-
indazol-3-yl]pyrimidin-2-
yl]azetidine-2-carbonitrile

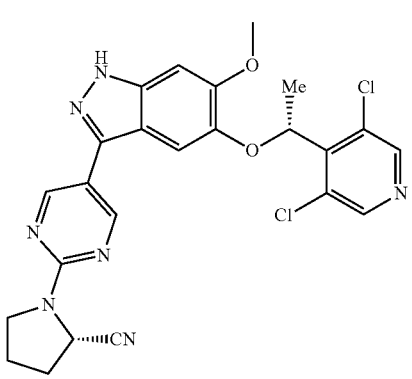 [SMILES: COc1cc2[nH]nc(-c3cnc(N4CCC[C@H]4C#N)nc3)c2cc1O[C@H](C)c1c(Cl)cncc1Cl]

(2S)-1-[5-[5-[(1R)-1-(3,5-dichloro-
4-pyridyl)ethoxy]-6-methoxy-1H-
indazol-3-yl]pyrimidin-2-
yl]pyrrolidine-2-carbonitrile

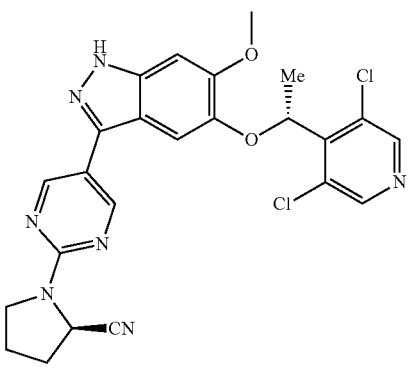 [SMILES: COc1cc2[nH]nc(-c3cnc(N4CCC[C@@H]4C#N)nc3)c2cc1O[C@H](C)c1c(Cl)cncc1Cl]

(2R)-1-[5-[5-[(1R)-1-(3,5-dichloro-
4-pyridyl)ethoxy]-6-methoxy-1H-
indazol-3-yl]pyrimidin-2-
yl]pyrrolidine-2-carbonitrile

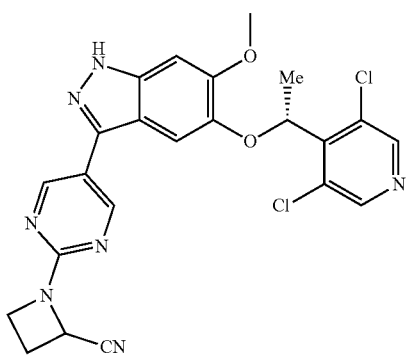 [SMILES: COc1cc2[nH]nc(-c3cnc(N4CCC4C#N)nc3)c2cc1O[C@H](C)c1c(Cl)cncc1Cl]

1-[5-[5-[(1R)-1-(3,5-dichloro-4-
pyridyl)ethoxy]-6-methoxy-1H-
indazol-3-yl]pyrimidin-2-
yl]azetidine-2-carbonitrile

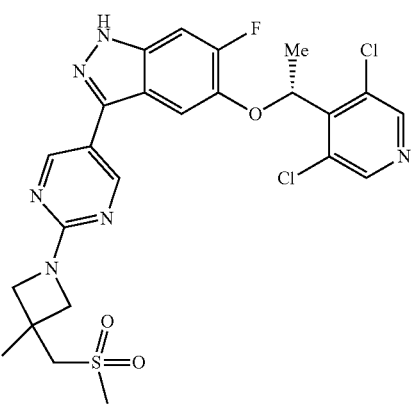 [SMILES: C[C@@H](Oc1cc2c(-c3cnc(N4CC(C)(CS(C)(=O)=O)C4)nc3)n[nH]c2cc1F)c1c(Cl)cncc1Cl]

5-[(1R)-1-(3,5-dichloro-4-
pyridyl)ethoxy]-6-fluoro-3-[3-
methyl-3-
(methylsulfonylmethyl)azetidin-1-
yl]pyrimidin-5-yl]-1H-indazole

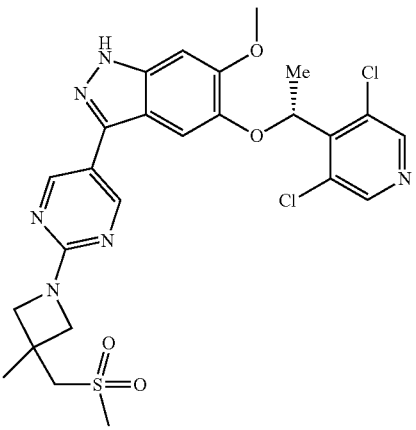 [SMILES: COc1cc2[nH]nc(-c3cnc(N4CC(C)(CS(C)(=O)=O)C4)nc3)c2cc1O[C@H](C)c1c(Cl)cncc1Cl]

5-[(1R)-1-(3,5-dichloro-4-
pyridyl)ethoxy]-6-methoxy-3-[2-[3-
methyl-3-
(methylsulfonylmethyl)azetidin-1-
yl]pyrimidin-5-yl]-1H-indazole

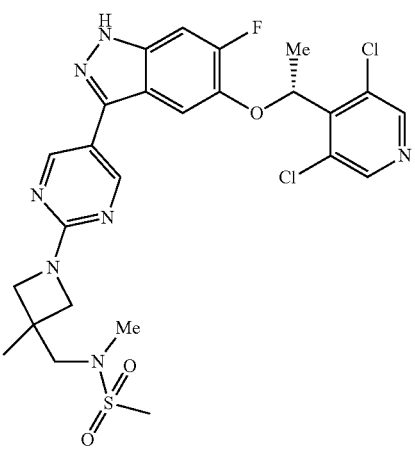 [SMILES: C[C@@H](Oc1cc2c(-c3cnc(N4CC(C)(CN(C)S(C)(=O)=O)C4)nc3)n[nH]c2cc1F)c1c(Cl)cncc1Cl]

N-[[1-[5-[5-[(1R)-1-(3,5-dichloro-4-
pyridyl)ethoxy]-6-fluoro-1H-
indazol-3-yl]pyrimidin-2-yl]-3-
methyl-azetidin-3-yl]methyl]-N-
methyl-methanesulfonamide

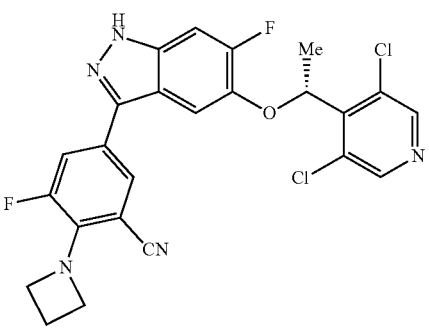 [SMILES: C[C@@H](Oc1cc2c(-c3cc(F)c(N4CCC4)c(C#N)c3)n[nH]c2cc1F)c1c(Cl)cncc1Cl]

2-(azetidin-1-yl)-5-[5-[(1R)-1-(3,5-
dichloro-4-pyridyl)ethoxy]-6-fluoro-
1H-indazol-3-yl]-3-fluoro-
benzonitrile

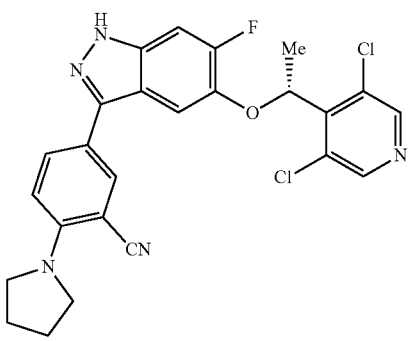 [SMILES: C[C@@H](Oc1cc2c(-c3ccc(N4CCCC4)c(C#N)c3)n[nH]c2cc1F)c1c(Cl)cncc1Cl]

5-[5-[(1R)-1-(3,5-dichloro-4-pyridyl)ethoxy]-6-fluoro-1H-indazol-3-yl]-2-pyrrolidin-1-yl-benzonitrile

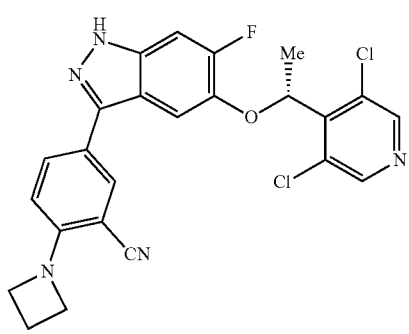 [SMILES: C[C@@H](Oc1cc2c(-c3ccc(N4CCC4)c(C#N)c3)n[nH]c2cc1F)c1c(Cl)cncc1Cl]

2-(azetidin-1-yl)-5-[5-[(1R)-1-(3,5-dichloro-4-pyridyl)ethoxy]-6-fluoro-1H-indazol-3-yl]benzonitrile

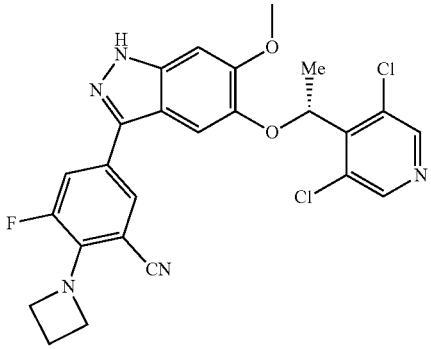 [SMILES: COc1cc2[nH]nc(-c3cc(F)c(N4CCC4)c(C#N)c3)c2cc1O[C@H](C)c1c(Cl)cncc1Cl]

2-(azetidin-1-yl)-5-[5-[(1R)-1-(3,5-dichloro-4-pyridyl)ethoxy]-6-methoxy-1H-indazol-3-yl]-3-fluoro-benzonitrile

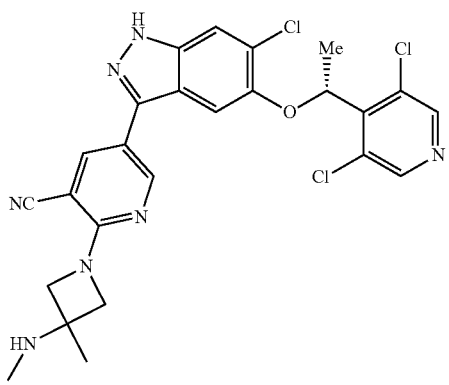 [SMILES: CNC1(C)CN(c2ncc(-c3n[nH]c4cc(Cl)c(O[C@H](C)c5c(Cl)cncc5Cl)cc34)cc2C#N)C1]

5-[6-chloro-5-[(1R)-1-(3,5-dichloro-4-pyridyl)ethoxy]-1H-indazol-3-yl]-2-[3-methyl-3-(methylamino)azetidin-1-yl]pyridine-3-carbonitrile

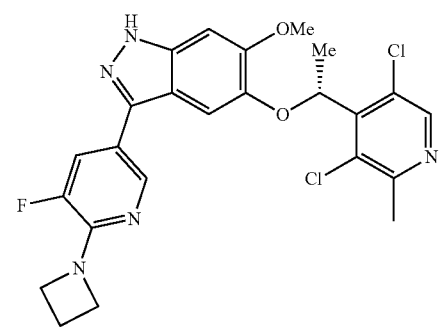 [SMILES: COc1cc2[nH]nc(-c3cnc(N4CCC4)c(F)c3)c2cc1O[C@H](C)c1c(Cl)cnc(C)c1Cl]

3-[6-(azetidin-1-yl)-5-fluoro-3-pyridyl]-5-[(1R)-1-(3,5-dichloro-2-methyl-4-pyridyl)ethoxy]-6-methoxy-1H-indazole

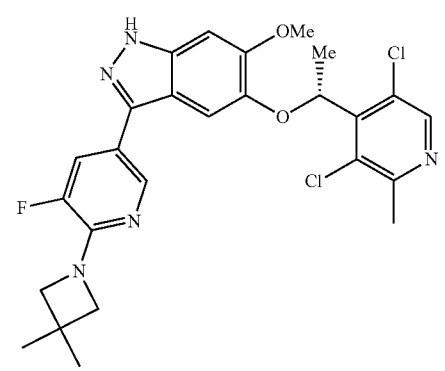 [SMILES: COc1cc2[nH]nc(-c3cnc(N4CC(C)(C)C4)c(F)c3)c2cc1O[C@H](C)c1c(Cl)cnc(C)c1Cl]

5-[(1R)-1-(3,5-dichloro-2-methyl-4-pyridyl)ethoxy]-3-[6-(3,3-dimethylazetidin-1-yl)-5-fluoro-3-pyridyl]-6-methoxy-1H-indazole

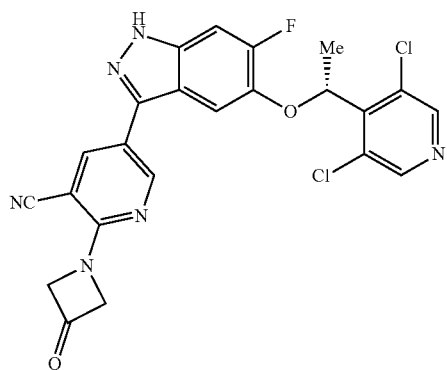 [SMILES: C[C@@H](Oc1cc2c(-c3cnc(N4CC(=O)C4)c(C#N)c3)n[nH]c2cc1F)c1c(Cl)cncc1Cl]

5-[5-[(1R)-1-(3,5-dichloro-4-
pyridyl)ethoxy]-6-fluoro-1H-
indazol-3-yl]-2-(3-oxoazetidin-1-
yl)pyridine-3-carbonitrile

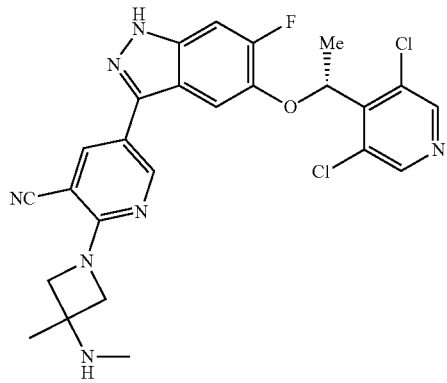 [SMILES: CNC1(C)CN(c2ncc(-c3n[nH]c4cc(F)c(O[C@H](C)c5c(Cl)cncc5Cl)cc34)cc2C#N)C1]

5-[5-[(1R)-1-(3,5-dichloro-4-
pyridyl)ethoxy]-6-fluoro-1H-
indazol-3-yl]-2-[3-methyl-3-
(methylamino)azetidin-1-
yl]pyridine-3-carbonitrile

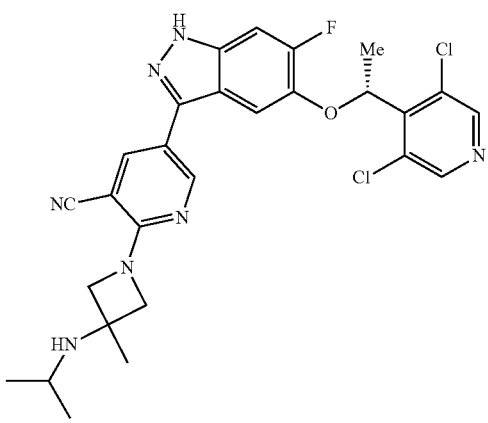 [SMILES: CC(C)NC1(C)CN(c2ncc(-c3n[nH]c4cc(F)c(O[C@H](C)c5c(Cl)cncc5Cl)cc34)cc2C#N)C1]

5-[5-[(1R)-1-(3,5-dichloro-4-
pyridyl)ethoxy]-6-fluoro-1H-
indazol-3-yl]-2-[3-(isopropylamino)-
3-methyl-azetidin-1-yl]pyridine-3-
carbonitrile

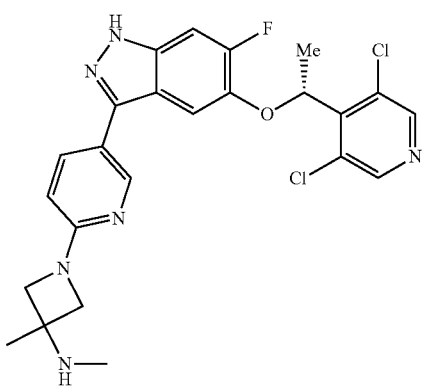 [SMILES: CNC1(C)CN(c2ccc(-c3n[nH]c4cc(F)c(O[C@H](C)c5c(Cl)cncc5Cl)cc34)cn2)C1]

1-[5-[5-[(1R)-1-(3,5-dichloro-4-
pyridyl)ethoxy]-6-fluoro-1H-
indazol-3-yl]-2-pyridyl]-N,3-
dimethyl-azetidin-3-amine

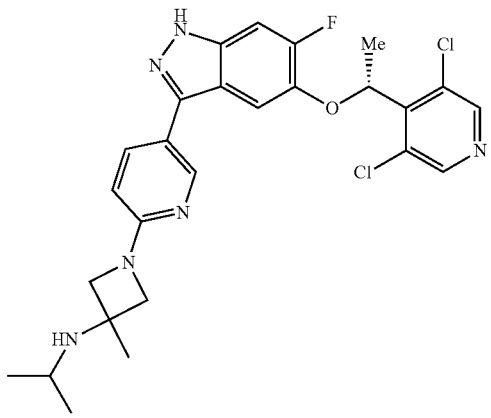 [SMILES: CC(C)NC1(C)CN(c2ccc(-c3n[nH]c4cc(F)c(O[C@H](C)c5c(Cl)cncc5Cl)cc34)cn2)C1]

1-[5-[5-[(1R)-1-(3,5-dichloro-4-
pyridyl)ethoxy]-6-fluoro-1H-
indazol-3-yl]-2-pyridyl]-N-
isopropyl-3-methyl-azetidin-3-
amine

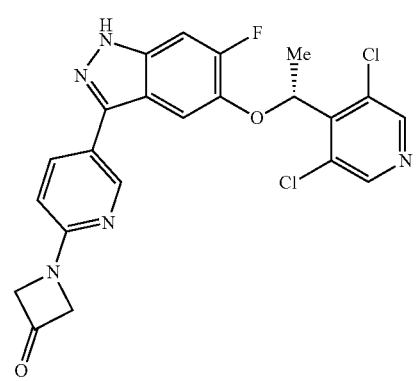 [SMILES: C[C@@H](Oc1cc2c(-c3ccc(N4CC(=O)C4)nc3)n[nH]c2cc1F)c1c(Cl)cncc1Cl]

1-[5-[5-[(1R)-1-(3,5-dichloro-4-
pyridyl)ethoxy]-6-fluoro-1H-
indazol-3-yl]-2-pyridyl]azetidin-3-
one

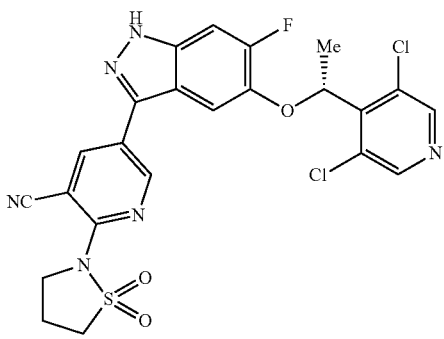 [SMILES: C[C@@H](Oc1cc2c(-c3cnc(N4CCCS4(=O)=O)c(C#N)c3)n[nH]c2cc1F)c1c(Cl)cncc1Cl]

5-[5-[(1R)-1-(3,5-dichloro-4-pyridyl)ethoxy]-6-fluoro-1H-indazol-3-yl]-2-(1,1-dioxo-1,2-thiazolidin-2-yl)pyridine-3-carbonitrile

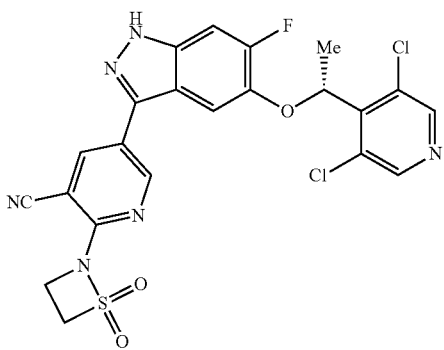 [SMILES: C[C@@H](Oc1cc2c(-c3cnc(N4CCS4(=O)=O)c(C#N)c3)n[nH]c2cc1F)c1c(Cl)cncc1Cl]

5-[5-[(1R)-1-(3,5-dichloro-4-pyridyl)ethoxy]-6-fluoro-1H-indazol-3-yl]-2-(1,1-dioxothiazetidin-2-yl)pyridine-3-carbonitrile

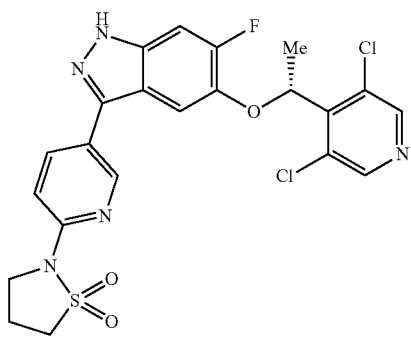 [SMILES: C[C@@H](Oc1cc2c(-c3ccc(N4CCCS4(=O)=O)nc3)n[nH]c2cc1F)c1c(Cl)cncc1Cl]

2-[5-[5-[(1R)-1-(3,5-dichloro-4-pyridyl)ethoxy]-6-fluoro-1H-indazol-3-yl]-2-pyridyl]-1,2-thiazolidine 1,1-dioxide

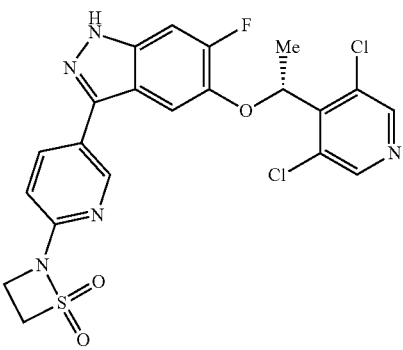 [SMILES: C[C@@H](Oc1cc2c(-c3ccc(N4CCS4(=O)=O)nc3)n[nH]c2cc1F)c1c(Cl)cncc1Cl]

2-[5-[5-[(1R)-1-(3,5-dichloro-4-pyridyl)ethoxy]-6-fluoro-1H-indazol-3-yl]-2-pyridyl]thiazetidine 1,1-dioxide

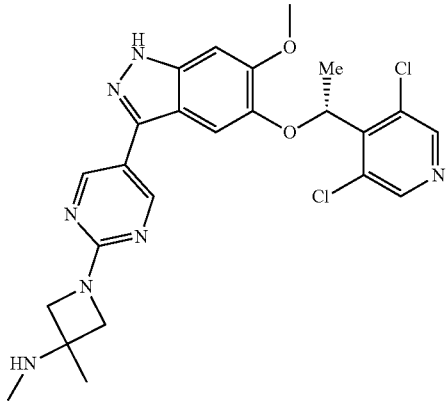 [SMILES: CNC1(C)CN(c2ncc(-c3n[nH]c4cc(OC)c(O[C@H](C)c5c(Cl)cncc5Cl)cc34)cn2)C1]

1-[5-[5-[(1R)-1-(3,5-dichloro-4-pyridyl)ethoxy]-6-methoxy-1H-indazol-3-yl]pyrimidin-2-yl]-N,3-dimethyl-azetidin-3-amine

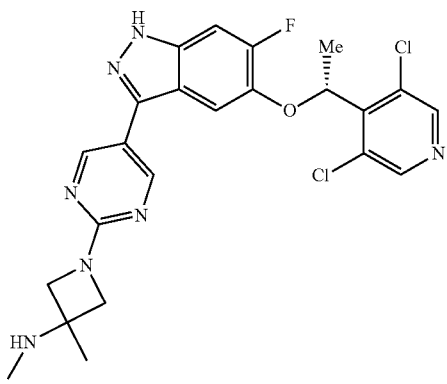 [SMILES: CNC1(C)CN(c2ncc(-c3n[nH]c4cc(F)c(O[C@H](C)c5c(Cl)cncc5Cl)cc34)cn2)C1]

1-[5-[5-[(1R)-1-(3,5-dichloro-4-pyridyl)ethoxy]-6-fluoro-1H-indazol-3-yl]pyrimidin-2-yl]-N,3-dimethyl-azetidin-3-amine

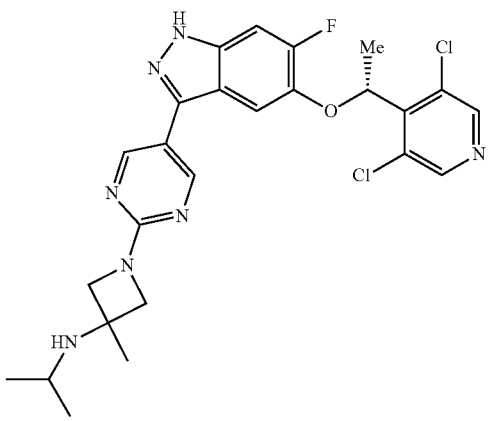 [SMILES: CC(C)NC1(C)CN(c2ncc(-c3n[nH]c4cc(F)c(O[C@H](C)c5c(Cl)cncc5Cl)cc34)cn2)C1]

1-[5-[5-[(1R)-1-(3,5-dichloro-4-pyridyl)ethoxy]-6-fluoro-1H-indazol-3-yl]pyrimidin-2-yl]-N-isopropyl-3-methyl-azetidin-3-amine

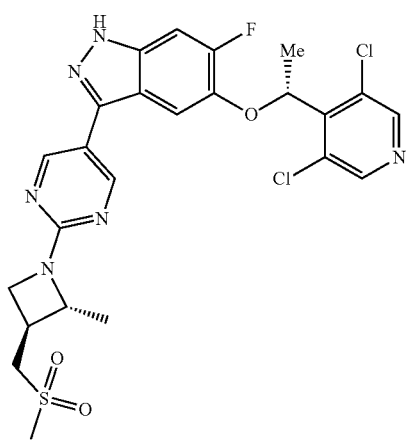 [SMILES: C[C@@H]1[C@@H](CS(C)(=O)=O)CN1c1ncc(-c2n[nH]c3cc(F)c(O[C@H](C)c4c(Cl)cncc4Cl)cc23)cn1]

5-[(1R)-1-(3,5-dichloro-4-pyridyl)ethoxy]-6-fluoro-3-[2-[(2R,3S)-2-methyl-3-(methylsulfonylmethyl)azetidin-1-yl]pyrimidin-5-yl]-1H-indazole

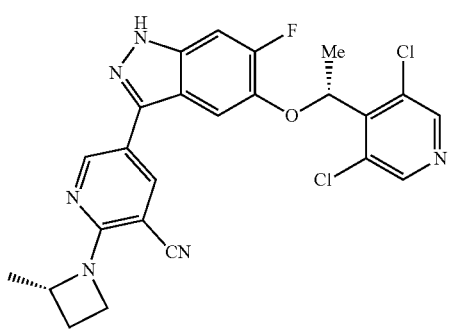 [SMILES: C[C@@H](Oc1cc2c(-c3cnc(N4CC[C@@H]4C)c(C#N)c3)n[nH]c2cc1F)c1c(Cl)cncc1Cl]

5-[5-[(1R)-1-(3,5-dichloro-4-pyridyl)ethoxy]-6-fluoro-1H-indazol-3-yl]-2-[(2S)-2-methylazetidin-1-yl]pyridine-3-carbonitrile

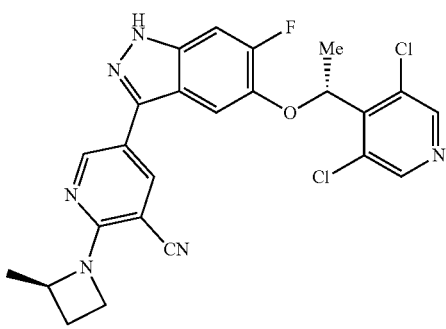 [SMILES: C[C@@H]1CCN1c1ncc(-c2n[nH]c3cc(F)c(O[C@H](C)c4c(Cl)cncc4Cl)cc23)cc1C#N]

5-[5-[(1R)-1-(3,5-dichloro-4-pyridyl)ethoxy]-6-fluoro-1H-indazol-3-yl]-2-[(2R)-2-methylazetidin-1-yl]pyridine-3-carbonitrile

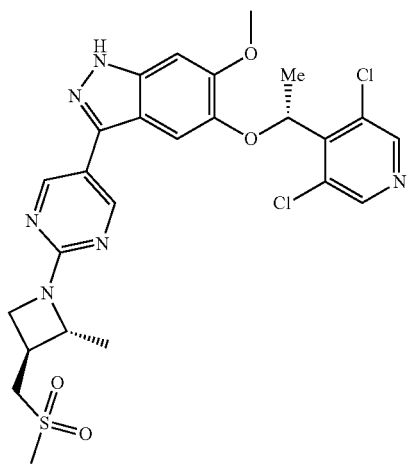

5-[(1R)-1-(3,5-dichloro-4-pyridyl)ethoxy]-6-methoxy-3-[2-[(2R,3S)-2-methyl-3-(methylsulfonylmethyl)azetidin-1-yl]pyrimidin-5-yl]-1H-indazole

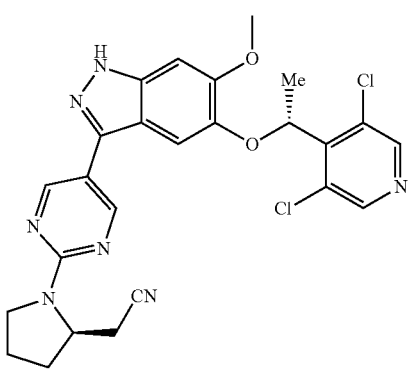 [SMILES: COc1cc2[nH]nc(-c3cnc(N4CCC[C@@H]4CC#N)nc3)c2cc1O[C@H](C)c1c(Cl)cncc1Cl]

2-[(2R)-1-[5-[5-[(1R)-1-(3,5-dichloro-4-pyridyl)ethoxy]-6-methoxy-1H-indazol-3-yl]pyrimidin-2-yl]pyrrolidin-2-yl]acetonitrile

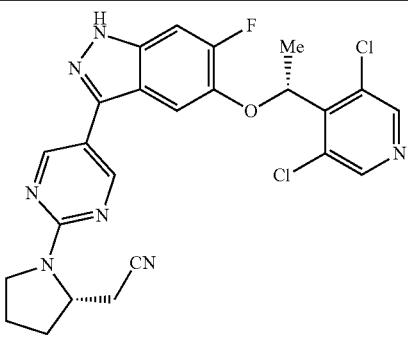

2-[(2S)-1-[5-[5-[(1R)-1-(3,5-dichloro-4-pyridyl)ethoxy]-6-fluoro-1H-indazol-3-yl]pyrimidin-2-yl]pyrrolidin-2-yl]acetonitrile

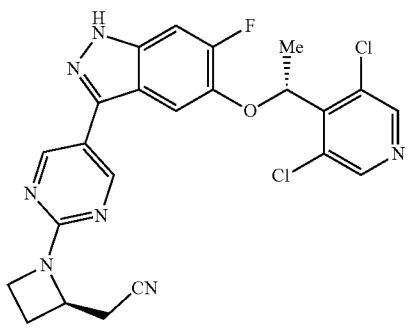 [SMILES: C[C@@H](Oc1cc2c(-c3cnc(N4CC[C@@H]4CC#N)nc3)n[nH]c2cc1F)c1c(Cl)cncc1Cl]

2-[(2R)-1-[5-[5-[(1R)-1-(3,5-dichloro-4-pyridyl)ethoxy]-6-fluoro-1H-indazol-3-yl]pyrimidin-2-yl]azetidin-2-yl]acetonitrile

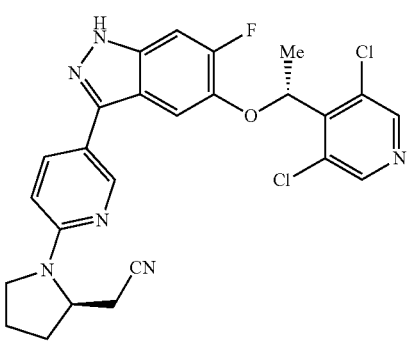 [SMILES: C[C@@H](Oc1cc2c(-c3ccc(N4CCC[C@@H]4CC#N)nc3)n[nH]c2cc1F)c1c(Cl)cncc1Cl]

2-[(2R)-1-[5-[5-[(1R)-1-(3,5-dichloro-4-pyridyl)ethoxy]-6-fluoro-1H-indazol-3-yl]-2-pyridyl]pyrrolidin-2-yl]acetonitrile

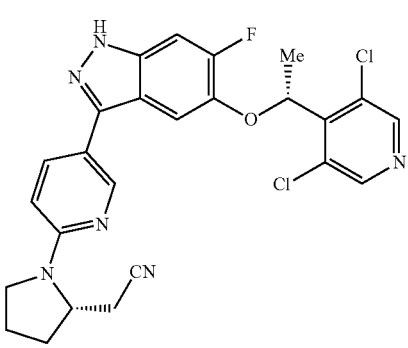 [SMILES: C[C@@H](Oc1cc2c(-c3ccc(N4CCC[C@H]4CC#N)nc3)n[nH]c2cc1F)c1c(Cl)cncc1Cl]

2-[(2S)-1-[5-[5-[(1R)-1-(3,5-dichloro-4-pyridyl)ethoxy]-6-fluoro-1H-indazol-3-yl]-2-pyridyl]pyrrolidin-2-yl]acetonitrile

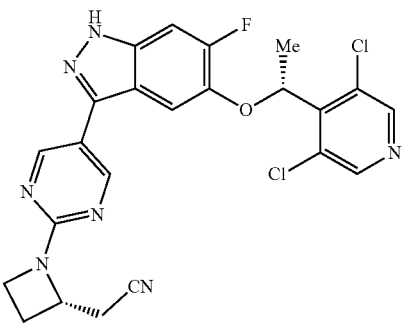 [SMILES: C[C@@H](Oc1cc2c(-c3cnc(N4CC[C@H]4CC#N)nc3)n[nH]c2cc1F)c1c(Cl)cncc1Cl]

2-[(2S)-1-[5-[5-[(1R)-1-(3,5-dichloro-4-pyridyl)ethoxy]-6-fluoro-1H-indazol-3-yl]pyrimidin-2-yl]azetidin-2-yl]acetonitrile

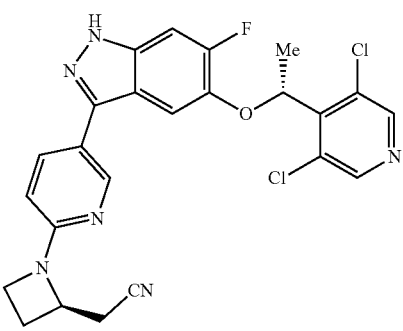 [SMILES: C[C@@H](Oc1cc2c(-c3ccc(N4CC[C@@H]4CC#N)nc3)n[nH]c2cc1F)c1c(Cl)cncc1Cl]

2-[(2R)-1-[5-[5-[(1R)-1-(3,5-dichloro-4-pyridyl)ethoxy]-6-fluoro-1H-indazol-3-yl]-2-pyridyl]azetidin-2-yl]acetonitrile

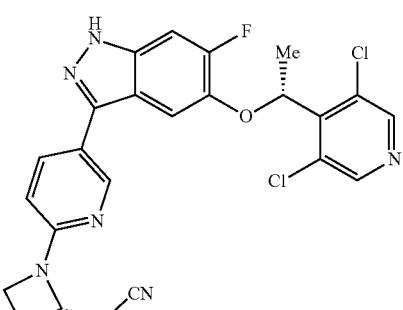

2-[(2S)-1-[5-[5-[(1R)-1-(3,5-dichloro-4-pyridyl)ethoxy]-6-fluoro-1H-indazol-3-yl]-2-pyridyl]azetidin-2-yl]acetonitrile

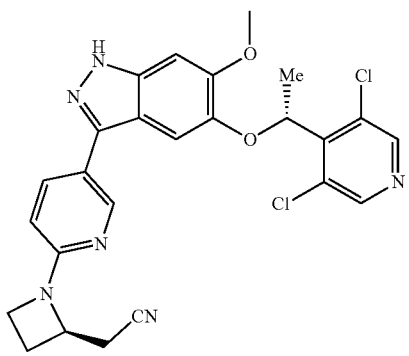 [SMILES: COc1cc2[nH]nc(-c3ccc(N4CC[C@@H]4CC#N)nc3)c2cc1O[C@H](C)c1c(Cl)cncc1Cl]

2-[(2R)-1-[5-[5-[(1R)-1-(3,5-
dichloro-4-pyridyl)ethoxy]-6-
methoxy-1H-indazol-3-yl]-2-
pyridyl]azetidin-2-yl]acetonitrile

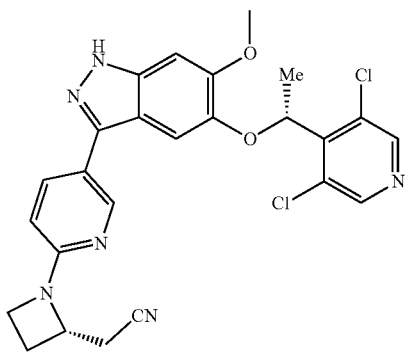 [SMILES: COc1cc2[nH]nc(-c3ccc(N4CC[C@H]4CC#N)nc3)c2cc1O[C@H](C)c1c(Cl)cncc1Cl]

2-[(2S)-1-[5-[5-[(1R)-1-(3,5-
dichloro-4-pyridyl)ethoxy]-6-
methoxy-1H-indazol-3-yl]-2-
pyridyl]azetidin-2-yl]acetonitrile

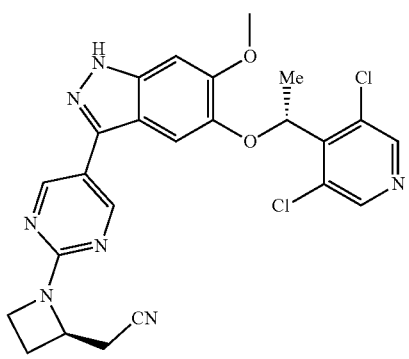 [SMILES: COc1cc2[nH]nc(-c3cnc(N4CC[C@@H]4CC#N)nc3)c2cc1O[C@H](C)c1c(Cl)cncc1Cl]

2-[(2R)-1-[5-[5-[(1R)-1-(3,5-
dichloro-4-pyridyl)ethoxy]-6-
methoxy-1H-indazol-3-yl]pyrimidin-
2-yl]azetidin-2-yl]acetonitrile

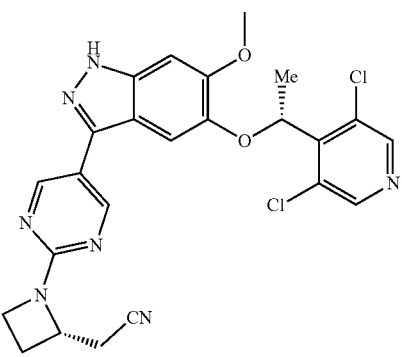 [SMILES: COc1cc2[nH]nc(-c3cnc(N4CC[C@H]4CC#N)nc3)c2cc1O[C@H](C)c1c(Cl)cncc1Cl]

2-[(2S)-1-[5-[5-[(1R)-1-(3,5-
dichloro-4-pyridyl)ethoxy]-6-
methoxy-1H-indazol-3-
yl]pyrimidin-2-yl]azetidin-2-
yl]acetonitrile In other aspects, the disclosure is directed to the following compounds, or pharmaceutically acceptable salts thereof:

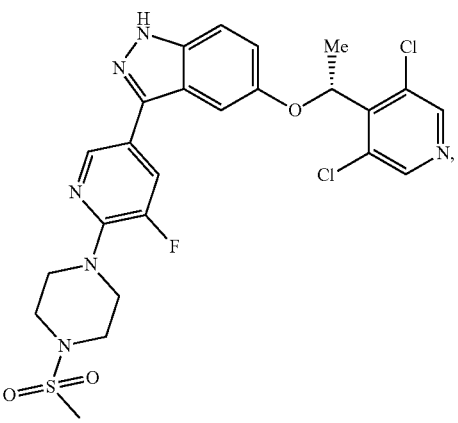

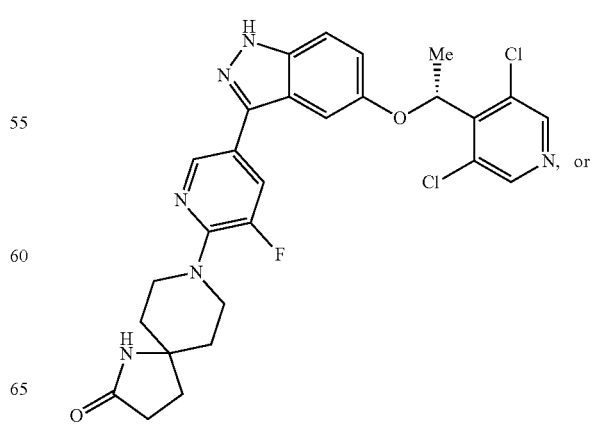

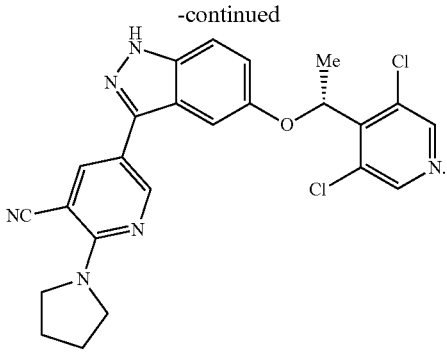

In some aspects, the disclosure is directed to the compounds shown in the Examples below, or pharmaceutically acceptable salts thereof.

References herein to formula (I) or formula (II) or subgenera thereof are meant to encompass the identified formula and any subgenera of those formula disclosed herein. For example, references to formula (I) also encompass subgenera formula IA, IA-1, IA-2, IA-3, IA-4, IA-5, IA-6, IA-7, IB, IB-1, and IB-2. Reference to formula (I) also encompass subgenera formula IA-8.

Stereoisomers of compounds of formula (I) or formula (II) are also contemplated by the present disclosure. Thus, the disclosure encompasses all stereoisomers and constitutional isomers of any compound disclosed or claimed herein, including all enantiomers and diastereomers, or mixtures thereof.

Pharmaceutically acceptable salts and solvates of the compounds of formula (I) or formula (II) are also within the scope of the disclosure.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. While an embodiment may be described as part of a series of steps or part of a more general structure, each said step may also be considered an independent embodiment in itself, combinable with others.

Pharmaceutical Compositions and Methods of Administration

The subject pharmaceutical compositions are typically formulated to provide a therapeutically effective amount of a compound of the present disclosure as the active ingredient, or a pharmaceutically acceptable salt, ester, prodrug, solvate, hydrate or derivative thereof. In some embodiments, the pharmaceutical compositions contain a compound of the present disclosure or a pharmaceutically acceptable salt thereof, and one or more pharmaceutically acceptable excipients, carriers, including inert solid diluents and fillers, diluents, including sterile aqueous solution and various organic solvents, permeation enhancers, solubilizers and adjuvants.

The subject pharmaceutical compositions can be administered alone or in combination with one or more other agents, which are also typically administered in the form of pharmaceutical compositions. Where desired, the one or more compounds of the invention and other agent(s) may be mixed into a preparation or both components may be formulated into separate preparations to use them in combination separately or at the same time.

In some embodiments, the concentration of one or more compounds provided in the pharmaceutical compositions of the present invention is less than 100%, 90%, 80%, 70%, 60%, 50%, 40%, 30%, 20%, 19%, 18%, 17%, 16%, 15%, 14%%, 13%, 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% (or a number in the range defined by and including any two numbers above) w/w, w/v or v/v.

In some embodiments, the concentration of one or more compounds of the invention is greater than 90%, 80%, 70%, 60%, 50%, 40%, 30%, 20%, 19.75%, 19.50%, 19.25%, 19%, 18.75%, 18.50%, 18.25% 18%, 17.75%, 17.50%, 17.25% 17%, 16.75%, 16.50%, 16.25%, 16%, 15.75%, 15.50%, 15.25% 15%, 14.75%, 14.50%, 14.25% 14%, 13.75%, 13.50%, 13.25%, 13%, 12.75%, 12.50%, 12.25%, 12%, 11.75%, 11.50%, 11.25% 11%, 10.75%, 10.50%, 10.25% 10%, 9.75%, 9.50%, 9.25%, 9%, 8.75%, 8.50%, 8.25% 8%, 7.75%, 7.50%, 7.25%, 7%, 6.75%, 6.50%, 6.25%, 6%, 5.75%, 5.50%, 5.25%, 5%, 4.75%, 4.50%, 4.25%, 4%, 3.75%, 3.50%, 3.25%, 3%, 2.75%, 2.50%, 2.25%, 2%, 1.75%, 1.50%, 1.25%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% (or a number in the range defined by and including any two numbers above) w/w, w/v, or v/v.

In some embodiments, the concentration of one or more compounds of the invention is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of one or more compounds of the invention is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more compounds of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g (or a number in the range defined by and including any two numbers above).

In some embodiments, the amount of one or more compounds of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g (or a number in the range defined by and including any two numbers above).

In some embodiments, the amount of one or more compounds of the invention is in the range of 0.0001-10 g, 0.0005-9 g, 0.001-8 g, 0.005-7 g, 0.01-6 g, 0.05-5 g, 0.1-4 g, 0.5-4 g, or 1-3 g.

In some embodiments, the compounds according to the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. An exemplary dosage is 10 to 30 mg per day. The exact dosage will depend upon the route of administration, the form in which the compound is administered, the subject to be treated, the body weight of the subject to be treated, and the preference and experience of the attending physician.

Unless otherwise noted, the amounts of the compounds described herein are set forth on a free base basis. That is, the amounts indicate that amount of the compound administered, exclusive of, for example, solvent (such as in solvates) or counterions (such as in pharmaceutically acceptable salts).

Described below are non-limiting exemplary pharmaceutical compositions and methods for preparing the same.

Pharmaceutical Compositions for Oral Administration.

In some embodiments, the invention provides a pharmaceutical composition for oral administration containing a compound of the invention, and a pharmaceutical excipient suitable for oral administration.

In some embodiments, the invention provides a solid pharmaceutical composition for oral administration containing: (i) an effective amount of a compound of the invention; optionally (ii) an effective amount of a second agent; and (iii) a pharmaceutical excipient suitable for oral administration. In some embodiments, the composition further contains: (iv) an effective amount of a third agent.

In some embodiments, the pharmaceutical composition may be a liquid pharmaceutical composition suitable for oral consumption. Pharmaceutical compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This invention further encompasses anhydrous pharmaceutical compositions and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions.

Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof, polyoxyethylated vitamins and derivatives thereof, polyoxyethylene-polyoxypropylene block copolymers; and mixtures thereof, polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose mono laurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition may include a solubilizer to ensure good solubilization and/or dissolution of the compound of the present invention and to minimize precipitation of the compound of the present invention. This can be especially important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, F-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, F-caprolactone and isomers thereof, 6-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a subject using conventional techniques, such as distillation or evaporation. Thus, if present, the solubilizer can be in a weight ratio of 10%, 25% o, 50%), 100% o, or up to about 200%> by weight, based on the combined weight of the drug, and other excipients. If desired, very small amounts of solubilizer may also be used, such as 5%>, 2%>, 1%) or even less. Typically, the solubilizer may be present in an amount of about 1%> to about 100%, more typically about 5%> to about 25%> by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Pharmaceutical Compositions for Injection.

In some embodiments, the invention provides a pharmaceutical composition for injection containing a compound of the present invention and a pharmaceutical excipient suitable for injection. Components and amounts of agents in the compositions are as described herein.

The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical compositions for topical (e.g. transdermal) delivery.

In some embodiments, the invention provides a pharmaceutical composition for transdermal delivery containing a compound of the present invention and a pharmaceutical excipient suitable for transdermal delivery.

Compositions of the present invention can be formulated into preparations in solid, semisolid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation.

Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such transdermal patches may be used to provide continuous or discontinuous infusion of a compound of the present invention in controlled amounts, either with or without another agent.

The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

Pharmaceutical compositions for inhalation.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

Other Pharmaceutical Compositions.

Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, New York, 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins, 2000; Martindale, The Extra Pharmacopoeia, Thirty-Second Edition (The Pharmaceutical Press, London, 1999); all of which are incorporated by reference herein in their entirety.

Administration of the compounds or pharmaceutical composition of the present invention can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g. transdermal application), rectal administration, via local delivery by catheter or stent or through inhalation. Compounds can also be administered intraadiposally or intrathecally.

The amount of the compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, e.g. by dividing such larger doses into several small doses for administration throughout the day.

In some embodiments, a compound of the invention is administered in a single dose.

Typically, such administration will be by injection, e.g., intravenous injection, in order to introduce the agent quickly. However, other routes may be used as appropriate. A single dose of a compound of the invention may also be used for treatment of an acute condition.

In some embodiments, a compound of the invention is administered in multiple doses. Dosing may be about once, twice, three times, four times, five times, six times, or more than six times per day. Dosing may be about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the compounds of the invention may continue as long as necessary. In some embodiments, a compound of the invention is administered for more than 1, 2, 3, 4, 5, 6, 7, 14, or 28 days. In some embodiments, a compound of the invention is administered for less than 28, 14, 7, 6, 5, 4, 3, 2, or 1 day. In some embodiments, a compound of the invention is administered chronically on an ongoing basis, e.g., for the treatment of chronic effects.

An effective amount of a compound of the invention may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

The compositions of the invention may also be delivered via an impregnated or coated device such as a stent, for example, or an artery-inserted cylindrical polymer. Such a method of administration may, for example, aid in the prevention or amelioration of restenosis following procedures such as balloon angioplasty. Without being bound by theory, compounds of the invention may slow or inhibit the migration and proliferation of smooth muscle cells in the arterial wall which contribute to restenosis. A compound of the invention may be administered, for example, by local delivery from the struts of a stent, from a stent graft, from grafts, or from the cover or sheath of a stent. In some embodiments, a compound of the invention is admixed with a matrix. Such a matrix may be a polymeric matrix, and may serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly (etherester) copolymers (e.g. PEO-PLLA); polydimethylsiloxane, poly(ethylene-vinylacetate), acrylate-based polymers or copolymers (e.g. polyhydroxyethyl methylmethacrylate, polyvinyl pyrrolidinone), fluorinated polymers such as polytetrafluoroethylene and cellulose esters. Suitable matrices may be nondegrading or may degrade with time, releasing the compound or compounds. Compounds of the invention may be applied to the surface of the stent by various methods such as dip/spin coating, spray coating, dip-coating, and/or brush-coating. The compounds may be applied in a solvent and the solvent may be allowed to evaporate, thus forming a layer of compound onto the stent. Alternatively, the compound may be located in the body of the stent or graft, for example in microchannels or micropores. When implanted, the compound diffuses out of the body of the stent to contact the arterial wall. Such stents may be prepared by dipping a stent manufactured to contain such micropores or microchannels into a solution of the compound of the invention in a suitable solvent, followed by evaporation of the solvent. Excess drug on the surface of the stent may be removed via an additional brief solvent wash. In yet other embodiments, compounds of the invention may be covalently linked to a stent or graft. A covalent linker may be used which degrades in vivo, leading to the release of the compound of the invention. Any bio-labile linkage may be used for such a purpose, such as ester, amide or anhydride linkages. Compounds of the invention may additionally be administered intravascularly from a balloon used during angioplasty. Extravascular administration of the compounds via the pericard or via advential application of formulations of the invention may also be performed to decrease restenosis.

A variety of stent devices which may be used as described are disclosed, for example, in the following references, all of which are hereby incorporated by reference: U.S. Pat. Nos. 5,451,233; 5,040,548; 5,061,273; 5,496,346; 5,292,331;

5,674,278; 3,657,744; 4,739,762; 5,195,984; 5,292,331; 5,674,278; 5,879,382; 6,344,053.

The compounds of the invention may be administered in dosages. It is known in the art that due to intersubject variability in compound pharmacokinetics, individualization of dosing regimen is necessary for optimal therapy. Dosing for a compound of the invention may be found by routine experimentation in light of the instant disclosure.

When a compound of the invention is administered in a composition that comprises one or more agents, and the agent has a shorter half-life than the compound of the invention unit dose forms of the agent and the compound of the invention may be adjusted accordingly.

The subject pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compound in sterile aqueous solutions, for example, aqueous propylene glycol or dextrose solutions. Such dosage forms can be suitably buffered, if desired.

Methods of Use

The FGFR receptors (FGFR1, FGFR2, FGFR3, and FGFR4) share several structural features in common, including three extracellular immunoglobulin-like (Ig) domains, a hydrophobic transmembrane domain, and an intracellular tyrosine kinase domain split by a kinase insert domain, followed by a cytoplasmic c-terminal tail (Johnson et al., Adv. Cancer Res. 60:1-40, 1993; and Wilkie et al., Curr. Biol. 5:500-507, 1995). In FGFR1, the kinase insert domain spans positions 582 to 595 of the alpha A1 isoform of FGFR1. In FGFR2, the kinase insert domain spans positions 585 to 598 of the FGFR2 IIIe isoform. In FGFR3, the kinase insert domain spans positions 576 to 589 of the FGFR3 IIIe isoform. In FGFR4, the kinase insert domain spans positions 571 to 584 of FGFR4 isoform 1. The c-terminal tail of FGFRs begins following the end of the tyrosine kinase domain and extends to the c-terminus of the protein. Several isoforms of each FGFR have been identified and are the result of alternative splicing of their mRNAs (Johnson et al., Mol. Cell. Biol. 11:4627-4634, 1995; and Chellaiah et al., J. Biol. Chem. 269:11620-11627, 1994).

A few of the receptor variants that result from this alternative splicing have different ligand binding specificities and affinities (Zimmer et al., J. Biol. Chem. 268:7899-7903, 1993; Cheon et al., Proc. Natl. Acad. Sci. U.S.A. 91:989-993, 1994; and Miki et al., Proc. Natl. Acad. Sci. U.S.A. 89:246-250, 1992). Protein sequences for FGFR proteins and nucleic acids encoding FGFR proteins are known in the art. Signaling by FGFRs regulates key biological processes including cell proliferation, survival, migration, and differentiation. Dysregulation of a FGFR gene, a FGFR protein, or expression or activity, or level of the same, has been associated with many types of cancer. For example, dysregulation of FGFRs can occur by multiple mechanisms, such as FGFR gene overexpression, FGFR gene amplification, activating mutations (e.g., point mutations or truncations), and chromosomal rearrangements that lead to FGFR fusion proteins. Dysregulation of a FGFR gene, a FGFR protein, or expression or activity, or level of the same, can result in (or cause in part) the development of a variety of different FGFR-associated cancers.

FGFR fusion proteins are known in the art. See, e.g., Baroy et al., *PloS One;* 11(9):e0163859. doi: 10.1371/journal.pone.0163859, 2016; Ren et al., *Int. J. Cancer,* 139(4):836-40, 2016; Marchwicka et al., *Cell Biosci.,* 6:7. doi: 10.1186/s13578-016-0075-9, 2016; PCT Patent Application Publication No. WO 2014/071419A2; U.S. Patent Application Publication No. 2015/0366866A1; PCT Patent Application Publication No. WO 2016/084883A1; PCT Patent Application Publication No. WO 2016/030509A1; PCT Patent Application Publication No. WO 2015/150900A2; PCT Patent Application Publication No. WO 2015/120094A2; Kasaian et al., *BMC Cancer.,* 15:984, 2015; Vakil et al., *Neuro-Oncology,* 18:Supp. Supplement 3, pp. iii93. Abstract Number: LG-64, 17$^{th}$ International Symposium on Pediatric Neuro-Oncology, Liverpool, United Kingdom, 2016; Astsaturov et al., *Journal of Clinical Oncology,* 34:Supp. Supplement 15, Abstract Number: 11504, 2016 Annual Meeting of the American Society of Clinical Oncology, Chicago, IL; Heinrich et al., *Journal of Clinical Oncology,* 34:Supp. Supplement 15, Abstract Number: 11012, 2016 Annual Meeting of the American Society of Clinical Oncology, Chicago, IL; Hall et al., *Molecular Cancer Therapeutics*, Vol. 14, No. 12, Supp.2, Abstract Number: B151, AACR-NCI-EORTC International Conference: Molecular Targets and Cancer Therapeutics, 2015; Reuther et al., *Journal of Molecular Diagnostics,* Vol. 17, No. 6, pp. 813, Abstract Number: ST02, 2015 Annual Meeting of the Association for Molecular Pathology, Austin, TX; Moeini et al., *Clin. Cancer. Res.,* 22(2):291-300, 2016; Schrock et al, *J Thorac. Oneal.* pii S1556-0864(18)30674-9, 2018. doi: 10.1016/j.jtho.2018.05.027; Pekmezci et al, *Acta Nurotaphol. Commun.* 6(1):47. doi: 10.1186/s40478-018-0551-z; Lowery et al. *Clin Cancer Res.* pii: clincanres.0078.2018. doi: 10.1158/1078-0432.CCR-18-0078; Ryland et al. *J Clin Pathol* pii: jclinpath-2018-205195, 2018. doi: 10.1136/jclinpath-2018-205195; Ferguson et al. *J Neuropathol Exp Neural* 77(6):437-442, 2018. doi: 10.1093/jnen/nly022; Wu et al, *BMC Cancer* 18(1):343, 2018. doi: 10.1186/s12885-018-4236-6; Shibata et al, *Cancer Sci* 109 (5):1282-1291, 2018. doi: 10.1111/cas.13582; Papdopoulos et al, *Br J Cancer,* 1117(11):1592-1599, 2017. doi: 10.1038/bjc.2017.330; Hall et al, *PLoS One,* 11(9):e1062594, 2016. doi: 10.1371/journal.pone.0162594; Johnson et al, *Oncologist,* 22(12):1478-1490, 2017. doi: 10.1634/theoncologist.2017-0242; Yang et al, *Am J Hum Genet,* 98(5):843-856, 2016. doi: 10.1016/j.ajhg.2016.03.017; U.S. Patent Application Publication No. 2013/009621; Babina and Turner, *Nat Rev Cancer* 17(5):318-332, 2017. doi: 10.1038/nrc.2017.8; Ryland et al, *J Clin Pathol.,* 2018 May 14. pii: jclinpath-2018-205195. doi: 10.1136/jclinpath-2018-205195; Kumar et al, *Am J Clin Pathol.* 143(5):738-748, 2015. doi: 10.1309/AJCPUD6W1JLQQMNA; Grand et al, *Genes Chromosomes Cancer* 40(1):78-83, 2004. doi: 10.1002/gcc.20023; Reeser, et al, *J Mol Diagn,* 19(5):682-696, 2017. doi: 10.1016/j.jmoldx.2017.05.006; Basturk, et al, *Mod Pathol,* 30(12):1760-1772, 2017. doi: 10.1038/modpathol.2017.60; Wang, et al, *Cancer* 123(20):3916-3924, 2017. doi: 10.1002/cncr.30837; Kim, et al, *Oncotarget,* 8(9):15014-15022, 2017. doi: 10.18632/oncotarget.14788; Busse, et al, *Genes Chromosomes Cancer,* 56(10):730-749, 2017. doi: 10.1002/gcc.22477; Shi, et al, *J Transl Med.*, 14(1):339, 2016. doi: 10.1186/s12967-016-1075-6, each of which is incorporated by reference herein.

FGFR point mutations are known in the art. See, e.g., UniParc entry UPI00000534B8; UniParc entry UPI0000001COF; UniParc entry UPI000002A99A; UniParc entry UPI000012A72A; UniParc entry UPI000059D1C2; UniParc entry UPI000002A9AC; Uniparc entry UPI000012A72C; Uniparc entry UPI000012A72D; Uniparc entry UPI000013EOB8; Uniparc entry UPI0001CE06A3; Gen bank entry BAD92868.1; Ang et al., *Diagn. Mol. Pathol.* Feb. 24, 2014; U.S. Patent Application Publication No. 2011/0008347; Gallo et al., *Cytokine Growth Factor Rev.* 26:425-449, 2015; Davies et al., *J. Cancer Res.* 65:7591, 2005; Kelleher et al., *Carcinogenesis* 34:2198, 2013; Cazier et al., *Nat. Commun.* 5:3756, 2014; Liu et al., *Genet. Mol. Res.* 13:1109, 2014; Trudel et al., *Blood* 107:4039, 2006; Gallo et al., *Cytokine Growth Factor Rev.* 26:425, 2015; Liao et al., *Cancer Res.* 73:5195-5205, 2013; Martincorena et al., *Science* 348:880 (2015); U.S. Patent Application Publication No. US2016/0235744A1; U.S. Pat. No. 9,254,288B2; U.S. Pat. No. 9,267,176B2; U.S. Patent Application Publication No. S2016/0215350A1; European Patent Application Publication No. EP3023101A1; PCT Patent Application Publication No. WO2016105503A1; Rivera et al., *Acta. Neuropathol.,* 131(6):847-63, 2016; Lo Iacono et al., *Oncotarget.*, 7(12): 14394-404, 2016; Deeken et al., *Journal of Clinical Oncology*, 34:Supp. Supplement 15, pp. iii93. Abstract Number: el 7520, 2016 Annual Meeting of the American Society of Clinical Oncology, Chicago, IL; Sullivan et al., *Journal of Clinical Oncology*, 34:Supp. Supplement 15, pp. iii93. Abstract Number: 11596, 2016 Annual Meeting of the American Society of Clinical Oncology, Chicago, IL; Nguyen et al., *Molecular Cancer Therapeutics*, Vol. 14, No. 12, Supp.2, Abstract Number: C199, AACR-NCI-EORTC International Conference: Molecular Targets and Cancer Therapeutics, 2015; Li et al., *Hum. Pathol.*, 55:143-50, 2016; European Patent No. EP2203449B1; Yoza et al., *Genes Cells.*, (10):1049-1058, 2016; U.S. Pat. No. 9,254,288B2; European Patent Application Publication No. 3023101A1; PCT Application Publication No. WO 2015/099127A1; European Patent No. EP2203449B1; Yoza et al., *Genes Cells.*, (10):1049-1058, 2016; Bunney et al., *EbioMedicine*, 2(3):194-204, 2015; Byron et al., *Neoplasia*, 15(8):975-88, 2013; European Patent Application Publication No. EP3023101A1; PCT Application Publication No. WO 2015/099127A1; Thussbas et al., *J. Clin. Oneal.*, 24(23):3747-55, 2006; Chell et al., *Oncogene*, 32(25):3059-70, 2013; Tanizaki et al, *Cancer Res.* 75(15):3149-3146 doi: 10.1158/0008-5472.CAN-14-3771; Yang et al, *EBioMedicine* pii S2352-3964(18)$_{30218}$-4. doi: 10.1016/j.ebiom.2018.06.011; Jakobsen, et al *Oncotarget* 9(40): 26195-26208, 2018. doi: 10.18632/oncotarget.25490; Stone, et al *Acta Neuropathol* 135(1):115-129, 2017. doi: 10.1007/s00401-017-1773-z; Pekmezci et al, *Acta Nurotaphol. Commun.* 6(1):47. doi: 10.1186/s40478-018-0551-z; De Mattos-Arruda et al, *Oncotarget* 9(29):20617-20630, 2018. doi: 10.18632/oncotarget.25041; Oliveira et al, *J Exp Clin Cancer Res* 37(1):84, 2018. doi: 10.1186/s13046-018-0746-y; Cha et al, *Mol Oneal* 12(7):993-1003, 2018. doi: 10.1002/1878-0261.12194; Ikeda et al, *Oncologist*, 23(5):586-593, 2018. doi: 10.1634/theoncologist.2017-0479; Pelaez-Garda et al, *PLoS One*, 8(5):e63695, 2013. doi: 10.1371/journal.pone.0063695; Shimada et al, *Oncotarget*, 8(55):93567-93579, 2017. doi: 10.18632/oncotarget.20510; Welander et al, *World J Surg*, 42(2):482-489, 2018. doi: 10.1007/s00268-017-4320-0; Chandrani et al, *Ann Oneal*, 28(3):597-603, 2017. doi: 10.1093/annonc/mdw636; Dalin et al, *Nat Commun*, 8(1):1197, 2017. doi: 10.1038/s41467-017-01178-z; Taurin et al, *Intl Gynecol Cancer*, 28(1):152-160, 2018. doi: 10.1097/IGC.0000000000001129; Haugh et al, *J Invest Dermatol* 138(2):384-393, 2018. doi: 10.1016/j.jid.2017.08.022; Babina and Turner, *Nat Rev Cancer* 17(5): 318-332, 2017. doi: 10.1038/nrc.2017.8; Greenman et al, *Nature* 446(7132):153-158, 2007. doi: 10.1038/nature05610; Helsten et al, *Clin Cancer Res*, 22(1):259-267, 2016. doi: 10.1158/1078-0432.CCR-14-3212; Kim et al, *BMC Urol*, 18:68, 2018. doi: 10.1186/s12894-018-0380-1; Goyal et al, *Cancer Discov*, 7(3):252-263, 2017. doi: 10.1158/2159-8290.CD-16-1000; Premov et al, *Oncogene*, 36(22):3168-3177, 2017. doi: 10.1038/onc.2016.464; Geelvink et al, *Int J Mol Sci.* 19(9): pii:E2548, 2018. doi: 10.3390/ijms19092548; Lee et al, *Exp Ther Med.* 16(2): 1343-1349, 2018. doi: 10.3892/etm.2018.6323; Kas et al, *Cancer Res*, 78(19):5668-5679, 2018. doi: 10.1158/0008-5472.CAN-18-0757; Chesi et al, *Blood*, 97(3):729-736, 2001. PMID: 11157491. Note that the deletion of FGFR3 isoform IIIe residues 795-808 also deletes the stop codon, elongating the protein by 99 amino acids (ATGPQQCEGSLAAHPAAGAQPLPGMRLSADGET-ATQSFGLCVCVCVCVCVCTSACACVRAH LASRCRGTLGVPAA VQRSPDWCCSTEGPLFWGDPVQNVSGPTRWDPVGQGAGPDMARPLPLHHGTSQGALGPSH TQS); Ge, et al, *Am J Cancer Res.* 7(7):1540-1553, 2017. PMID: 28744403; Jiao et al, *Nat Genet*, 45(12):1470-1473, 2013. doi: 10.1038/ng.2813; Jusakul et al, *Cancer Discov.* 7(10):1116-1135, 2017. doi: 10.1158/2159-8290.CD-17-0368; Guyard et al, *Respir Res.*, 18(1):120, 2018. doi: 10.1186/s12931-017-0605-y; Paik et al, *Clin Cancer Res.*, 23(18):5366-5373, 2017. doi: 10.1158/1078-0432.CCR-17-0645; Roy et al, *Mod Pathol.*, 30(8):1133-1143, 2017. doi: 10.1038/modpathol.2017.33; Chakrabarty et al, *Br J Cancer*, 117(1):136-143, 2017. doi: 10.1038/bjc.2017.148; Hoang et al, *Sci Transl Med.*, 5(197):197ra102. doi: 10.1126/scitranslmed.3006200; Kim et al, *Ann Oneal.*, 28(6):1250-1259. doi: 10.1093/annonc/mdx098, each of which is incorporated by reference herein.

Compounds of the disclosure have been found to inhibit FGFR1, FGFR2, FGFR3, and/or FGFR4 and are therefore believed to be useful for treating diseases and disorders which can be treated with an inhibitor of FGFR1, FGFR2, FGFR3 and/or FGFR4. For example, compounds of the disclosure can be useful in treating FGFR-associated diseases and disorders, e.g., proliferative disorders such as cancers, including hematological cancers and solid tumor, and angiogenesis-related disorders. Compounds of the disclosure may also be useful in treating disorders arising from autosomal dominant mutations in FGFR, e.g., FGFR3, including, for example, developmental disorders. Developmental disorders to be treated with compounds of the disclosure include Achondroplasia (Ach) and related chondrodysplasia syndromes, including Hypochondroplasia (Hch), Severe Achondroplasia with Developmental Delay and Acanthosis Nigricans (SADDAN), and Thanatophoric dysplasia (TD).

Non-limiting examples of FGFR-associated diseases and disorders include Acanthosis nigricans, Achondroplasia, Apert syndrome, Beare-Stevenson syndrome (BSS), Camptodactyly, tall stature, and hearing loss syndrome (CATSHL) syndrome, cleft lip and palate, congenital heart disease (e.g., associated with ambiguous genitalia), craniosynostosis, Crouzon syndrome, ectrodactyly, encephalocraniocutaneous lipomatosis, Hartsfield syndrome, hypochondroplasia, hypogonadoropic hypogonadism (e.g., hypogonadotropic hypogonadism 2 with or without anosmia, Kallman syndrome), ichthyosis vulgaris and/or atopic dermatitis, Jackson-Weiss syndrome, lethal pulmonary acinar dysplasia, microphthalmia, Muenke coronal craniosynostosis, osteoglophonic dysplasia, Pfeiffer syndrome, seborrheic keratosis, syndactyly, thanatophoric dysplasia (e.g., type I or type II), trigonocephaly 1 (also called metopic craniosynostosis), and tumor-induced osteomalacia.

Non-limiting examples of FGFR1 associated diseases and disorders include congenital heart disease (e.g., associated with ambiguous genitalia), craniosynostosis, encephalocraniocutaneous lipomatosis, Hartsfield syndrome, hypogonadoropic hypogonadism (e.g., hypogonadotropic hypogonadism 2 with or without anosmia, Kallman syndrome), ichthyosis vulgaris and/or atopic dermatitis, Jackson-Weiss syndrome, osteoglophonic dysplasia, Pfeiffer syndrome, trigonocephaly 1 (also called metopic craniosynostosis), and tumor-induced osteomalacia.

Non-limiting examples of FGFR2-associated diseases and disorders include Apert syndrome, Beare-Stevenson syndrome (BSS), Crouzon syndrome, ectrodactyly, Jackson-Weiss syndrome, lethal pulmonary acinar dysplasia, Pfeiffer syndrome, and syndactyly. Non-limiting examples of FGFR3-associated diseases and disorders include acanthosis nigricans, achondroplasia, Camptodactyly, tall stature, and hearing loss syndrome (CATSHL) syndrome, cleft lip and palate, craniosynostosis, hypochondroplasia, microphthalmia, Muenke coronal craniosynostosis, seborrheic keratosis, and thanatophoric dysplasia (e.g., type I or type II). See also, See UniParc entry UPI00000534B8; UniParc entry UPI0000001COF; Uni Pare entry UPI000002A99A; UniParc entry UPI000012A72A; Yong-Xing et al., Hum. Mol. Genet. 9(13):2001-2008, 2000; Eeva-Maria Laitinen et al., PLoS One 7(6):e39450, 2012; Hart et al., Oncogene 19(29): 3309-3320, 2000; Shiang et al., Cell 76:335-342, 1994; Rosseau et al., Nature 371:252-254, 1994; Tavormina et al., Nature Genet. 9:321-328, 1995; Bellus et al., Nature Genet. 10:357-359, 1995; Muenke et al., Nature Genet. 8:269-274, 1994; Rutland et al., Nature Genet. 9:173-176, 1995; Reardon et al., Nature Genet. 8:98-103, 1994; Wilkie et al., Nature Genet. 9:165-172, 1995; Jabs et al., Nature Genet. 8:275-279, 1994; Japanese Patent No. JP05868992B2; Ye et al., Plast. Reconstr. Surg., 137(3):952-61, 2016; U.S. Pat. No. 9,447,098B2; Bellus et al., Am. J. Med. Genet. 85(1): 53-65, 1999; PCT Patent Application Publication No. WO2016139227A1; Australian Patent Application Publication No. AU2014362227A1; Chinese Patent No. CN102741256B; Ohishi et al., Am. J. Med. Genet. A., doi: 10.1002/ajmg.a.37992, 2016; Nagahara et al., Clin. Pediatr. Endocrinol., 25(3): 103-106, 2016; Hibberd et al., Am. J. Med. Genet. A., doi: 10.1002/ajmg.a.37862, 2016; Dias et al., Exp. Mol. Pathol., 101(1):116-23, 2016; Lin et al., Mol. Med. Rep., 14(3):1941-6, 2016; Barnett et al., Hum. Mutat., 37(9):955-63, 2016; Krstevska-Konstantinova et al., Med. Arch., 70(2):148-50, 2016; Kuentz et al., Br. J. Dermatol., doi: 10.1111/bjd.14681, 2016; Ron et al., Am. J. Case Rep., 15; 17:254-8, 2016; Fernandes et al., Am. J. Med. Genet. A., 170(6):1532-7, 2016; Lindy et al., Am. J. Med. Genet. A., 170(6):1573-9, 2016; Bennett et al., Am. J. Hum. Genet., 98(3):579-87, 2016; Ichiyama et al., J. Eur. Acad. Dermatol. Venereal., 30(3):442-5, 2016; Zhao et al., Int. J. Clin. Exp. Med., 8(10):19241-9, 2015; Hasegawa et al., Am. J. Med. Genet. A., 170A(5):1370-2, 2016; Legeai-Mallet, Endocr. Dev., 30:98-105, 2016; Takagi, Am. J. Med. Genet. A., 167A(11):2851-4, 2015; Goncalves, Fertil. Steril., 104(5): 1261-7.el, 2015; Miller et al., Journal of Clinical Oncology, 34:Supp. Supplement 15, pp. iii93. Abstract Number: e22500, 2016 Annual Meeting of the American Society of Clinical Oncology, Chicago, IL; Sarabipour et al., J. Mol. Biol., 428(20):3903-3910, 2016; Escobar et al., Am. J. Med. Genet. A., 170(7):1908-11, 2016; Mazen et al., Sex Dev., 10(1):16-22, 2016; Taylan et al., *J Allergy Clin Immunol*, 136(2):507-9, 2015. doi: 10.1016/j.jaci.2015.02.010; Kant et al, *EuroJourn Endocrinol*, 172(6):763-770, 2015. doi: 10.1530/EJE-14-0945; Gonzalez-Del Angel et al, *Am J med Genet A*, 176(1):161-166, 2018. doi: 10.1002/ajmg.a.38526; Lei and Deng, *Int J Biol Sci* 13(9):1163:1171, 2017. doi: 10.7150/ijbs.20792; Lajeunie et al, *Eur J Hum Genet*, 14(3): 289-298, 2006. doi: 10.1038/sj.ejhg.5201558; Karadimas et al, *Prenat Diagn*, 26(3):258-261, 2006. doi: 10.1002/pd.1392; Ibrahimi et al, *Hum Mol Genet* 13(19):2313-2324, 2004. doi: 10.1093/hmg/ddh235; Trarbach et al, *J Clin Endocrinol Metab.*, 91(10):4006-4012, 2006. doi: 10.1210/jc.2005-2793; Dode et al, *Nat Genet*, 33(4):463-465, 2003. doi: 10.1038/ng1122, each of which is incorporated by reference herein.

The term "angiogenesis-related disorder" means a disease characterized in part by an increased number or size of blood vessels in a tissue in a subject or patient, as compared to a similar tissue from a subject not having the disease. Non-limiting examples of angiogenesis-related disorders include: cancer (e.g., any of the exemplary cancers described herein, such as prostate cancer, lung cancer, breast cancer, bladder cancer, renal cancer, colon cancer, gastric cancer, pancreatic cancer, ovarian cancer, melanoma, hepatoma, sarcoma, and lymphoma), exudative macular degeneration, proliferative diabetic retinopathy, ischemic retinopathy, retinopathy of prematurity, neovascular glaucoma, iritis rubeosis, corneal neovascularization, cyclitis, sickle cell retinopathy, and pterygium.

Compounds of the disclosure inhibit wild-type FGFR1, FGFR2, FGFR3, and/or FGFR4. In other aspects, compounds of the disclosure inhibit a mutated FGFR1, FGFR2, FGFR3, and/or FGFR4. In other aspects, compounds of the disclosure inhibit FGFR1, FGFR2, FGFR3, and/or FGFR4 that includes an FGFR kinase inhibitor mutation.

In some embodiments of any of the methods or uses described herein, the cancer (e.g., FGFR-associated cancer) is a hematological cancer. In some embodiments of any of the methods or uses described herein, the cancer (e.g., FGFR-associated cancer) is a solid tumor.

In some embodiments of any of the methods or uses described herein, the cancer (e.g., FGFR-associated cancer) is a lung cancer (e.g., small cell lung carcinoma, non-small cell lung carcinoma, squamous cell carcinoma, lung adenocarcinoma, large cell carcinoma, mesothelioma, lung neuroendocrine carcinoma, smoking-associated lung cancer), prostate cancer, colorectal cancer (e.g., rectal adenocarcinoma), endometrial cancer (e.g., endometrioid endometrial cancer, endometrial adenocarcinoma), breast cancer (e.g., hormone-receptor-positive breast cancer, triple-negative breast cancer, neuroendodrine carcinoma of the breast), skin cancer (e.g., melanoma, cutaneous squamous cell carcinoma, basal cell carcinoma, large squamous cell carcinoma), gallbladder cancer, liposarcoma (e.g., dedifferentiated liposarcoma, myxoid liposarcoma), pheochromocytoma, myoepithelial carcinoma, urothelial carcinoma, spermatocytic seminoma, stomach cancer, head and neck cancer (e.g., head and neck (squamous) carcinoma, head and neck adenoid cystic adenocarcinoma), brain cancer (e.g., glialneural tumors, glioma, neuroblastoma, glioblastoma, pilocytic astrocytoma, Rosette forming glioneural tumor, dysembryoplastic neuroepithelial tumor, anaplastic astrocytoma, medulloblastoma, ganglioglioma, oligodendroglioma), malignant peripheral nerve sheath tumor, sarcoma (e.g., soft tissue sarcoma (e.g., leiomyosarcoma), osteosarcoma), esophageal cancer (e.g., esophageal adenocarcinoma), lymphoma, bladder cancer (e.g., bladder urothelial (transition cell) carcinoma), cervical cancer (e.g., cervical squamous cell carcinoma, cervical adenocarcinoma), fallopian tube cancer (e.g., fallopian tube carcinoma), ovarian cancer (e.g., ovarian serous cancer, ovarian mucinous carcinoma), cholangiocarcinoma, adenoid cystic carcinoma, pancreatic cancer (e.g., pancreatic exocrine carcinoma, pancreatic ductal adenocarcinoma, pancreatic cancer intraepithelial neoplasia), salivary gland cancer (e.g., pleomorphic salivary gland adenocarcinoma, salivary adenoid cystic cancer), oral cancer (e.g., oral squamous cell carcinoma), uterine cancer, gastric or stomach cancer (e.g., gastric adenocarcinoma), gastrointestinal stromal tumors, myeloma (e.g., multiple myeloma), lymphoepithelioma, anal cancer (e.g., anal squamous cell carcinoma), prostate cancer (e.g., prostate adenocarcinoma), renal cell carcinoma, thymic cancer, gastroesophogeal junction adenocarcinoma, testicular cancer, rhabdomyosarcoma (e.g., alveolar rhabdomyosarcoma, embryonic rhabomyosarcoma), renal papillary carcinoma, liver cancer (e.g., hepatocellular carcinoma, intrahepatic cholangiocarcinoma), carcinoid, myeloid proliferative disorders (also called myeloid proliferative neoplasms (MPN); e.g., 8p11 myeloproliferative syndrome (EMS, also called stem cell leukemia/lymphoma), acute myeloid leukemia (AML), chronic myeloid leukemia (CVL)), lymphoma (e.g., T-cell lymphoma, T-lymphoblastic lymphoma, acute lymphoblastic leukemia (ALL), B-cell lymphoma), myeloid and lymphoid neoplasms, chronic neutrophilic leukemia, phosphaturic mesenchymal tumor, thyroid cancer (e.g. anaplastic thyroid carcinoma), or biliary duct cancer.

In some embodiments of any of the methods or uses described herein, the cancer (e.g., FGFR-associated cancer) is selected from the group of: acute lymphoblastic leukemia (ALL), acute myeloid leukemia (AML), cancer in adolescents, adrenocortical carcinoma, anal cancer, appendix cancer, astrocytoma, atypical teratoid/rhabdoid tumor, basal cell carcinoma, bile duct cancer, bladder cancer, bone cancer, brain stem glioma, brain tumor, breast cancer, bronchial tumor, Burkitt lymphoma, carcinoid tumor, unknown primary carcinoma, cardiac tumors, cervical cancer, childhood cancers, chordoma, chronic lymphocytic leukemia (CLL), chronic myelogenous leukemia (CML), chronic myeloproliferative neoplasms, neoplasms by site, neoplasms, colon cancer, colorectal cancer, craniopharyngioma, cutaneous T-cell lymphoma, cutaneous angiosarcoma, bile duct cancer, ductal carcinoma in situ, embryonal tumors, endometrial cancer, ependymoma, esophageal cancer, esthesioneuroblastoma, Ewing sarcoma, extracranial germ cell tumor, extragonadal germ cell tumor, extrahepatic bile duct cancer, eye cancer, fallopian tube cancer, fibrous histiocytoma of bone, gallbladder cancer, gastric cancer, gastrointestinal carcinoid tumor, gastrointestinal stromal tumors (GIST), germ cell tumor, gestational trophoblastic disease, glioma, hairy cell tumor, hairy cell leukemia, head and neck cancer, thoracic neoplasms, head and neck neoplasms, CNS tumor, primary CNS tumor, heart cancer, hepatocellular cancer, histiocytosis, Hodgkin's lymphoma, hypopharyngeal cancer, intraocular melanoma, islet cell tumors, pancreatic neuroendocrine tumors, Kaposi sarcoma, kidney cancer, Langerhans cell histiocytosis, laryngeal cancer, leukemia, lip and oral cavity cancer, liver cancer, lung cancer, lymphoma, macroglobulinemia, malignant fibrous histiocytoma of bone, osteocarcinoma, melanoma, Merkel cell carcinoma, mesothelioma, metastatic squamous neck cancer, midline tract carcinoma, mouth cancer, multiple endocrine neoplasia syndromes, multiple myeloma, mycosis fungoides, myelodysplastic syndromes, myelodysplastic/myeloproliferative neoplasms, neoplasms by site, neoplasms, myelogenous leukemia, myeloid leukemia, multiple myeloma, myeloproliferative neoplasms, nasal cavity and para nasal sinus cancer, nasopharyngeal cancer, neuroblastoma, non-Hodgkin's lymphoma, non-small cell lung cancer, lung neoplasm, pulmonary cancer, pulmonary neoplasms, respiratory tract neoplasms, bronchogenic carcinoma, bronchial neoplasms, oral cancer, oral cavity cancer, lip cancer, oropharyngeal cancer, osteosarcoma, ovarian cancer, pancreatic cancer, papillomatosis, paraganglioma, para nasal sinus and nasal cavity cancer, parathyroid cancer, penile cancer, pharyngeal cancer, pheochromosytoma, pituitary cancer, plasma cell neoplasm, pleuropulmonary blastoma, pregnancy-associated breast cancer, primary central nervous system lymphoma, primary peritoneal cancer, prostate cancer, rectal cancer, colon cancer, colonic neoplasms, renal cell cancer, retinoblastoma, rhabdomyosarcoma, salivary gland cancer, sarcoma, Sezary syndrome, skin cancer, Spitz tumors, small cell lung cancer, small intestine cancer, soft tissue sarcoma, squamous cell carcinoma, squamous neck cancer, stomach cancer, T-cell lymphoma, testicular cancer, throat cancer, thymoma and thymic carcinoma, thyroid cancer, transitional cell cancer of the renal pelvis and ureter, unknown primary carcinoma, urethral cancer, uterine cancer, uterine sarcoma, vaginal cancer, vulvar cancer, and Wilms' tumor.

In some embodiments, a hematological cancer (e.g., hematological cancers that are FGFR associated cancers) is selected from the group consisting of leukemias, lymphomas (non-Hodgkin's lymphoma), Hodgkin's disease (also called Hodgkin's lymphoma), and myeloma, for instance, acute lymphocytic leukemia (ALL), acute myeloid leukemia (AML), acute promyelocytic leukemia (APL), chronic lymphocytic leukemia (CLL), chronic myeloid leukemia (CMIL), chronic myelomonocytic leukemia (CMML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult Tcell ALL, AML with trilineage myelodysplasia (AML/TMDS), mixed lineage leukemia (MLL), myelodysplastic syndromes (MDSs), myeloproliferative disorders (MPD), and multiple myeloma (MM).

Additional examples of hematological cancers include myeloproliferative disorders (MPD) such as polycythemia vera (PV), essential thrombocytopenia (ET) and idiopathic primary myelofibrosis (IMF/IPF/PMF). In some embodiments, the hematological cancer (e.g., the hematological cancer that is a FGFR-associated cancer) is AML or CMML. In some embodiments, the cancer (e.g., the FGFR-associated cancer) is a solid tumor. Examples of solid tumors (e.g., solid tumors that are FGFR-associated cancers) include, for example, lung cancer (e.g., lung adenocarcinoma, non-small-cell lung carcinoma, squamous cell lung cancer), bladder cancer, colorectal cancer, brain cancer, testicular cancer, bile duct cancer cervical cancer, prostate cancer, and sparmatocytic seminomas. See, for example, Turner and Grose, Nat. Rev. Cancer, 10(2):116-129, 2010.

In some embodiments, the cancer is selected from the group consisting of bladder cancer, brain cancer, breast cancer, cholangiocarcinoma, head and neck cancer, lung cancer, multiple myeloma, rhabdomyosarcoma, urethral cancer, and uterine cancer. In some embodiments, the cancer is selected from the group consisting of lung cancer, breast cancer, and brain cancer.

In some embodiments, a FGFR1-associated cancer is selected from the group consisting of lung cancer, breast cancer, and brain cancer.

In some embodiments, the cancer is selected from the group consisting of breast cancer, uterine cancer, cholangiocarcinoma, and lung cancer.

In some embodiments, a FGFR2-associated cancer is selected from the group consisting of breast cancer, uterine cancer, cholangiocarcinoma, and lung cancer. In some embodiments, the cancer is selected from the group consisting of lung cancer, bladder cancer, urethral cancer, multiple myeloma, and head and neck cancer.

In some embodiments, a FGFR3-associated cancer is selected from the group consisting of lung cancer, bladder cancer, urethral cancer, multiple myeloma, and head and neck cancer.

In some embodiments, the cancer is selected from lung cancer, rhabdomyosarcoma, and breast cancer.

In some embodiments, a FGFR4-associated cancer is selected from lung cancer, rhabdomyosarcoma, and breast cancer.

In some aspects, the compounds of the disclosure are useful in treating cancers associated with amplification or overexpression of FGFR1, for example, Breast cancer or carcinoma (e.g., hormone receptor-positive breast cancer, ductal carcinoma in situ (breast)), pancreatic ductal adenocarcinoma, pancreatic exocrine carcinoma, smoking-associated lung cancer, small cell lung cancer, lung adenocarcinoma, non-small cell lung cancer, squamous cell lung cancer or carcinoma, prostate cancer or carcinoma, ovarian cancer, fallopian tube carcinoma, bladder cancer, rhabdomyosarcoma, head and neck carcinoma (e.g., head and neck squamous cell carcinoma), esophageal cancer (e.g., esophageal squamous cell carcinoma), sarcoma (e.g., osteosarcoma), hepatocellular carcinoma, renal cell carcinoma, colorectal cancer (e.g., colorectal adenocarcinoma), prostate cancer, salivary gland tumors, glioblastoma multiforme, urinary bladder cancer, urothelial carcinoma, carcinoma of unknown primary, squamous non-lung tumors, gastric cancer, gastroesophageal junction carcinoma, adenoid cystic carcinoma, anal squamous cell carcinoma, oral squamous cell carcinoma, cholangiocarcinoma, hemangioendothelioma, leiomyosarcoma, melanoma, neuroendocrine carcinoma, squamous cell carcinoma, uterine carcinosarcoma.

In some aspects, the compounds of the disclosure are useful in treating cancers associated with amplification of FGFR2, for example, Gastric cancer, gastroesophageal junction adenocarcinoma, breast cancer (e.g., triple negative breast cancer), colon cancer, colorectal cancer (e.g., colorectal adenocarcinoma), urothelial cancer, bladder adenocarcinoma, carcinoma of unknown primary, cholangiocarcinoma, endometrial adenocarcinoma, esophageal adenocarcinoma, gallbladder carcinoma, ovarian cancer, fallopian tube carcinoma, pancreatic exocrine carcinoma, sarcoma, squamous cell carcinoma.

In some aspects, the compounds of the disclosure are useful in treating cancers associated with overexpression of FGFR2, for example, Myxoid lipocarcinoma, rectal cancer, renal cell carcinoma, breast cancer.

In some aspects, the compounds of the disclosure are useful in treating cancers associated with upregulation of activity of FGFR3, for example, Colorectal cancer, hepatocellular carcinoma, pancreatic exocrine carcinoma. In some aspects, the compounds of the disclosure are useful in treating cancers associated with overexpression of activity of FGFR3, for example, Multiple myeloma, thyroid carcinoma. In some aspects, the compounds of the disclosure are useful in treating cancers associated with amplification of activity of FGFR3, for example, Bladder cancer and salivary adenoid cystic cancer, urothelial cancer, breast cancer, carcinoid, carcinoma of unknown primary, colorectal cancer (e.g., colorectal adenocarcinoma), gallbladder carcinoma, gastric cancer, gastroesophageal junction adenocarcinoma, glioma, mesothelioma, non-small cell lung carcinoma, small cell lung cancer, ovarian cancer, fallopian tube carcinoma, pancreatic exocrine carcinoma.

In some aspects, the compounds of the disclosure are useful in treating cancers associated with amplification of FGFR4, for example, Rhabdomyosarcoma, prostate cancer or carcinoma, breast cancer, urothelial cancer, carcinoid, carcinoma of unknown primary, esophageal adenocarcinoma, head and neck carcinoma, hepatocellular carcinoma, non-small cell lung carcinoma, ovarian cancer, fallopian tube carcinoma, peritoneal carcinoma, renal cell carcinoma.

In some aspects, the compounds of the disclosure are useful in treating cancers associated with upregulation of activity of FGFR4, for example, Colorectal cancer, hepatocellular carcinoma, adrenal carcinoma, breast cancer.

In some aspects, the compounds of the disclosure are useful in treating cancers associated with overexpression of activity of FGFR4, for example, Pancreatic intraepithelial neoplasia, and pancreatic ductal adenocarcinoma.

In some aspects, the compounds of the disclosure are more selective for one FGFR than for another. As used herein, the "selectivity" of a compound for a first target over a second target means that the compound has more potent activity at the first target than the second target. A fold selectivity can be calculated by any method known in the art. For example, a fold selectivity can be calculated by dividing the IC50 value (or Kd value) of a compound for the second target (e.g., FGFR1) by the IC50 value of the same compound for the first target (e.g., FGFR2 or FGFR3). An IC50 value can be determined by any method known in the art. In some embodiments, a compound is first determined to have an activity of less than 500 nM for the first target. In some embodiments, a compound is first determined to have an activity of less than 500 nM for the second target.

For example, in some aspects, the compounds of the disclosure are more selective for FGFR3 than for FGFR1. In some aspects, the compounds are at least 3-fold more selective for FGFR3 than for FGFR1. In some aspects, the compounds are 4, 5, 6, 7, 8, 9, 10, 15, 20, 30, 40, 50, 75, 100, 200, 500, or 1000 fold more selective for FGFR3 than for FGFR1.

In some aspects, the compounds of the disclosure are more selective for FGFR2 than for FGFR1. In some aspects, the compounds are at least 3-fold more selective for FGFR2 than for FGFR1. In some aspects, the compounds are 4, 5, 6, 7, 8, 9, 10, 15, 20, 30, 40, 50, 75, 100, 200, 500, or 1000 fold more selective for FGFR2 than for FGFR1.

In some aspects, the compounds of the disclosure are more selective for a first FGFR family member (e.g., FGFR2 or FGFR3) over a second FGFR family member (e.g., FGFR1 or FGFR4). In some aspects, the compounds of the disclosure are at least 3-fold more selective for a first FGFR family member over a second FGFR family member. In some aspects, the compounds are at least 10, 20, 30, 40, 50, 60, 70, 80, 90, 200, 300, 400, 500, 600, 700, 800, 900, or at least 1000 fold more selective for a first FGFR family member over a second FGFR family member.

In some aspects, the compounds of the disclosure are more selective for an FGFR kinase over another kinase that is not an FGFR kinase. For example, the compounds of the disclosure are at least 3-fold more selective for an FGFR kinase over another kinase that is not an FGFR kinase. In some aspects, the compounds of the disclosure are at least 10, 20, 30, 40, 50, 60, 70, 80, 90, 200, 300, 400, 500, 600, 700, 800, 900, or at least 1000 fold more selective for an FGFR kinase over another kinase that is not an FGFR kinase. Kinases that are not FGFR kinases include, for example, KDR kinase and Aurora B kinase.

In some embodiments, the compounds of the disclosure exhibit brain and/or central nervous system (CNS) penetrance. Such compounds are capable of crossing the blood brain barrier and inhibiting a FGFR kinase in the brain and/or other CNS structures. In some embodiments, the compounds provided herein are capable of crossing the blood brain barrier in a therapeutically effective amount. For example, treatment of a subject with cancer (e.g., a FGFR-associated cancer such as a FGFR-associated brain or CNS cancer) can include administration (e.g., oral administration) of the compound to the subject. In some such embodiments, the compounds provided herein are useful for treating a primary brain tumor or metastatic brain tumor. For example, a FGFR-associated primary brain tumor or metastatic brain tumor.

In some embodiments, the compounds of the disclosure, exhibit one or more of high GI absorption, low clearance, and low potential for drug-drug interactions.

In some aspects, compounds of the disclosure can be used for treating a subject diagnosed with (or identified as having) a FGFR-associated disease or disorder (e.g., a FGFR-associated cancer) that include administering to the subject a therapeutically effective amount of a compound of the disclosure. Also provided herein are methods for treating a subject identified or diagnosed as having a FGFR-associated disease or disorder (e.g., a FGFR-associated cancer) that include administering to the subject a therapeutically effective amount of a compound of the disclosure. In some embodiments, the subject that has been identified or diagnosed as having a FGFR-associated disease or disorder (e.g., a FGFR-associated cancer) through the use of a regulatory agency-approved, e.g., FDA-approved test or assay for identifying dysregulation of a FGFR gene, a FGFR kinase, or expression or activity or level of any of the same, in a subject or a biopsy sample from the subject or by performing any of the non-limiting examples of assays described herein. In some embodiments, the test or assay is provided as a kit. In some embodiments, the FGFR-associated disease or disorder is a FGFR-associated cancer. For example, the FGFR-associated cancer can be a cancer that includes one or more FGFR inhibitor resistance mutations.

Also provided are methods for treating a disease or disorder in a subject in need thereof, the method comprising: (a) detecting a FGFR-associated disease or disorder in the subject; and (b) administering to the subject a therapeutically effective amount of a compound of the disclosure. Some embodiments of these methods further include administering to the subject an additional therapy or therapeutic agent (e.g., a second FGFR inhibitor, a second compound of the disclosure, or an immunotherapy. In some embodiments, the subject was previously treated with a first FGFR inhibitor or previously treated with another treatment. In some embodiments, the subject is determined to have a FGFR-associated disease or disorder through the use of a regulatory agency-approved, e.g., FDA approved test or assay for identifying dysregulation of a FGFR gene, a FGFR kinase, or expression or activity or level of any of the same, in a subject or a biopsy sample from the subject or by performing any of the non-limiting examples of assays described herein. In some embodiments, the test or assay is provided as a kit.

Also provided are methods for treating cancer in a subject in need thereof, the method comprising: (a) detecting a FGFR-associated cancer in the subject; and (b) administering to the subject a therapeutically effective amount of a compound of the disclosure. Some embodiments of these methods further include administering to the subject an additional therapy or therapeutic agent (e.g., a second FGFR inhibitor, a second compound of the disclosure, or an immunotherapy). In some embodiments, the subject was previously treated with a first FGFR inhibitor or previously treated with another anticancer treatment, e.g., at least partial resection of the tumor or radiation therapy. In some embodiments, the subject is determined to have a FGFR-associated cancer through the use of a regulatory agency-approved, e.g., FDA-approved test or assay for identifying dysregulation of a FGFR gene, a FGFR kinase, or expression or activity or level of any of the same, in a subject or a biopsy sample from the subject or by performing any of the non-limiting examples of assays described herein. In some embodiments, the test or assay is provided as a kit. In some embodiments, the cancer is a FGFR associated cancer. For example, the FGFR-associated cancer can be a cancer that includes one or more FGFR inhibitor resistance mutations. In some embodiments, the cancer is a FGFR associated cancer. For example, the FGFR-associated cancer can be a cancer that includes one or more FGFR activating mutations.

Also provided are methods of treating a subject that include performing an assay on a sample obtained from the subject to determine whether the subject has a dysregulation of a FGFR gene, a FGFR kinase, or expression or activity or level of any of the same, and administering (e.g., specifically or selectively administering) a therapeutically effective amount of a compound of the disclosure or pharmaceutically acceptable salt or solvate thereof to the subject determined to have a dysregulation of a FGFR gene, a FGFR kinase, or expression or activity or level of any of the same. Some embodiments of these methods further include administering to the subject an additional therapy or therapeutic agent (e.g., a second FGFR inhibitor, a second compound of the disclosure, or immunotherapy). In some embodiments of these methods, the subject was previously treated with a first FGFR inhibitor or previously treated with another anticancer treatment, e.g., at least partial resection of a tumor or radiation therapy. In some embodiments, the subject is a subject suspected of having a FGFR-associated disease or disorder (e.g., a FGFR-associated cancer), a subject presenting with one or more symptoms of a FGFR-associated disease or disorder (e.g., a FGFR-associated cancer), or a subject having an elevated risk of developing a FGFR-associated disease or disorder (e.g., a FGFR-associated cancer). In some embodiments, the assay utilizes next generation sequencing, pyrosequencing, immunohistochemistry, or break apart FISH analysis. In some embodiments, the assay is a regulatory agency-approved assay, e.g., FDA-approved kit. In some embodiments, the assay is a liquid biopsy. Additional, non-limiting assays that may be used in these methods are described herein. Additional assays are also known in the art. In some embodiments, the dysregulation of a FGFR gene, a FGFR kinase, or expression or activity or level of any of the same includes one or more FGFR inhibitor resistance mutations.

Also provided herein are methods of selecting a treatment for a subject, wherein the methods include a step of performing an assay on a sample obtained from the subject to determine whether the subject has a dysregulation of a FGFR gene, a FGFR kinase, or expression or activity or level of any of the same (e.g., one or more FGFR inhibitor resistance mutations), and identifying or diagnosing a subject determined to have a dysregulation of a FGFR gene, a FGFR kinase, or expression or activity or level of any of the same, as having a FGFR-associated cancer. Some embodiments further include administering the selected treatment to the subject identified or diagnosed as having a FGFR-associated cancer. For example, in some embodiments, the selected treatment can include administration of a therapeutically effective amount of a compound of the disclosure to the subject identified or diagnosed as having a FGFR-associated cancer. In some embodiments, the assay is an in vitro assay. For example, an assay that utilizes the next generation sequencing, immunohistochemistry, or break apart FISH analysis. In some embodiments, the assay is a regulatory agency-approved, e.g., FDA-approved, kit. In some embodiments, the assay is a liquid biopsy.

Also provided herein are methods of treating a FGFR-associated cancer in a subject that include (a) administering one or more (e.g., two or more, three or more, four or more, five or more, or ten or more) doses of a first FGFR kinase inhibitor to a subject identified or diagnosed as having a FGFR associated cancer (e.g., any of the types of FGFR-associated cancers described herein) (e.g., identified or diagnosed as having a FGFR-associated cancer using any of the exemplary methods described herein or known in the art); (b) after step (a), determining a level of circulating tumor DNA in a biological sample (e.g., a biological sample comprising blood, serum, or plasma) obtained from the subject; (c) administering a therapeutically effective amount of a second FGFR inhibitor or a compound of the disclosure as a monotherapy or in conjunction with an additional therapy or therapeutic agent to a subject identified as having about the same or an elevated level of circulating tumor DNA as compared to a reference level of circulating tumor DNA (e.g., any of the reference levels of circulating tumor DNA described herein). In some examples of these methods, the reference level of circulating tumor DNA is a level of circulating tumor DNA in a biological sample obtained from the subject prior to step (a). Some embodiments of these methods further include determining the level of circulating tumor DNA in the biological sample obtained from the subject prior to step (a). In some examples of these methods, the reference level of circulating tumor DNA is a threshold level of circulating tumor DNA (e.g., an average level of circulating tumor DNA in a population of subjects having a similar FGFR-associated cancer and having a similar stage of the FGFR-associated cancer, but receiving a non-effective treatment or a placebo, or not yet receiving therapeutic treatment, or a level of circulating tumor DNA in a subject having a similar FGFR-associated cancer and having a similar stage of the FGFR-associated cancer, but receiving a non-effective treatment or a placebo, or not yet receiving therapeutic treatment). In some examples of these methods, the first FGFR inhibitor is: ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, TAS-120 or RLY-4008.

Compounds of the disclosure can also be administered with additional therapy or therapeutic agents. In some aspects, the additional therapy or therapeutic agent includes one or more of radiation therapy, a chemotherapeutic agent (e.g., any of the exemplary chemotherapeutic agents described herein or known in the art), a checkpoint inhibitor (e.g., any of the exemplary checkpoint inhibitors described herein or known in the art), surgery (e.g., at least partial resection of the tumor), and one or more other kinase inhibitors (e.g., any of the kinase inhibitors described herein or known in the art).

Compounds of the disclosure may also be useful as adjuvants to cancer treatment, that is, they can be used in combination with one or more additional therapies or therapeutic agents, for example a chemotherapeutic agent that works by the same or by a different mechanism of action. In some embodiments, a compound of the disclosure can be used prior to administration of an additional therapeutic agent or additional therapy. For example, a subject in need thereof can be administered one or more doses of a compound of the disclosure for a period of time and then under go at least partial resection of the tumor. In some embodiments, the treatment with one or more doses of a compound of the disclosure reduces the size of the tumor (e.g., the tumor burden) prior to the at least partial resection of the tumor. In some embodiments, a subject has a cancer (e.g., a locally advanced or metastatic tumor) that is refractory or intolerant to standard therapy (e.g., administration of a chemotherapeutic agent, such as a first FGFR inhibitor or a multikinase inhibitor, immunotherapy, radiation, or a platinum-based agent (e.g., cisplatin)). In some embodiments, a subject has a cancer (e.g., a locally advanced or metastatic tumor) that is refractory or intolerant to prior therapy (e.g., administration of a chemotherapeutic agent, such as a first FGFR inhibitor or a multikinase inhibitor, immunotherapy, radiation, or a platinum-based agent (e.g., cisplatin)).

In some embodiments of any the methods described herein, the compound of the disclosure is administered in combination with a therapeutically effective amount of at least one additional therapeutic agent selected from one or more additional therapies or therapeutic (e.g., chemotherapeutic) agents. Non-limiting examples of additional therapeutic agents include: other FGFR-targeted therapeutic agents (i.e. a first or second FGFR kinase inhibitor), other kinase inhibitors (e.g., receptor tyrosine kinase targeted therapeutic agents (e.g., Trk inhibitors or EGFR inhibitors)), signal transduction pathway inhibitors, checkpoint inhibitors, modulators of the apoptosis pathway (e.g. obataclax); cytotoxic chemotherapeutics, angiogenesis-targeted therapies, immune-targeted agents, including immunotherapy, and radiotherapy.

Also provided herein are methods of treating a disease or disorder, comprising administering to a subject in need thereof a pharmaceutical combination for treating the disease or disorder which comprises (a) a compound of the disclosure, (b) an additional therapeutic agent, and (c) optionally at least one pharmaceutically acceptable carrier for simultaneous, separate or sequential use for the treatment of the disease or disorder, wherein the amounts of the compound of the disclosure and the additional therapeutic agent are together effective in treating the disease or disorder. In some embodiments, the compound of the disclosure, and the additional therapeutic agent are administered simultaneously as separate dosages. In some embodiments, the compound of the disclosure, and the additional therapeutic agent are administered as separate dosages sequentially in any order, in jointly therapeutically effective amounts, e.g. in daily or intermittently dosages. In some embodiments, the compound of the disclosure, and the additional therapeutic agent are administered simultaneously as a combined dosage. In some embodiments, the disease or disorder is a FGFR-associated disease or disorder. In some embodiments, the subject has been administered one or more doses of a compound of the disclosure, prior to administration of the pharmaceutical composition.

In some embodiments, the treatment period is at least 7 days (e.g., at least or about 8 days, at least or about 9 days, at least or about 10 days, at least or about 11 days, at least or about 12 days, at least or about 13 days, at least or about 14 days, at least or about 15 days, at least or about 16 days, at least or about 17 days, at least or about 18 days, at least or about 19 days, at least or about 20 days, at least or about 21 days, at least or about 22 days, at least or about 23 days, at least or about 24 days, at least or about 25 days, at least or about 26 days, at least or about 27 days, at least or about 28 days, at least or about 29 days, or at least or about 30 days).

In some embodiments, the treatment period is at least 21 days (e.g., at least or about 22 days, at least or about 23 days, at least or about 24 days, at least or about 25 days, at least or about 26 days, at least or about 27 days, at least or about 28 days, at least or about 29 days, at least or about 30 days, at least or about 31 days, at least or about 32 days, at least or about 33 days, at least or about 34 days, at least or about 35 days, at least or about 36 days, at least or about 37 days, at least or about 38 days, at least or about 39 days, or at least or about 40 days).

Also provided herein are pharmaceutical compositions that contain, as the active ingredient, a compound of the disclosure, in combination with one or more pharmaceutically acceptable carriers (excipients). In some embodiments, the composition is suitable for topical administration. In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. In some embodiments, the composition is formulated for oral administration. In some embodiments, the composition is formulated as a tablet or capsule.

The compositions comprising a compound of the disclosure can be formulated in a unit dosage form, each dosage containing from about 5 to about 1,000 mg (1 g), more usually about 100 mg to about 500 mg, of the active ingredient. The term "unit dosage form" refers to physically discrete units for human subjects and other subjects, each unit containing a predetermined quantity of active material (i.e., a compound of the disclosure) to produce the desired therapeutic effect, with a suitable pharmaceutical excipient.

In some embodiments, the compositions provided herein contain from about 5 mg to about 50 mg of the active ingredient, i.e., the compound of the disclosure. One having ordinary skill in the art will appreciate that this embodies compounds or compositions containing about 5 mg to about 10 mg, about 10 mg to about 15 mg, about 15 mg to about 20 mg, about 20 mg to about 25 mg, about 25 mg to about 30 mg, about 30 mg to about 35 mg, about 35 mg to about 40 mg, about 40 mg to about 45 mg, or about 45 mg to about 50 mg of the active ingredient. In some embodiments, the compositions provided herein contain from about 50 mg to about 500 mg of the active ingredient. One having ordinary skill in the art will appreciate that this embodies compounds or compositions containing about 50 mg to about 100 mg, about 100 mg to about 150 mg, about 150 mg to about 200 mg, about 200 mg to about 250 mg, about 250 mg to about 300 mg, about 350 mg to about 400 mg, or about 450 mg to about 500 mg of the active ingredient. In some embodiments, the compositions provided herein contain from about 500 mg to about 1,000 mg of the active ingredient. One having ordinary skill in the art will appreciate that this embodies compounds or compositions containing about 500 mg to about 550 mg, about 550 mg to about 600 mg, about 600 mg to about 650 mg, about 650 mg to about 700 mg, about 700 mg to about 750 mg, about 750 mg to about 800 mg, about 800 mg to about 850 mg, about 850 mg to about 900 mg, about 900 mg to about 950 mg, or about 950 mg to about 1,000 mg of the active ingredient.

The active compound may be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual subject, the severity of the subject's symptoms, and the like.

In some embodiments, the compounds provided herein can be administered in an amount ranging from about 1 mg/kg to about 100 mg/kg. In some embodiments, the compound provided herein can be administered in an amount of about 1 mg/kg to about 20 mg/kg, about 5 mg/kg to about 50 mg/kg, about 10 mg/kg to about 40 mg/kg, about 15 mg/kg to about 45 mg/kg, about 20 mg/kg to about 60 mg/kg, or about 40 mg/kg to about 70 mg/kg. For example, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg. In some embodiments, such administration can be once-daily or twice-daily (BID) administration.

EXAMPLES

The examples and preparations provided below further illustrate and exemplify the compounds of the present invention and methods of preparing such compounds. It is to be understood that the scope of the present invention is not limited in any way by the scope of the following examples and preparations.

In several embodiments, where single enantiomers are provided, the enantiomers may be separated by conventional means (chiral chromatography, preparing diastereomeric salts, chiral derivatization, crystallization, enzymatic reactions, etc.). In several embodiments, a chiral intermediate compound is purified to prepare an enantiomerically pure (or substantially enantiomerically pure, enantiomerically enriched, etc.) intermediate.

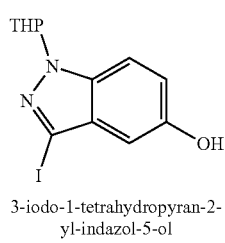

3-iodo-1-tetrahydropyran-2-yl-indazol-5-ol

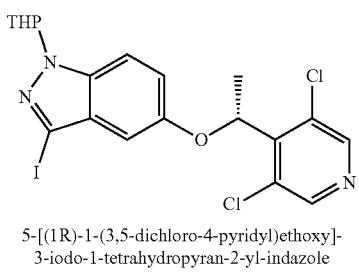

5-[(1R)-1-(3,5-dichloro-4-pyridyl)ethoxy]-3-iodo-1-tetrahydropyran-2-yl-indazole

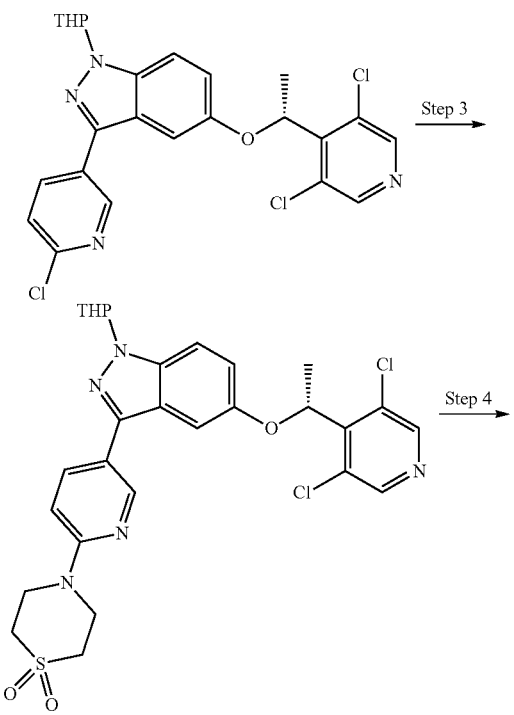

Example 1

Example 1. 4-[5-[5-[(1R)-1-(3,5-dichloro-4-pyridyl)ethoxy]-1H-indazol-3-yl]-2-pyridyl]-1,4-thiazinane 1,1-dioxide

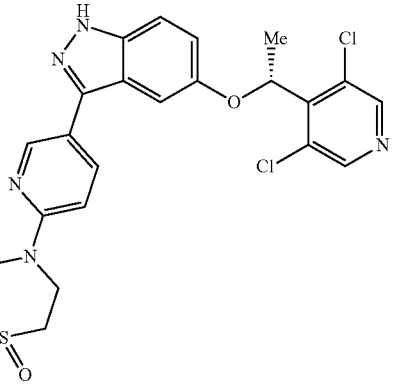

Step 1. 5-((R)-1-(3,5-Dichloropyridin-4-yl)ethoxy)-3-iodo-1-(tetrahydro-2H-pyran-2-yl)-1H-indazole. A mixture of 3-iodo-1-tetrahydropyran-2-yl-indazol-5-ol (1.0 g, 2.90 mmol, 1.0 equiv), [(1S)-1-(3,5-dichloro-4-pyridyl)ethyl] methanesulfonate (780 mg, 2.90 mmol, 1.0 equiv) and cesium carbonate (1.41 g, 14.45 mmol, 1.5 equiv) in N,N-dimethylformamide (20 mL) was heated at 130° C. for 16 h. The volatiles were removed under reduced pressure and the residue was suspended in saturated ammonium chloride (50 mL). The solution was extracted with ethyl acetate (3×50 mL). The combined organic layers were dried over sodium sulfate, filtered and concentrated under reduced pressure. The crude product was purified on a Büchi automated chromatography system (Sorbtech 40 g silica gel column), eluting with a gradient of 0 to 30% ethyl acetate in heptanes to give a white solid (1.01 g, 88% yield). Analysis: LCMS: m/z=517.2 (M+H).

Step 2. 3-(6-chloro-3-pyridyl)-5-[(1R)-1-(3,5-dichloro-4-pyridyl)ethoxy]-1-tetrahydropyran-2-yl-indazole. A solution of 5-((R)-1-(3,5-dichloropyridin-4-yl)ethoxy)-3-iodo-1-(tetrahydro-2H-pyran-2-yl)-1H-indazole (1.32 g, 2.55 mmol, 1.0 equiv), 2-chloro-5-(4,4,5,5-tetramethyl-1,3,2-dioxaborolan-2-yl)pyridine (790 mg, 3.31 mmol, 1.3 equiv), [1,1' bis(diphenylphosphino) ferrocene]dichloropalladium(II) (190 mg, 0.255 mmol, 0.1 equiv) and potassium carbonate (700 mg, 5.1 mmol, 2.0 equiv) in 1,4-dioxane (20 mL) and water (1 mL) was sparged with nitrogen for 15 minutes. After heating at 90° C. for 16 h, the reaction was cooled to room temperature and filtered through Celite. The filtrate was concentrated under reduced pressure. The residue was suspended in saturated sodium bicarbonate (20 mL) and extracted with ethyl acetate (3×30 mL). The combined organic layers were dried over sodium sulfate, filtered and concentrated under reduced pressure. The residue was purified on a Büchi automated chromatography system (Sorbtech 25 g silica gel column), eluting with a gradient of 0 to 50% ethyl acetate in heptanes to give a white solid (870 mg, 68% yield). Analysis: LCMS: m/z=503.1 (M+H).

Step 3. 4-(5-(5-((R)-1-(3,5-Dichloropyridin-4-yl)ethoxy)-1-(tetrahydro-2H-pyran-2-yl)-1H-indazol-3-yl)pyridin-2-yl)thiomorpholine 1,1-dioxide. A solution of product from step 2 (280 mg, 0.56 mmol, 1.0 equiv), (150 mg, 1.12 mmol, 2.0 equiv), Xantphos (64 mg, 0.11 mmol, 0.2 equiv), tris(dibenzylideneacetone)dipalladium(0) (51 mg, 0.06 mmol, 0.1 equiv) and cesium carbonate (364 mg, 1.1 mmol, 2.0 equiv)

in N,N-dimethylformamide (10 mL) was sparged with nitrogen for 15 minutes. After heating at 95° C. for 16 hours, the reaction was cooled to room temperature and filtered through Celite. The filtrate was concentrated under reduced pressure. The residue was purified on a Büchi automated chromatography system (Sorbtech 40 g column), eluting with a gradient of 0 to 100% ethyl acetate in heptanes to give a brown solid (290 mg, 89% yield) as. Analysis: LCMS: m/z=601.2 (M+H).

Step 4. 4-[5-[5-[(1R)-1-(3,5-dichloro-4-pyridyl)ethoxy]-1H-indazol-3-yl]-2-pyridyl]-1,4-thiazinane 1,1-dioxide. A solution of step 3 product (290 mg, 0.47 mmol, 1.0 equiv) in 1,4-dioxane (2.0 mL) and water (0.5 mL) was treated with 4M HCl in 1,4-dioxane (0.95 mL, 3.79 mmol, 8.0 equiv) and heated at 100° C. in a CEM microwave reactor for 1 hour. The volatiles were removed under reduced pressure. The residue was dissolved in 20% methanol in dichloromethane (10 mL) followed by the addition of MP-carbonate (1.0 g). After stirring at room temperature for 1 hour, the suspension was filtered and the filtrate was concentrated under reduced pressure. The residue was purified on a Büchi automated chromatography system (RediSep Rf Gold HP C18, 50 g column), eluting with a gradient of 0 to 80% acetonitrile in water to give a white solid (29 mg, 12% yield). Analysis: LCMS: m/z=518.1 (M+H); $^1$H NMR (400 MHz, DMSO-d6) δ 13.04 (s, 1H), 8.60 (s, 2H), 8.59 (d, J=2.1 Hz, 1H), 7.93 (dd, J=2.4, 8.9 Hz, 1H), 7.47 (d, J=9.0 Hz, 1H), 7.20-7.15 (m, 2H), 7.10 (dd, J=2.3, 9.0 Hz, 1H), 6.10 (q, J=6.7 Hz, 1H), 4.18-4.11 (m, 4H), 3.20-3.15 (m, 4H), 1.76 (d, J=6.6 Hz, 3H).

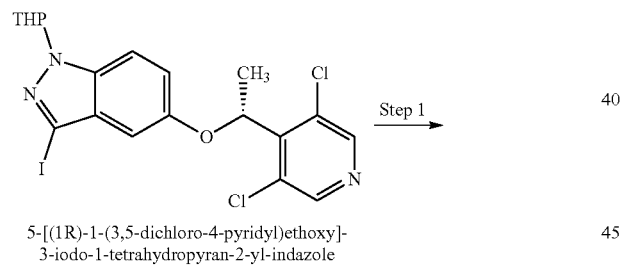

5-[(1R)-1-(3,5-dichloro-4-pyridyl)ethoxy]-3-iodo-1-tetrahydropyran-2-yl-indazole

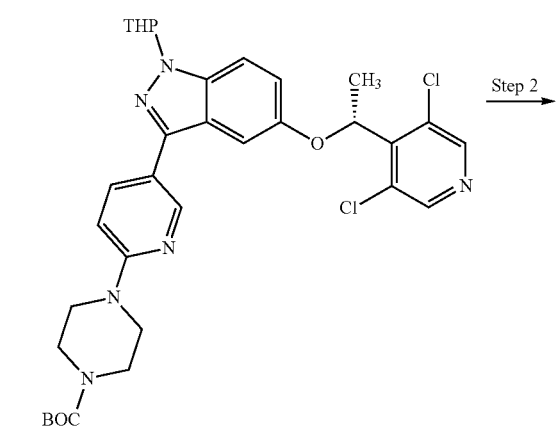

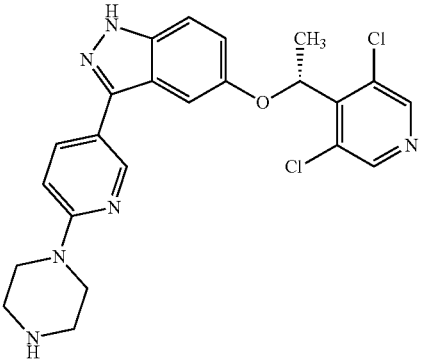

Example 2

Example 2. (R)-5-(1-(3,5-Dichloropyridin-4-yl)ethoxy)-3-(6-(piperazin-1-yl)pyridin-3-yl)-1H-indazole dihydrochloride

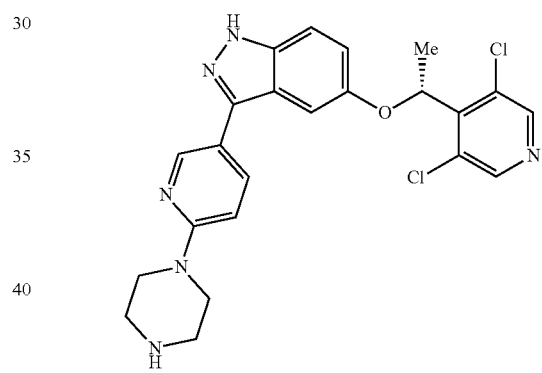

Step 1. tert-Butyl 4-(5-(5-((R)-1-(3,5-dichloropyridin-4-yl)ethoxy)-1-(tetrahydro-2H-pyran-2-yl)-1H-indazol-3-yl)pyridin-2-yl)piperazine-1-carboxylate. A solution of 5-((R)-1-(3,5-dichloropyridin-4-yl)ethoxy)-3-iodo-1-(tetrahydro-2H-pyran-2-yl)-1H-indazole (3.1 g, 5.99 mmol, 1 equiv) and tert-butyl 4-[5-(4,4,5,5-tetramethyl-1,3,2-dioxaborolan-2-yl)-2-pyridyl]piperazine-1-carboxylate (3.03 g, 7.78 mmol, 1.3 equiv) in a 20 to 1 mixture of 1,4-dioxane and water (50 mL) was sparged with nitrogen for 10 minutes. Potassium carbonate (1.65 g, 11.98 mmol, 2.0 equiv) and [1,1' bis(diphenylphosphino)ferrocene]palladium(II) dichloride (0.44 g, 0.6 mmol, 0.1 equiv) were added and the reaction mixture was sparged with nitrogen for an additional 5 minutes. The reaction was heated at 90° C. for 16 hours. After cooling to room temperature, the reaction was concentrated under reduced pressure. The residue was diluted with water (100 mL) and dichloromethane (100 mL). The organic layer was separated, dried over sodium sulfate,- filtered and concentrated under reduced pressure. The crude product was pre-absorbed onto silica gel (5 g) and purified on an Interchim automated chromatography system (Sorbtech 120 g silica gel cartridge), eluting with a gradient of 0 to 30% ethyl acetate in heptanes to give a white solid (2.19 g, 56% yield). Analysis: LCMS: m/z=653 (M+H).

Step 2. (R)-5-(1-(3,5-Dichloropyridin-4-yl)ethoxy)-3-(6-(piperazin-1-yl)pyridin-3-yl)-1H-indazole dihydrochloride. A solution of step 1 product (70.0 mg, 0.11 mmol, 1.0 equiv) in 1,4-dioxane (1.0 mL) was treated with 4M HCl in dioxane (0.27 mL, 1.1 mmol, 10.0 equiv) at room temperature overnight. The volatiles were removed under reduced pressure. The residue was triturated with a 1 to 3 mixture of dichloromethane and methanol (2.8 mL) to give a white solid (23.0 mg, 40% yield). Analysis: LCMS: m/z=469.2 (free base M+H). $^1$H NMR (400 MHz, DMSO-d6) δ 9.47 (br s, 2H), 8.59 (s, 2H), 8.50 (d, J=2.1 Hz, 1H), 8.13 (dd, J=2.0, 9.0 Hz, 1H), 7.50 (d, J=9.0 Hz, 1H), 7.29 (d, J=9.2 Hz, 1H), 7.18 (d, J=1.8 Hz, 1H), 7.11 (dd, J=2.2, 9.0 Hz, 1H), 6.12 (q, J=6.6 Hz, 1H), 3.97-3.93 (m, 4H), 3.27 (br s, 4H), 1.76 (d, J=6.6 Hz, 3H).

Example 3. [4-[5-[5-[(1R)-1-(3,5-dichloro-4-pyridyl)ethoxy]-1H-indazol-3-yl]-2-pyridyl]piperazin-1-yl]-morpholino-methanone

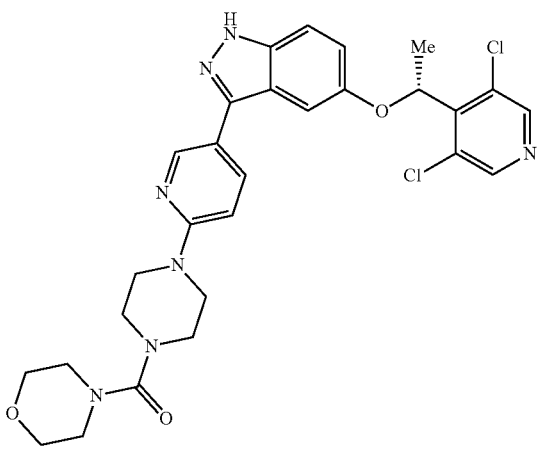 [SMILES: C[C@@H](Oc1ccc2[nH]nc(-c3ccc(N4CCN(C(=O)N5CCOCC5)CC4)nc3)c2c1)c1c(Cl)cncc1Cl]

Step 1. (4-(5-(5-((R)-1-(3,5-Dichloropyridin-4-yl)ethoxy)-1-(tetrahydro-2H-pyran-2-yl)-1H-indazol-3-yl)pyridin-2-yl)piperazin-1-yl)(morpholino)methanone. Triethylamine (28.0 uL, 0.204 mmol, 1.1 equiv) and morpholine-4-carbonyl chloride (30.5 mg, 0.204 mmol, 1.1 equiv) were added to a solution of example 2 (102.6 mg, 0.185 mmol, 1 equiv) in anhydrous THF (3 mL at room temperature. After stirring for 1 hour, the reaction was diluted with saturated brine (20 mL) and dichloromethane (20 mL). The organic layer was separated, dried over sodium sulfate, filtered and concentrated under reduced pressure to give a yellow solid (90 mg, 73% yield). Analysis: LCMS: m/z=666 (M+H).

Step 2. (R)-(4-(5-(5-(1-(3,5-Dichloropyridin-4-yl)ethoxy)-1H-indazol-3-yl)pyridin-2-yl)piperazin-1-yl)(morpholino)methanone. Example 3 step 1 (90 mg, 0.135 mmol, 1 equiv) in 1,4-dioxane (4.0 mL) and water (1 mL) was treated with 4M HCl in 1,4-dioxane (0.27 mL, 1.08 mmol, 8.0 equiv) and heated at 60° C. in a CEM microwave reactor for 20 minutes. Additional 4M HCl in 1,4-dioxane (0.27 mL, 1.08 mmol, 8.0 equiv) was added and the reaction was heated at 60° C. in a CEM microwave reactor for 20 additional minutes. After cooling to room temperature, the volatiles were removed under reduced pressure. The residue was dissolved in methanol (20 mL), treated with MP-carbonate resin (3.2 mmol/g, 1 g), stirred for 30 minutes, filtered and concentrated under reduced pressure. The residue was pre-absorbed onto Celite (1 g) and purified on an Interchim automated chromatography system (RediSep Rf Gold HP C18, 15.5 g cartridge), eluting with a gradient of 0 to 100% acetonitrile in water. The fractions containing product were collected and lyophilized to give a white solid (36.9 mg, 47% yield). Analysis: LCMS: m/z=582.2 (M+H); $^1$H NMR (400 MHz, DMSO-d6) δ 13.01 (br s, 1H), 8.60 (s, 2H), 8.56 (d, J=2.2 Hz, 1H), 7.89 (dd, J=2.4, 8.9 Hz, 1H), 7.47 (d, J=9.0 Hz, 1H), 7.16 (d, J=2.1 Hz, 1H), 7.09 (dd, J=2.3, 9.0 Hz, 1H), 6.98 (d, J=8.8 Hz, 1H), 6.10 (q, J=6.6 Hz, 1H), 3.63-3.57 (m, 8H), 3.33-3.30 (m, 4H), 3.22-3.18 (m, 4H), 1.76 (d, J=6.6 Hz, 3H).

Examples 4-9 were synthesized using the procedure for example 3.

| Example 4 [4-[5-[5-[(1R)-1-(3,5-dichloro-4-pyridyl)ethoxy]-1H-indazol-3-yl]-2-pyridyl]piperazin-1-yl]-(4-methylpiperazin-1-yl)methanone | 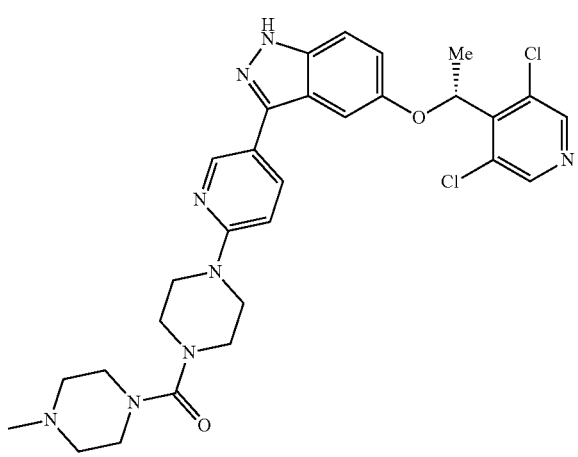 [SMILES: C[C@@H](Oc1ccc2[nH]nc(-c3ccc(N4CCN(C(=O)N5CCN(C)CC5)CC4)nc3)c2c1)c1c(Cl)cncc1Cl] | LCMS: m/z = 595.2 (M + H); $^1$H NMR (400 MHz, CDCl3) δ 8.68 (d, J = 2.0 Hz, 1H), 8.42 (s, 2H), 7.94 (dd, J = 2.4, 8.8 Hz, 1H), 7.35 (d, J = 8.9 Hz, 1H), 7.22 (d, J = 2.1 Hz, 1H), 7.12 (dd, J = 2.3, 9.0 Hz, 1H), 6.76 (d, J = 8.8 Hz, 1H), 6.05 (q, J = 6.7 Hz, 1H), 3.69-3.63 (m, 4H), 3.46-3.41 (m, 4H), 3.41-3.34 (m, 4H), 2.44 (t, J = 4.8 Hz, 4H), 2.33 (s, 3H), 1.81 (d, J = 6.7 Hz, 3H) |

| | | |
|---|---|---|
| Example 5<br>4-[5-[5-[(1R)-1-(3,5-dichloro-4-pyridyl)ethoxy]-1H-indazol-3-yl]-2-pyridyl]-N,N-dimethyl-piperazine-1-carboxamide | 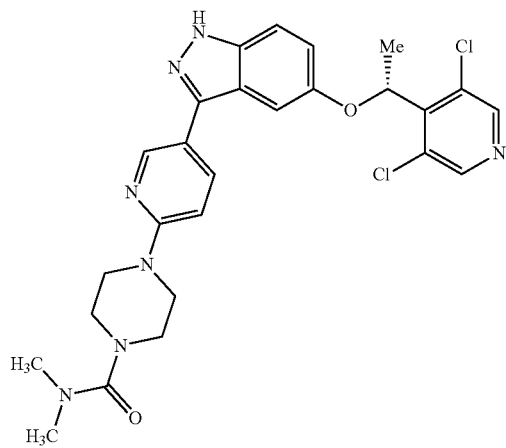 [SMILES: C[C@@H](Oc1ccc2[nH]nc(-c3ccc(N4CCN(C(=O)N(C)C)CC4)nc3)c2c1)c1c(Cl)cncc1Cl] | LCMS: m/z = 540.2 (M + H); ¹H NMR (400 MHz, DMSO-d6) δ 13.01 (br s, 1H), 8.60 (s, 2H), 8.56 (d, J = 2.0 Hz, 1H), 7.89 (dd, J = 2.4, 8.8 Hz, 1H), 7.46 (d, J = 9.0 Hz, 1H), 7.16 (d, J = 2.1 Hz, 1H), 7.09 (dd, J = 2.3, 9.0 Hz, 1H), 6.99 (d, J = 8.8 Hz, 1H), 6.11 (q, J = 6.7 Hz, 1H), 3.60 (dd, J = 4.1, 6.2 Hz, 4H), 3.28-3.23 (m, 4H), 2.80 (s, 6H), 1.76 (d, J = 6.6 Hz, 3H) |
| Example 6<br>5-[(1R)-1-(3,5-dichloro-4-pyridyl)ethoxy]-3-[6-(4-methylsulfonyl-piperazin-1-yl)-3-pyridyl]-1H-indazole | 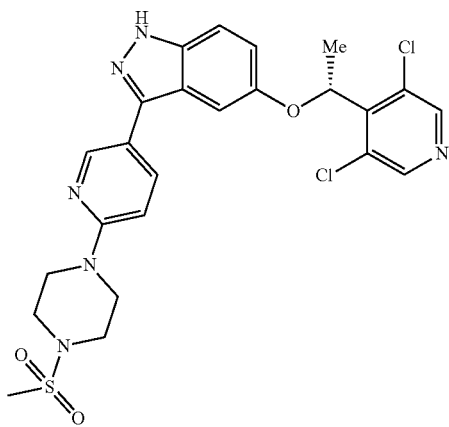 | LCMS: m/z = 525.2 (M + H); 1H NMR (400 MHz, DMSO-d6) δ 13.01 (s, 1H), 8.60 (s, 2H), 8.57 (d, J = 2.1 Hz, 1H), 7.89 (dd, J = 2.4, 8.8 Hz, 1H), 7.46 (d, J = 8.9 Hz, 1H), 7.17 (d, J = 1.8 Hz, 1H), 7.09 (dd, J = 2.3, 9.0 Hz, 1H), 7.00 (d, J = 8.7 Hz, 1H), 6.10 (q, J = 6.7 Hz, 1H), 3.66-3.54 (m, 8H), 2.39 (q, J = 7.4 Hz, 2H), 1.76 (d, J = 6.7 Hz, 3H), 1.03 (t, J = 7.4 Hz, 3H) |
| Example 7<br>Methyl 4-[5-[5-[(1R)-1-(3,5-dichloro-4-pyridyl)ethoxy]-1H-indazol-3-yl]-2-pyridyl]piperazine-1-carboxylate | 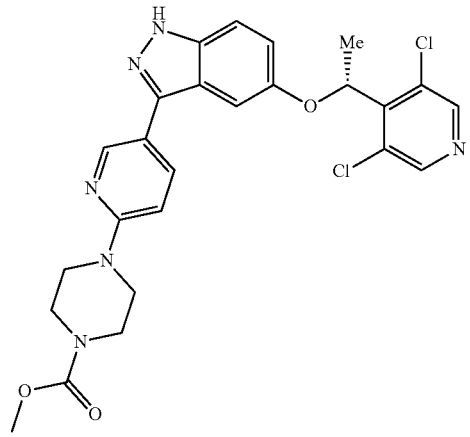 [SMILES: COC(=O)N1CCN(c2ccc(-c3n[nH]c4ccc(O[C@H](C)c5c(Cl)cncc5Cl)cc34)cn2)CC1] | LCMS: m/z = 527.2 (M + H); ¹H NMR (400 MHz, DMSO-d6) δ 13.02 (br s, 1H), 8.60 (s, 2H), 8.56 (d, J = 2.0 Hz, 1H), 7.89 (dd, J = 2.4, 8.9 Hz, 1H), 7.46 (d, J = 9.0 Hz, 1H), 7.16 (d, J = 2.1 Hz, 1H), 7.09 (dd, J = 2.3, 9.0 Hz, 1H), 7.00 (d, J = 8.7 Hz, 1H), 6.10 (q, J = 6.7 Hz, 1H), 3.65 (s, 3H), 3.63-3.57 (m, 4H), 3.56-3.49 (m, 4H), 1.76 (d, J = 6.6 Hz, 3H) |

| Example 8<br>5-[(1R)-1-(3,5-dichloro-4-pyridyl)ethoxy]-3-[6-[4-(4-methylpiperazin-1-yl)sulfonylpiperazin-1-yl]-3-pyridyl]-1H-indazole | 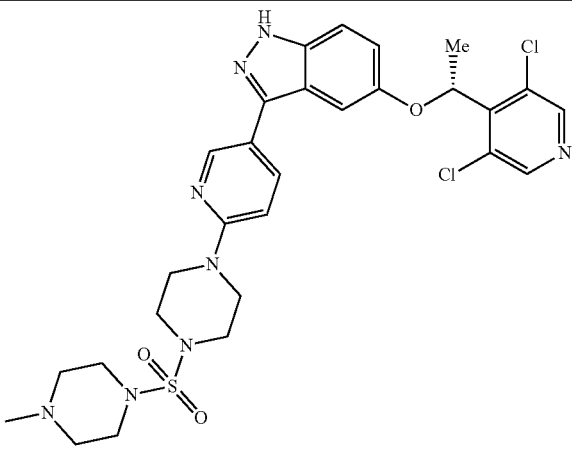 | LCMS: m/z = 631.2 (M + H); $^1$H NMR (400 MHz, DMSO-d6) δ 8.60 (s, 2H), 8.57 (d, J = 2.2 Hz, 1H), 7.90 (dd, J = 2.4, 8.9 Hz, 1H), 7.47 (d, J = 9.0 Hz, 1H), 7.16 (d, J = 2.1 Hz, 1H), 7.09 (dd, J = 2.3, 9.0 Hz, 1H), 7.02 (d, J = 8.8 Hz, 1H), 6.11 (q, J = 6.6 Hz, 1H), 3.68-3.63 (m, 4H), 3.32-3.27 (m, 4H), 3.25-3.19 (m, 4H), 2.47-2.39 (m, 4H), 2.24 (s, 3H), 1.76 (d, J = 6.7 Hz, 3H) |
|---|---|---|
| Example 9<br>1-[4-[5-[5-[(1R)-1-(3,5-dichloro-4-pyridyl)ethoxy]-1H-indazol-3-yl]-2-pyridyl]piperazin-1-yl]propan-1-one | 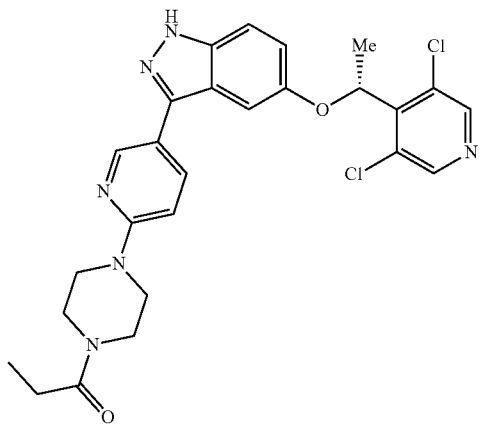 [SMILES: CCC(=O)N1CCN(c2ccc(-c3n[nH]c4ccc(O[C@H](C)c5c(Cl)cncc5Cl)cc34)cn2)CC1] | LCMS: m/z = 525.2 (M + H); $^1$H NMR (400 MHz, DMSO-d6) δ 13.01 (s, 1H), 8.60 (s, 2H), 8.57 (d, J = 2.1 Hz, 1H), 7.89 (dd, J = 2.4, 8.8 Hz, 1H), 7.46 (d, J = 8.9 Hz, 1H), 7.17 (d, J = 1.8 Hz, 1H), 7.09 (dd, J = 2.3, 9.0 Hz, 1H), 7.00 (d, J = 8.7 Hz, 1H), 6.10 (q, J = 6.7 Hz, 1H), 3.66-3.54 (m, 8H), 2.39 (q, J = 7.4 Hz, 2H), 1.76 (d, J = 6.7 Hz, 3H), 1.03 (t, J = 7.4 Hz, 3H) |

Example 10. 5-[(1R)-1-(3,5-Dichloro-4-pyridyl)ethoxy]-3-(5-fluoro-6-piperazin-1-yl-3-pyridyl)-1H-indazole

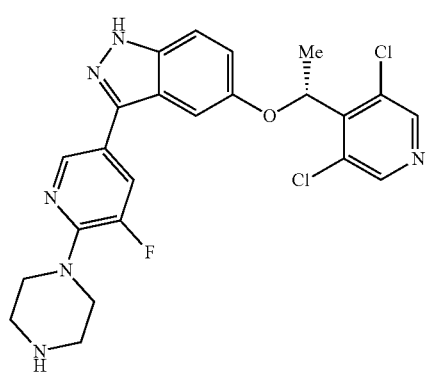 [SMILES: C[C@@H](Oc1ccc2[nH]nc(-c3cnc(N4CCNCC4)c(F)c3)c2c1)c1c(Cl)cncc1Cl]

This example was synthesized using the procedure for example 1 using 2-chloro-3-fluoro-5-(4,4,5,5-tetramethyl-1,3,2-dioxaborolan-2-yl)pyridine and BOC-piperazine to give a white solid. Analysis: LCMS: m/z=487.0 (M+H); $^1$H NMR (400 MHz, CDCl$_3$) δ 8.50 (s, 1H), 8.44 (s, 2H), 7.66 (dd, J=1.7, 14.1 Hz, 1H), 7.38 (d, J=8.9 Hz, 1H), 7.19 (d, J=2.0 Hz, 1H), 7.15 (dd, J=2.2, 9.0 Hz, 1H), 6.06 (q, J=6.6 Hz, 1H), 3.61-3.53 (m, 4H), 3.12-3.01 (m, 4H), 1.83 (d, J=6.7 Hz, 3H).

Example 11. 5-[(1R)-1-(3,5-dichloro-4-pyridyl)ethoxy]-3-(2-piperazin-1-ylpyrimidin-5-yl)-1H-indazole

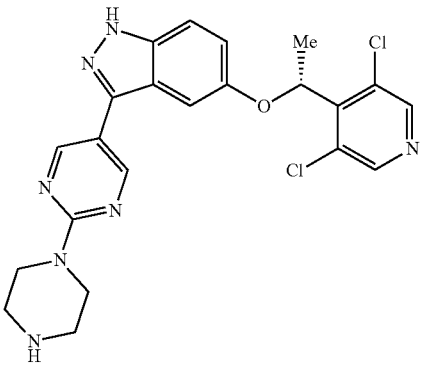

Example 11 was synthesized using tert-butyl 4-[5-(4,4,5,5-tetramethyl-1,3,2-dioxaborolan-2-yl)pyrimidin-2-yl]piperazine-1-carboxylate and the procedure for example 2 to give an off-white solid (150 mg, 64% yield). Analysis: LCMS: m/z=470.1 (M+H); $^1$H NMR (400 MHz, DMSO-d6)

δ 13.11 (br s, 1H), 8.75 (s, 2H), 8.57 (s, 2H), 7.47 (d, J=8.9 Hz, 1H), 7.24 (d, J=2.0 Hz, 1H), 7.09 (dd, J=2.2, 9.0 Hz, 1H), 6.14 (q, J=6.6 Hz, 1H), 3.82-3.67 (m, 4H), 2.87-2.68 (m, 4H), 1.75 (d, J=6.7 Hz, 3H).

Example 12. 4-[5-[5-[(1R)-1-(3,5-dichloro-4-pyridyl)ethoxy]-1H-indazol-3-yl]-2-pyridyl]piperazine-1-carboxamide

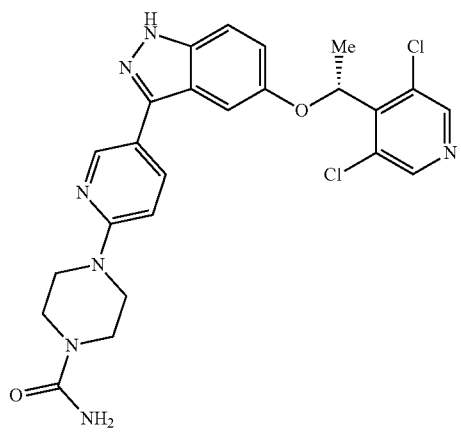 [SMILES: C[C@@H](Oc1ccc2[nH]nc(-c3ccc(N4CCN(C(N)=O)CC4)nc3)c2c1)c1c(Cl)cncc1Cl]

(R)-4-(5-(5-(1-(3,5-Dichloropyridin-4-yl)ethoxy)-1H-indazol-3-yl)pyridin-2-yl)piperazine-1-carboxamide. (Trimethylsilyl)isocyanate (66 μL, 0.49 mmol, 1.1 equiv) and triethylamine (68 μL, 0.49 mmol, 1.1 equiv) were sequentially added to a solution of example 2 (208 mg, 0.45 mmol, 1 equiv) in anhydrous THF (5 mL) at room temperature. After stirring for 20 hours, the volatiles were removed under reduced pressure and the crude product was pre-absorbed on Celite (0.5 g) then purified on Interchim automated chromatography system (RediSep Rf Gold HP C18, 15.5 g cartridge), eluting with a gradient of 0 to 100% acetonitrile in water. The fractions containing product were collected and lyophilized to give a white solid (36.0 mg, 16% yield). Analysis: LCMS: m/z=512.2 (M+H); $^1$H NMR (400 MHz, DMSO-d6) δ 13.02 (br s, 1H), 8.60 (s, 2H), 8.56 (d, J=2.0 Hz, 1H), 7.87 (dd, J=2.4, 8.8 Hz, 1H), 7.46 (d, J=8.9 Hz, 1H), 7.16 (d, J=2.1 Hz, 1H), 7.09 (dd, J=2.3, 9.0 Hz, 1H), 7.01 (d, J=8.9 Hz, 1H), 6.14-6.02 (m, 3H), 3.62-3.50 (m, 5H), 3.50-3.39 (m, 4H), 1.76 (d, J=6.6 Hz, 3H).

Example 13. [4-[5-[5-[(1R)-1-(3,5-Dichloro-4-pyridyl)ethoxy]-1H-indazol-3-yl]-3-fluoro-2-pyridyl]piperazin-1-yl]-(4-methylpiperazin-1-yl)methanone

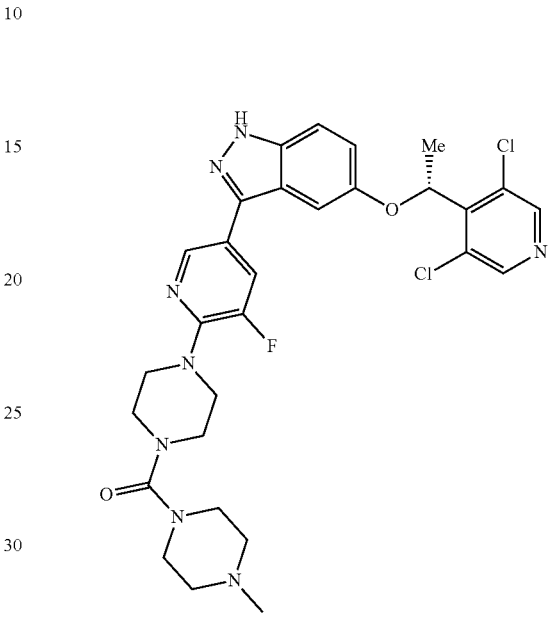

(R)-(4-(5-(5-(1-(3,5-Dichloropyridin-4-yl)ethoxy)-1H-indazol-3-yl)-3-fluoropyridin-2-yl)piperazin-1-yl)(4-methylpiperazin-1-yl)methanone. Triethylamine (21.6 μL, 0.156 mmol, 2.0 equiv) and 4-methylpiperazine-1-carbonyl chloride hydrochloride (17.6 mg, 0.089 mmol, 1.0 equiv) were sequentially added to a solution of example 10 (43 mg, 0.089 mmol, 1 equiv) in anhydrous THF (5 mL) at room temperature. After stirring for 1-hour, additional triethylamine (21.6 μL, 0.156 mmol, 2.0 equiv) and 4-methylpiperazine-1-carbonyl chloride hydrochloride (17.6 mg, 0.089 mmol, 1.0 equiv) were added and the reaction was stirred at room temperature for 20 hours. The volatiles were removed under reduced pressure. The crude product was pre-absorbed on Celite (0.5 g) and purified on an Interchim automated chromatography system (RediSep Rf Gold HP C18, 15.5 g cartridge), eluting with a gradient of 0 to 100% acetonitrile in water. Further purification on an Interchim automated chromatography system (Sorbtech 25 g silica gel cartridge), eluting with a gradient of 0 to 15% methanol in dichloromethane to give a white solid gave (12.0 mg, 22% yield). Analysis: LCMS: m/z=613.2 (M+H); $^1$H NMR (400 MHz, CDCl$_3$) δ 10.51 (br s, 1H), 8.50 (t, J=1.5 Hz, 1H), 8.43 (s, 2H), 7.69 (dd, J=1.8, 13.9 Hz, 1H), 7.37 (dd, J=0.4, 8.9 Hz, 1H), 7.17 (d, J=1.8 Hz, 1H), 7.14 (d, J=9.3 Hz, 1H), 6.05 (q, J=6.7 Hz, 1H), 3.62-3.57 (m, 4H), 3.47-3.42 (m, 4H), 3.40-3.34 (m, 4H), 2.44 (br t, J=4.8 Hz, 4H), 2.33 (s, 3H), 1.82 (d, J=6.7 Hz, 3H).

Example 14. 5-[(1R)-1-(3,5-Dichloro-4-pyridyl)ethoxy]-3-[2-(4-methylsulfonylpiperazin-1-yl)pyrimidin-5-yl]-1H-indazole

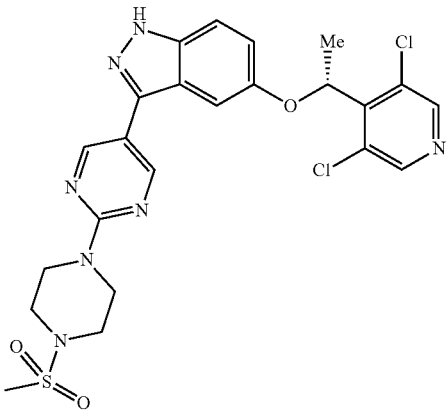 [SMILES: C[C@@H](Oc1ccc2[nH]nc(-c3cnc(N4CCN(S(C)(=O)=O)CC4)nc3)c2c1)c1c(Cl)cncc1Cl]

(R)-5-(1-(3,5-Dichloropyridin-4-yl)ethoxy)-3-(2-(4-(methylsulfonyl)piperazin-1-yl)pyrimidin-5-yl)-1H-indazole. Methanesulfonyl chloride (25 mg, 0.22 mmol, 1 equiv) in acetonitrile (1 mL) was added dropwise to a solution of example 11 (104 mg, 0.22 mmol, 1 equiv) in pyridine (10 mL) at 0° C. After stirring for 16 hours at room temperature, additional methanesulfonyl chloride (13 mg, 0.11 mmol, 0.5 equiv) in acetonitrile (0.5 mL) was added. After stirring for 70 hours, the reaction was concentrated under reduced pressure. The residue was dissolved in DMSO (6 mL) and purified on an InterChim automated chromatography system (RediSep Rf GOLD 100 g HP C18 column), eluting with a gradient of 0 to 100% acetonitrile in water to give an off-white solid (20 mg, 17% yield). Analysis: LCMS: m/z=548.1 (M+H); $^1$H NMR (400 MHz, DMSO-d6) δ=13.12 (br s, 1H), 8.82 (s, 2H), 8.57 (s, 2H), 7.48 (d, J=9.0 Hz, 1H), 7.26 (d, J=2.1 Hz, 1H), 7.11 (dd, J=2.3, 9.0 Hz, 1H), 6.15 (q, J=6.7 Hz, 1H), 4.00-3.91 (m, 4H), 3.27-3.22 (m, 4H), 2.92 (s, 3H), 1.76 (d, J=6.6 Hz, 3H).

Example 15. [4-[5-[5-[(1R)-1-(3,5-dichloro-4-pyridyl)ethoxy]-1H-indazol-3-yl]pyrimidin-2-yl]piperazin-1-yl]-(4-methylpiperazin-1-yl)methanone

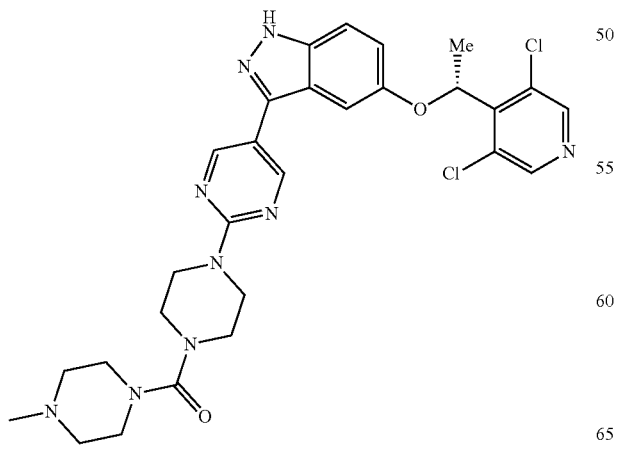

4-Methylpiperazine-1-carbonyl chloride (44 mg, 0.22 mmol, 1 equiv) was added a solution of example 11 (104 mg, 0.22 mmol, 1 equiv) in pyridine (10 mL) at room temperature. After stirring for 16 hours, the mixture was concentrated under reduced pressure. The residue was dissolved in DMSO (6 mL) and purified on an InterChim automated chromatography system ((RediSep Rf GOLD 100 g HP C18 column), eluting with a gradient of 0 to 100% acetonitrile in water to give an off-white solid (30 mg, 23% yield). Analysis: LCMS: m/z=596.2 (M+H); $^1$H NMR (400 MHz, DMSO-d6) δ 13.05 (br s, 1H), 8.79 (s, 2H), 8.57 (s, 2H), 7.48 (d, J=9.2 Hz, 1H), 7.25 (d, J=2.1 Hz, 1H), 7.10 (dd, J=2.3, 9.0 Hz, 1H), 6.14 (q, J=6.7 Hz, 1H), 3.88-3.79 (m, 4H), 3.29-3.25 (m, 4H), 3.24-3.17 (m, 4H), 2.31 (br t, J=4.6 Hz, 4H), 2.19 (s, 3H), 1.76 (d, J=6.6 Hz, 3H).

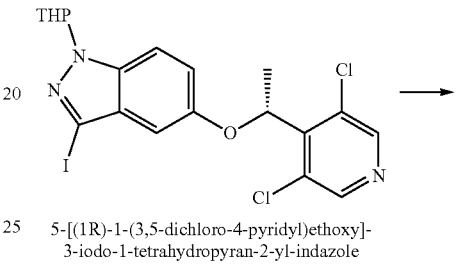

5-[(1R)-1-(3,5-dichloro-4-pyridyl)ethoxy]-3-iodo-1-tetrahydropyran-2-yl-indazole

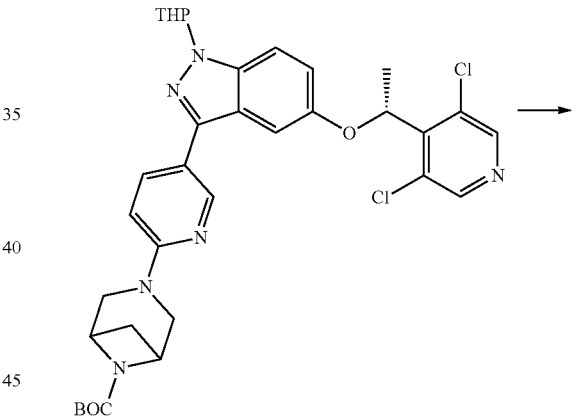

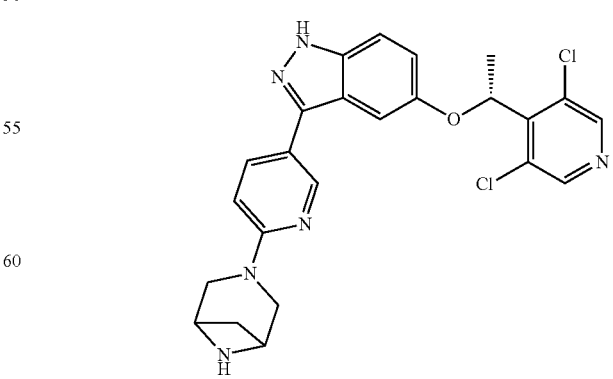

Example 16

Example 16. 3-[6-(3,6-Diazabicyclo[3.1.1]heptan-3-yl)-3-pyridyl]-5-[(1R)-1-(3,5-dichloro-4-pyridyl)ethoxy]-1H-indazole

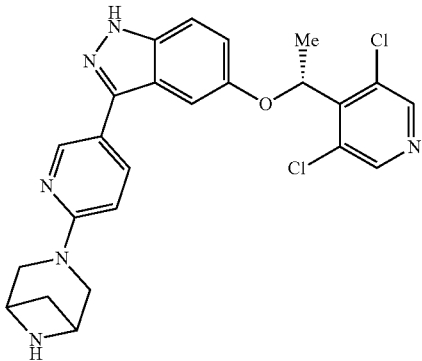 [SMILES: C[C@@H](Oc1ccc2[nH]nc(-c3ccc(N4CC5CC(C4)N5)nc3)c2c1)c1c(Cl)cncc1Cl]

Step 1. tert-Butyl 3-(5-(5-((R)-1-(3,5-Dichloropyridin-4-yl)ethoxy)-1-(tetrahydro-2H-pyran-2-yl)-1H-indazol-3-yl)pyridin-2-yl)-3,6-diazabicyclo[3.1.1]heptane-6-carboxylate. A solution of 5-[(1R)-1-(3,5-dichloro-4-pyridyl)ethoxy]-3-iodo-1-tetrahydropyran-2-yl-indazole (170 mg, 0.33 mmol, 1.0 equiv), tert-butyl 3-[5-(4,4,5,5-tetramethyl-1,3,2-dioxaborolan-2-yl)-2-pyridyl]-3,6-diazabicyclo[3.1.1]heptane-6-carboxylate (128 mg, 0.40 mmol, 1.2 equiv), [1,1' bis(diphenylphosphino)ferrocene]dichloropalladium(II) (24 mg, 0.04 mmol, 0.1 equiv) and potassium carbonate (91 mg, 0.66 mmol, 2.0 equiv) in 1,4-dioxane (10 mL) and water (1 mL) was sparged with nitrogen for 15 minutes and then heated at 90° C. for 16 hours. After cooling to room temperature, the reaction mixture was filtered through Celite and the filtrate was concentrated under reduced pressure. The residue was purified on a Büchi automated chromatography system (Sorbtech 25 g silica gel column), eluting with a gradient of 0 to 70% ethyl acetate in heptanes to give a white solid (80 mg, 36% yield). Analysis: LCMS: m/z=665.1 (M+H).

Step 2. 3-(5-(5-((R)-1-(3,5-Dichloropyridin-4-yl)ethoxy)-1H-indazol-3-yl)pyridin-2-yl)-3,6-diazabicyclo[3.1.1]heptane. A solution of product step 1 (80 mg, 0.13 mmol, 1.0 equiv) in 1,4-dioxane (2.0 mL) and water (0.5 mL) was treated with 4M HCl in 1,4-dioxane (0.65 mL, 2.65 mmol, 20.0 equiv) and heated at 100° C. in a CEM microwave reactor for 1 hour. After cooling to room temperature, the volatiles were removed under reduced pressure. The residue was dissolved in 20% methanol in dichloromethane (10 mL) followed by the addition of MP-carbonate resin (1.0 g). After stirring at room temperature for 1 hour, the suspension was filtered, and the filtrate was concentrated under reduced pressure. The residue was purified on a Büchi automated chromatography system (RediSep Rf Gold HP C18, 50 g column), eluting with a gradient of 0 to 100% acetonitrile in water. Product containing fractions were lyophilized to give an off-white solid (8 mg, 14% yield). Analysis: LCMS: m/z=481.1 (M+H); $^1$H NMR (400 MHz, METHANOL-d4) δ 8.55 (dd, J=0.5, 2.3 Hz, 1H), 8.46 (s, 2H), 7.97 (ddd, J=2.0, 4.5, 8.6 Hz, 2H), 7.48-7.35 (m, 2H), 7.17 (dd, J=2.3, 9.0 Hz, 1H), 7.11 (d, J=2.1 Hz, 1H), 6.87 (d, J=8.4 Hz, 1H), 6.12 (q, J=6.6 Hz, 1H), 4.52 (br d, J=6.1 Hz, 2H), 4.12-3.99 (m, 4H), 3.18-3.06 (m, 1H), 1.97 (d, J=10.3 Hz, 1H), 1.82 (d, J=6.7 Hz, 3H).

Example 17. 5-[(1R)-1-(3,5-Dichloro-4-pyridyl)ethoxy]-3-[5-fluoro-6-(4-methylsulfonyl-piperazin-1-yl)-3-pyridyl]-1H-indazole

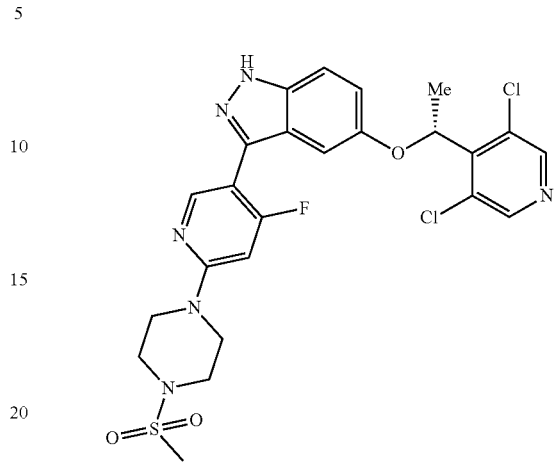

Step 1. 3-(6-Chloro-4-fluoropyridin-3-yl)-5-((R)-1-(3,5-dichloropyridin-4-yl)ethoxy)-1-(tetrahydro-2H-pyran-2-yl)-1H-indazole. A solution of 5-[(1R)-1-(3,5-dichloro-4-pyridyl)ethoxy]-3-iodo-1-tetrahydropyran-2-yl-indazole (0.4 g, 0.77 mmol, 1 equiv) and 2-chloro-4-fluoro-5-(4,4,5,5-tetramethyl-1,3,2-dioxaborolan-2-yl)pyridine (0.258 g, 1.0 mmol, 1.3 equiv) in 20 to 1 mixture of 1,4-dioxane and water (10 mL) was sparged with nitrogen for 15 minutes. Potassium carbonate (0.28 g, 2.0 mmol, 2.6 equiv) and (1,1'-bis(diphenylphosphino)ferrocene)palladium(II) dichloride (56 mg, 0.077 mmol, 0.01 equiv) were added and the reaction mixture was sparged with nitrogen for an additional 5 minutes. The reaction was heated at 90° C. for 16 h. After cooling to room temperature, the reaction was concentrated under reduced pressure and diluted with saturated brine (20 mL) and dichloromethane (20 mL). The layers were separated and the organic layer was dried over sodium sulfate, filtered and concentrated under reduced pressure. The crude product was pre-absorbed on silica gel (1 g) and purified on an Interchim automated chromatography system (Sorbtech 40 g silica gel cartridge), eluting with a gradient of 5 to 50% ethyl acetate in heptanes to give a white solid (360 mg, 89% yield). Analysis: LCMS: m/z=521.8 (M+H).

Step 2. tert-Butyl 4-(5-(5-((R)-1-(3,5-Dichloropyridin-4-yl)ethoxy)-1-(tetrahydro-2H-pyran-2-yl)-1H-indazol-3-yl)pyridin-2-yl)piperazine-1-carboxylate. A solution of step 1 product (360 mg, 0.69 mmol, 1 equiv), BOC-piperazine (193 mg, 1.04 mmol, 1.5 equiv), Xantphos (80 mg, 0.14 mmol, 0.2 equiv), tris(dibenzylideneacetone)dipalladium (O) (63 mg, 0.07 mmol, 0.1 equiv) and cesium carbonate (450 mg, 1.4 mmol, 2.0 equiv) in N,N-dimethylformamide (10 mL) was sparged with nitrogen for 10 minutes. After heating at 95° C. for 16 hours, the reaction was cooled to room temperature and filtered through Celite. The filtrate was concentrated under reduced pressure. The residue was purified on a Büchi automated chromatography system (Sorbtech 25 g silica gel column), eluting with a gradient of 0 to 15% methanol in dichloromethane to give a brown solid (107 mg, 23% yield). Analysis: LCMS: m/z=653.1 (M+H).

Step 3. (R)-5-(1-(3,5-Dichloropyridin-4-yl)ethoxy)-3-(4-fluoro-6-(piperazin-1-yl)pyridin-3-yl)-1H-indazole. A solution of step 2 product (90 mg, 0.14 mmol, 1 equiv) in 1,4-dioxane (2.0 mL) and water (0.2 mL) was treated with 4M HCl in 1,4-dioxane (0.7 mL, 2.68 mmol, 20 equiv) and heated at 100° C. in a CEM microwave reactor for 1 hour. The volatiles were removed under reduced pressure. The residue was dissolved in 20% methanol in dichloromethane (10 mL) followed by the addition of MP-carbonate (1.0 g). After stirring at room temperature for 1 hour, the suspension was filtered and the filtrate was concentrated under reduced pressure. The residue was purified on a Büchi automated chromatography system (RediSep Rf Gold HP C18, 25 g column), eluting with a gradient of 0 to 80% acetonitrile in water to give an off-white solid (15 mg, 20% yield). Analysis: LCMS: m/z=487.1 (M+H).

Step 4. (R)-5-(1-(3,5-Dichloropyridin-4-yl)ethoxy)-3-(4-fluoro-6-(4-(methylsulfonyl)piperazin-1-yl)pyridin-3-yl)-1H-indazole. Methanesulfonyl chloride (3 μL, 0.04 mmol, 1.5 equiv) was added to a solution of solution of step 3 product (15 mg, 0.03 mmol, 1.0 equiv) in pyridine (2.0 mL) at room temperature. After stirring for 16 hours, the volatiles were removed under reduced pressure. The residue was first purified on a Büchi automated chromatography system (RediSep Rf Gold HP C18, 50 g column), eluting with a gradient of 0 to 80% acetonitrile in water then repurified on a Teledyne ACCQPrep automated chromatography system (Waters Atlantis T3 Prep OBD column, 5 μm, 19×250 mm), eluting with a gradient of 0 to 80% acetonitrile in water with 0.1% formic acid. Product containing fractions were lyophilized to give a white solid (R)-ADE-163 (12 mg, 70% yield). Analysis: LCMS: m/z=565.1 (M+H); $^1$H NMR (400 MHz, CD3OD) δ 8.47 (s, 2H), 8.36 (d, J=10.8 Hz, 1H), 7.45 (d, J=9.0 Hz, 1H), 7.17 (dd, J=2.4, 9.0 Hz, 1H), 6.86 (t, J=2.4 Hz, 1H), 6.78 (d, J=13.7 Hz, 1H), 6.05 (q, J=6.7 Hz, 1H), 3.81-3.76 (m, 4H), 3.38-3.34 (m, 4H), 2.89 (s, 3H), 1.80 (d, J=6.6 Hz, 3H).

Example 18. 3-(6-Chloro-3-pyridyl)-5-[(1R)-1-(3,5-dichloro-4-pyridyl)ethoxy]-1H-indazole

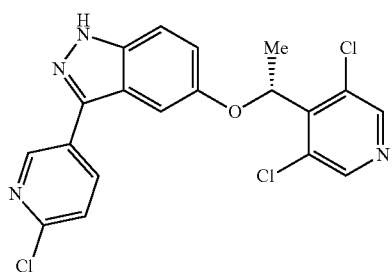 [SMILES: C[C@@H](Oc1ccc2[nH]nc(-c3ccc(Cl)nc3)c2c1)c1c(Cl)cncc1Cl]

5-[(1R)-1-(3,5-dichloro-4-pyridyl)ethoxy]-3-chloro-1-tetrahydropyran-2-yl-indazole was deprotected using conditions for example 1 step 4. Analysis: LCMS: m/z=421.1 (M+H); $^1$H NMR (400 MHz, DMSO) δ 13.42 (br s, 1H), 8.84 dd, J=0.6, 2.4 Hz, 1H), 8.59 (s, 2H), 8.21 (dd, J=2.6, 8.3 Hz, 1H), 7.67 (dd, J=0.6, 8.3 Hz, 1H), 7.54 (d, J=9.2 Hz, 1H), 7.24 d, J=2.2 Hz, 1H), 7.13 (dd, J=2.2, 9 Hz, 1H), 6.14 (q, J=6.6 Hz, 1H), 1.77 (d, J=6.6 Hz, 3H).

Example 19. 4-[5-[5-[(1R)-1-(3,5-Dichloro-4-pyridyl)ethoxy]-1H-indazol-3-yl]pyrimidin-2-yl]-N,N-dimethyl-piperazine-1-carboxamide

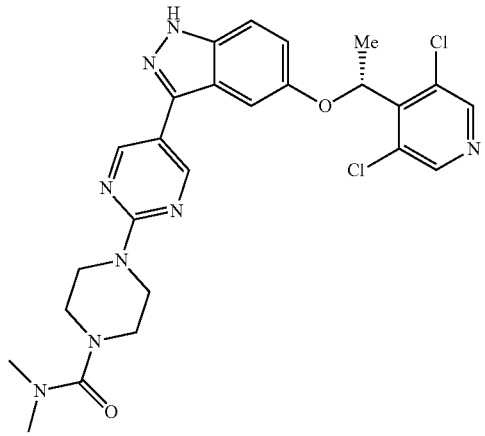 [SMILES: C[C@@H](Oc1ccc2[nH]nc(-c3cnc(N4CCN(C(=O)N(C)C)CC4)nc3)c2c1)c1c(Cl)cncc1Cl]

4-[5-[5-[(1R)-1-(3,5-Dichloro-4-pyridyl)ethoxy]-1H-indazol-3-yl]pyrimidin-2-yl]-N,N-dimethyl-piperazine-1-carboxamide. Triethylamine (65 mg, 0.638 mmol, 3 equiv) and N,N-dimethylcarbamoyl chloride (23 mg, 0.213 mmol, 1 equiv) in acetonitrile (1 mL) were added dropwise to a solution of example 11 (100 mg, 0.213 mmol, 1 equiv) in THF (10 mL) at room temperature. After stirring for 16 hours, the mixture was concentrated under reduced pressure. The residue was dissolved in DMSO (6 mL) and purified on an InterChim automated chromatography system (RediSep Rf GOLD 100 g HP C18 column), eluting with a gradient of 0 to 100% acetonitrile in water to give an off-white solid (40 mg, 35% yield). Analysis: LCMS: m/z=541.2 (M+H); $^1$H NMR (400 MHz, DMSO-d6) δ 13.13 (br s, 1H), 8.79 (s, 2H), 8.57 (s, 2H), 7.47 (d, J=9.0 Hz, 1H), 7.25 (d, J=2.1 Hz, 1H), 7.10 (dd, J=2.2, 9.0 Hz, 1H), 6.14 (q, J=6.7 Hz, 1H), 3.87-3.80 (m, 4H), 3.26-3.21 (m, 4H), 2.80 (s, 6H), 1.76 (d, J=6.6 Hz, 3H).

Example 20. 5-[(1R)-1-(3,5-dichloro-4-pyridyl)ethoxy]-3-[6-(6-methylsulfonyl-3,6-diazabicyclo[3.1.1]heptan-3-yl)-3-pyridyl]-1H-indazole

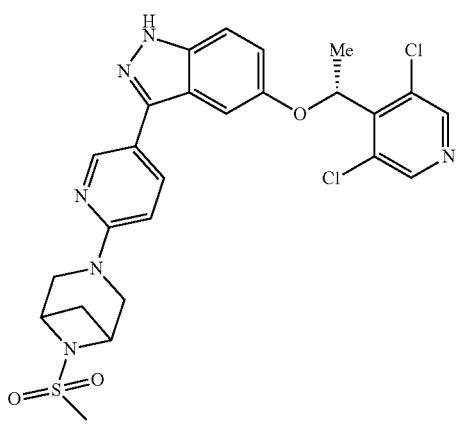 [SMILES: C[C@@H](Oc1ccc2[nH]nc(-c3ccc(N4CC5CC(C4)N5S(C)(=O)=O)nc3)c2c1)c1c(Cl)cncc1Cl]

5-[(1R)-1-(3,5-dichloro-4-pyridyl)ethoxy]-3-[6-(6-methylsulfonyl-3,6-diazabicyclo[3.1.1]heptan-3-yl)-3-pyridyl]-1H-indazole. Triethylamine (24.8 µL, 0.178 mmol, 1.2 equiv) and methanesulfonyl chloride (11.5 µL, 0.149 mmol, 1 equiv) were sequentially added to a solution of example 16 (71 mg, 0.149 mmol, 1 equiv) in anhydrous THF (2 mL) at room temperature. After stirring for 16 hours, additional methanesulfonyl chloride (2×11.5 µL, 0.149 mmol, 2 equiv) and triethylamine (24.8 µL, 0.178 mmol, 1.2 equiv) were added at 24 hours intervals and stirred in total for 72 hours. The volatiles were removed under reduced pressure and the crude product was pre-absorbed on Celite (0.5 g) then purified on Interchim automated chromatography system (RediSep Rf Gold HP C18, 15.5 g cartridge), eluting with a gradient of 0 to 100% acetonitrile in water. The fractions containing product were collected and lyophilized to give a white solid. Analysis: LCMS: m/z=559.1 (M+H); $^1$H NMR (400 MHz, CDCl$_3$) δ 8.71 (d, J=2.3 Hz, 1H), 8.43 (s, 2H), 7.97 (dd, J=2.1, 8.7 Hz, 1H), 7.35 (d, J=9.0 Hz, 1H), 7.26 (s, 1H), 7.24 (d, J=2.1 Hz, 1H), 7.13 (dd, J=1.9, 9.0 Hz, 1H), 6.64 (d, J=8.8 Hz, 1H), 6.05 (q, J=6.7 Hz, 1H), 4.57 (br d, J=6.2 Hz, 2H), 4.10 (br d, J=11.7 Hz, 2H), 3.88 (br d, J=11.7 Hz, 2H), 3.14-3.08 (m, 1H), 2.95 (s, 3H), 1.82 (d, J=6.6 Hz, 3H).

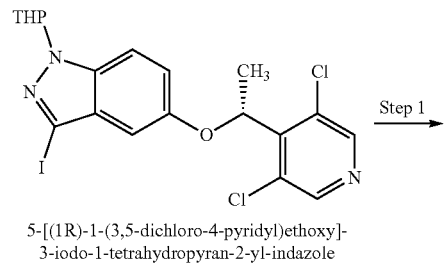

5-[(1R)-1-(3,5-dichloro-4-pyridyl)ethoxy]-
3-iodo-1-tetrahydropyran-2-yl-indazole

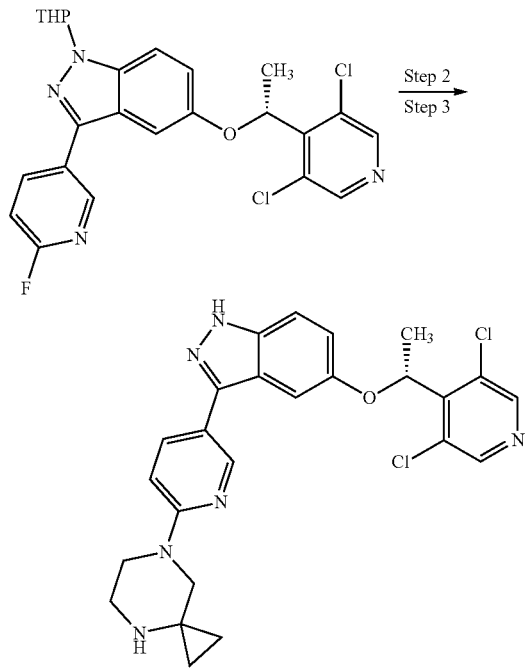

Example 21

Example 21. 3-[6-(4,7-diazaspiro[2.5]octan-7-yl)-3-pyridyl]-5-[(1R)-1-(3,5-dichloro-4-pyridyl)ethoxy]-1H-indazole

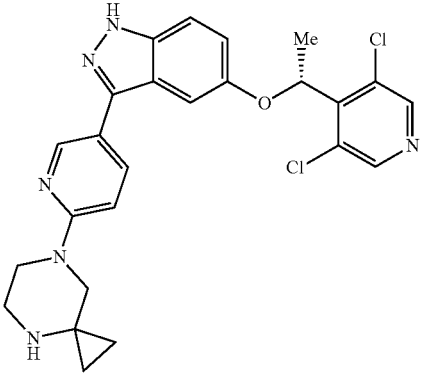 [SMILES: C[C@@H](Oc1ccc2[nH]nc(-c3ccc(N4CCNC5(CC5)C4)nc3)c2c1)c1c(Cl)cncc1Cl]

Step 1. (R)-5-(1-(3,5-Dichloropyridin-4-yl)ethoxy)-3-(6-fluoropyridin-3-yl)-1H-indazole. A solution of 5-[(1R)-1-(3,5-dichloro-4-pyridyl)ethoxy]-3-iodo-1-tetrahydropyran-2-yl-indazole (3.0 g, 5.80 mmol, 1.0 equiv), 2-fluoro-5-(4,4,5,5-tetramethyl-1,3,2-dioxaborolan-2-yl)pyridine (1.6 g, 6.96 mmol, 1.2 equiv), [1,1' bis(diphenylphosphino) ferrocene]dichloropalladium(II) (430 mg, 0.58 mmol, 0.1 equiv) and potassium carbonate (1.6 g, 11.66 mmol, 2.0 equiv) in 1,4-dioxane (30 mL) and water (3 mL) was sparged with nitrogen for 15 minutes and then heated at 100° C. for 16 hours. After cooling to room temperature, the reaction mixture was filtered through Celite and the filtrate was concentrated under reduced pressure. The residue was purified on a Büchi automated chromatography system (Sorbtech 40 g silica gel column), eluting with a gradient of 0 to 60% ethyl acetate in heptanes to give a white solid (2.5 g, 88% yield). Analysis: LCMS: m/z=487.1 (M+H).

Step 2. tert-Butyl 7-(5-(5-((R)-1-(3,5-dichloropyridin-4-yl)ethoxy)-1-(tetrahydro-2H-pyran-2-yl)-1H-indazol-3-yl)pyridin-2-yl)-4,7-diazaspiro[2.5]octane-4-carboxylate. A suspension of product step 1 (350 mg, 0.72 mmol, 1.0 equiv), tert-butyl 4,7-diazaspiro[2.5]octane-4-carboxylate (310 mg, 1.44 mmol, 2.0 equiv) and potassium carbonate (400 mg, 2.88 mmol, 4.0 equiv) in DMSO (5.0 mL) was heated at 120° C. in a sealed tube for 20 hours. After cooling to room temperature, the reaction mixture was filtered through Celite and the filtrate was concentrated under reduced pressure. The residue was purified on a Büchi automated chromatography system (RediSep Rf Gold HP C18, 50 g column), eluting with a gradient of 0 to 100% acetonitrile in water to give an off-white solid (417 mg, 87% yield). Analysis: LCMS: m/z=679.1 (M+H).

Step 3. 3-[6-(4,7-diazaspiro[2.5]octan-7-yl)-3-pyridyl]-5-[(1R)-1-(3,5-dichloro-4-pyridyl)ethoxy]-1H-indazole. A solution of step 2 product (25 mg, 0.04 mmol, 1.0 equiv) in 1,4-dioxane (1.0 mL) and water (0.4 mL) was treated with 4M HCl in 1,4-dioxane (0.2 mL, 0.75 mmol, 20.0 equiv) and heated at 100° C. in a microwave for 1 hour. After cooling to room temperature, the volatiles were removed under reduced pressure. The residue was dissolved in 20% methanol in dichloromethane (10 mL) followed by the addition of MP-carbonate (1.0 g). After stirring at room temperature for 1 hour, the suspension was filtered, and the filtrate was concentrated under reduced pressure. The residue was purified on a Büchi automated chromatography system (RediSep Rf Gold HP C18, 50 g column), eluting with a gradient of 0 to 80% acetonitrile. Product fractions were lyophilized to give an off-white solid (7.5 mg, 20% yield). Analysis: LCMS: m/z=495.1 (M+H); $^1$H NMR (400 MHz, CD3OD) δ 8.50-8.44 (m, 3H), 7.88 (dd, J=2.4, 8.8 Hz, 1H), 7.43 (d, J=9.0 Hz, 1H), 7.16 (dd, J=2.3, 9.0 Hz, 1H), 7.11 (d, J=2.0 Hz, 1H), 6.91 (d, J=8.4 Hz, 1H), 6.13 (q, J=6.6 Hz, 1H), 3.66-3.62 (m, 2H), 3.51 (s, 2H), 3.08-3.02 (m, 2H), 1.82 (d, J=6.6 Hz, 3H), 0.72-0.65 (m, 4H).

Example 22. 5-[(1R)-1-(3,5-dichloro-4-pyridyl)ethoxy]-3-[6-(4-methylsulfonyl-4,7-diazaspiro[2.5]octan-7-yl)-3-pyridyl]-1H-indazole

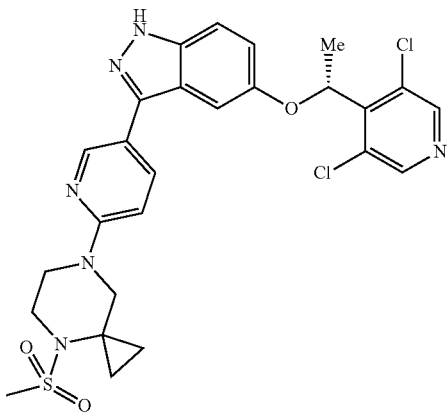 [SMILES: C[C@@H](Oc1ccc2[nH]nc(-c3ccc(N4CCN(S(C)(=O)=O)C5(CC5)C4)nc3)c2c1)c1c(Cl)cncc1Cl]

Methanesulfonyl chloride (21 µL, 0.26 mmol, 1.5 equiv) was added to a solution of example 21 (100 mg, 0.17 mmol, 1.0 equiv) in pyridine (5.0 mL) at room temperature. After stirring for 16 hours additional methanesulfonyl chloride (21 µL, 0.26 mmol, 1.5 equiv) along with N,N-diisopropylethylamine (0.1 mL) were added at room temperature. After stirring for 2 additional hours, the volatiles were removed under reduced pressure. The residue was first purified on a Büchi automated chromatography system (RediSep Rf Gold HP C18, 50 g column), eluting with a gradient of 0 to 80% acetonitrile in water, then repurified on a Büchi automated chromatography system (RediSep Rf Gold HP C18, 4 g column), eluting with a gradient of 0 to 80% acetonitrile in water. Product containing fractions were lyophilized to give an off-white solid (16.0 mg, 16% yield). Analysis: LCMS: m/z=573.2 (M+H); $^1$H NMR (400 MHz, CD3OD) δ 8.48 (s, 3H), 7.90 (dd, J=2.4, 8.9 Hz, 1H), 7.44 (d, J=8.9 Hz, 1H), 7.17 (dd, J=2.3, 9.0 Hz, 1H), 7.11 (d, J=1.7 Hz, 1H), 6.93 (dd, J=0.5, 8.9 Hz, 1H), 6.13 (q, J=6.6 Hz, 1H), 3.80-3.74 (m, 4H), 3.04 (s, 3H), 1.82 (d, J=6.7 Hz, 3H), 1.29 (s, 3H), 1.23-1.20 (m, 2H), 1.00-0.96 (m, 2H).

Example 23. (R)-7-(5-(5-(1-(3,5-dichloropyridin-4-yl)ethoxy)-1H-indazol-3-yl)pyridin-2-yl)-N,N-dimethyl-4,7-diazaspiro[2.5]octane-4-carboxamide

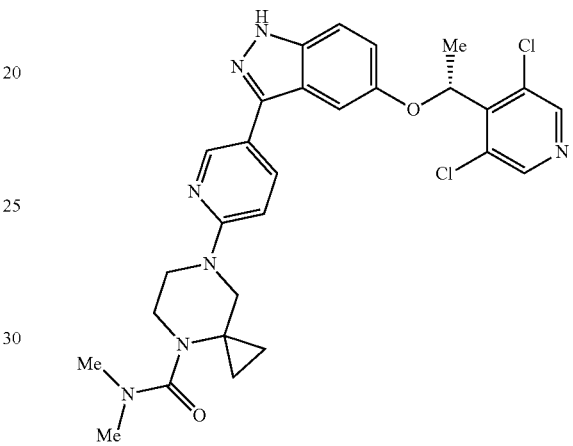

Dimethylcarbamic chloride (23 µL, 0.26 mmol, 1.5 equiv) was added to a solution of example 21 (100 mg, 0.17 mmol, 1.0 equiv) in pyridine (5.0 mL) at room temperature. After stirring for 16 hours, additional dimethylcarbamic chloride (23 µL, 0.26 mmol, 1.5 equiv) along with N,N-diisopropylethylamine (0.1 mL) were added at room temperature. After stirring for 2 additional hours, the volatiles were removed under reduced pressure. The residue was first purified on a Büchi automated chromatography system (RediSep Rf Gold HP C18, 50 g column), eluting with a gradient of 0 to 80% acetonitrile in water then repurified on a Büchi automated chromatography system (RediSep Rf Gold HP C18, 4 g column), eluting with a gradient of 0 to 80% acetonitrile in water to give an off white solid (5 mg, 5% yield). Analysis: LCMS: m/z=566.3 (M+H); $^1$H NMR (400 MHz, CD3OD) δ 8.52 (dd, J=0.6, 2.4 Hz, 1H), 8.47 (s, 2H), 7.93 (dd, J=2.4, 8.9 Hz, 1H), 7.88 (dd, J=0.4, 9.2 Hz, 1H), 7.24 (dd, J=2.4, 9.1 Hz, 1H), 7.16 (d, J=2.3 Hz, 1H), 6.92 (dd, J=0.5, 8.9 Hz, 1H), 6.16 (q, J=6.6 Hz, 1H), 3.70-3.65 (m, 2H), 3.55 (s, 2H), 3.24 (s, 6H), 3.08-3.01 (m, 2H), 1.83 (d, J=6.7 Hz, 3H), 0.76-0.61 (m, 4H).

Example 24. 7-[5-[5-[(1R)-1-(3,5-dichloro-4-pyridyl)ethoxy]-1H-indazol-3-yl]-2-pyridyl]-4,7-diazaspiro[2.5]octane-4-carboxamide

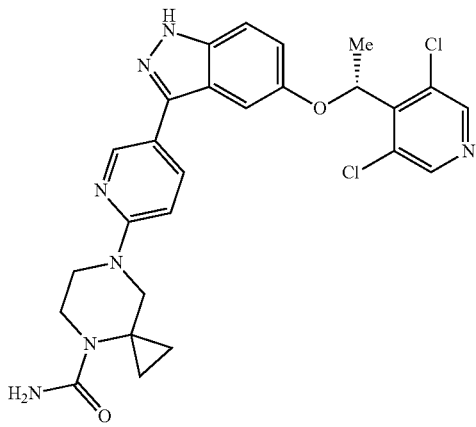 [SMILES: C[C@@H](Oc1ccc2[nH]nc(-c3ccc(N4CCN(C(N)=O)C5(CC5)C4)nc3)c2c1)c1c(Cl)cncc1Cl]

Step 1. 4-Nitrophenyl (R)-7-(5-(5-(1-(3,5-dichloropyridin-4-yl)ethoxy)-1H-indazol-3-yl)pyridin-2-yl)-4,7-diazaspiro[2.5]octane-4-carboxylate. p-Nitrophenylchloroformate (48.8 mg, 0.242 mmol, 1.1 equiv) and triethylamine (150 µL, 1.1 mmol, 5 equiv) were sequentially added to a solution of example 21 (119 mg, 0.22 mmol, 1 equiv) in anhydrous THF (3 mL) at room temperature. After stirring overnight, the brown solution was diluted with water (10 mL) and ethyl acetate (10 mL). The layers were separated and the aqueous layer was extracted with ethyl acetate (3×5 mL). The combined organic layers were dried over sodium sulfate and concentrated under reduced pressure. The residue was purified on an Interchim automated chromatography system (RediSep Rf Gold HP C18, 4 g column), eluting with a gradient of 0 to 100% acetonitrile in water to give a white solid (40 mg, 28% yield). Analysis: LCMS: m/z=660.1 (M+H).

Step 2. 7-[5-[5-[(1R)-1-(3,5-dichloro-4-pyridyl)ethoxy]-1H-indazol-3-yl]-2-pyridyl]-4,7-diazaspiro[2.5]octane-4-carboxamide. Concentrated ammonium hydroxide (71 µL, 0.515 mmol, 10 equiv) was added to a solution of product step 1 (34 mg, 0.0515 mmol, 1 equiv) in DMSO (2 mL). The yellow solution was heated at 90° C. overnight, cooled to room temperature and diluted with water (5 mL) and ethyl acetate (5 mL). The layers were separated and the aqueous layer was extracted with ethyl acetate (3×5 mL). The combined organic layers were dried over sodium sulfate and concentrated under reduced pressure. The residue was purified on Interchim automated chromatography system (RediSep Rf Gold HP C18, 4 g column), eluting with a gradient of 0 to 100% acetonitrile in water to give a white solid (40 mg, 28% yield). Analysis: LCMS: m/z=538.2 (M+H). $^1$H NMR (400 MHz, CDCl$_3$) δ 10.12 (br s, 1H), 8.64 (d, J=1.8 Hz, 1H), 8.42 (s, 2H), 7.93 (dd, J=2.3, 8.8 Hz, 1H), 7.36 (d, J=9.0 Hz, 1H), 7.21 (d, J=2.2 Hz, 1H), 7.13 (dd, J=2.3, 9.0 Hz, 1H), 6.72 (d, J=8.4 Hz, 1H), 6.05 (q, J=6.6 Hz, 1H), 5.08 (s, 2H), 3.85 (br s, 2H), 3.61 (s, 4H), 1.81 (d, J=6.7 Hz, 3H), 1.14-1.05 (m, 4H).

Example 25. 5-[(1R)-1-(3,5-Dichloro-4-pyridyl)ethoxy]-3-(6-fluoro-3-pyridyl)-1H-indazole

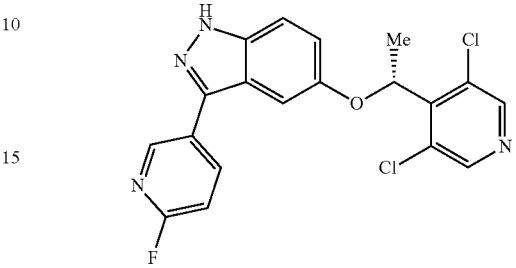

Step 1. (R)-5-(1-(3,5-Dichloropyridin-4-yl)ethoxy)-3-iodo-1H-indazole. A mixture of 5-[(1R)-1-(3,5-dichloro-4-pyridyl)ethoxy]-3-iodo-1-tetrahydropyran-2-yl-indazole (1.0 g, 1.93 mmol, 1 equiv) in dichloromethane (10 mL) was treated with trifluoroacetic acid (3 mL, 39.2 mmol, 20 equiv) at room temperature for 24 hours. The mixture was concentrated under reduced pressure. The residue was dissolved in dichloromethane (100 mL), washed with saturated sodium bicarbonate (100 mL), dried over sodium sulfate, filtered and concentrated under reduced pressure. The product was dried at room temperature under vacuum overnight to give an orange solid (1.05 g), which was used subsequently. Analysis: LCMS (ESI) m/z=434 (M+H); $^1$H NMR (400 MHz, DMSO-d6) δ 13.37 (br s, 1H), 8.60 (s, 2H), 7.46 (d, J=8.9 Hz, 1H), 7.13 (dd, J=2.4, 9.0 Hz, 1H), 6.59 (d, J=2.3 Hz, 1H), 6.07 (q, J=6.6 Hz, 1H), 1.75 (d, J=6.6 Hz, 3H).

Step 2. (R)-5-(1-(3,5-Dichloropyridin-4-yl)ethoxy)-3-(6-fluoropyridin-3-yl)-1H-indazole. A solution of product step 1 (1.0 g, 2.3 mmol, 1 equiv) and 2-fluoro-5-(4,4,5,5-tetramethyl-1,3,2-dioxaborolan-2-yl)pyridine (0.67 g, 2.995 mmol, 1.3 equiv) in 20 to 1 mixture of 1,4-dioxane and water (21 mL) was sparged with nitrogen for 15 minutes. Potassium carbonate (0.825 g, 5.98 mmol, 2.6 equiv) and (1,1'-bis(diphenylphosphino) ferrocene)palladium(II) dichloride (168 mg, 0.23 mmol, 0.01 equiv) were added and the reaction mixture was sparged with nitrogen for an additional 5 minutes. The reaction was heated at 90° C. for 2 hours. After cooling to room temperature, the reaction was concentrated under reduced pressure and diluted with saturated brine (30 mL) and dichloromethane (30 mL). The layers were separated and the organic layer was dried over sodium sulfate, filtered and concentrated under reduced pressure. The residue was absorbed onto silica gel (2 g) and purified on an Interchim automated chromatography system (Sorbtech 40 g silica gel cartridge), eluting with a gradient of 20 to 80% ethyl acetate in heptanes to give a yellow solid (0.42 g, 45% yield). Analysis: LCMS (ESI) m/z=403.1 (M+H); $^1$H NMR (400 MHz, CDCl$_3$) δ 10.55 (br s, 1H), 8.68 (d, J=2.1 Hz, 1H), 8.43 (s, 2H), 8.24 (dt, J=2.4, 8.1 Hz, 1H), 7.39 (dd, J=0.8, 8.7 Hz, 1H), 7.20-7.14 (m, 2H), 7.06 (dd, J=2.8, 8.4 Hz, 1H), 6.06 (q, J=6.7 Hz, 1H), 1.82 (d, J=6.6 Hz, 3H).

Example 26. 8-[5-[5-[(1R)-1-(3,5-dichloro-4-pyridyl)ethoxy]-1H-indazol-3-yl]-2-pyridyl]-1-oxa-8-azaspiro[4.5]decane

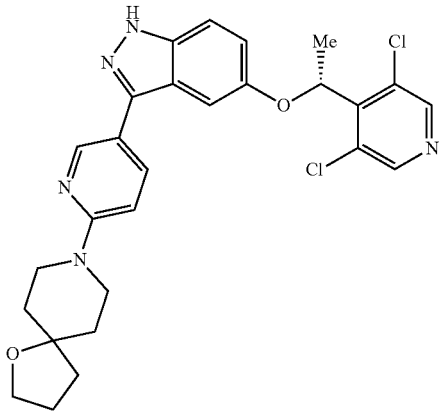 [SMILES: C[C@@H](Oc1ccc2[nH]nc(-c3ccc(N4CCC5(CCCO5)CC4)nc3)c2c1)c1c(Cl)cncc1Cl]

Step 1. 8-(5-(5-((R)-1-(3,5-Dichloropyridin-4-yl)ethoxy)-1-(tetrahydro-2H-pyran-2-yl)-1H-indazol-3-yl)pyridin-2-yl)-1-oxa-8-azaspiro[4.5]decane. A suspension of 5-[(1R)-1-(3,5-dichloro-4-pyridyl)ethoxy]-3-(6-fluoro-3-pyridyl)-1-tetrahydropyran-2-yl-indazole (100 mg, 0.21 mmol, 1.0 equiv), 1-oxa-8-azaspiro[4.5]decane (110 mg, 0.42 mmol, 3.0 equiv) and potassium carbonate (145 mg, 1.05 mmol, 5.0 equiv) in 1-methyl-2-pyrrolidone (5 mL) was heated in a sealed tube at 120° C. for 16 hours. The reaction mixture was cooled to room temperature and absorbed over celite under reduced pressure. The residue was purified on a Büchi automated chromatography system (RediSep Rf Gold HP C18, 50 g column), eluting with a gradient of 0 to 100% acetonitrile in water to give a white solid (105 mg, 84% yield). Analysis: LCMS (ESI) m/z=608.1 (M+H), Step 2. (R)-8-(5-(5-(1-(3,5-Dichloropyridin-4-yl)ethoxy)-1H-indazol-3-yl)pyridin-2-yl)-1-oxa-8-azaspiro[4.5]decane. A solution of step 1 product (105 mg, 0.18 mmol, 1.0 equiv) in 1,4-dioxane (2.0 mL) and water (0.1 mL) was treated with 4M HCl in 1,4-dioxane (0.86 mL, 3.45 mmol, 20.0 equiv) and heated at 100° C. in a microwave for 1 hour. After cooling to room temperature, the volatiles were removed under reduced pressure. The residue was dissolved in 20% methanol in dichloromethane (10 mL) followed by the addition of MP-carbonate resin (1.0 g). After stirring at room temperature for 1 hour, the suspension was filtered and the filtrate was concentrated under reduced pressure. The residue was purified on a Büchi automated chromatography system (RediSep Rf Gold HP C18, 50 g column), eluting with a gradient of 0 to 80% acetonitrile in water. Product containing fractions were lyophilized to give a white solid (40.1 mg, 44% yield). Analysis: LCMS (ESI) m/z=524.2 (M+H); $^1$H NMR (400 MHz, DMSO-d6) δ 13.01 (br s, 1H), 8.60 (s, 2H), 8.53 (d, J=2.1 Hz, 1H), 7.83 (dd, J=2.4, 8.9 Hz, 1H), 7.46 (d, J=9.0 Hz, 1H), 7.16 (d, J=2.1 Hz, 1H), 7.08 (dd, J=2.3, 8.9 Hz, 1H), 6.98 (d, J=8.8 Hz, 1H), 6.10 (q, J=6.7 Hz, 1H), 3.80-3.73 (m, 4H), 3.58-3.51 (m, 2H), 1.94-1.86 (m, 2H), 1.76 (d, J=6.6 Hz, 3H), 1.74-1.68 (m, 2H), 1.61 (t, J=5.6 Hz, 4H).

Examples 27-34 were synthesized using the procedure for Example 26.

| Example 27<br>8-[5-[5-[(1R)-1-(3,5-dichloro-4-pyridyl)ethoxy]-1H-indazol-3-yl]-2-pyridyl]-2,8-diazaspiro[4.5]decan-1-one | 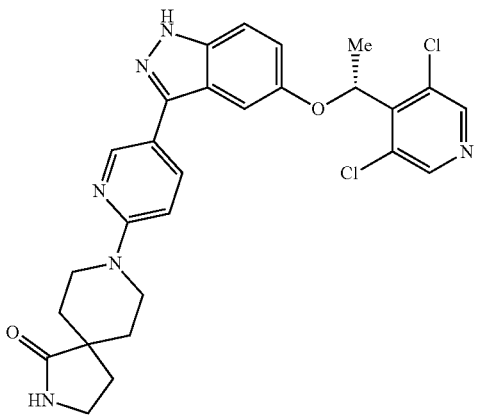 [SMILES: C[C@@H](Oc1ccc2[nH]nc(-c3ccc(N4CCC5(CCNC5=O)CC4)nc3)c2c1)c1c(Cl)cncc1Cl] | LCMS m/z = 537.2 (M + H); $^1$H NMR (400 MHz, CD$_3$OD) δ 8.48 (s, 3H), 7.89 (dd, J = 2.4, 8.8 Hz, 1H), 7.43 (d, J = 9.0 Hz, 1H), 7.16 (dd, J = 2.3, 8.9 Hz, 1H), 7.12 (d, J = 2.0 Hz, 1H), 6.98 (d, J = 8.8 Hz, 1H), 6.13 (q, J = 6.6 Hz, 1H), 4.55 (br s, 1H), 4.31 (td, J = 3.8, 13.7 Hz, 2H), 3.43-3.37 (m, 2H), 3.23-3.15 (m, 2H), 2.23 (t, J = 6.9 Hz, 2H), 1.99-1.91 (m, 2H), 1.82 (d, J = 6.7 Hz, 3H), 1.59 (br d, J = 13.3 Hz, 2H) |
| --- | --- | --- |
| Example 28<br>8-[5-[5-[(1R)-1-(3,5-dichloro-4-pyridyl)ethoxy]-1H-indazol-3-yl]-2-pyridyl]-2-oxa-8-azaspiro[4.5]decane | 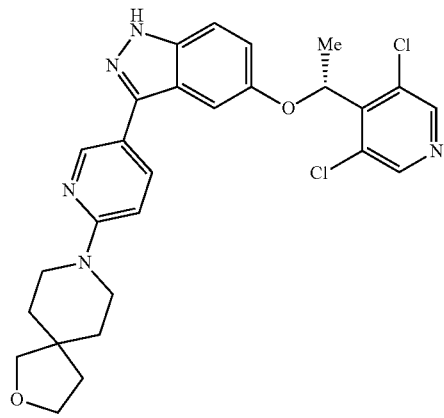 [SMILES: C[C@@H](Oc1ccc2[nH]nc(-c3ccc(N4CCC5(CCOC5)CC4)nc3)c2c1)c1c(Cl)cncc1Cl] | LCMS m/z = 524.2 (M + H); $^1$H NMR (400 MHz, CD3OD) δ 8.47 (d, J = 2.0 Hz, 1H), 8.45 (s, 2H), 7.85 (dd, J = 2.4, 8.9 Hz, 1H), 7.41 (d, J = 9.0 Hz, 1H), 7.13 (dd, J = 2.3, 9.0 Hz, 1H), 7.09 (d, J = 2.0 Hz, 1H), 6.87 (d, J = 8.7 Hz, 1H), 6.08 (q, J = 6.6 Hz, 1H), 3.88 (t, J = 7.2 Hz, 2H), 3.69-3.61 (m, 2H), 3.58 (s, 2H), 3.56-3.48 (m, 2H), 1.82 (t, J = 7.2 Hz, 2H), 1.79 (d, J = 6.6 Hz, 3H), 1.65 (t, J = 5.7 Hz, 4H) |

| | | |
|---|---|---|
| Example 29<br>8-[5-[5-[(1R)-1-(3,5-dichloro-4-pyridyl)ethoxy]-1H-indazol-3-yl]-2-pyridyl]-1,8-diazaspiro[4.5]decan-2-one | 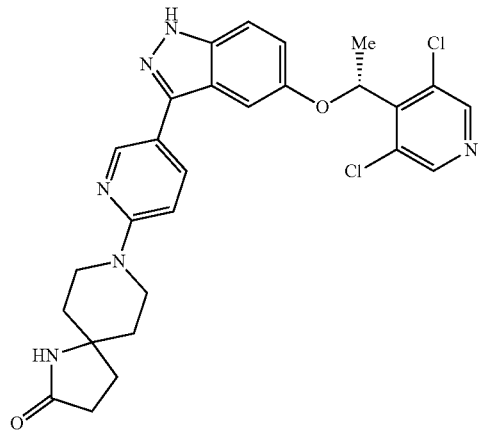 [SMILES: C[C@@H](Oc1ccc2[nH]nc(-c3ccc(N4CCC5(CCC(=O)N5)CC4)nc3)c2c1)c1c(Cl)cncc1Cl] | LCMS m/z = 537 (M + H); 1H NMR (400 MHz, DMSO-d6) δ 12.97 (s, 1H), 8.60 (s, 2H), 8.53 (d, J = 2.0 Hz, 1H), 8.01 (s, 1H), 7.84 (dd, J = 2.3, 8.9 Hz, 1H), 7.45 (d, J = 8.9 Hz, 1H), 7.16 (s, 1H), 7.09 (dd, J = 2.1, 9.0 Hz, 1H), 7.00 (d, J = 8.8 Hz, 1H), 6.10 (q, J = 6.5 Hz, 1H), 3.88-3.77 (m, 2H), 3.60-3.49 (m, 2H), 2.24 (t, J = 8.0 Hz, 2H), 1.93 (t, J = 8.0 Hz, 2H), 1.76 (d, J = 6.6 Hz, 3H), 1.64 (br t, J = 5.3 Hz, 4H). |
| Example 30<br>1-[5-[5-[(1R)-1-(3,5-dichloro-4-pyridyl)ethoxy]-1H-indazol-3-yl]-2-pyridyl]-1,4-diazepan-5-one | 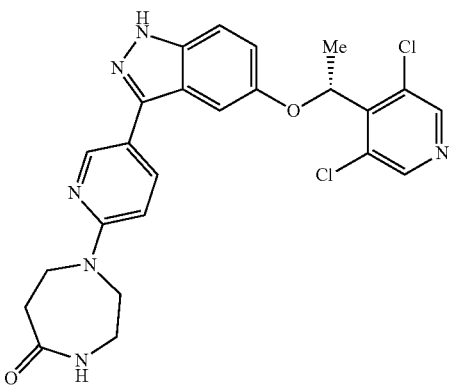 [SMILES: C[C@@H](Oc1ccc2[nH]nc(-c3ccc(N4CCNC(=O)CC4)nc3)c2c1)c1c(Cl)cncc1Cl] | LCMS m/z = 497 (M + H); 1H NMR (400 MHz, DMSO-d6) δ 12.98 (s, 1H), 8.60 (s, 2H), 8.54 (d, J = 2.2 Hz, 1H), 7.86 (dd, J = 2.4, 8.8 Hz, 1H), 7.64 (t, J = 5.3 Hz, 1H), 7.45 (d, J = 8.9 Hz, 1H), 7.17 (d, J = 2.0 Hz, 1H), 7.09 (dd, J = 2.3, 9.0 Hz, 1H), 6.97 (d, J = 8.9 Hz, 1H), 6.10 (q, J = 6.6 Hz, 1H), 3.89-3.81 (m, 4H), 3.24 (ddd, J = 1.3, 5.6, 7.2 Hz, 2H), 2.58-2.53 (m, 2H), 1.76 (d, J = 6.7 Hz, 3H) |
| Example 31<br>5-[(1R)-1-(3,5-dichloro-4-pyridyl)ethoxy]-3-[6-(2-isopropyl-2,6-diazaspiro[3.3]heptan-6-yl)-3-pyridyl]-1H-indazole | 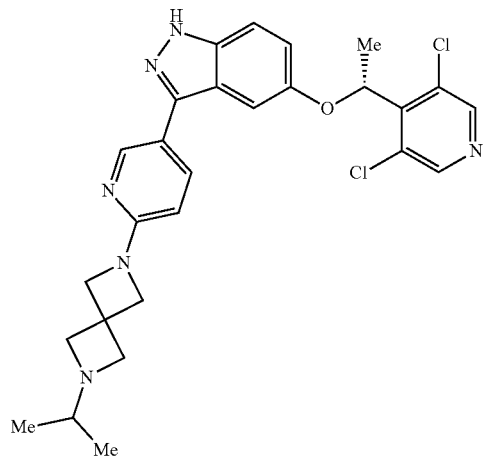 [SMILES: CC(C)N1CC2(CN(c3ccc(-c4n[nH]c5ccc(O[C@H](C)c6c(Cl)cncc6Cl)cc45)cn3)C2)C1] | LCMS m/z = 523.2 (M + H); 1H NMR (400 MHz, CDCl3) δ 10.40 (br s, 1H), 8.64 (d, J = 1.7 Hz, 1H), 8.41 (s, 2H), 7.89 (dd, J = 2.3, 8.6 Hz, 1H), 7.33 (d, J = 8.9 Hz, 1H), 7.24-7.20 (m, 1H), 7.11 (dd, J = 2.3, 9.0 Hz, 1H), 6.39 (d, J = 8.6 Hz, 1H), 6.04 (q, J = 6.7 Hz, 1H), 4.17 (s, 4H), 3.40 (s, 4H), 2.29 (spt, J = 6.2 Hz, 1H), 1.80 (d, J = 6.7 Hz, 3H), 0.96 (d, J = 6.2 Hz, 6H). |

| | | |
|---|---|---|
| Example 32<br>8-[5-[5-[(1R)-1-(3,5-dichloro-4-pyridyl)ethoxy]-1H-indazol-3-yl]-2-pyridyl]-2-methyl-2,8-diazaspiro[4.5]decane | 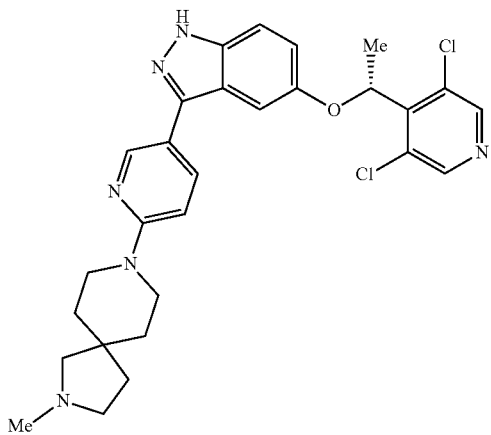 [SMILES: C[C@@H](Oc1ccc2[nH]nc(-c3ccc(N4CCC5(CCN(C)C5)CC4)nc3)c2c1)c1c(Cl)cncc1Cl] | LCMS m/z = 537 (M + H); 1H NMR (400 MHz, DMSO-d6) δ 12.97 (br s, 1H), 8.60 (s, 2H), 8.53 (d, J = 2.2 Hz, 1H), 8.19 (s, 1H), 7.83 (dd, J = 2.4, 8.9 Hz, 1H), 7.45 (d, J = 9.0 Hz, 1H), 7.15 (d, J = 2.0 Hz, 1H), 7.09 (dd, J = 2.2, 9.0 Hz, 1H), 6.97 (d, J = 8.9 Hz, 1H), 6.10 (q, J = 6.6 Hz, 1H), 3.67-3.51 (m, 4H), 2.74 (br t, J = 7.0 Hz, 2H), 2.59 (s, 2H), 2.40 (s, 3H), 1.78-1.70 (m, 5H), 1.66-1.55 (m, 4H), 19F NMR (376 MHz, DMSO-d6) δ −73.42 (s, 1F). |
| Example 33<br>8-[5-[5-[(1R)-1-(3,5-dichloro-4-pyridyl)ethoxy]-1H-indazol-3-yl]-2-pyridyl]-1-methyl-1,8-diazaspiro[4.5]decane | 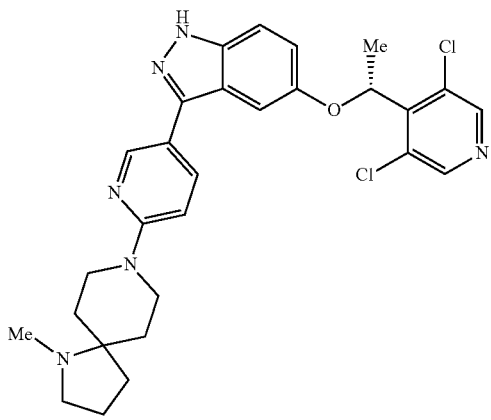 [SMILES: C[C@@H](Oc1ccc2[nH]nc(-c3ccc(N4CCC5(CCCN5C)CC4)nc3)c2c1)c1c(Cl)cncc1Cl] | LCMS m/z = 537.2 (M + H); 1H NMR (400 MHz, CD3OD) δ 8.52-8.44 (m, 3H), 7.90 (dd, J = 2.4, 8.9 Hz, 1H), 7.44 (dd, J = 0.4, 9.0 Hz, 1H), 7.17 (dd, J = 2.3, 9.0 Hz, 1H), 7.12 (d, J = 2.1 Hz, 1H), 6.98 (d, J = 8.6 Hz, 1H), 6.13 (q, J = 6.8 Hz, 1H), 4.49-4.41 (m, 2H), 3.05-2.94 (m, 4H), 2.40 (s, 3H), 2.07-1.84 (m, 6H), 1.82 (d, J = 6.7 Hz, 3H), 1.54 (br d, J = 12.6 Hz, 2H) |
| Example 34<br>9-[5-[5-[(1R)-1-(3,5-dichloro-4-pyridyl)ethoxy]-1H-indazol-3-yl]-2-pyridyl]-1-methyl-1,4,9-triazaspiro[5.5]undecan-5-one | 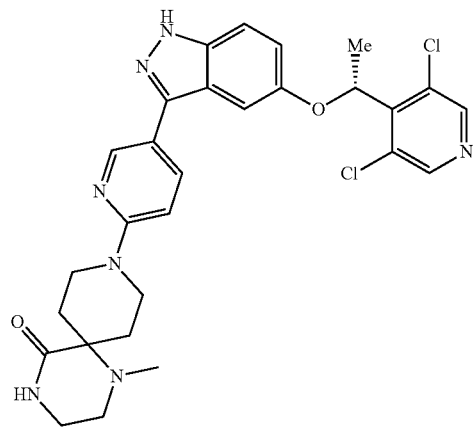 [SMILES: C[C@@H](Oc1ccc2[nH]nc(-c3ccc(N4CCC5(CC4)C(=O)NCCN5C)nc3)c2c1)c1c(Cl)cncc1Cl] | LCMS m/z = 566.2 (M + H); 1H NMR (400 MHz, DMSO-d6) δ 12.97 (s, 1H), 8.60 (s, 2H), 8.54 (d, J = 2.2 Hz, 1H), 7.85 (dd, J = 2.4, 8.8 Hz, 1H), 7.49-7.42 (m, 2H), 7.17 (d, J = 2.0 Hz, 1H), 7.09 (dd, J = 2.3, 9.0 Hz, 1H), 6.95 (d, J = 9.0 Hz, 1H), 6.11 (q, J = 6.8 Hz, 1H), 4.05 (td, J = 4.0, 12.8 Hz, 2H), 3.29-3.22 (m, 2H), 3.06 (t, J = 5.9 Hz, 2H), 2.41 (s, 3H), 1.98-1.87 (m, 4H), 1.76 (d, J = 6.6 Hz, 3H) |

-continued

| | | |
|---|---|---|
| Example 35<br>4-[5-[5-[(1R)-1-(3,5-dichloro-4-pyridyl)ethoxy]-1H-indazol-3-yl]-2-pyridyl]-1,4-diazepan-2-one | 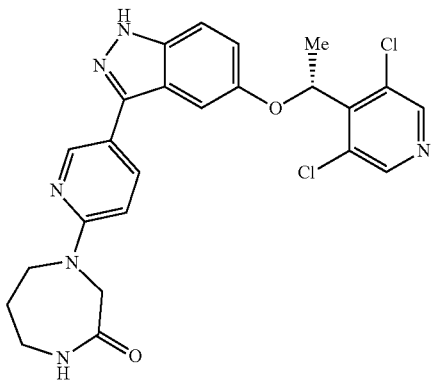 [SMILES: C[C@@H](Oc1ccc2[nH]nc(-c3ccc(N4CCCNC(=O)C4)nc3)c2c1)c1c(Cl)cncc1Cl] | LCMS m/z = 497 (M + H); 1H NMR (400 MHz, DMSO-d6) δ 12.99 (s, 1H), 8.58 (s, 2H), 8.52 (d, J = 2.1 Hz, 1H), 8.32 (br s, 1H), 7.87 (dd, J = 2.4, 8.8 Hz, 1H), 7.50 (t, J = 5.0 Hz, 1H), 7.45 (d, J = 8.9 Hz, 1H), 7.18 (d, J = 1.7 Hz, 1H), 7.08 (dd, J = 2.3, 9.0 Hz, 1H), 6.89 (d, J = 8.8 Hz, 1H), 6.11 (q, J = 6.8 Hz, 1H), 4.24 (s, 2H), 3.99 (br s, 2H), 3.25 (br s, 2H), 1.78-1.72 (m, 5H) |
| Example 36<br>4-[5-[5-[(1R)-1-(3,5-dichloro-4-pyridyl)ethoxy]-1H-indazol-3-yl]-2-pyridyl]piperazin-2-one | 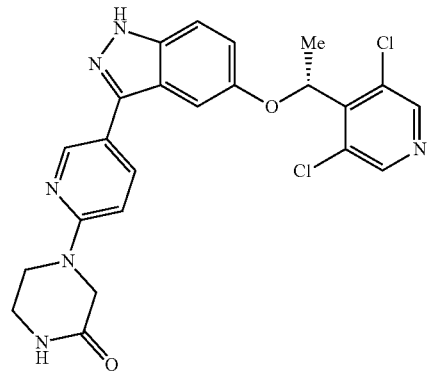 [SMILES: C[C@@H](Oc1ccc2[nH]nc(-c3ccc(N4CCNC(=O)C4)nc3)c2c1)c1c(Cl)cncc1Cl] | LCMS m/z = 483.1 (M + H); 1H NMR (400 MHz, DMSO-d6) δ 13.02 (s, 1H), 8.61 (s, 2H), 8.57 (d, J = 2.1 Hz, 1H), 8.11 (br s, 1H), 7.90 (dd, J = 2.4, 8.8 Hz, 1H), 7.46 (d, J = 8.9 Hz, 1H), 7.16 (d, J = 1.8 Hz, 1H), 7.09 (dd, J = 2.3, 9.0 Hz, 1H), 6.97 (d, J = 8.7 Hz, 1H), 6.10 (q, J = 6.7 Hz, 1H), 4.09 (s, 2H), 3.86-3.77 (m, 2H), 3.36-3.33 (m, 2H), 1.76 (d, J = 6.7 Hz, 3H). |
| Example 37<br>1-[5-[5-[(1R)-1-(3,5-dichloro-4-pyridyl)ethoxy]-1H-indazol-3-yl]-2-pyridyl]piperazin-2-one | 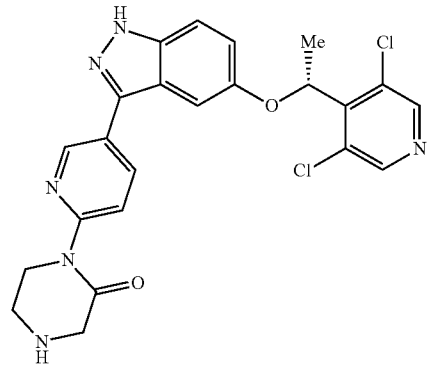 [SMILES: C[C@@H](Oc1ccc2[nH]nc(-c3ccc(N4CCNCC4=O)nc3)c2c1)c1c(Cl)cncc1Cl] | LCMS m/z = 483.1 (M + H); 1H NMR (400 MHz, DMSO-d6) δ 13.35 (s, 1H), 9.29 (br s, 2H), 8.90 (dd, J = 0.7, 2.4 Hz, 1H), 8.58 (s, 2H), 8.26 (dd, J = 2.4, 8.6 Hz, 1H), 8.04 (dd, J = 0.7, 8.6 Hz, 1H), 7.53 (d, J = 9.0 Hz, 1H), 7.28 (d, J = 2.0 Hz, 1H), 7.13 (dd, J = 2.3, 9.0 Hz, 1H), 6.15 (q, J = 6.7 Hz, 1H), 4.23-4.15 (m, 2H), 4.01 (s, 2H), 3.58 (t, J = 5.6 Hz, 2H), 1.77 (d, J = 6.6 Hz, 3H) |
| Example 38<br>1-[5-[5-[(1R)-1-(3,5-dichloro-4-pyridyl)ethoxy]-1H-indazol-3-yl]-2-pyridyl]-4-methyl-piperazin-2-one | 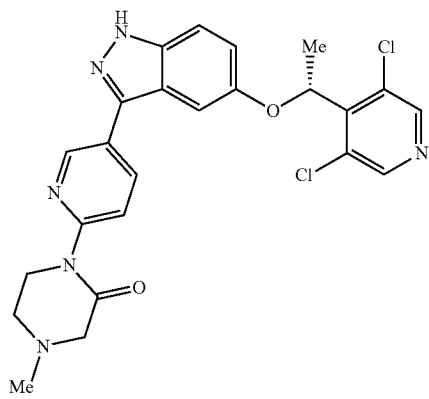 [SMILES: C[C@@H](Oc1ccc2[nH]nc(-c3ccc(N4CCN(C)CC4=O)nc3)c2c1)c1c(Cl)cncc1Cl] | LCMS m/z = 497.1 (M + H); 1H NMR (400 MHz, DMSO-d6) δ 13.29 (s, 1H), 8.87 (dd, J = 0.6, 2.3 Hz, 1H), 8.58 (s, 2H), 8.18 (dd, J = 2.4, 8.7 Hz, 1H), 8.03 (dd, J = 0.7, 8.6 Hz, 1H), 7.52 (d, J = 9.0 Hz, 1H), 7.28 (d, J = 2.1 Hz, 1H), 7.12 (dd, J = 2.3, 9.0 Hz, 1H), 6.15 (q, J = 6.6 Hz, 1H), 3.96 (dd, J = 4.8, 6.7 Hz, 2H), 3.23 (s, 2H), 2.78 (t, J = 5.5 Hz, 2H), 2.31 (s, 3H), 1.77 (d, J = 6.6 Hz, 3H) |

Example 39
1-[5-[5-[(1R)-1-(3,5-dichloro-4-pyridyl)ethoxy]-1H-indazol-3-yl]-2-pyridyl]-4-methylsulfonyl-piperazin-2-one

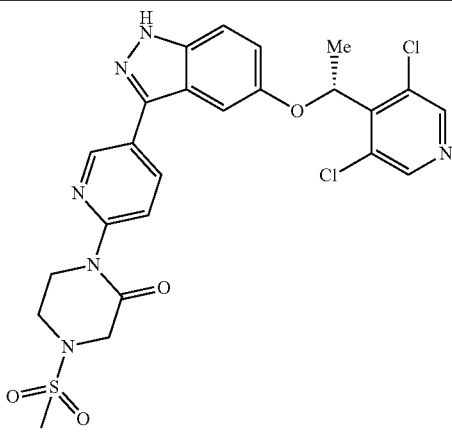

LCMS m/z = 561.1 (M + H); 1H NMR (400 MHz, DMSO-d6) δ 13.32 (s, 1H), 8.89 (dd, J = 0.7, 2.4 Hz, 1H), 8.59 (s, 2H), 8.22 (dd, J = 2.4, 8.7 Hz, 1H), 8.04 (dd, J = 0.7, 8.6 Hz, 1H), 7.52 (d, J = 9.0 Hz, 1H), 7.29 (d, J = 2.1 Hz, 1H), 7.13 (dd, J = 2.3, 9.0 Hz, 1H), 6.15 (q, J = 6.6 Hz, 1H), 4.15 (dd, J = 4.7, 6.4 Hz, 2H), 4.09 (s, 2H), 3.66-3.61 (m, 2H), 3.08 (s, 3H), 1.77 (d, J = 6.7 Hz, 3H)

Example 40
8-[5-[5-[(1R)-1-(3,5-dichloro-4-pyridyl)ethoxy]-1H-indazol-3-yl]-2-pyridyl]-1-methyl-1,8-diazaspiro[4.5]decan-2-one

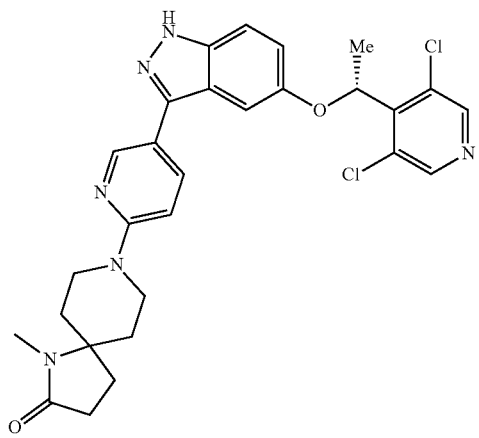 [SMILES: C[C@@H](Oc1ccc2[nH]nc(-c3ccc(N4CCC5(CCC(=O)N5C)CC4)nc3)c2c1)c1c(Cl)cncc1Cl]

LCMS m/z = 551.1 (M + H); 1H NMR (400 MHz, DMSO-d6) δ 12.99 (s, 1H), 8.60 (s, 2H), 8.55 (d, J = 2.2 Hz, 1H), 7.86 (dd, J = 2.4, 8.9 Hz, 1H), 7.46 (d, J = 9.0 Hz, 1H), 7.16 (d, J = 2.0 Hz, 1H), 7.09 (dd, J = 2.3, 9.0 Hz, 1H), 7.03 (d, J = 8.9 Hz, 1H), 6.10 (q, J = 6.6 Hz, 1H), 4.44 (br d, J = 13.2 Hz, 2H), 2.99 (br t, J = 12.4 Hz, 2H), 2.60 (s, 3H), 2.30 (t, J = 7.9 Hz, 2H), 2.02 (t, J = 7.9 Hz, 2H), 1.89 (dt, J = 4.4, 12.7 Hz, 2H), 1.76 (d, J = 6.6 Hz, 3H), 1.48 (br d, J = 12.6 Hz, 2H).

Example 41. 8-[5-[5-[(1R)-1-(3,5-dichloro-4-pyridyl)ethoxy]-1H-indazol-3-yl]-3-fluoro-2-pyridyl]-1,8-diazaspiro[4.5]decan-2-one

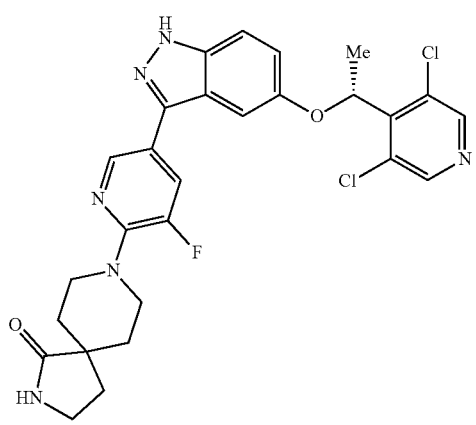 [SMILES: C[C@@H](Oc1ccc2[nH]nc(-c3cnc(N4CCC5(CCNC5=O)CC4)c(F)c3)c2c1)c1c(Cl)cncc1Cl]

This example was synthesized using 3-(6-chloro-4-fluoropyridin-3-yl)-5-((R)-1-(3,5-dichloropyridin-4-yl)ethoxy)-1-(tetrahydro-2H-pyran-2-yl)-1H-indazole by the method for example 17 to give a white solid (49 mg, 35% yield). Analysis: LCMS: m/z=555.2 (M+H); 1H NMR (400 MHz, CDCL3) δ 10.57 (br s, 1H), 8.47 (t, J=1.6 Hz, 1H), 8.44 (s, 2H), 7.64 (dd, J=2.0, 14.1 Hz, 1H), 7.37 (d, J=9.0 Hz, 1H), 7.17 (d, J=2.0 Hz, 1H), 7.13 (dd, J=2.3, 9.0 Hz, 1H), 6.09-5.97 (m, 2H), 4.16 (td, J=3.8, 13.4 Hz, 2H), 3.40 (t, J=6.8 Hz, 2H), 3.21 (br t, J=11.7 Hz, 2H), 2.22-2.10 (m, 4H), 1.82 (d, J=6.7 Hz, 3H), 1.66-1.52 (m, 2H).

Example 42. 8-[5-[5-[(1R)-1-(3,5-dichloro-4-pyridyl)ethoxy]-1H-indazol-3-yl]-3-fluoro-2-pyridyl]-1,8-diazaspiro[4.5]decan-2-one

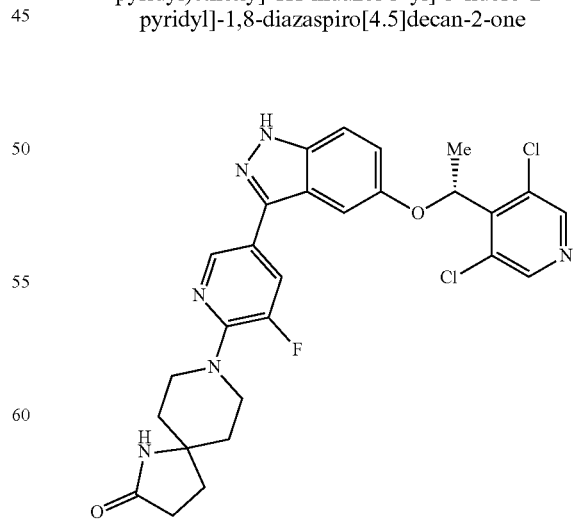

This example was synthesized using 3-(6-chloro-4-fluoropyridin-3-yl)-5-((R)-1-(3,5-dichloropyridin-4-yl)ethoxy)-

1-(tetrahydro-2H-pyran-2-yl)-1H-indazole by the method for example 17 to give a white solid (45 mg, 58% yield). Analysis: LCMS: m/z=555.2 (M+H); 1H NMR (400 MHz, CDCl$_3$) δ 11.91 (br s, 1H), 8.42 (s, 2H), 8.39 (t, J=1.6 Hz, 1H), 7.80 (s, 1H), 7.57 (dd, J=1.9, 14.0 Hz, 1H), 7.42 (d, J=8.9 Hz, 1H), 7.14 (dd, J=2.2, 8.9 Hz, 1H), 7.11 (d, J=2.0 Hz, 1H), 6.03 (q, J=6.7 Hz, 1H), 3.84-3.71 (m, 2H), 3.36-3.24 (m, 2H), 2.51 (t, J=8.1 Hz, 2H), 2.05 (t, J=8.1 Hz, 2H), 1.90-1.78 (m, 7H).

Example 43. 8-[5-[5-[(1R)-1-(3,5-dichloro-4-pyridyl)ethoxy]-1H-indazol-3-yl]-3-fluoro-2-pyridyl]-1-methyl-1,8-diazaspiro[4.5]decan-2-one

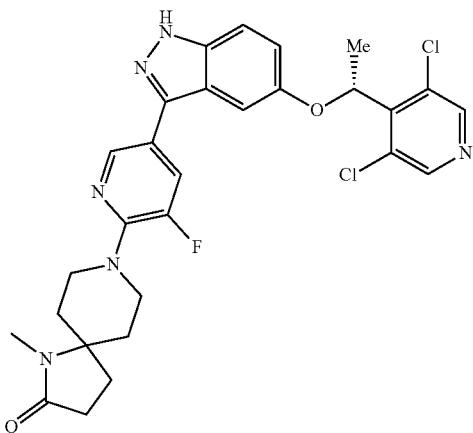 [SMILES: C[C@@H](Oc1ccc2[nH]nc(-c3cnc(N4CCC5(CCC(=O)N5C)CC4)c(F)c3)c2c1)c1c(Cl)cncc1Cl]

This example was synthesized using 3-(6-chloro-4-fluoropyridin-3-yl)-5-((R)-1-(3,5-dichloropyridin-4-yl)ethoxy)-1-(tetrahydro-2H-pyran-2-yl)-1H-indazole by the method for example 17. Analysis: LCMS: m/z=569.2 (M+H); 1H NMR (400 MHz, DMSO-d6) δ 13.17 (s, 1H), 8.57 (s, 2H), 8.46 (t, J=1.7 Hz, 1H), 7.78 (dd, J=2.0, 14.4 Hz, 1H), 7.49 (d, J=8.9 Hz, 1H), 7.21 (d, J=2.1 Hz, 1H), 7.11 (dd, J=2.3, 9.0 Hz, 1H), 6.13 (q, J=6.6 Hz, 1H), 4.11 (br d, J=13.4 Hz, 2H), 3.12-3.03 (m, 2H), 2.64 (s, 3H), 2.32-2.26 (m, 2H), 2.06-1.97 (m, 4H), 1.76 (d, J=6.6 Hz, 3H), 1.49 (br d, J=12.5 Hz, 2H).

Example 44. 9-[5-[5-[(1R)-1-(3,5-dichloro-4-pyridyl)ethoxy]-1H-indazol-3-yl]-3-fluoro-2-pyridyl]-1-methyl-1,4,9-triazaspiro[5.5]undecan-5-one

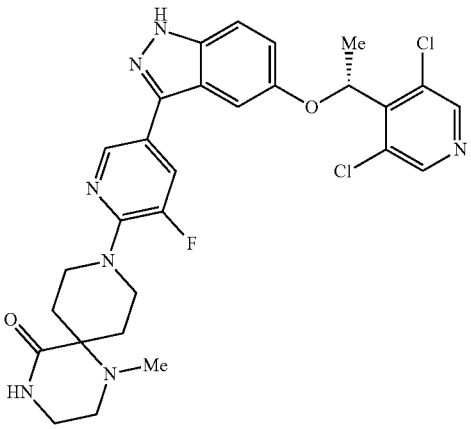 [SMILES: C[C@@H](Oc1ccc2[nH]nc(-c3cnc(N4CCC5(CC4)C(=O)NCCN5C)c(F)c3)c2c1)c1c(Cl)cncc1Cl]

This example was synthesized using 3-(6-chloro-4-fluoropyridin-3-yl)-5-((R)-1-(3,5-dichloropyridin-4-yl)ethoxy)-1-(tetrahydro-2H-pyran-2-yl)-1H-indazole by the method for example 17. Analysis: LCMS: m/z=584.2 (M+H); 1H NMR (400 MHz, DMSO-d6) δ 13.16 (br s, 1H), 8.57 (s, 2H), 8.44 (t, J=1.7 Hz, 1H), 7.74 (dd, J=2.0, 14.5 Hz, 1H), 7.48 (d, J=9.2 Hz, 1H), 7.45 (s, 1H), 7.20 (d, J=2.2 Hz, 1H), 7.10 (dd, J=2.3, 9.0 Hz, 1H), 6.14 (q, J=6.6 Hz, 1H), 3.85 (br d, J=12.8 Hz, 2H), 3.38-3.32 (m, 2H), 3.06 (t, J=5.9 Hz, 2H), 2.41 (s, 3H), 2.05-1.91 (m, 4H), 1.76 (d, J=6.7 Hz, 3H).

Example 45. 3-[6-(2,6-diazaspiro[3.3]heptan-2-yl)-3-pyridyl]-5-[(1R)-1-(3,5-dichloro-4-pyridyl)ethoxy]-1H-indazole Step 1. tert-Butyl (R)-6-(5-(5-(1-(3,5-dichloropyridin-4-yl)ethoxy)-1H-indazol-3-yl)pyridin-2-yl)-2,6-diazaspiro[3.3]heptane-2-carboxylate. A mixture of example 25 (0.295 g, 0.732 mmol, 1 equiv), tert-butyl 2,6-diazaspiro[3.3]heptane-2-carboxylate (0.29 g, 1.464 mmol, 2 equiv), and potassium carbonate (0.4 g, 2.93 mmol, 4 equiv) in anhydrous N-methylpyrrolidone was heated at 120° C. for 16 hours. The reaction mixture was filtered through a syringe filter and the filtrate was pre-absorbed on Celite (5 g). The material was purified on an Interchim automated chromatography system (RediSep Rf Gold HP C18, 15.5 g cartridge), eluting with a gradient of 0 to 100% acetonitrile in water. The fractions containing product were collected and lyophilized to give a yellowish solid (0.3 g, 71% yield) Analysis: LCMS (ESI) m/z=581 (M+H).

Step 2. 3-[6-(2,6-diazaspiro[3.3]heptan-2-yl)-3-pyridyl]-5-[(1R)-1-(3,5-dichloro-4-pyridyl)ethoxy]-1H-indazole. A solution of step 1 product (50 mg, 0.086 mmol, 1 equiv) in anhydrous dichloromethane (2 mL) was treated with trifluoroacetic acid (0.53 mL, 6.88 mmol, 80 equiv) at room temperature for 16 hours. Additional trifluoroacetic acid (0.23 mL, 3.01 mmol, 35 equiv) was added and stirred for 1 hour. The reaction mixture was concentrated under reduced pressure to dryness. The residue was dissolved in methanol (10 mL), treated with MP-carbonate resin (3.2 mmol/g, 1 g), stirred for 30 minutes, filtered and concentrated under reduced pressure. The residue was absorbed onto Celite (1 g) and purified on an Interchim automated chromatography system (RediSep Rf Gold HP C18, 15.5 g cartridge), eluting with a gradient of 0 to 100% acetonitrile in water. The fractions containing product were collected and lyophilized to give a white solid (30 mg, 73% yield). Analysis: LCMS: m/z=481.1 (M+H); 1H NMR (400 MHz, DMSO-d6) δ 13.00 (br s, 1H), 8.59 (s, 2H), 8.50 (d, J=1.8 Hz, 1H), 7.84 (dd, J=2.3, 8.7 Hz, 1H), 7.45 (d, J=9.0 Hz, 1H), 7.16 (d, J=2.1 Hz, 1H), 7.08 (dd, J=2.3, 9.0 Hz, 1H), 6.51 (d, J=8.4 Hz, 1H), 6.10 (q, J=6.6 Hz, 1H), 4.20-3.82 (m, 5H), 3.66 (br s, 4H), 1.76 (d, J=6.6 Hz, 3H).

Example 46. 5-[(1R)-1-(3,5-dichloro-4-pyridyl)ethoxy]-3-[6-(2-methylsulfonyl-2,6-diazaspiro[3.3]heptan-6-yl)-3-pyridyl]-1H-indazole

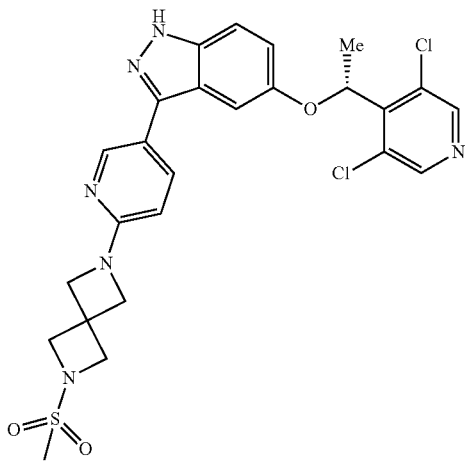 [SMILES: C[C@@H](Oc1ccc2[nH]nc(-c3ccc(N4CC5(C4)CN(S(C)(=O)=O)C5)nc3)c2c1)c1c(Cl)cncc1Cl]

(5-[(1R)-1-(3,5-dichloro-4-pyridyl)ethoxy]-3-[6-(2-methylsulfonyl-2,6-diazaspiro[3.3]heptan-6-yl)-3-pyridyl]-1H-indazole. Triethylamine (20.5 uL, 0.148 mmol, 1.2 equiv) and methylsulfonyl chloride (9.5 uL, 0.123 mmol, 1.0 equiv) were sequentially added at room temperature to a solution of example 45 (59.0 mg, 0.123 mmol, 1 equiv) in anhydrous THF (3 mL). After stirring for 2 hours, the reaction mixture was concentrated under reduced pressure and diluted with saturated brine (30 mL) and dichloromethane (30 mL). The layers were separated. The organic layer was dried over sodium sulfate, filtered and concentrated under reduced pressure on to Celite (1 g). The product was purified on an Interchim automated chromatography system (RediSep Rf Gold HP C18, 15.5 g cartridge), eluting with a gradient of 0 to 100% acetonitrile in water. The fractions containing product were collected and lyophilized to give a white solid (45.0 mg, 65% yield). Analysis: LCMS: m/z=559.2 (M+H); 1H NMR (400 MHz, DMSO-d6) δ 13.02 (br s, 1H), 8.59 (s, 2H), 8.52 (dd, J=0.6, 2.2 Hz, 1H), 7.87 (dd, J=2.4, 8.6 Hz, 1H), 7.46 (d, J=8.9 Hz, 1H), 7.16 (d, J=2.1 Hz, 1H), 7.09 (dd, J=2.3, 9.0 Hz, 1H), 6.54 (dd, J=0.4, 8.6 Hz, 1H), 6.10 (q, J=6.6 Hz, 1H), 4.17 (s, 4H), 4.12 (s, 4H), 3.03 (s, 3H), 1.76 (d, J=6.6 Hz, 3H).

Example 47. 6-[5-[5-[(1R)-1-(3,5-dichloro-4-pyridyl)ethoxy]-1H-indazol-3-yl]-2-pyridyl]-N,N-dimethyl-2,6-diazaspiro[3.3]heptane-2-carboxamide

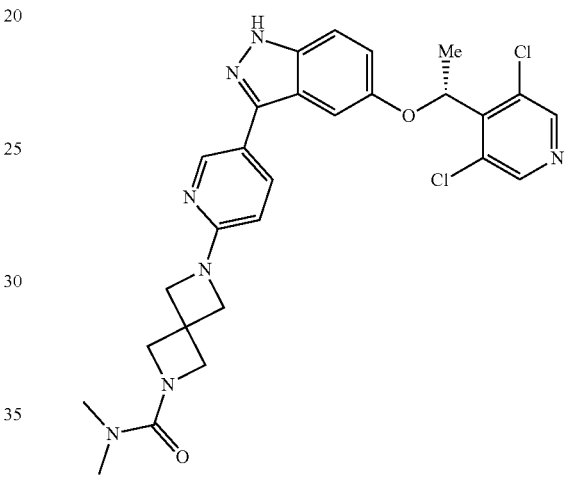

6-[5-[5-[(1R)-1-(3,5-dichloro-4-pyridyl)ethoxy]-1H-indazol-3-yl]-2-pyridyl]-N,N-dimethyl-2,6-diazaspiro[3.3]heptane-2-carboxamide. Triethylamine (24.4 μL, 0.175 mmol, 1.2 equiv) and dimethylcarbamic chloride (14.8 μL, 0.161 mmol, 1.1 equiv) were sequentially added at room temperature to a solution of example 45 (70.0 mg, 0.146 mmol, 1 equiv) in anhydrous THF (3 mL). After stirring for 2 hours, additional dimethylcarbamic chloride (4 μL, 0.044 mmol, 0.3 equiv) and triethylamine (8.1 μL, 0.058 mmol, 0.4 equiv) were added and the reaction was stirred for 16 hours at room temperature. The reaction mixture was concentrated under reduced pressure and diluted with saturated brine (30 mL) and dichloromethane (30 mL). The layers were separated. The organic layer was dried over sodium sulfate, filtered and concentrated under reduced pressure. The crude product was absorbed onto Celite (1 g) and purified on an Interchim automated chromatography system (RediSep Rf Gold HP C18, 15.5 g cartridge), eluting with a gradient of 0 to 100% acetonitrile in water. The fractions containing product were collected and lyophilized to give a white solid (33.0 mg, 41% yield). Analysis: LCMS: m/z=552.2 (M+H); 1H NMR (400 MHz, DMSO-d6) δ 8.59 (s, 2H), 8.51 (dd, J=0.7, 2.3 Hz, 1H), 7.86 (dd, J=2.3, 8.6 Hz, 1H), 7.46 (d, J=8.9 Hz, 1H), 7.16 (d, J=2.1 Hz, 1H), 7.09 (dd, J=2.3, 9.0 Hz, 1H), 6.53 (dd, J=0.6, 8.7 Hz, 1H), 6.11 (q, J=6.6 Hz, 1H), 4.14 (s, 4H), 4.10 (s, 4H), 2.77 (s, 6H), 1.76 (d, J=6.6 Hz, 3H), 1.36 (s, 1H).

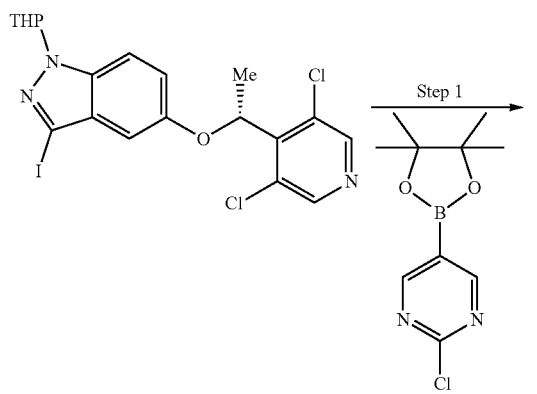

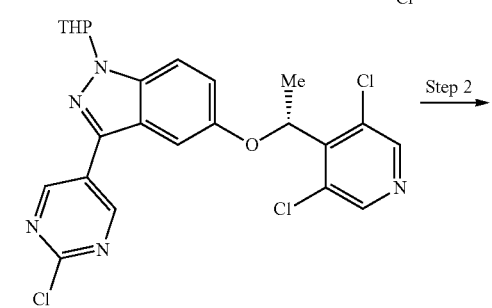

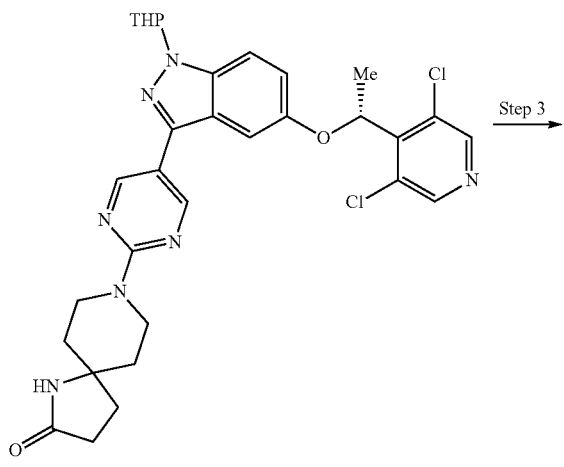

Example 48

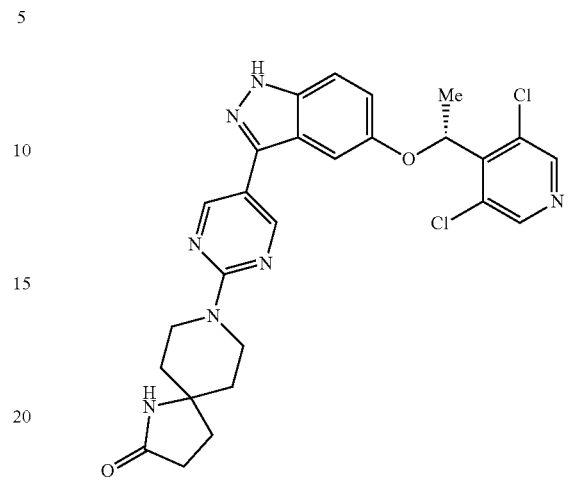

Example 48. 8-[5-[5-[(1R)-1-(3,5-dichloro-4-pyridyl)ethoxy]-1H-indazol-3-yl]pyrimidin-2-yl]-1,8-diazaspiro[4.5]decan-2-one Step 1. 3-(2-Chloropyrimidin-5-yl)-5-((R)-1-(3,5-dichloropyridin-4-yl)ethoxy)-1-(tetrahydro-2H-pyran-2-yl)-1H-indazole. A mixture of 5-[(1R)-1-(3,5-dichloro-4-pyridyl)ethoxy]-3-iodo-1-tetrahydropyran-2-yl-indazole (1.5 g, 2.89 mmol, 1 equiv), 2-chloro-5-(4,4,5,5-tetramethyl-1,3,2-dioxaborolan-2-yl)pyrimidine (904 mg, 3.76 mmol, 1.3 equiv), [1,1'-bis(diphenylphosphino)ferrocene]-dichloropalladium(II) (211 mg, 0.289 mmol, 0.1 equiv), potassium carbonate (798 mg, 5.79 mmol, 2 equiv) and water (2 mL) in 1,4-dioxane (24 mL) was sparged with nitrogen for 10 minutes. The mixture was vigorously stirred under a nitrogen atmosphere at 90° C. overnight. The brown reaction mixture was cooled to room temperature and diluted with water (20 mL) and ethyl acetate (20 mL). The layers were separated and the aqueous layer was extracted with ethyl acetate (3×10 mL). The combined organic layers were dried over sodium sulfate and concentrated under reduced pressure. The residue was absorbed onto Celite (10 g) and purified on an Interchim automated chromatography system (Sorbtech 80 g silica gel cartridge), eluting with a gradient of 0 to 50% ethyl acetate in heptanes to give a white solid (1.17 g, 80% yield). Analysis: LCMS: m/z=504.1 (M+H).

Step 2. 8-(5-(5-((R)-1-(3,5-Dichloropyridin-4-yl)ethoxy)-1-(tetrahydro-2H-pyran-2-yl)-1H-indazol-3-yl)pyrimidin-2-yl)-1,8-diazaspiro[4.5]decan-2-one. A mixture of product step 1 (185 mg, 0.366 mmol, 1 equiv), 1,8-diazaspiro[4.5]decan-2-one (62 mg, 0.403 mmol, 1.1 equiv), and potassium carbonate (76 mg, 0.549 mmol, 1.5 equiv) in anhydrous NMP (3 mL) was heated at 120° C. overnight. The reaction mixture was cooled to room temperature and was diluted with water (10 mL) and ethyl acetate (10 mL). The layers were separated and the aqueous layer was extracted with ethyl acetate (3×5 mL). The combined organic layers were dried over sodium sulfate and concentrated under reduced pressure to give a white solid (290 mg) that was used subsequently. Analysis: LCMS m/z=622.1 (M+H).

Step 3. 8-[5-[5-[(1R)-1-(3,5-dichloro-4-pyridyl)ethoxy]-1H-indazol-3-yl]pyrimidin-2-yl]-1,8-diazaspiro[4.5]decan-2-one. Product step 2 (290 mg) was dissolved in a 1 to 1 mixture of trifluoroacetic acid and dichloromethane (2 mL) at room temperature and the red solution was stirred at room temperature for 3 hours. The reaction mixture was concentrated under reduced pressure. The residue was diluted with saturated sodium bicarbonate (5 mL) and ethyl acetate (5 mL). The layers were separated and the aqueous layer was extracted with ethyl acetate (3×5 mL). The combined organic layers were dried over sodium sulfate and concentrated under reduced pressure. The brown residue was adsorbed to Celite (1 g) and purified on an Interchim automated chromatography system (RediSep Rf GOLD HP C18, 15 g column), eluting with a gradient of 0 to 100% methanol in water to give a white solid after lyophilzation (100 mg, 40% yield two steps). Analysis: LCMS: m/z=538.2 (M+H); $^1$H NMR (400 MHz, CDCl$_3$) δ 12.24 (br s, 1H), 8.61 (s, 2H), 8.55 (s, 1H), 8.41 (s, 2H), 7.43 (dd, J=0.5, 9.0 Hz, 1H), 7.14 (dd, J=2.3, 9.0 Hz, 1H), 7.10 (d, J=2.1 Hz, 1H), 6.03 (q, J=6.7 Hz, 1H), 4.44-4.34 (m, 2H), 3.36-3.21 (m, 2H), 2.51 (t, J=8.1 Hz, 2H), 2.02 (t, J=8.1 Hz, 2H), 1.80 (d, J=6.7 Hz, 3H), 1.74-1.69 (m, 4H).

Examples 49-58 were synthesized using the procedure for Example 26.

Example 49
8-[5-[5-[(1R)-1-(3,5-dichloro-4-pyridyl)ethoxy]-1H-indazol-3-yl]pyrimidin-2-yl]-2,8-diazaspiro[4.5]decan-3-one

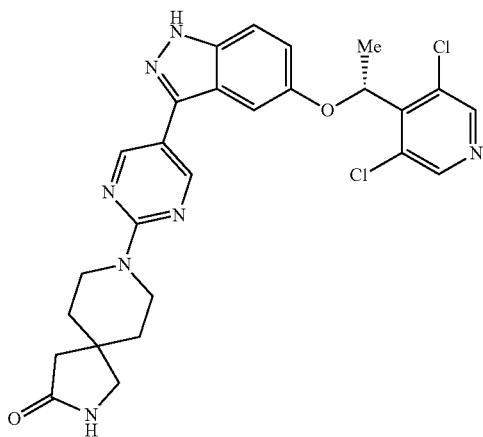 [SMILES: C[C@@H](Oc1ccc2[nH]nc(-c3cnc(N4CCC5(CC4)CNC(=O)C5)nc3)c2c1)c1c(Cl)cncc1Cl]

LCMS: m/z = 538.2 (M + H); 1H NMR (400 MHz, DMSO-d6) δ 13.09 (s, 1H), 8.76 (s, 2H), 8.57 (s, 2H), 7.56 (s, 1H), 7.47 (d, J = 9.0 Hz, 1H), 7.25 (d, J = 2.0 Hz, 1H), 7.09 (dd, J = 2.3, 9.0 Hz, 1H), 6.14 (q, J = 6.6 Hz, 1H), 3.97 (td, J = 5.3, 13.6 Hz, 2H), 3.77-3.68 (m, 2H), 3.13 (s, 2H), 2.16 (s, 2H), 1.76 (d, J = 6.7 Hz, 3H), 1.62 (t, J = 5.6 Hz, 4H)

Example 50
8-[5-[5-[(1R)-1-(3,5-dichloro-4-pyridyl)ethoxy]-1H-indazol-3-yl]pyrimidin-2-yl]-2,8-diazaspiro-[4.5]decane-1,3-dione

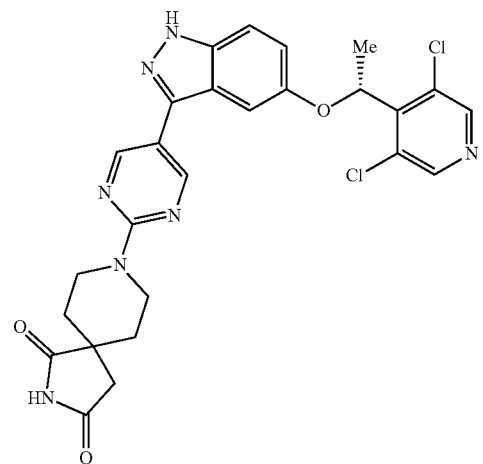 [SMILES: C[C@@H](Oc1ccc2[nH]nc(-c3cnc(N4CCC5(CC4)CC(=O)NC5=O)nc3)c2c1)c1c(Cl)cncc1Cl]

LCMS: m/z = 552.2 (M + H); 1H NMR (400 MHz, DMSO-d6) δ 13.11 (br s, 1H), 11.19 (br s, 1H), 8.78 (s, 2H), 8.57 (s, 2H), 7.47 (d, J = 9.0 Hz, 1H), 7.25 (d, J = 2.1 Hz, 1H), 7.10 (dd, J = 2.3, 9.0 Hz, 1H), 6.14 (q, J = 6.6 Hz, 1H), 4.67-4.58 (m, 2H), 3.21-3.14 (m, 2H), 2.74 (s, 2H), 1.82-1.66 (m, 7H)

Example 51
8-[5-[5-[(1R)-1-(3,5-dichloro-4-pyridyl)ethoxy]-1H-indazol-3-yl]pyrimidin-2-yl]-2-methyl-2,8-diazaspiro[4.5]decan-1-one

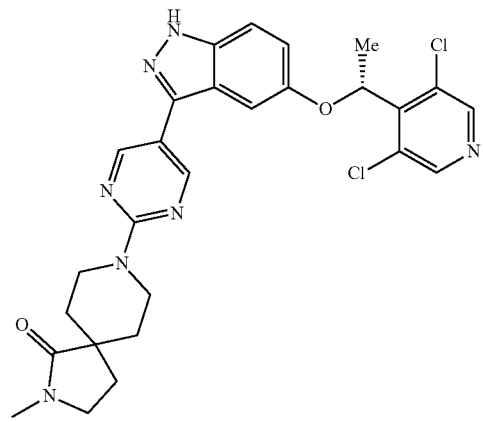 [SMILES: C[C@@H](Oc1ccc2[nH]nc(-c3cnc(N4CCC5(CCN(C)C5=O)CC4)nc3)c2c1)c1c(Cl)cncc1Cl]

LCMS: m/z = 553 (M + H); 1H NMR (400 MHz, DMSO-d6) δ 13.10 (s, 1H), 8.77 (s, 2H), 8.57 (s, 2H), 7.47 (d, J = 9.0 Hz, 1H), 7.26 (d, J = 2.1 Hz, 1H), 7.10 (dd, J = 2.3, 9.0 Hz, 1H), 6.15 (q, J = 6.6 Hz, 1H), 4.58 (td, J = 3.8, 13.4 Hz, 2H), 3.36-3.32 (m, 2H), 3.28-3.21 (m, 2H), 2.75 (s, 3H), 2.05 (t, J = 6.9 Hz, 2H), 1.76 (d, J = 6.6 Hz, 3H), 1.67 (dt, J = 3.7, 12.3 Hz, 2H), 1.45 (br d, J = 13.4 Hz, 2H)

-continued

| Example 52<br>8-[5-[5-[(1R)-1-(3,5-dichloro-4-pyridyl)ethoxy]-1H-indazol-3-yl]pyrimidin-2-yl]-1-methyl-1,8-diazaspiro[4.5]decane | 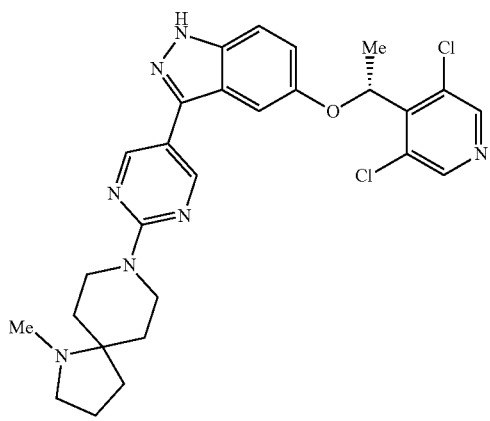 [SMILES: C[C@@H](Oc1ccc2[nH]nc(-c3cnc(N4CCC5(CCCN5C)CC4)nc3)c2c1)c1c(Cl)cncc1Cl] | LCMS: m/z = 538.2 (M + H); 1H NMR (400 MHz, Methanol-d4) δ 8.72 (s, 2H), 8.46 (s, 2H), 7.45 (d, J = 9.0 Hz, 1H), 7.17 (dd, J = 2.3, 9.0 Hz, 1H), 7.07 (d, J = 2.2 Hz, 1H), 6.12 (q, J = 6.6 Hz, 1H), 5.00 (ddd, J = 2.1, 4.3, 14.1 Hz, 2H), 4.57 (br s, 1H), 3.47 (br t, J = 5.4 Hz, 2H), 3.15-3.04 (m, 2H), 2.79 (s, 3H), 2.40-2.23 (m, 2H), 2.22-2.14 (m, 2H), 1.96 (dt, J = 4.5, 12.4 Hz, 2H), 1.85-1.78 (m, 5H) |
| --- | --- | --- |
| Example 53<br>8-[5-[5-[(1R)-1-(3,5-dichloro-4-pyridyl)ethoxy]-1H-indazol-3-yl]pyrimidin-2-yl]-1,3,8-triazaspiro[4.5]decan-2-one | 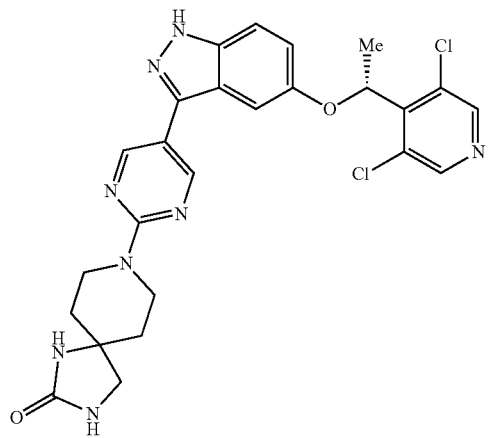 [SMILES: C[C@@H](Oc1ccc2[nH]nc(-c3cnc(N4CCC5(CC4)CNC(=O)N5)nc3)c2c1)c1c(Cl)cncc1Cl] | LCMS: m/z = 539.2 (M + H); 1H NMR (400 MHz, DMSO-d6) δ 13.10 (br s, 1H), 8.76 (s, 2H), 8.57 (s, 2H), 7.47 (d, J = 9.0 Hz, 1H), 7.24 (d, J = 2.2 Hz, 1H), 7.09 (dd, J = 2.3, 9.0 Hz, 1H), 6.79 (s, 1H), 6.20 (s, 1H), 6.14 (q, J = 6.7 Hz, 1H), 3.97-3.82 (m, 4H), 3.20-3.17 (m, 2H), 1.76 (d, J = 6.6 Hz, 3H), 1.70-1.62 (m, 4H) |
| Example 54<br>8-[5-[5-[(1R)-1-(3,5-dichloro-4-pyridyl)ethoxy]-1H-indazol-3-yl]pyrimidin-2-yl]-1-methyl-1,8-diazaspiro[4.5]decan-2-one | 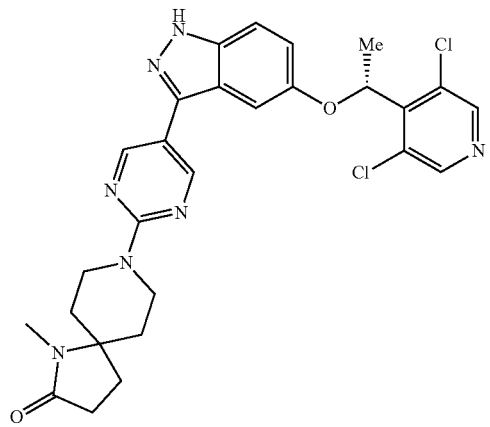 [SMILES: C[C@@H](Oc1ccc2[nH]nc(-c3cnc(N4CCC5(CCC(=O)N5C)CC4)nc3)c2c1)c1c(Cl)cncc1Cl] | LCMS: m/z = 552.2 (M + H); 1H NMR (400 MHz, DMSO-d6) δ 13.11 (br s, 1H), 8.78 (s, 2H), 8.57 (s, 2H), 7.47 (d, J = 9.0 Hz, 1H), 7.25 (d, J = 2.1 Hz, 1H), 7.10 (dd, J = 2.3, 9.0 Hz, 1H), 6.19-6.10 (m, 1H), 4.81 (br dd, J = 2.2, 11.5 Hz, 2H), 3.07 (dt, J = 2.0, 1.3 Hz, 2H), 2.60 (s, 3H), 2.34-2.27 (m, 2H), 2.08-2.01 (m, 2H), 1.85 (dt, J = 4.6, 12.8 Hz, 2H), 1.75 (d, J = 6.7 Hz, 3H), 1.49 (br d, J = 13.0 Hz, 2H). |

| Example | Structure | Data |
|---|---|---|
| Example 55<br>8-[5-[5-[(1R)-1-(3,5-dichloro-4-pyridyl)ethoxy]-1H-indazol-3-yl]pyrimidin-2-yl]-2,8-diazaspiro[4.5]decan-1-one | 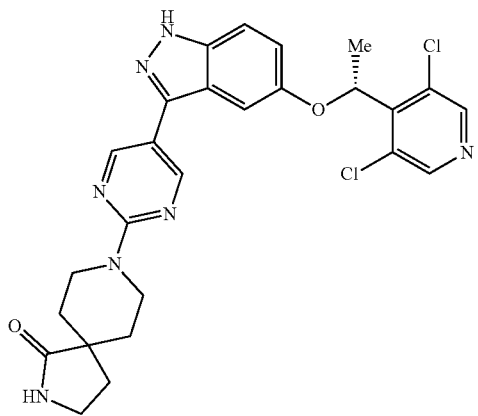 [SMILES: C[C@@H](Oc1ccc2[nH]nc(-c3cnc(N4CCC5(CCNC5=O)CC4)nc3)c2c1)c1c(Cl)cncc1Cl] | LCMS: m/z = 538.2 (M + H); 1H NMR (400 MHz, CDCl3) δ = 10.32 (br s, 1H), 8.75 (s, 2H), 8.43 (s, 2H), 7.37 (d, J = 9.0 Hz, 1H), 7.19 (d, J = 2.2 Hz, 1H), 7.13 (dd, J = 2.3, 8.9 Hz, 1H), 6.05 (q, J = 6.6 Hz, 1H), 5.86 (br s, 1H), 4.68 (td, J = 4.3, 13.5 Hz, 2H), 3.44-3.32 (m, 4H), 2.20 (t, J = 6.9 Hz, 2H), 2.05-1.97 (m, 2H), 1.81 (d, J = 6.7 Hz, 3H), 1.57 (td, J = 3.1, 13.4 Hz, 3H) |
| Example 56<br>8-[5-[5-[(1R)-1-(3,5-dichloro-4-pyridyl)ethoxy]-1H-indazol-3-yl]pyrimidin-2-yl]-1,8-diazaspiro[4.5]decane | 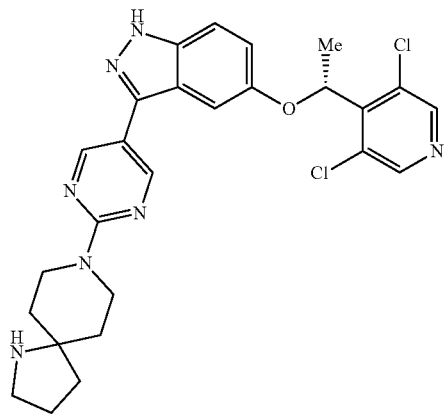 [SMILES: C[C@@H](Oc1ccc2[nH]nc(-c3cnc(N4CCC5(CCCN5)CC4)nc3)c2c1)c1c(Cl)cncc1Cl] | LCMS: m/z = 524.2 (M + H); 1H NMR (400 MHz, Methanol-d4) δ 8.72 (s, 2H), 8.47 (s, 2H), 7.46 (dd, J = 0.5, 9.0 Hz, 1H), 7.18 (dd, J = 2.3, 9.0 Hz, 1H), 7.08 (d, J = 2.2 Hz, 1H), 6.14 (q, J = 6.7 Hz, 1H), 4.49 (td, J = 4.7, 14.1 Hz, 2H), 3.56 (ddd, J = 4.3, 9.1, 13.9 Hz, 2H), 3.40-3.36 (m, 2H), 2.22-2.10 (m, 4H), 1.97-1.88 (m, 4H), 1.82 (d, J = 6.6 Hz, 3H) |
| Example 57<br>8-[5-[5-[(1R)-1-(3,5-dichloro-4-pyridyl)ethoxy]-1H-indazol-3-yl]pyrimidin-2-yl]-2λ⁶-thia-8-azaspiro[4.5]decane 2,2-dioxide | 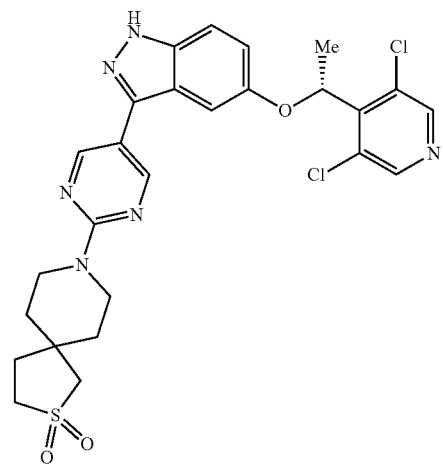 [SMILES: C[C@@H](Oc1ccc2[nH]nc(-c3cnc(N4CCC5(CC4)CCS(=O)(=O)C5)nc3)c2c1)c1c(Cl)cncc1Cl] | LCMS: m/z = 573.2 (M + H); 1H NMR (400 MHz, CDCl3) δ = 10.01 (br s, 1H), 8.77 (s, 2H), 8.43 (s, 2H), 7.38 (dd, J = 0.5, 8.9 Hz, 1H), 7.17 (d, J = 1.7 Hz, 1H), 7.15 (d, J = 9.2 Hz, 1H), 6.06 (q, J = 6.7 Hz, 1H), 4.39 (td, J = 4.7, 14.2 Hz, 2H), 3.53-3.45 (m, 2H), 3.24 (t, J = 7.5 Hz, 2H), 3.13 (s, 2H), 2.19 (t, J = 7.5 Hz, 2H), 1.93-1.87 (m, 2H), 1.82 (d, J = 6.6 Hz, 3H), 1.75 (ddd, J = 4.0, 9.8, 13.7 Hz, 2H) |

| Example 58<br>9-[5-[5-[(1R)-1-(3,5-dichloro-4-pyridyl)ethoxy]-1H-indazol-3-yl]pyrimidin-2-yl]-1-methyl-1,4,9-triazaspiro[5.5]undecan-5-one | 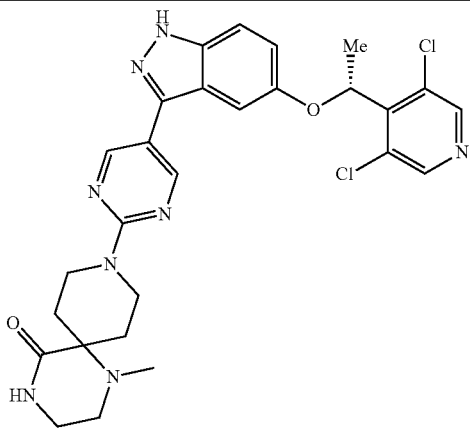 | LCMS: m/z = 567.2 (M + H); 1H NMR (400 MHz, CDCl3) δ = 10.45 (br s, 1H), 8.75 (s, 2H), 8.43 (s, 2H), 7.36 (dd, J = 0.3, 9.0 Hz, 1H), 7.19 (d, J = 2.2 Hz, 1H), 7.12 (dd, J = 2.3, 9.0 Hz, 1H), 6.05 (q, J = 6.7 Hz, 1H), 5.96 (br s, 1H), 4.46 (td, J = 4.4, 13.2 Hz, 2H), 3.61 (ddd, J = 3.1, 10.5, 13.1 Hz, 2H), 3.52 (dt, J = 1.9, 5.9 Hz, 2H), 3.19 (t, J = 5.9 Hz, 2H), 2.54 (s, 3H), 2.20-2.11 (m, 2H), 2.08-2.01 (m, 2H), 1.83-1.79 (m, 3H) |

Example 59. 3-(2-Chloropyrimidin-5-yl)-5-[(1R)-1-(3,5-dichloro-4-pyridyl)ethoxy]-1H-indazole

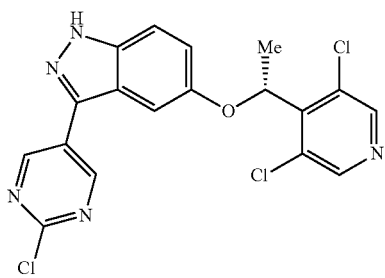 [SMILES: C[C@@H](Oc1ccc2[nH]nc(-c3cnc(Cl)nc3)c2c1)c1c(Cl)cncc1Cl]

Example 48 step 1 product (60 mg, 0.12 mmol, 1 equiv) in dichloromethane (0.6 mL) was treated with trifluoroacetic acid (0.6 mL, 7.84 mmol, 65 equiv) at room temperature overnight. The volatiles were removed under reduced pressure. The residue was dissolved in a 3 to 1 mixture of dichloromethane and methanol (2.4 mL) and treated with MP-Carbonate® (2.42 g) for 2 hours. Resin was filtered and filtrate was concentrated onto Celite directly. The residue was purified with Biotage automated chromatography system (RediSep HP Gold C18 50 g column), eluting with a gradient of 0 to 100% acetonitrile in water to give an off white solid (17.6 mg, 36% yield). Analysis: LCMS: m/z=422.0 (M+H); $^1$H NMR (400 MHz, CDCl3) δ 10.41 (br s, 1H), 9.11 (s, 2H), 8.45 (s, 2H), 7.45 (dd, J=0.5, 9.0 Hz, 1H), 7.21 (dd, J=2.3, 9.0 Hz, 1H), 7.15 (d, J=2.1 Hz, 1H), 6.08 (q, J=6.6 Hz, 1H), 1.84 (d, J=6.6 Hz, 3H).

Example 60. 5-[(1R)-1-(3,5-Dichloro-4-pyridyl)ethoxy]-3-[2-[4-(oxetan-3-yl)-1,4-diazepan-1-yl]pyrimidin-5-yl]-1H-indazole

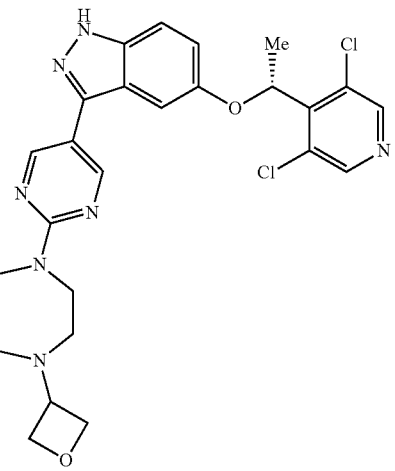

5-[(1R)-1-(3,5-Dichloro-4-pyridyl)ethoxy]-3-[2-[4-(oxetan-3-yl)-1,4-diazepan-1-yl]pyrimidin-5-yl]-1H-indazole. A mixture of example 59 (135 mg, 0.321 mmol, 1.0 equiv), 1-(oxetan-3-yl)-1,4-diazepane (136 mg, 0354 mmol, 1.1 equiv), and potassium carbonate (444 mg, 3.22 mmol, 10 equiv) in N-methylpyrrolidinone was heated at 120° C. overnight. The brown reaction mixture was cooled to room temperature and diluted with water (5 mL) and ethyl acetate (5 mL). The layers were separated and the aqueous layer was extracted with ethyl acetate (3×5 mL). The combined organic layers were dried over sodium sulfate and concentrated under reduced pressure. The brown oil was adsorbed to Celite (1 g) and purified on an Interchim automated chromatography system (RediSep Rf Gold HP C18 15 g column), eluting with a gradient of 0 to 100% methanol and water to give a white solid (100 mg, 57% yield). Analysis: LCMS: m/z=541.2 (M+H); $^1$H NMR (400 MHz, CDCl$_3$) δ 10.11 (br s, 1H), 8.75 (s, 2H), 8.42 (s, 2H), 7.36 (dd, J=0.6, 9.0 Hz, 1H), 7.19 (d, J=2.1 Hz, 1H), 7.13 (dd, J=2.3, 9.0 Hz, 1H), 6.05 (q, J=6.7 Hz, 1H), 4.69-4.63 (m, 2H), 4.63-4.56 (m, 2H), 4.03-3.98 (m, 2H), 3.95 (t, J=6.4 Hz, 2H), 3.71

(quin, J=6.5 Hz, 1H), 2.65-2.58 (m, 2H), 2.49-2.42 (m, 2H), 2.07-2.00 (m, 2H), 1.82 (d, J=6.6 Hz, 3H).

Example 61. 3-[2-(1,4-Diazepan-1-yl)pyrimidin-5-yl]-5-[(1R)-1-(3,5-dichloro-4-pyridyl)ethoxy]-1H-indazole

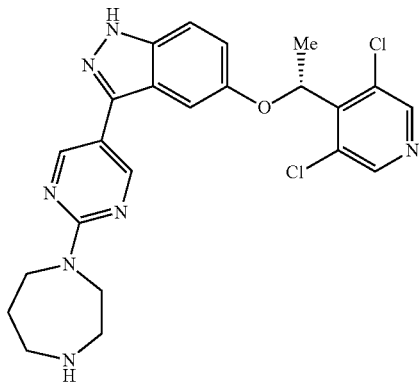 [SMILES: C[C@@H](Oc1ccc2[nH]nc(-c3cnc(N4CCCNCC4)nc3)c2c1)c1c(Cl)cncc1Cl]

Step 1. tert-Butyl 4-(5-(5-((R)-1-(3,5-Dichloropyridin-4-yl)ethoxy)-1-(tetrahydro-2H-pyran-2-yl)-1H-indazol-3-yl)pyrimidin-2-yl)-1,4-diazepane-1-carboxylate. Potassium carbonate (164.1 mg, 1.2 mmol, 4 equiv) and 1-Boc-hexahydro-1,4-diazepine (117 µL, 0.6 mmol, 2 equiv) were sequentially added at room temperature to a nitrogen purged solution of 3-(2-chloropyrimidin-5-yl)-5-[(1R)-1-(3,5-dichloro-4-pyridyl)ethoxy]-1-tetrahydropyran-2-yl-indazole (149.8 mg, 0.30 mmol, 1 equiv) in N-methyl-2-pyrrolidone (3.0 mL). The resulting mixture was heated at 120° C. overnight. After cooling to room temperature, the reaction was concentrated under reduced pressure. The residue was purified on a Biotage automated chromatography system (Biotage Sfär 60 µm 15.5 g silica gel cartridge), eluting with a gradient of 0 to 100% ethyl acetate in heptane to give a yellow solid (179 mg, 90% yield). Analysis: LCMS: m/z=668.2 (M+H).

Step 2. 3-[2-(1,4-Diazepan-1-yl)pyrimidin-5-yl]-5-[(1R)-1-(3,5-dichloro-4-pyridyl)ethoxy]-1H-indazole trifluoroacetic acid salt. Product step 1 (178.6 mg, 0.27 mmol, 1 equiv) in dichloromethane (2.0 mL) was treated with trifluoroacetic acid (2.0 mL, 26.1 mmol, 96 equiv) at room temperature for 2 hours. The reaction mixture was concentrated onto Celite directly and purified an a Biotage automated chromatography system (RediSep Gold HP C18 column 50 g), eluting with a gradient of 0 to 100% acetonitrile in water to give an off white solid (103 mg, 72% yield). Analysis: LCMS: m/z=484.2 (M+H), $^1$H NMR (400 MHz, CD3OD) δ 8.76 (s, 2H), 8.47 (s, 2H), 7.47 (dd, J=0.4, 9.1 Hz, 1H), 7.19 (dd, J=2.3, 9.0 Hz, 1H), 7.09 (d, J=2.1 Hz, 1H), 6.14 (q, J=6.6 Hz, 1H), 4.56 (br s, 1H), 4.22-4.17 (m, 2H), 4.06 (t, J=6.2 Hz, 2H), 3.49-3.46 (m, 2H), 3.38-3.35 (m, 2H), 2.21 (td, J=5.9, 11.5 Hz, 2H), 1.83 (d, J=6.6 Hz, 3H).

Example 62. 4-[5-[5-[(1R)-1-(3,5-Dichloro-4-pyridyl)ethoxy]-1H-indazol-3-yl]pyrimidin-2-yl]-1,4-diazepane-1-carboxamide

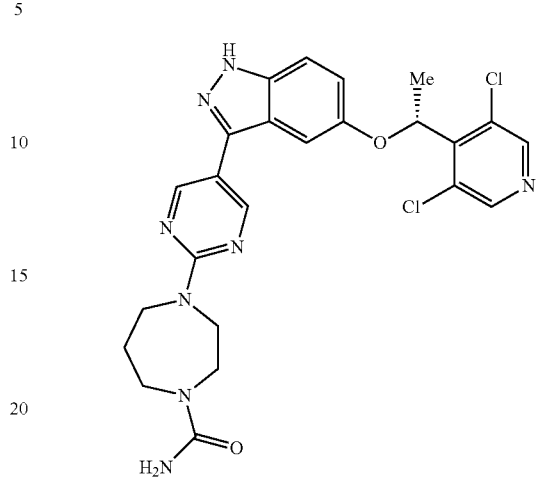

Step 1. 3-(2-(1,4-Diazepan-1-yl)pyrimidin-5-yl)-5-((R)-1-(3,5-dichloropyridin-4-yl)ethoxy)-1-(tetrahydro-2H-pyran-2-yl)-1H-indazole: A suspension of 3-(2-chloropyrimidin-5-yl)-5-[(1R)-1-(3,5-dichloro-4-pyridyl)ethoxy]-1-tetrahydropyran-2-yl-indazole (145 mg, 0.28 mmol, 1 equiv) and potassium carbonate (160 mg, 1.12 mmol, 4 equiv) in 1-methyl-2-pyrrolidone (2 mL) was treated with 1,4-diazepane dihydrochloride (97 mg, 0.57 mmol, 2 equiv). After heating at 120° C. for 16 hours, the reaction mixture was cooled to room temperature and diluted with water (10 mL). The resulting solids were stirred at room temperature for 30 minutes and filtered to give a light brown solid (86 mg, 53% yield), which was used subsequently. Analysis: LCMS (ESI) m/z=568.1 (M+H).

Step 2. 4-(5-(5-((R)-1-(3,5-Dichloropyridin-4-yl)ethoxy)-1-(tetrahydro-2H-pyran-2-yl)-1H-indazol-3-yl)pyrimidin-2-yl)-1,4-diazepane-1-carboxamide (209-4): Trimethylsilyl) isocyanate (23 µL, 0.17 mmol, 1.1 equiv) was added at room temperature to a solution of product step 1 (86 mg, 0.15 mmol, 1 equiv) and triethylamine (24 µL, 0.17 mmol, 1.1 equiv) in THF (2 mL). After 4 hours, the volatiles were removed under reduced pressure. The residue was purified on a Büchi automated chromatography system (Sorbtech 24 g silica gel column), eluting with a gradient of 0 to 80% ethyl acetate in heptanes to give a light brown solid (25 mg, 27% yield). Analysis: LCMS (ESI) m/z=611.1 (M+H).

Step 3. (4-[5-[5-[(1R)-1-(3,5-Dichloro-4-pyridyl)ethoxy]-1H-indazol-3-yl]pyrimidin-2-yl]-1,4-diazepane-1-carboxamide. Product step 2 (25 mg, 0.04 mmol, 1 equiv) was treated with a 1 to 1 mixture of dichloromethane-trifluoracetic acid (0.5 mL) at room temperature for 2 hours. The volatiles were removed under reduced pressure. The residue was diluted with saturated sodium bicarbonate (10 mL) and extracted with ethyl acetate (3×20 mL). The combined organic layers were dried over sodium sulfate, filtered and concentrated under reduced pressure. The residue was purified on a Büchi automated chromatography system (RediSep Rf Gold HP C18, 50 g column), eluting with a gradient of 0 to 80% acetonitrile in water. Product containing fractions were lyophilized to give a white solid (11 mg, 53% yield). Analysis: LCMS (ESI) m/z=527.2 (M+H); $^1$H NMR (400 MHz, CD3OD) δ 8.70-8.67 (m, 2H), 8.48 (s, 2H), 7.45 (d, J=9.0 Hz, 1H), 7.17 (dd, J=2.3, 9.0 Hz, 1H), 7.09 (d, J=2.2 Hz, 1H), 6.14 (q, J=6.6 Hz, 1H), 4.55 (br s, 2H), 4.02 (t, J=5.5 Hz, 2H), 3.91 (t, J=6.1 Hz, 2H), 3.69-3.64 (m, 2H), 3.49-3.45 (m, 2H), 2.05-1.99 (m, 2H), 1.82 (d, J=6.6 Hz, 3H).

Example 63. 5-[(1R)-1-(3,5-Dichloro-4-pyridyl)ethoxy]-3-[2-(4-methylsulfonyl-1,4-diazepan-1-yl)pyrimidin-5-yl]-1H-indazole

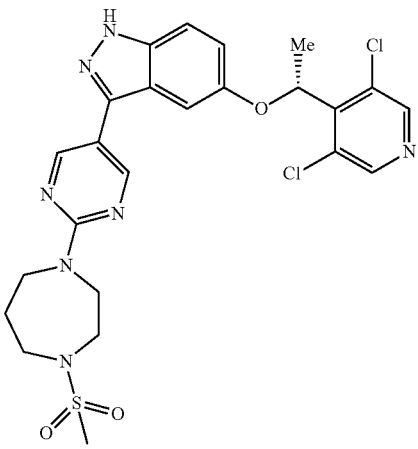 [SMILES: C[C@@H](Oc1ccc2[nH]nc(-c3cnc(N4CCCN(S(C)(=O)=O)CC4)nc3)c2c1)c1c(Cl)cncc1Cl]

Example 61 (76.5 mg, 0.16 mmol, 1 equiv) in THF (1.6 mL) was treated with triethylamine (22.0 µL, 0.63 mmol, 4 equiv) and methanesulfonyl chloride (12.2 µL, 0.63 mmol, 4 equiv) at 40° C. for 4 days. The reaction mixture was concentrated onto Celite directly, then purified on a Biotage automated chromatography system (RediSep Gold HP C18 50 g column), eluting with a gradient of 0 to 100% acetonitrile in water to give a white solid (14.8 mg, 17% yield). Analysis: LCMS: m/z=562.2 (M+H); $^1$H NMR (400 MHz, DMSO-d6) δ 13.13 (s, 1H), 8.77 (s, 2H), 8.56 (s, 2H), 7.47 (d, J=8.9 Hz, 1H), 7.23 (d, J=1.7 Hz, 1H), 7.09 (dd, J=2.3, 9.0 Hz, 1H), 6.14 (q, J=6.7 Hz, 1H), 3.97 (t, J=5.6 Hz, 2H), 3.91 (t, J=6.0 Hz, 2H), 3.50 (t, J=5.5 Hz, 2H), 3.34-3.31 (m, 2H), 2.84 (s, 3H), 1.90 (quin, J=5.7 Hz, 2H), 1.76 (d, J=6.7 Hz, 3H).

Examples 64-68 were synthesized using the procedure and methods for examples 3-9 using tert-butyl 4-[4-(4,4,5,5-tetramethyl-1,3,2-dioxaborolan-2-yl)pyrazol-1-yl]piperidine-1-carboxylate or 1-methyl-4-[4-(4,4,5,5-tetramethyl-1,3,2-dioxaborolan-2-yl)pyrazol-1-yl]piperidine.

| | | |
|---|---|---|
| Example 64<br>5-[(1R)-1-(3,5-dichloro-4-pyridyl)ethoxy]-3-[1-(4-piperidyl)pyrazol-4-yl]-1H-indazole | 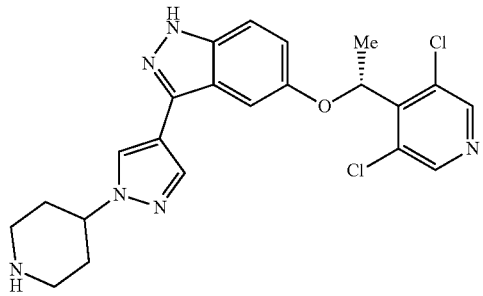 [SMILES: C[C@@H](Oc1ccc2[nH]nc(-c3cnn(C4CCNCC4)c3)c2c1)c1c(Cl)cncc1Cl] | LCMS: m/z = 457.1 (M + H); 1H NMR (400 MHz, DMSO-d6) δ = 12.86 (br s, 1H), 8.59 (s, 2H), 8.35 (s, 1H), 8.13 (s, 1H), 7.84 (s, 1H), 7.42 (d, J = 8.9 Hz, 1H), 7.14 (d, J = 2.1 Hz, 1H), 7.06 (dd, J = 2.3, 8.9 Hz, 1H), 6.14 (q, J = 6.6 Hz, 1H), 4.42-4.34 (m, 1H), 3.21 (br d, J = 12.3 Hz, 2H), 2.79 (br t, J = 11.9 Hz, 2H), 2.10 (br d, J = 11.4 Hz, 2H), 2.04-1.93 (m, 2H), 1.76 (d, J = 6.7 Hz, 3H). |
| Example 65<br>5-[(1R)-1-(3,5-dichloro-4-pyridyl)ethoxy]-3-[1-(1-methyl-4-piperidyl)pyrazol-4-yl]-1H-indazole | 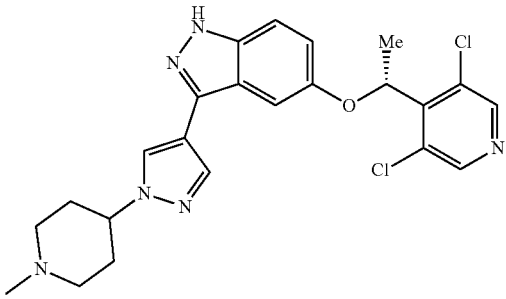 [SMILES: C[C@@H](Oc1ccc2[nH]nc(-c3cnn(C4CCN(C)CC4)c3)c2c1)c1c(Cl)cncc1Cl] | LCMS: m/z = 471.2 (M + H); 1H NMR (400 MHz, DMSO-d6) δ = 12.85 (br s, 1H), 8.58 (s, 2H), 8.18 (s, 1H), 7.87 (s, 1H), 7.42 (d, J = 8.9 Hz, 1H), 7.16 (d, J = 2.1 Hz, 1H), 7.06 (dd, J = 2.3, 9.0 Hz, 1H), 6.14 (q, J = 6.7 Hz, 1H), 4.37 (tt, J = 5.2, 10.0 Hz, 1H), 3.21 (br d, J = 11.9 Hz, 2H), 2.64 (br s, 2H), 2.56-2.51 (m, 3H), 2.23-2.12 (m, 4H), 1.76 (d, J = 6.7 Hz, 3H). |
| Example 66<br>5-[(1R)-1-(3,5-dichloro-4-pyridyl)ethoxy]-3-[1-(1-methylsulfonyl-4-piperidyl)pyrazol-4-yl]-1H-indazole | 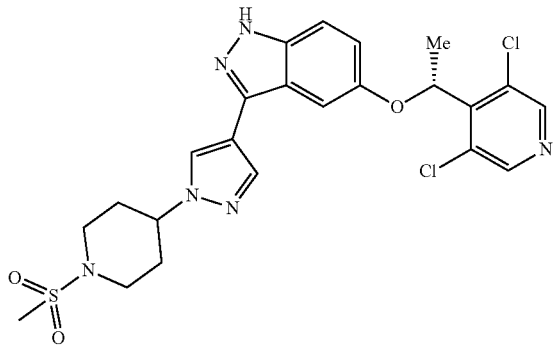 [SMILES: C[C@@H](Oc1ccc2[nH]nc(-c3cnn(C4CCN(S(C)(=O)=O)CC4)c3)c2c1)c1c(Cl)cncc1Cl] | LCMS: m/z = 535.2 (M + H); 1H NMR (400 MHz, DMSO-d6) δ = 12.84 (s, 1H), 8.58 (s, 2H), 8.22 (s, 1H), 7.87 (s, 1H), 7.42 (d, J = 9.0 Hz, 1H), 7.18 (d, J = 1.8 Hz, 1H), 7.06 (dd, J = 2.3, 9.0 Hz, 1H), 6.15 (q, J = 6.7 Hz, 1H), 4.42 (tt, J = 4.1, 11.2 Hz, 1H), 3.73 (br d, J = 12.0 Hz, 2H), 3.03-2.96 (m, 2H), 2.95 (s, 3H), 2.24-2.18 (m, 2H), 2.14-2.04 (m, 2H), 1.76 (d, J = 6.7 Hz, 3H). |

| Example 67<br>4-[4-[5-[(1R)-1-(3,5-dichloro-4-pyridyl)ethoxy]-1H-indazol-3-yl]pyrazol-1-yl]-N,N-dimethyl-piperidine-1-carboxamide | 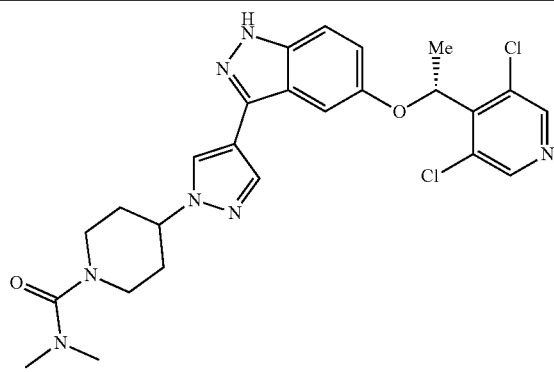 | LCMS: m/z = 528.2 (M + H); ¹H NMR (400 MHz, DMSO-d6) δ = 12.83 (s, 1H), 8.59 (s, 2H), 8.15 (d, J = 0.4 Hz, 1H), 7.84 (d, J = 0.5 Hz, 1H), 7.42 (d, J = 8.9 Hz, 1H), 7.13 (d, J = 2.1 Hz, 1H), 7.06 (dd, J = 2.3, 8.9 Hz, 1H), 6.14 (q, J = 6.7 Hz, 1H), 4.44 (tt, J = 4.2, 11.3 Hz, 1H), 3.70 (br d, J = 13.0 Hz, 2H), 2.97-2.88 (m, 2H), 2.79 (s, 6H), 2.11-2.04 (m, 2H), 2.03-1.92 (m, 2H), 1.76 (d, J = 6.7 Hz, 3H). |
|---|---|---|
| Example 68.<br>4-[4-[5-[(1R)-1-(3,5-dichloro-4-pyridyl)ethoxy]-1H-indazol-3-yl]pyrazol-1-yl]piperidine-1-carboxamide | 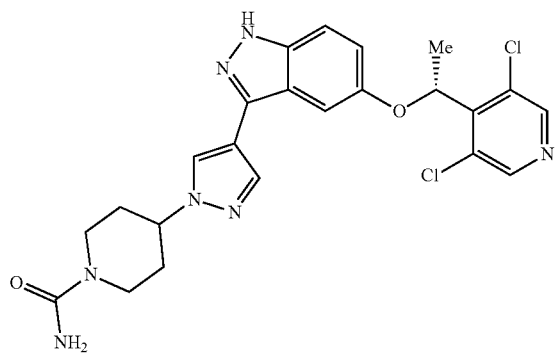 [SMILES: C[C@@H](Oc1ccc2[nH]nc(-c3cnn(C4CCN(C(N)=O)CC4)c3)c2c1)c1c(Cl)cncc1Cl] | LCMS: m/z = 500.2 (M + H); ¹H NMR (400 MHz, DMSO-d6) δ = H NMR (400 MHz, DMSO-d6) δ = 12.82 (s, 1H), 8.58 (s, 2H), 8.15 (s, 1H), 7.84 (s, 1H), 7.41 (d, J = 9.0 Hz, 1H), 7.15 (d, J = 2.0 Hz, 1H), 7.06 (dd, J = 2.3, 9.0 Hz, 1H), 6.14 (q, J = 6.7 Hz, 1H), 6.04 (s, 2H), 4.44 (tt, J = 4.0, 11.4 Hz, 1H), 4.11 (br d, J = 13.1 Hz, 2H), 3.32-3.30 (m, 1H), 2.89 (br t, J = 11.9 Hz, 2H), 2.10-1.99 (m, 2H), 1.93-1.79 (m, 2H), 1.76 (d, J = 6.6 Hz, 3H). |

Examples 69-72 were synthesized using the procedure and methods for examples 3-9 using tert-butyl 4-[5-(4,4,5,5-tetramethyl-1,3,2-dioxaborolan-2-yl)-2-pyridyl]piperidine-1-carboxylate.

| Example 69.<br>5-[(1R)-1-(3,5-dichloro-4-pyridyl)ethoxy]-3-[6-(4-piperidyl)-3-pyridyl]-1H-indazole | 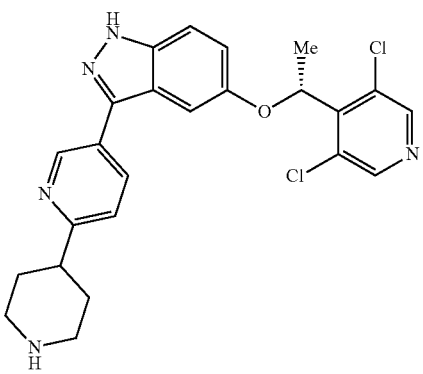 [SMILES: C[C@@H](Oc1ccc2[nH]nc(-c3ccc(C4CCNCC4)nc3)c2c1)c1c(Cl)cncc1Cl] | LCMS: m/z = 468.1 (M + H); ¹H NMR (400 MHz, DMSO-d6) δ = 13.29 (br s, 1H), 8.95 (dd, J = 0.7, 2.3 Hz, 1H), 8.59 (s, 2H), 8.46 (br s, 2H), 8.09 (dd, J = 2.3, 8.2 Hz, 1H), 7.52 (d, J = 9.3 Hz, 1H), 7.45 (d, J = 7.8 Hz, 1H), 7.23 (d, J = 2.2 Hz, 1H), 7.13 (dd, J = 2.3, 9.0 Hz, 1H), 6.16-6.10 (m, 1H), 3.45-3.40 (m, 2H), 3.14-3.03 (m, 3H), 2.13-2.05 (m, 2H), 2.03-1.92 (m, 2H), 1.77 (d, J = 6.7 Hz, 3H) |
|---|---|---|

-continued

| | | |
|---|---|---|
| Example 70. 5-[(1R)-1-(3,5-dichloro-4-pyridyl)ethoxy]-3-[6-(1-methylsulfonyl-4-piperidyl)-3-pyridyl]-1H-indazole | 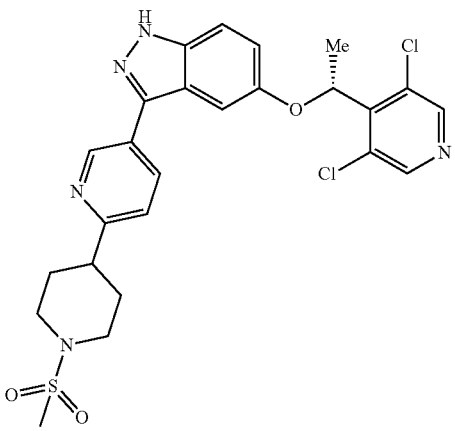 [SMILES: C[C@@H](Oc1ccc2[nH]nc(-c3ccc(C4CCN(S(C)(=O)=O)CC4)nc3)c2c1)c1c(Cl)cncc1Cl] | LCMS: m/z = 546.1 (M + H); $^1$H NMR (400 MHz, DMSO-d6) δ = 8.99-8.91 (m, 1H), 8.59 (s, 2H), 8.05 (dd, J = 2.1, 8.1 Hz, 1H), 7.55-7.44 (m, 2H), 7.22 (d, J = 1.6 Hz, 1H), 7.11 (dd, J = 2.1, 9.0 Hz, 1H), 6.12 (q, J = 6.5 Hz, 1H), 3.72 (br d, J = 11.7 Hz, 2H), 2.93-2.85 (m, 6H), 2.07-2.00 (m, 2H), 1.88-1.79 (m, 2H), 1.76 (d, J = 6.6 Hz, 3H) |
| Example 71. 4-[5-[5-[(1R)-1-(3,5-dichloro-4-pyridyl)ethoxy]-1H-indazol-3-yl]-2-pyridyl]-N,N-dimethyl-piperidine-1-carboxamide | 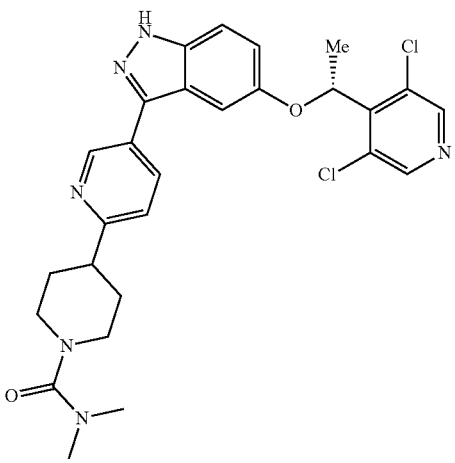 | LCMS: m/z = 4539.2 (M + H); $^1$H NMR (400 MHz, DMSO-d6) δ = 13.28 (br s, 1H), 8.94 (d, J = 1.8 Hz, 1H), 8.60 (s, 2H), 8.04 (dd, J = 2.2, 8.1 Hz, 1H), 7.52 (d, J = 9.0 Hz, 1H), 7.45 (d, J = 8.1 Hz, 1H), 7.23 (d, J = 2.0 Hz, 1H), 7.12 (dd, J = 2.2, 8.9 Hz, 1H), 6.13 (q, J = 6.6 Hz, 1H), 3.70 (br d, J = 13.0 Hz, 2H), 2.96-2.81 (m, 3H), 2.78 (s, 6H), 1.93-1.86 (m, 2H), 1.81-1.72 (m, 5H) |
| Example 72. 4-[5-[5-[(1R)-1-(3,5-dichloro-4-pyridyl)ethoxy]-1H-indazol-3-yl]-2-pyridyl]piperidine-1-carboxamide | 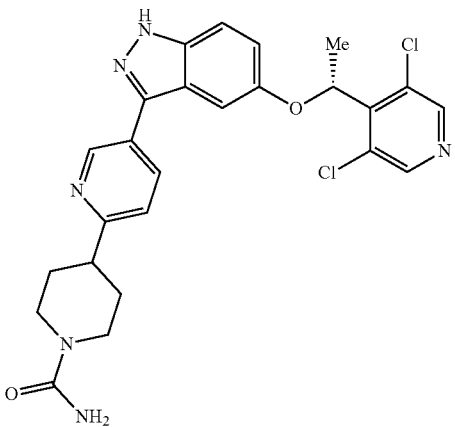 [SMILES: C[C@@H](Oc1ccc2[nH]nc(-c3ccc(C4CCN(C(N)=O)CC4)nc3)c2c1)c1c(Cl)cncc1Cl] | LCMS: m/z = 511.2 (M + H); $^1$H NMR (400 MHz, DMSO-d6) δ = 13.25 (s, 1H), 8.93 (d, J = 1.7 Hz, 1H), 8.60 (s, 2H), 8.03 (dd, J = 2.3, 8.1 Hz, 1H), 7.51 (d, J = 9.0 Hz, 1H), 7.44 (d, J = 7.8 Hz, 1H), 7.22 (d, J = 2.0 Hz, 1H), 7.12 (dd, J = 2.3, 9.0 Hz, 1H), 6.12 (q, J = 6.6 Hz, 1H), 5.93 (s, 2H), 4.10 (br d, J = 13.2 Hz, 2H), 2.93 (tt, J = 3.5, 11.8 Hz, 1H), 2.81 (dt, J = 2.1, 12.7 Hz, 2H), 1.85 (br dd, J = 2.3, 12.7 Hz, 2H), 1.76 (d, J = 6.6 Hz, 3H), 1.65 (dq, J = 3.7, 12.3 Hz, 2H) |

Examples 73-76 were synthesized using the procedure and methods for examples 3-9 using tert-butyl 6-oxo-5-oxa-2,7-diazaspiro[3.4]octane-2-carboxylate and tert-butyl 2-oxo-1-oxa-3,8-diazaspiro[4.5]decane-8-carboxylate.

| | | |
|---|---|---|
| Example 73. 7-[5-[5-[(1R)-1-(3,5-dichloro-4-pyridyl)ethoxy]-1H-indazol-3-yl]-2-pyridyl]-5-oxa-2,7-diazaspiro [3.4]octan-6-one | 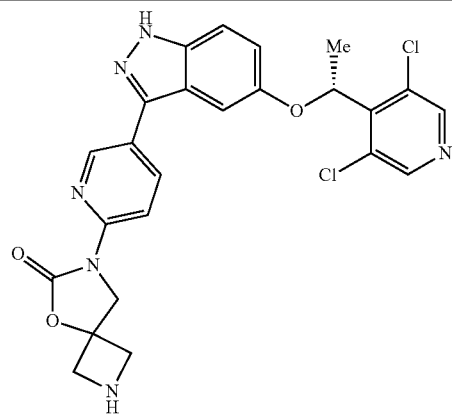 | LCMS: m/z = 511.1 (M + H); ¹H NMR (400 MHz, DMSO-d6) δ = 13.27 (br s, 1H), 8.80 (dd, J = 0.9, 2.3 Hz, 1H), 8.58 (s, 2H), 8.24 (dd, J = 2.3, 8.8 Hz, 1H), 8.20-8.17 (m, 1H), 7.51 (d, J = 9.0 Hz, 1H), 7.27 (d, J = 2.1 Hz, 1H), 7.12 (dd, J = 2.3, 9.0 Hz, 1H), 6.15 (q, J = 6.7 Hz, 1H), 4.48 (s, 2H), 3.96-3.85 (m, 4H), 1.77 (d, J = 6.6 Hz, 3H) |
| Example 74. 3-[5-[5-[(1R)-1-(3,5-dichloro-4-pyridyl)ethoxy]-1H-indazol-3-yl]-2-pyridyl]-1-oxa-3,8-diazaspiro[4.5] decan-2-one | 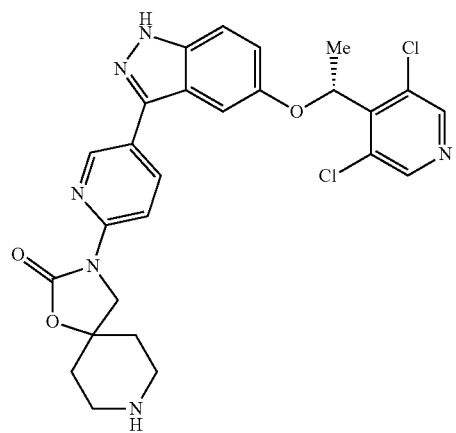 [SMILES: C[C@@H](Oc1ccc2[nH]nc(-c3ccc(N4CC5(CCNCC5)OC4=O)nc3)c2c1)c1c(Cl)cncc1Cl] | LCMS: m/z = 539.1 (M + H); ¹H NMR (400 MHz, CD3OD) δ = 8.73 (dd, J = 0.9, 2.3 Hz, 1H), 8.47 (s, 2H), 8.29 (dd, J = 0.8, 8.7 Hz, 1H), 8.14 (dd, J = 2.3, 8.8 Hz, 1H), 7.47 (dd, J = 0.6, 9.0 Hz, 1H), 7.18 (dd, J = 2.3, 9.0 Hz, 1H), 7.14 (d, J = 2.1 Hz, 1H), 6.14 (q, J = 6.7 Hz, 1H), 4.13 (s, 2H), 3.10-3.01 (m, 2H), 2.98-2.90 (m, 2H), 2.04-1.98 (m, 2H), 1.96-1.88 (m, 2H), 1.82 (d, J = 6.6 Hz, 3H) |
| Example 75. 3-[5-[5-[(1R)-1-(3,5-dichloro-4-pyridyl)ethoxy]-1H-indazol-3-yl]-2-pyridyl]-8-methyl-1-oxa-3,8-diazaspiro [4.5]decan-2-one | 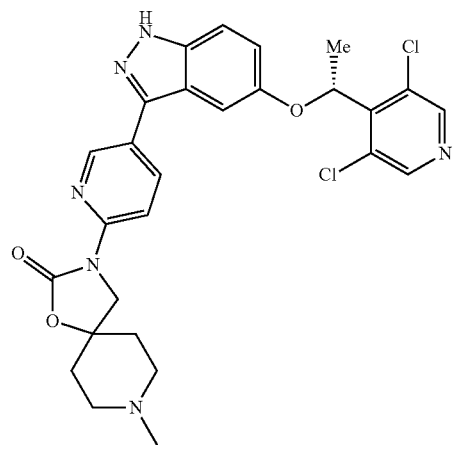 [SMILES: C[C@@H](Oc1ccc2[nH]nc(-c3ccc(N4CC5(CCN(C)CC5)OC4=O)nc3)c2c1)c1c(Cl)cncc1Cl] | LCMS: m/z = 553.1 (M + H); ¹H NMR (400 MHz, DMSO-d6) δ = 13.25 (br s, 1H), 8.79 (dd, J = 1.1, 2.0 Hz, 1H), 8.57 (s, 2H), 8.26-8.20 (m, 2H), 7.51 (d, J = 9.0 Hz, 1H), 7.27 (d, J = 2.1 Hz, 1H), 7.12 (dd, J = 2.2, 9.0 Hz, 1H), 6.14 (q, J = 6.7 Hz, 1H), 4.04 (s, 2H), 2.43 (br s, 4H), 2.21 (s, 3H), 1.96-1.88 (m, 4H), 1.76 (d, J = 6.6 Hz, 3H) |

| Example 76. 3-[5-[5-[(1R)-1-(3,5-dichloro-4-pyridyl)ethoxy]-1H-indazol-3-yl]-2-pyridyl]-8-methylsulfonyl-1-oxa-3,8-diazaspiro[4.5]decan-2-one | 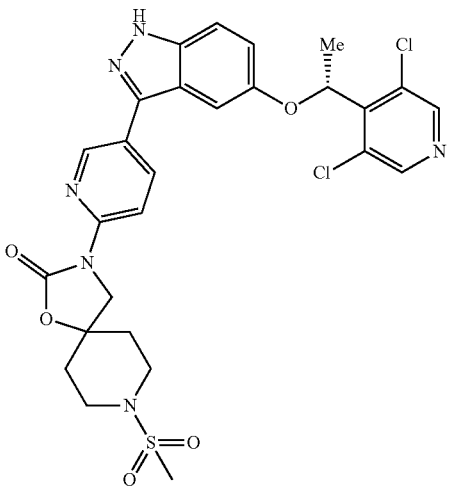 | LCMS: m/z = 627.2 (M + H); $^1$H NMR (400 MHz, DMSO-d6) δ = 13.26 (br s, 1H), 8.82-8.78 (m, 1H), 8.58 (s, 2H), 8.27-8.22 (m, 2H), 7.51 (d, J = 9.2 Hz, 1H), 7.28 (d, J = 2.1 Hz, 1H), 7.13 (dd, J = 2.3, 9.0 Hz, 1H), 6.16 (q, J = 6.7 Hz, 1H), 4.10 (s, 2H), 3.47-3.41 (m, 2H), 3.20-3.12 (m, 2H), 2.95 (s, 3H), 2.12-2.00 (m, 4H), 1.77 (d, J = 6.7 Hz, 3H) |
|---|---|---|

Example 77. 8-[5-[5-[(1R)-1-(3,5-dichloro-4-pyridyl)ethoxy]-1H-indazol-3-yl]-3-fluoro-2-pyridyl]-2λ$^6$-thia-8-azaspiro[4.5]decane 2,2-dioxide Example 78. 8-[5-[5-[(1R)-1-(3,5-dichloro-4-pyridyl)ethoxy]-1H-indazol-3-yl]-2-pyridyl]-2λ$^6$-thia-8-azaspiro[4.5]decane 2,2-dioxide

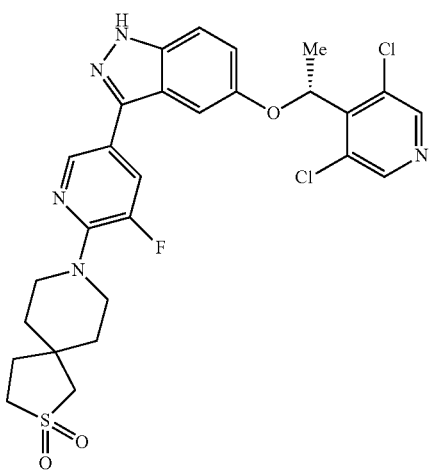 [SMILES: C[C@@H](Oc1ccc2[nH]nc(-c3cnc(N4CCC5(CC4)CCS(=O)(=O)C5)c(F)c3)c2c1)c1c(Cl)cncc1Cl]

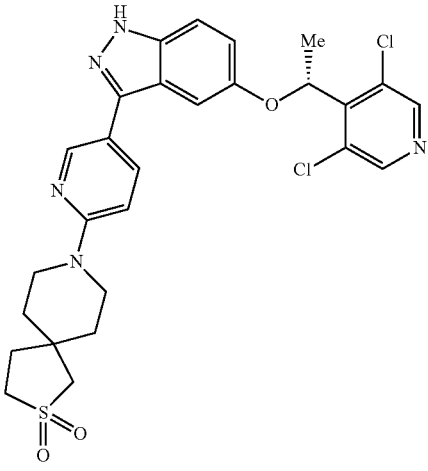 [SMILES: C[C@@H](Oc1ccc2[nH]nc(-c3ccc(N4CCC5(CC4)CCS(=O)(=O)C5)nc3)c2c1)c1c(Cl)cncc1Cl]

This example was synthesized using 3-(6-chloro-4-fluoropyridin-3-yl)-5-((R)-1-(3,5-dichloropyridin-4-yl)ethoxy)-1-(tetrahydro-2H-pyran-2-yl)-1H-indazole and 2λ$^6$-thia-8-azaspiro[4.5]decane 2,2-dioxide using the method for examples 17 and 42. LCMS: m/z=590.2 (M+H); $^1$H NMR (400 MHz, DMSO-d6) δ=13.18 (br s, 1H), 8.57 (s, 2H), 8.44 (t, J=1.7 Hz, 1H), 7.76 (dd, J=1.9, 14.5 Hz, 1H), 7.49 (d, J=9.0 Hz, 1H), 7.20 (d, J=2.1 Hz, 1H), 7.10 (dd, J=2.3, 9.0 Hz, 1H), 6.13 (q, J=6.6 Hz, 1H), 3.77-3.69 (m, 2H), 3.35-3.28 (m, 4H), 3.24 (t, J=7.6 Hz, 2H), 2.10 (t, J=7.6 Hz, 2H), 1.88-1.81 (m, 2H), 1.78-1.70 (m, 5H).

This example was synthesized using 3-(6-chloro-pyridin-3-yl)-5-((R)-1-(3,5-dichloropyridin-4-yl)ethoxy)-1-(tetrahydro-2H-pyran-2-yl)-1H-indazole and 2λ$^6$-thia-8-azaspiro[4.5]decane 2,2-dioxide using the method for examples 17 and 42. LCMS: m/z=572.2 (M+H). $^1$H NMR (400 MHz, DMSO-d6) δ=12.97 (s, 1H), 8.60 (s, 2H), 8.54 (d, J=2.2 Hz, 1H), 7.84 (dd, J=2.4, 8.9 Hz, 1H), 7.45 (d, J=8.9 Hz, 1H), 7.16 (d, J=1.6 Hz, 1H), 7.09 (dd, J=2.3, 9.0 Hz, 1H), 7.00 (d, J=8.9 Hz, 1H), 6.10 (q, J=6.7 Hz, 1H), 3.96-3.87 (m, 2H), 3.40-3.32 (m, 2H), 3.24 (t, J=7.5 Hz, 2H), 3.18 (s, 2H), 2.09 (t, J=7.6 Hz, 2H), 1.81 (br d, J=4.9 Hz, 2H), 1.76 (d, J=6.6 Hz, 3H), 1.65 (ddd, J=3.9, 9.6, 13.4 Hz, 2H).

(R)-1-(3,5-dichloro-2-methyl-4-pyridyl)ethanol and (S)-1-(3,5-dichloro-2-methyl-4-pyridyl)ethanol

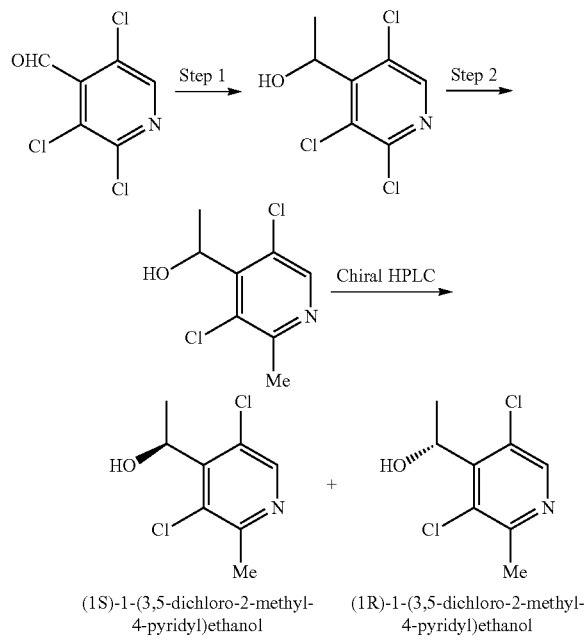

(1S)-1-(3,5-dichloro-2-methyl-4-pyridyl)ethanol (1R)-1-(3,5-dichloro-2-methyl-4-pyridyl)ethanol Step 1. (Trichloro-4-pyridyl)ethanol. A 500 mL three-neck round bottom flask was charged with 2,3,5-trichloro-pyridine-4-carbaldehyde (40 g, 0.19 mol) and THF (200 mL). MeMgBr (70 mL, 0.21 mol) was added in portions and the mixture was stirred at −70° C. for 1 h. The reaction was quenched with aqueous ammonium chloride solution, extracted with ethyl acetate (200 mL×3), dried over $Na_2SO_4$ and concentrated. The residue was purified by silica gel column (PE/EA=30/1) to give (33 g) a yellow liquid (33 g, 77%). Analysis: LCMS: m/z=227 (M+H).

Step 2. 1-(3,5-Dichloro-2-methyl-4-pyridyl)ethanol. A mixture of product step 1 (33 g, 0.147 mmol), methylboronic acid (26.3 g, 0.429 mmol) $K_2CO_3$ (40 g, 0.290 mmol) and $Pd(PPh_3)_2Cl_2$ (3 g) in dioxane (300 mL) was stirred at 110° C. overnight. The resulting mixture was filtered and the filtrate was concentrated in vacuo to give the crude product, which was further purified by silica gel column chromatography to give a yellow liquid (15 g, 50%). LCMS: m/z=206.1 (M+H). The product was separated by Prep-HPLC (Chiralpak ID 5×25 cm, hexanes/ethanol (80/20), 60 mL/min. 38 C.°) to give (S)-1-(3,5-dichloro-2-methyl-4-pyridyl)ethanol (5 g) and (R)-1-(3,5-dichloro-2-methyl-4-pyridyl)ethanol R (5 g) as yellow liquid. Peak 1 5.5 min; (S)-1-(3,5-dichloro-2-methyl-4-pyridyl)ethanol. Analysis: LCMS: m/z=206.1 (M+H). $^1$H NMR (400 MHz, $CDCl_3$) δ 8.36 (s, 1H), 5.57 (m, 1H), 2.93 (b, 1H), 2.64 (s, 3H), 1.65 (d, 3H). Peak 2 6.9 min; (R)-1-(3,5-dichloro-2-methyl-4-pyridyl)ethanol. Analysis: LCMS: m/z=206.1 (M+H). $^1$H NMR (400 MHz, $CDCl_3$) δ 8.36 (s, 1H), 5.57 (m, 1H), 2.93 (b, 1H), 2.64 (s, 3H), 1.65 (d, 3H).

Examples 79-95 were synthesized using the procedure and methods for examples 64 using tert-butyl 4-[4-(4,4,5,5-tetramethyl-1,3,2-dioxaborolan-2-yl)pyrazol-1-yl]piperidine-1-carboxylate, tert-butyl (3S)-3-[4-(4,4,5,5-tetramethyl-1,3,2-dioxaborolan-2-yl)pyrazol-1-yl]pyrrolidine-1-carboxylate, tert-butyl (3R)-3-[4-(4,4,5,5-tetramethyl-1,3,2-dioxaborolan-2-yl)pyrazol-1-yl]pyrrolidine-1-carboxylate or tert-butyl 3-[4-(4,4,5,5-tetramethyl-1,3,2-dioxaborolan-2-yl)pyrazol-1-yl]azetidine-1-carboxylate and (1R)-1-(3,5-dichloro-4-pyridyl)ethanol or (1R)-1-(3,5-dichloro-2-methyl-4-pyridyl)ethanol.

| Example 79 2-[4-[4-[5-[(1R)-1-(3,5-dichloro-4-pyridyl)ethoxy]-1H-indazol-3-yl]pyrazol-1-yl]-1-piperidyl]ethanol | 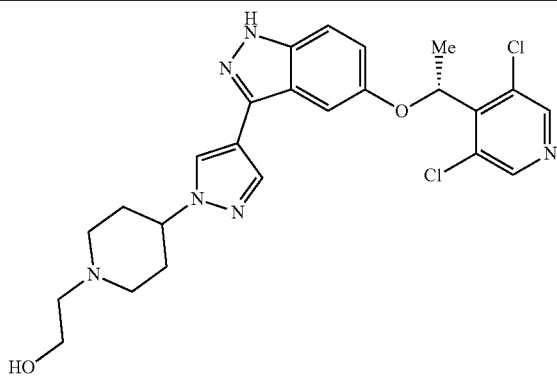 | LCMS: m/z = 501.2 (free base, M + H); $^1$H NMR (400 MHz, DMSO-d6) δ = 12.82 (br s, 1H), 8.58 (s, 2H), 8.15 (s, 1H), 7.83 (d, J = 0.6 Hz, 1H), 7.41 (d, J = 9.0 Hz, 1H), 7.16 (d, J = 2.1 Hz, 1H), 7.05 (dd, J = 2.3, 8.9 Hz, 1H), 6.15 (q, J = 6.6 Hz, 1H), 4.22 (tt, J = 5.3, 10.3 Hz, 1H), 3.55 (t, J = 6.3 Hz, 2H), 3.03 (br d, J = 11.7 Hz, 2H), 2.49 - 2.46 (m, 2H), 2.21 (dt, J = 3.5, 11.0 Hz, 2H), 2.10 - 2.00 (m, 4H), 1.76 (d, J = 6.6 Hz, 3H |
|---|---|---|
| Example 80 5-[(1R)-1-(3,5-dichloro-2-methyl-4-pyridyl)ethoxy]-3-[1-(1-methyl-4-piperidyl)pyrazol-4-yl]-1H-indazole | 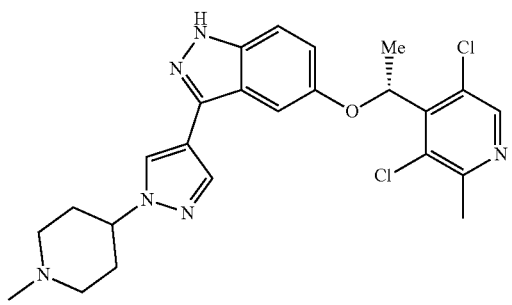 [SMILES: Cc1ncc(Cl)c([C@@H](C)Oc2ccc3[nH]nc(-c4cnn(C5CCN(C)CC5)c4)c3c2)c1Cl] | LCMS: m/z = 485.2 (M + H); $^1$H NMR (400 MHz, DMSO-d6) δ = 12.83 (br s, 1H), 8.43 (s, 1H), 8.20 (s, 1H), 8.15 (d, J = 0.5 Hz, 1H), 7.80 (d, J = 0.6 Hz, 1H), 7.41 (d, J = 8.9 Hz, 1H), 7.11 (d, J = 2.1 Hz, 1H), 7.05 (dd, J = 2.3, 9.0 Hz, 1H), 6.15 (q, J = 6.8 Hz, 1H), 4.26 - 4.18 (m, 1H), 2.94 (br d, J = 11.2 Hz, 2H), 2.27 (s, 3H), 2.19 - 2.11 (m, 2H), 2.10 - 2.03 (m, 4H), 1.76 (d, J = 6.6 Hz, 3H) |

| | | |
|---|---|---|
| Example 81<br>1-[4-[4-[5-[(1R)-1-(3,5-dichloro-4-pyridyl)ethoxy]-1H-indazol-3-yl]pyrazol-1-yl]-1-piperidyl]-2-(dimethylamino)ethanone | 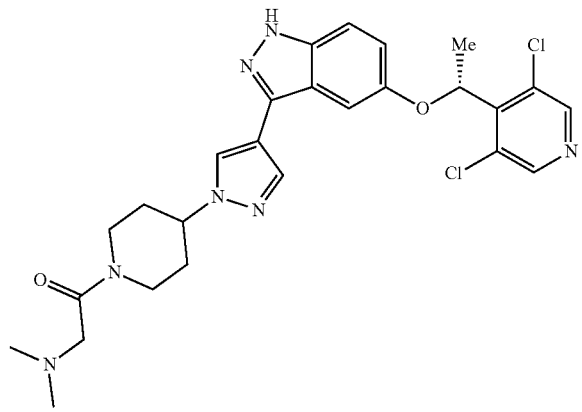 [SMILES: C[C@@H](Oc1ccc2[nH]nc(-c3cnn(C4CCN(C(=O)CN(C)C)CC4)c3)c2c1)c1c(Cl)cncc1Cl] | LCMS: m/z = 542.2 (M + H); $^1$H NMR (400 MHz, DMSO-d6) δ = 12.84 (br s, 1H), 8.64 - 8.51 (m, 2H), 8.19 (s, 1H), 8.16 (d, J = 3.3 Hz, 1H), 7.85 (d, J = 0.5 Hz, 1H), 7.42 (d, J = 9.0 Hz, 1H), 7.14 (s, 1H), 7.06 (dd, J = 2.3, 8.9 Hz, 1H), 6.18 - 6.10 (m, 1H), 4.58 - 4.46 (m, 2H), 4.20 (br d, J = 13.6 Hz, 1H), 3.29 - 3.20 (m, 2H), 3.18 - 3.14 (m, 1H), 2.80 (br t, J = 12.0 Hz, 1H), 2.30 - 2.21 (m, 6H), 2.13 (br s, 2H), 2.02 - 1.92 (m, 1H), 1.88 - 1.78 (m, 1H), 1.76 (d, J = 6.6 Hz, 3H) |
| Example 82<br>1-[4-[4-[5-[(1R)-1-(3,5-dichloro-4-pyridyl)ethoxy]-1H-indazol-3-yl]pyrazol-1-yl]-1-piperidyl]-3-(dimethylamino)propan-1-one | 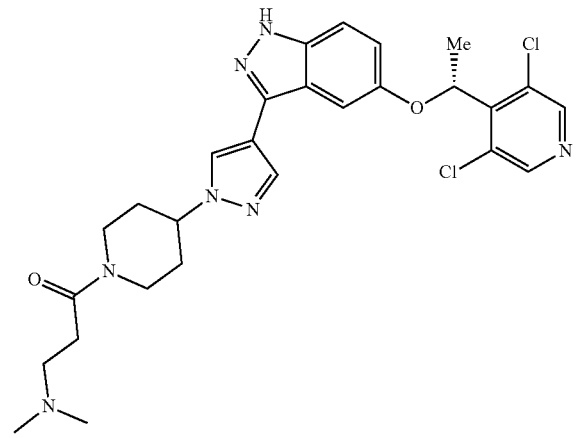 [SMILES: C[C@@H](Oc1ccc2[nH]nc(-c3cnn(C4CCN(C(=O)CCN(C)C)CC4)c3)c2c1)c1c(Cl)cncc1Cl] | LCMS: m/z = 556.2 (free base, M + H); $^1$H NMR (400 MHz, DMSO-d6) δ = 12.83 (br s, 1H), 8.58 (s, 2H), 8.19 (s, 1H), 8.17 (d, J = 4.0 Hz, 1H), 7.84 (d, J = 0.4 Hz, 1H), 7.42 (d, J = 9.2 Hz, 1H), 7.14 (s, 1H), 7.06 (dd, J = 2.3, 8.9 Hz, 1H), 6.14 (br dd, J = 3.0, 6.7 Hz, 1H), 4.58 - 4.50 (m, 2H), 4.05 (br d, J = 12.5 Hz, 1H), 3.25 (br t, J = 12.3 Hz, 1H), 2.83 - 2.69 (m, 3H), 2.64 (br d, J = 6.8 Hz, 2H), 2.32 (s, 6H), 2.14 - 2.07 (m, 2H), 2.02 - 1.92 (m, 1H), 1.87 - 1.79 (m, 1H), 1.76 (d, J = 6.7 Hz, 3H) |
| Example 83<br>5-[(1R)-1-(3,5-dichloro-4-pyridyl)ethoxy]-3-[1-(1-isopropyl-4-piperidyl)pyrazol-4-yl]-1H-indazole | 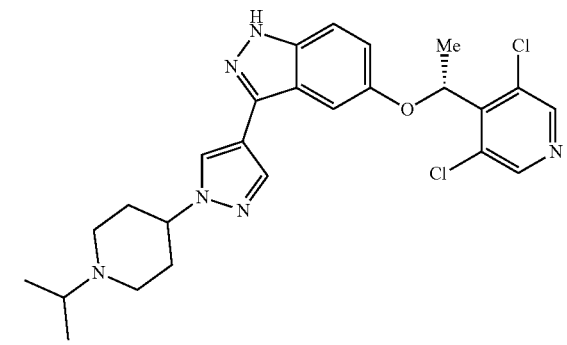 [SMILES: CC(C)N1CCC(n2cc(-c3n[nH]c4ccc(O[C@H](C)c5c(Cl)cncc5Cl)cc34)cn2)CC1] | LCMS: m/z = 499.2 (free base, M + H); $^1$H NMR (400 MHz, DMSO-d6) δ = 12.82 (br s, 1H), 8.58 (s, 2H), 8.14 (s, 1H), 7.82 (d, J = 0.6 Hz, 1H), 7.41 (d, J = 9.0 Hz, 1H), 7.16 (d, J = 2.1 Hz, 1H), 7.05 (dd, J = 2.3, 9.0 Hz, 1H), 6.15 (q, J = 6.7 Hz, 1H), 4.19 (tt, J = 4.3, 11.4 Hz, 1H), 2.94 (br d, J = 11.7 Hz, 2H), 2.80 (spt, J = 6.5 Hz, 1H), 2.33 (brt, J = 11.5 Hz, 2H), 2.11 - 2.06 (m, 2H), 2.04 - 1.93 (m, 2H), 1.76 (d, J = 6.7 Hz, 3H), 1.02 (d, J = 6.6 Hz, 6H) |
| Example 84<br>5-[(1R)-1-(3,5-dichloro-4-pyridyl)ethoxy]-3-[(1R)-1-(1-isopropylpyrrolidin-3-yl)pyrazol-4-yl]-1H-indazole | 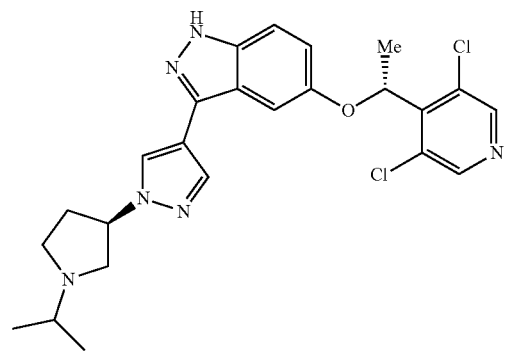 [SMILES: CC(C)N1CC[C@@H](n2cc(-c3n[nH]c4ccc(O[C@H](C)c5c(Cl)cncc5Cl)cc34)cn2)C1] | LCMS: m/z = 485.1 (M + H); $^1$H NMR (400 MHz, DMSO-d6) δ = 12.83 (s, 1H), 8.59 (s, 2H), 8.16 (d, J = 0.6 Hz, 1H), 7.82 (d, J = 0.5 Hz, 1H), 7.42 (d, J = 8.9 Hz, 1H), 7.13 (d, J = 1.7 Hz, 1H), 7.07 (dd, J = 2.3, 8.9 Hz, 1H), 6.18 - 6.11 (m, 1H), 4.99 - 4.92 (m, 1H), 3.05 (dd, J = 7.5, 9.5 Hz, 1H), 2.88 - 2.82 (m, 2H), 2.71 - 2.65 (m, 1H), 2.47 - 2.32 (m, 2H), 2.21 - 2.13 (m, 1H), 1.77 (d, J = 6.6 Hz, 3H), 1.07 (t, J = 6.4 Hz, 6H) |

-continued

| | | |
|---|---|---|
| Example 85<br>3-[1-(azetidin-3-yl)pyrazol-4-yl]-5-[(1R)-1-(3,5-dichloro-4-pyridyl)ethoxy]-1H-indazole | 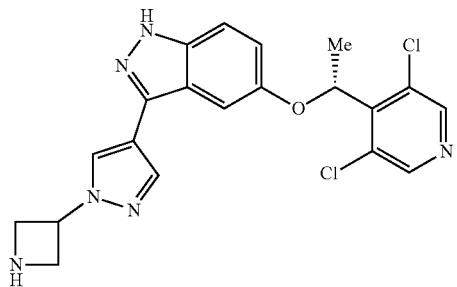 [SMILES: C[C@@H](Oc1ccc2[nH]nc(-c3cnn(C4CNC4)c3)c2c1)c1c(Cl)cncc1Cl] | LCMS: m/z = 429.1 (M + H); $^1$H NMR (400 MHz, DMSO-d6) δ = 12.94 (s, 1H), 9.12 (br s, 2H), 8.59 (s, 2H), 8.34 (d, J = 0.6 Hz, 1H), 8.06 (s, 1H), 7.44 (d, J = 8.9 Hz, 1H), 7.19 (d, J = 2.0 Hz, 1H), 7.06 (dd, J = 2.3, 9.0 Hz, 1H), 6.13 (q, J = 6.7 Hz, 1H), 5.52 (quin, J = 7.6 Hz, 1H), 4.51 - 4.40 (m, 4H), 1.77 (d, J = 6.6 Hz, 3H) |
| Example 86<br>5-[(1R)-1-(3,5-dichloro-4-pyridyl)ethoxy]-3-[1-(1-isopropylazetidin-3-yl)pyrazol-4-yl]-1H-indazole | 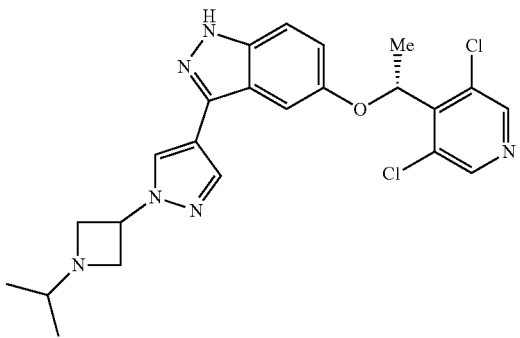 [SMILES: CC(C)N1CC(n2cc(-c3n[nH]c4ccc(O[C@H](C)c5c(Cl)cncc5Cl)cc34)cn2)C1] | LCMS: m/z = 471.1 (M + H); $^1$H NMR (400 MHz, DMSO-d6) δ = 12.86 (s, 1H), 8.58 (s, 2H), 8.27 (d, J = 0.5 Hz, 1H), 7.89 (s, 1H), 7.42 (d, J = 9.0 Hz, 1H), 7.16 (d, J = 1.8 Hz, 1H), 7.06 (dd, J = 2.3, 9.0 Hz, 1H), 6.15 (q, J = 6.6 Hz, 1H), 5.00 (quin, J = 6.9 Hz, 1H), 3.74 - 3.69 (m, 2H), 3.41 (dd, J = 6.8, 7.8 Hz, 2H), 2.46 (spt, J = 6.2 Hz, 1H), 1.77 (d, J = 6.6 Hz, 3H), 0.93 (d, J = 6.1 Hz, 6H) |
| Example 87<br>5-[(1R)-1-(3,5-dichloro-4-pyridyl)ethoxy]-3-[1-[1-(oxetan-3-yl)-4-piperidyl]pyrazol-4-yl]-1H-indazole | 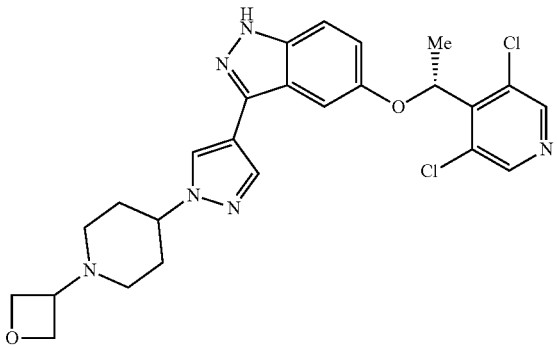 [SMILES: C[C@@H](Oc1ccc2[nH]nc(-c3cnn(C4CCN(C5COC5)CC4)c3)c2c1)c1c(Cl)cncc1Cl] | LCMS: m/z = 513.2 (M + H); $^1$H NMR (400 MHz, DMSO-d6) δ = 12.82 (br s, 1H), 8.59 (s, 2H), 8.17 (s, 1H), 7.84 (d, J = 0.6 Hz, 1H), 7.41 (d, J = 8.9 Hz, 1H), 7.18 (d, J = 1.8 Hz, 1H), 7.05 (dd, J = 2.3, 9.0 Hz, 1H), 6.15 (q, J = 6.6 Hz, 1H), 4.60 - 4.54 (m, 2H), 4.52 - 4.44 (m, 2H), 4.25 (tt, J = 4.8, 10.1 Hz, 1H), 3.47 (quin, J = 6.4 Hz, 1H), 2.85 (br d, J = 9.3 Hz, 2H), 2.12 - 1.96 (m, 6H), 1.77 (d, J = 6.7 Hz, 3H). |
| Example 88<br>5-[(1R)-1-(3,5-dichloro-4-pyridyl)ethoxy]-3-[1-[(3S)-pyrrolidin-3-yl]pyrazol-4-yl]-1H-indazole | 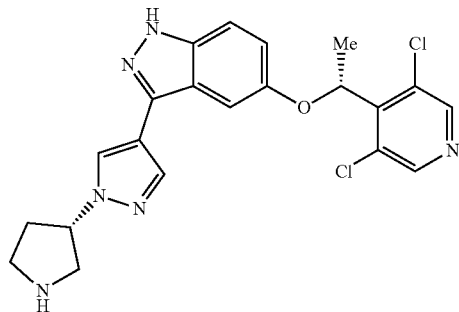 | LCMS: m/z = 443.1 (M + H); $^1$H NMR (400 MHz, DMSO-d6) δ = 12.91 (s, 1H), 9.15 (br s, 2H), 8.59 (s, 2H), 8.32 (s, 1H), 7.95 (s, 1H), 7.43 (d, J = 8.9 Hz, 1H), 7.18 (d, J = 2.1 Hz, 1H), 7.07 (dd, J = 2.3, 9.0 Hz, 1H), 6.13 (q, J = 6.7 Hz, 1H), 5.31 - 5.25 (m, 1H), 3.74 - 3.61 (m, 2H), 3.53 - 3.38 (m, 2H), 2.49 - 2.44 (m, 1H), 2.41 - 2.33 (m, 1H), 1.77 (d, J = 6.6 Hz, 3H) |

| | | |
|---|---|---|
| Example 89<br>5-[(1R)-1-(3,5-dichloro-4-pyridyl)ethoxy]-3-[1-[(3S)-1-ethylpyrrolidin-3-yl]pyrazol-4-yl]-1H-indazole | 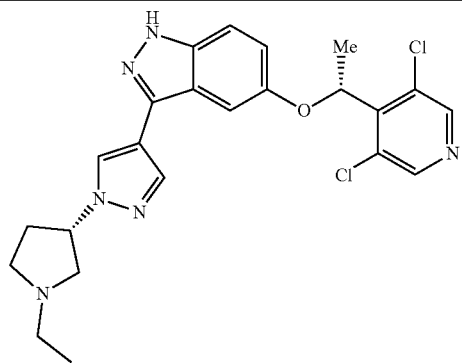 | LCMS: m/z = 471.1 (M + H); $^1$H NMR (400 MHz, DMSO-d6) δ = 12.84 (s, 1H), 8.58 (s, 2H), 8.19 (s, 1H), 7.83 (s, 1H), 7.42 (d, J = 8.9 Hz, 1H), 7.13 (d, J = 1.6 Hz, 1H), 7.07 (dd, J = 2.3, 9.0 Hz, 1H), 6.15 (q, J = 6.6 Hz, 1H), 5.05 - 4.94 (m, 1H), 2.99 (br s, 1H), 2.88 (br s, 2H), 2.70 - 2.51 (m, 3H), 2.46 - 2.37 (m, 1H), 2.22 - 2.13 (m, 1H), 1.77 (d, J = 6.6 Hz, 3H), 1.09 (t, J = 7.2 Hz, 3H) |
| Example 90<br>3-[1-(1-cyclobutyl-4-piperidyl)pyrazol-4-yl]-5-[(1R)-1-(3,5-dichloro-4-pyridyl)ethoxy]-1H-indazole | 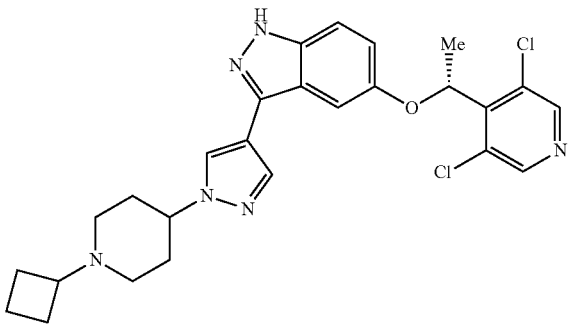 [SMILES: C[C@@H](Oc1ccc2[nH]nc(-c3cnn(C4CCN(C5CCC5)CC4)c3)c2c1)c1c(Cl)cncc1Cl] | LCMS: m/z = 511.2 (free base, M + H); $^1$H NMR (400 MHz, DMSO-d6) δ = 12.82 (br s, 1H), 8.58 (s, 2H), 8.15 (s, 1H), 7.82 (s, 1H), 7.41 (d, J = 9.0 Hz, 1H), 7.17 (d, J = 2.1 Hz, 1H), 7.05 (dd, J = 2.3, 8.9 Hz, 1H), 6.15 (q, J = 6.6 Hz, 1H), 4.25 - 4.17 (m, 1H), 2.92 (br d, J = 10.3 Hz, 2H), 2.76 (quin, J = 7.8 Hz, 1H), 2.11 - 1.96 (m, 6H), 1.95 - 1.88 (m, 2H), 1.86 - 1.78 (m, 2H), 1.76 (d, J = 6.6 Hz, 3H), 1.69 - 1.60 (m, 2H) |
| Example 91<br>5-[(1R)-1-(3,5-dichloro-4-pyridyl)ethoxy]-3-[1-[(3R)-1-ethylpyrrolidin-3-yl]pyrazol-4-yl]-1H-indazole | 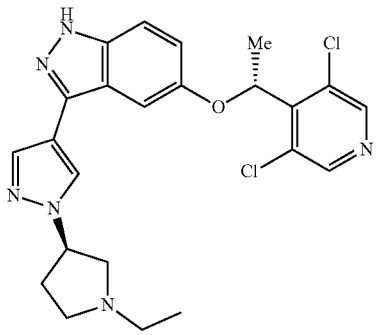 [SMILES: CCN1CC[C@@H](n2cc(-c3n[nH]c4ccc(O[C@H](C)c5c(Cl)cncc5Cl)cc34)cn2)C1] | LCMS: m/z = 471.2 (M + H); $^1$H NMR (400 MHz, DMSO-d6) δ = 12.85 (s, 1H), 8.59 (s, 2H), 8.17 (s, 1H), 7.84 (s, 1H), 7.42 (d, J = 8.9 Hz, 1H), 7.13 (d, J = 1.6 Hz, 1H), 7.07 (dd, J = 2.3, 9.0 Hz, 1H), 6.14 (q, J = 6.7 Hz, 1H), 5.06 - 4.97 (m, 1H), 3.08 - 3.00 (m, 1H), 2.91 (br d, J = 4.0 Hz, 2H), 2.73 - 2.64 (m, 1H), 2.59 (br d, J = 6.0 Hz, 2H), 2.48 - 2.38 (m, 1H), 2.24 - 2.14 (m, 1H), 1.76 (d, J = 6.7 Hz, 3H), 1.10 (t, J = 7.2 Hz, 3H) |
| Example 92<br>5-[(1R)-1-(3,5-dichloro-2-methyl-4-pyridyl)ethoxy]-3-[1-(4-piperidyl)pyrazol-4-yl]-1H-indazole | 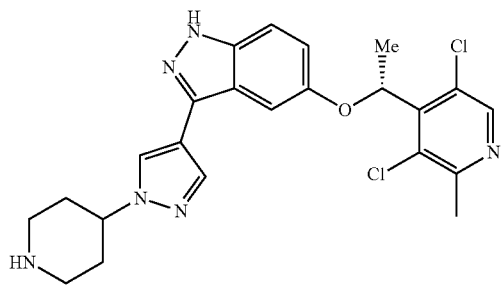 [SMILES: Cc1ncc(Cl)c([C@@H](C)Oc2ccc3[nH]nc(-c4cnn(C5CCNCC5)c4)c3c2)c1Cl] | LCMS m/z = 471.3 (M + H) (free base); $^1$H NMR (400 MHz, DMSO-d6) δ = 12.87 (br s, 1H), 8.80 (br d, J = 8.3 Hz, 1H), 8.53 (br d, J = 9.7 Hz, 1H), 8.45 (s, 1H), 8.17 (s, 1H), 7.86 (s, 1H), 7.43 (d, J = 9.0 Hz, 1H), 7.11 (d, J = 2.1 Hz, 1H), 7.06 (dd, J = 2.3, 9.0 Hz, 1H), 6.14 (q, J = 6.7 Hz, 1H), 4.63 - 4.56 (m, 1H), 3.47 (br d, J = 12.8 Hz, 2H), 3.14 (q, J = 10.8 Hz, 2H), 2.54 - 2.51 (m, 3H), 2.31 - 2.25 (m, 2H), 2.20 (br d, J = 12.3 Hz, 2H), 1.76 (d, J = 6.7 Hz, 3H) |
| Example 93<br>5-[(1R)-1-(3,5-dichloro-2-methyl-4-pyridyl)ethoxy]-3-[1-(1-isopropyl-4-piperidyl)pyrazol-4-yl]-1H-indazole | 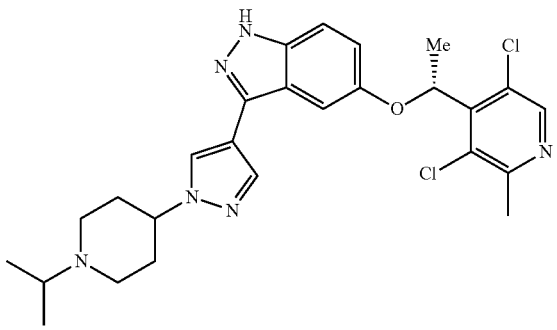 [SMILES: Cc1ncc(Cl)c([C@@H](C)Oc2ccc3[nH]nc(-c4cnn(C5CCN(C(C)C)CC5)c4)c3c2)c1Cl] | LCMS: m/z = 513.2 (M + H); $^1$H NMR (400 MHz, DMSO-d6) δ = 12.83 (br s, 1H), 8.43 (s, 1H), 8.15 - 8.11 (m, 1H), 7.79 (s, 1H), 7.41 (d, J = 8.9 Hz, 1H), 7.11 (d, J = 2.2 Hz, 1H), 7.05 (dd, J = 2.3, 8.9 Hz, 1H), 6.15 (q, J = 6.7 Hz, 1H), 4.18 (tt, J = 4.3, 11.5 Hz, 1H), 2.92 (br d, J = 11.7 Hz, 2H), 2.77 (spt, J = 6.6 Hz, 1H), 2.54 - 2.52 (m, 3H), 2.36 - 2.22 (m, 2H), 2.12 - 1.92 (m, 4H), 1.75 (d, J = 6.6 Hz, 3H), 1.01 (d, J = 6.5 Hz, 6H) |

-continued

| Example 94<br>5-[(1R)-1-(3,5-dichloro-2-methyl-4-pyridyl)ethoxy]-3-[1-[1-(oxetan-3-yl)-4-piperidyl]pyrazol-4-yl]-1H-indazole | 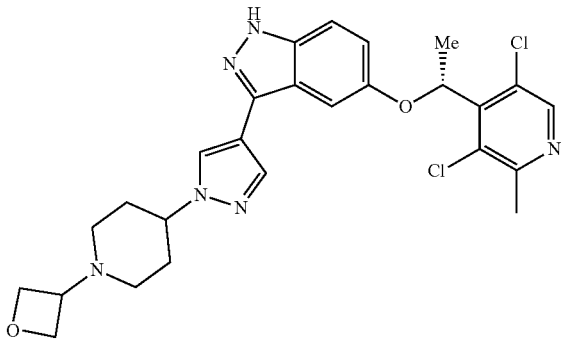 [SMILES: Cc1ncc(Cl)c([C@@H](C)Oc2ccc3[nH]nc(-c4cnn(C5CCN(C6COC6)CC5)c4)c3c2)c1Cl] | LCMS: m/z = 527.2 (M + H); $^1$H NMR (400 MHz, DMSO-d6) δ = 12.84 (br s, 1H), 8.44 (s, 1H), 8.16 (s, 1H), 7.80 (d, J = 0.6 Hz, 1H), 7.42 (br d, J = 8.9 Hz, 1H), 7.12 (d, J = 2.1 Hz, 1H), 7.05 (dd, J = 2.3, 9.0 Hz, 1H), 6.18 - 6.12 (m, 1H), 4.57 (t, J = 6.5 Hz, 2H), 4.47 (t, J = 6.1 Hz, 2H), 4.25 (tt, J = 5.1, 10.0 Hz, 1H), 3.51 - 3.42 (m, 1H), 2.84 (br d, J = 9.0 Hz, 2H), 2.57 - 2.51 (m, 3H), 2.11 - 1.95 (m, 6H), 1.76 (d, J = 6.7 Hz, 3H) |
| --- | --- | --- |
| Example 95<br>3-[1-(1-cyclobutyl-4-piperidyl)pyrazol-4-yl]-5-[(1R)-1-(3,5-dichloro-2-methyl-4-pyridyl)ethoxy]-1H-indazole | 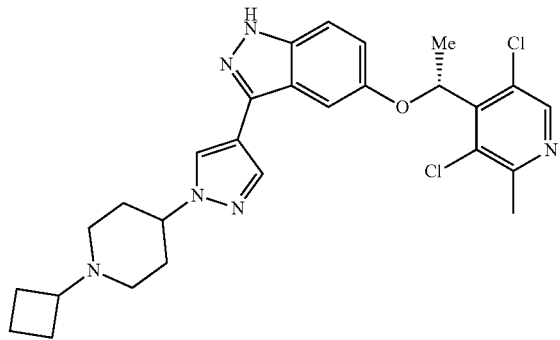 [SMILES: Cc1ncc(Cl)c([C@@H](C)Oc2ccc3[nH]nc(-c4cnn(C5CCN(C6CCC6)CC5)c4)c3c2)c1Cl] | LCMS: m/z = 525.2 (M + H); $^1$H NMR (400 MHz, DMSO-d6) δ = 12.82 (br s, 1H), 8.43 (s, 1H), 8.14 (s, 1H), 7.79 (s, 1H), 7.41 (d, J = 8.9 Hz, 1H), 7.12 (d, J = 2.1 Hz, 1H), 7.05 (dd, J = 2.3, 9.0 Hz, 1H), 6.15 (q, J = 6.6 Hz, 1H), 4.25 - 4.16 (m, 1H), 2.91 (br d, J = 11.2 Hz, 2H), 2.74 (quin, J = 7.8 Hz, 1H), 2.55 - 2.51 (m, 3H), 2.08 - 1.86 (m, 8H), 1.85 - 1.74 (m, 5H), 1.69 - 1.59 (m, 2H) |

Examples 96-140 were synthesized using the previously described procedures.

| Example 96<br>5-[(1R)-1-(3,5-dichloro-4-pyridyl)ethoxy]-3-[6-(1-methyl-1,6-diazaspiro[3.3]heptan-6-yl)-3-pyridyl]-1H-indazole | 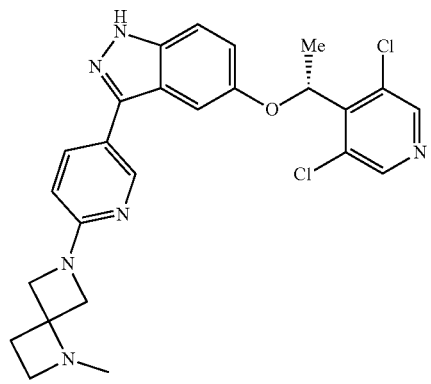 [SMILES: C[C@@H](Oc1ccc2[nH]nc(-c3ccc(N4CC5(CCN5C)C4)nc3)c2c1)c1c(Cl)cncc1Cl] | LCMS: m/z = 495.1 (M + H); $^1$H NMR (400 MHz, DMSO-d6) δ = 13.00 (br s, 1H), 8.59 (s, 2H), 8.54 - 8.50 (m, 1H), 8.13 (s, 1H), 7.87 (dd, J = 2.3, 8.6 Hz, 1H), 7.46 (d, J = 8.9 Hz, 1H), 7.17 (d, J = 2.0 Hz, 1H), 7.09 (dd, J = 2.3, 9.0 Hz, 1H), 6.58 (d, J = 8.7 Hz, 1H), 6.11 (q, J = 6.6 Hz, 1H), 4.23 (d, J = 9.4 Hz, 2H), 4.03 (d, J = 9.7 Hz, 2H), 2.48 - 2.37 (m, 5H), 1.76 (d, J = 6.6 Hz, 3H) |
| --- | --- | --- |

-continued

Example 97
9-[5-[5-[(1R)-1-(3,5-dichloro-4-pyridyl)ethoxy]-1H-indazol-3-yl]-2-pyridyl]-4-methyl-1,4,9-triazaspiro[5.5]undecan-2-one

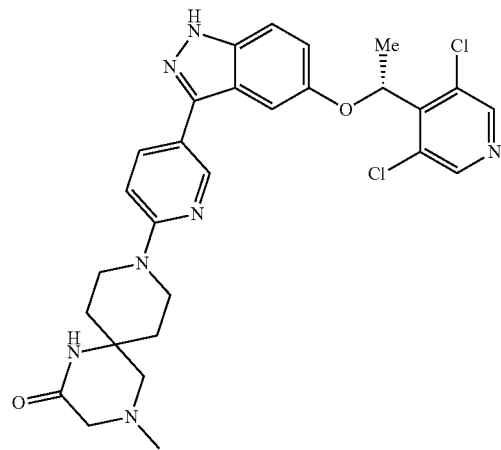 [SMILES: C[C@@H](Oc1ccc2[nH]nc(-c3ccc(N4CCC5(CC4)CN(C)CC(=O)N5)nc3)c2c1)c1c(Cl)cncc1Cl]

LCMS: m/z = 566.2 (M + H); $^1$H NMR (400 MHz, DMSO-d6) δ = 12.97 (s, 1H), 8.61 (s, 2H), 8.53 (d, J = 2.3 Hz, 1H), 7.90 (s, 1H), 7.84 (dd, J = 2.4, 8.8 Hz, 1H), 7.46 (d, J = 9.0 Hz, 1H), 7.16 (s, 1H), 7.09 (dd, J = 2.3, 9.0 Hz, 1H), 6.98 (d, J = 8.8 Hz, 1H), 6.10 (q, J = 6.6 Hz, 1H), 3.99 (br d, J = 13.7 Hz, 2H), 3.45 - 3.35 (m, 2H), 2.85 (s, 2H), 2.58 - 2.52 (m, 2H), 2.25 (s, 3H), 1.80 - 1.64 (m, 7H)

Example 98
9-[5-[5-[(1R)-1-(3,5-dichloro-4-pyridyl)ethoxy]-1H-indazol-3-yl]-2-pyridyl]-1,4-dimethyl-1,4,9-triazaspiro[5.5]undecan-2-one

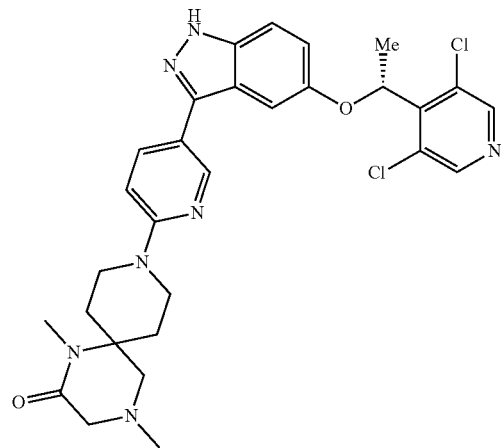 [SMILES: C[C@@H](Oc1ccc2[nH]nc(-c3ccc(N4CCC5(CC4)CN(C)CC(=O)N5C)nc3)c2c1)c1c(Cl)cncc1Cl]

LCMS m/z = 580.2 (M + H); $^1$H NMR (400 MHz, DMSO-d6) δ = 12.99 (s, 1H), 8.60 (s, 2H), 8.55 (d, J = 2.2 Hz, 1H), 7.86 (dd, J = 2.4, 8.9 Hz, 1H), 7.46 (d, J = 9.0 Hz, 1H), 7.16 (s, 1H), 7.09 (dd, J = 2.3, 9.0 Hz, 1H), 7.00 (d, J = 8.8 Hz, 1H), 6.10 (q, J = 6.7 Hz, 1H), 4.32 (br d, J = 14.7 Hz, 2H), 3.10 - 3.01 (m, 2H), 2.98 (s, 2H), 2.78 - 2.71 (m, 5H), 2.27 (s, 3H), 2.08 - 1.97 (m, 2H), 1.80 - 1.72 (m, 5H)

Example 99
3-[6-(1,6-diazaspiro[3.3]heptan-6-yl)-3-pyridyl]-5-[(1R)-1-(3,5-dichloro-4-pyridyl)ethoxy]-1H-indazole

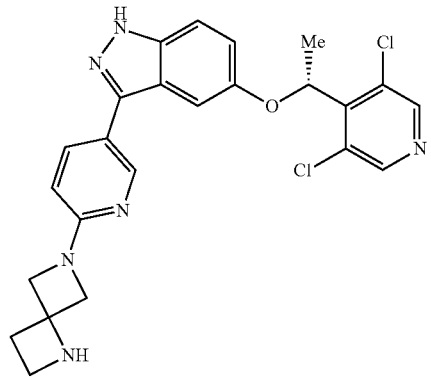 [SMILES: C[C@@H](Oc1ccc2[nH]nc(-c3ccc(N4CC5(CCN5)C4)nc3)c2c1)c1c(Cl)cncc1Cl]

LCMS m/z = 481.1 (M + H); $^1$H NMR (400 MHz, DMSO-d6) δ = 12.99 (br s, 1H), 8.59 (s, 2H), 8.50 (dd, J = 0.7, 2.3 Hz, 1H), 8.21 (s, 1H), 7.84 (dd, J = 2.3, 8.7 Hz, 1H), 7.45 (d, J = 9.0 Hz, 1H), 7.16 (d, J = 2.1 Hz, 1H), 7.08 (dd, J = 2.3, 9.0 Hz, 1H), 6.53 (dd, J = 0.6, 8.6 Hz, 1H), 6.11 (q, J = 6.7 Hz, 1H), 4.16 (d, J = 9.7 Hz, 2H), 4.03 (d, J = 9.0 Hz, 2H), 3.38 (t, J = 7.2 Hz, 2H), 2.55 - 2.51 (m, 1H), 1.76 (d, J = 6.7 Hz, 3H)

-continued

Example 100
5-[(1R)-1-(3,5-dichloro-4-pyridyl)ethoxy]-3-[6-(1-methylsulfonyl-1,6-diazaspiro[3.3]heptan-6-yl)-3-pyridyl]-1H-indazole

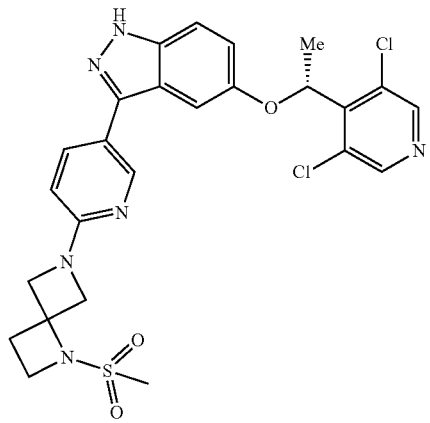 [SMILES: C[C@@H](Oc1ccc2[nH]nc(-c3ccc(N4CC5(CCN5S(C)(=O)=O)C4)nc3)c2c1)c1c(Cl)cncc1Cl]

LCMS m/z = 559.1 (M + H); $^1$H NMR (400 MHz, DMSO-d6) δ = 13.01 (br s, 1H), 8.59 (s, 2H), 8.53 (dd, J = 0.6, 2.3 Hz, 1H), 8.17 (s, 1H), 7.88 (dd, J = 2.4, 8.6 Hz, 1H), 7.46 (d, J = 9.0 Hz, 1H), 7.18 (d, J = 2.1 Hz, 1H), 7.09 (dd, J = 2.3, 9.0 Hz, 1H), 6.59 (d, J = 8.2 Hz, 1H), 6.11 (q, J = 6.6 Hz, 1H), 4.43 (d, J = 9.7 Hz, 2H), 4.21 (d, J = 9.8 Hz, 2H), 3.87 (t, J = 7.4 Hz, 2H), 3.07 (s, 3H), 2.64 (t, J = 7.4 Hz, 2H), 1.76 (d, J = 6.6 Hz, 3H)

Example 101
4-[5-[5-[(1R)-1-(3,5-dichloro-4-pyridyl)ethoxy]-1H-indazol-3-yl]-3-methyl-2-pyridyl]morpholine

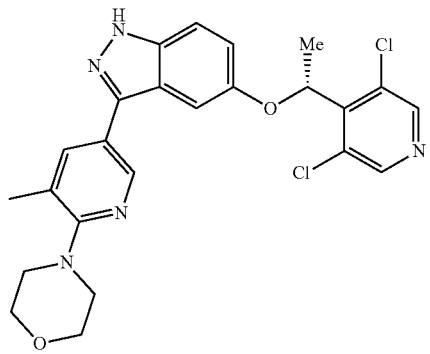 [SMILES: Cc1cc(-c2n[nH]c3ccc(O[C@H](C)c4c(Cl)cncc4Cl)cc23)cnc1N1CCOCC1]

LCMS m/z = 484.1 (M + H); 1H NMR (400 MHz, DMSO-d6) δ = 8.66 - 8.48 (m, 3H), 7.82 (dd, J = 0.7, 2.3 Hz, 1H), 7.49 (d, J = 9.0 Hz, 1H), 7.16 (d, J = 2.1 Hz, 1H), 7.10 (dd, J = 2.3, 9.0 Hz, 1H), 6.11 (q, J = 6.7 Hz, 1H), 3.82 - 3.73 (m, 4H), 3.17 - 3.10 (m, 4H), 2.36 (s, 3H), 1.75 (d, J = 6.6 Hz, 3H)

Example 102
5-[5-[(1R)-1-(3,5-dichloro-4-pyridyl)ethoxy]-1H-indazol-3-yl]-2-morpholino-pyridine-3-carbonitrile

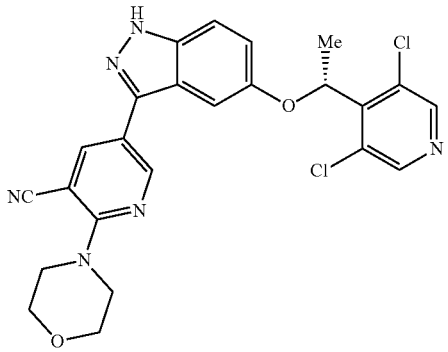 [SMILES: C[C@@H](Oc1ccc2[nH]nc(-c3cnc(N4CCOCC4)c(C#N)c3)c2c1)c1c(Cl)cncc1Cl]

LCMS m/z = 495.1 (M + H); $^1$H NMR (400 MHz, DMSO-d6) δ = 13.24 (br s, 1H), 8.85 (d, J = 2.4 Hz, 1H), 8.56 (s, 2H), 8.27 (d, J = 2.4 Hz, 1H), 7.50 (d, J = 9.0 Hz, 1H), 7.18 (d, J = 2.2 Hz, 1H), 7.11 (dd, J = 2.3, 9.0 Hz, 1H), 6.13 (q, J = 6.7 Hz, 1H), 3.80 - 3.67 (m, 8H), 1.76 (d, J = 6.6 Hz, 3H)

Example 103
4-[6-[5-[(1R)-1-(3,5-dichloro-4-pyridyl)ethoxy]-1H-indazol-3-yl]-3-pyridyl]morpholine

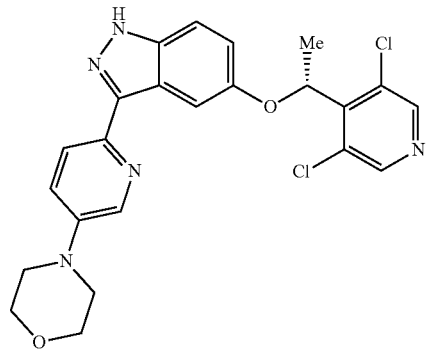 [SMILES: C[C@@H](Oc1ccc2[nH]nc(-c3ccc(N4CCOCC4)cn3)c2c1)c1c(Cl)cncc1Cl]

LCMS: m/z = 470 (M + H); $^1$H NMR (400 MHz, DMSO-d6) δ = 13.03 (br s, 1H), 8.61 (s, 2H), 8.35 (br s, 1H), 7.90 (br d, J = 8.8 Hz, 1H), 7.83 (br s, 1H), 7.43 (br d, J = 8.7 Hz, 2H), 7.07 (br d, J = 7.9 Hz, 1H), 6.03 (q, J = 6.6 Hz, 1H), 3.81 (t, J = 4.5 Hz, 4H), 3.25 (br s, 4H), 1.76 (d, J = 6.7 Hz, 3H)

-continued

Example 104
5-[(1R)-1-(3,5-dichloro-2-methyl-4-pyridyl)ethoxy]-3-(1-tetrahydropyran-4-ylpyrazol-4-yl)-1H-indazole

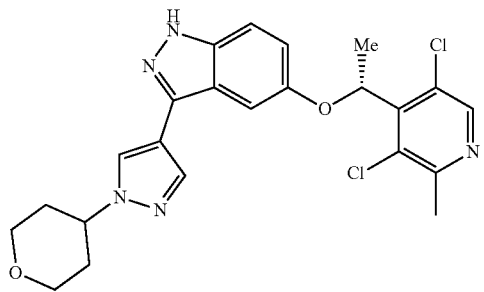 [SMILES: Cc1ncc(Cl)c([C@@H](C)Oc2ccc3[nH]nc(-c4cnn(C5CCOCC5)c4)c3c2)c1Cl]

LCMS: m/z = 472.1 (M + H); $^1$H NMR (400 MHz, DMSO-d6) δ = 12.84 (br s, 1H), 8.43 (s, 1H), 8.18 (s, 1H), 7.82 (s, 1H), 7.42 (d, J = 9.0 Hz, 1H), 7.12 (d, J = 2.0 Hz, 1H), 7.05 (dd, J = 2.2, 8.9 Hz, 1H), 6.15 (q, J = 6.6 Hz, 1H), 4.49 (td, J = 7.9, 15.4 Hz, 1H), 4.07 - 3.96 (m, 2H), 3.56 - 3.46 (m, 2H), 2.52 (s, 3H), 2.11 - 1.98 (m, 4H), 1.75 (d, J = 6.6 Hz, 3H)

Example 105
4-[5-[5-[(1R)-1-(3,5-dichloro-4-pyridyl)ethoxy]-1H-indazol-3-yl]-3-methoxy-2-pyridyl]morpholine

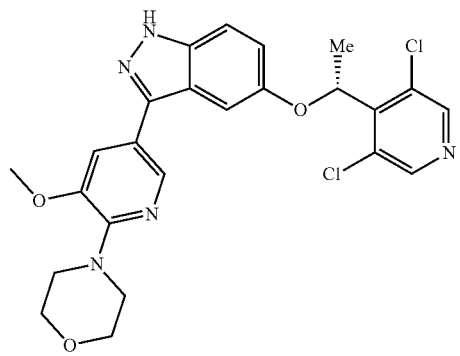 [SMILES: COc1cc(-c2n[nH]c3ccc(O[C@H](C)c4c(Cl)cncc4Cl)cc23)cnc1N1CCOCC1]

LCMS: m/z = 500.1 (M + H); 1H NMR (400 MHz, DMSO-d6) δ = 13.12 (br s, 1H), 8.56 (s, 2H), 8.21 (d, J = 1.8 Hz, 1H), 7.58 (d, J = 1.8 Hz, 1H), 7.48 (d, J = 9.0 Hz, 1H), 7.26 (d, J = 2.0 Hz, 1H), 7.11 (dd, J = 2.3, 9.0 Hz, 1H), 6.14 (q, J = 6.7 Hz, 1H), 3.89 (s, 3H), 3.80 - 3.71 (m, 4H), 3.42 - 3.36 (m, 4H), 1.75 (d, J = 6.6 Hz, 3H)

Example 106
5-[(1R)-1-(3,5-dichloro-4-pyridyl)ethoxy]-3-(1-tetrahydropyran-4-ylpyrazol-4-yl)-1H-indazole

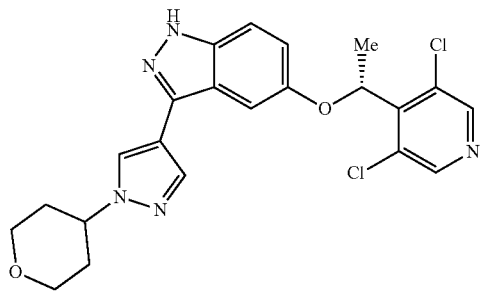 [SMILES: C[C@@H](Oc1ccc2[nH]nc(-c3cnn(C4CCOCC4)c3)c2c1)c1c(Cl)cncc1Cl]

LCMS: m/z = 458.1 (M + H); 1H NMR (400 MHz, DMSO-d6) δ = 12.83 (br s, 1H), 8.58 (s, 2H), 8.18 (s, 1H), 7.85 (d, J = 0.6 Hz, 1H), 7.42 (d, J = 8.9 Hz, 1H), 7.17 (d, J = 1.8 Hz, 1H), 7.06 (dd, J = 2.3, 8.9 Hz, 1H), 6.15 (q, J = 6.6 Hz, 1H), 4.54 - 4.45 (m, 1H), 4.05 - 3.98 (m, 2H), 3.56 - 3.47 (m, 2H), 2.08 - 2.00 (m, 4H), 1.76 (d, J = 6.6 Hz, 3H)

Example 107
5-[(1R)-1-(3,5-dichloro-2-methyl-4-pyridyl)ethoxy]-3-[6-(2-methylsulfonyl-2,6-diazaspiro[3.3]heptan-6-yl)-3-pyridyl]-1H-indazole

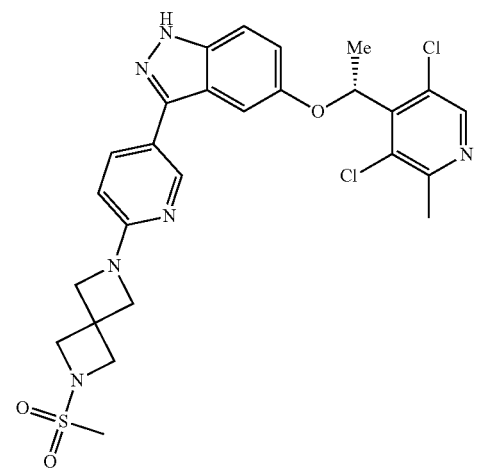 [SMILES: Cc1ncc(Cl)c([C@@H](C)Oc2ccc3[nH]nc(-c4ccc(N5CC6(C5)CN(S(C)(=O)=O)C6)nc4)c3c2)c1Cl]

LCMS: m/z = 573.1 (M + H); 1H NMR (400 MHz, DMSO-d6) δ = 13.00 (s, 1H), 8.47 - 8.37 (m, 2H), 7.87 (dd, J = 2.2, 8.6 Hz, 1H), 7.46 (d, J = 8.9 Hz, 1H), 7.11 - 7.03 (m, 2H), 6.53 (d, J = 8.6 Hz, 1H), 6.09 (q, J = 6.6 Hz, 1H), 4.17 (s, 4H), 4.12 (s, 4H), 3.03 (s, 3H), 2.58 (s, 3H), 1.75 (d, J = 6.6 Hz, 3H)

-continued

| Example 108 5-[1-(2,4-dichloro-3-pyridyl)ethoxy]-3-[1-[1-(oxetan-3-yl)-4-piperidyl]pyrazol-4-yl]-1H-indazole | 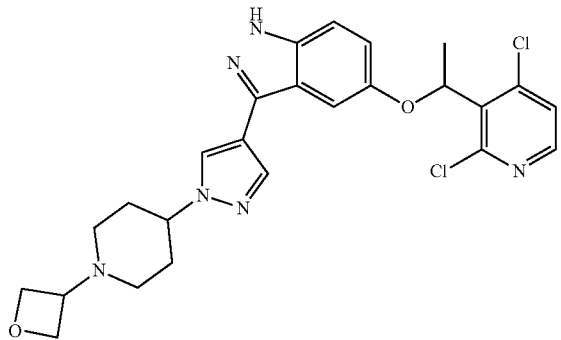 | LCMS: m/z = 513.2 (M + H); 1H NMR (400 MHz, DMSO-d6) δ = 12.81 (s, 1H), 8.25 (d, J = 5.3 Hz, 1H), 8.19 (d, J = 0.5 Hz, 1H), 7.84 (d, J = 0.5 Hz, 1H), 7.56 (d, J = 5.3 Hz, 1H), 7.41 (d, J = 9.0 Hz, 1H), 7.20 (d, J = 1.7 Hz, 1H), 7.06 (dd, J = 2.3, 9.0 Hz, 1H), 6.16 (q, J = 6.7 Hz, 1H), 4.57 (t, J = 6.5 Hz, 2H), 4.47 (t, J = 6.0 Hz, 2H), 4.25 (tt, J = 4.9, 10.0 Hz, 1H), 3.48 (quin, J = 6.4 Hz, 1H), 2.84 (br d, J = 9.8 Hz, 2H), 2.12 - 1.96 (m, 6H), 1.79 (d, J = 6.6 Hz, 3H). |
| Example 109 5-[1-(2,4-dichloro-3-pyridyl)ethoxy]-3-[6-(2-methylsulfonyl-2,6-diazaspiro[3.3]heptan-6-yl)-3-pyridyl]-1H-indazole | 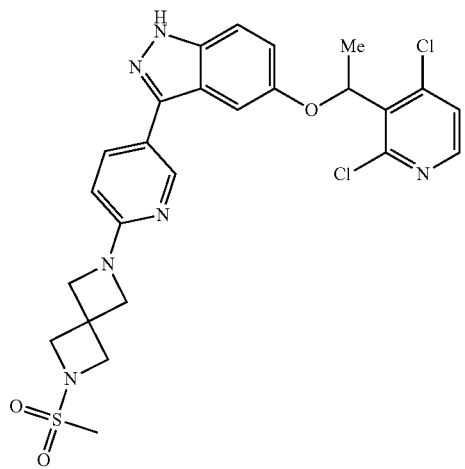 [SMILES: CC(Oc1ccc2[nH]nc(-c3ccc(N4CC5(C4)CN(S(C)(=O)=O)C5)nc3)c2c1)c1c(Cl)ccnc1Cl] | LCMS: m/z = 559.1 (M + H); 1H NMR (400 MHz, DMSO-d6) δ = 12.99 (s, 1H), 8.54 (d, J = 1.7 Hz, 1H), 8.26 (d, J = 5.3 Hz, 1H), 7.90 (dd, J = 2.3, 8.6 Hz, 1H), 7.57 (d, J = 5.3 Hz, 1H), 7.45 (d, J = 8.9 Hz, 1H), 7.20 (d, J = 1.6 Hz, 1H), 7.09 (dd, J = 2.3, 9.0 Hz, 1H), 6.53 (d, J = 8.1 Hz, 1H), 6.12 (q, J = 6.7 Hz, 1H), 4.17 (s, 4H), 4.11 (s, 4H), 3.02 (s, 3H), 1.78 (d, J = 6.6 Hz, 3H) |
| Example 110 3-[6-(2,7-diazaspiro[3.5]nonan-2-yl)-3-pyridyl]-5-[(1R)-1-(3,5-dichloro-4-pyridyl)ethoxy]-1H-indazole | 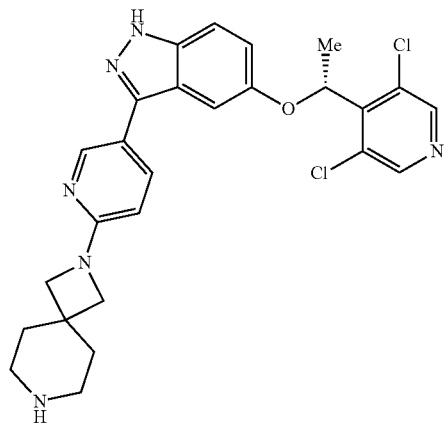 [SMILES: C[C@@H](Oc1ccc2[nH]nc(-c3ccc(N4CC5(CCNCC5)C4)nc3)c2c1)c1c(Cl)cncc1Cl] | LCMS: m/z = 509.2 (free base, M + H); 1H NMR (400 MHz, DMSO-d6) δ = 13.00 (br s, 1H), 8.59 (s, 2H), 8.50 (dd, J = 0.6, 2.3 Hz, 1H), 8.34 (d, 1H), 7.85 (dd, J = 2.3, 8.6 Hz, 1H), 7.45 (d, J = 9.0 Hz, 1H), 7.16 (d, J = 2.2 Hz, 1H), 7.09 (dd, J = 2.3, 9.0 Hz, 1H), 6.51 (d, J = 8.6 Hz, 1H), 6.13 - 6.08 (m, 1H), 3.77 (s, 4H), 2.87 (br s, 4H), 1.84 - 1.79 (m, 4H), 1.76 (d, J = 6.6 Hz, 3H) |

| | | |
|---|---|---|
| Example 111<br>5-[(1R)-1-(3,5-dichloro-4-pyridyl)ethoxy]-3-[6-(7-methylsulfonyl-2,7-diazaspiro[3.5]nonan-2-yl)-3-pyridyl]-1H-indazole | 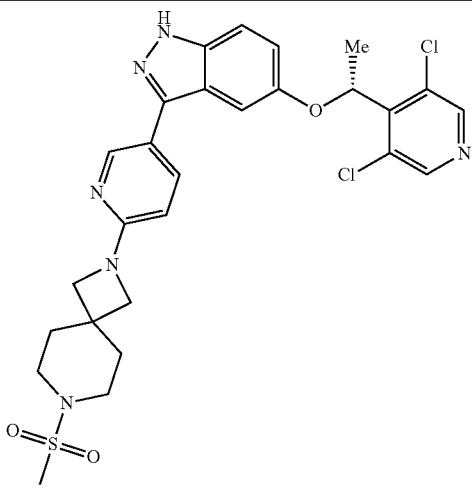 | LCMS: m/z = 587.2 (M + H); 1H NMR (400 MHz, DMSO-d6) δ = 12.98 (br s, 1H), 8.59 (s, 2H), 8.50 (d, J = 1.8 Hz, 1H), 7.86 (dd, J = 2.3, 8.6 Hz, 1H), 7.45 (d, J = 8.9 Hz, 1H), 7.16 (d, J = 1.8 Hz, 1H), 7.09 (dd, J = 2.2, 9.0 Hz, 1H), 6.51 (d, J = 8.6 Hz, 1H), 6.10 (q, J = 6.7 Hz, 1H), 3.78 (s, 4H), 3.18 - 3.12 (m, 4H), 2.88 (s, 3H), 1.92 - 1.85 (m, 4H), 1.76 (d, J = 6.6 Hz, 3H) |
| Example 112<br>6-[5-[[(1R)-1-(3,5-dichloro-4-pyridyl)ethoxy]-1H-indazol-3-yl]-2-pyridyl]-2$\lambda^6$-thia-6-azaspiro[3.3]heptane 2,2-dioxide | 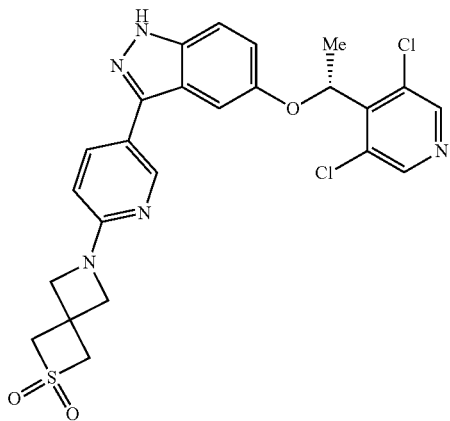 [SMILES: C[C@@H](Oc1ccc2[nH]nc(-c3ccc(N4CC5(C4)CS(=O)(=O)C5)nc3)c2c1)c1c(Cl)cncc1Cl] | LCMS: m/z = 530 (M + H); 1H NMR (400 MHz, DMSO-d6) δ = 13.02 (s, 1H), 8.59 (s, 2H), 8.53 (d, J = 1.6 Hz, 1H), 7.88 (dd, J = 2.3, 8.6 Hz, 1H), 7.46 (d, J = 9.0 Hz, 1H), 7.16 (d, J = 2.0 Hz, 1H), 7.09 (dd, J = 2.3, 9.0 Hz, 1H), 6.60 (d, J = 8.1 Hz, 1H), 6.11 (q, J = 6.7 Hz, 1H), 4.53 (s, 4H), 4.25 (s, 4H), 1.76 (d, J = 6.6 Hz, 3H) |
| Example 113<br>2-[5-[5-[[(1R)-1-(3,5-dichloro-4-pyridyl)ethoxy]-1H-indazol-3-yl]-2-pyridyl]-7$\lambda^6$-thia-2-azaspiro[3.5]nonane 7,7-dioxide | 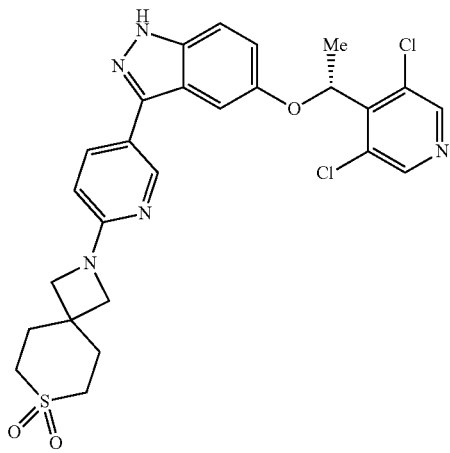 [SMILES: C[C@@H](Oc1ccc2[nH]nc(-c3ccc(N4CC5(CCS(=O)(=O)CC5)C4)nc3)c2c1)c1c(Cl)cncc1Cl] | LCMS: m/z = 558.1 (M + H); 1H NMR (400 MHz, DMSO-d6) δ = 12.99 (s, 1H), 8.64 - 8.55 (m, 2H), 8.51 (d, J = 1.8 Hz, 1H), 7.88 (dd, J = 2.3, 8.6 Hz, 1H), 7.46 (d, J = 8.9 Hz, 1H), 7.17 (d, J = 1.6 Hz, 1H), 7.11 - 7.06 (m, 1H), 6.50 (d, J = 8.7 Hz, 1H), 6.10 (q, J = 6.6 Hz, 1H), 3.84 (s, 4H), 3.18 - 3.12 (m, 4H), 2.29 - 2.22 (m, 4H), 1.75 (d, J = 6.6 Hz, 3H) |

| | | |
|---|---|---|
| Example 114<br>4-[4-[5-[(1R)-1-(3,5-dichloro-4-pyridyl)ethoxy]-1H-indazol-3-yl]pyrazol-1-yl]thiane 1,1-dioxide | 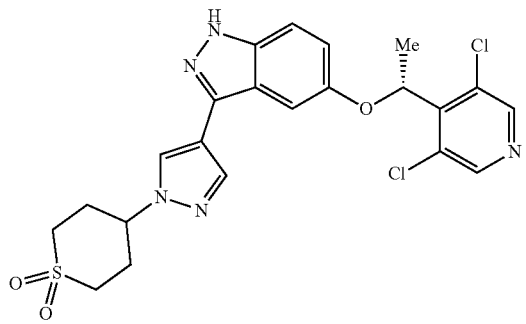 [SMILES: C[C@@H](Oc1ccc2[nH]nc(-c3cnn(C4CCS(=O)(=O)CC4)c3)c2c1)c1c(Cl)cncc1Cl] | LCMS: m/z = 506.1 (M + H); 1H NMR (400 MHz, DMSO-d6) δ = 12.86 (br s, 1H), 8.59 (s, 2H), 8.19 (s, 1H), 7.89 (s, 1H), 7.42 (d, J = 8.9 Hz, 1H), 7.16 (d, J = 1.8 Hz, 1H), 7.06 (dd, J = 2.3, 9.0 Hz, 1H), 6.14 (q, J = 6.6 Hz, 1H), 4.72 (tt, J = 3.7, 10.8 Hz, 1H), 3.52 - 3.43 (m, 2H), 3.31 - 3.24 (m, 2H), 2.62 - 2.50 (m, 2H), 2.46 - 2.37 (m, 2H), 1.76 (d, J = 6.6 Hz, 3H) |
| Example 115<br>5-[(1R)-1-(3,5-dichloro-4-pyridyl)ethoxy]-3-[6-(7-methylsulfonyl-2,7-diazaspiro[3.4]octan-2-yl)-3-pyridyl]-1H-indazole | 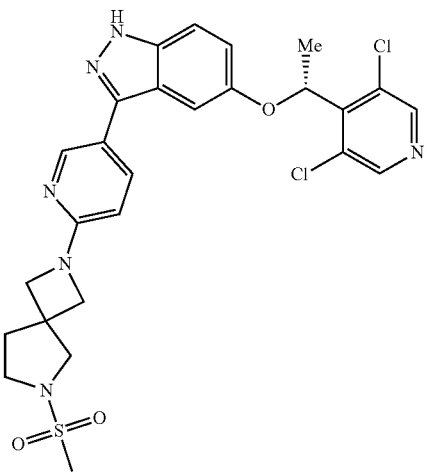 [SMILES: C[C@@H](Oc1ccc2[nH]nc(-c3ccc(N4CC5(CCN(S(C)(=O)=O)C5)C4)nc3)c2c1)c1c(Cl)cncc1Cl] | LCMS: m/z = 573.1 (M + H); 1H NMR (400 MHz, DMSO-d6) δ = 12.76 (br s, 1H), 8.24 (s, 1H), 7.89 (s, 1H), 7.40 (d, J = 8.9 Hz, 1H), 7.30 (d, J = 2.0 Hz, 1H), 7.23 (dd, J = 2.1, 8.3 Hz, 2H), 7.12 - 7.05 (m, 2H), 5.70 (q, J = 6.2 Hz, 1H), 4.25 - 4.14 (m, 1H), 2.92 (br d, J = 10.0 Hz, 2H), 2.75 (quin, J = 7.3 Hz, 1H), 2.09 - 1.87 (m, 8H), 1.85 - 1.76 (m, 2H), 1.69 - 1.60 (m, 2H), 1.59 (d, J = 6.4 Hz, 3H) |
| Example 116<br>4-[4-[5-[(1R)-1-(3,5-dichloro-2-methyl-4-pyridyl)ethoxy]-1H-indazol-3-yl]pyrazol-1-yl]thiane 1,1-dioxide | 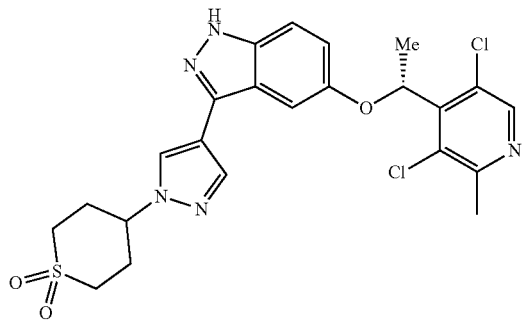 | LCMS: m/z = 506.1 (M + H); 1H NMR (400 MHz, DMSO-d6) δ = 12.85 (s, 1H), 8.45 (s, 1H), 8.21 (s, 1H), 7.86 (s, 1H), 7.42 (d, J = 9.0 Hz, 1H), 7.14 (d, J = 2.0 Hz, 1H), 7.05 (dd, J = 2.3, 9.0 Hz, 1H), 6.15 (q, J = 6.6 Hz, 1H), 4.72 (tt, J = 3.7, 10.7 Hz, 1H), 3.52 - 3.41 (m, 2H), 3.31 - 3.23 (m, 2H), 2.61 - 2.52 (m, 2H), 2.52 (s, 3H), 2.48 - 2.35 (m, 2H), 1.76 (d, J = 6.7 Hz, 3H) |
| Example 117<br>2-[5-[5-[(1R)-1-(3,5-dichloro-4-pyridyl)ethoxy]-1H-indazol-3-yl]-2-pyridyl]-6λ$^6$-thia-2-azaspiro[3.4]octane 6,6-dioxide | 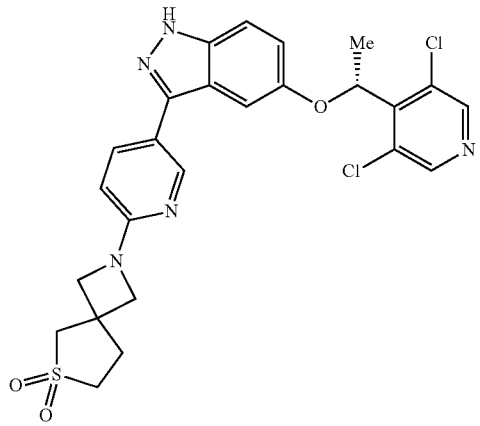 [SMILES: C[C@@H](Oc1ccc2[nH]nc(-c3ccc(N4CC5(CCS(=O)(=O)C5)C4)nc3)c2c1)c1c(Cl)cncc1Cl] | LCMS: m/z = 544.1 (M + H); 1H NMR (400 MHz, DMSO-d6) δ = 13.01 (s, 1H), 8.59 (s, 2H), 8.54 (d, J = 1.8 Hz, 1H), 7.88 (dd, J = 2.3, 8.6 Hz, 1H), 7.47 (d, J = 8.9 Hz, 1H), 7.17 (d, J = 1.7 Hz, 1H), 7.10 (dd, J = 2.2, 9.0 Hz, 1H), 6.57 (d, J = 8.6 Hz, 1H), 6.10 (q, J = 6.7 Hz, 1H), 4.07 (d, J = 8.3 Hz, 2H), 3.99 (d, J = 8.2 Hz, 2H), 3.50 (s, 3H), 3.27 (t, J = 7.6 Hz, 2H), 2.55 - 2.50 (m, 1H), 2.50 - 2.46 (m, 1H), 1.76 (d, J = 6.6 Hz, 3H) |

-continued

| Example 118 3-[2-(2,6-diazaspiro[3.3]heptan-2-yl)pyrimidin-5-yl]-5-[(1R)-1-(3,5-dichloro-4-pyridyl)ethoxy]-1H-indazole | 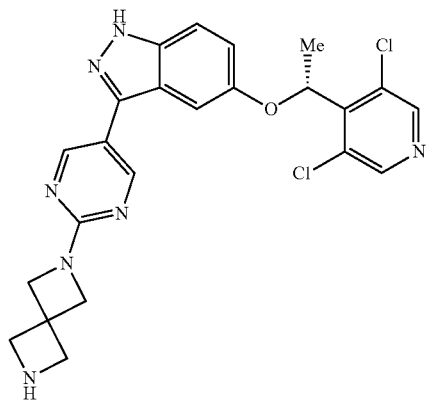 [SMILES: C[C@@H](Oc1ccc2[nH]nc(-c3cnc(N4CC5(CNC5)C4)nc3)c2c1)c1c(Cl)cncc1Cl] | LCMS: m/z = 482.1 (M + H) (free base); 1H NMR (400 MHz, DMSO-d6) δ = 13.16 (s, 1H), 8.78 (s, 2H), 8.70 (br s, 2H), 8.60 - 8.51 (m, 2H), 7.48 (d, J = 9.0 Hz, 1H), 7.24 (d, J = 2.1 Hz, 1H), 7.10 (dd, J = 2.3, 9.0 Hz, 1H), 6.14 (q, J = 6.6 Hz, 1H), 4.30 (s, 4H), 4.22 (s, 4H), 1.75 (d, J = 6.6 Hz, 3H) |
| --- | --- | --- |
| Example 119 5-[(1R)-1-(3,5-dichloro-4-pyridyl)ethoxy]-3-[2-(2-methylsulfonyl-2,6-diazaspiro[3.3]heptan-6-yl)pyrimidin-5-yl]-1H-indazole | 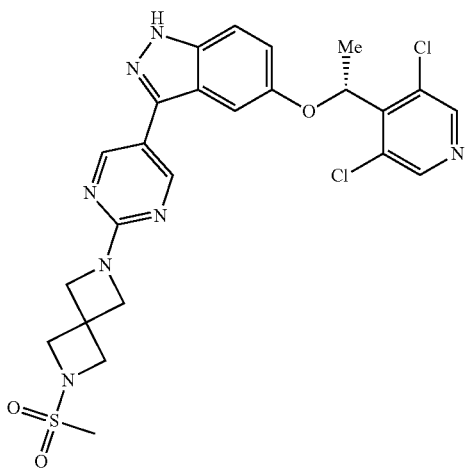 [SMILES: C[C@@H](Oc1ccc2[nH]nc(-c3cnc(N4CC5(C4)CN(S(C)(=O)=O)C5)nc3)c2c1)c1c(Cl)cncc1Cl] | LCMS: m/z = 560 (M + H); 1H NMR (400 MHz, DMSO-d6) δ = 13.13 (s, 1H), 8.77 (s, 2H), 8.56 (s, 2H), 7.47 (d, J = 9.0 Hz, 1H), 7.25 (d, J = 2.1 Hz, 1H), 7.10 (dd, J = 2.3, 9.0 Hz, 1H), 6.15 (q, J = 6.7 Hz, 1H), 4.29 (s, 4H), 4.12 (s, 4H), 3.02 (s, 3H), 1.76 (d, J = 6.6 Hz, 3H) |
| Example 120 5-[(1R)-1-(3,5-dichloro-4-pyridyl)ethoxy]-3-[2-(2-isopropylsulfonyl-2,6-diazaspiro[3.3]heptan-6-yl)pyrimidin-5-yl]-1H-indazole | 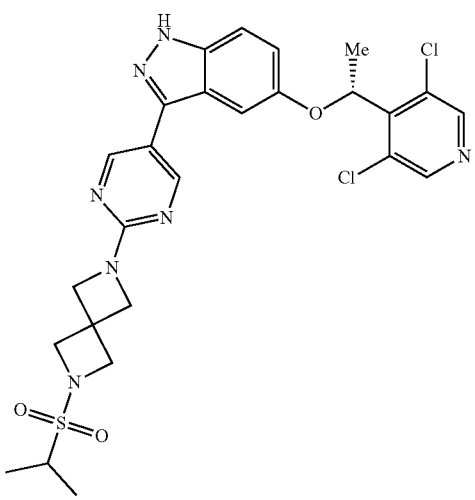 [SMILES: CC(C)S(=O)(=O)N1CC2(CN(c3ncc(-c4n[nH]c5ccc(O[C@H](C)c6c(Cl)cncc6Cl)cc45)cn3)C2)C1] | LCMS: m/z = 588.1 (M + H); 1H NMR (400 MHz, DMSO-d6) δ = 13.14 (br s, 1H), 8.77 (s, 2H), 8.56 (s, 2H), 7.47 (d, J = 9.0 Hz, 1H), 7.25 (d, J = 2.1 Hz, 1H), 7.10 (dd, J = 2.3, 9.0 Hz, 1H), 6.15 (q, J = 6.6 Hz, 1H), 4.29 (s, 4H), 4.11 (s, 4H), 3.24 (spt, J = 6.8 Hz, 1H), 1.75 (d, J = 6.6 Hz, 3H), 1.24 (d, J = 6.8 Hz, 6H) |

| | | |
|---|---|---|
| Example 121<br>ethyl 6-[5-[5-[(1R)-1-(3,5-dichloro-4-pyridyl)ethoxy]-1H-indazol-3-yl]-2-pyridyl]-2,6-diazaspiro[3.3]heptane-2-carboxylate | 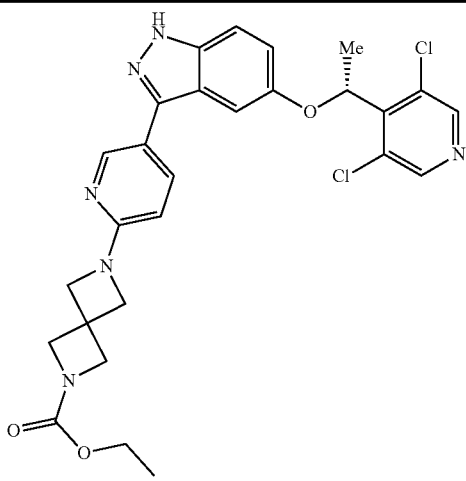 | LCMS: m/z = 553.2 (M + H); 1H NMR (400 MHz, DMSO-d6) δ = 13.00 (br s, 1H), 8.58 (s, 2H), 8.51 (d, J = 2.0 Hz, 1H), 7.86 (dd, J = 2.3, 8.6 Hz, 1H), 7.46 (d, J = 9.0 Hz, 1H), 7.19 - 7.13 (m, 1H), 7.09 (dd, J = 2.2, 8.9 Hz, 1H), 6.52 (d, J = 8.6 Hz, 1H), 6.10 (q, J = 6.7 Hz, 1H), 4.14 (s, 4H), 4.13 (br s, 4H), 4.01 (q, J = 7.1 Hz, 2H), 1.75 (d, J = 6.6 Hz, 3H), 1.17 (t, J = 7.1 Hz, 3H) |
| Example 122<br>2-[5-[5-[(1R)-1-(3,5-dichloro-4-pyridyl)ethoxy]-1H-indazol-3-yl]pyrimidin-2-yl]-6λ$^6$-thia-2-azaspiro[3.4]octane 6,6-dioxide | 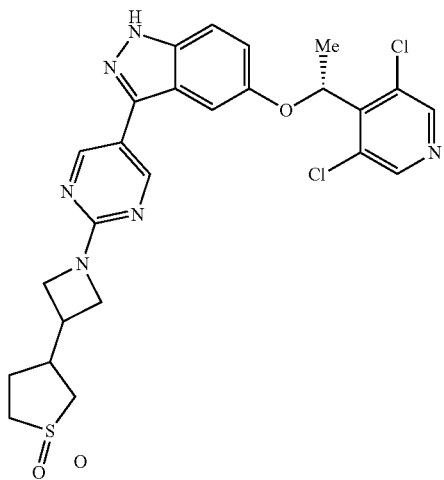 | LCMS: m/z = 545.1 (M + H); 1H NMR (400 MHz, DMSO-d6) δ = 13.14 (s, 1H), 8.79 (s, 2H), 8.57 (s, 2H), 7.48 (d, J = 9.0 Hz, 1H), 7.25 (d, J = 2.0 Hz, 1H), 7.11 (dd, J = 2.3, 9.0 Hz, 1H), 6.15 (q, J = 6.7 Hz, 1H), 4.17 (d, J = 8.9 Hz, 2H), 4.09 (d, J = 8.8 Hz, 2H), 3.51 (s, 2H), 3.30 - 3.24 (m, 2H), 2.52 - 2.51 (m, 1H), 2.48 (s, 1H), 1.76 (d, J = 6.7 Hz, 3H) |
| Example 123<br>methyl 6-[5-[5-[(1R)-1-(3,5-dichloro-4-pyridyl)ethoxy]-1H-indazol-3-yl]-2-pyridyl]-2,6-diazaspiro[3.3]heptane-2-carboxylate | 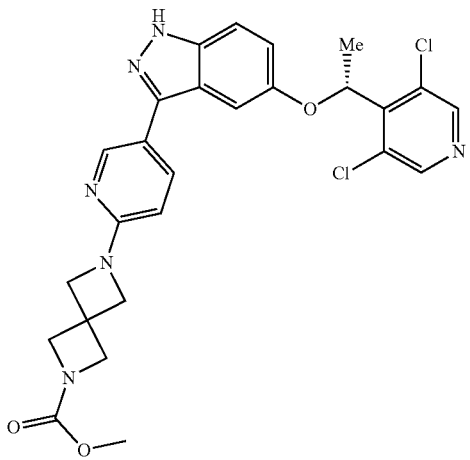 [SMILES: COC(=O)N1CC2(C1)CN(c1ccc(-c3n[nH]c4ccc(O[C@H](C)c5c(Cl)cncc5Cl)cc34)cn1)C2] | LCMS: m/z = 539.1 (M + H); 1H NMR (400 MHz, DMSO-d6) δ = 13.00 (br s, 1H), 8.58 (s, 2H), 8.51 (d, J = 1.8 Hz, 1H), 7.86 (dd, J = 2.2, 8.6 Hz, 1H), 7.45 (d, J = 9.0 Hz, 1H), 7.19 - 7.13 (m, 1H), 7.09 (dd, J = 2.2, 8.9 Hz, 1H), 6.52 (d, J = 8.6 Hz, 1H), 6.10 (q, J = 6.6 Hz, 1H), 4.14 (s, 8H), 3.57 (s, 3H), 1.75 (d, J = 6.7 Hz, 3H) |

-continued

| Example 124 5-[(1R)-1-(3,5-dichloro-4-pyridyl)ethoxy]-3-[6-(2-ethylsulfonyl-2,6-diazaspiro[3.3]heptan-6-yl)-3-pyridyl]-1H-indazole | 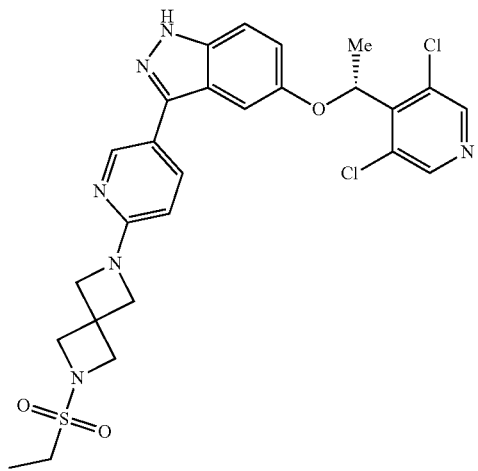 [SMILES: CCS(=O)(=O)N1CC2(CN(c3ccc(-c4n[nH]c5ccc(O[C@H](C)c6c(Cl)cncc6Cl)cc45)cn3)C2)C1] | LCMS: m/z = 573.1 (M + H); 1H NMR (400 MHz, DMSO-d6) δ = 12.99 (s, 1H), 8.59 (s, 2H), 8.52 (d, J = 1.8 Hz, 1H), 7.87 (dd, J = 2.3, 8.7 Hz, 1H), 7.45 (d, J = 9.0 Hz, 1H), 7.16 (d, J = 1.7 Hz, 1H), 7.09 (dd, J = 2.3, 9.0 Hz, 1H), 6.54 (d, J = 8.7 Hz, 1H), 6.11 (q, J = 6.6 Hz, 1H), 4.17 (s, 4H), 4.11 (s, 4H), 3.14 (q, J = 7.3 Hz, 2H), 1.76 (d, J = 6.6 Hz, 3H), 1.24 (br t, J = 7.4 Hz, 3H) |
|---|---|---|
| Example 125 methyl 2-[5-[5-[(1R)-1-(3,5-dichloro-4-pyridyl)ethoxy]-1H-indazol-3-yl]-2-pyridyl]-2,7-diazaspiro[3.5]nonane-7-carboxylate | 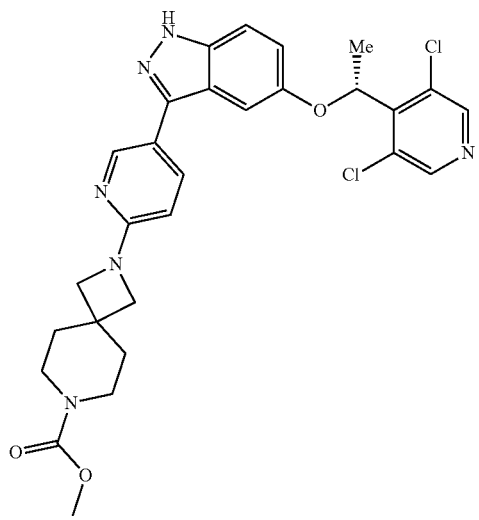 | LCMS: m/z = 560.1 (M + H); 1H NMR (400 MHz, DMSO-d6) δ = 12.97 (s, 1H), 8.59 (s, 2H), 8.50 (d, J = 2.0 Hz, 1H), 7.85 (dd, J = 2.3, 8.6 Hz, 1H), 7.45 (d, J = 9.0 Hz, 1H), 7.16 (d, J = 1.7 Hz, 1H), 7.09 (dd, J = 2.2, 8.9 Hz, 1H), 6.50 (d, J = 8.7 Hz, 1H), 6.10 (q, J = 6.6 Hz, 1H), 3.77 (s, 4H), 3.60 (s, 3H), 3.42 - 3.36 (m, 4H), 1.77 - 1.71 (m, 7H) |
| Example 126 ethyl 2-[5-[5-[(1R)-1-(3,5-dichloro-4-pyridyl)ethoxy]-1H-indazol-3-yl]pyrimidin-2-yl]-2,7-diazaspiro[3.5]nonane-7-carboxylate | 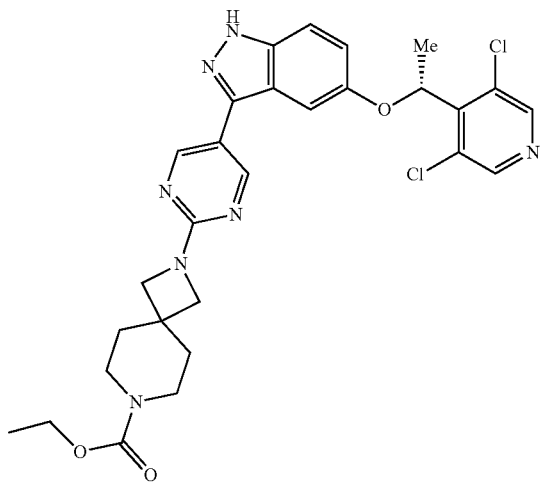 [SMILES: CCOC(=O)N1CCC2(CC1)CN(c1ncc(-c3n[nH]c4ccc(O[C@H](C)c5c(Cl)cncc5Cl)cc34)cn1)C2] | LCMS: m/z = 582.2 (M + H); 1H NMR (400 MHz, DMSO-d6) δ = 13.11 (s, 1H), 8.75 (s, 2H), 8.57 (s, 2H), 7.47 (d, J = 8.9 Hz, 1H), 7.24 (d, J = 2.0 Hz, 1H), 7.10 (dd, J = 2.3, 9.0 Hz, 1H), 6.15 (q, J = 6.5 Hz, 1H), 4.04 (q, J = 7.1 Hz, 2H), 3.87 (s, 4H), 3.43 - 3.36 (m, 4H), 1.78 - 1.71 (m, 7H), 1.19 (t, J = 7.1 Hz, 3H) |

| Example 127 7-[5-[5-[(1R)-1-(3,5-dichloro-4-pyridyl)ethoxy]-1H-indazol-3-yl]pyrimidin-2-yl]-2λ⁶-thia-7-azaspiro[4.4]nonane 2,2-dioxide | 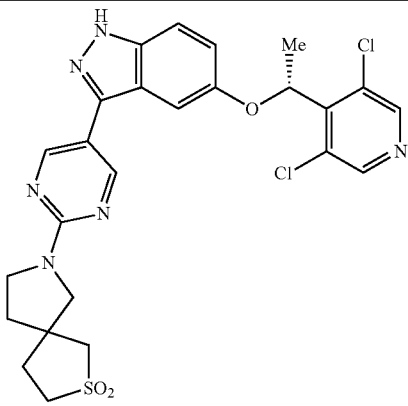 | LCMS: m/z = 559.47 (M + H); 1H NMR (400 MHz, DMSO-d6) δ = 13.09 (s, 1H), 8.78 (d, J = 1.0 Hz, 2H), 8.57 (s, 2H), 7.47 (d, J = 8.9 Hz, 1H), 7.26 (d, J = 2.1 Hz, 1H), 7.10 (dd, J = 2.3, 9.0 Hz, 1H), 6.15 (q, J = 6.7 Hz, 1H), 3.79 - 3.58 (m, 4H), 3.31 (s, 5H), 3.29 - 3.25 (m, 2H), 2.32 - 2.15 (m, 3H), 2.12 - 2.05 (m, 1H), 1.76 (d, J = 6.6 Hz, 3H) |
|---|---|---|
| Example 128 5-[(1R)-1-(3,5-dichloro-4-pyridyl)ethoxy]-3-[2-(2-ethylsulfonyl-2,6-diazaspiro[3.3]heptan-6-yl)pyrimidin-5-yl]-1H-indazole | 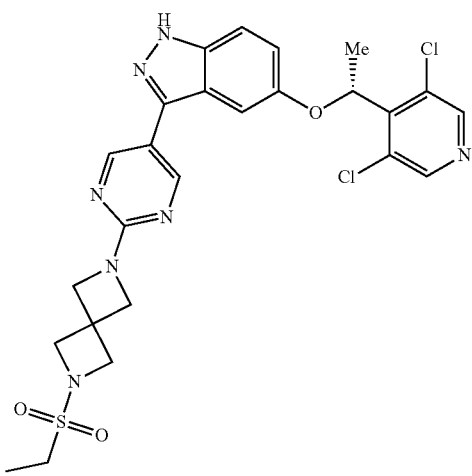 [SMILES: CCS(=O)(=O)N1CC2(CN(c3ncc(-c4n[nH]c5ccc(O[C@H](C)c6c(Cl)cncc6Cl)cc45)cn3)C2)C1] | LCMS: m/z = 574.1 (M + H); 1H NMR (400 MHz, DMSO-d6) δ = 13.13 (s, 1H), 8.77 (s, 2H), 8.56 (s, 2H), 7.47 (d, J = 9.0 Hz, 1H), 7.25 (d, J = 2.0 Hz, 1H), 7.10 (dd, J = 2.3, 9.0 Hz, 1H), 6.15 (q, J = 6.6 Hz, 1H), 4.28 (s, 4H), 4.11 (s, 4H), 3.14 (q, J = 7.3 Hz, 2H), 1.76 (d, J = 6.7 Hz, 3H), 1.24 (t, J = 7.3 Hz, 3H) |
| Example 129 2-[5-[5-[(1R)-1-(3,5-dichloro-4-pyridyl)ethoxy]-1H-indazol-3-yl]pyrimidin-2-yl]-6λ⁶-thia-2-azaspiro[3.5]nonane 6,6-dioxide | 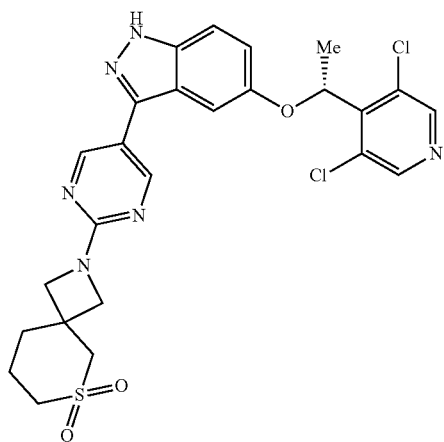 [SMILES: C[C@@H](Oc1ccc2[nH]nc(-c3cnc(N4CC5(CCCS(=O)(=O)C5)C4)nc3)c2c1)c1c(Cl)cncc1Cl] | LCMS: m/z = 559.1 (M + H); 1H NMR (400 MHz, DMSO-d6) δ = 13.13 (br s, 1H), 8.77 (s, 2H), 8.57 (s, 2H), 7.47 (d, J = 9.0 Hz, 1H), 7.24 (d, J = 2.0 Hz, 1H), 7.10 (dd, J = 2.2, 9.0 Hz, 1H), 6.15 (q, J = 6.5 Hz, 1H), 4.08 (d, J = 8.9 Hz, 2H), 3.87 (d, J = 8.7 Hz, 2H), 3.48 (s, 2H), 3.05 (br s, 2H), 2.00 (br s, 2H), 1.97 - 1.93 (m, 2H), 1.76 (d, J = 6.6 Hz, 3H) |

-continued

| Example 130 ethyl 2-[5-[5-[(1R)-1-(3,5-dichloro-4-pyridyl)ethoxy]-1H-indazol-3-yl]-2-pyridyl]-2,7-diazaspiro[3.5]nonane-7-carboxylate | 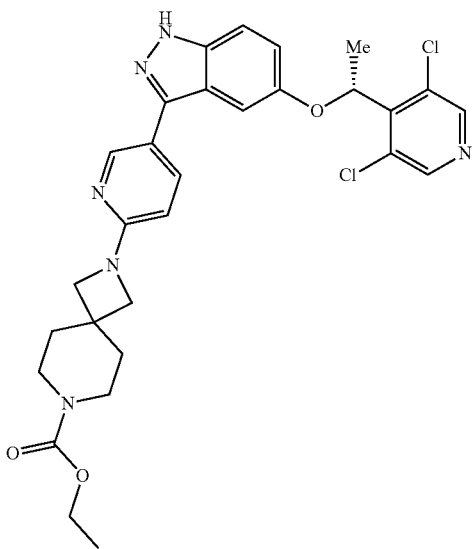 [SMILES: CCOC(=O)N1CCC2(CC1)CN(c1ccc(-c3n[nH]c4ccc(O[C@H](C)c5c(Cl)cncc5Cl)cc34)cn1)C2] | LCMS: m/z = 581.2 (M + H); 1H NMR (400 MHz, DMSO-d6) δ = 12.98 (br s, 1H), 8.59 (s, 2H), 8.50 (d, J = 1.7 Hz, 1H), 8.20 (s, 1H), 7.85 (dd, J = 2.3, 8.6 Hz, 1H), 7.45 (d, J = 9.0 Hz, 1H), 7.16 (d, J = 2.0 Hz, 1H), 7.09 (dd, J = 2.3, 9.0 Hz, 1H), 6.51 (d, J = 8.2 Hz, 1H), 6.10 (q, J = 6.6 Hz, 1H), 4.04 (q, J = 7.1 Hz, 2H), 3.77 (s, 4H), 3.41 - 3.38 (m, J = 5.1 Hz, 4H), 1.78 - 1.72 (m, 7H), 1.19 (t, J = 7.1 Hz, 3H) |
|---|---|---|
| Example 131 ethyl 2-[5-[5-[(1R)-1-(3,5-dichloro-4-pyridyl)ethoxy]-1H-indazol-3-yl]pyrimidin-2-yl]-2,8-diazaspiro[3.5]nonane-8-carboxylate | 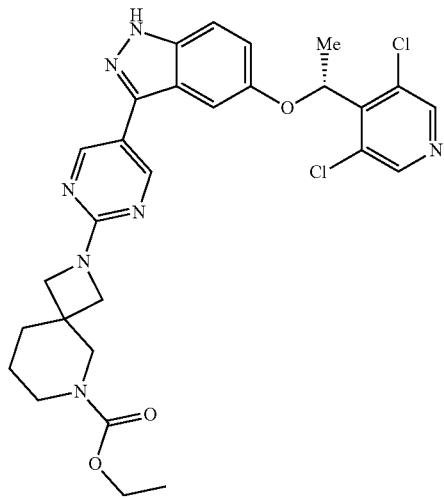 [SMILES: CCOC(=O)N1CCCC2(C1)CN(c1ncc(-c3n[nH]c4ccc(O[C@H](C)c5c(Cl)cncc5Cl)cc34)cn1)C2] | LCMS: m/z = 582.2 (M + H); 1H NMR (400 MHz, DMSO-d6) δ = 13.13 (br s, 1H), 8.76 (s, 2H), 8.56 (s, 2H), 7.47 (d, J = 8.9 Hz, 1H), 7.24 (d, J = 2.0 Hz, 1H), 7.10 (dd, J = 2.2, 9.0 Hz, 1H), 6.14 (q, J = 6.6 Hz, 1H), 4.07 (q, J = 7.0 Hz, 2H), 3.79 (q, J = 8.8 Hz, 4H), 3.57 (s, 2H), 3.39 - 3.34 (m, 2H), 1.85 - 1.77 (m, 2H), 1.75 (d, J = 6.6 Hz, 3H), 1.57 - 1.43 (m, 2H), 1.19 (t, J = 7.1 Hz, 3H) |
| Example 132 3-[2-(2,8-diazaspiro[3.5]nonan-2-yl)pyrimidin-5-yl]-5-[(1R)-1-(3,5-dichloro-4-pyridyl)ethoxy]-1H-indazole | 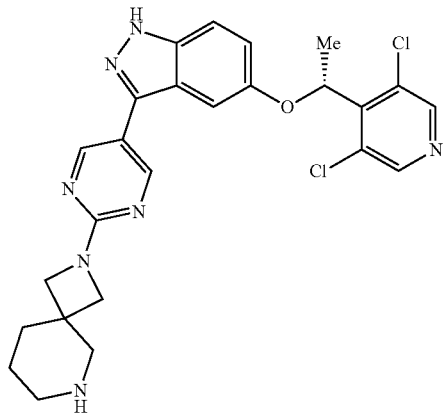 [SMILES: C[C@@H](Oc1ccc2[nH]nc(-c3cnc(N4CC5(CCCNC5)C4)nc3)c2c1)c1c(Cl)cncc1Cl] | LCMS: m/z = 510.2 (free base, M + H); 1H NMR (400 MHz, DMSO-d6) δ = 13.15 (br s, 1H), 8.78 (s, 2H), 8.61 (br s, 2H), 8.56 (s, 2H), 7.48 (d, J = 9.0 Hz, 1H), 7.24 (d, J = 2.1 Hz, 1H), 7.11 (dd, J = 2.3, 9.0 Hz, 1H), 6.15 (q, J = 6.5 Hz, 1H), 4.02 (d, J = 8.9 Hz, 2H), 3.84 (d, J = 8.9 Hz, 2H), 3.34 (br s, 2H), 3.02 (br s, 2H), 1.94 - 1.87 (m, 2H), 1.78 - 1.70 (m, 5H) |

| Example 133 3-[2-(2,7-diazaspiro[3.5]nonan-2-yl)pyrimidin-5-yl]-5-[(1R)-1-(3,5-dichloro-4-pyridyl)ethoxy]-1H-indazole | 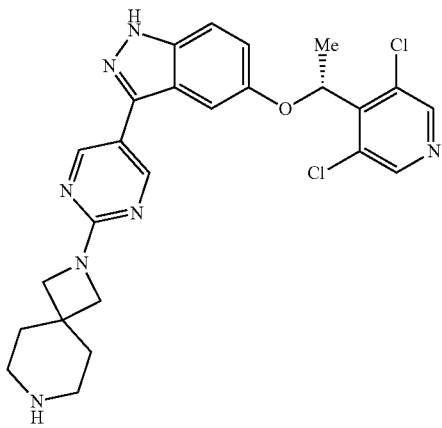 | LCMS: m/z = 510.2 (M + H); 1H NMR (400 MHz, DMSO-d6) δ = 13.15 (br s, 1H), 8.74 (s, 2H), 8.57 (s, 2H), 7.47 (d, J = 8.9 Hz, 1H), 7.24 (d, J = 2.1 Hz, 1H), 7.10 (dd, J = 2.3, 9.0 Hz, 1H), 6.15 (q, J = 6.7 Hz, 1H), 3.81 (s, 4H), 2.77 - 2.56 (m, 4H), 1.75 (d, J = 6.6 Hz, 3H), 1.69 - 1.63 (m, 4H) |
| Example 134 5-[(1R)-1-(3,5-dichloro-4-pyridyl)ethoxy]-3-[2-(8-methylsulfonyl-2,8-diazaspiro[3.5]nonan-2-yl)pyrimidin-5-yl]-1H-indazole | 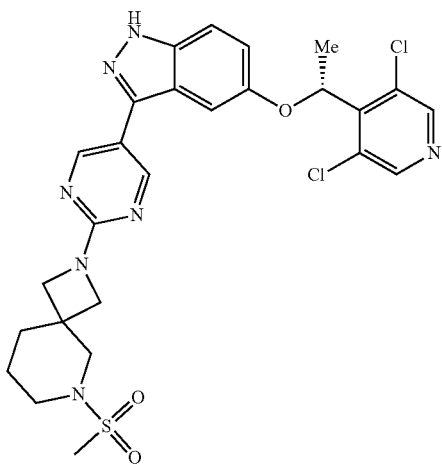 [SMILES: C[C@@H](Oc1ccc2[nH]nc(-c3cnc(N4CC5(CCCN(S(C)(=O)=O)C5)C4)nc3)c2c1)c1c(Cl)cncc1Cl] | LCMS: m/z = 588.1 (free base, M + H); 1H NMR (400 MHz, DMSO-d6) δ = 13.12 (s, 1H), 8.77 (s, 2H), 8.57 (s, 2H), 7.47 (d, J = 9.0 Hz, 1H), 7.26 (d, J = 1.8 Hz, 1H), 7.10 (dd, J = 2.3, 9.0 Hz, 1H), 6.15 (q, J = 6.6 Hz, 1H), 3.84 (s, 4H), 3.29 - 3.26 (m, 2H), 3.09 (br t, J = 5.3 Hz, 2H), 2.90 (s, 3H), 1.81 - 1.77 (m, 2H), 1.76 (d, J = 6.7 Hz, 3H), 1.63 (br s, 2H) |
| Example 135 isopropyl 2-[5-[5-[(1R)-1-(3,5-dichloro-4-pyridyl)ethoxy]-1H-indazol-3-yl]pyrimidin-2-yl]-2,8-diazaspiro[3.5]nonane-8-carboxylate | 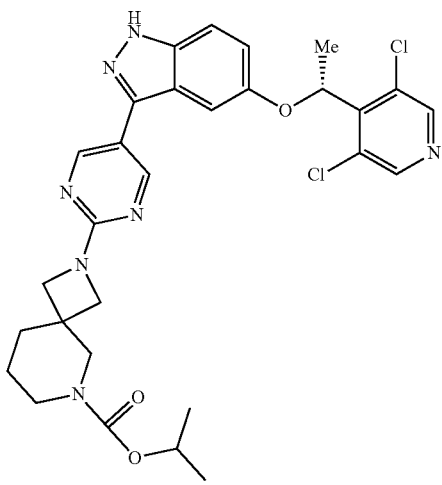 [SMILES: CC(C)OC(=O)N1CCCC2(C1)CN(c1ncc(-c3n[nH]c4ccc(O[C@H](C)c5c(Cl)cncc5Cl)cc34)cn1)C2] | LCMS: m/z = 596.2 (M + H); 1H NMR (400 MHz, DMSO-d6) δ = 13.12 (s, 1H), 8.76 (s, 2H), 8.56 (s, 2H), 7.47 (d, J = 9.0 Hz, 1H), 7.25 (d, J = 1.8 Hz, 1H), 7.10 (dd, J = 2.3, 9.0 Hz, 1H), 6.15 (q, J = 6.6 Hz, 1H), 4.81 (td, J = 6.2, 12.4 Hz, 1H), 3.83 - 3.75 (m, 4H), 3.56 (s, 2H), 3.36 - 3.32 (m, 2H), 1.85 - 1.79 (m, 2H), 1.76 (d, J = 6.7 Hz, 3H), 1.50 (br d, J = 3.3 Hz, 2H), 1.20 (d, J = 6.2 Hz, 6H) |

| | | |
|---|---|---|
| Example 136<br>methyl 2-[5-[5-[(1R)-1-(3,5-dichloro-4-pyridyl)ethoxy]-1H-indazol-3-yl]pyrimidin-2-yl]-2,7-diazaspiro[3.5]nonane-7-carboxylate | 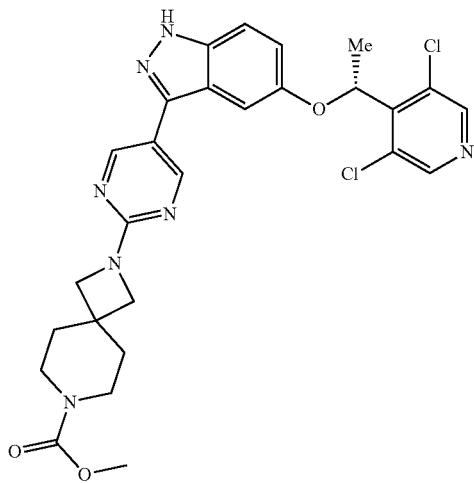 [SMILES: COC(=O)N1CCC2(CC1)CN(c1ncc(-c3n[nH]c4ccc(O[C@H](C)c5c(Cl)cncc5Cl)cc34)cn1)C2] | LCMS: m/z = 568.2 (M + H); 1H NMR (400 MHz, DMSO-d6) δ = 13.11 (br s, 1H), 8.77 - 8.73 (m, 2H), 8.57 (s, 2H), 7.47 (d, J = 9.0 Hz, 1H), 7.24 (d, J = 2.1 Hz, 1H), 7.10 (dd, J = 2.3, 9.0 Hz, 1H), 6.15 (q, J = 6.6 Hz, 1H), 3.87 (s, 4H), 3.60 (s, 3H), 3.41 - 3.37 (m, 4H), 1.77 - 1.73 (m, 7H) |
| Example 137<br>5-[(1R)-1-(3,5-dichloro-4-pyridyl)ethoxy]-3-[2-(7-methylsulfonyl-2,7-diazaspiro[3.5]nonan-2-yl)pyrimidin-5-yl]-1H-indazole | 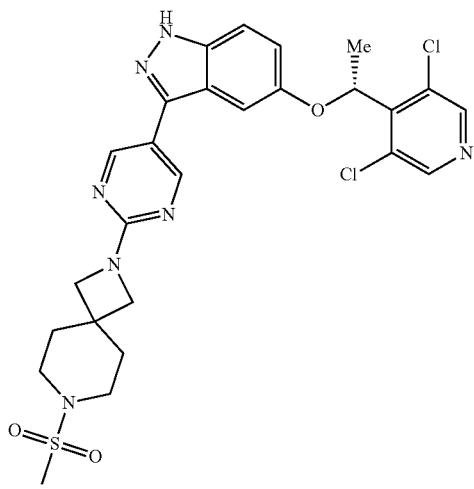 | LCMS: m/z = 559.1 (free base, M + H); 1H NMR (400 MHz, DMSO-d6) δ = 13.25 (br s, 1H), 8.58 (s, 2H), 8.39 - 8.36 (m, 1H), 8.21 (br d, J = 8.3 Hz, 1H), 7.51 (d, J = 9.0 Hz, 1H), 7.21 (d, J = 2.1 Hz, 1H), 7.13 (dd, J = 2.2, 9.0 Hz, 1H), 6.91 (br d, J = 8.6 Hz, 1H), 6.14 (q, J = 6.6 Hz, 1H), 4.41 (s, 4H), 4.15 (s, 4H), 3.04 (s, 3H), 2.87 (d, J = 14.7 Hz, 1H), 2.73 - 2.65 (m, 1H), 2.37 (d, J = 14.8 Hz, 1H), 2.23 (td, J = 3.6, 18.0 Hz, 1H), 1.94 - 1.75 (m, 6H), 1.31 - 1.23 (m, 2H), 1.05 (s, 3H), 0.74 (s, 3H). |
| Example 138<br>methyl 2-[5-[5-[(1R)-1-(3,5-dichloro-4-pyridyl)ethoxy]-1H-indazol-3-yl]pyrimidin-2-yl]-2,8-diazaspiro[3.5]nonane-8-carboxylate | 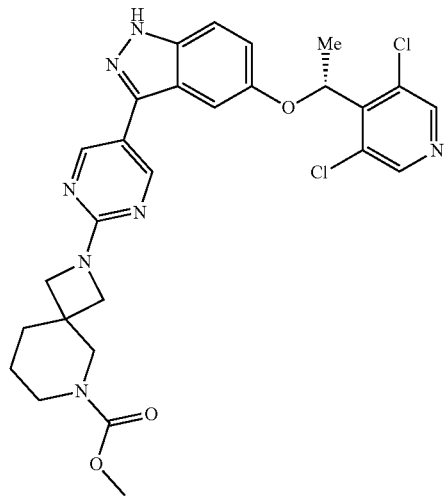 [SMILES: COC(=O)N1CCCC2(C1)CN(c1ncc(-c3n[nH]c4ccc(O[C@H](C)c5c(Cl)cncc5Cl)cc34)cn1)C2] | LCMS: m/z = 568.2 (M + H); 1H NMR (400 MHz, DMSO-d6) δ = 13.12 (br s, 1H), 8.76 (s, 2H), 8.57 (s, 2H), 7.47 (d, J = 9.0 Hz, 1H), 7.25 (d, J = 2.0 Hz, 1H), 7.10 (dd, J = 2.3, 9.0 Hz, 1H), 6.15 (q, J = 6.6 Hz, 1H), 3.83 - 3.75 (m, 4H), 3.64 - 3.61 (m, 3H), 3.59 - 3.53 (m, 2H), 3.37 - 3.33 (m, 2H), 1.85 - 1.79 (m, 2H), 1.76 (d, J = 6.6 Hz, 3H), 1.55 - 1.47 (m, 2H) |

-continued

Example 139
5-[(1R)-1-(3,5-dimethyl-4-pyridyl)ethoxy]-3-[6-(2-methylsulfonyl-2,6-diazaspiro[3.3]heptan-6-yl)-3-pyridyl]-1H-indazole

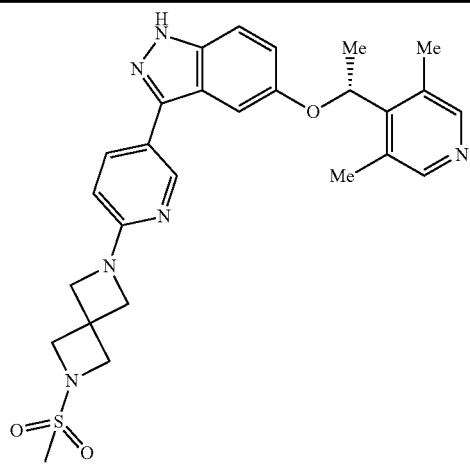

LCMS: m/z = 519.2 (M + H); 1H NMR (400 MHz, DMSO-d6) δ = 12.94 (s, 1H), 8.46 (d, J = 1.8 Hz, 1H), 8.16 (s, 2H), 7.79 (dd, J = 2.3, 8.6 Hz, 1H), 7.44 (d, J = 8.9 Hz, 1H), 7.05 (dd, J = 2.3, 9.0 Hz, 1H), 6.99 - 6.93 (m, 1H), 6.52 (d, J = 8.2 Hz, 1H), 5.78 (q, J = 6.7 Hz, 1H), 4.17 (s, 4H), 4.12 (s, 4H), 3.03 (s, 3H), 2.41 (s, 6H), 1.64 (d, J = 6.7 Hz, 3H)

Example 140
5-[(1S)-1-(3,5-dimethyl-4-pyridyl)ethoxy]-3-[6-(2-methylsulfonyl-2,6-diazaspiro[3.3]heptan-6-yl)-3-pyridyl]-1H-indazole

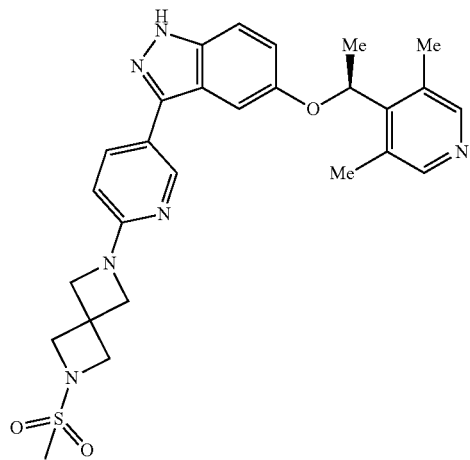 [SMILES: Cc1cncc(C)c1[C@H](C)Oc1ccc2[nH]nc(-c3ccc(N4CC5(C4)CN(S(C)(=O)=O)C5)nc3)c2c1]

LCMS: m/z = 519.2 (M + H); 1H NMR (400 MHz, DMSO-d6) δ = 12.94 (s, 1H), 8.46 (d, J = 1.8 Hz, 1H), 8.16 (s, 2H), 7.79 (dd, J = 2.3, 8.6 Hz, 1H), 7.44 (d, J = 8.9 Hz, 1H), 7.05 (dd, J = 2.3, 9.0 Hz, 1H), 6.99 - 6.93 (m, 1H), 6.52 (d, J = 8.2 Hz, 1H), 5.78 (q, J = 6.7 Hz, 1H), 4.17 (s, 4H), 4.12 (s, 4H), 3.03 (s, 3H), 2.41 (s, 6H), 1.64 (d, J = 6.7 Hz, 3H)

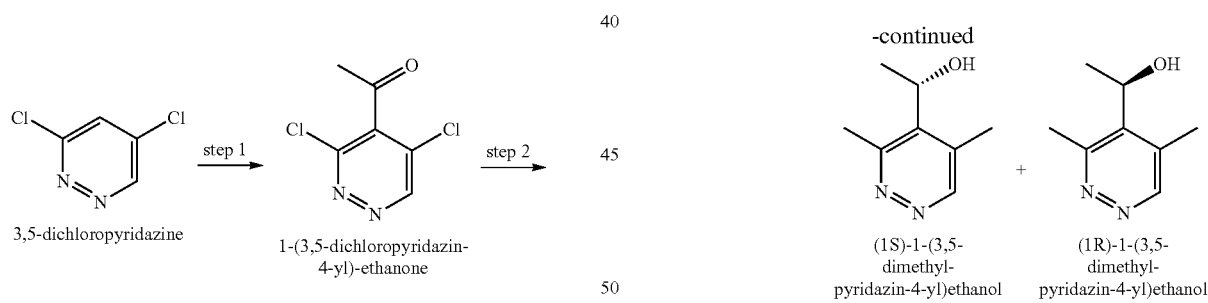

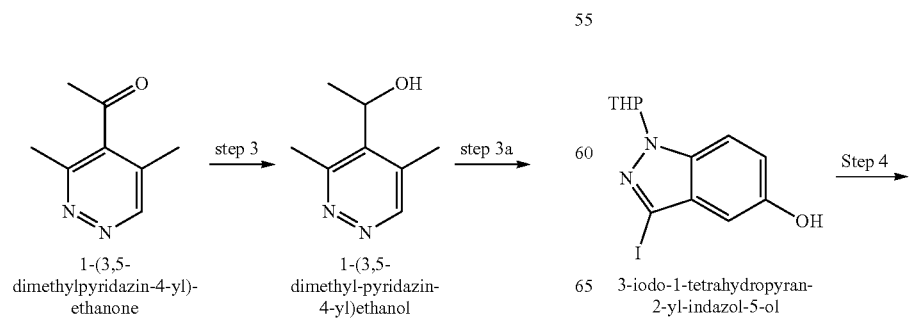

205

-continued

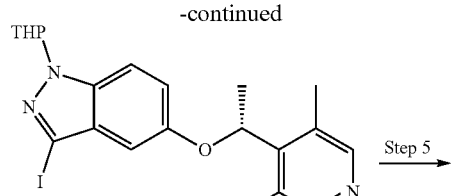

5-[(1R)-1-(3,5-dimethylpyridazin-4-yl)
ethoxy]-3-iodo-1-tetrahydropyran-2-yl-indazole Step 5 →

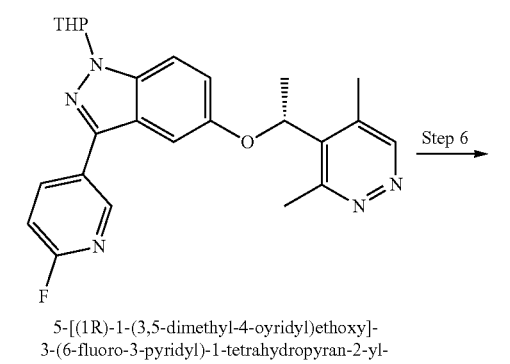

5-[(1R)-1-(3,5-dimethyl-4-oyridyl)ethoxy]-
3-(6-fluoro-3-pyridyl)-1-tetrahydropyran-2-yl-
indazole Step 6 →

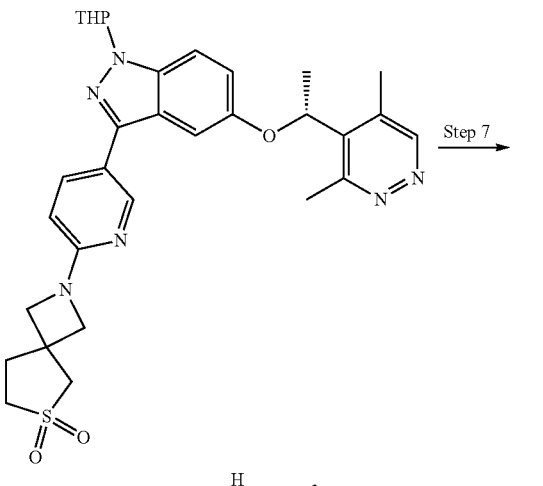

Step 7 →

Example 144

206

Example 144. 2-[5-[5-[(1R)-1-(3,5-Dimethylpyridazin-4-yl)ethoxy]-1H-indazol-3-yl]-2-pyridyl]-6λ⁶-thia-2-azaspiro[3.4]octane 6,6-dioxide

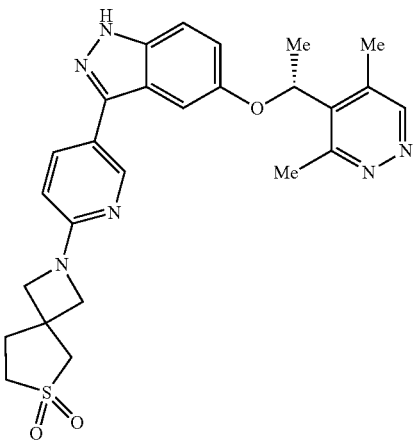 [SMILES: Cc1cnnc(C)c1[C@@H](C)Oc1ccc2[nH]nc(-c3ccc(N4CC5(CCS(=O)(=O)C5)C4)nc3)c2c1]

Step 1. 1-(3,5-dichloropyridazin-4-yl)ethanone. To a solution of 3,5-dichloropyridazine (50.0 g, 0.336 mol) in CH$_3$CN (500 mL) and water (500 mL) was added 2-oxo-propanoic acid (37.0 g, 0.403 mol), K$_2$S$_2$O$_8$ (136.0 g, 0.504 mol) and AgNO$_3$ (11.4 g, 0.067 mol). The reaction mixture was stirred at 70° C. for 6 h. After completion, the reaction was cooled to room temperature, and the ACN was removed. The aqueous solution was extracted with EtOAc (3×500 mL). The combined organic layers were washed with brine (2×300 mL), dried over Na$_2$SO$_4$ and concentrated. The residue was purified by silica gel flash column chromatography (petroleum Ether/EtOAc=4/1) to give 1-(3,5-dichloropyridazin-4-yl)ethanone as a light yellow solid (35.0 g, 56%). LCMS m/z=191 (M+1).

Step 2. 1-(3,5-Dimethylpyridazin-4-yl)ethanone. To a solution of 1-(3,5-dichloropyridazin-4-yl)ethanone (35.0 g, 0.184 mol) in dioxane (700 mL) and water (35 mL) was added 2,4,6-trimethyl-1,3,5,2,4,6-trioxatriborinane (157 mL, 3.5 mol/L in THF, 0.552 mol), K$_2$CO$_3$ (63.5 g, 0.460 mol) and Pd(dppf)Cl$_2$ (5.3 g, 0.0074 mol). The mixture was stirred for 36 h at 110° C. under a N$_2$ atmosphere. After completion, the reaction was cooled to room temperature and concentrated. The crude product was purified by silica gel flash column chromatography (DCM/MeOH=60/1) to give a brown oil (17.5 g, 63.2%). LCMS m/z—151 (M+1).

Step 3. 1-(3,5-Dimethylpyridazin-4-yl)ethanol. To a solution of 1-(3,5-dimethylpyridazin-4-yl)ethanone (17.5 g, 0.12 mol) in THF (180 mL) was added NaBH$_4$ (5.06 g, 0.132 mol) at 0° C., then MeOH (18 mL) was added dropwise at the same temperature. The reaction mixture was stirred for 2 h at 0° C. When the reaction was completed, silica (80 g) was added to the mixture at 0° C. and concentrated in vacuum. The crude product was purified by silica gel flash column chromatography (DCM/MeOH=40/1) to give a light brown solid afford the racemic product 1-6 (9.5 g, 52.0% yield). The racemate was separated by SFC to afford Peak 1 (4.0 g, 23% yield, S-enantiomer) as a white solid LCMS m/z=153[M+1]; $^1$H NMR (400 MHz, CDCl$_3$) δ 8.65 (s, 1H), 5.31-5.26 (m, 1H), 3.37 (s, 1H), 2.67 (s, 3H), 2.43 (s, 3H), 1.49 (d, J=6.8 Hz, 3H), [α]D=47.092. Peak 2 (4.3 g, 24% yield, R-enantiomer) as a white solid. LCMS m/z=153 (M+1); $^1$H NMR (400 MHz, CDCl$_3$) δ 8.61 (s, 1H), 5.30-

5.25 (m, 1H), 3.71 (s, 1H), 2.68 (s, 3H), 2.41 (s, 3H), 1.48 (d, J=6.8 Hz, 3H), [α]D=+44.534.

Step 4. 5-[(1R)-1-(3,5-Dimethylpyridazin-4-yl)ethoxy]-3-iodo-1-tetrahydropyran-2-yl-indazole. To a solution of 3-iodo-1-tetrahydropyran-2-yl-indazol-5-ol (678 mg, 1.97 mmol) and (S)-1-(3,5-dimethylpyridazin-4-yl)ethanol (200 mg, 1.31 mmol), in dry THF (5 mL) was added PPh₃ (517 mg, 2.62 mmol) at 0° C. under N₂. Then, a solution of DIAD (398 mg, 1.70 mmol, 1.3 eq) in THF (2.5 mL) was added dropwise and the resulting mixture was stirred at rt for 16 h. After completion, the reaction solvent was removed. The residue was purified by silica gel flash column chromatography (Petroleum Ether/THF=3/1) to give a white solid (53% yield). LCMS m/z=479 (M+1); ¹H NMR (400 MHz, DMSO-d6) δ 8.85 (s, 1H), 7.67 (d, J=8.8 Hz, 1H), 7.19 (d, J=9.2 Hz, 1H), 6.46 (s, 1H), 5.86 (q, J=4.0 Hz, 1H), 5.76 (t, J=7.2 Hz, 1H), 3.83-3.81 (m, 1H), 3.70-3.65 (m, 1H), 2.79 (s, 3H), 2.44 (s, 3H), 2.40-2.21 (m, 1H), 1.99-1.88 (m, 2H), 1.68-1.66 (m, 4H), 1.65-1.54 (m, 2H).

Step 5. 5-[(1R)-1-(3,5-Dimethyl-4-pyridyl)ethoxy]-3-(6-fluoro-3-pyridyl)-1-tetrahydropyran-2-yl-indazole. To a solution of 5-[(1R)-1-(3,5-dimethylpyridazin-4-yl)ethoxy]-3-iodo-1-tetrahydropyran-2-yl-indazole (500 mg, 1.05 mmol, 1.0 eq), 2-fluoro-5-(4,4,5,5-tetramethyl-1,3,2-dioxaborolan-2-yl)pyridine (439 mg, 1.57 mmol, 1.5 eq) in dioxane (5.0 mL) and H₂O (0.5 mL) were added K₂CO₃ (288 mg, 2.09 mmol, 2.0 eq), and Pd(dppf)Cl₂ (50 mg, 0.1 w/w). The reaction mixture was stirred for 2 h at 90° C. under N2 protection. After the reaction was completed, the solid was filtered out and the filtrate was concentrated in vacuum. The crude product was purified by silica gel flash column chromatography (Petroleum Ether/EtOAc=3/7) to give a yellow solid (410 mg, 88%). LCMS m/z=448 (M+1).

Step 6. 2-[5-[5-[(1R)-1-(3,5-Dimethyl-4-pyridyl)ethoxy]-1-tetrahydropyran-2-yl-indazol-3-yl]-2-pyridyl]-6λ⁶-thia-2-azaspiro[3.4]octane 6,6-dioxide. To a solution of product step 5 (160 mg, 0.36 mmol, 1.0 eq) in DMSO (3.0 mL) was added DIEA (231 mg, 1.79 mmol, 5.0 eq) and 6λ⁶-thia-2-azaspiro[3.4]octane 6,6-dioxide hydrochloride (106 mg, 0.54 mmol, 1.5 eq). The reaction mixture was stirred for 16 h at 100° C. under N₂. After cooling to room temperature, the solution was diluted with EtOAc (30 mL) and washed with brine (2×15 mL). The organic layer was concentrated and the crude product was purified by Prep-TLC (EtOAc) to give a yellow solid (120 mg, 57%). LCMS m/z=589 (M+1).

Step 7. 2-[5-[5-[(1R)-1-(3,5-Dimethylpyridazin-4-yl)ethoxy]-1H-indazol-3-yl]-2-pyridyl]-6λ⁶-thia-2-azaspiro [3.4]octane 6,6-dioxide. To a solution of product step 6 (110 mg, 0.19 mmol, 1.0 eq) in DCM (3 mL) was added TFA (0.6 mL). The reaction mixture was stirred at rt for 4 h. After completion, the solution was concentrated in vacuum. The residue was diluted with EtOAc (10 mL) and washed with the saturated sodium bicarbonate solution (5 mL). The organic layer was concentrated and purified by Prep-HPLC (Prep-C18, 5 µM Triart column, 20×150 mm, YMC-Actus; gradient elution of 40% MeCN in water to 60% MeCN in water over an 8 min period, where both solvents contain 0.05% NH₃·H₂O) to give a white solid (58 mg, 62%). LCMS m/z=505[M+1]; ¹HNMR (400 MHz, DMSO-d6) δ 13.00 (s, 1H), 8.83 (s, 1H), 8.51 (s, 1H), 7.86 (d, J=7.6 Hz, 1H), 7.46 (d, J=9.2 Hz, 1H), 7.08-7.03 (m, 2H), 6.54 (d, J=8.0 Hz, 1H), 5.87 (q, J=6.0 Hz, 1H), 4.07-3.97 (m, 4H), 3.50 (s, 2H), 3.28-3.24 (m, 2H), 2.78 (s, 3H), 2.50-2.44 (m, 2H), 2.44 (s, 3H), 1.67 (d, J=6.4 Hz, 3H).

Example 145. 2-[5-[5-[(1S)-1-(3,5-Dimethylpyridazin-4-yl)ethoxy]-1H-indazol-3-yl]-2-pyridyl]-6λ⁶-thia-2-azaspiro[3.4]octane 6,6-dioxide

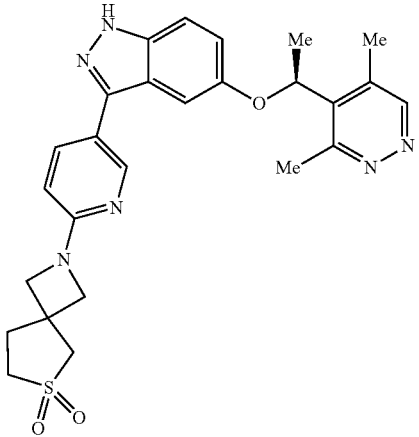 [SMILES: Cc1cnnc(C)c1[C@H](C)Oc1ccc2[nH]nc(-c3ccc(N4CC5(CCS(=O)(=O)C5)C4)nc3)c2c1]

Step 1. 5-[(1S)-1-(3,5-Dimethylpyridazin-4-yl)ethoxy]-3-iodo-1-tetrahydropyran-2-yl-indazole. To a solution of (R)-1-(3,5-dimethylpyridazin-4-yl)ethanol (200 mg, 1.31 mmol, 1.0 eq) and 3-iodo-1-tetrahydropyran-2-yl-indazol-5-ol (678 mg, 1.97 mmol, 1.5 eq) in DCM (7.5 mL) was added PPh₃ (862 mg, 3.28 mmol, 2.5 eq) at 0° C. under N2. Then, a solution of DIAD (398 mg, 1.97 mmol, 1.5 eq) in DCM (2.5 mL) was added dropwise and the resulting mixture was stirred at rt for 3 h. After completion, the reaction mixture was concentrated. The residue was purified by silica gel flash column chromatography (petroleum Ether/THF=3/1) to give a white solid (56% yield). LCMS m/z=479 (M+1); 1H NMR (400 MHz, DMSO-d6) δ 8.85 (s, 1H), 7.66 (d, J=8.8 Hz, 1H), 7.19 (dd, J=9.2 Hz, 2.4 Hz, 1H), 6.47 (s, 1H), 5.86 (q, J=4.0 Hz, 1H), 5.76 (t, J=7.2 Hz, 1H), 3.83-3.81 (m, 1H), 3.70-3.65 (m, 1H), 2.79 (s, 3H), 2.44 (s, 3H), 2.32-2.25 (m, 1H), 1.99-1.87 (m, 2H), 1.68-1.66 (m, 4H), 1.65-1.54 (m, 2H).

Step 2. 5-[(1S)-1-(3,5-Dimethyl-4-pyridyl)ethoxy]-3-(6-fluoro-3-pyridyl)-1-tetrahydropyran-2-yl-indazole. To a solution of 5-[(1S)-1-(3,5-dimethylpyridazin-4-yl)ethoxy]-3-iodo-1-tetrahydropyran-2-yl-indazole (900 mg, 1.88 mmol, 1.0 eq), 2-fluoro-5-(4,4,5,5-tetramethyl-1,3,2-dioxaborolan-2-yl)pyridine (545 mg, 2.44 mmol, 1.3 eq) in dioxane (30.0 mL) and H₂O (3 mL) were added K₂CO₃ (518.6 mg, 3.76 mmol, 2.0 eq), and Pd(dppf)Cl₂ (153 mg, 0.19 mmol, 0.1 eq). The reaction mixture was stirred for 3 h at 90° C. under N2 protection. After the reaction was completed, the solid was filtered out and the filtrate was concentrated in vacuum. The crude product was purified by silica gel flash column chromatography (Petroleum Ether/ EtOAc=1/1) to afford the product Example 7c (800 mg, 95.0% yield) as a yellow solid. LCMS m/z=448 (M+1).

Step 3: 2-[5-[5-[(1S)-1-(3,5-Dimethyl-4-pyridyl)ethoxy]-1-tetrahydropyran-2-yl-indazol-3-yl]-2-pyridyl]-6λ⁶-thia-2-azaspiro[3.4]octane 6,6-dioxide. To a solution of 5-[(1S)-1-(3,5-Dimethyl-4-pyridyl)ethoxy]-3-(6-fluoro-3-pyridyl)-1-tetrahydropyran-2-yl-indazole (170 mg, 0.38 mmol, 1.0 eq) in DMSO (5.0 mL) were added DIEA (245 mg, 1.90 mmol, 5.0 eq) and 6λ⁶-thia-2-azaspiro[3.4]octane 6,6-dioxide hydrochloride (90 mg, 0.46 mmol, 1.2 eq). The reaction mixture was stirred for 16 h at 105° C. under N2. After cooling to room temperature, the solution was diluted with EtOAc (30 mL) and washed with brine (2×15 mL). The organic layer was concentrated and the product was purified by Prep-TLC (EtOAc) to give a yellow solid (170 mg, 76%). LCMS m/z=589 [M+1].

Step 3: 2-[5-[5-[(1S)-1-(3,5-Dimethylpyridazin-4-yl) ethoxy]-1H-indazol-3-yl]-2-pyridyl]-6λ⁶-thia-2-azaspiro [3.4]octane 6,6-dioxide. To a solution of 2-[5-[5-[(1S)-1-(3, 5-dimethyl-4-pyridyl)ethoxy]-1-tetrahydropyran-2-yl-indazol-3-yl]-2-pyridyl]-6λ⁶-thia-2-azaspiro[3.4]octane 6,6-dioxide (170 mg, 0.29 mmol, 1.0 eq) in DCM (10 mL) was added TFA (2.0 mL). The reaction mixture was stirred at rt for 2 h. After completion, the solution was concentrated in vacuum. The crude product was treated with MeOH (5 mL), and NaHCO₃ (excess) was added to the solution, which was stirred at r.t. for 20 min. Then DCM (20 mL) was added, the precipitate was filtered out and the filtrate was concentrated. The crude product was purified by Prep-HPLC (Prep-C18, 5 µM Triart column, 20×150 mm, YMC-Actus; gradient elution of 20% MeCN in water to 56% MeCN in water over an 8 min period, where both solvents contain 0.05% NH₃·H₂O) to give a white solid (45 mg, 31%). LCMS m/z=505 (M+1); ¹HNMR (400 MHz, DMSO-d6) δ 13.00 (s, 1H), 8.84 (s, 1H), 8.51 (d, J=1.6 Hz, 1H), 7.86 (dd, J=8.8 Hz, 2.4 Hz, 1H), 7.46 (d, J=8.8 Hz, 1H), 7.07 (dd, J=9.2 Hz, 2.4 Hz, 1H), 7.03-7.02 (m, 1H), 6.54 (d, J=8.4 Hz, 1H), 5.88 (q, J=6.4 Hz, 1H), 4.06 (d, J=8.4 Hz, 2H), 3.99 (d, J=8.0 Hz, 2H), 3.50 (s, 2H), 3.26 (t, J=7.2 Hz, 2H), 2.78 (s, 3H), 2.50-2.47 (m, 2H), 2.44 (s, 3H), 1.67 (d, J=6.8 Hz, 3H).

Examples 141-156 were synthesized using procedures and intermediates described for Example 144 and Example 145.

Example 141
2-[5-[5-[(1R)-1-(3,5-dimethylpyridazin-4-yl)ethoxy]-1H-indazol-3-yl]pyrimidin-2-yl]-6λ⁶-thia-2-azaspiro[3.4]octane 6,6-dioxide

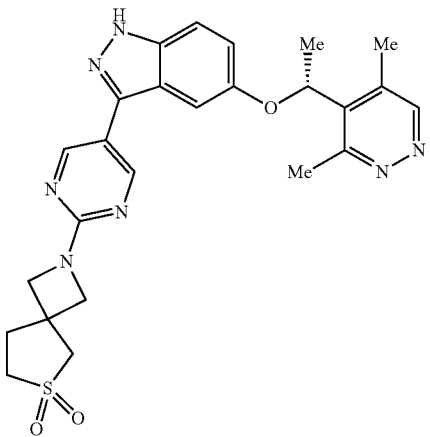 [SMILES: Cc1cnnc(C)c1[C@@H](C)Oc1ccc2[nH]nc(-c3cnc(N4CC5(CCS(=O)(=O)C5)C4)nc3)c2c1]

LCMS: m/z = 506 (M + H); 1H NMR (400 MHz, DMSO-d6) δ 13.13 (s, 1H), 8.82 (s, 1H), 8.79 (s, 2H), 7.48 (d, J = 8.8 Hz, 1H), 7.13 (s, 1H), 7.09 (dd, J = 9.2 Hz, 2.0 Hz, 1H), 5.91 (q, J = 6.0 Hz, 1H), 4.16 (d, J = 8.8 Hz, 2H), 4.08 (d, J = 8.0 Hz, 2H), 3.51 (s, 2H), 3.26 (t, J = 7.6 Hz, 2H), 2.78 (s, 3H), 2.50-2.48 (m, 2H), 2.44 (s, 3H), 1.66 (d, J = 6.4 Hz, 3H).

Example 142
ethyl 6-[5-[5-[(1R)-1-(3,5-dimethylpyridazin-4-yl)ethoxy]-1H-indazol-3-yl]-2-pyridyl]-2,6-diazaspiro[3.3]heptane-2-carboxylate

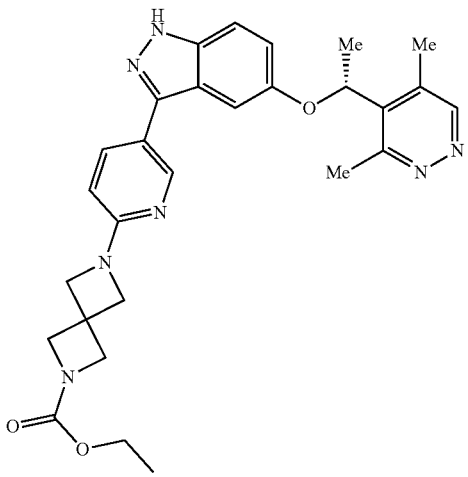 [SMILES: CCOC(=O)N1CC2(C1)CN(c1ccc(-c3n[nH]c4ccc(O[C@H](C)c5c(C)cnnc5C)cc34)cn1)C2]

LCMS: m/z = 514 (M + H); 1H NMR (400 MHz, DMSO-d6) δ 12.98 (s, 1H), 8.83 (s, 1H), 8.50 (d, J = 2.4 Hz, 1H), 7.83 (dd, J = 8.8 Hz, 2.4 Hz, 1H), 7.45 (d, J = 8.8 Hz, 1H), 7.08-7.05 (m, 1H), 7.03 (s, 1H), 6.51 (d, J = 8.0 Hz, 1H), 5.88 (q, J = 6.8 Hz, 1H), 4.15-4.12 (m, 8H), 4.02 (q, J = 7.2 Hz, 2H), 2.78 (s, 3H), 2.44 (s, 3H), 1.67 (d, J = 6.8 Hz, 3H), 1.17 (t, J = 7.6 Hz, 3H)

| | | |
|---|---|---|
| Example 143<br>methyl 6-[5-[5-[(1R)-1-(3,5-dimethylpyridazin-4-yl)ethoxy]-1H-indazol-3-yl]pyrimidin-2-yl]-2,6-diazaspiro[3.3]heptane-2-carboxylate | 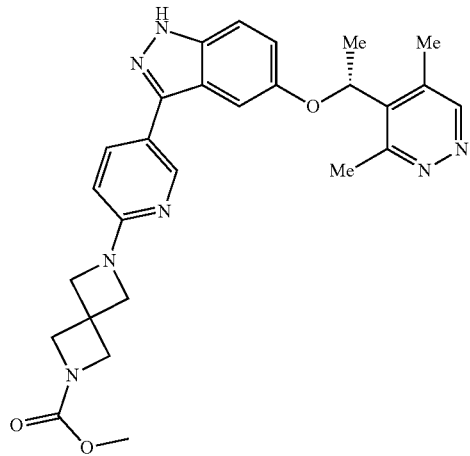 [SMILES: COC(=O)N1CC2(C1)CN(c1ccc(-c3n[nH]c4ccc(O[C@H](C)c5c(C)cnnc5C)cc34)cn1)C2] | LCMS: m/z = 501.3 (M + H); 1H NMR (400 MHz, DMSO-d6) δ 13.12 (s, 1H), 8.82 (s, 1H), 8.76 (s, 2H), 7.48 (d, J = 8.8 Hz, 1H), 7.12 (s, 1H), 7.08 (dd, J = 8.4 Hz, 1.2 Hz, 1H), 5.90 (q, J = 6.4 Hz, 1H), 4.26 (s, 4H), 4.14 (s, 4H), 3.57 (s, 3H), 2.78 (s, 3H), 2.44 (s, 3H), 1.66 (d, J = 6.8 Hz, 3H). |
| Example 144<br>2-[5-[5-[(1R)-1-(3,5-dimethylpyridazin-4-yl)ethoxy]-1H-indazol-3-yl]-2-pyridyl]-6λ⁶-thia-2-azaspiro[3.4]octane 6,6-dioxide | 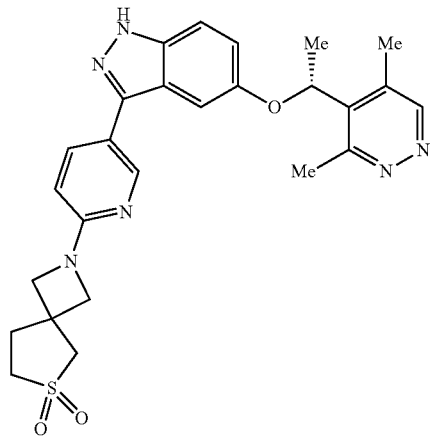 [SMILES: Cc1cnnc(C)c1[C@@H](C)Oc1ccc2[nH]nc(-c3ccc(N4CC5(CCS(=O)(=O)C5)C4)nc3)c2c1] | LCMS: m/z = 505 (M + H); 1H NMR (400 MHz, DMSO-d6) δ 13.00 (s, 1H), 8.83 (s, 1H), 8.51 (s, 1H), 7.86 (d, J = 7.6 Hz, 1H), 7.46 (d, J = 9.2 Hz, 1H), 7.08-7.03 (m, 2H), 6.54 (d, J = 8.0 Hz, 1H), 5.87 (q, J = 6.0 Hz, 1H), 4.07-3.97 (m, 4H), 3.50 (s, 2H), 3.28-3.24 (m, 2H), 2.78 (s, 3H), 2.50-2.44 (m, 2H), 2.44 (s, 3H), 1.67 (d, J = 6.4 Hz, 3H). |
| Example 145<br>2-[5-[5-[(1S)-1-(3,5-dimethylpyridazin-4-yl)ethoxy]-1H-indazol-3-yl]-2-pyridyl]-6λ⁶-thia-2-azaspiro[3.4]octane 6,6-dioxide | 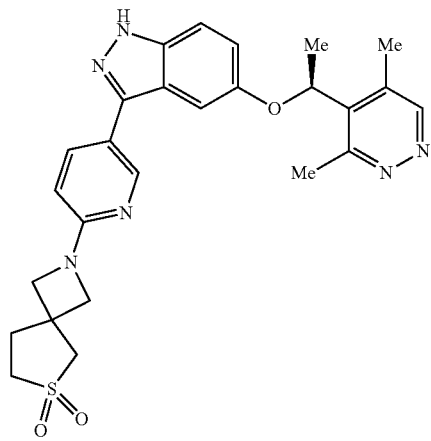 [SMILES: Cc1cnnc(C)c1[C@H](C)Oc1ccc2[nH]nc(-c3ccc(N4CC5(CCS(=O)(=O)C5)C4)nc3)c2c1] | LCMS: m/z = 506 (M + H); 1H NMR (400 MHz, DMSO-d6) δ 13.00 (s, 1H), 8.84 (s, 1H), 8.51 (d, J = 1.6 Hz, 1H), 7.86 (dd, J = 8.8 Hz, 2.4 Hz, 1H), 7.46 (d, J = 8.8 Hz, 1H), 7.07 (dd, J = 9.2 Hz, 2.4 Hz, 1H), 7.03-7.02 (m, 1H), 6.54 (d, J = 8.4 Hz, 1H), 5.88 (q, J = 6.4 Hz, 1H), 4.06 (d, J = 8.4 Hz, 2H), 3.99 (d, J = 8.0 Hz, 2H), 3.50 (s, 2H), 3.26 (t, J = 7.2 Hz, 2H), 2.78 (s, 3H), 2.50-2.47 (m, 2H), 2.44 (s, 3H), 1.67 (d, J = 6.8 Hz, 3H). |

| Example 146 ethyl 6-[5-[5-[(1R)-1-(3,5-dimethylpyridazin-4-yl)ethoxy]-1H-indazol-3-yl]pyrimidin-2-yl]-2,6-diazaspiro[3.3]heptane-2-carboxylate | 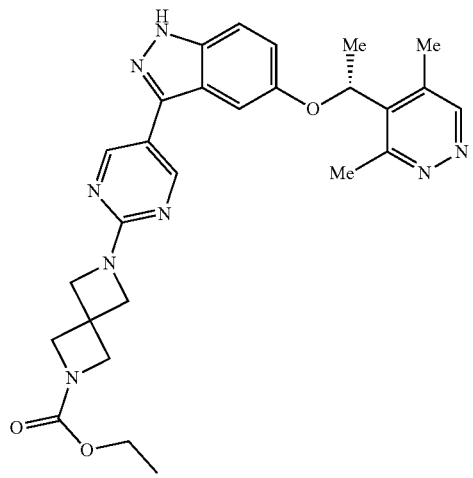 [SMILES: CCOC(=O)N1CC2(C1)CN(c1ncc(-c3n[nH]c4ccc(O[C@H](C)c5c(C)cnnc5C)cc34)cn1)C2] | LCMS: m/z = 515.3 (M + H); 1H NMR (400 MHz, DMSO-d6) δ 13.12 (s, 1H), 8.82 (s, 1H), 8.76 (s, 2H), 7.48 (d, J = 8.8 Hz, 1H), 7.12 (d, J = 2.0 Hz, 1H), 7.09 (dd, J = 8.8 Hz, 2.4 Hz, 1H), 5.92 (q, J = 6.8 Hz, 1H), 4.26 (s, 4H), 4.13 (s, 4H), 4.02 (q, J = 7.6 Hz, 2H), 2.78 (s, 3H), 2.44 (s, 3H), 1.65 (d, J = 6.8 Hz, 3H), 1.17 (t, J = 6.8 Hz, 3H) |
|---|---|---|
| Example 147 2-[5-[5-[(1S)-1-(3,5-dimethylpyridazin-4-yl)ethoxy]-1H-indazol-3-yl]pyrimidin-2-yl]-6λ$^6$-thia-2-azaspiro[3.4]octane 6,6-dioxide | 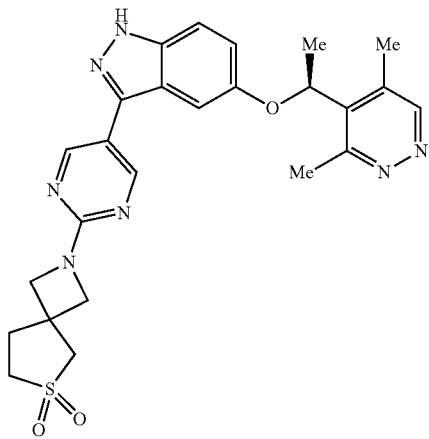 [SMILES: Cc1cnnc(C)c1[C@H](C)Oc1ccc2[nH]nc(-c3cnc(N4CC5(CCS(=O)(=O)C5)C4)nc3)c2c1] | LCMS: m/z = 506 (M + H); 1H NMR (400 MHz, DMSO-d6) δ 13.11 (s, 1H), 8.82 (s, 1H), 8.79 (s, 2H), 7.48 (d, J = 9.6 Hz, 1H), 7.13~7.12 (m, 1H), 7.09 (dd, J = 8.8 Hz, 2.0 Hz, 1H), 5.93 (q, J = 6.4 Hz, 1H), 4.17 (d, J = 9.2 Hz, 2H), 4.08 (dd, J = 8.8 Hz, 1.6 Hz, 2H), 3.51 (s, 2H), 3.26 (t, J = 8.0 Hz, 2H), 2.79 (s, 3H), 2.50~2.48 (m, 2H), 2.45 (s, 3H), 1.66 (d, J = 6.8 Hz, 3H) |
| Example 148 5-[(1R)-1-(3,5-dimethylpyridazin-4-yl)ethoxy]-3-[6-(2-methylsulfonyl-2,6-diazaspiro[3.3]heptan-6-yl)-3-pyridyl]-1H-indazole | 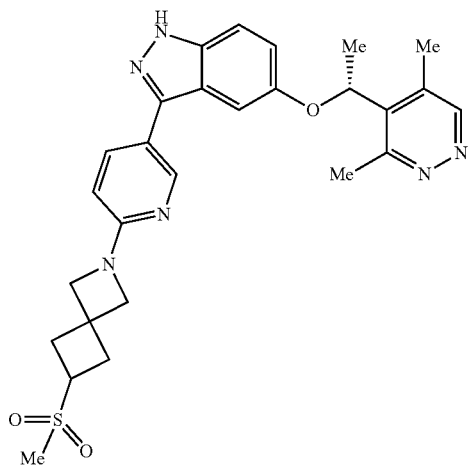 [SMILES: Cc1cnnc(C)c1[C@@H](C)Oc1ccc2[nH]nc(-c3ccc(N4CC5(CC(S(C)(=O)=O)C5)C4)nc3)c2c1] | LCMS: m/z = 520.6 (M + H); 1H NMR (400 MHz, DMSO-d6) δ 12.99 (s, 1H), 8.83 (s, 1H), 8.50 (d, J = 2.0 Hz, 1H), 7.85 (dd, J = 8.8 Hz, 2.4 Hz, 1H), 7.46 (d, J = 8.8 Hz, 1H), 7.08-7.04 (m, 2H), 6.52 (d, J = 8.8 Hz, 1H), 5.87 (q, J = 6.8 Hz, 1H), 4.17 (s, 4H), 4.12 (s, 4H), 3.03 (s, 3H), 2.78 (s, 3H), 2.44 (s, 3H), 1.67 (d, J = 6.4 Hz, 3H) |

| Example 149 5-[(1S)-1-(3,5-dimethylpyridazin-4-yl)ethoxy]-3-[6-(2-methylsulfonyl-2,6-diazaspiro[3.3]heptan-6-yl)-3-pyridyl]-1H-indazole | 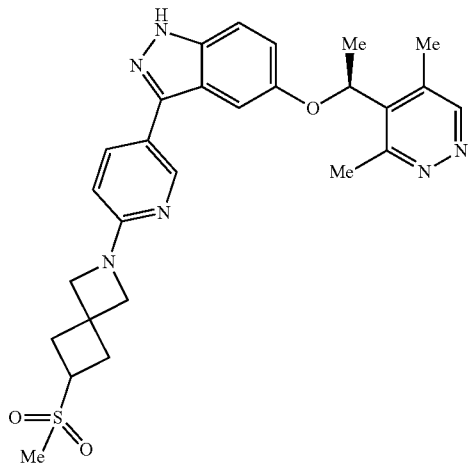 [SMILES: Cc1cnnc(C)c1[C@H](C)Oc1ccc2[nH]nc(-c3ccc(N4CC5(CC(S(C)(=O)=O)C5)C4)nc3)c2c1] | LCMS: m/z = 520.3 (M + H); 1H NMR (400 MHz, DMSO-d6) δ 12.99 (s, 1H), 8.83 (s, 1H), 8.50 (d, J = 2.0 Hz, 1H), 7.85 (dd, J = 8.4 Hz, 2.0 Hz, 1H), 7.46 (d, J = 9.2 Hz, 1H), 7.07 (dd, J = 9.2 Hz, 2.4 Hz, 1H), 7.08-7.07 (m, 1H), 6.52 (d, J = 8.4 Hz, 1H), 5.87 (q, J = 6.8 Hz, 1H), 4.17 (s, 4H), 4.12 (s, 4H), 3.03 (s, 3H), 2.78 (s, 3H), 2.44 (s, 3H), 1.66 (d, J = 6.8 Hz, 3H) |
|---|---|---|
| Example 150 methyl 6-[5-[5-[(1R)-1-(3,5-dimethylpyridazin-4-yl)ethoxy]-1H-indazol-3-yl]-2-pyridyl]-2,6-diazaspiro[3.3]heptane-2-carboxylate | 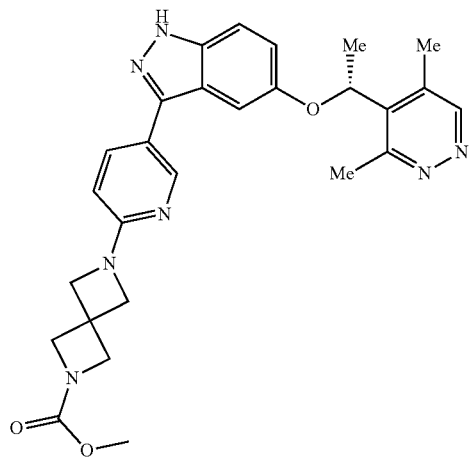 [SMILES: COC(=O)N1CC2(C1)CN(c1ccc(-c3n[nH]c4ccc(O[C@H](C)c5c(C)cnnc5C)cc34)cn1)C2] | LCMS: m/z = 500.6 (M + H); 1H NMR (400 MHz, DMSO-d6) δ 12.98 (s, 1H), 8.83 (s, 1H), 8.50 (d, J = 1.2 Hz, 1H), 7.84 (dd, J = 8.8 Hz, 2.4 Hz, 1H), 7.46 (d, J = 8.8 Hz, 1H), 7.08-7.03 (m, 2H), 6.50 (d, J = 8.0 Hz, 1H), 5.87 (q, J = 6.4 Hz, 1H), 4.15 (s, 8H), 3.57 (s, 3H), 2.78 (s, 3H), 2.44 (s, 3H), 1.66 (d, J = 6.8 Hz, 3H) |
| Example 151 ethyl 6-[5-[5-[(1S)-1-(3,5-dimethylpyridazin-4-yl)ethoxy]-1H-indazol-3-yl]-2-pyridyl]-2,6-diazaspiro[3.3]heptane-2-carboxylate | 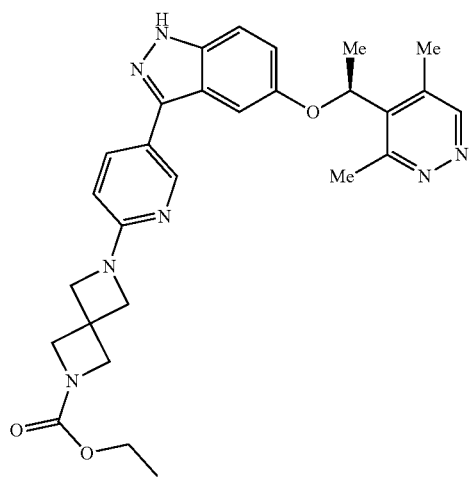 [SMILES: CCOC(=O)N1CC2(C1)CN(c1ccc(-c3n[nH]c4ccc(O[C@@H](C)c5c(C)cnnc5C)cc34)cn1)C2] | LCMS: m/z = 514.3 (M + H); 1H NMR (400 MHz, DMSO-d6) δ 12.99 (s, 1H), 8.83 (s, 1H), 8.50 (d, J = 2.0 Hz, 1H), 7.83 (dd, J = 8.4 Hz, 2.0 Hz, 1H), 7.45 (d, J = 8.8 Hz, 1H), 7.08-7.05 (m, 1H), 7.03 (s, 1H), 6.51 (d, J = 8.8 Hz, 1H), 5.88 (q, J = 6.8 Hz, 1H), 4.15-4.12 (m, 8H), 4.02 (q, J = 6.8 Hz, 2H), 2.78 (s, 3H), 2.44 (s, 3H), 1.67 (d, J = 6.0 Hz, 3H), 1.17 (t, J = 7.6 Hz, 3H) |

| Example 152 8-[5-[5-[(1R)-1-(3,5-dimethylpyridazin-4-yl)ethoxy]-1H-indazol-3-yl]pyrimidin-2-yl]-2λ⁶-thia-8-azaspiro[4.5]decane 2,2-dioxide | 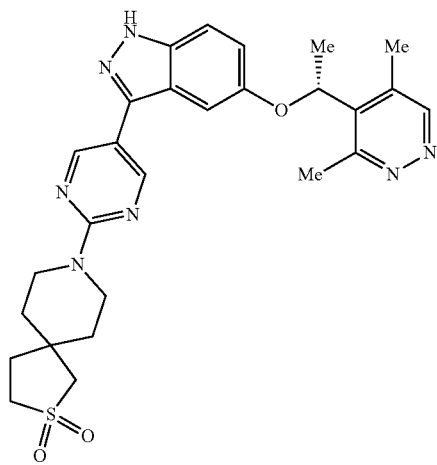 [SMILES: Cc1cnnc(C)c1[C@@H](C)Oc1ccc2[nH]nc(-c3cnc(N4CCC5(CC4)CCS(=O)(=O)C5)nc3)c2c1] | LCMS: m/z = 534.3 (M + H); 1H NMR (400 MHz, CDCl3) δ 8.80 (s, 1H), 8.71 (s, 2H), 7.41 (d, J = 9.2 Hz, 1H), 7.02-6.97 (m, 2H), 5.63 (q, J = 6.8 Hz, 1H), 4.38-4.34 (m, 2H), 3.50-3.43 (m, 2H), 3.23 (t, J = 8.0 Hz, 2H), 3.12 (s, 2H), 2.88 (s, 3H), 2.48 (s, 3H), 2.18 (t, J = 7.6 Hz, 2H), 1.90-1.86 (m, 2H), 1.77-1.71 (m, 5H) |
|---|---|---|
| Example 153 methyl 6-[5-[5-[(1S)-1-(3,5-dimethylpyridazin-4-yl)ethoxy]-1H-indazol-3-yl]-2-pyridyl]-2,6-diazaspiro[3.3]heptane-2-carboxylate | 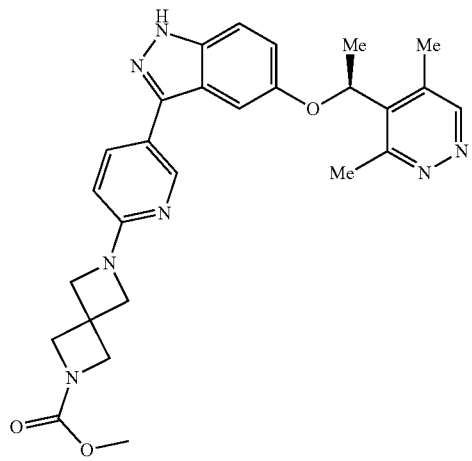 [SMILES: COC(=O)N1CC2(C1)CN(c1ccc(-c3n[nH]c4ccc(O[C@@H](C)c5c(C)cnnc5C)cc34)cn1)C2] | LCMS: m/z = 500.3 (M + H); 1H NMR (400 MHz, DMSO-d6) δ 12.99 (s, 1H), 8.83 (s, 1H), 8.49 (d, J = 1.6 Hz, 1H), 7.84 (dd, J = 8.8 Hz, 2.4 Hz, 1H), 7.46 (d, J = 9.2 Hz, 1H), 7.08 - 7.02 (m, 2H), 6.50 (d, J = 9.2 Hz, 1H), 5.87 (q, J = 6.8 Hz, 1H), 4.15 (s, 8H), 3.57 (s, 3H), 2.78 (s, 3H), 2.44 (s, 3H), 1.66 (d, J = 6.8 Hz, 3H) |
| Example 154 8-[5-[5-[(1S)-1-(3,5-dimethylpyridazin-4-yl)ethoxy]-1H-indazol-3-yl]pyrimidin-2-yl]-2λ⁶-thia-8-azaspiro[4.5]decane 2,2-dioxide | 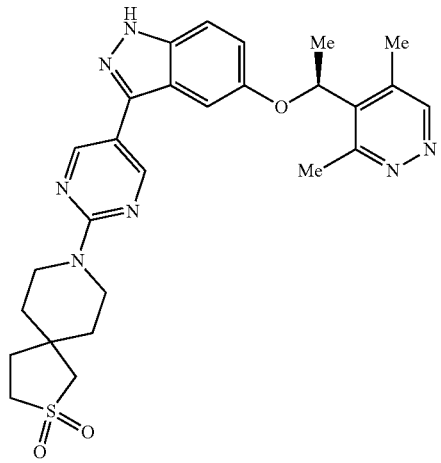 [SMILES: Cc1cnnc(C)c1[C@H](C)Oc1ccc2[nH]nc(-c3cnc(N4CCC5(CC4)CCS(=O)(=O)C5)nc3)c2c1] | LCMS: m/z = 534.3 (M + H); 1H NMR (400 MHz, DMSO-d6) δ 13.09 (s, 1H), 8.83 (s, 1H), 8.76 (s, 2H), 7.47 (d, J = 8.8 Hz, 1H), 7.14 (s, 1H), 7.09 (d, J = 9.2 Hz, 1H), 5.90 (q, J = 6.4 Hz, 1H), 4.23-4.15 (m, 2H), 3.58-3.50 (m, 2H), 3.29-3.23 (m, 2H), 3.21-3.19 (m, 2H), 2.79 (s, 3H), 2.45 (s, 3H), 2.13-2.07 (m, 2H), 1.83-1.76 (m, 2H), 1.68-1.60 (m, 5H) |

-continued

| Example 155<br>5-[(1S)-1-(3,5-dimethylpyridazin-4-yl)ethoxy]-3-[2-(2-methylsulfonyl-2,6-diazaspiro[3.3]heptan-6-yl)pyrimidin-5-yl]-1H-indazole | 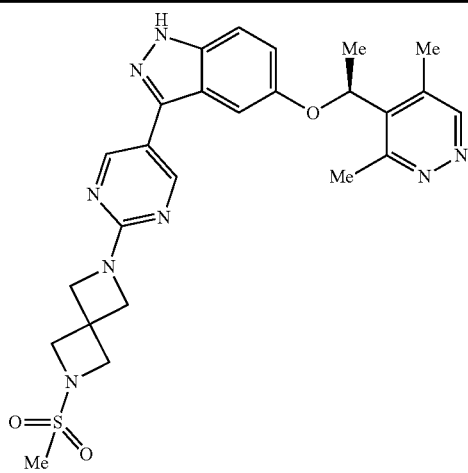 | LCMS: m/z = 521.3 (M + H); 1H NMR (400 MHz, DMSO-d6) δ 12.91 (brs, 1H), 8.82 (s, 1H), 8.78 (s, 2H), 7.48 (d, J = 8.8 Hz, 1H), 7.12 (d, J = 2.0 Hz, 1H), 7.08 (dd, J = 8.8 Hz, 2.4 Hz, 1H), 5.90 (q, J = 6.8 Hz, 1H), 4.28 (s, 4H), 4.12 (s, 4H), 3.03 (s, 3H), 2.80 (s, 3H), 2.44 (s, 3H), 1.66 (d, J = 6.8 Hz, 3H) |
| --- | --- | --- |
| Example 156<br>5-[(1R)-1-(3,5-dimethylpyridazin-4-yl)ethoxy]-3-[2-(2-methylsulfonyl-2,6-diazaspiro[3.3]heptan-6-yl)pyrimidin-5-yl]-1H-indazole | 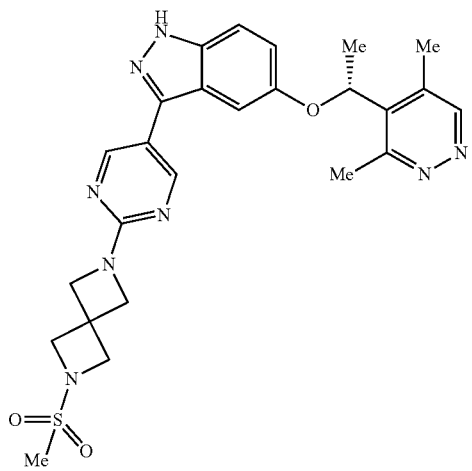 [SMILES: Cc1cnnc(C)c1[C@@H](C)Oc1ccc2[nH]nc(-c3cnc(N4CC5(C4)CN(S(C)(=O)=O)C5)nc3)c2c1] | LCMS: m/z = 521.4 (M + H); 1H NMR (400 MHz, DMSO-d6) δ 13.14 (s, 1H), 8.82 (s, 1H), 8.78 (s, 2H), 7.49 (d, J = 8.8 Hz, 1H), 7.12-7.07 (m, 2H), 5.91 (q, J = 6.8 Hz, 1H), 4.29 (s, 4H), 4.12 (s, 4H), 3.03 (s, 3H), 2.79 (s, 3H), 2.44 (s, 3H), 1.67 (d, J = 6.0 Hz, 3H). |

Examples 157-165 were synthesized using procedures and intermediates previously described.

| Example 157<br>5-[(1R)-1-(3,5-dichloro-4-pyridyl)ethoxy]-3-[2-(7-methylsulfonyl-2,7-diazaspiro[3.4]octan-2-yl)pyrimidin-5-yl]-1H-indazole | 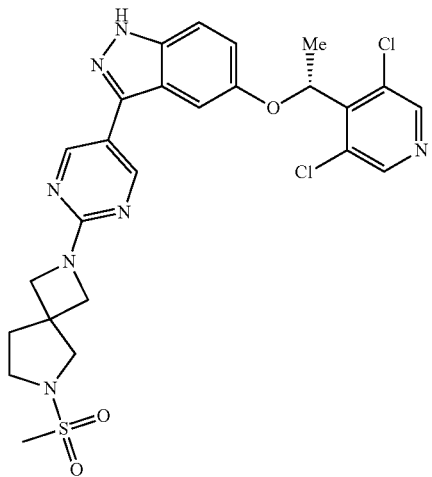 [SMILES: C[C@@H](Oc1ccc2[nH]nc(-c3cnc(N4CC5(CCN(S(C)(=O)=O)C5)C4)nc3)c2c1)c1c(Cl)cncc1Cl] | LCMS: m/z = 574.1 (M + H); 1H NMR (400 MHz, CDCl3) δ = 10.50 (br s, 1H), 8.80 (s, 2H), 8.41 (s, 2H), 7.37 (d, J = 8.9 Hz, 1H), 7.21 - 7.09 (m, 2H), 6.04 (q, J = 6.7 Hz, 1H), 4.23 - 4.12 (m, 4H), 3.60 (s, 2H), 3.48 (t, J = 6.9 Hz, 2H), 2.88 (s, 3H), 2.27 (t, J = 6.9 Hz, 2H), 1.81 (d, J = 6.7 Hz, 3H) |
| --- | --- | --- |

| Example 158 3-[2-(2,7-diazaspiro[3.4]octan-2-yl)pyrimidin-5-yl]-5-[(1R)-1-(3,5-dichloro-4-pyridyl)ethoxy]-1H-indazole | 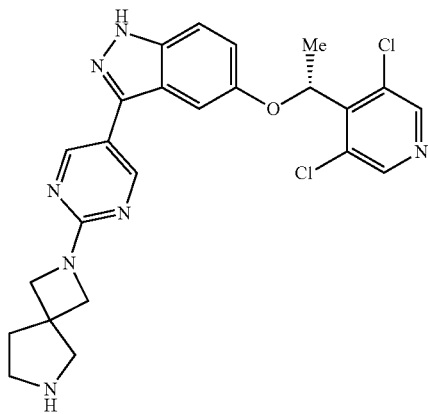 [SMILES: C[C@@H](Oc1ccc2[nH]nc(-c3cnc(N4CC5(CCNC5)C4)nc3)c2c1)c1c(Cl)cncc1Cl] | LCMS: m/z = 496.2 (M + H); 1H NMR (400 MHz, CD3OD) δ = 8.70 (s, 2H), 8.47 (s, 2H), 7.45 (dd, J = 0.5, 9.0 Hz, 1H), 7.18 (dd, J = 2.3, 9.0 Hz, 1H), 7.09 (d, J = 2.2 Hz, 1H), 6.15 (q, J = 6.7 Hz, 1H), 4.16 (d, J = 1.7 Hz, 4H), 3.20 (s, 2H), 3.07 (t, J = 7.2 Hz, 2H), 2.18 (t, J = 7.2 Hz, 2H), 1.82 (d, J = 6.7 Hz, 3H) |
|---|---|---|
| Example 159 2-[5-[5-[(1R)-1-(3,5-dichloro-4-pyridyl)ethoxy]-1H-indazol-3-yl]-2-pyridyl]-6λ6-thia-2-azaspiro[3.5]nonane 6,6-dioxide | 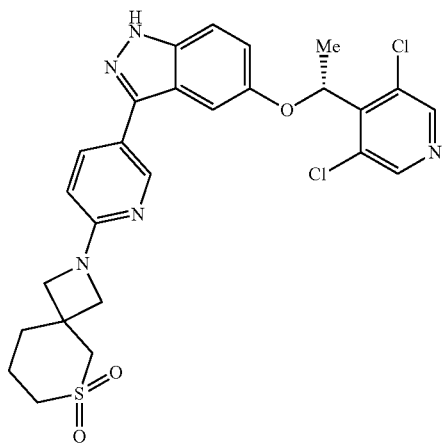 [SMILES: C[C@@H](Oc1ccc2[nH]nc(-c3ccc(N4CC5(CCCS(=O)(=O)C5)C4)nc3)c2c1)c1c(Cl)cncc1Cl] | LCMS: m/z = 558.1 (M + H); 1H NMR (400 MHz, DMSO-d6) δ = 12.98 (s, 1H), 8.60 (s, 2H), 8.51 (d, J = 1.8 Hz, 1H), 7.85 (dd, J = 2.3, 8.6 Hz, 1H), 7.45 (d, J = 8.9 Hz, 1H), 7.15 (d, J = 2.1 Hz, 1H), 7.09 (dd, J = 2.3, 9.0 Hz, 1H), 6.56 (d, J = 8.6 Hz, 1H), 6.11 (q, J = 6.7 Hz, 1H), 3.96 (d, J = 8.2 Hz, 2H), 3.80 (d, J = 8.2 Hz, 2H), 3.46 (s, 2H), 3.09 - 3.03 (m, 2H), 2.01 (br s, 2H), 1.96 (br d, J = 5.1 Hz, 2H), 1.76 (d, J = 6.7 Hz, 3H) |
| Example 160 5-[(1S)-1-(3,5-dichloro-4-pyridyl)ethoxy]-3-[6-(2-methylsulfonyl-2,6-diazaspiro[3.3]heptan-6-yl)-3-pyridyl]-1H-indazole | 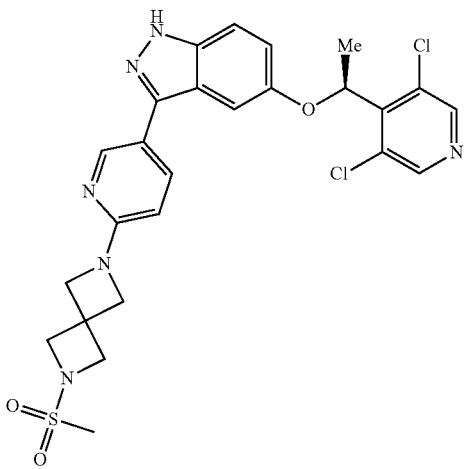 [SMILES: C[C@H](Oc1ccc2[nH]nc(-c3ccc(N4CC5(C4)CN(S(C)(=O)=O)C5)nc3)c2c1)c1c(Cl)cncc1Cl] | LCMS: m/z = 559.1 (M + H); 1H NMR (400 MHz, DMSO-d6) δ = 12.99 (s, 1H), 8.59 (s, 2H), 8.52 (d, J = 1.7 Hz, 1H), 7.87 (dd, J = 2.3, 8.7 Hz, 1H), 7.46 (d, J = 9.0 Hz, 1H), 7.17 (d, J = 2.1 Hz, 1H), 7.09 (dd, J = 2.3, 8.9 Hz, 1H), 6.54 (d, J = 8.3 Hz, 1H), 6.11 (q, J = 6.6 Hz, 1H), 4.17 (s, 4H), 4.12 (s, 4H), 3.03 (s, 3H), 1.76 (d, J = 6.7 Hz, 3H) |

-continued

| | | |
|---|---|---|
| Example 161<br>3-[6-(2,8-diazaspiro[3.5]nonan-2-yl)-3-pyridyl]-5-[(1R)-1-(3,5-dichloro-4-pyridyl)ethoxy]-1H-indazole | 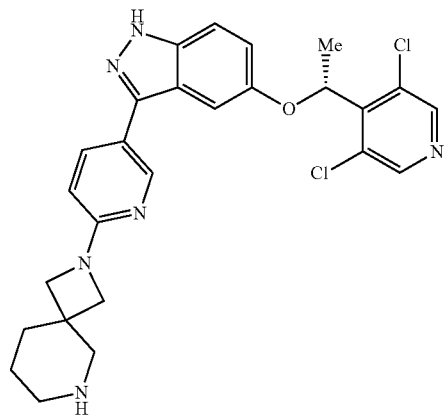 [SMILES: C[C@@H](Oc1ccc2[nH]nc(-c3ccc(N4CC5(CCCNC5)C4)nc3)c2c1)c1c(Cl)cncc1Cl] | LCMS: m/z = 509 (M + H)+ (free base); 1H NMR (400 MHz, DMSO-d6) δ = 13.04 (br s, 1H), 8.72 (br s, 2H), 8.59 (s, 2H), 8.52 (dd, J = 0.6, 2.2 Hz, 1H), 7.91 (dd, J = 2.3, 8.6 Hz, 1H), 7.47 (d, J = 8.9 Hz, 1H), 7.17 (d, J = 2.1 Hz, 1H), 7.10 (dd, J = 2.3, 9.0 Hz, 1H), 6.56 (d, J = 8.7 Hz, 1H), 6.11 (q, J = 6.7 Hz, 1H), 3.96 - 3.90 (m, 2H), 3.77 (d, J = 8.3 Hz, 2H), 3.36 - 3.32 (m, 2H), 3.03 (br s, 2H), 1.95 - 1.87 (m, 2H), 1.79 - 1.71 (m, 5H) |
| Example 162<br>5-[(1R)-1-(3,5-dichloro-4-pyridyl)ethoxy]-3-[6-(8-methylsulfonyl-2,8-diazaspiro[3.5]nonan-2-yl)-3-pyridyl]-1H-indazole | 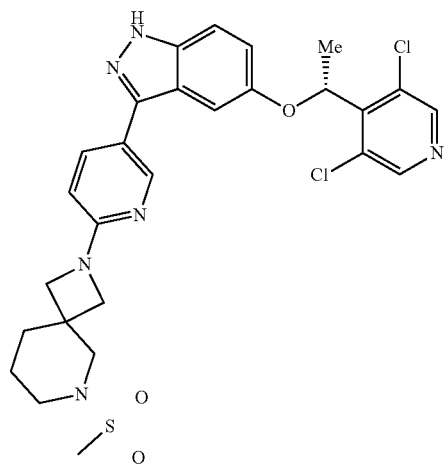 | LCMS: m/z = 587.2 (M + H); 1H NMR (400 MHz, DMSO-d6) δ = 12.98 (br s, 1H), 8.59 (s, 2H), 8.52 (s, 1H), 7.85 (br d, J = 8.3 Hz, 1H), 7.46 (br d, J = 8.9 Hz, 1H), 7.16 (br s, 1H), 7.09 (br d, J = 8.9 Hz, 1H), 6.55 (br d, J = 8.6 Hz, 1H), 6.10 (q, J = 6.3 Hz, 1H), 3.74 (q, J = 8.0 Hz, 4H), 3.30 - 3.24 (m, 2H), 3.09 (br s, 2H), 2.90 (s, 3H), 1.75 (br d, J = 6.2 Hz, 5H), 1.62 (br s, 2H) |
| Example 163<br>5-[(1R)-1-(3,5-dichloro-4-pyridyl)ethoxy]-3-[6-(7-methylsulfonyl-2,7-diazaspiro[3.4]octan-2-yl)-3-pyridyl]-1H-indazole | 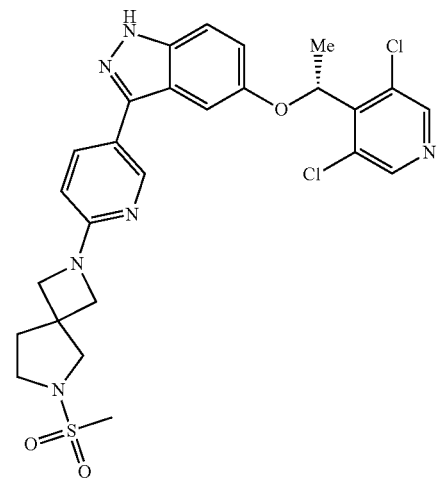 [SMILES: C[C@@H](Oc1ccc2[nH]nc(-c3ccc(N4CC5(CCN(S(C)(=O)=O)C5)C4)nc3)c2c1)c1c(Cl)cncc1Cl] | LCMS: m/z = 573.2 (M + H); 1H NMR (400 MHz, CD3OD) δ = 8.47 (s, 2H), 8.44 (d, J = 1.7 Hz, 1H), 7.90 (dd, J = 2.3, 8.6 Hz, 1H), 7.43 (d, J = 9.0 Hz, 1H), 7.16 (dd, J = 2.3, 9.0 Hz, 1H), 7.11 (d, J = 2.1 Hz, 1H), 6.57 (dd, J = 0.7, 8.7 Hz, 1H), 6.13 (q, J = 6.7 Hz, 1H), 4.10 - 4.08 (m, 2H), 4.06 - 4.02 (m, 2H), 3.58 (s, 2H), 3.46 (t, J = 7.0 Hz, 2H), 2.94 (s, 3H), 2.29 (t, J = 7.0 Hz, 2H), 1.81 (d, J = 6.6 Hz, 3H) |

-continued

| | | |
|---|---|---|
| Example 164<br>3-[6-(2,7-diazaspiro[3.4]octan-2-yl)-3-pyridyl]-5-[(1R)-1-(3,5-dichloro-4-pyridyl)ethoxy]-1H-indazole | 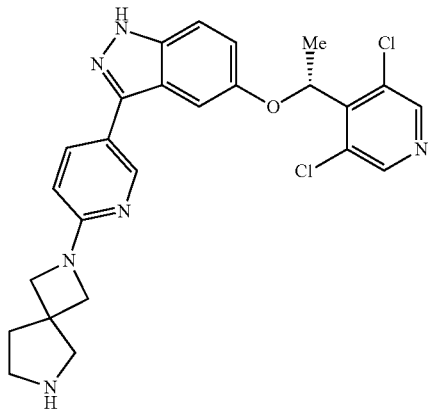 [SMILES: C[C@@H](Oc1ccc2[nH]nc(-c3ccc(N4CC5(CCNC5)C4)nc3)c2c1)c1c(Cl)cncc1Cl] | LCMS: m/z = 495.2 (M + H); 1H NMR (400 MHz, CD3OD) δ = 8.47 (s, 2H), 8.45 (dd, J = 0.7, 2.2 Hz, 1H), 7.94 (dd, J = 2.3, 8.7 Hz, 1H), 7.45 (dd, J = 0.5, 9.0 Hz, 1H), 7.18 (dd, J = 2.3, 9.0 Hz, 1H), 7.10 (d, J = 2.2 Hz, 1H), 6.61 (dd, J = 0.7, 8.7 Hz, 1H), 6.13 (q, J = 6.7 Hz, 1H), 4.13 (q, J = 8.2 Hz, 4H), 3.56 (s, 2H), 3.41 (t, J = 7.3 Hz, 2H), 2.40 (t, J = 7.3 Hz, 2H), 1.82 (d, J = 6.6 Hz, 3H) |
| Example 165<br>methyl 2-[5-[5-[(1R)-1-(3,5-dichloro-4-pyridyl)ethoxy]-1H-indazol-3-yl]-2-pyridyl]-2,8-diazaspiro[3.5]nonane-8-carboxylate | 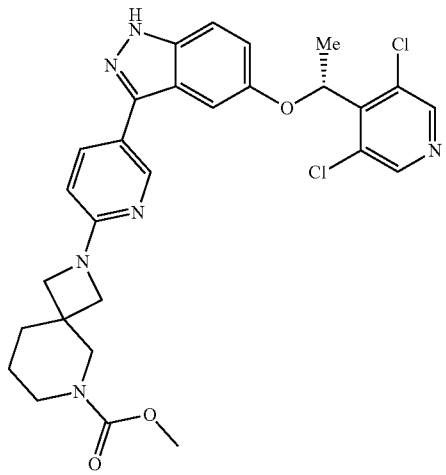 [SMILES: COC(=O)N1CCCC2(C1)CN(c1ccc(-c3n[nH]c4ccc(O[C@H](C)c5c(Cl)cncc5Cl)cc34)cn1)C2] | LCMS: m/z = (M + H); 1H NMR (400 MHz, DMSO-d6) δ = 12.98 (s, 1H), 8.59 (s, 2H), 8.50 (d, J = 1.8 Hz, 1H), 7.85 (dd, J = 2.2, 8.6 Hz, 1H), 7.45 (d, J = 8.9 Hz, 1H), 7.16 (s, 1H), 7.09 (dd, J = 2.2, 8.9 Hz, 1H), 6.54 (d, J = 8.6 Hz, 1H), 6.11 (q, J = 6.7 Hz, 1H), 3.75 - 3.70 (m, 2H), 3.69 - 3.65 (m, 2H), 3.63 (s, 3H), 3.58 (s, 2H), 3.37 - 3.33 (m, 2H), 1.84 - 1.78 (m, 2H), 1.76 (d, J = 6.7 Hz, 3H), 1.55 - 1.46 (m, 2H) |
| Example 166<br>5-[(1R)-1-(3,5-difluorophenyl)ethoxy]-3-[1-(4-piperidyl)pyrazol-4-yl]-1H-indazole | 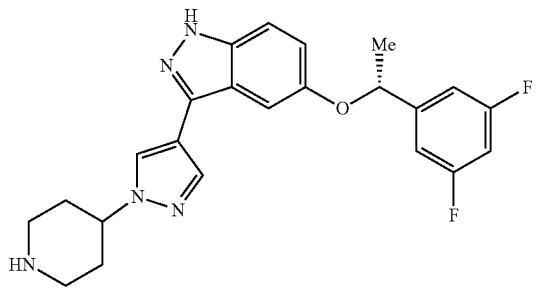 [SMILES: C[C@@H](Oc1ccc2[nH]nc(-c3cnn(C4CCNCC4)c3)c2c1)c1cc(F)cc(F)c1] | LCMS: m/z = 424.2 (M + H) (free base); 1H NMR (400 MHz, DMSO-d6) δ = 12.80 (br s, 1H), 8.23 (s, 1H), 7.93 (s, 1H), 7.41 (d, J = 8.9 Hz, 1H), 7.30 (d, J = 1.8 Hz, 1H), 7.23 (br d, J = 6.5 Hz, 2H), 7.15 - 7.03 (m, 2H), 5.69 (q, J = 6.1 Hz, 1H), 4.39 (tt, J = 4.0, 11.1 Hz, 1H), 3.24 (br d, J = 12.3 Hz, 2H), 2.90 - 2.77 (m, 2H), 2.15 - 1.95 (m, 4H), 1.58 (d, J = 6.4 Hz, 3H) |
| Example 167<br>3-[1-(1-cyclobutyl-4-piperidyl)pyrazol-4-yl]-5-[(1R)-1-(3,5-difluorophenyl)ethoxy]-1H-indazole | 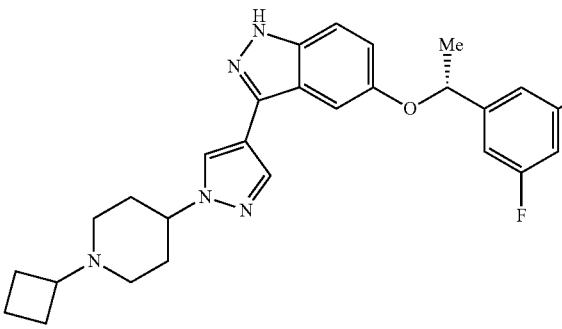 | LCMS: m/z = 478.2 (M + H); 1H NMR (400 MHz, DMSO-d6) δ = 12.76 (br s, 1H), 8.24 (s, 1H), 7.89 (s, 1H), 7.40 (d, J = 8.9 Hz, 1H), 7.30 (d, J = 2.0 Hz, 1H), 7.23 (dd, J = 2.1, 8.3 Hz, 2H), 7.12 - 7.05 (m, 2H), 5.70 (q, J = 6.2 Hz, 1H), 4.25 - 4.14 (m, 1H), 2.92 (br d, J = 10.0 Hz, 2H), 2.75 (quin, J = 7.3 Hz, 1H), 2.09 - 1.87 (m, 8H), 1.85 - 1.76 (m, 2H), 1.69 - 1.60 (m, 2H), 1.59 (d, J = 6.4 Hz, 3H) |

| Example | Structure | Data |
|---|---|---|
| Example 168<br>5-[(1R)-1-(3,5-difluorophenyl)ethoxy]-3-[1-[1-(oxetan-3-yl)-4-piperidyl]pyrazol-4-yl]-1H-indazole | 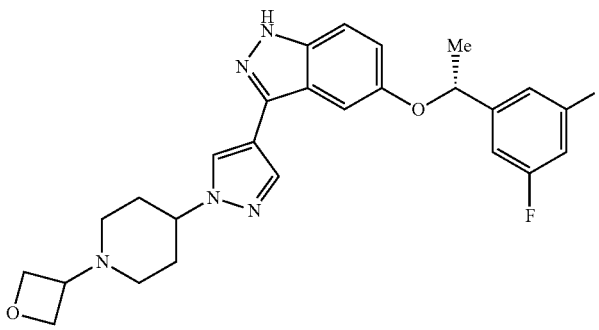 | LCMS: m/z = 480.2 (M + H); 1H NMR (400 MHz, DMSO-d6) δ = 12.72 (br s, 1H), 8.19 (s, 1H), 7.84 (s, 1H), 7.34 (d, J = 8.9 Hz, 1H), 7.24 (d, J = 1.7 Hz, 1H), 7.16 (br d, J = 6.5 Hz, 2H), 7.07 - 6.96 (m, 2H), 5.63 (q, J = 6.2 Hz, 1H), 4.49 (t, J = 6.5 Hz, 2H), 4.39 (t, J = 6.1 Hz, 2H), 4.22 - 4.11 (m, 1H), 3.38 (quin, J = 6.4 Hz, 1H), 2.76 (br d, J = 10.4 Hz, 2H), 2.08 - 1.85 (m, 6H), 1.52 (d, J = 6.2 Hz, 3H) |
| Example 169<br>3-[6-(2,6-diazaspiro[3.3]heptan-2-yl)-3-pyridyl]-5-[(1R)-1-(3,5-difluorophenyl)ethoxy]-1H-indazole | 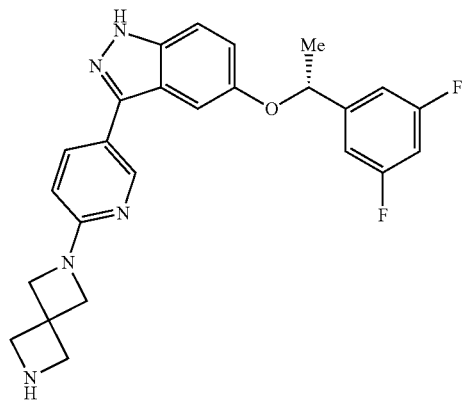 [SMILES: C[C@@H](Oc1ccc2[nH]nc(-c3ccc(N4CC5(CNC5)C4)nc3)c2c1)c1cc(F)cc(F)c1] | LCMS: m/z = 448.2 (M + H) (free base); 1H NMR (400 MHz, DMSO-d6) δ = 12.99 (br s, 1H), 8.60 (dd, J = 0.6, 2.2 Hz, 2H), 7.99 (dd, J = 2.3, 8.6 Hz, 1H), 7.45 (d, J = 9.0 Hz, 1H), 7.33 (d, J = 2.1 Hz, 1H), 7.23 - 7.16 (m, 2H), 7.13 - 7.06 (m, 2H), 6.53 (dd, J = 0.5, 8.7 Hz, 1H), 5.69 (q, J = 6.3 Hz, 1H), 4.18 (d, J = 3.1 Hz, 8H), 1.57 (d, J = 6.4 Hz, 3H) |
| Example 170<br>5-[(1R)-1-(2,6-dichlorophenyl)ethoxy]-3-[6-(2-methylsulfonyl-2,6-diazaspiro[3.3]heptan-6-yl)-3-pyridyl]-1H-indazole | 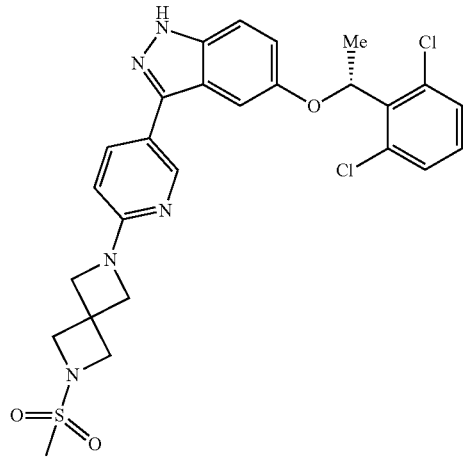 [SMILES: C[C@@H](Oc1ccc2[nH]nc(-c3ccc(N4CC5(C4)CN(S(C)(=O)=O)C5)nc3)c2c1)c1c(Cl)cccc1Cl] | LCMS: m/z = 558.1 (M + H); 1H NMR (400 MHz, DMSO-d6) δ = 12.95 (s, 1H), 8.57 - 8.48 (m, 1H), 7.85 (dd, J = 2.3, 8.6 Hz, 1H), 7.48 - 7.38 (m, 3H), 7.31 - 7.25 (m, 1H), 7.14 (d, J = 2.0 Hz, 1H), 7.08 (dd, J = 2.3, 9.0 Hz, 1H), 6.53 (d, J = 8.6 Hz, 1H), 6.12 (q, J = 6.7 Hz, 1H), 4.17 (s, 4H), 4.12 (s, 4H), 3.03 (s, 3H), 1.76 (d, J = 6.6 Hz, 3H) |
| Example 171<br>4-[4-[5-[(1R)-1-(3,5-difluorophenyl)ethoxy]-1H-indazol-3-yl]pyrazol-1-yl]thiane 1,1-dioxide | 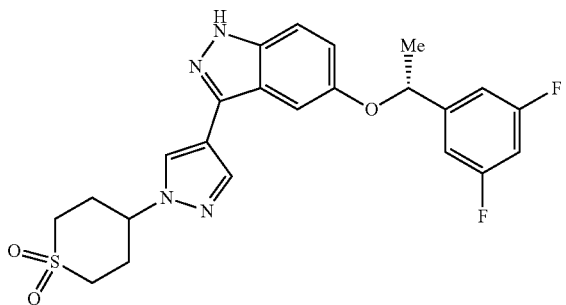 [SMILES: C[C@@H](Oc1ccc2[nH]nc(-c3cnn(C4CCS(=O)(=O)CC4)c3)c2c1)c1cc(F)cc(F)c1] | LCMS: m/z = 473.1 (M + H) (free base); 1H NMR (400 MHz, DMSO-d6) δ = 12.64 (br s, 1H), 8.33 (s, 1H), 7.97 (s, 1H), 7.41 (d, J = 8.9 Hz, 1H), 7.36 (d, J = 2.0 Hz, 1H), 7.26 - 7.18 (m, 2H), 7.13 - 7.04 (m, 2H), 5.70 (q, J = 6.3 Hz, 1H), 4.70 (tt, J = 3.6, 10.6 Hz, 1H), 3.50 - 3.39 (m, 2H), 3.25 - 3.21 (m, 1H), 2.63 - 2.51 (m, 2H), 2.45 - 2.37 (m, 2H), 1.58 (d, J = 6.2 Hz, 3H) |

| Example 172<br>5-[(1R)-1-(3,5-difluorophenyl)ethoxy]-3-[6-(2-methylsulfonyl-2,6-diazaspiro[3.3]heptan-6-yl)-3-pyridyl]-1H-indazole | 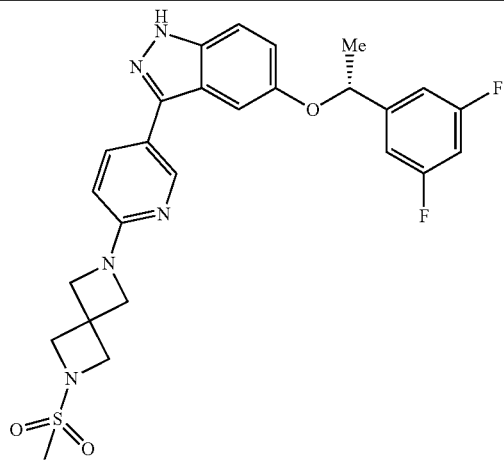 | LCMS: m/z = 526.2 (M + H); 1H NMR (400 MHz, DMSO-d6) δ = 12.98 (br s, 1H), 8.60 (d, J = 1.7 Hz, 1H), 7.99 (dd, J = 2.3, 8.7 Hz, 1H), 7.45 (d, J = 8.9 Hz, 1H), 7.34 (d, J = 2.0 Hz, 1H), 7.24 - 7.17 (m, 2H), 7.13 - 7.06 (m, 2H), 6.51 (d, J = 8.2 Hz, 1H), 5.69 (q, J = 6.3 Hz, 1H), 4.17 (s, 4H), 4.11 (s, 4H), 3.02 (s, 3H), 1.57 (d, J = 6.4 Hz, 3H) |
|---|---|---|
| Example 173<br>5-[5-[(1R)-1-(3,5-dimethylpyridazin-4-yl)ethoxy]-1H-indazol-3-yl]-2-pyrrolidin-1-yl-pyridine-3-carbonitrile | 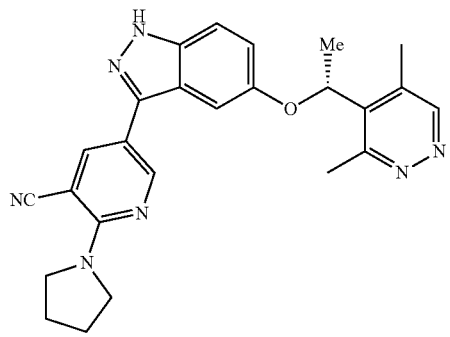 | LCMS: m/z = 430.3 (M + H); 1H NMR (400 MHz, DMSO-d6) δ 13.12 (s, 1H), 8.82 (s, 1H), 8.76 (d, J = 2.0 Hz, 1H), 8.16 (d, J = 2.4 Hz, 1H), 7.48 (d, J = 8.8 Hz, 1H), 7.09 (dd, J = 8.8 Hz, J = 2.4 Hz, 1H), 7.03 (d, J = 2.0 Hz, 1H), 5.91 (q, J = 6.0 Hz, 1H), 3.75 (t, J = 6.4 Hz, 4H), 2.79 (s, 3H), 2.47 (s, 3H), 1.99-1.96 (m, 4H), 1.67 (d, J = 6.8 Hz, 3H) |

Synthesis of (R)-1-(3,5-dichloropyridazin-4-yl)ethanol and (S)-1-(3,5-dichloropyridazin-4-yl)ethanol Step 1. 1-(3,5-Dichloropyridazin-4-yl)ethenone. To a solution of 3,5-dichloropyridazine (25.0 g, 168.9 mmol), 2-oxopropanoic acid (18.6 g, 202.7 mmol) in MeCN (200 mL)/H$_2$O (200 mL) was added AgNO$_3$ (5.74 g, 33.8 mmol) and K$_2$S$_2$O$_8$ (68.4 g, 253.4 mmol). The mixture was heated to 70° C. and stirred for 8 h. After the reaction completed, MeCN was removed under vacuo and the resulting aqueous solution was adjusted to pH=7-8 with saturated aqueous NaHCO$_3$. The solution was extracted with ethyl acetate (400 mL×2). The organic layers were dried over Na$_2$SO$_4$ and concentrated in vacuo. The residue was purified by silica gel flash column chromatography (ethyl acetate/PE=1:4) to afford a light-yellow solid (14.0 g, 43% yield). LCMS=191 (M+1).

Step 2. To a solution of 1-(3,5-dichloropyridazin-4-yl)ethanone (14.0 g, 73.3 mmol) in MeOH (30 mL) was added NaBH$_4$ (3.06 g, 80.6 mmol) at −10° C. and stirred for 10 min. After the reaction completed, the solution was added to DCM (300 mL)/saturated NH$_4$Cl (100 mL). The organic layer was separated, dried over Na$_2$SO$_4$ and concentrated under vacuo. The residue was purified by silica gel flash column chromatography (ethyl acetate/PE=1:3) to afford the racemate that was separated by Chiral-HPLC to afford (R)-1-(3,5-dichloropyridazin-4-yl) ethanol (4.0 g, 28.6; [α]D=+8.1) and (S)-1-(3,5-dichloropyridazin-4-yl)ethanol (3.4 g, 24.3%; [α]D=−11.9) as a light yellow solid. 1H NMR (300 MHz, CDCl$_3$) δ 9.05 (s, 1H), 5.70-5.49 (m, 1H), 2.77 (s, 1H), 1.68 (d, J=6.9 Hz, 3H); LCMS=193.1 (M+1).

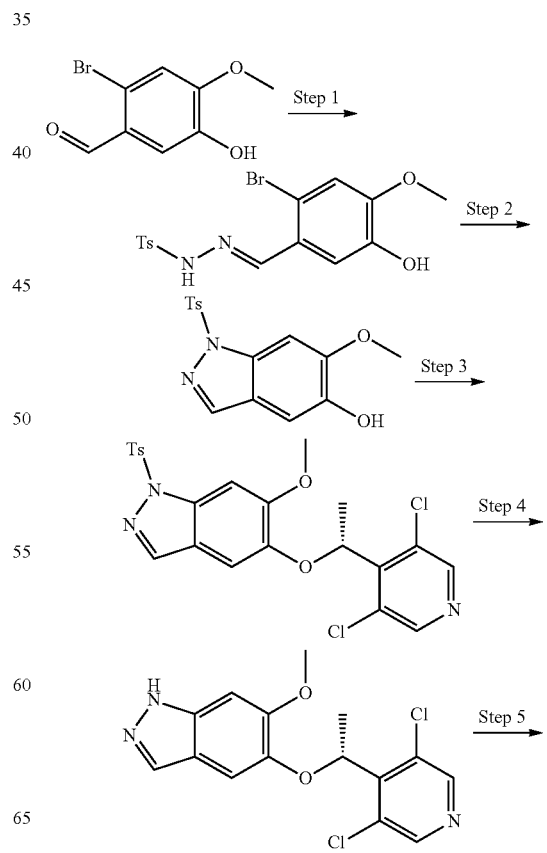

-continued

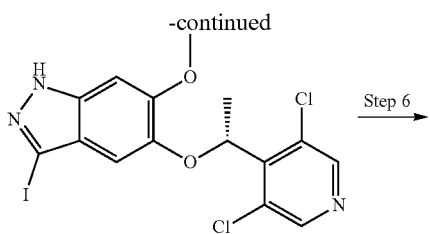

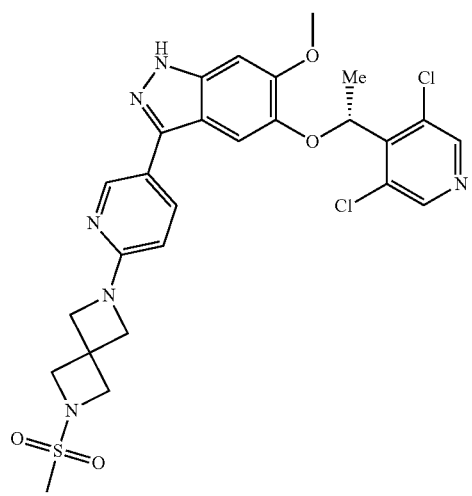

Example 191

Example 191. 5-[(1R)-1-(3,5-dichloro-4-pyridyl)ethoxy]-6-methoxy-3-[6-(2-methylsulfonyl-2,6-diazaspiro[3.3]heptan-6-yl)-3-pyridyl]-1H-indazole Step 1. (E)-N'-(2-Bromo-5-hydroxy-4-methoxybenzylidene)-4-methylbenzenesulfonohydrazide. p-Toluenesulfonyl hydrazide (0.56 g, 3.0 mmol, 1.0 equiv) was added to a solution of 2-bromo-5-hydroxy-4-methoxy-benzaldehyde (0.7 g, 3.0 mmol, 1.0 equiv) in methanol (7.0 mL) at rt. The resulting mixture was heated at 60° C. for 2 h. The reaction was cooled to rt and the solvent was removed under reduced pressure. The residue was dissolved in ethyl acetate (20 mL), then heptanes (80 mL) was added to give a light-yellow solid (1.21 g, 100%). LCMS: m/z=399.0 (M+H).

Step 2. 6-Methoxy-1-tosyl-1H-indazol-5-ol. Copper(I) oxide (0.22 g, 1.5 mmol, 0.5 equiv) was added to a solution of (E)-N'-(2-Bromo-5-hydroxy-4-methoxybenzylidene)-4-methylbenzenesulfonohydrazide (1.2 g, 3.0 mmol, 1.0 equiv) in isoamyl alcohol (30 mL) at room temperature. After heating at 132° C. for 2 hours, the mixture was cooled to room temperature and diluted with water (80 mL). The mixture was extract with ethyl acetate (4×50 mL). The combined organic layers were dried over sodium sulfate and filtered. The filtrate was concentrated onto silica gel (8.0 g) and purified on a Biotage automated purification system (Biotage Sfär Silica, 50 g; 0% to 100% ethyl acetate in heptanes) to give a light yellow solid (0.66 g, 70% yield). LCMS: m/z=319.1 (M+H).

Step 3. (R)-5-(1-(3,5-Dichloropyridin-4-yl)ethoxy)-6-methoxy-1-tosyl-1H-indazole. (1S)-1-(3,5-dichloro-4-pyridyl)ethyl]methanesulfonate (0.57 g, 2.1 mmol, 1.0 equiv) and cesium carbonate (1.03 g, 3.2 mmol, 1.5 equiv) were added to a solution of 6-methoxy-1-tosyl-1H-indazol-5-ol (0.67 g, 2.1 mmol, 1.0 equiv) in acetonitrile (21 mL) at room temperature. After heating at 90° C. overnight, the mixture was cooled to room temperature and concentrated onto silica gel (6.0 g) under reduced pressure. The product was purified on a Biotage automated purification system (Sorbtech silica, 40 g), eluting with a gradient of 0% to 60% ethyl acetate in heptanes to give a white solid (0.71 g, 70% yield). LCMS m/z=492.1 (M+H).

Step 4. (R)-5-(1-(3,5-Dichloropyridin-4-yl)ethoxy)-6-methoxy-1H-indazole. 1M Tetrabutylammonium fluoride in THF (7.2 mL, 7.2 mmol, 18.0 equiv) was added to a solution of (R)-5-(1-(3,5-dichloropyridin-4-yl)ethoxy)-6-methoxy-1-tosyl-1H-indazole (0.20 g, 0.4 mmol, 1.0 equiv) in tetrahydrofuran (4 mL) at room temperature. After heating at 50° C. for 4 days, the solvent was removed under reduced pressure. The residue was concentrated onto silica gel (2.0 g) and purified on a Biotage automated purification system (Sorbtech silica, 12 g), eluting with a gradient of 0% to 100% ethyl acetate in heptanes to give a white solid (74.7 mg, 54%). LCMS m/z=338.0 (M+H).

Step 5. (R)-5-(1-(3,5-Dichloropyridin-4-yl)ethoxy)-3-iodo-6-methoxy-1H-indazole. Potassium hydroxide (27.9 mg, 0.50 mmol, 2.25 equiv) and iodine (84.1 mg, 0.33 mmol, 1.5 equiv) were added to a solution of (R)-5-(1-(3,5-dichloropyridin-4-yl)ethoxy)-6-methoxy-1H-indazole (74.7 mg, 0.22 mmol, 1.0 equiv) in N,N-dimethylformamide (2.2 mL) at 0° C. The resulting mixture was allowed to warm up to room temperature and stirred overnight. The reaction was diluted with ethyl acetate (10 mL) and washed with water (4×5 mL). The organic layer was dried over sodium sulfate and concentrated onto silica gel (1.5 g) under reduced pressure. The product was purified on a Biotage automated purification system (Sorbtech silica, 12 g), eluting with a gradient of 0% to 100% ethyl acetate in heptanes to give an off-white solid (80 mg, 77%). LCMS m/z=463.9 (M+H).

Step 6. (R)-5-(1-(3,5-Dichloropyridin-4-yl)ethoxy)-6-methoxy-3-(6-(6-(methylsulfonyl)-2,6-diazaspiro[3.3]heptan-2-yl)pyridin-3-yl)-1H-indazole. A mixture of (R)-5-(1-(3,5-dichloropyridin-4-yl)ethoxy)-3-iodo-6-methoxy-1H-indazole (80 mg, 0.17 mmol, 1.0 equiv), 2-methylsulfonyl-6-[5-(4,4,5,5-tetramethyl-1,3,2-dioxaborolan-2-yl)-2-pyridyl]-2,6-diazaspiro[3.3]heptane (71.9 mg, 0.19 mmol, 1.1 equiv), tetrakis(triphenylphosphine)-palladium(O) (20.0 mg, 0.02 mol, 0.1 equiv), and potassium carbonate (47.6 mg, 0.35 mmol, 2.0 equiv) in 1.4-dioxane (4.0 mL) and water (0.4 mL) was sparged with nitrogen for 10 minutes. After heating for 10 hours at 100° C., the reaction was cooled to room temperature, diluted with ethyl acetate (10 mL) and washed with water (4 mL). The organic layer was dried over sodium sulfate and concentrated under reduced pressure onto silica gel (1 g). The product was purified on a Biotage automated purification system (Sorbtech silica, 4 g), eluting with a gradient of 0% to 100% ethyl acetate in heptanes then with a gradient of 0% to 10% methanol in ethyl acetate to give a white solid (31.0 mg, 31% yield, 98.1%). LCMS m/z=589.1 (M+H); 1H NMR (400 MHz, DMSO-d6) δ=12.81 (s, 1H), 8.60 (s, 2H), 8.45 (d, J=1.8 Hz, 1H), 7.81 (dd, J=2.3, 8.6 Hz, 1H), 7.06 (s, 1H), 6.99 (s, 1H), 6.52 (d, J=8.1 Hz, 1H), 5.99-5.93 (m, 1H), 4.16 (s, 4H), 4.11 (s, 4H), 3.86 (s, 3H), 3.02 (s, 3H), 1.75 (d, J=6.7 Hz, 3H).

Example 192. 5-[(1S)-1-(3,5-dimethylpyridazin-4-yl)ethoxy]-6-methoxy-3-[6-(2-methylsulfonyl-2,6-diazaspiro[3.3]heptan-6-yl)-3-pyridyl]-1H-indazole

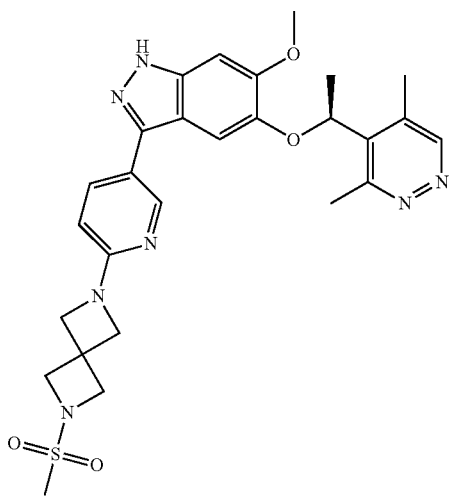 [SMILES: COc1cc2[nH]nc(-c3ccc(N4CC5(C4)CN(S(C)(=O)=O)C5)nc3)c2cc1O[C@@H](C)c1c(C)cnnc1C]

Step 1. 5-[(1S)-1-(3,5-Dimethylpyridazin-4-yl)ethoxy]-3-(6-fluoro-3-pyridyl)-6-methoxy-1-tetrahydropyran-2-yl-indazole. To a solution of 5-[(1S)-1-(3,5-dimethylpyridazin-4-yl)ethoxy]-3-iodo-6-methoxy-1-tetrahydropyran-2-yl-indazole (150 mg, 0.30 mmol, 1.0 eq) and 2-fluoro-5-(4,4,5,5-tetramethyl-1,3,2-dioxaborolan-2-yl)pyridine (86 mg, 0.38 mmol, 1.3 eq) in dioxane (4 mL) and water (0.4 mL) were added $K_2CO_3$ (122 mg, 0.88 mmol, 3.0 eq) and Pd(dppf)Cl$_2$ (25 mg, 0.030 mmol, 0.1 eq). The reaction mixture was stirred for 3 h at 90° C. under $N_2$ protection. After the reaction was completed, the solid was filtered out and the filtrate was concentrated in vacuo. The crude product was purified by prep-TLC (DCM/MeOH=30/1) to afford the product a brown solid (130 mg, 92%). LCMS m/z=478.4 (M+1).

Step 2: 5-[(1S)-1-(3,5-Dimethylpyridazin-4-yl)ethoxy]-6-methoxy-3-[6-(2-methylsulfonyl-2,6-diazaspiro[3.3]heptan-6-yl)-3-pyridyl]-1-tetrahydropyran-2-yl-indazole. To a solution of step 1 product (130 mg, 0.27 mmol) and 2-methylsulfonyl-2,6-diazaspiro[3.3]heptane TFA salt (95 mg, 0.33 mol) in DMSO (5 mL) was added DIEA (176 mg, 1.36 mmol, 5.0 eq). The reaction mixture was stirred for 16 h at 100° C. After the reaction was completed, the mixture was diluted with EtOAc (20 mL) and washed with brine (20 mL×3). The organic layer was dried over $Na_2SO_4$ and concentrated. The crude product was purified by prep-TLC (DCM/MeOH=20/1) to afford a brown solid (122 mg, 69.6%). LCMS m/z=634.4 (M+1).

Step 3. 5-[(1S)-1-(3,5-dimethylpyridazin-4-yl)ethoxy]-6-methoxy-3-[6-(2-methylsulfonyl-2,6-diazaspiro[3.3]heptan-6-yl)-3-pyridyl]-1H-indazole. To a solution of product step 2 (100 mg, 0.16 mmol, 1.0 eq) in DCM (4 mL) was added TFA (1 mL), which was stirred at rt for 3 h. After the reaction completed, the reaction mixture was concentrated in vacuum. The crude product was treated with MeOH (3 mL), and excess NaHCO$_3$ was added. The mixture was stirred for 20 minutes then DCM (30 mL) was added. The solid was filtered out and filtrate was concentrated. The residue was purified by Prep-HPLC (Prep-C18, 5 μM Triart column, 20×150 mm, YMC-Actus; gradient elution of 35% MeCN in water to 50% MeCN in water over a 8 min period, where both solvents contain 0.05% $NH_3 \cdot H_2O$) to give a light-red solid (30.4 mg, 35%). LCMS m/z=550.3 (M+H); 1H NMR (400 MHz, DMSO-d6) δ 12.78 (s, 1H), 8.84 (s, 1H), 8.48 (d, J=2.0 Hz, 1H), 7.83 (dd, J=8.8 Hz, 2.4 Hz, 1H), 7.02 (s, 1H), 6.99 (s, 1H), 6.52-6.49 (m, 1H), 5.79 (q, J=6.8 Hz, 1H), 4.17 (s, 4H), 4.11 (s, 4H), 3.87 (s, 3H), 3.03 (s, 3H), 2.77 (s, 3H), 2.43 (s, 3H), 1.65 (d, J=6.8 Hz, 3H).

Example 193. Ethyl 6-[5-[5-[(1S)-1-(3,5-dichloro-2-fluoro-4-pyridyl)ethoxy]-1H-indazol-3-yl]-2-pyridyl]-2,6-diazaspiro[3.3]heptane-2-carboxylate

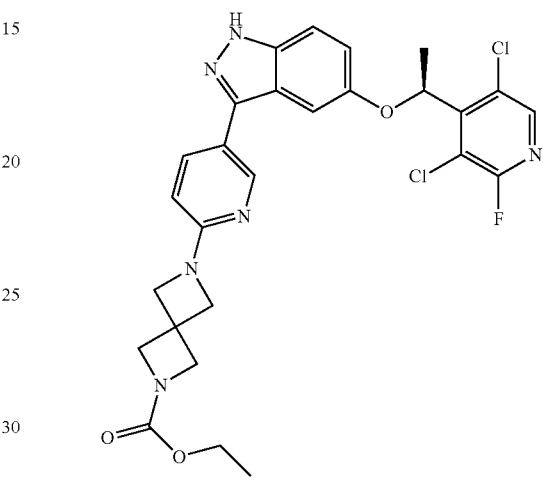

Step 1. [6-(2-ethoxycarbonyl-2,6-diazaspiro[3.3]heptan-6-yl)-3-pyridyl]boronic acid. To a solution of ethyl 2,6-diazaspiro[3.3]heptane-2-carboxylate TFA salt (400 mg, 2.35 mmol, 1.0 eq) and 2-fluoro-5-(4,4,5,5-tetramethyl-1,3,2-dioxaborolan-2-yl)pyridine (524 mg, 2.35 mmol, 1.0 eq) in DMSO (6 mL) was added DIEA (1.52 g, 11.75 mmol, 5.0 eq). The reaction mixture was stirred for 3 h at 110° C. After the reaction was completed, the mixture was diluted with EtOAc (100 mL) and washed with brine (50 mL×3). The organic layer was dried over $Na_2SO_4$ and concentrated in vacuo. The crude product was purified by prep-TLC (DCM/MeOH=20/1) to afford a yellow oil (150 mg, 17%). LCMS m/z=292 (M+1).

Step 2. Ethyl 6-[5-[5-[(1S)-1-(3,5-dichloro-2-fluoro-4-pyridyl)ethoxy]-1-tetrahydropyran-2-yl-indazol-3-yl]-2-pyridyl]-2,6-diazaspiro[3.3]heptane-2-carboxylate. To a solution of 5-[(1S)-1-(3,5-dichloro-2-fluoro-4-pyridyl)ethoxy]-3-iodo-1-tetrahydropyran-2-yl-indazole (138 mg, 0.26 mmol, 1.0 eq) and [6-(2-ethoxycarbonyl-2,6-diazaspiro[3.3]heptan-6-yl)-3-pyridyl]boronic acid (75 mg, 0.26 mmol, 1.0 eq) in dioxane (2 mL) and water (0.2 mL) was added $K_2CO_3$ (71 mg, 0.52 mmol, 2.0 eq) and Pd(dppf)Cl$_2$ (19 mg, 0.026 mmol, 0.1 eq). The reaction mixture was stirred for 2 h at 90° C. under $N_2$ protection. After the reaction was completed, the mixture was cooled to room temperature and concentrated in vacuum. The crude product was purified by prep-TLC (DCM/MeOH=30/1) to give a yellow oil (75 mg, 44.4%). LCMS m/z=655.3 (M+1).

Step 3. Ethyl 6-[5-[5-[(1S)-1-(3,5-dichloro-2-fluoro-4-pyridyl)ethoxy]-1H-indazol-3-yl]-2-pyridyl]-2,6-diazaspiro[3.3]heptane-2-carboxylate. To a solution of product step 2 (70 mg, 0.11 mmol, 1.0 eq) in DCM (2 mL) was added TFA (1 mL). The reaction mixture was stirred for 3 h at room temperature. After the reaction was complete, the mixture was concentrated in vacuo. The crude product was treated with MeOH (3 mL), NaHCO$_3$ (excess) was added to the solution and stirred for 20 minutes at rt, then DCM (20 mL) was added. The solid was filtered out and filtrate was concentrated in vacuo. The crude product was purified by Pre-TLC (DCM/MeOH=10/1) to give a white solid (25.3 mg, 41.5%). LCMS m/z=571.2 (M+H); 1H NMR (400 MHz, DMSO-d6) δ 13.02 (s, 1H), 8.52 (d, J=2.0 Hz, 1H), 8.34 (s, 1H), 7.88 (dd, J=1.6 Hz, 8.8 Hz, 1H), 7.46 (d, J=8.8 Hz, 1H), 7.19 (s, 1H), 7.09 (dd, J=8.8 Hz, 2.0 Hz, 1H), 6.51 (d, J=8.8 Hz, 1H), 6.13 (q, J=6.8 Hz, 1H), 4.19-4.09 (m, 8H), 4.01 (q, J=7.2 Hz, 2H), 1.76 (d, J=6.8 Hz, 3H), 1.7 (t, J=7.2 Hz, 3H).

Example 194. 5-[(1R)-1-(3,5-dimethylpyridazin-4-yl)ethoxy]-6-methoxy-3-[6-(2-methylsulfonyl-2,6-diazaspiro[3.3]heptan-6-yl)-3-pyridyl]-1H-indazole

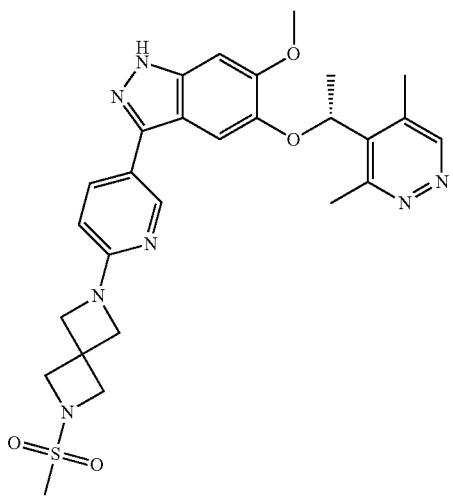 [SMILES: COc1cc2[nH]nc(-c3ccc(N4CC5(C4)CN(S(C)(=O)=O)C5)nc3)c2cc1O[C@H](C)c1c(C)cnnc1C]

Step 1. 5-[(1R)-1-(3,5-dimethylpyridazin-4-yl)ethoxy]-3-(6-fluoro-3-pyridyl)-6-methoxy-1-tetrahydropyran-2-yl-indazole. To a solution of 5-[(1R)-1-(3,5-dimethylpyridazin-4-yl)ethoxy]-3-iodo-6-methoxy-1-tetrahydropyran-2-yl-indazole (135 mg, 0.27 mmol, 1.0 eq) and 2-fluoro-5-(4,4,5,5-tetramethyl-1,3,2-dioxaborolan-2-yl)pyridine (89 mg, 0.40 mmol, 1.5 eq) in dioxane (2.0 mL) and H$_2$O (0.2 mL) was added K$_2$CO$_3$ (110 mg, 0.81 mmol, 3.0 eq) and Pd(dppf)Cl$_2$ (27 mg, 20% wt) at room temperature. The mixture was stirred for 2 h at 90° C. under N2 protection. After the reaction was completed, the solid was filtered out and the filtrate was concentrated in vacuo. The crude product was purified by prep-TLC (DCM/MeOH=20/1) to afford an off-white solid (120 mg, 94.6%). LCMS m/z=478.3 (M+1).

Step 2. 5-[(1R)-1-(3,5-dimethylpyridazin-4-yl)ethoxy]-6-methoxy-3-[6-(2-methylsulfonyl-2,6-diazaspiro[3.3]heptan-6-yl)-3-pyridyl]-1-tetrahydropyran-2-yl-indazole. To a solution of Example 79c (110 mg, 0.230 mmol, 1.0 eq) and 2-methylsulfonyl-2,6-diazaspiro[3.3]heptane TFA salt (100 mg, 0.345 mmol) in DMSO (3 mL) was added DIEA (148 mg, 1.15 mmol). The reaction mixture was stirred for 16 h at 110° C. After the reaction was completed, the mixture was diluted with EtOAc (10 mL) and washed with brine (10 mL×5). The organic layer was dried over Na$_2$SO$_4$ and concentrated. The crude product was purified by prep-TLC (DCM/MeOH=20/1) to afford a yellow solid (93 mg, 63.7%). LCMS m/z=634.4 (M+1).

Step 3. 5-[(1R)-1-(3,5-dimethylpyridazin-4-yl)ethoxy]-6-methoxy-3-[6-(2-methylsulfonyl-2,6-diazaspiro[3.3]heptan-6-yl)-3-pyridyl]-1H-indazole. To a solution of product step 2 (83 mg, 0.131 mmol) in DCM (2 mL) was added TFA (0.4 mL). The solution was stirred at rt for 3 h. After the reaction completion, the mixture was concentrated in vacuum. The crude product was made basic with the saturate NaHCO$_3$ solution, and then was extracted into DCM (20 mL×3). The combined organic layers were washed with brine (20 mL×2), dried over Na$_2$SO$_4$ and concentrated in vacuo. The residue was purified by Prep-HPLC (Prep-C18, 5 μM Triart column, 20×150 mm, YMC-Actus; gradient elution of 15% MeCN in water to 30% MeCN in water over a 11 min period, both solvents contained 0.05% NH$_3$·H$_2$O) to give a white solid (40.6 mg, 56.2%). LCMS: m/z=550.2 (M+H); 1H NMR (400 MHz, DMSO-d6) δ 12.78 (s, 1H), 8.84 (s, 1H), 8.49 (d, J=2.0 Hz, 1H), 7.83 (dd, J=8.4 Hz, 2.4 Hz, 1H), 7.01 (s, 1H), 6.99 (s, 1H), 6.50 (d, J=8.8 Hz, 1H), 5.79 (q, J=6.8 Hz, 1H), 4.17 (s, 4H), 4.11 (s, 4H), 3.87 (s, 3H), 3.03 (s, 3H), 2.77 (s, 3H), 2.43 (s, 3H), 1.65 (d, J=6.8 Hz, 3H).

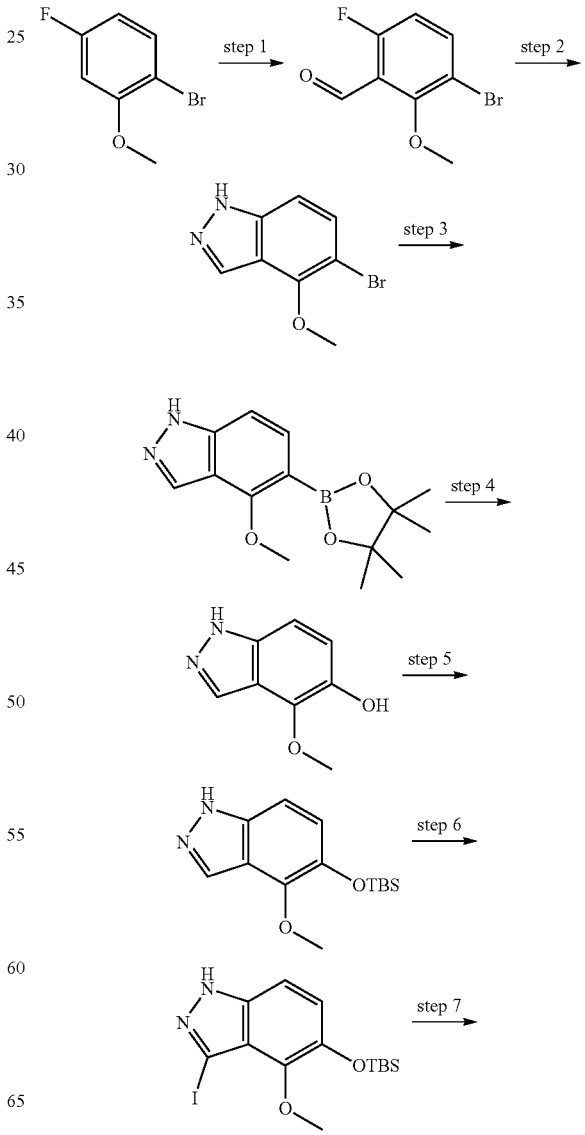

-continued

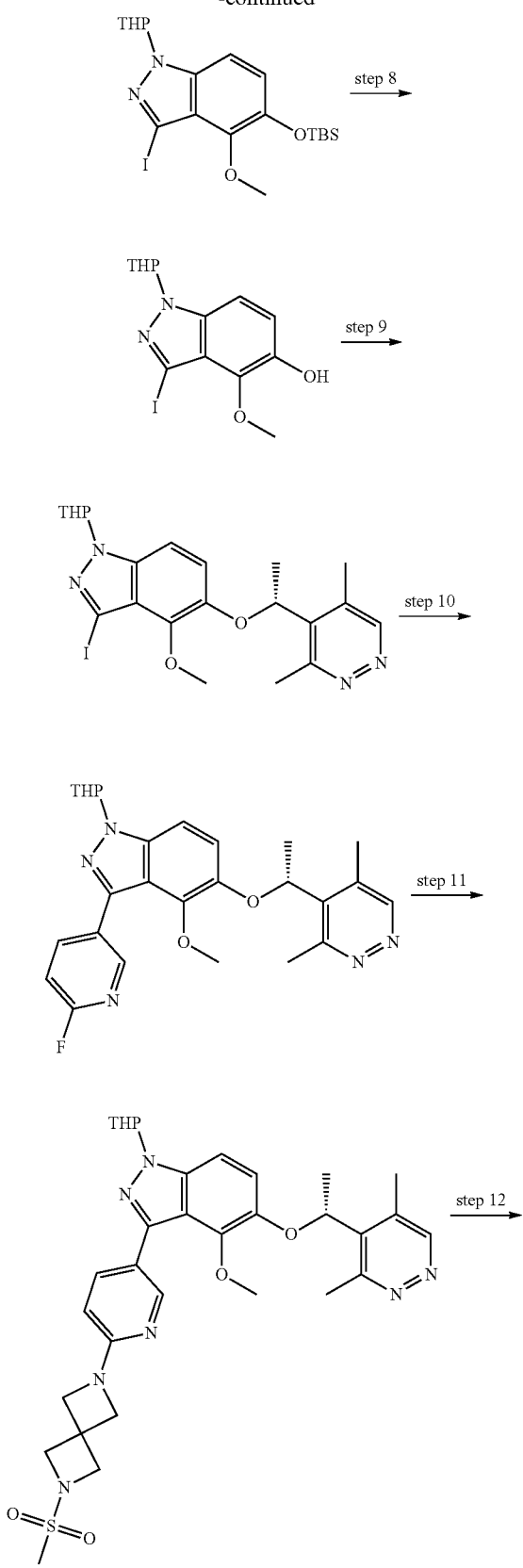

Example 200

Example 200. 5-[(1R)-1-(3,5-dimethylpyridazin-4-yl)ethoxy]-4-methoxy-3-[6-(2-methylsulfonyl-2,6-diazaspiro[3.3]heptan-6-yl)-3-pyridyl]-1H-indazole

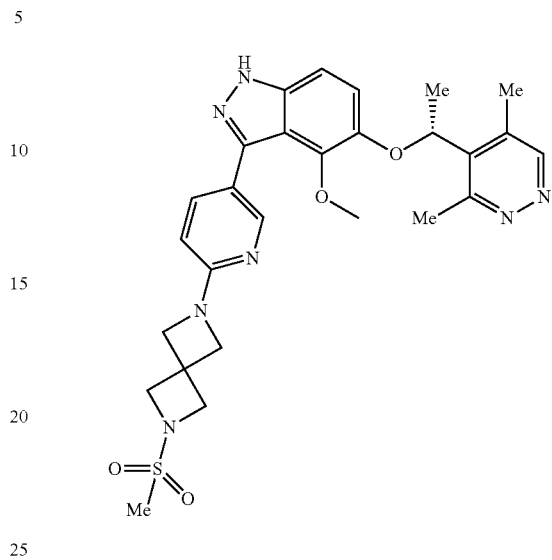

Step 1. 3-Bromo-6-fluoro-2-methoxy-benzaldehyde. To a solution of 1-bromo-4-fluoro-2-methoxy-benzene (85.0 g, 0.42 mol, 1.0 eq) in THF (1 L) was added LDA (2 mol/L, 250 mL, 0.50 mol, 1.2 eq) dropwise over 30 min at −70° C. The reaction mixture was stirred for 1 h at same temperature. Then DMF (42.4 g, 0.58 mol, 1.4 eq) was added to the solution dropwise at −70° C. The reaction mixture was stirred for another 2 h at the same temperature. The reaction mixture was then quenched with aqueous HCl solution (4 mol/L, 300 mL), and extracted with ethyl acetate (300 mL×2). The combined organic layers were washed with $H_2O$ (500 mL), brine (500 mL), dried over $Na_2SO_4$ and concentrated in vacuum. The crude product was purified by silica gel chromatography (ethyl acetate/petroleum ether=1/10) to give a light yellow solid (80.0 g, 82.8% yield). LCMS m/z=233 (M+1).

Step 2. 5-Bromo-4-methoxy-1H-indazole. To a solution of 3-bromo-6-fluoro-2-methoxy-benzaldehyde (38.0 g, 0.16 mol) in DMSO (450 mL) was added $N_2H_4$—$H_2O$ (57.1 g, 1.14 mol, 7.0 eq). The mixture was heated to 125° C. for 16 h. The reaction mixture was cooled to room temperature and diluted with $H_2O$ (1 L), and extracted with ethyl acetate (500 mL×3). The combined organic layers were dried over $Na_2SO_4$ and concentrated. The crude product was purified by silica gel chromatography, eluted with ethyl acetate/petroleum ether (1/10) to give a brown solid (5.0 g, 13.5%). LCMS m/z=227.1 (M+1).

Step 3. 4-Methoxy-5-(4,4,5,5-tetramethyl-1,3,2-dioxaborolan-2-yl)-1H-indazole. To a solution of 5-bromo-4-methoxy-1H-indazole (2.5 g, 11.0 mmol, 1.0 eq) in dioxane (50 mL) was added KOAc (3.24 g, 33.0 mmol, 3.0 eq) and Pd(dppf)Cl$_2$ (1.6 g, 2.2 mmol, 0.2 eq). The mixture was stirred for 24 h at 90° C. and then concentrated to obtain brown crude product (3.5 g); LCMS m/z=275.2 (M+1). This material was used directly in the next step.

Step 4. 4-Methoxy-1H-indazol-5-ol. A solution of 4-methoxy-5-(4,4,5,5-tetramethyl-1,3,2-dioxaborolan-2-yl)-1H-indazole (3.5 g) in THF (20 mL) was added NaOH (0.4 g) and $H_2O_2$ (30% aq., 3.7 g) at 0° C. The resulting mixture was stirred at rt for 2 h, quenched with 50 mL of saturated aqueous NaHSO$_3$ (30 mL), and then extracted with ethyl acetate (30 mL×3). The combined organic layers were dried over Na$_2$SO$_4$ and concentrated. The crude product was purified by silica gel chromatography eluted with ethyl acetate/petroleum ether (1:1) to give a light brown solid (700 mg, 38.8% yield). LCMS m/z=165 (M+1).

Step 5. tert-Butyl-[(4-methoxy-1H-indazol-5-yl)oxy]-dimethyl-silane. To a solution of 4-methoxy-1H-indazol-5-ol (0.86 g, 5.2 mmol, 1.0 eq) in THF (10 mL) was added TBSCl (1.73 g, 21 mmol, 4.0 eq) and imidazole (1.43 g, 21 mmol, 4 eq). The resulting mixture was stirred at 25° C. for 16 h. The reaction mixture was quenched with 50 mL of H$_2$O and extracted with ethyl acetate (50 mL×2). The combined organic layers were washed with brine (30 mL), dried over Na$_2$SO$_4$ and concentrated. The crude product was purified by Prep-TLC (ethyl acetate/petroleum ether=1:1) to give a yellow solid (800 mg, 54.9% yield). LCMS m/z=279.2 (M+1).

Step 6. tert-butyl-[(3-iodo-4-methoxy-1H-indazol-5-yl)oxy]-dimethyl-silane. To a solution of tert-butyl-[(4-methoxy-1H-indazol-5-yl)oxy]-dimethyl-silane (0.74 g, 2.66 mmol, 1.0 eq) in DMF (15 mL) was added NIS (598 mg, 2.66 mmol, 1.0 eq) at 0° C. The resulting solution was stirred for 3 h at 0° C. The reaction mixture was then diluted with H$_2$O (50 mL), and extracted with ethyl acetate (50 mL×2). The combined organic layers were washed with water (30 mL), brine (30 mL), then dried over Na$_2$SO$_4$ and concentrated. The crude product was purified by silica gel chromatography eluted with ethyl acetate/petroleum ether (5:1) to give an off-white solid (570 mg, 53%). LCMS m/z=405.1 (M+1).

Step 7. tert-Butyl-(3-iodo-4-methoxy-1-tetrahydropyran-2-yl-indazol-5-yl)oxy-dimethyl-silane. To a solution of tert-butyl-[(3-iodo-4-methoxy-1H-indazol-5-yl)oxy]-dimethyl-silane (0.58 g, 1.43 mmol, 1.0 eq) in THF (15 mL) was added 3,4-dihydro-2H-pyran (241 mg, 2.87 mmol, 2.0 eq) and TsOH (74 mg, 0.43 mol, 0.3 eq) at 25° C. The resulting mixture was stirred for 16 h at 50° C., quenched with 50 mL of water and extracted with ethyl acetate (30 mL×2). The combined organic layers were washed with water (30 mL), brine (30 mL), dried over Na$_2$SO$_4$ and concentrated. The crude product was purified by silica gel chromatography eluted with ethyl acetate/petroleum ether (10:1) to give an off-white solid (500 mg, 82.8%). LCMS m/z=489.2 (M+1).

Step 8. 3-Iodo-4-methoxy-1-tetrahydropyran-2-yl-indazol-5-ol. To a solution of tert-butyl-(3-iodo-4-methoxy-1-tetrahydropyran-2-yl-indazol-5-yl)oxy-dimethyl-silane (0.8 g, 1.64 mmol, 1.0 eq) in THF (15 mL) was added TBAF (1 mol/L in THF, 1.8 mL, 1.8 mmol, 1.1 eq) at rt. The resulting mixture was stirred at rt for 5 h, diluted with H$_2$O (50 mL) and extracted with ethyl acetate (50 mL×3). The combined organic layers were washed with water (50 mL), brine (50 mL), dried over Na$_2$SO$_4$ and concentrated. The crude product was purified by silica gel chromatography eluted with ethyl acetate/petroleum ether (5:1) to give an off-white solid (450 mg, 73.4%). LCMS m/z=375.1 (M+1).

Step 9. 5-[(1R)-1-(3,5-Dimethylpyridazin-4-yl)ethoxy]-3-iodo-4-methoxy-1-tetrahydropyran-2-yl-indazole. To a solution 3-iodo-4-methoxy-1-tetrahydropyran-2-yl-indazol-5-ol (50 mg, 0.14 mmol, 1.0 eq) in DCM (2 mL) was added PPh$_3$ (70 mg, 0.26 mmol, 2.0 eq) and DEAD (35 mg, 0.2 mmol, 1.4 eq) at 0° C. The mixture was warmed to rt, stirred for 16 h and then was concentrated. The crude was purified by Prep-TLC (ethyl acetate/petroleum ether=1:2) to give a light brown solid (40 mg, 58.9%). LCMS m/z=509.2 (M+1).

Step 10: 5-[(1R)-1-(3,5-Dimethylpyridazin-4-yl)ethoxy]-3-(6-fluoro-3-pyridyl)-4-methoxy-1-tetrahydropyran-2-yl-indazole. To a solution of 5-[(1R)-1-(3,5-dimethylpyridazin-4-yl)ethoxy]-3-iodo-4-methoxy-1-tetrahydropyran-2-yl-indazole (90 mg, 0.18 mmol) in dioxane (4 mL) and H$_2$O (0.4 mL) was added 2-fluoro-5-(4,4,5,5-tetramethyl-1,3,2-dioxaborolan-2-yl)pyridine (59 mg, 0.27 mmol, 1.5 eq), Pd(dppf)Cl$_2$ (40 mg, 0.055 mmol, 0.3 eq) and K$_2$CO$_3$ (49 mg, 0.36 mmol, 2.0 eq) at 25° C. under N$_2$ protection. The resulting mixture was stirred at 100° C. for 2 h, cooled to rt, diluted with 10 mL of water and extracted with ethyl acetate (10 mL×2). The combined organic layers were washed with water (20 mL), brine (20 mL), dried over Na$_2$SO$_4$ and concentrated. The crude product was purified by Prep-TLC (ethyl acetate/petroleum ether=3:1) to give a light brown solid (70 mg, 82.8%). LCMS m/z=478.3 (M+1).

Step 11. 5-[(1R)-1-(3,5-Dimethylpyridazin-4-yl)ethoxy]-4-methoxy-3-[6-(2-methylsulfonyl-2,6-diazaspiro[3.3]heptan-6-yl)-3-pyridyl]-1-tetrahydropyran-2-yl-indazole. To a solution of 5-[(1R)-1-(3,5-dimethylpyridazin-4-yl)ethoxy]-3-(6-fluoro-3-pyridyl)-4-methoxy-1-tetrahydropyran-2-yl-indazole (70 mg, 0.15 mmol, 1.0 eq) in DMSO (4 mL) was added 2-methylsulfonyl-2,6-diazaspiro[3.3]heptane (182 mg, 0.66 mmol, 4.4 eq) and DIEA (190 mg, 1.5 mmol, 10 eq) at 25° C. The resulting mixture was stirred at 130° C. for 10 h, cooled to rt and quenched with water (15 mL). The precipitate was collected by filtration, washed with water, and dried over under vacuum to afford a brown solid (70 mg, 75.4%). LCMS m/z=634.4 (M+1).

Step 12: 5-[(1R)-1-(3,5-dimethylpyridazin-4-yl)ethoxy]-4-methoxy-3-[6-(2-methylsulfonyl-2,6-diazaspiro[3.3]heptan-6-yl)-3-pyridyl]-1H-indazole. To a solution of 5-[(1R)-1-(3,5-dimethylpyridazin-4-yl)ethoxy]-4-methoxy-3-[6-(2-methylsulfonyl-2,6-diazaspiro[3.3]heptan-6-yl)-3-pyridyl]-1-tetrahydropyran-2-yl-indazole (100 mg, 0.16 mmol, 1.0 eq) in DCM (3 mL) was added TFA (1 mL) at rt. The resulting mixture was stirred at rt for 10 h. The solvent was concentrated and the resulting mixture was diluted with DCM/MeOH (5:1, 3 mL). Solid NaHCO$_3$ was added and the mixture was stirred for 30 minutes. The solid was filtered out and the filtrate was concentrated under vacuum. The crude product was purified by Prep-TLC (DCM:MeOH=20:1) to give an off-white solid (22.7 mg, 26.5%). LCMS: m/z=550.3 (M+H); 1H-NMR (400 MHz, DMSO-d6) δ 13.09 (s, 1H), 8.88 (s, 1H), 8.52 (d, J=1.6 Hz, 1H), 7.96 (dd, J=8.4 Hz, 2.0 Hz, 1H), 7.15 (d, J=8.8 Hz, 1H), 6.97 (d, J=8.8 Hz, 1H), 6.51 (d, J=8.8 Hz, 1H), 5.65 (q, J=7.2 Hz, 1H), 4.16 (s, 4H), 4.11 (s, 4H), 3.55 (s, 3H), 3.02 (s, 3H), 2.76 (s, 3H), 2.46 (s, 3H), 1.65 (d, J=6.8 Hz, 3H).

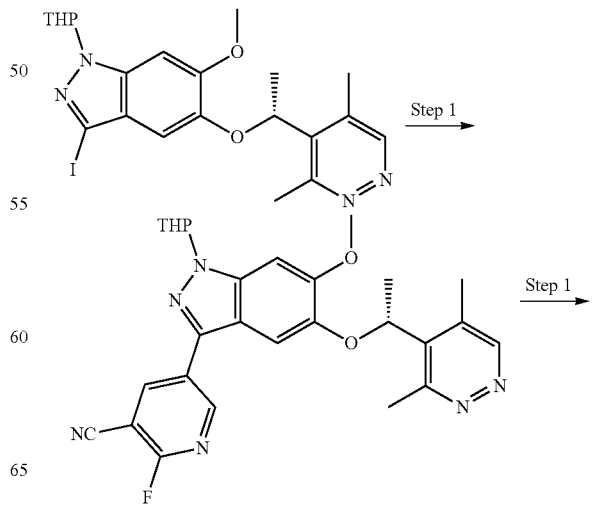

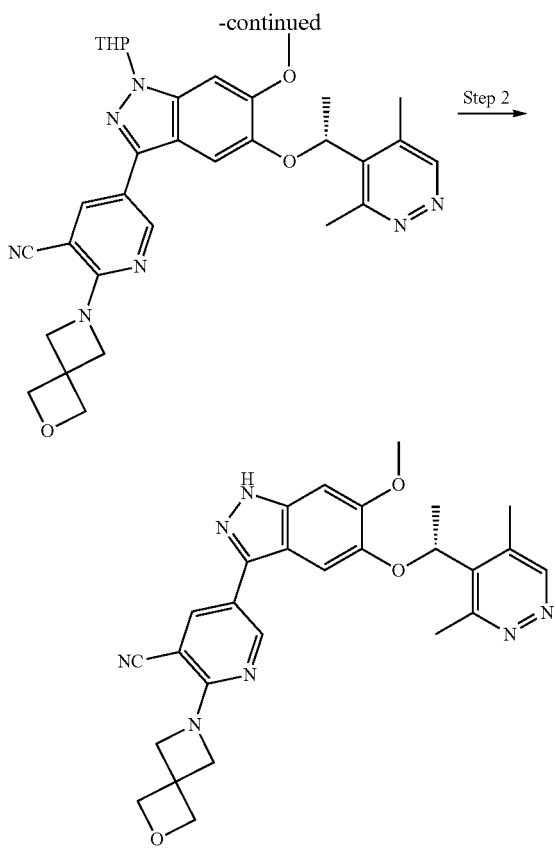

Example 218

Example 218. (R)-5-(5-(1-(3,5-dimethylpyridazin-4-yl)ethoxy)-6-methoxy-1H-indazol-3-yl)-2-(2-oxa-6-azaspiro[3.3]heptan-6-yl)nicotinonitrile

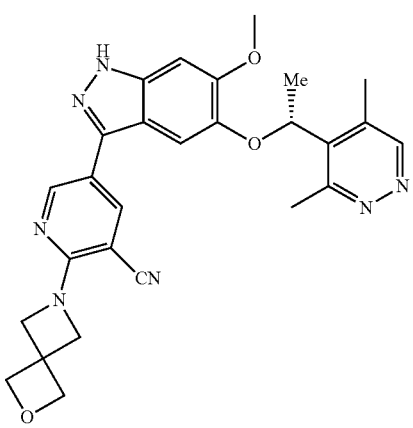 [SMILES: COc1cc2[nH]nc(-c3cnc(N4CC5(COC5)C4)c(C#N)c3)c2cc1O[C@H](C)c1c(C)cnnc1C]

Step 1. 5-[5-[(1R)-1-(3,5-dimethylpyridazin-4-yl)ethoxy]-6-methoxy-1-tetrahydropyran-2-yl-indazol-3-yl]-2-fluoro-pyridine-3-carbonitrile. This intermediate was synthesized using 2-fluoro-5-(4,4,5,5-tetramethyl-1,3-dioxolan-2-yl)pyridine-3-carbonitrile and 5-[(1R)-1-(3,5-dimethylpyridazin-4-yl)ethoxy]-3-iodo-6-methoxy-1-tetrahydropyran-2-yl-indazole using conditions described previously.

Step 2. 5-[5-[(1R)-1-(3,5-dimethylpyridazin-4-yl)ethoxy]-6-methoxy-1-tetrahydropyran-2-yl-indazol-3-yl]-2-fluoro-pyridine-3-carbonitrile. To a solution of 5-[5-[(1R)-1-(3,5-dimethylpyridazin-4-yl)ethoxy]-6-methoxy-1-tetrahydropyran-2-yl-indazol-3-yl]-2-fluoro-pyridine-3-carbonitrile (150 mg, 0.298 mmol, 1.0 eq) and 2-oxa-6-azaspiro[3.3]heptane oxalic acid salt (84 mg, 0.447 mmol) in DMSO (3 mL) was added DIEA (192 mg, 1.49 mmol, 5.0 eq). The reaction mixture was stirred for 6 h at 100° C. After the reaction was complete, the mixture was diluted with EtOAc (60 mL) and washed with brine (20 mL×2). The organic layer was dried over $Na_2SO_4$ and concentrated. The crude product was purified by prep-TLC (PE/EA=1/1) to afford a yellow solid (100 mg, 57.6%). LCMS m/z=582.4 (M+1).

Step 3. (R)-5-(5-(1-(3,5-dimethylpyridazin-4-yl)ethoxy)-6-methoxy-1H-indazol-3-yl)-2-(2-oxa-6-azaspiro[3.3]heptan-6-yl)nicotinonitrile. To a solution of 5-[5-[(1R)-1-(3,5-dimethylpyridazin-4-yl)ethoxy]-6-methoxy-1-tetrahydropyran-2-yl-indazol-3-yl]-2-fluoro-pyridine-3-carbonitrile (90 mg, 0.155 mmol, 1.0 eq) in DCM (1 mL) was added TFA (0.4 mL). The solution was stirred at rt for 2 h and was concentrated in vacuum. The crude product was basified with the saturate aqueous $NaHCO_3$ solution, and extracted with DCM (30 mL×3). The combined organic layers were washed with brine (20 mL×2), dried over $Na_2SO_4$ and concentrated. The residue was purified by Prep-HPLC (Prep-C18, 5 μM Triart column, 20×150 mm, YMC-Actus; gradient elution of 20% MeCN in water to 45% MeCN in water over a 11 min period, both solvents contain 0.05% $NH_3·H_2O$) to give a white solid (20.3 mg, 26.4%). LCMS: m/z=498.2 (M+H); 1H NMR (400 MHz, DMSO-d6) δ 12.96 (s, 1H), 8.82 (s, 1H), 8.75 (d, J=2.4 Hz, 1H), 8.18 (d, J=2.4 Hz, 1H), 7.01 (d, J=6.0 Hz, 2H), 5.84 (q, J=6.4 Hz, 1H), 4.76 (s, 4H), 4.48 (s, 4H), 3.87 (s, 3H), 2.78 (s, 3H), 2.45 (s, 3H), 1.66 (d, J=6.8 Hz, 3H).

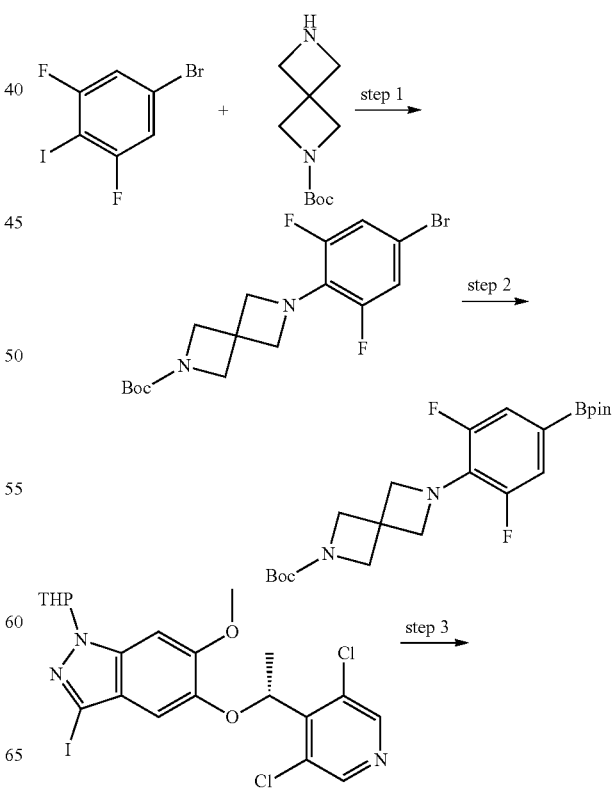

243
-continued

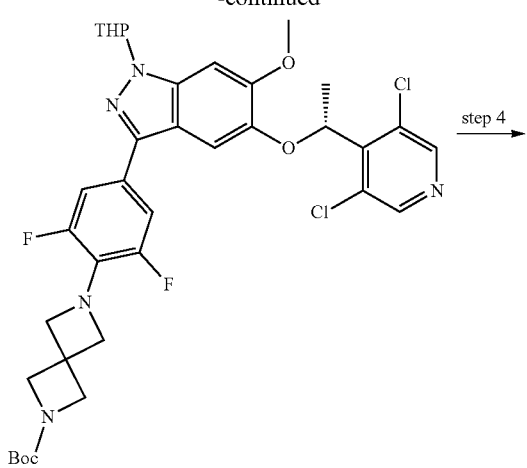

step 4 →

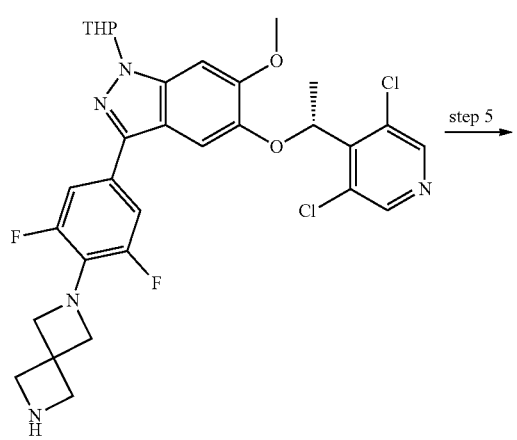

step 5 →

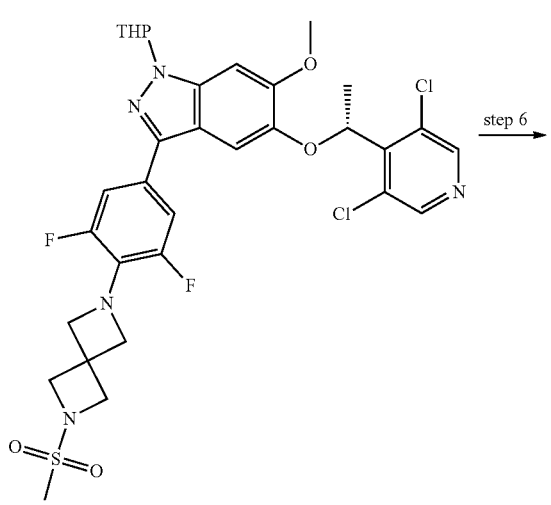

step 6 →

244
-continued

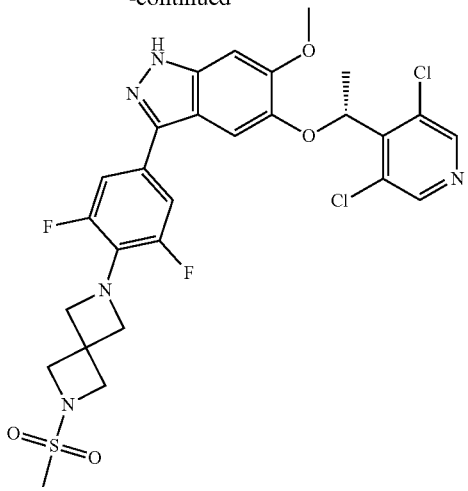

Example 279

Example 279. (R)-5-(1-(3,5-dichloropyridin-4-yl)ethoxy)-3-(3,5-difluoro-4-(6-(methylsulfonyl)-2,6-diazaspiro[3.3]heptan-2-yl)phenyl)-6-methoxy-1H-indazole

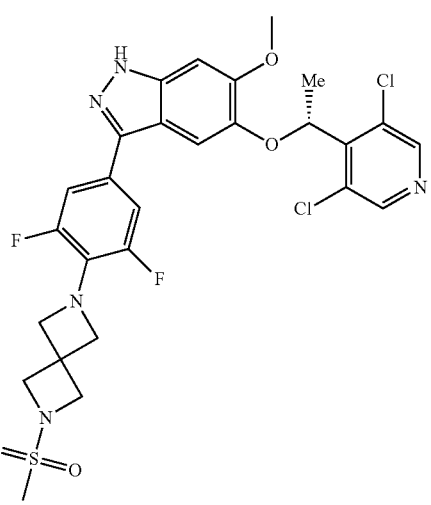

Step 1. tert-butyl 6-(4-bromo-2,6-difluoro-phenyl)-2,6-diazaspiro[3.3]heptane-2-carboxylate. To a solution of 5-bromo-1,3-difluoro-2-iodo-benzene (1.0 g, 3.14 mmol, 1.0 eq) and tert-butyl 2,6-diazaspiro[3.3]heptane-2-carboxylate oxylate salt (1.1 g, 3.76 mmol, 1.2 eq) in dioxane (20 mL) was added Xantphos (151 mg, 0.31 mmol, 0.1 eq), Pd$_2$(dba)$_3$ (146 mg, 0.16 mmol, 0.05 eq) and Cs$_2$CO$_3$ (2.04 g, 6.28 mmol, 2.0 eq). The resulting mixture was stirred at 100° C. for 3 h under N$_2$ protection. After cooled to room temperature, the reaction mixture was diluted with 50 mL of water and extracted with EtOAc (20 mL×3). The combined organic layers were washed with water (30 ml), brine (30 mL), dried over Na$_2$SO$_4$ and concentrated under reduced pressure. The crude product was purified by silica gel chromatography (petroleum ether/EtOAc=10/1) to give a white solid (900 mg, 73.73% yield). LCMS m/z=389.2 (M+1).

Step 2. tert-butyl 6-[2,6-difluoro-4-(4,4,5,5-tetramethyl-1,3,2-dioxaborolan-2-yl)phenyl]-2,6-diazaspiro[3.3]heptane-2-carboxylate. To a solution of tert-butyl 6-(4-bromo-2,6-difluoro-phenyl)-2,6-diazaspiro[3.3]heptane-2-carboxylate (860 mg, 2.21 mmol, 1.0 eq) and BPD (673 mg, 2.65 mmol, 1.2 eq) in dioxane (20 mL) was added KOAc (433 mg, 4.42 mmol, 2.0 eq) and Pd(dppf)Cl$_2$ (81 mg, 0.11 mmol, 0.05 eq) at 25° C. The resulting mixture was stirred at 100° C. for 3 h under N$_2$ protection. After cooled to room temperature, the reaction mixture was diluted with 50 mL of water and extracted with EtOAc (30 mL×2). The combined organic layers were washed with water (50 ml), brine (50 mL), dried over Na$_2$SO$_4$ and concentrated under reduced pressure. The crude product was purified by silica gel chromatography (petroleum ether/EtOAc=10/1) to give an off-white solid (550 mg, 57.05% yield). LCMS m/z=437.3 (M+1).

Step 3. tert-butyl 6-[4-[5-[(1R)-1-(3,5-dichloro-4-pyridyl)ethoxy]-6-methoxy-1-tetrahydropyran-2-yl-indazol-3-yl]-2,6-difluoro-phenyl]-2,6-diazaspiro[3.3]heptane-2-carboxylate. To a solution of tert-butyl 6-[2,6-difluoro-4-(4,4,5,5-tetramethyl-1,3,2-dioxaborolan-2-yl)phenyl]-2,6-diazaspiro[3.3]heptane-2-carboxylate (176 mg, 0.403 mmol, 1.2 eq) and 5-[(1R)-1-(3,5-dichloro-4-pyridyl)ethoxy]-3-iodo-6-methoxy-1-tetrahydropyran-2-yl-indazole (185 mg, 0.336 mmol, 1.0 eq) in dioxane (6 mL) and H$_2$O (0.6 mL) was added K$_2$CO$_3$ (93 mg, 0.672 mmol, 2.0 eq) and Pd(dppf)Cl$_2$ (50 mg, 0.067 mmol, 0.2 eq) at 25° C., the resulting mixture was stirred at 100° C. for 2 h under N$_2$ protection. After cooled to room temperature, the reaction mixture was diluted with 20 mL of water, extracted with EtOAc (10 mL×3). The combined organic layers were washed with brine (20 mL×2), dried over Na$_2$SO$_4$, and concentrated under reduced pressure. The crude product was purified by silica gel chromatography (Petroleum Ether/EtOAc=4/1) to give a white solid (180 mg, 74%). LCMS m/z=730.3 (M+1).

Step 4. 3-[4-(2,6-diazaspiro[3.3]heptan-2-yl)-3,5-difluoro-phenyl]-5-[(1R)-1-(3,5-dichloro-4-pyridyl)ethoxy]-6-methoxy-1-tetrahydropyran-2-yl-indazole. To a solution of tert-butyl 6-[4-[5-[(1R)-1-(3,5-dichloro-4-pyridyl)ethoxy]-6-methoxy-1-tetrahydropyran-2-yl-indazol-3-yl]-2,6-difluoro-phenyl]-2,6-diazaspiro[3.3]heptane-2-carboxylate (120 mg, 0.165 mmol, 1.0 eq) in DCM (3 mL) was added TMSOTf (370 mg, 1.65 mmol, 10.0 eq) at 0° C. The resulting mixture was stirred at 25° C. for 5 h. After completion, the reaction mixture was quenched with aqueous NaHCO$_3$ (20 mL) and extracted with DCM (10 mL×3). The combined organic layers were washed with brine (20 mL×2), dried over Na$_2$SO$_4$, and concentrated under reduced pressure. The crude product was purified by Prep-TLC (DCM/MeOH=15/1) to give an off-white solid (120 mg). LCMS m/z=630.3 (M+1).

Step 5. 5-[(1R)-1-(3,5-Dichloro-4-pyridyl)ethoxy]-3-[3,5-difluoro-4-(2-methylsulfonyl-2,6-diazaspiro[3.3]heptan-6-yl)phenyl]-6-methoxy-1-tetrahydropyran-2-yl-indazole. To a solution of 3-[4-(2,6-diazaspiro[3.3]heptan-2-yl)-3,5-difluoro-phenyl]-5-[(1R)-1-(3,5-dichloro-4-pyridyl)ethoxy]-6-methoxy-1-tetrahydropyran-2-yl-indazole (120 mg, crude) in DCM (3 mL) was added MsCl (40 mg, 0.35 mmol, 1.8 eq) and TEA (84 mg, 0.83 mmol, 4.4 eq) at 0° C. The resulting mixture was stirred at 0° C. for 3 h. After completion, the reaction mixture was quenched with H$_2$O (20 mL) and extracted with DCM (10 mL×3). The combined organic layers were washed with brine (20 mL), dried over Na$_2$SO$_4$, and concentrated under reduced pressure. The crude product was purified by Prep-TLC (DCM/MeOH=20/1) to give as a white solid (78 mg, 58.4% yield, two steps). LCMS m/z=708.20 (M+1).

Step 6. (R)-5-(1-(3,5-dichloropyridin-4-yl)ethoxy)-3-(3,5-difluoro-4-(6-(methylsulfonyl)-2,6-diazaspiro[3.3]heptan-2-yl)phenyl)-6-methoxy-1H-indazole. To a solution of 5-[(1R)-1-(3,5-dichloro-4-pyridyl)ethoxy]-3-[3,5-difluoro-4-(2-methylsulfonyl-2,6-diazaspiro[3.3]heptan-6-yl)phenyl]-6-methoxy-1-tetrahydropyran-2-yl-indazole (73 mg, 0.103 mmol, 1.0 eq) in DCM (4 mL) was added TFA (1 mL) at 0° C. The resulting mixture was stirred at 25° C. for 3 h. After completion, the reaction solution was added to a mixed solution of DCM and NaHCO$_3$ aqueous dropwise, the organic layer was separated, and the aqueous was extracted with DCM (10 mL*3). The combined organic layers were washed with brine (20 mL×2), dried over Na$_2$SO$_4$, then filtered and concentrated under reduced pressure. The crude product was purified by Prep-TLC (DCM/MeOH=15/1) to give a white solid (23.3 mg, 36.3% yield). LCMS: m/z=624.2 (M+H); 1H-NMR (400 MHz, DMSO-d6) δ 8.59 (s, 2H), 7.19 (dd, J=8.8 Hz, 2.4 Hz, 2H), 6.99 (s, 1H), 6.95 (s, 1H), 5.99 (q, J=6.4 Hz, 1H), 4.34 (s, 4H), 4.10 (s, 4H), 3.87 (s, 3H), 3.02 (s, 3H), 1.76 (d, J=6.4 Hz, 3H).

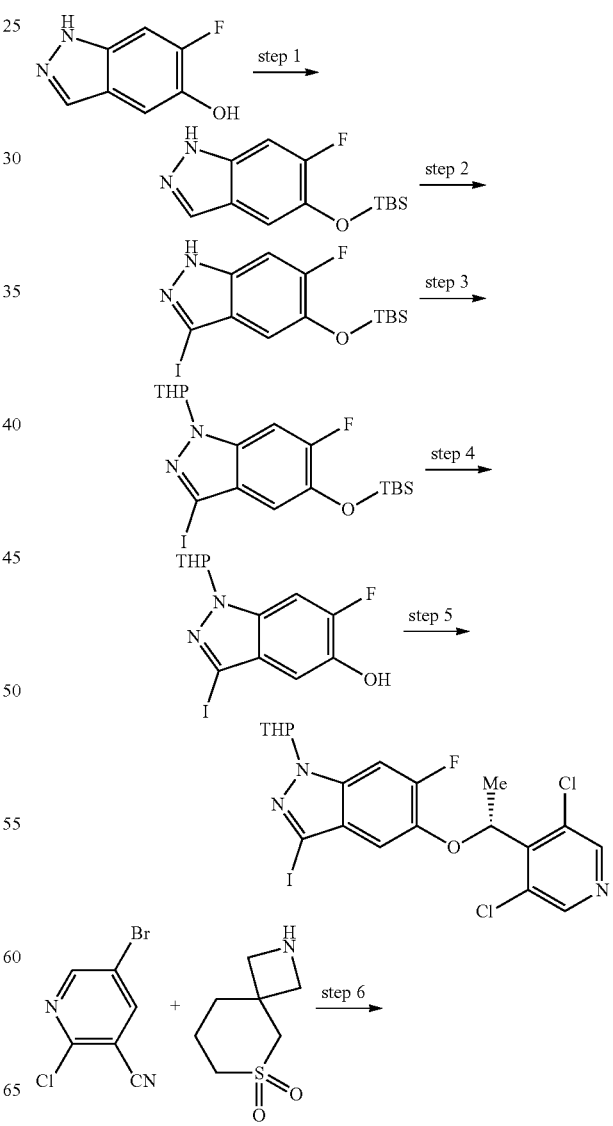

247

-continued

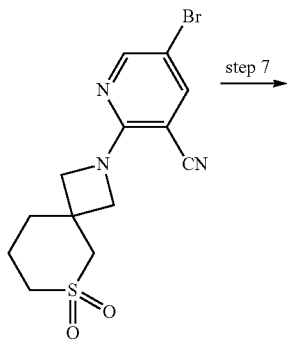

step 7 →

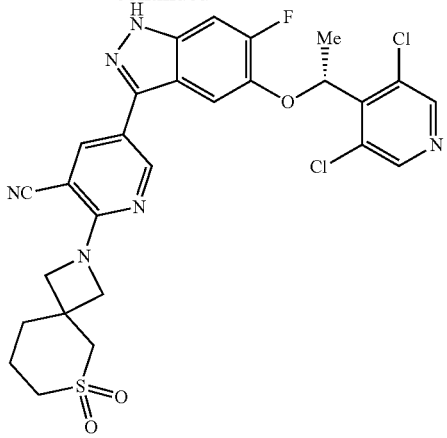

Example 362

Example 362. 5-[5-[(1R)-1-(3,5-dichloro-4-pyridyl)ethoxy]-6-fluoro-1H-indazol-3-yl]-2-(6,6-dioxo-6),6-thia-2-azaspiro[3.5]nonan-2-yl)pyridine-3-carbonitrile

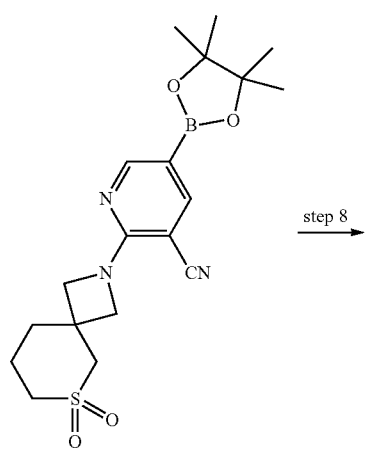

step 8 →

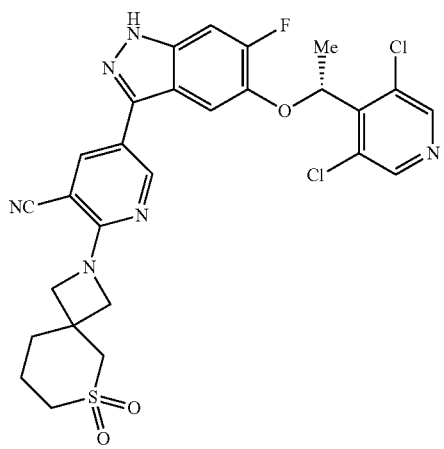 [SMILES: C[C@@H](Oc1cc2c(-c3cnc(N4CC5(CCCS(=O)(=O)C5)C4)c(C#N)c3)n[nH]c2cc1F)c1c(Cl)cncc1Cl]

step 9 →

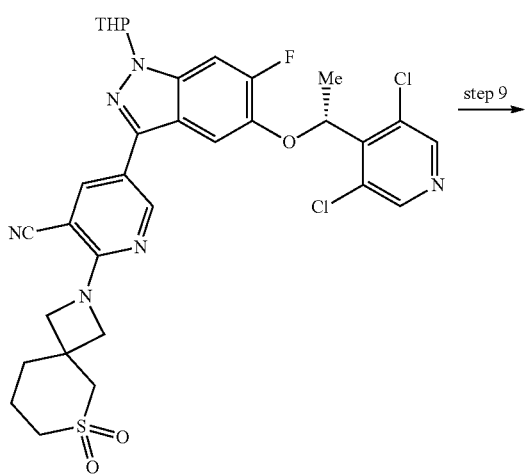

Step 1. 5-((tert-Butyldimethylsilyl)oxy)-6-fluoro-1H-indazole. Imidazole (10 g, 148 mmol) and tert-butyldimethylsilyl chloride (10.7 g, 71 mmol, 1.2 equiv) were sequentially added at 0° C. to a solution of 6-fluoro-1H-indazol-5-ol (9 g, 59 mmol, 1.0 equiv) in N,N-dimethylformamide (59 mL). After stirring at room temperature for 3 hours. The mixture was diluted with ethyl acetate (120 mL), washed with water (4×60 mL) and the organic layer was dried over sodium sulfate, filtered and concentrated under reduced pressure to give a brown oil (15.1 g, 99%). LCMS (ESI) m/z=267.1 (M+H). This material was used directly in the next step.

Step 2. 5-((tert-Butyldimethylsilyl)oxy)-6-fluoro-3-iodo-1H-indazole. 5-((tert-Butyldimethylsilyl)oxy)-6-fluoro-1H-indazole (15.1 g, 57 mmol, 1.0 equiv) in dichloromethane (590 mL) was treated with potassium hydroxide (7.5 g, 128 mmol, 2.25 equiv) and iodine (22.6 g, 85 mmol, 1.5 equiv) at room temperature. After stirring overnight, the reaction was diluted with dichloromethane (1 L) and washed with water (1 L). The organic layer was separated, filtered through a silica gel pad (20 g), which was washed with a 1:1 mixture of ethyl acetate in heptanes (1 L). The filtrate was dried over sodium sulfate, filtered, and concentrated under reduced pressure to give a brown oil (16.5 g, 71% crude yield over 2 steps). LCMS m/z=393.0 (M+H). This material was used directly in the next step.

Step 3. 5-((tert-Butyldimethylsilyl)oxy)-6-fluoro-3-iodo-1-(tetrahydro-2H-pyran-2-yl)-1H-indazole. 5-((tert-Butyldimethylsilyl)oxy)-6-fluoro-3-iodo-1H-indazole (16.5 g, 42 mmol, 1.0 equiv) in dichloromethane (420 mL) was treated with 3,4-dihydro-2H-pyran (7.7 mL, 84 mmol, 2.0 equiv) and p-toluenesulfonic acid (0.4 g, 2 mmol, 0.05 equiv) at room temperature. After stirring overnight, the reaction was diluted with dichloromethane (400 mL) and washed with a saturated sodium bicarbonate (100 mL). The organic layer was dried over sodium sulfate, filtered and concentrated under reduced pressure onto silica gel (60 g). The residue was purified on a Biotage automated chromatography system (Biotage Sfär HC, 200 g, silica gel), eluting with a gradient of 0 to 20% ethyl acetate in heptanes to give a yellow oil (11.2 g, 56% yield over 3 steps). LCMS m/z=477.1 (M+H).

Step 4. 6-Fluoro-3-iodo-1-(tetrahydro-2H-pyran-2-yl)-1H-indazol-5-ol. 5-((tert-Butyldimethylsilyl)oxy)-6-fluoro-3-iodo-1-(tetrahydro-2H-pyran-2-yl)-1H-indazole (11.2 g, 23.5 mmol, 1.0 equiv) in tetrahydrofuran (235 mL) was treated with 1M tetrabutylammonium fluoride in THF (47 mL, 47 mmol, 2.0 equiv) at 0° C. After stirring at 0° C. for 4 hours, the reaction was diluted with dichloromethane (800 mL) and washed with saturated sodium bicarbonate (300 mL). The organic layer was dried over sodium sulfate, filtered and concentrated under reduced pressure onto silica gel (30 g). The residue was purified on a Biotage automated chromatography system (Biotage Sfär HC, 200 g, silica gel), eluting with a gradient of 0 to 10% methanol in dichloromethane to give a white solid (8.07 g, 95%). LCMS m/z=363.0 (M+H).

Step 5. 5-((R)-1-(3,5-Dichloropyridin-4-yl)ethoxy)-6-fluoro-3-iodo-1-(tetrahydro-2H-pyran-2-yl)-1H-indazole. A mixture of 6-fluoro-3-iodo-1-(tetrahydro-2H-pyran-2-yl)-1H-indazol-5-ol (3.0 g, 8.3 mmol, 1.0 equiv), (1S)-1-(3,5-dichloro-4-pyridyl)ethyl]methanesulfonate (2.3 g, 8.3 mmol, 1.0 equiv) and cesium carbonate (4.1 g, 12.4 mmol, 1.5 equiv) in acetonitrile (82 mL) was heated at 90° C. overnight. After cooling to room temperature, the reaction was diluted with ethyl acetate (200 mL) and washed with water (200 mL). The organic layer was dried over sodium sulfate, filtered and concentrated under reduced pressure onto silica gel (30 g). The residue was purified on a Biotage automated chromatography system (Biotage Sfär HC, 200 g, silica gel), eluting with a gradient of 0 to 100% ethyl acetate in heptanes to give a white solid (3.0 g, 68% yield). LCMS m/z=M+H).

Step 6. 5-Bromo-2-(6,6-dioxido-6-thia-2-azaspiro[3.5]nonan-2-yl)nicotinonitrile. A solution of 5-bromo-2-chloropyridine-3-carbonitrile (327 mg, 1.5 mmol, 1.0 equiv), $6\lambda^6$-thia-2-azaspiro[3.5]nonane 6,6-dioxide (318 mg, 1.5 mmol, 1.0 equiv) and N,N-diisopropylethylamine (1.21 mL, 6.9 mmol, 4.6 equiv) in acetonitrile (8 mL) was heated at 60° C. for 16 hours, and then stirred at room temperature for an additional 16 hours. The resulting solids were filtered and washed with cold acetonitrile (4 mL). The solid was dried under vacuum at room temperature overnight to give a white solid (399 mg, 74% yield). LCMS m/z=356 (M+H).

Step 7 and Step 8. 2-(6,6-dioxo-$6\lambda^6$-thia-2-azaspiro[3.5]nonan-2-yl)-5-(4,4,5,5-tetramethyl-1,3,2-dioxaborolan-2-yl)pyridine-3-carbonitrile and Step 8. 5-(5-((R)-1-(3,5-Dichloropyridin-4-yl)ethoxy)-6-fluoro-1-(tetrahydro-2H-pyran-2-yl)-1H-indazol-3-yl)-2-(6,6-dioxido-6-thia-2-azaspiro[3.5]nonan-2-yl)nicotinonitrile. A solution of 5-bromo-2-(6,6-dioxido-6-thia-2-azaspiro[3.5]nonan-2-yl) nicotinonitrile (243 mg, 0.68 mmol, 1.0 equiv), potassium acetate (81 mg, 0.83 mmol, 1.2 equiv), bis(pinacolato)diboron (190 mg, 0.75 mmol, 1.10 equiv) and [1,1'-bis(diphenylphosphino)ferrocene]dichloropalladium(II) (35 mg, 0.04 mmol, 0.07 equiv) in 1,4-dioxane (10 mL) was sparged with nitrogen for 5 minutes then heated at 97° C. for 18 hours. After cooling to room temperature, 5-((R)-1-(3,5-dichloropyridin-4-yl)ethoxy)-6-fluoro-3-iodo-1-(tetrahydro-2H-pyran-2-yl)-1H-indazole (200 mg, 0.37 mmol, 1.0 equiv), [1,1'-bis(diphenylphosphino)ferrocene]-dichloropalladium(II) (19 mg, 0.02 mmol, 0.07 equiv), potassium carbonate (103 mg, 0.75 mmol, 2.0 equiv) and water (1.0 mL) were added. The resulting mixture was sparged with nitrogen for 5 minutes then heated at 90° C. for 4 hours. The mixture was cooled to room temperature and diluted with ethyl acetate (20 mL) and water (10 mL). The layers were separated and the aqueous layer was extracted with ethyl acetate (2×20 mL). The combined organic layers were washed with saturated brine (25 mL), dried over magnesium sulfate, filtered and concentrated under reduced pressure. The residue was purified on a Biotage automated chromatography system (Biotage HC, 50 g silica gel column), eluting with a gradient of 0 to 100% ethyl acetate in heptanes to give an off-white solid (310 mg, >100% yield). LCMS m/z=685 (M+H).

Step 9. (R)-5-(5-(1-(3,5-Dichloropyridin-4-yl)ethoxy)-6-fluoro-1H-indazol-3-yl)-2-(6,6-dioxido-6-thia-2-azaspiro[3.5]nonan-2-yl)nicotinonitrile. 5-(5-((R)-1-(3,5-Dichloropyridin-4-yl)ethoxy)-6-fluoro-1-(tetrahydro-2H-pyran-2-yl)-1H-indazol-3-yl)-2-(6,6-dioxido-6-thia-2-azaspiro[3.5]nonan-2-yl)nicotinonitrile (124 mg, 0.18 mmol) in dichloromethane (4 mL) was treated with trifluoroacetic acid (3 mL). After stirring at room temperature overnight, the reaction was quenched with saturated sodium carbonate (25 mL) and 6N sodium hydroxide (20 mL) at 0° C. The layers were separated and the aqueous layer was extracted with dichloromethane (2×25 mL). The combined organic layers were washed with saturated brine (20 mL), dried over magnesium sulfate, filtered and concentrated under reduced pressure. The residue was purified on a Biotage automated chromatography system (RediSep Rf GOLD 100 g HP C18 column), eluting with a gradient of 0 to 90% acetonitrile in water. The product fractions were concentrated under reduced pressure and then precipitated from a mixture of ethyl acetate (3 mL), methanol (0.5 mL), MTBE (7 mL) and heptanes (15 mL) to give an off-white solid (88 mg, 81% yield, 99.3% purity). LCMS m/z=601.1 (M+H); 1H NMR (400 MHz, DMSO-d6) δ=13.23 (s, 1H), 8.75 (d, J=2.3 Hz, 1H), 8.60 (s, 2H), 8.14 (d, J=2.3 Hz, 1H), 7.47 (d, J=10.9 Hz, 1H), 7.24 (d, J=7.9 Hz, 1H), 6.18 (q, J=6.6 Hz, 1H), 4.29 (d, J=9.0 Hz, 2H), 4.07 (d, J=8.9 Hz, 2H), 3.51 (s, 2H), 3.11-3.00 (m, 2H), 1.99 (br s, 4H), 1.81 (d, J=6.6 Hz, 3H).

The Examples below may be prepared using methods and procedures described herein.

| Example 174 3-[6-[(8aS)-3,4,6,7,8,8a-hexahydro-1H-pyrrolo[1,2-a]pyrazin-2-yl]-3-pyridyl]-5-[(1R)-1-(3,5-dimethylpyridazin-4-yl)ethoxy]-1H-indazole | 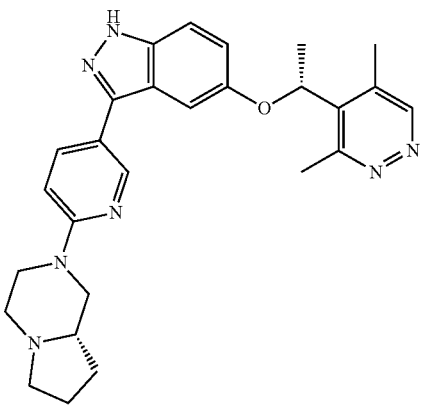 [SMILES: Cc1cnnc(C)c1[C@@H](C)Oc1ccc2[nH]nc(-c3ccc(N4CCN5CCC[C@H]5C4)nc3)c2c1] | LCMS: m/z = 470.4 (M + H); 1H NMR (400 MHz DMSO-d6) δ 12.90 (brs, 1H), 8.85 (s, 1H), 8.52 (d, J = 2.4 Hz, 1H), 7.83 (dd, J = 8.8 Hz, 2.4 Hz, 1H), 7.46 (d, J = 8.8 Hz, 1H), 7.07 (dd, J = 8.8 Hz, 2.4 Hz, 1H), 7.04-7.03 (m, 1H), 6.96 (d, J = 8.8 Hz, 1H), 5.88 (q, J = 6.8 Hz, 1H), 4.48 (d, J = 11.2 Hz, 1H), 4.31 (d, J = 12.8 Hz, 1H), 3.10-3.01 (m, 2H), 2.91 (td, J = 12.0 Hz, 3.2 Hz, 1H), 2.78 (s, 3H), 2.60-2.53 (m, 1H), 2.45 (s, 3H), 2.16 (td, J = 11.2 Hz, 3.6 Hz, 1H), 2.07 (q, J = 8.8 Hz, 1H), 2.00-1.92 (m, 1H), 1.90-1.82 (m, 1H), 1.78-1.65 (m, 5H), 1.45-1.35 (m, 1H) |
|---|---|---|
| Example 175 3-[6-[(8aR)-3,4,6,7,8,8a-hexahydro-1H-pyrrolo[1,2-a]pyrazin-2-yl]-3-pyridyl]-5-[(1R)-1-(3,5-dimethylpyridazin-4-yl)ethoxy]-1H-indazole | 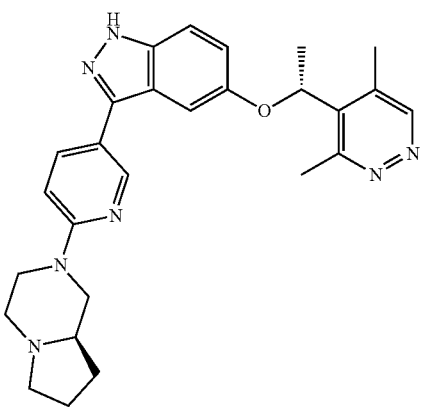 [SMILES: Cc1cnnc(C)c1[C@@H](C)Oc1ccc2[nH]nc(-c3ccc(N4CCN5CCC[C@@H]5C4)nc3)c2c1] | LCMS: m/z = 470.4 (M + H); 1H NMR (400 MHz, DMSO-d6) δ 12.98 (s, 1H), 8.85 (s, 1H), 8.52 (s, 1H), 7.83 (d, J = 6.8 Hz, 1H), 7.47 (d, J = 8.8 Hz, 1H), 7.08 - 7.04 (m, 2H), 6.96 (d, J = 9.2 Hz, 1H), 5.87 (q, J = 6.8 Hz, 1H), 4.48 (d, J = 12.4 Hz, 1H), 4.31 (d, J = 12.0 Hz, 1H), 3.10-3.04 (m, 2H), 2.91 - 2.90 (m, 1H), 2.79 (s, 3H), 2.57 (q, J = 9.2 Hz, 1H), 2.45 (s, 3H), 2.16 - 2.15 (m, 1H), 2.07 (q, J = 8.4 Hz, 1H), 2.00 - 1.94 (m, 1H), 1.90 - 1.83 (m, 1H), 1.77 - 1.69 (m, 2H), 1.67 (d, J = 6.4 Hz, 3H), 1.45 - 1.35 (m, 1H). |
| Example 176 (7R,8aS)-2-[5-[5-[(1R)-1-(3,5-dimethylpyridazin-4-yl)ethoxy]-1H-indazol-3-yl]-2-pyridyl]-3,4,6,7,8,8a-hexahydro-1H-pyrrolo[1,2-a]pyrazin-7-ol | 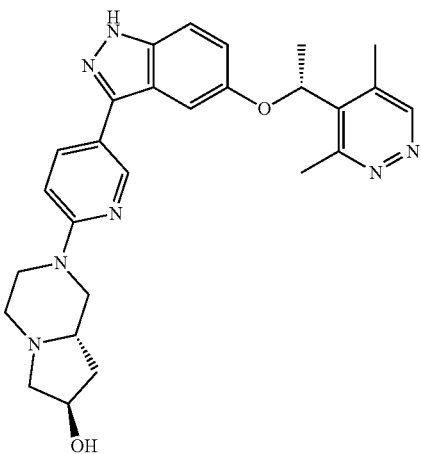 [SMILES: Cc1cnnc(C)c1[C@@H](C)Oc1ccc2[nH]nc(-c3ccc(N4CCN5C[C@H](O)C[C@H]5C4)nc3)c2c1] | LCMS: m/z = 486.3 (M + H); 1H NMR (400 MHz, DMSO-d6) δ 12.96 (brs, 1H), 8.85 (s, 1H), 8.52 (d, J = 2.0 Hz, 1H), 7.83 (dd, J = 9.2 Hz, 2.4 Hz, 1H), 7.46 (d, J = 8.8 Hz, 1H), 7.08 - 7.03 (m, 2H), 6.96 (d, J = 8.8 Hz, 1H), 5.88 (q, J = 6.8 Hz, 1H), 4.85 (brs, 1H), 4.45 (d, J = 10.8 Hz, 1H), 4.32 - 4.26 (m, 2H), 3.49 - 3.38 (m, 2H), 3.01 (d, J = 11.2 Hz, 1H), 2.91 - 2.84 (m, 1H), 2.78 (s, 3H), 2.45 (s, 3H), 2.32 - 2.19 (m, 2H), 2.01 - 1.97 (m, 1H), 1.73 - 1.66 (m, 5H). |
| Example 177 3-[6-(2,6-diazaspiro[3.3]heptan-2-yl)-3-pyridyl]-5-[(1R)-1-(3,5-dichloro-2-methyl-4-pyridyl)ethoxy]-1H-indazole | 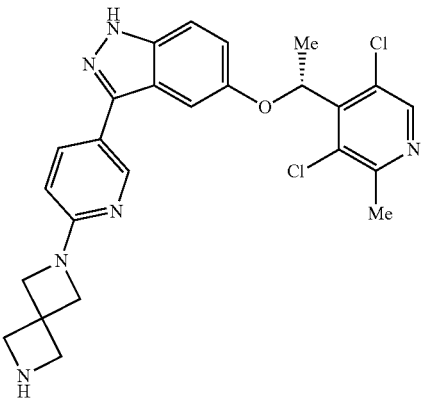 [SMILES: Cc1ncc(Cl)c([C@@H](C)Oc2ccc3[nH]nc(-c4ccc(N5CC6(CNC6)C5)nc4)c3c2)c1Cl] | LCMS: m/z = 495.1 (M + H); 1H NMR (400 MHz, DMSO-d6) δ = 13.04 (br s, 1H), 8.58 (br s, 2H), 8.43 (s, 1H), 8.39 (d, J = 1.8 Hz, 1H), 7.93 (dd, J = 2.2, 8.7 Hz, 1H), 7.47 (d, J = 9.0 Hz, 1H), 7.09 (d, J = 8.7 Hz, 1H), 7.06 (d, J = 2.0 Hz, 1H), 6.60 (d, J = 8.6 Hz, 1H), 6.09 (q, J = 6.7 Hz, 1H), 4.24 - 4.19 (m, 8H), 2.59 (s, 3H), 1.76 (d, J = 6.6 Hz, 3H) |

Example 178
(7R,8aS)-2-[5-[5-[(1R)-1-(3,5-dichloro-4-pyridyl)ethoxy]-1H-indazol-3-yl]-2-pyridyl]-3,4,6,7,8,8a-hexahydro-1H-pyrrolo[1,2-a]pyrazin-7-ol

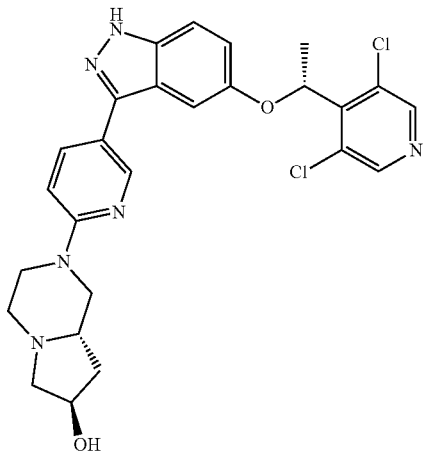 [SMILES: C[C@@H](Oc1ccc2[nH]nc(-c3ccc(N4CCN5C[C@H](O)C[C@H]5C4)nc3)c2c1)c1c(Cl)cncc1Cl]

LCMS: m/z = 525.2 (M + H); 1H NMR (400 MHz, DMSO-d6) δ 13.00 (s, 1H), 8.61-8.59 (m, 2H), 8.54 (s, 1H), 7.84 (d, J = 8.8 Hz, 1H), 7.46 (dd, J = 8.4 Hz, 1.6 Hz, 1H), 7.15 (s, 1H), 7.09 (dd, J = 9.2 Hz, 2.4 Hz, 1H), 7.00-6.96 (m, 1H), 6.11 (q, J = 6.4 Hz, 1H), 4.83 (s, 1H), 4.45 (d, J = 12.0 Hz, 1H), 4.33 - 4.27 (m, 2H), 3.43 - 3.35 (m, 2H), 3.01 (d, J = 11.2 Hz, 1H), 2.91 - 2.85 (m, 1H) , 2.32 - 2.20 (m, 2H), 2.00 (s, 1H), 1.78 (d, J = 7.2 Hz, 3H), 1.70- 1.65 (m, 2H)

Example 179
3-[2-(2,6-diazaspiro[3.3]heptan-2-yl)pyrimidin-5-yl]-5-[(1R)-1-(3,5-dichloro-2-methyl-4-pyridyl)ethoxy]-1H-indazole

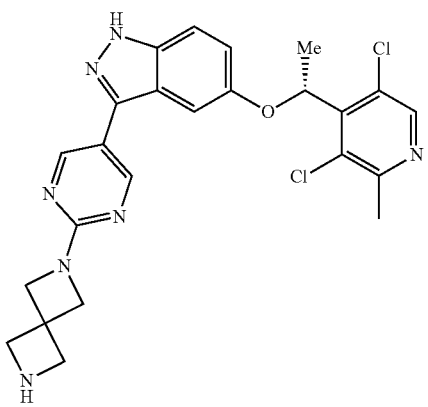

LCMS: m/z = 496.2 (M + H); 1H NMR (400 MHz, DMSO-d6) δ = 13.14 (s, 1H), 8.69 (s, 2H), 8.57 (br s, 2H), 8.42 (s, 1H), 7.48 (d, J = 9.0 Hz, 1H), 7.10 (d, J = 9.3 Hz, 1H), 7.07 (s, 1H), 6.14 - 6.07 (m, 1H), 4.30 (s, 4H), 4.22 (br s, 4H), 2.59 (s, 3H), 1.76 (d, J = 6.7 Hz, 3H)

Example 180
5-[(1R)-1-(3,5-dichloro-2-methyl-4-pyridyl)ethoxy]-3-[6-(2-ethylsulfonyl-2,6-diazaspiro[3.3]heptan-6-yl)-3-pyridyl]-1H-indazole

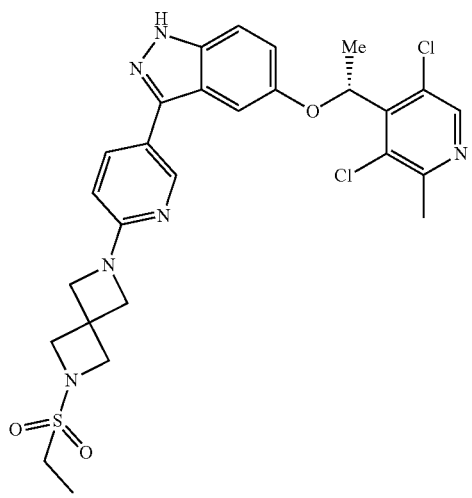 [SMILES: CCS(=O)(=O)N1CC2(CN(c3ccc(-c4n[nH]c5ccc(O[C@H](C)c6c(Cl)cnc(C)c6Cl)cc45)cn3)C2)C1]

LCMS: m/z = 587.2 (M + H); 1H NMR (400 MHz, DMSO-d6) δ = 12.99 (s, 1H), 8.43 (s, 1H), 8.40 (d, J = 2.0 Hz, 1H), 7.87 (dd, J = 2.3, 8.6 Hz, 1H), 7.45 (d, J = 9.0 Hz, 1H), 7.11 - 7.04 (m, 2H), 6.53 (dd, J = 0.6, 8.6 Hz, 1H), 6.12 - 6.06 (m, 1H), 4.17 (s, 4H), 4.11 (s, 4H), 3.14 (q, J = 7.3 Hz, 2H), 2.58 (s, 3H), 1.75 (d, J = 6.7 Hz, 3H), 1.24 (t, J = 7.4 Hz, 3H)

| | | |
|---|---|---|
| Example 181<br>5-[(1R)-1-(3,5-dichloro-2-methyl-4-pyridyl)ethoxy]-3-[2-(2-ethylsulfonyl-2,6-diazaspiro[3.3]heptan-6-yl)pyrimidin-5-yl]-1H-indazole | 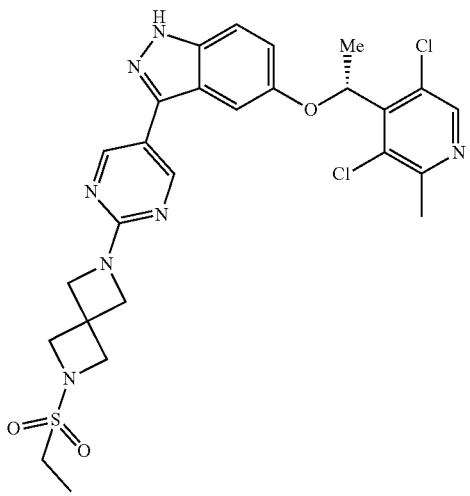 [SMILES: CCS(=O)(=O)N1CC2(CN(c3ncc(-c4n[nH]c5ccc(O[C@H](C)c6c(Cl)cnc(C)c6Cl)cc45)cn3)C2)C1] | LCMS: m/z = 588.1 (M + H); 1H NMR (400 MHz, DMSO-d6) δ = 13.12 (s, 1H), 8.69 (s, 2H), 8.41 (s, 1H), 7.47 (d, J = 9.7 Hz, 1H), 7.12 - 7.07 (m, 2H), 6.14 - 6.08 (m, 1H), 4.28 (s, 4H), 4.11 (s, 4H), 3.14 (q, J = 7.3 Hz, 2H), 2.58 (s, 3H), 1.75 (d, J = 6.7 Hz, 3H), 1.24 (t, J = 7.3 Hz, 3H) |
| Example 182<br>ethyl 2-[5-[5-[(1R)-1-(3,5-dimethylpyridazin-4-yl)ethoxy]-1H-indazol-3-yl]-2-pyridyl]-2,8-diazaspiro[3.5]nonane-8-carboxylate | 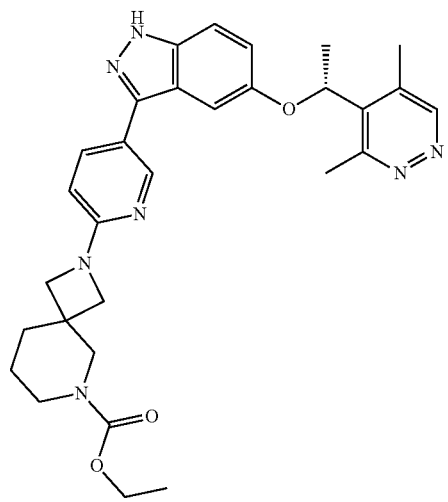 [SMILES: CCOC(=O)N1CCCC2(C1)CN(c1ccc(-c3n[nH]c4ccc(O[C@H](C)c5c(C)cnnc5C)cc34)cn1)C2] | LCMS: m/z = 542.5 (M + H); 1H NMR (400 MHz, DMSO-d6) δ 12.97 (s, 1H), 8.84 (s, 1H), 8.49 (d, J = 2.0 Hz, 1H), 7.83 (dd, J = 8.4 Hz, 2.0 Hz, 1H), 7.46 (d, J = 8.8 Hz, 1H), 7.07 (dd, J = 8.8 Hz, 2.0 Hz, 1H), 7.05-7.04 (m, 1H), 6.51 (d, J = 8.8 Hz, 1H), 5.87 (q, J = 6.8 Hz, 1H), 4.07 (q, J = 7.2 Hz, 2H), 3.74 (d, J = 7.6 Hz, 2H), 3.68 (d, J = 8.0 Hz, 2H), 3.57 (s, 2H), 3.38-3.33 (m, 2H), 2.78 (s, 3H), 2.44 (s, 3H), 1.82-1.79 (m, 2H), 1.66 (d, J = 6.8 Hz, 3H), 1.51-1.50 (m, 2H), 1.20 (t, J = 6.8 Hz, 3H). |
| Example 183<br>3-[6-[(8aS)-3,4,6,7,8,8a-hexahydro-1H-pyrrolo[1,2-a]pyrazin-2-yl]-3-pyridyl]-5-[(1R)-1-(3,5-dichloro-4-pyridyl)ethoxy]-1H-indazole | 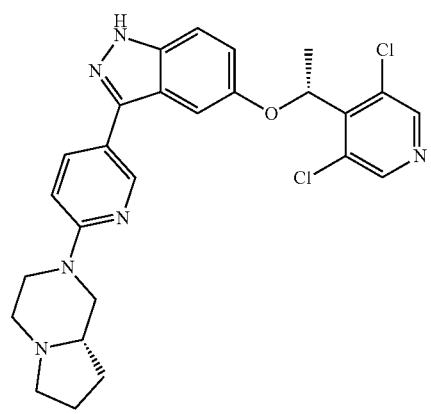 [SMILES: C[C@@H](Oc1ccc2[nH]nc(-c3ccc(N4CCN5CCC[C@H]5C4)nc3)c2c1)c1c(Cl)cncc1Cl] | LCMS: m/z = 509.2 (M + H); 1H NMR (400 MHz, DMSO-d6) δ 12.99 (s, 1H), 8.61 (s, 2H), 8.54 (d, J = 2.0 Hz, 1H), 7.85 (dd, J = 8.8 Hz, 2.4 Hz, 1H), 7.46 (d, J = 8.8 Hz, 1H), 7.16 (s, 1H), 7.09 (dd, J = 8.8 Hz, 1.0 Hz, 1H), 6.99 (d, J = 9.2 Hz, 1H), 6.11 (q, J = 6.4 Hz, 1H), 4.48 (d, J = 11.6 Hz, 1H), 4.31 (d, J = 12.4 Hz, 1H), 3.11-3.03 (m, 2H), 3.03-2.93 (m, 1H), 2.58-2.50 (m, 1H), 2.18-1.86 (m, 4H), 1.77-1.70 (m, 5H), 1.44-1.39 (m, 1H). |

| Example 184 3-[6-[(8aR)-3,4,6,7,8,8a-hexahydro-1H-pyrrolo[1,2-a]pyrazin-2-yl]-3-pyridyl]-5-[(1R)-1-(3,5-dichloro-4-pyridyl)ethoxy]-1H-indazole | 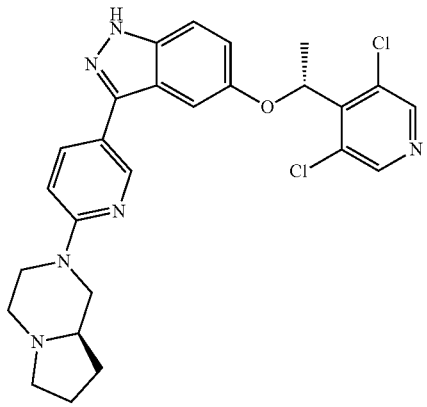 [SMILES: C[C@@H](Oc1ccc2[nH]nc(-c3ccc(N4CCN5CCC[C@@H]5C4)nc3)c2c1)c1c(Cl)cncc1Cl] | LCMS: m/z = 509.3 (M + H); 1H NMR (400 MHz, DMSO-d6) δ 13.00 (s, 1H), 8.61 (s, 2H), 8.54 (d, J = 2.0 Hz, 1H), 7.85 (dd, J = 8.8 Hz, 2.4 Hz, 1H), 7.46 (d, J = 9.2 Hz, 1H), 7.16 (d, J = 1.6 Hz, 1H), 7.01 (dd, J = 8.8 Hz, 2.4 Hz, 1H), 6.99 (d, J = 8.8 Hz, 1H), 6.11 (q, J = 6.8 Hz, 1H), 4.48 (d, J = 12.0 Hz, 1H), 4.31 (d, J = 12.0 Hz, 1H), 3.12-3.06 (m, 2H), 2.97-2.88 (m, 1H), 2.67-2.54 (m, 2H), 2.28-1.94 (m, 3H), 1.77-1.67 (m, 5H), 1.50-1.38 (m, 1H). |
|---|---|---|
| Example 185 ethyl 6-[5-[5-[(1R)-1-(3,5-dichloro-2-methyl-4-pyridyl)ethoxy]-1H-indazol-3-yl]pyrimidin-2-yl]-2,6-diazaspiro[3.3]heptane-2-carboxylate | 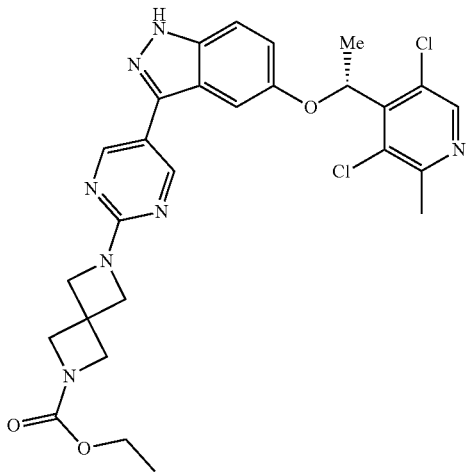 [SMILES: CCOC(=O)N1CC2(C1)CN(c1ncc(-c3n[nH]c4ccc(O[C@H](C)c5c(Cl)cnc(C)c5Cl)cc34)cn1)C2] | LCMS: m/z = 568.2 (M + H); 1H NMR (400 MHz, DMSO-d6) δ = 13.11 (s, 1H), 8.68 (s, 2H), 8.41 (s, 1H), 7.47 (d, J = 9.7 Hz, 1H), 7.12 - 7.07 (m, 2H), 6.11 (q, J = 6.6 Hz, 1H), 4.26 (s, 4H), 4.13 (br s, 4H), 4.05 - 3.98 (m, 2H), 2.57 (s, 3H), 1.75 (d, J = 6.6 Hz, 3H), 1.20 - 1.14 (m, 3H) |
| Example 186 5-[(1R)-1-(3,5-dimethylpyridazin-4-yl)ethoxy]-3-[6-(8-ethylsulfonyl-2,8-diazaspiro[3.5]nonan-2-yl)-3-pyridyl]-1H-indazole | 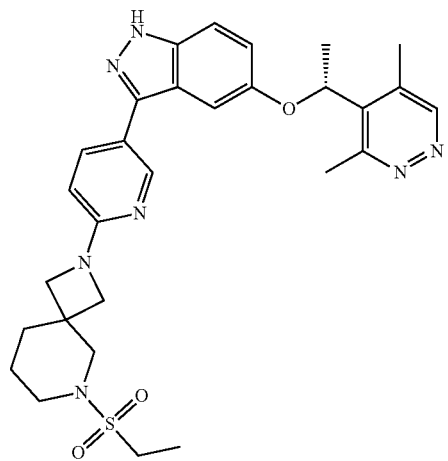 [SMILES: CCS(=O)(=O)N1CCCC2(CN(c3ccc(-c4n[nH]c5ccc(O[C@H](C)c6c(C)cnnc6C)cc45)cn3)C2)C1] | LCMS: m/z = 562.4 (M + H); 1H NMR (400 MHz, DMSO-d6) δ 12.96 (s, 1H), 8.84 (s, 1H), 8.49 (d, J = 2.0 Hz, 1H), 7.83 (dd, J = 8.8 Hz, 2.4 Hz, 1H), 7.75 (d, J = 8.8 Hz, 1H), 7.08-7.04 (m, 2H), 6.52 (d, J = 8.4 Hz, 1H), 5.87 (q, J = 6.8 Hz, 1H), 3.78-3.70 (m, 4H), 3.36 (s, 2H), 3.17-3.15 (m, 2H), 3.09 (q, J = 7.2 Hz, 2H), 2.78 (s, 3H), 2.45 (s, 3H), 1.79-1.77 (m, 2H), 1.66 (d, J = 6.8 Hz, 3H), 1.63-1.56 (m, 2H), 1.23 (t, J = 7.2 Hz, 3H). |

-continued

| Example 187 methyl 2-[5-[5-[(1R)-1-(3,5-dimethylpyridazin-4-yl)ethoxy]-1H-indazol-3-yl]-2-pyridyl]-2,8-diazaspiro[3.5]nonane-8-carboxylate | 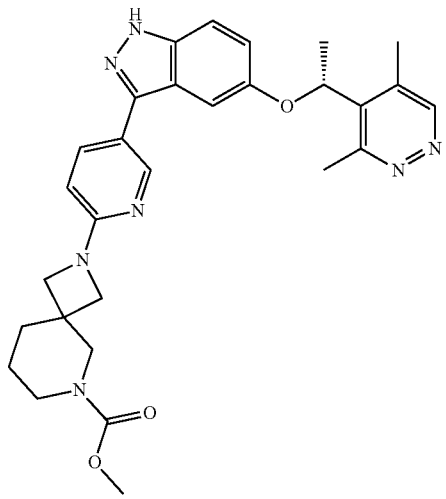 [SMILES: COC(=O)N1CCCC2(C1)CN(c1ccc(-c3n[nH]c4ccc(O[C@H](C)c5c(C)cnnc5C)cc34)cn1)C2] | LCMS: m/z = 528.5 (M + H); 1H NMR (400 MHz, DMSO-d6) δ 12.97 (s, 1H), 8.84 (s, 1H), 8.49 (d, J = 2.0 Hz, 1H), 7.83 (dd, J = 8.8 Hz, 2.4 Hz, 1H), 7.46 (d, J = 8.8 Hz, 1H), 7.07 (dd, J = 8.8 Hz, 2.4 Hz, 1H), 7.05-7.04 (m, 1H), 6.51 (d, J = 8.8 Hz, 1H), 5.87 (q, J = 7.2 Hz, 1H), 3.72 (d, J = 7.6 Hz, 2H), 3.66 (d, J = 8.4 Hz, 2H), 3.63 (s, 3H), 3.57 (s, 2H), 3.36-3.34 (m, 2H), 2.78 (s, 3H), 2.45 (s, 3H), 1.81-1.78 (m, 2H), 1.66 (d, J = 6.8 Hz, 3H), 1.51-1.50 (m, 2H). |
|---|---|---|
| Example 188 5-[(1R)-1-(3,5-dimethylpyridazin-4-yl)ethoxy]-3-[6-(8-methylsulfonyl-2,8-diazaspiro[3.5]nonan-2-yl)-3-pyridyl]-1H-indazole | 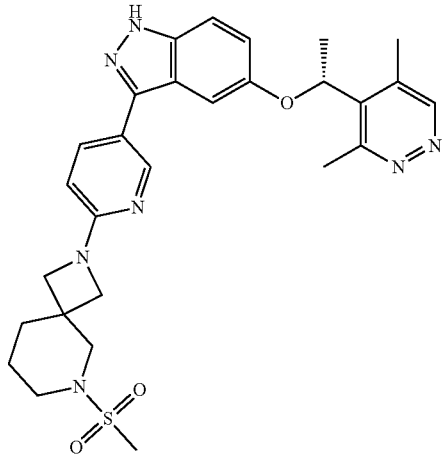 [SMILES: Cc1cnnc(C)c1[C@@H](C)Oc1ccc2[nH]nc(-c3ccc(N4CC5(CCCN(S(C)(=O)=O)C5)C4)nc3)c2c1] | LCMS: m/z = 548.4 (M + H); 1H NMR (400 MHz, DMSO-d6) δ 12.96 (s, 1H), 8.84 (s, 1H), 8.49 (d, J = 2.4 Hz, 1H), 7.83 (dd, J = 8.8 Hz, 2.4 Hz, 1H), 7.45 (d, J = 8.8 Hz, 1H), 7.08-7.05 (m, 2H), 6.53 (d, J = 8.4 Hz, 1H), 5.87 (q, J = 6.8 Hz, 1H), 3.77-3.71 (m, 4H), 3.29-3.28 (m, 2H), 3.11-3.08 (m, 2H), 2.90 (s, 3H), 2.78 (s, 3H), 2.45 (s, 3H), 1.78-1.76 (m, 2H), 1.67-1.63 (m, 5H). |
| Example 189 isopropyl 2-[5-[5-[(1R)-1-(3,5-dimethylpyridazin-4-yl)ethoxy]-1H-indazol-3-yl]-2-pyridyl]-2,8-diazaspiro[3.5]nonane-8-carboxylate | 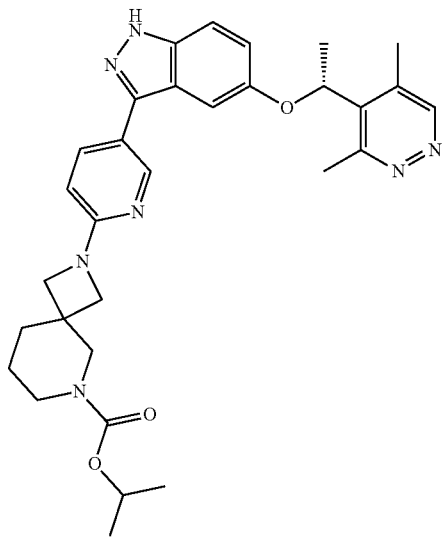 | LCMS: m/z = 566.4 (M + H); 1H NMR (400 MHz, DMSO-d6) δ 12.96 (s, 1H), 8.84 (s, 1H), 8.49 (d, J = 2.0 Hz, 1H), 7.81 (dd, J = 8.4 Hz, 2.0 Hz, 1H), 7.45 (d, J = 8.8 Hz, 1H), 7.08-7.04 (m, 2H), 6.51 (d, J = 8.8 Hz, 1H), 5.87 (q, J = 6.8 Hz, 1H), 4.84-4.78 (m, 1H), 3.74-3.3.66 (m, 4H), 3.57 (s, 2H), 3.36-3.32 (m, 2H), 2.78 (s, 3H), 2.45 (s, 3H), 1.82-1.79 (m, 2H), 1.63 (d, J = 6.8 Hz, 3H), 1.52-1.23 (m, 2H), 1.87 (d, J = 6.4 Hz, 6H). |

| | | |
|---|---|---|
| Example 190<br>ethyl 6-[5-[5-[(1R)-1-(3,5-dichloro-2-methyl-4-pyridyl)ethoxy]-1H-indazol-3-yl]-2-pyridyl]-2,6-diazaspiro[3.3]heptane-2-carboxylate | 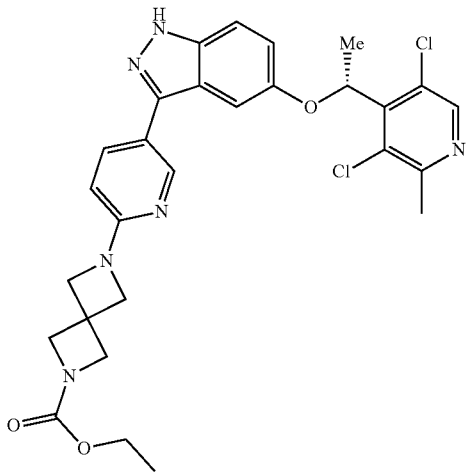 [SMILES: CCOC(=O)N1CC2(C1)CN(c1ccc(-c3n[nH]c4ccc(O[C@H](C)c5c(Cl)cnc(C)c5Cl)cc34)cn1)C2] | LCMS: m/z = 567 (M + H); 1H NMR (400 MHz, DMSO-d6) δ = 12.99 (s, 1H), 8.43 (s, 1H), 8.40 (d, J = 1.8 Hz, 1H), 7.86 (dd, J = 2.3, 8.6 Hz, 1H), 7.45 (d, J = 9.2 Hz, 1H), 7.10 - 7.04 (m, 2H), 6.51 (d, J = 8.1 Hz, 1H), 6.09 (q, J = 6.6 Hz, 1H), 4.15 (s, 4H), 4.13 (br s, 4H), 4.02 (q, J = 7.1 Hz, 2H), 2.58 (s, 3H), 1.75 (d, J = 6.6 Hz, 3H), 1.17 (t, J = 7.1 Hz, 3H) |
| Example 191<br>5-[(1R)-1-(3,5-dichloro-4-pyridyl)ethoxy]-6-methoxy-3-[6-(2-methylsulfonyl-2,6-diazaspiro[3.3]heptan-6-yl)-3-pyridyl]-1H-indazole | 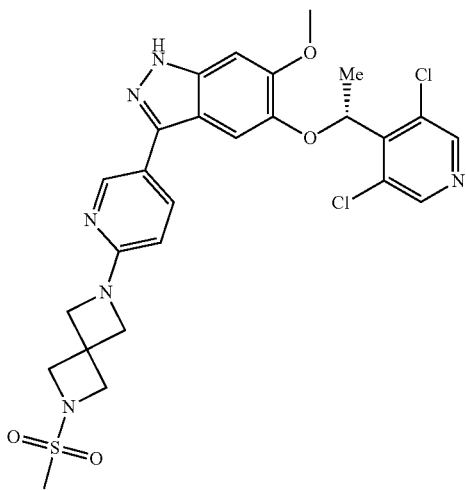 [SMILES: COc1cc2[nH]nc(-c3ccc(N4CC5(C4)CN(S(C)(=O)=O)C5)nc3)c2cc1O[C@H](C)c1c(Cl)cncc1Cl] | LCMS: m/z = 589.1 (M + H); 1H NMR (400 MHz, DMSO-d6) δ = 12.81 (s, 1H), 8.60 (s, 2H), 8.45 (d, J = 1.8 Hz, 1H), 7.81 (dd, J = 2.3, 8.6 Hz, 1H), 7.06 (s, 1H), 6.99 (s, 1H), 6.52 (d, J = 8.1 Hz, 1H), 5.99 - 5.93 (m, 1H), 4.16 (s, 4H), 4.11 (s, 4H), 3.86 (s, 3H), 3.02 (s, 3H), 1.75 (d, J = 6.7 Hz, 3H) |
| Example 192<br>5-[(1S)-1-(3,5-dimethylpyridazin-4-yl)ethoxy]-6-methoxy-3-[6-(2-methylsulfonyl-2,6-diazaspiro[3.3]heptan-6-yl)-3-pyridyl]-1H-indazole | 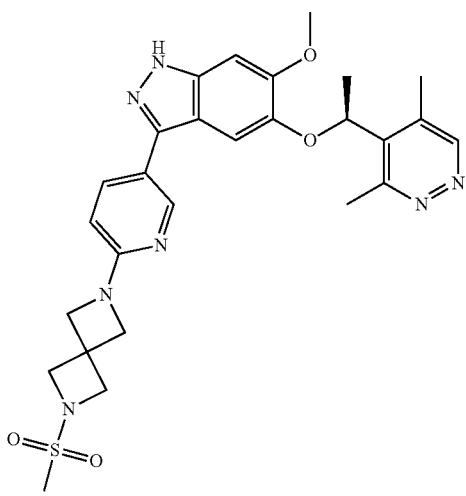 [SMILES: COc1cc2[nH]nc(-c3ccc(N4CC5(C4)CN(S(C)(=O)=O)C5)nc3)c2cc1O[C@@H](C)c1c(C)cnnc1C] | LCMS: m/z = 550.3 (M + H); 1H NMR (400 MHz, DMSO-d6) δ 12.78 (s, 1H), 8.84 (s, 1H), 8.48 (d, J = 2.0 Hz, 1H), 7.83 (dd, J = 8.8 Hz, 2.4 Hz, 1H), 7.02 (s, 1H), 6.99 (s, 1H), 6.52-6.49 (m, 1H), 5.79 (q, J = 6.8 Hz, 1H), 4.17 (s, 4H), 4.11 (s, 4H), 3.87 (s, 3H), 3.03 (s, 3H), 2.77 (s, 3H), 2.43 (s, 3H), 1.65 (d, J = 6.8 Hz, 3H) |

| | | |
|---|---|---|
| Example 193<br>ethyl 6-[5-[5-[(1S)-1-(3,5-dichloro-2-fluoro-4-pyridyl)ethoxy]-1H-indazol-3-yl]-2-pyridyl]-2,6-diazaspiro[3.3]heptane-2-carboxylate | 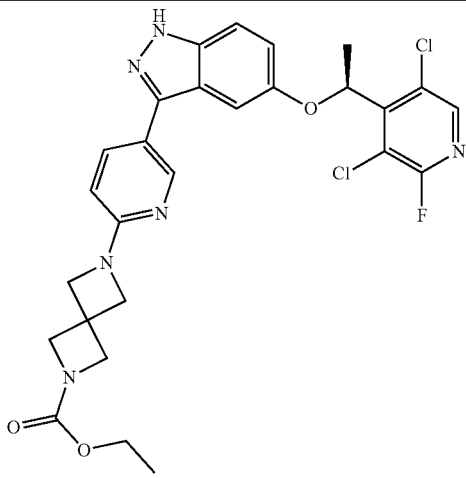 | LCMS: m/z = 571.2 (M + H); 1H NMR (400 MHz,DMSO-d6) δ 13.02 (s, 1H), 8.52 (d, J = 2.0 Hz, 1H), 8.34 (s, 1H), 7.88 (dd, J = 1.6 Hz, 8.8 Hz, 1H), 7.46 (d, J = 8.8 Hz, 1H), 7.19 (s, 1H), 7.09 (dd, J = 8.8 Hz, 2.0 Hz, 1H), 6.51 (d, J = 8.8 Hz, 1H), 6.13 (q, J = 6.8 Hz, 1H), 4.19-4.09 (m, 8H), 4.01 (q, J = 7.2 Hz, 2H ), 1.76 (d, J = 6.8 Hz, 3H), 1.7 (t, J = 7.2 Hz, 3H). |
| Example 194<br>5-[(1R)-1-(3,5-dimethylpyridazin-4-yl)ethoxy]-6-methoxy-3-[6-(2-methylsulfonyl-2,6-diazaspiro[3.3]heptan-6-yl)-3-pyridyl]-1H-indazole | 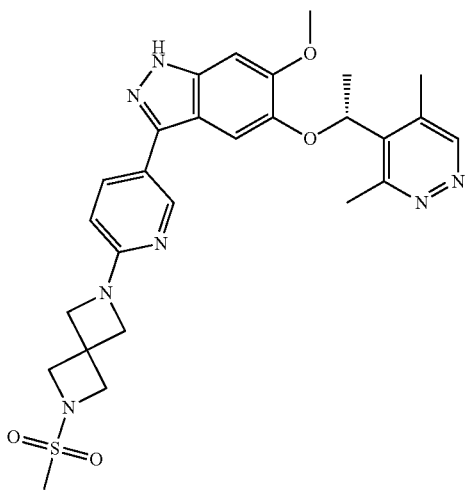 [SMILES: COc1cc2[nH]nc(-c3ccc(N4CC5(C4)CN(S(C)(=O)=O)C5)nc3)c2cc1O[C@H](C)c1c(C)cnnc1C] | LCMS: m/z = 550.2 (M + H); 1H NMR (400 MHz, DMSO-d6) δ 12.78 (s, 1H), 8.84 (s, 1H), 8.49 (d, J = 2.0 Hz, 1H), 7.83 (dd, J = 8.4 Hz, 2.4 Hz, 1H), 7.01 (s, 1H), 6.99 (s, 1H), 6.50 (d, J = 8.8 Hz, 1H), 5.79 (q, J = 6.8 Hz, 1H), 4.17 (s, 4H), 4.11 (s, 4H), 3.87 (s, 3H), 3.03 (s, 3H), 2.77 (s, 3H), 2.43 (s, 3H), 1.65 (d, J = 6.8 Hz, 3H). |
| Example 195<br>methyl 6-[5-[5-[(1R)-1-(3,5-dichloro-2-fluoro-4-pyridyl)ethoxy]-1H-indazol-3-yl]-2-pyridyl]-2,6-diazaspiro[3.3]heptane-2-carboxylate | 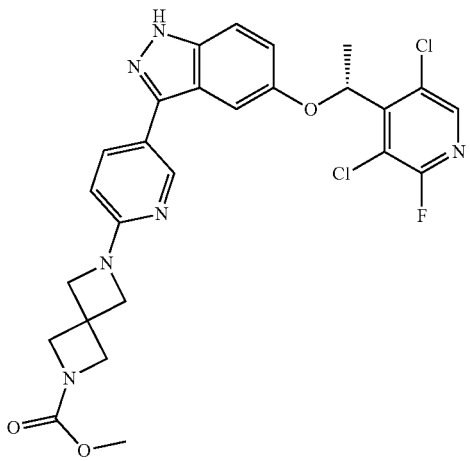 [SMILES: COC(=O)N1CC2(C1)CN(c1ccc(-c3n[nH]c4ccc(O[C@H](C)c5c(Cl)cnc(F)c5Cl)cc34)cn1)C2] | LCMS: m/z = 557.2 (M + H); 1H NMR (400 MHz, DMSO-d6) δ 13.01 (s, 1H), 8.52 (d, J = 2.0 Hz, 1H), 8.34 (s, 1H), 7.90 (dd, J = 8.8 Hz, 2.4 Hz, 1H), 7.45 (d, J = 9.2 Hz, 1H), 7.20 (d, J = 2.0 Hz, 1H), 7.10 (dd, J = 9.2 Hz, 2.4 Hz, 1H), 6.52 (d, J = 8.4 Hz, 1H), 6.14 (q, J = 6.4 Hz, 1H), 4.14 (s, 8H), 3.57 (s, 3H), 1.77 (d, J = 6.4 Hz, 3H). |

| Example | Structure | Data |
|---|---|---|
| Example 196<br>ethyl 6-[5-[5-[(1R)-1-(3,5-dichloro-2-fluoro-4-pyridyl)ethoxy]-1H-indazol-3-yl]-2-pyridyl]-2,6-diazaspiro[3.3]heptane-2-carboxylate | 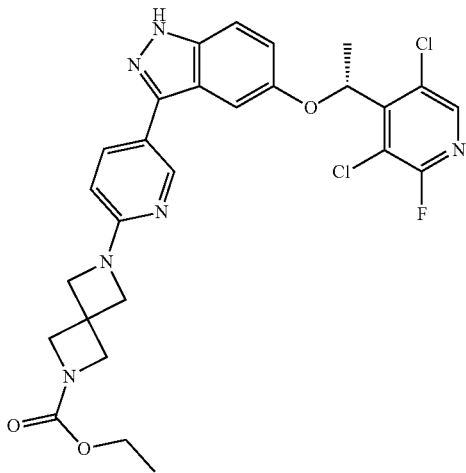 [SMILES: CCOC(=O)N1CC2(C1)CN(c1ccc(-c3n[nH]c4ccc(O[C@H](C)c5c(Cl)cnc(F)c5Cl)cc34)cn1)C2] | LCMS: m/z = 571.3 (M + H); 1H NMR (400 MHz, DMSO-d6) δ 13.03 (s, 1H), 8.52 (d, J = 1.6 Hz, 1H), 8.34 (s, 1H), 7.89 (dd, J = 8.8 Hz, 2.4 Hz, 1H), 7.45 (d, J = 9.2 Hz, 1H), 7.20 (d, J = 2.0 Hz, 1H), 7.10 (dd, J = 9.2 Hz, 2.4 Hz, 1H), 6.52 (d, J = 8.0 Hz, 1H), 6.14 (q, J = 6.8 Hz, 1H), 4.15-4.13 (m, 8H), 4.00 (q, J = 6.8 Hz, 2H), 1.77 (d, J = 6.4 Hz, 3H), 1.72 (t, J = 7.2 Hz, 3H). |
| Example 197<br>5-[(1R)-1-(3,5-dichloro-2-fluoro-4-pyridyl)ethoxy]-3-[6-(2-methylsulfonyl-2,6-diazaspiro[3.3]heptan-6-yl)-3-pyridyl]-1H-indazole | 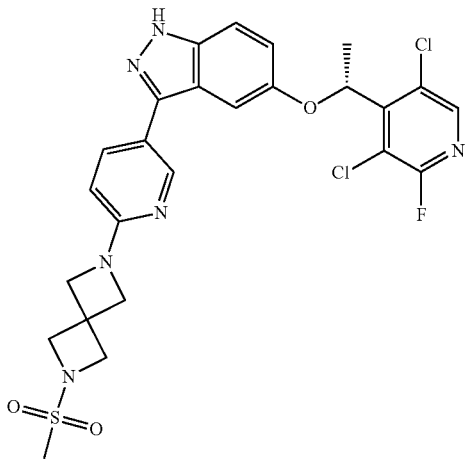 [SMILES: C[C@@H](Oc1ccc2[nH]nc(-c3ccc(N4CC5(C4)CN(S(C)(=O)=O)C5)nc3)c2c1)c1c(Cl)cnc(F)c1Cl] | LCMS: m/z = 577.2 (M + H); 1H NMR (400 MHz, DMSO-d6) δ 13.05 (s, 1H), 8.52 (d, J = 2.0 Hz, 1H), 8.34 (s, 1H), 7.94 (d, J = 8.0 Hz, 1H), 7.48 (d, J = 9.2 Hz, 1H), 7.20 (d, J = 1.6 Hz, 1H), 7.10 (dd, J = 9.2 Hz, 2.4 Hz, 1H), 6.57 (d, J = 8.4 Hz, 1H), 6.14 (q, J = 6.4 Hz, 1H), 4.19 (s, 4H), 4.12 (s, 4H), 3.03 (s, 3H), 1.76 (d, J = 6.8 Hz, 3H). |
| Example 198<br>methyl 6-[5-[5-[(1S)-1-(3,5-dichloro-2-fluoro-4-pyridyl)ethoxy]-1H-indazol-3-yl]-2-pyridyl]-2,6-diazaspiro[3.3]heptane-2-carboxylate | 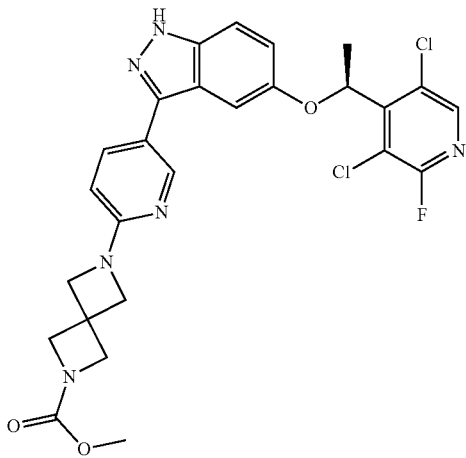 [SMILES: COC(=O)N1CC2(C1)CN(c1ccc(-c3n[nH]c4ccc(O[C@@H](C)c5c(Cl)cnc(F)c5Cl)cc34)cn1)C2] | LCMS: m/z = 557.1 (M + H); 1H NMR (400 MHz, DMSO-d6) δ 13.02 (s, 1H), 8.52 (d, J = 1.6 Hz, 1H), 8.34 (d, J = 1.2 Hz, 1H), 7.88 (dd, J = 8.8 Hz, 2.4 Hz, 1H), 7.46 (d, J = 8.8 Hz, 1H), 7.19 (d, J = 2.0 Hz, 1H), 7.09 (dd, J = 6.8 Hz, 2.4 Hz, 1H), 6.50 (d, J = 8.4 Hz, 1H), 6.13 (q, J = 6.8 Hz, 1H), 4.14 (s, 8H), 3.56 (s, 3H), 1.76 (d, J = 6.8 Hz, 3H). |

| Example 199<br>5-[(1S)-1-(3,5-dichloro-2-fluoro-4-pyridyl)ethoxy]-3-[6-(2-methylsulfonyl-2,6-diazaspiro[3.3]heptan-6-yl)-3-pyridyl]-1H-indazole | 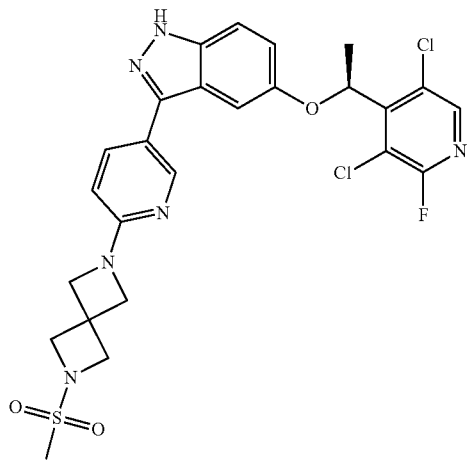 [SMILES: C[C@H](Oc1ccc2[nH]nc(-c3ccc(N4CC5(C4)CN(S(C)(=O)=O)C5)nc3)c2c1)c1c(Cl)cnc(F)c1Cl] | LCMS: m/z = 577.1 (M + H); 1H NMR (400 MHz, DMSO-d6) δ 13.02 (s, 1H), 8.53 (d, J = 2.0 Hz, 1H), 8.34 (s, 1H), 7.89 (dd, J = 8.4 Hz, 2.0 Hz, 1H), 7.46 (d, J = 9.2 Hz, 1H), 7.20 (d, J = 1.6 Hz, 1H), 7.09 (dd, J = 9.2 Hz, 2.4 Hz, 1H), 6.53 (d, J = 8.8 Hz, 1H), 6.13 (q, J = 6.4 Hz, 1H), 4.17 (s, 4H), 4.12 (s, 4H), 3.03 (s, 3H), 1.76 (d, J = 6.4 Hz, 3H). |
|---|---|---|
| Example 200<br>5-[(1R)-1-(3,5-dimethylpyridazin-4-yl)ethoxy]-4-methoxy-3-[6-(2-methylsulfonyl-2,6-diazaspiro[3.3]heptan-6-yl)-3-pyridyl]-1H-indazole | 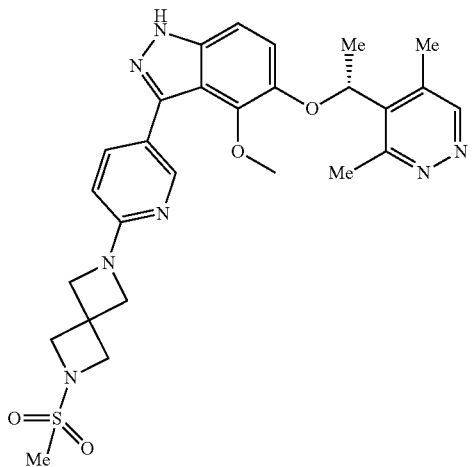 [SMILES: COc1c(O[C@H](C)c2c(C)cnnc2C)ccc2[nH]nc(-c3ccc(N4CC5(C4)CN(S(C)(=O)=O)C5)nc3)c12] | LCMS: m/z = 550.3 (M + H); 1H-NMR (400 MHz, DMSO-d6) δ 13.09 (s, 1H), 8.88 (s, 1H), 8.52 (d, J = 1.6 Hz, 1H), 7.96 (dd, J = 8.4 Hz, 2.0 Hz, 1H), 7.15 (d, J = 8.8 Hz, 1H), 6.97 (d, J = 8.8 Hz, 1H), 6.51 (d, J = 8.8 Hz, 1H), 5.65 (q, J = 7.2 Hz, 1H), 4.16 (s, 4H), 4.11 (s, 4H), 3.55 (s, 3H), 3.02 (s, 3H), 2.76 (s, 3H), 2.46 (s, 3H), 1.65 (d, J = 6.8 Hz, 3H). |
| Example 201<br>6-[5-[5-[(1R)-1-(3,5-dichloro-2-methyl-4-pyridyl)ethoxy]-1H-indazol-3-yl]-2-pyridyl]-2-oxa-6-azaspiro[3.3]heptane | 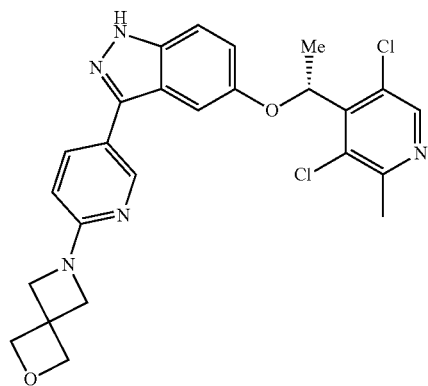 [SMILES: Cc1ncc(Cl)c([C@@H](C)Oc2ccc3[nH]nc(-c4ccc(N5CC6(COC6)C5)nc4)c3c2)c1Cl] | LCMS: m/z = 496.1 (M + H); 1H NMR (400 MHz, DMSO-d6) δ = 12.98 (s, 1H), 8.43 (s, 1H), 8.40 (d, J = 1.8 Hz, 1H), 7.86 (dd, J = 2.3, 8.6 Hz, 1H), 7.45 (d, J = 8.9 Hz, 1H), 7.12 - 7.02 (m, 2H), 6.51 (d, J = 8.6 Hz, 1H), 6.08 (q, J = 6.7 Hz, 1H), 4.75 (s, 4H), 4.18 (s, 4H), 2.58 (s, 3H), 1.75 (d, J = 6.6 Hz, 3H). |

| | | |
|---|---|---|
| Example 202<br>6-[5-[5-[(1R)-1-(3,5-dimethylpyridazin-4-yl)ethoxy]-6-methoxy-1H-indazol-3-yl]-2-pyridyl]-2-oxa-6-azaspiro[3.3]heptane | 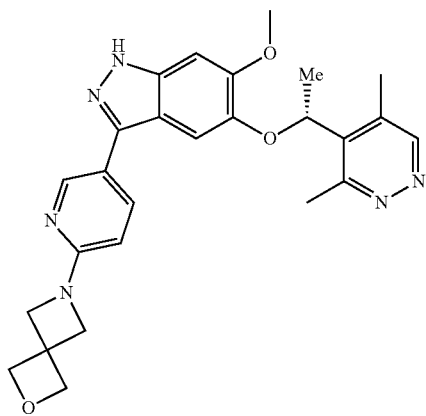 [SMILES: COc1cc2[nH]nc(-c3ccc(N4CC5(COC5)C4)nc3)c2cc1O[C@H](C)c1c(C)cnnc1C] | LCMS: m/z = 473.2 (M + H); 1H NMR (400 MHz, DMSO-d6) δ 12.78 (s, 1H), 8.84 (s, 1H), 8.47 (d, J = 2.0 Hz, 1H), 7.81 (dd, J = 8.8 Hz, 2.0 Hz, 1H), 7.01 (s, 1H), 6.98 (s, 1H), 6.50 (d, J = 8.4 Hz, 1H), 5.89 (q, J = 6.4 Hz, 1H), 4.75 (s, 4H), 4.18 (s, 4H), 3.87 (s, 3H), 2.77 (s, 3H), 2.43 (s, 3H), 1.65 (d, J = 6.8 Hz, 3H). |
| Example 203<br>6-[5-[5-[(1R)-1-(3,5-dichloro-2-fluoro-4-pyridyl)ethoxy]-1H-indazol-3-yl]-2-pyridyl]-2-oxa-6-azaspiro[3.3]heptane | 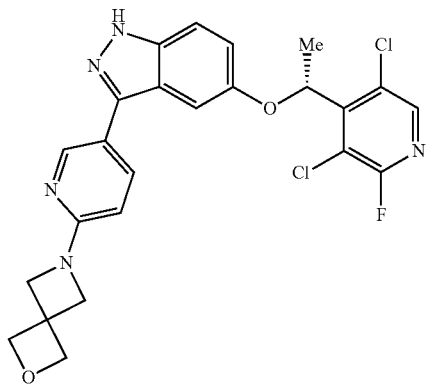 [SMILES: C[C@@H](Oc1ccc2[nH]nc(-c3ccc(N4CC5(COC5)C4)nc3)c2c1)c1c(Cl)cnc(F)c1Cl] | LCMS: m/z = 500.13 (M + H); 1H NMR (400 MHz, DMSO-d6) δ 12.98 (s, 1H), 8.49 (s, 1H), 8.30 (s, 1H), 7.85 (dd, J = 8.4 Hz, 2.4 Hz, 1H), 7.44 (d, J = 9.2 Hz, 1H), 7.16 (s, 1H), 7.06 (dd, J = 9.2 Hz, 2.4 Hz, 1H), 6.48 (d, J = 8.4 Hz, 1H), 6.11 (q, J = 6.8 Hz, 1H), 4.72 (s, 4H), 4.14 (s, 4H), 1.73 (d, J = 6.8 Hz, 3H). |
| Example 204<br>(R)-2-(5-(5-(1-(3,5-dichloro-2-fluoropyridin-4-yl)ethoxy)-1H-indazol-3-yl)pyridin-2-yl)-6-oxa-2-azaspiro[3.4]octane | 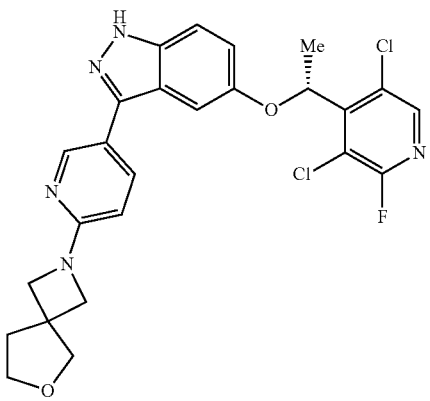 [SMILES: C[C@@H](Oc1ccc2[nH]nc(-c3ccc(N4CC5(CCOC5)C4)nc3)c2c1)c1c(Cl)cnc(F)c1Cl] | LCMS: m/z = 514.1 (M + H); 1H NMR (400 MHz, DMSO-d6) δ 13.01 (s, 1H), 8.53 (d, J = 2.0 Hz, 1H), 8.34 (s, 1H), 7.89 (dd, J = 8.4 Hz, 2.0 Hz, 1H), 7.46 (d, J = 8.8 Hz, 1H), 7.20 (d, J = 2.0 Hz, 1H), 7.09 (dd, J = 9.2 Hz, 2.8 Hz, 1H), 6.52 (d, J = 8.8 Hz, 1H), 6.13 (q, J = 6.8 Hz, 1H), 3.99 (s, 4H), 3.84 (s, 2H), 3.76 (t, J = 7.2 Hz, 2H), 2.18 (t, J = 7.2 Hz, 2H), 1.76 (d, J = 6.8 Hz, 3H). |
| Example 205<br>6-[5-[5-[(1R)-1-(3,5-dimethylpyridazin-4-yl)ethoxy]-1H-indazol-3-yl]-2-pyridyl]-2-oxa-6-azaspiro[3.3]heptane | 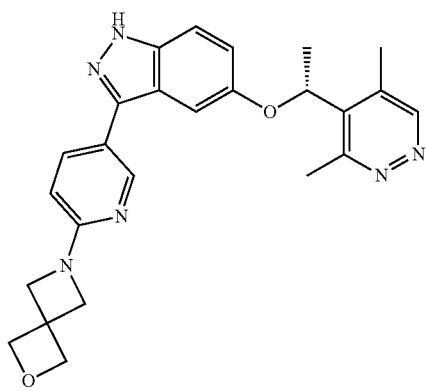 [SMILES: Cc1cnnc(C)c1[C@@H](C)Oc1ccc2[nH]nc(-c3ccc(N4CC5(COC5)C4)nc3)c2c1] | LCMS: m/z = 443.3 (M + H); 1H NMR (400 MHz, DMSO-d6) δ 12.98 (s, 1H), 8.83 (s, 1H), 8.50 (d, J = 2.0 Hz, 1H), 7.84 (dd, J = 8.4 Hz, 2.0 Hz, 1H), 7.46 (d, J = 9.2 Hz, 1H), 7.07 (dd, J = 9.2 Hz, 2.4 Hz, 1H), 7.03 (d, J = 2.0 Hz, 1H), 6.51 (d, J = 8.4 Hz, 1H), 5.87 (q, J = 6.8 Hz, 1H), 4.76 (s, 4H), 4.18 (s, 4H), 2.78 (s, 3H), 2.44 (s, 3H), 1.67 (d, J = 6.8 Hz, 3H). |

| Example 206
(R)-2-(5-(5-(1-(3,5-dimethylpyridazin-4-yl)ethoxy)-1H-indazol-3-yl)pyridin-2-yl)-6-oxa-2-azaspiro[3.4]octane | 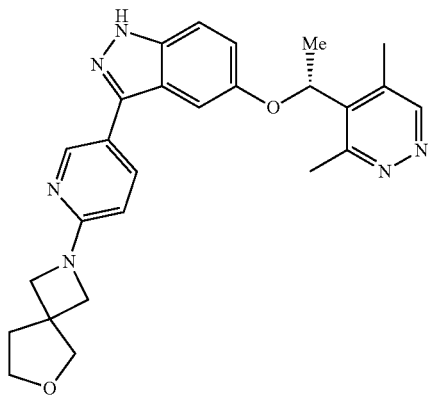 [SMILES: Cc1cnnc(C)c1[C@@H](C)Oc1ccc2[nH]nc(-c3ccc(N4CC5(CCOC5)C4)nc3)c2c1] | LCMS: m/z = 457.3 (M + H); 1H NMR (400 MHz, DMSO-d6) δ 12.98 (s, 1H), 8.83 (s, 1H), 8.50 (d, J = 2.4 Hz, 1H), 7.84 (dd, J = 8.4 Hz, 2.0 Hz 1H), 7.45 (d, J = 8.8 Hz, 1H), 7.07 (dd, J = 8.8 Hz, 2.4 Hz, 1H), 7.05-7.03 (m, 1H), 6.51 (d, J = 8.8 Hz, 1H), 5.87 (q, J = 6.4 Hz, 1H), 3.99 (s, 4H), 3.85 (s, 2H), 3.76 (t, J = 6.8 Hz, 2H), 2.78 (s, 3H), 2.44 (s, 3H), 2.19 (t, J = 6.8 Hz, 2H), 1.66 (d, J = 6.4 Hz, 3H). |
|---|---|---|
| Example 207
5-[(1R)-1-(3,5-dichloro-2-methyl-4-pyridyl)ethoxy]-6-methoxy-3-[6-(2-methylsulfonyl-2,6-diazaspiro[3.3]heptan-6-yl)-3-pyridyl]-1H-indazole | 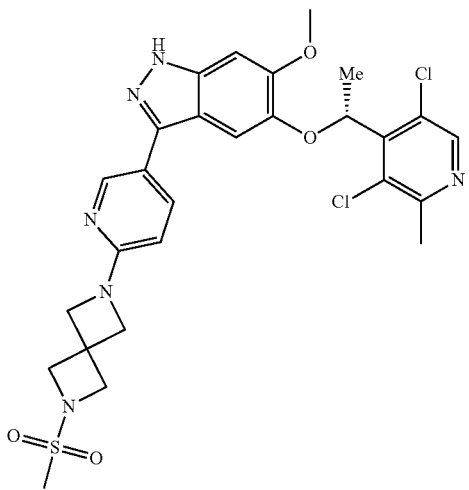 [SMILES: COc1cc2[nH]nc(-c3ccc(N4CC5(C4)CN(S(C)(=O)=O)C5)nc3)c2cc1O[C@H](C)c1c(Cl)cnc(C)c1Cl] | LCMS: m/z = 603.1 (M + H); 1H NMR (400 MHz, DMSO-d6) δ = 12.80 (s, 1H), 8.45 (s, 1H), 8.33 (d, J = 2.0 Hz, 1H), 7.82 (dd, J = 2.3, 8.6 Hz, 1H), 6.98 (s, 1H), 6.95 (s, 1H), 6.50 (d, J = 8.7 Hz, 1H), 5.96 (q, J = 6.7 Hz, 1H), 4.16 (s, 4H), 4.11 (s, 4H), 3.86 (s, 3H), 3.02 (s, 3H), 2.60 (s, 3H), 1.75 (d, J = 6.7 Hz, 3H) |
| Example 208
1-[5-[5-[(1R)-1-(3,5-dichloro-2-methyl-4-pyridyl)ethoxy]-6-methoxy-1H-indazol-3-yl]-2-pyridyl]azetidin-3-ol | 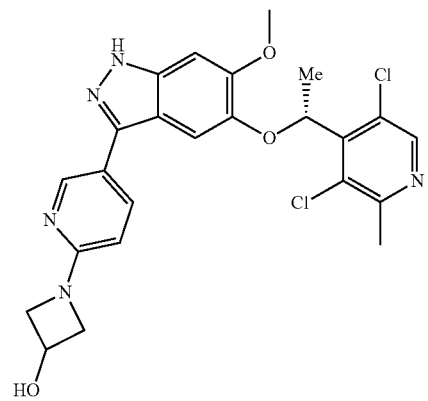 [SMILES: COc1cc2[nH]nc(-c3ccc(N4CC(O)C4)nc3)c2cc1O[C@H](C)c1c(Cl)cnc(C)c1Cl] | LCMS: m/z = 500.1 (M + H); 1H NMR (400 MHz, DMSO-d6) δ = 12.78 (s, 1H), 8.45 (s, 1H), 8.33 (d, J = 1.8 Hz, 1H), 7.79 (dd, J = 2.3, 8.6 Hz, 1H), 6.98 (s, 1H), 6.95 (s, 1H), 6.49 (d, J = 8.6 Hz, 1H), 5.96 (q, J = 6.7 Hz, 1H), 5.67 (d, J = 6.6 Hz, 1H), 4.65 - 4.58 (m, 1H), 4.22 (t, J = 7.5 Hz, 2H), 3.86 (s, 3H), 3.74 (dd, J = 4.6, 8.6 Hz, 2H), 3.31 - 3.28 (m, 2H), 2.69 (s, 3H), 2.60 (s, 3H), 2.20 - 2.14 (m, 2H), 1.94 - 1.86 (m, 2H), 1.75 (d, J = 6.7 Hz, 3H) |

-continued

| Example 209<br>(3R)-1-[5-[5-[(1R)-1-(3,5-dichloro-2-methyl-4-pyridyl)ethoxy]-6-methoxy-1H-indazol-3-yl]-2-pyridyl]pyrrolidin-3-ol | 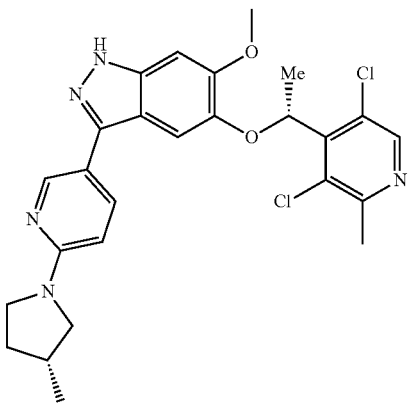 | LCMS: m/z = 414.2 (M + H); 1H NMR (400 MHz, DMSO-d6) δ = 12.72 (br s, 1H), 8.45 (s, 1H), 8.31 (d, J = 2.1 Hz, 1H), 7.78 (dd, J = 2.4, 8.7 Hz, 1H), 6.98 (s, 1H), 6.94 (s, 1H), 6.53 (d, J = 8.7 Hz, 1H), 5.96 (q, J = 6.7 Hz, 1H), 4.98 (d, J = 3.5 Hz, 1H), 4.42 (br s, 1H), 3.87 (s, 3H), 3.58 - 3.48 (m, 3H), 3.40 - 3.35 (m, 1H), 2.62 (s, 3H), 2.06 (dtd, J = 4.7, 8.5, 12.9 Hz, 1H), 1.96 - 1.89 (m, 1H), 1.75 (d, J = 6.7 Hz, 3H) |
| --- | --- | --- |
| Example 210<br>5-[(1R)-1-(3,5-dichloro-2-methyl-4-pyridyl)ethoxy]-3-[6-(3-methoxy-3-methyl-azetidin-1-yl)-3-pyridyl]-1H-indazole | 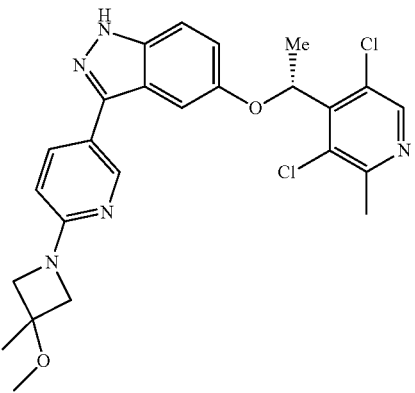 [SMILES: COC1(C)CN(c2ccc(-c3n[nH]c4ccc(O[C@H](C)c5c(Cl)cnc(C)c5Cl)cc34)cn2)C1] | LCMS: m/z = 498.1 (M + H); 1H NMR (400 MHz, DMSO-d6) δ = 13.00 (br s, 1H), 8.43 (s, 1H), 8.41 (d, J = 1.8 Hz, 1H), 7.89 (dd, J = 2.2, 8.6 Hz, 1H), 7.46 (d, J = 8.9 Hz, 1H), 7.11 - 7.05 (m, 2H), 6.57 (d, J = 8.6 Hz, 1H), 6.12 - 6.06 (m, 1H), 3.96 (d, J = 8.6 Hz, 2H), 3.86 (d, J = 8.6 Hz, 2H), 3.24 - 3.22 (m, 3H), 2.57 (s, 3H), 1.75 (d, J = 6.7 Hz, 3H), 1.51 (s, 3H) |
| Example 211<br>6-[5-[5-[(1R)-1-(3,5-dichloro-2-methyl-4-pyridyl)ethoxy]-6-methoxy-1H-indazol-3-yl]-2-pyridyl]-2-oxa-6-azaspiro[3.3]heptane | 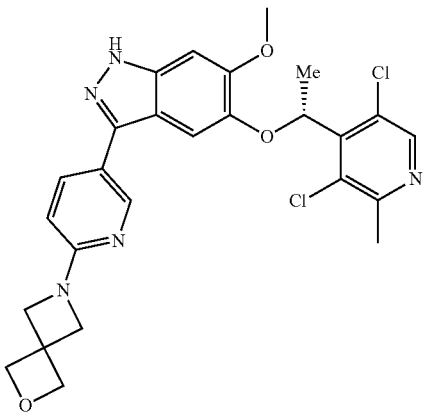 [SMILES: COc1cc2[nH]nc(-c3ccc(N4CC5(COC5)C4)nc3)c2cc1O[C@H](C)c1c(Cl)cnc(C)c1Cl] | LCMS: m/z = 526.1 (M + H); 1H NMR (400 MHz, DMSO-d6) δ = 12.78 (br s, 1H), 8.45 (s, 1H), 8.33 (d, J = 2.0 Hz, 1H), 7.80 (dd, J = 2.3, 8.7 Hz, 1H), 6.98 (s, 1H), 6.95 (s, 1H), 6.49 (dd, J = 0.6, 8.6 Hz, 1H), 5.96 (q, J = 6.7 Hz, 1H), 4.75 (s, 4H), 4.17 (s, 4H), 3.86 (s, 3H), 2.60 (s, 3H), 1.75 (d, J = 6.6 Hz, 3H) |
| Example 212<br>3-[6-(2-azaspiro[3.3]-heptan-2-yl)-3-pyridyl]-5-[(1R)-1-(3,5-dichloro-2-methyl-4-pyridyl)ethoxy]-1H-indazole | 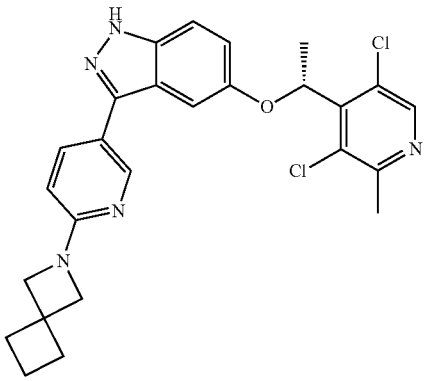 [SMILES: Cc1ncc(Cl)c([C@@H](C)Oc2ccc3[nH]nc(-c4ccc(N5CC6(CCC6)C5)nc4)c3c2)c1Cl] | LCMS: m/z = 494.2 (M + H); 1H NMR (400 MHz, DMSO-d6) δ = 12.96 (s, 1H), 8.43 (s, 1H), 8.38 (d, J = 1.8 Hz, 1H), 7.83 (dd, J = 2.3, 8.6 Hz, 1H), 7.45 (d, J = 9.0 Hz, 1H), 7.10 - 7.04 (m, 2H), 6.46 (d, J = 8.6 Hz, 1H), 6.08 (q, J = 6.6 Hz, 1H), 3.97 (s, 4H), 2.58 (s, 3H), 2.21 (t, J = 7.6 Hz, 4H), 1.84 (quin, J = 7.5 Hz, 2H), 1.75 (d, J = 6.6 Hz, 3H) |

-continued

| Example 213
3-(5-(5-((R)-1-(3,5-dimethylpyridazin-4-yl)ethoxy)-6-methoxy-1H-indazol-3-yl)pyridin-2-yl)-6-ethyl-3,6-diazabicyclo[3.1.1]heptane | 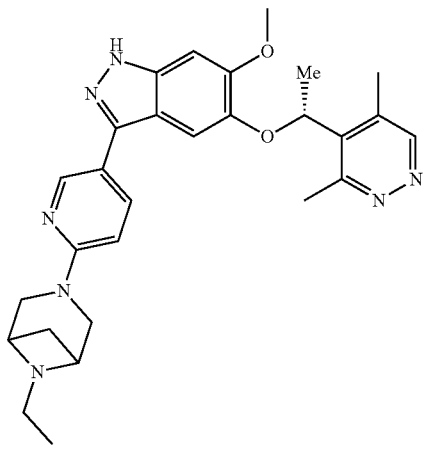 [SMILES: CCN1C2CC1CN(c1ccc(-c3n[nH]c4cc(OC)c(O[C@H](C)c5c(C)cnnc5C)cc34)cn1)C2] | LCMS: m/z = 500.2 (M + H); 1H-NMR (400 MHz, DMSO-d6) δ 12.76 (s, 1H), 8.85 (d, J = 3.2 Hz, 1H), 8.53 (s, 1H), 7.84 (d, J = 8.0 Hz, 1H), 7.03 (s, 1H), 7.00 (s, 1H), 6.73 (d, J = 8.8 Hz, 1H), 5.82 (q, J = 6.0 Hz, 1H), 3.87 (s, 3H), 3.68-3.63 (m, 4H), 3.54-3.46 (m, 2H), 2.78 (s, 3H), 2.45-2.43 (m, 4H), 2.36-2.30 (m, 2H), 1.65 (d, J = 2.8 Hz, 3H), 1.55 (d, J = 8.4 Hz, 1H), 0.94 (t, J = 6.8 Hz, 3H). |
| Example 214
1-(3-(5-(5-((R)-1-(3,5-dimethylpyridazin-4-yl)ethoxy)-6-methoxy-1H-indazol-3-yl)-3-methylpyridin-2-yl)-3,6-diazabicyclo[3.1.1]heptan-6-yl)-2-methylpropan-2-ol | 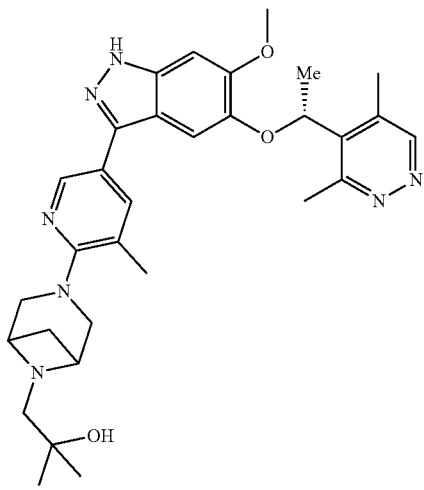 [SMILES: COc1cc2[nH]nc(-c3cnc(N4CC5CC(C4)N5CC(C)(C)O)c(C)c3)c2cc1O[C@H](C)c1c(C)cnnc1C] | LCMS: m/z = 558.4 (M + H); 1H-NMR (400 MHz, DMSO-d6) δ 12.80 (s, 1H), 8.84 (s, 1H), 8.40 (d, J = 1.6 Hz, 1H), 7.61 (s, 1H), 7.00 (s, 1H), 6.97 (s, 1H), 5.81 (q, J = 6.8 Hz, 1H), 4.12 (brs, 1H), 4.04-3.96 (m, 2H), 3.88 (s, 3H), 3.72-3.60 (m, 4H), 2.78 (s, 3H), 2.56-2.52 (m, 1H), 2.49 (s, 3H), 2.43 (s, 3H), 2.30 (s, 2H), 1.71-1.61 (m, 4H), 1.10 (s, 6H). |
| Example 215
2-[5-[5-[(1R)-1-(3,5-dichloro-2-methyl-4-pyridyl)ethoxy]-6-methoxy-1H-indazol-3-yl]-2-pyridyl]-1,3,4,7,8,8a-hexahydropyrrolo[1,2-a]pyrazin-6-one | 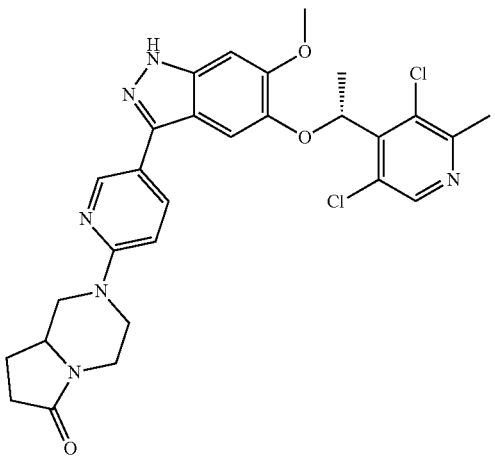 [SMILES: COc1cc2[nH]nc(-c3ccc(N4CCN5C(=O)CCC5C4)nc3)c2cc1O[C@H](C)c1c(Cl)cnc(C)c1Cl] | LCMS: m/z = 567.2 (M + H); 1H NMR (400 MHz, DMSO-d6) δ = 12.83 (br s, 1 H) 8.47 (s, 1 H) 8.39 (d, J = 2.2 Hz, 1 H) 7.85 (dd, J = 8.9, 2.4 Hz, 1 H) 7.04 (d, J = 8.9 Hz, 1 H) 6.99 (s, 1 H) 6.96 (s, 1 H) 5.97 (q, J = 6.8 Hz, 1 H) 4.58 (br d, J = 9.7 Hz, 1 H) 4.45 (br d, J = 10.6 Hz, 1 H) 3.90 (br d, J = 12.0 Hz, 1 H) 3.87 (s, 3 H) 3.58 - 3.66 (m, 2 H) 2.75 - 2.87 (m, 2 H) 2.61 - 2.70 (m, 1 H) 2.59 (d, J = 1.1 Hz, 3 H) 2.27 - 2.34 (m, 2 H) 2.14 - 2.26 (m, 2 H) 1.76 (d, J = 6.7 Hz, 3 H) 1.61 - 1.69 (m, 1 H) |

-continued

| | | |
|---|---|---|
| Example 216<br>2-[5-[5-[(1R)-1-(3,5-dichloro-2-methyl-4-pyridyl)ethoxy]-1H-indazol-3-yl]-2-pyridyl]-6-oxa-2-azaspiro[3.4]octane | 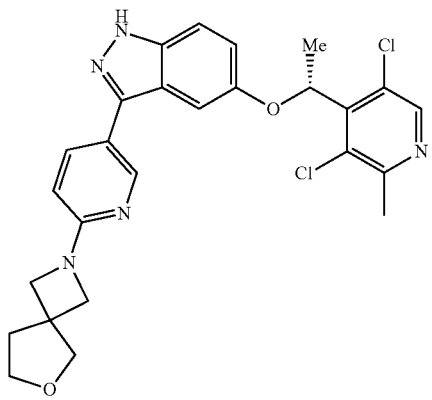 [SMILES: Cc1ncc(Cl)c([C@@H](C)Oc2ccc3[nH]nc(-c4ccc(N5CC6(CCOC6)C5)nc4)c3c2)c1Cl] | LCMS: m/z = 510.1 (M + H); 1H NMR (400 MHz, DMSO-d6) δ = 12.98 (s, 1H), 8.43 (s, 1H), 8.41 (d, J = 1.8 Hz, 1H), 7.86 (dd, J = 2.3, 8.6 Hz, 1H), 7.45 (d, J = 9.0 Hz, 1H), 7.12 - 7.04 (m, 2H), 6.52 (dd, J = 0.6, 8.7 Hz, 1H), 6.09 (q, J = 6.7 Hz, 1H), 3.99 (s, 4H), 3.85 (s, 2H), 3.76 (t, J = 7.0 Hz, 2H), 2.58 (s, 3H), 2.19 (t, J = 7.0 Hz, 2H), 1.75 (d, J = 6.7 Hz, 3H). |
| Example 217<br>2-[5-[5-[(1R)-1-(3,5-dichloro-2-methyl-4-pyridyl)ethoxy]-1H-indazol-3-yl]-3-methyl-2-pyridyl]-6-oxa-2-azaspiro[3.4]octane | 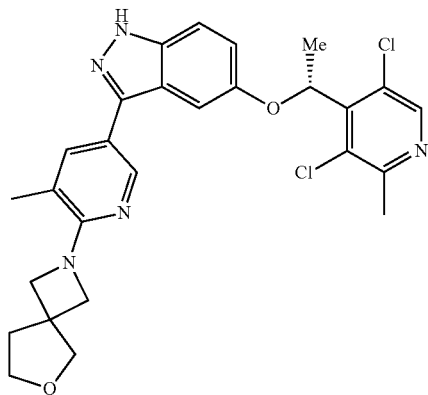 [SMILES: Cc1cc(-c2n[nH]c3ccc(O[C@H](C)c4c(Cl)cnc(C)c4Cl)cc23)cnc1N1CC2(CCOC2)C1] | LCMS: m/z = 524.2 (M + H); 1H NMR (400 MHz, DMSO-d6) δ 13.00 (s, 1 H) 8.43 (s, 1 H) 8.27 (d, J = 1.8 Hz, 1 H) 7.69 (s, 1 H) 7.46 (d, J = 8.9 Hz, 1 H) 7.04 - 7.12 (m, 2 H) 6.10 (q, J = 6.7 Hz, 1 H) 4.12 (s, 4 H) 3.84 (s, 2 H) 3.76 (t, J = 7.0 Hz, 2 H) 2.58 (s, 3 H) 2.27 (s, 3 H) 2.17 (t, J = 7.0 Hz, 2 H) 1.75 (d, J = 6.6 Hz, 3 H) |
| Example 218<br>(R)-5-(5-(1-(3,5-dimethylpyridazin-4-yl)ethoxy)-6-methoxy-1H-indazol-3-yl)-2-(2-oxa-6-azaspiro[3.3]heptan-6-yl)nicotinonitrile | 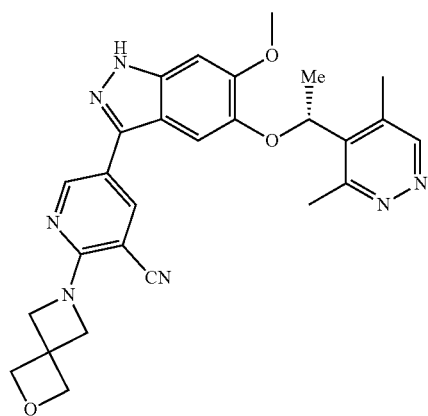 [SMILES: COc1cc2[nH]nc(-c3cnc(N4CC5(COC5)C4)c(C#N)c3)c2cc1O[C@H](C)c1c(C)cnnc1C] | LCMS: m/z = 498.2 (M + H); 1H NMR (400 MHz, DMSO-d6) δ 12.96 (s, 1H), 8.82 (s, 1H), 8.75 (d, J = 2.4 Hz, 1H), 8.18 (d, J = 2.4 Hz, 1H), 7.01(d, J = 6.0 Hz, 2H), 5.84 (q, J = 6.4 Hz, 1H), 4.76 (s, 4H), 4.48 (s, 4H), 3.87 (s, 3H), 2.78 (s, 3H), 2.45 (s, 3H), 1.66 (d, J = 6.8 Hz, 3H). |
| Example 219<br>(R)-6-(5-(5-(1-(3,5-dimethylpyridazin-4-yl)ethoxy)-6-methoxy-1H-indazol-3-yl)-3-methylpyridin-2-yl)-2-oxa-6-azaspiro[3.3]heptane | 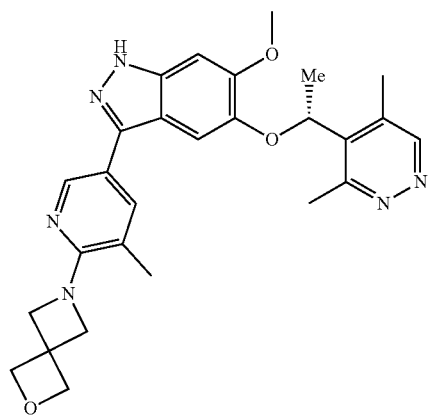 [SMILES: COc1cc2[nH]nc(-c3cnc(N4CC5(COC5)C4)c(C)c3)c2cc1O[C@H](C)c1c(C)cnnc1C] | LCMS: m/z = 487.3 (M + H); 1H NMR (400 MHz, DMSO-d6) δ 12.78 (s, 1H), 8.83 (s, 1H), 8.35 (d, J = 1.6 Hz, 1H), 7.55 (s, 1H), 6.98 (s, 1H), 6.95 (s, 1H), 5.80 (q, J = 6.4 Hz, 1H), 4.74 (s, 4H), 4.28 (s, 4H), 3.87 (s, 3H), 2.77 (s, 3H), 2.42 (s, 3H), 2.24 (s, 3H), 1.66 (d, J = 6.8 Hz, 3H). |

| | | |
|---|---|---|
| Example 220<br>5-[(1R)-1-(3,5-dichloro-2-methyl-4-pyridyl)ethoxy]-6-methoxy-3-(6-pyrrolidin-1-yl-3-pyridyl)-1H-indazole | 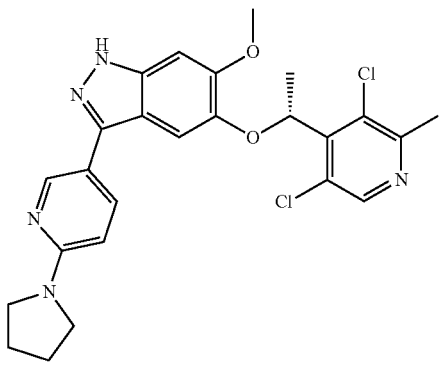 [SMILES: COc1cc2[nH]nc(-c3ccc(N4CCCC4)nc3)c2cc1O[C@H](C)c1c(Cl)cnc(C)c1Cl] | LCMS: m/z = 498 (M + H); 1H NMR (400 MHz, DMSO-d6) δ = 12.72 (br s, 1 H) 8.45 (s, 1 H) 8.32 (d, J = 2.1 Hz, 1 H) 7.77 (dd, J = 8.7, 2.4 Hz, 1 H) 6.98 (s, 1 H) 6.95 (s, 1 H) 6.54 (d, J = 8.7 Hz, 1 H) 5.96 (q, J = 6.6 Hz, 1 H) 3.87 (s, 3 H) 3.37 - 3.53 (m, 5 H) 2.62 (s, 3 H) 1.93 - 2.03 (m, 4 H) 1.75 (d, J = 6.7 Hz, 3 H) |
| Example 221<br>(3S)-1-[5-[5-[(1R)-1-(3,5-dichloro-2-methyl-4-pyridyl)ethoxy]-6-methoxy-1H-indazol-3-yl]-2-pyridyl]pyrrolidin-3-ol | 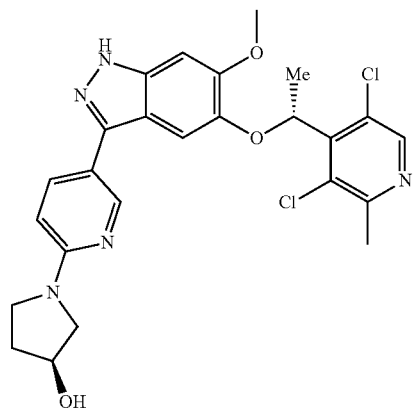 [SMILES: COc1cc2[nH]nc(-c3ccc(N4CC[C@H](O)C4)nc3)c2cc1O[C@H](C)c1c(Cl)cnc(C)c1Cl] | LCMS: m/z = 514.1 (M + H); 1H NMR (400 MHz, DMSO-d6) δ 12.74 (br s, 1 H) 8.45 (s, 1 H) 8.30 (d, J = 2.1 Hz, 1 H) 7.81 (br d, J = 7.6 Hz, 1 H) 6.95 - 7.00 (m, 2 H) 6.58 (br d, J = 8.7 Hz, 1 H) 5.93 - 5.99 (m, 1 H) 5.00 (br s, 1 H) 4.44 (br s, 1 H) 3.87 (s, 3 H) 3.51 - 3.60 (m, 3 H) 3.36 - 3.42 (m, 2 H) 2.62 (s, 3 H) 2.07 (dtd, J = 12.9, 8.5, 8.5, 4.6 Hz, 1 H) 1.90 - 1.99 (m, 1 H) 1.76 (d, J = 6.7 Hz, 3 H) |
| Example 222<br>1-[5-[5-[(1R)-1-(3,5-dichloro-2-methyl-4-pyridyl)ethoxy]-1H-indazol-3-yl]-2-pyridyl]-3-methyl-azetidin-3-ol | 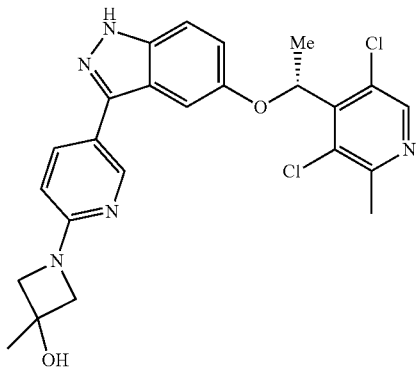 [SMILES: Cc1ncc(Cl)c([C@@H](C)Oc2ccc3[nH]nc(-c4ccc(N5CC(C)(O)C5)nc4)c3c2)c1Cl] | LCMS: m/z = 484.1 (M + H); 1H NMR (400 MHz, DMSO-d6) δ = 12.97 (s, 1H), 8.43 (s, 1H), 8.40 (d, J = 2.0 Hz, 1H), 7.85 (dd, J = 2.3, 8.6 Hz, 1H), 7.45 (d, J = 9.2 Hz, 1H), 7.11 - 7.04 (m, 2H), 6.51 (d, J = 8.1 Hz, 1H), 6.09 (q, J = 6.7 Hz, 1H), 5.59 (s, 1H), 3.92 - 3.83 (m, 4H), 2.58 (s, 3H), 1.75 (d, J = 6.7 Hz, 3H), 1.48 (s, 3H) |
| Example 223<br>(R)-2-(5-(5-(1-(3,5-dichloropyridazin-4-yl)ethoxy)-1H-indazol-3-yl)pyridin-2-yl)-6-oxa-2-azaspiro[3.4]octane | 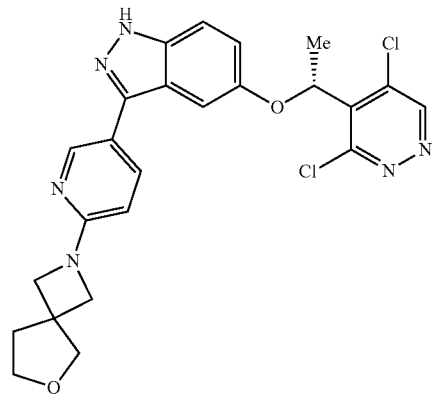 [SMILES: C[C@@H](Oc1ccc2[nH]nc(-c3ccc(N4CC5(CCOC5)C4)nc3)c2c1)c1c(Cl)cnnc1Cl] | LCMS: m/z = 498 (M + H); 1H NMR (400 MHz, DMSO-d6) δ 13.02 (s, 1H), 9.36 (s, 1H), 8.55 (d, J = 2.0 Hz, 1H), 7.91 (dd, J = 8.4, 2.0 Hz, 1H), 7.47 (d, J = 8.8 Hz, 1H), 7.24 (s, 1H), 7.10 (dd, J = 8.8, 2.0 Hz, 1H), 6.53 (d, J = 8.8 Hz, 1H), 6.12 (q, J = 6.4 Hz, 1H), 3.99 (s, 4H), 3.85 (s, 2H), 3.76 (t, J = 7.2 Hz, 2H), 2.19 (t, J = 6.8 Hz, 2H), 1.77 (d, J = 6.8 Hz, 3H). |

-continued

Example 224
(R)-5-(1-(3,5-dichloropyridin-4-yl)ethoxy)-3-(6-(6-(2,2,2-trifluoroethyl)-2,6-diazaspiro[3.3]heptan-2-yl)pyridin-3-yl)-1H-indazole

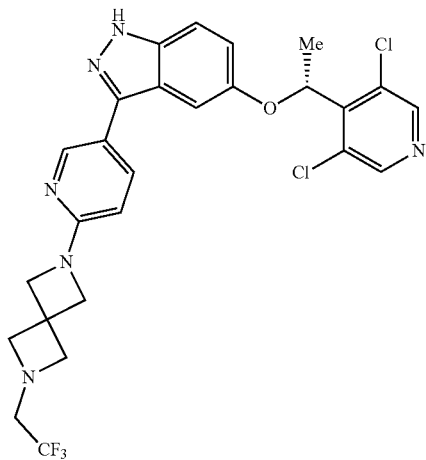 [SMILES: C[C@@H](Oc1ccc2[nH]nc(-c3ccc(N4CC5(CN(CC(F)(F)F)C5)C4)nc3)c2c1)c1c(Cl)cncc1Cl]

LCMS: m/z = 564 (M + H); 1H NMR (400 MHz, DMSO-d6) δ13.00 (s, 1H), 8.59 (s, 2H), 8.50 (d, J = 2.0 Hz, 1H), 7.85 (dd, J = 8.4 Hz, 2.0 Hz, 1H), 7.45 (d, J = 9.2 Hz, 1H), 7.17 (d, J = 2.0 Hz, 1H), 7.09 (dd, J = 8.8 Hz, 2.0 Hz, 1H), 6.52 (d, J = 8.4 Hz, 1H), 6.11 (q, J = 6.8 Hz, 1H), 4.10 (s, 4H), 3.55 (s, 4H), 3.20 (q, J = 10.4 Hz, 2H), 1.75 (d, J = 6.4 Hz, 3H).

Example 225
2-[5-[5-[(1R)-1-(3,5-dichloro-2-methyl-4-pyridyl)ethoxy]-1H-indazol-3-yl]-2-pyridyl]-1,3,4,7,8,8a-hexahydropyrrolo[1,2-a]pyrazin-6-one

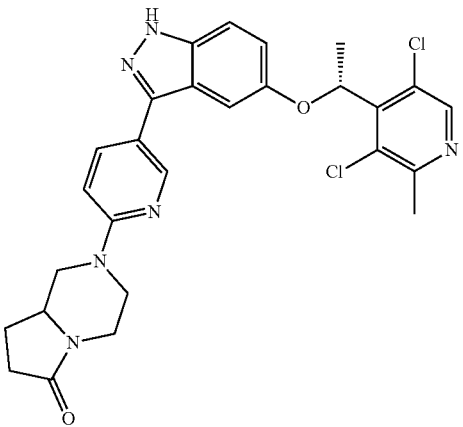 [SMILES: Cc1ncc(Cl)c([C@@H](C)Oc2ccc3[nH]nc(-c4ccc(N5CCN6C(=O)CCC6C5)nc4)c3c2)c1Cl]

LCMS: m/z = 438 (M + H); 1H NMR (400 MHz, DMSO-d6) δ = 13.00 (s, 1H), 8.53 - 8.39 (m, 2H), 7.96 - 7.85 (m, 1H), 7.46 (d, J = 9.2 Hz, 1H), 7.14 - 7.00 (m, 3H), 6.09 (q, J = 6.7 Hz, 1H), 4.63 - 4.55 (m, 1H), 4.46 (br d, J = 11.0 Hz, 1H), 3.95 - 3.86 (m, 1H), 3.63 (br dd, J = 1.8, 7.1 Hz, 1H), 2.91 - 2.77 (m, 2H), 2.68 - 2.61 (m, 1H), 2.58 (d, J = 1.3 Hz, 3H), 2.35 - 2.26 (m, 2H), 2.22 - 2.14 (m, 1H), 1.76 (d, J = 6.6 Hz, 3H), 1.70 - 1.60 (m, 1H)

Example 226
2-[5-[5-[(1R)-1-(3,5-dichloro-2-methyl-4-pyridyl)ethoxy]-1H-indazol-3-yl]-2-pyridyl]-5-oxa-2-azaspiro[3.4]octane

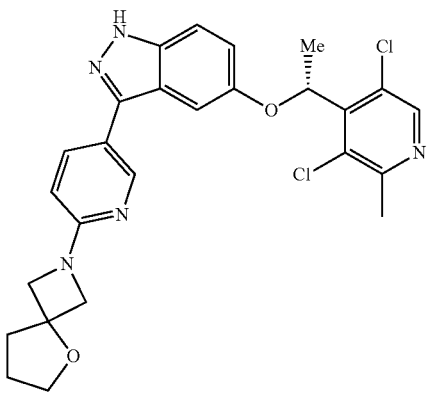 [SMILES: Cc1ncc(Cl)c([C@@H](C)Oc2ccc3[nH]nc(-c4ccc(N5CC6(CCCO6)C5)nc4)c3c2)c1Cl]

LCMS: m/z = 511 (M + H); 1H NMR (400 MHz, DMSO-d6) δ = 12.98 (s, 1H), 8.43 (s, 1H), 8.40 (d, J = 1.8 Hz, 1H), 7.86 (dd, J = 2.3, 8.6 Hz, 1H), 7.45 (d, J = 9.3 Hz, 1H), 7.12 - 7.04 (m, 2H), 6.53 (d, J = 8.6 Hz, 1H), 6.09 (q, J = 6.7 Hz, 1H), 4.05 (d, J = 8.7 Hz, 2H), 3.96 (d, J = 8.7 Hz, 2H), 3.80 (t, J = 6.8 Hz, 2H), 2.57 (s, 3H), 2.17 - 2.11 (m, 2H), 1.91 (quin, J = 7.0 Hz, 2H), 1.75 (d, J = 6.6 Hz, 3H)

| Example | Structure | Data |
|---|---|---|
| Example 227<br>2-[5-[5-[(1R)-1-(3,5-dichloro-2-methyl-4-pyridyl)ethoxy]-1H-indazol-3-yl]-2-pyridyl]-2-azaspiro[3.3]heptan-6-ol | 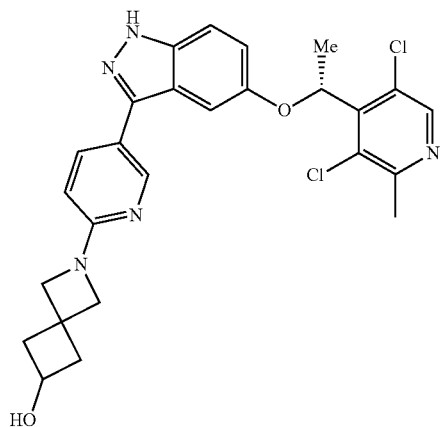 [SMILES: Cc1ncc(Cl)c([C@@H](C)Oc2ccc3[nH]nc(-c4ccc(N5CC6(CC(O)C6)C5)nc4)c3c2)c1Cl] | LCMS: m/z = 510 (M + H); 1H NMR (400 MHz, DMSO-d6) δ = 12.96 (s, 1H), 8.43 (s, 1H), 8.38 (d, J = 2.0 Hz, 1H), 7.83 (dd, J = 2.3, 8.6 Hz, 1H), 7.45 (d, J = 9.0 Hz, 1H), 7.10 - 7.03 (m, 2H), 6.45 (d, J = 8.4 Hz, 1H), 6.08 (q, J = 6.6 Hz, 1H), 5.05 (d, J = 6.1 Hz, 1H), 4.09 - 4.00 (m, 1H), 3.98 (s, 2H), 3.93 (s, 2H), 2.58 (s, 3H), 2.54 - 2.51 (m, 1H), 2.49 - 2.44 (m, 1H), 2.08 - 2.01 (m, 2H), 1.75 (d, J = 6.6 Hz, 3H). |
| Example 228<br>7-(5-(5-((R)-1-(3,5-dimethylpyridazin-4-yl)ethoxy)-6-methoxy-1H-indazol-3-yl)pyridin-2-yl)hexahydroimidazo[1,5-a]pyrazin-3(2H)-one | 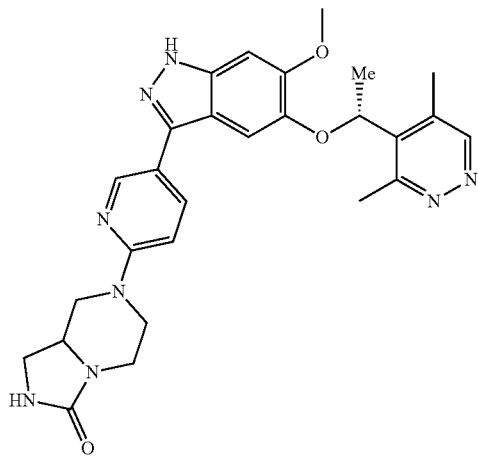 [SMILES: COc1cc2[nH]nc(-c3ccc(N4CCN5C(=O)NCC5C4)nc3)c2cc1O[C@H](C)c1c(C)cnnc1C] | LCMS: m/z = 515.3 (M + H); 1H-NMR (400 MHz, DMSO-d6) δ 12.81 (s, 1H), 8.86 (s, 1H), 8.51 (s, 1H), 7.85-7.82 (m, 1H), 7.00 (d, J = 7.6 Hz, 3H), 6.53 (s, 1H), 5.80 (q, J = 6.4 Hz, 1H), 4.45-4.47 (m, 1H), 4.44-4.43 (m, 1H), 3.87 (s, 3H), 3.70-3.66 (m, 2H), 3.48-3.41 (m, 1H), 3.03-3.00 (m, 1H), 2.90-2.87 (m, 1H), 2.82-2.73 (m, 5H), 2.44 (s, 3H), 1.65 (d, J = 6.8 Hz, 3H). |
| Example 229<br>(R)-6-(5-(5-(1-(3,5-dichloropyridazin-4-yl)ethoxy)-1H-indazol-3-yl)pyridin-2-yl)-2-oxa-6-azaspiro[3.3]heptane | 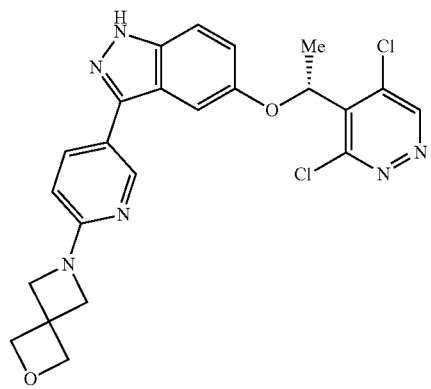 [SMILES: C[C@@H](Oc1ccc2[nH]nc(-c3ccc(N4CC5(COC5)C4)nc3)c2c1)c1c(Cl)cnnc1Cl] | LCMS: m/z = 483.1 (M + H); 1H NMR (400 MHz, DMSO-d6) δ 13.02 (s, 1H), 9.35 (s, 1H), 8.53 (d, J = 2.0 Hz, 1H), 7.90 (dd, J = 8.4 Hz, 2.4 Hz, 1H), 7.46 (d, J = 8.8 Hz, 1H), 7.22 (d, J = 2.0 Hz, 1H), 7.09 (dd, J = 8.8 Hz, 2.0 Hz, 1H), 6.52 (d, J = 8.4 Hz, 1H), 6.12 (q, J = 6.4 Hz, 1H), 4.75 (s, 4H), 4.18 (s, 4H), 1.76 (d, J = 7.2 Hz, 3H). |

| | | |
|---|---|---|
| Example 230<br>(R)-5-(1-(3,5-dichloropyridin-4-yl)ethoxy)-3-(6-(6-(2,2-difluoroethyl)-2,6-diazaspiro[3.3]heptan-2-yl)pyridin-3-yl)-1H-indazole | 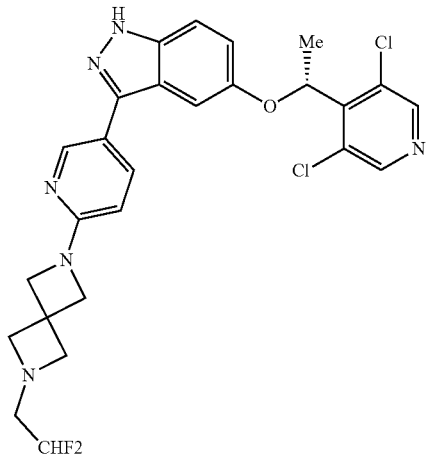 [SMILES: C[C@@H](Oc1ccc2[nH]nc(-c3ccc(N4CC5(CN(CC(F)F)C5)C4)nc3)c2c1)c1c(Cl)cncc1Cl] | LCMS: m/z = 545.2 (M + H); 1H NMR (400 MHz, DMSO-d6) δ 13.00 (s, 1H), 8.59 (s, 2H), 8.50 (s, 1H), 7.85 (d, J = 8.0 Hz, 1H), 7.46 (d, J = 8.8 Hz, 1H), 7.16 (s, 1H), 7.10 (d, J = 8.8 Hz, 1H), 6.52 (d, J = 8.4 Hz, 1H), 6.11 (q, J = 6.4 Hz, 1H), 5.96 (t, J = 55.6.0 Hz, 1H), 4.08 (s, 4H), 3.46 (s, 4H), 2.85-2.76 (m, 2H), 1.76 (d, J = 6.4 Hz, 3H). |
| Example 231<br>7-(5-(5-((R)-1-(3,5-dimethylpyridazin-4-yl)ethoxy)-1H-indazol-3-yl)-3-methylpyridin-2-yl)hexahydroimidazo[1,5-a]pyrazin-3(2H)-one | 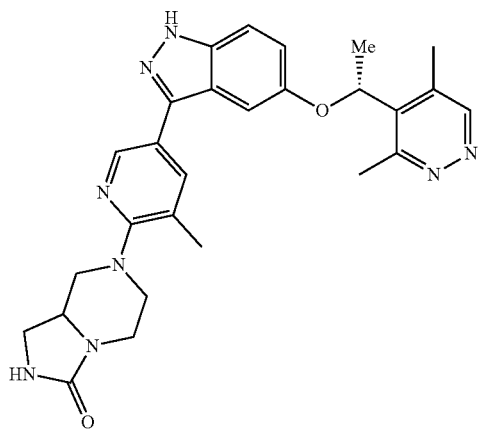 [SMILES: Cc1cc(-c2n[nH]c3ccc(O[C@H](C)c4c(C)cnnc4C)cc23)cnc1N1CCN2C(=O)NCC2C1] | LCMS: m/z = 499.3 (M + H); 1H-NMR (400 MHz, DMSO-d6) δ 13.13 (s, 1H), 8.83 (s, 1H), 8.53 (s, 1H), 7.79 (s, 1H), 7.49 (d, J = 9.2 Hz, 1H), 7.09 (d, J = 8.8 Hz, 1H), 7.02 (s, 1H), 6.49 (s, 1H), 5.88 (q, J = 6.4 Hz, 1H), 3.91-3.79 (m, 1H), 3.75-3.67 (m, 1H), 3.53-3.41 (m, 3H), 3.10-2.97 (m, 2H), 2.79 (s, 3H), 2.72-2.60 (m, 2H), 2.44 (s, 3H), 2.37 (s, 3H), 1.67 (d, J = 6.4 Hz, 3H). |
| Example 232<br>[(2R)-1-[5-[5-[(1R)-1-(3,5-dichloro-2-methyl-4-pyridyl)ethoxy]-1H-indazol-3-yl]-2-pyridyl]pyrrolidin-2-yl]methanol | 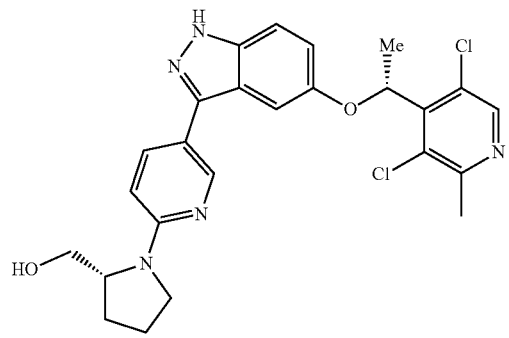 [SMILES: Cc1ncc(Cl)c([C@@H](C)Oc2ccc3[nH]nc(-c4ccc(N5CCC[C@@H]5CO)nc4)c3c2)c1Cl] | LCMS: m/z = 498.1 (M + H); 1H NMR (400 MHz, DMSO-d6) δ = 12.93 (s, 1H), 8.42 (s, 1H), 8.38 (d, J = 2.0 Hz, 1H), 7.85 (dd, J = 2.3, 8.7 Hz, 1H), 7.45 (d, J = 8.9 Hz, 1H), 7.08 (d, J = 9.6 Hz, 1H), 7.05 (s, 1H), 6.63 (d, J = 8.8 Hz, 1H), 6.08 (q, J = 6.6 Hz, 1H), 4.93 (br s, 1H), 4.11 (br d, J = 3.5 Hz, 1H), 3.64 (dd, J = 4.0, 10.5 Hz, 1H), 3.53 (br t, J = 8.0 Hz, 1H), 3.39 - 3.34 (m, 1H), 2.58 (s, 3H), 2.10 - 1.99 (m, 2H), 1.99 - 1.90 (m, 2H), 1.76 (d, J = 6.6 Hz, 3H). |

| | | |
|---|---|---|
| Example 233<br>(R)-5-(1-(3,5-dichloropyridazin-4-yl)ethoxy)-3-(6-(6-(methylsulfonyl)-2,6-diazaspiro[3.3]heptan-2-yl)pyridin-3-yl)-1H-indazole | 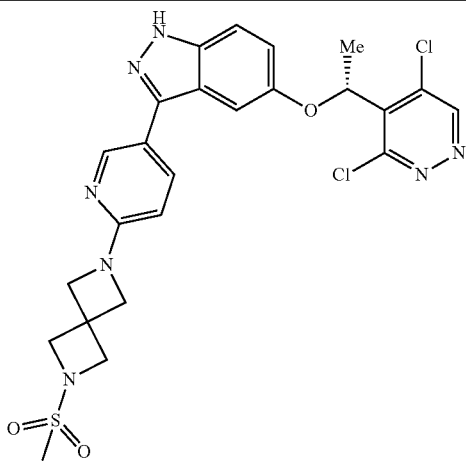 | LCMS: m/z = 560.2 (M + H); 1H NMR (400 MHz, DMSO-d6) δ 13.03 (s, 1H), 9.36 (s, 1H), 8.55 (d, J = 2.4 Hz, 1H), 7.93 (dd, J = 8.8 Hz, 2.4 Hz, 1H), 7.48 (d, J = 9.2 Hz, 1H), 7.23 (d, J = 2.0 Hz, 1H), 7.11 (dd, J = 9.2 Hz, 2.4 Hz, 1H), 6.55 (d, J = 8.8 Hz, 1H), 6.13 (q, J = 6.4 Hz, 1H), 4.18 (s, 4H), 4.12 (s, 4H), 3.03 (s, 3H), 1.78 (d, J = 6.8 Hz, 3H). |
| Example 234<br>[1-[5-[5-[(1R)-1-(3,5-dichloro-2-methyl-4-pyridyl)ethoxy]-1H-indazol-3-yl]-3-methyl-2-pyridyl]-3-(hydroxymethyl)azetidin-3-yl]methanol | 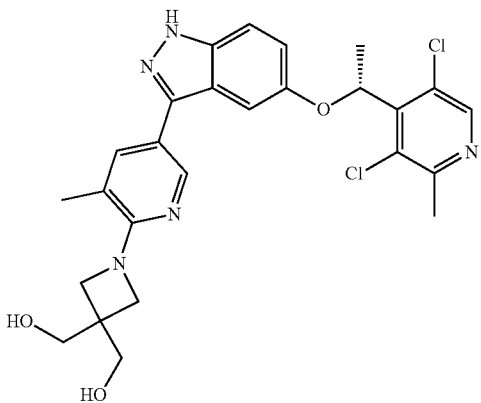 [SMILES: Cc1cc(-c2n[nH]c3ccc(O[C@H](C)c4c(Cl)cnc(C)c4Cl)cc23)cnc1N1CC(CO)(CO)C1] | LCMS: m/z = 528.2 (M + H); 1H NMR (400 MHz, DMSO-d6) δ = 12.99 (br s, 1H), 8.43 (s, 1H), 8.24 (d, J = 1.8 Hz, 1H), 7.63 (d, J = 1.2 Hz, 1H), 7.45 (d, J = 9.0 Hz, 1H), 7.08 (dd, J = 2.3, 8.9 Hz, 1H), 7.05 (s, 1H), 6.12 - 6.06 (m, 1H), 3.86 (s, 4H), 3.59 (s, 4H), 2.58 (s, 3H), 2.26 (s, 3H), 1.75 (d, J = 6.7 Hz, 3H) |
| Example 235<br>5-[(1R)-1-(3,5-dichloro-2-methyl-4-pyridyl)ethoxy]-3-[5-methyl-6-(2-methylsulfonyl-2,6-diazaspiro[3.3]heptan-6-yl)-3-pyridyl]-1H-indazole | 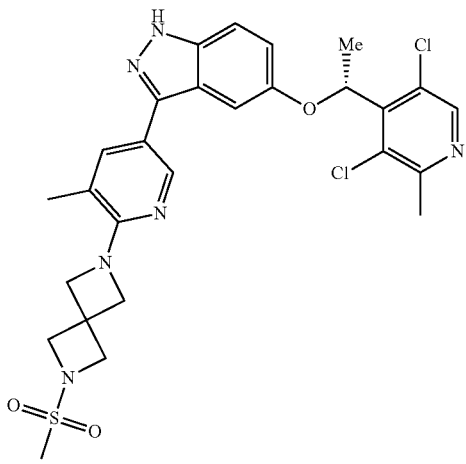 [SMILES: Cc1cc(-c2n[nH]c3ccc(O[C@H](C)c4c(Cl)cnc(C)c4Cl)cc23)cnc1N1CC2(C1)CN(S(C)(=O)=O)C2] | LCMS: m/z = 587.2 (M + H); 1H NMR (400 MHz, DMSO-d6) δ = 13.00 (s, 1H), 8.43 (s, 1H), 8.28 (d, J = 2.0 Hz, 1H), 7.69 (d, J = 1.2 Hz, 1H), 7.46 (d, J = 9.0 Hz, 1H), 7.09 (dd, J = 2.3, 8.9 Hz, 1H), 7.05 (d, J = 1.5 Hz, 1H), 6.09 (q, J = 6.7 Hz, 1H), 4.27 (s, 4H), 4.10 (s, 4H), 3.02 (s, 3H), 2.58 (s, 3H), 2.25 (s, 3H), 1.75 (d, J = 6.6 Hz, 3H) |

-continued

| Example 236 ((R)-1-(5-(5-((R)-1-(3,5-dichloropyridin-4-yl)ethoxy)-1H-indazol-3-yl)pyridin-2-yl)pyrrolidin-2-yl)methanol | 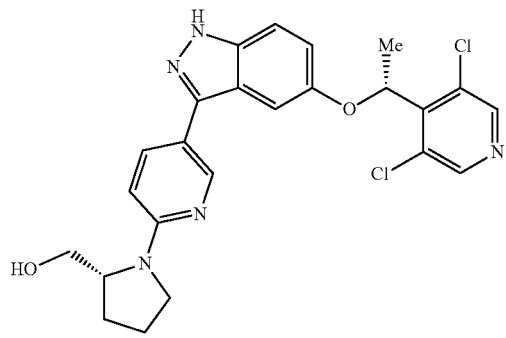 [SMILES: C[C@@H](Oc1ccc2[nH]nc(-c3ccc(N4CCC[C@@H]4CO)nc3)c2c1)c1c(Cl)cncc1Cl] | LCMS: m/z = 484.2 (M + H); 1H NMR (400 MHz, DMSO-d6) δ 12.94 (s, 1H), 8.60 (s, 2H), 8.45 (d, J = 2.0 Hz, 1H), 7.82 (dd, J = 8.8 Hz, 2.4 Hz, 1H), 7.44 (d, J = 9.2 Hz, 1H), 7.15 (d, J = 1.6 Hz, 1H), 7.08 (dd, J = 9.2 Hz, 2.4 Hz, 1H), 6.63 (d, J = 8.8 Hz, 1H), 6.10 (q, J = 6.8 Hz, 1H), 4.95 (t, J = 4.2 Hz, 1H), 4.11-4.08 (m, 1H), 3.67-3.63 (m, 1H), 3.54-3.50 (m, 1H), 3.37-3.28 (m, 2H), 2.07-1.91 (m, 4H), 1.75 (d, J = 6.8 Hz, 3H). |
|---|---|---|
| Example 237 ((S)-1-(5-(5-((R)-1-(3,5-dichloropyridin-4-yl)ethoxy)-1H-indazol-3-yl)pyridin-2-yl)pyrrolidin-2-yl)methanol | 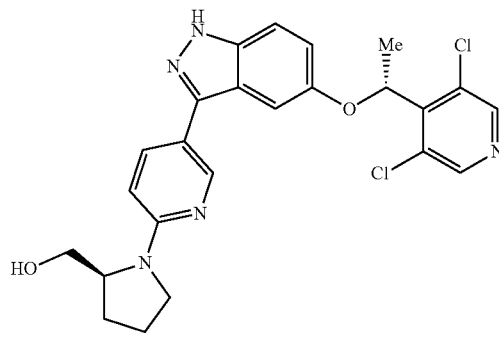 | LCMS: m/z = 484.2 (M + H); 1H NMR (400 MHz, DMSO-d6) δ 12.94 (s, 1H), 8.59 (s, 2H), 8.49 (d, J = 2.4 Hz, 1H), 7.83 (dd, J = 8.8 Hz, 2.4 Hz, 1H), 7.45 (d, J = 8.8 Hz, 1H), 7.16 (s, 1H), 7.08 (dd, J = 8.8 Hz, 2.4 Hz, 1H), 6.63 (d, J = 8.8 Hz, 1H), 6.11 (q, J = 6.8 Hz, 1H), 4.96 (t, J = 5.2 Hz, 1H), 4.12 - 4.11 (m,1H), 3.67 - 3.62 (m, 1H), 3.53-3.50 (m, 1H), 3.38 - 3.32 (m, 2H), 2.07 - 1.93 (m, 4H), 1.76 (d, J = 6.8 Hz, 3H). |
| Example 238 5-[(1R)-1-(3,5-dichloro-2-methyl-4-pyridyl)ethoxy]-3-[6-(6-methoxy-2-azaspiro[3.3]heptan-2-yl)-3-pyridyl]-1H-indazole | 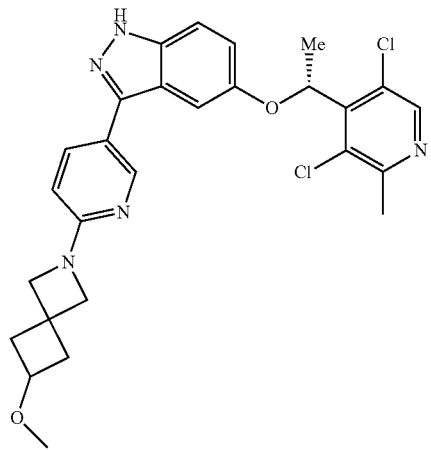 [SMILES: COC1CC2(C1)CN(c1ccc(-c3n[nH]c4ccc(O[C@H](C)c5c(Cl)cnc(C)c5Cl)cc34)cn1)C2] | LCMS: m/z = 524 (M + H); 1H NMR (400 MHz, DMSO-d6) δ = 12.96 (s, 1H), 8.43 (s, 1H), 8.38 (d, J = 2.0 Hz, 1H), 7.84 (dd, J = 2.3, 8.7 Hz, 1H), 7.45 (d, J = 9.2 Hz, 1H), 7.10 - 7.06 (m, 1H), 7.06 (s, 1H), 6.46 (dd, J = 0.5, 8.7 Hz, 1H), 6.08 (q, J = 6.7 Hz, 1H), 4.00 (s, 2H), 3.95 (s, 2H), 3.81 (quin, J = 6.9 Hz, 1H), 3.14 (s, 3H), 2.58 (s, 3H), 2.55 - 2.50 (m, 2H), 2.12 - 2.05 (m, 2H), 1.75 (d, J = 6.7 Hz, 3H) |
| Example 239 5-[(1R)-1-(3,5-dichloro-4-pyridyl)ethoxy]-6-methoxy-3-[2-(2-methylsulfonyl-2,6-diazaspiro[3.3]heptan-6-yl)pyrimidin-5-yl]-1H-indazole | 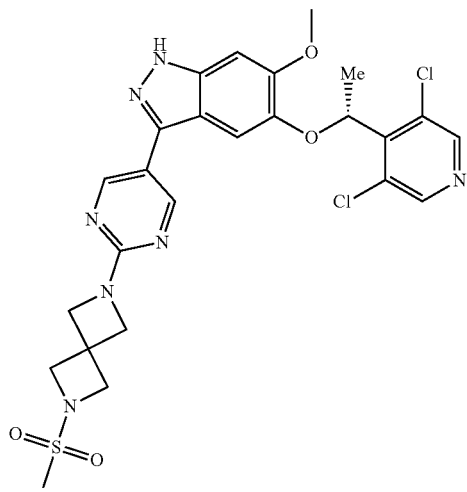 | LCMS: m/z = 559.1 (M + H); 1H NMR (400 MHz, DMSO-d6) δ = 12.94 (s, 1H), 8.72 (s, 2H), 8.58 (s, 2H), 7.14 (s, 1H), 7.00 (s, 1H), 5.98 (q, J = 6.7 Hz, 1H), 4.28 (s, 4H), 4.11 (s, 4H), 3.85 (s, 3H), 3.02 (s, 3H), 1.75 (d, J = 6.7 Hz, 3H) |

| | | |
|---|---|---|
| Example 240<br>5-[(1R)-1-(3,5-dichloro-2-methyl-4-pyridyl)ethoxy]-6-methoxy-3-[2-(2-methylsulfonyl-2,6-diazaspiro[3.3]heptan-6-yl)pyrimidin-5-yl]-1H-indazole | 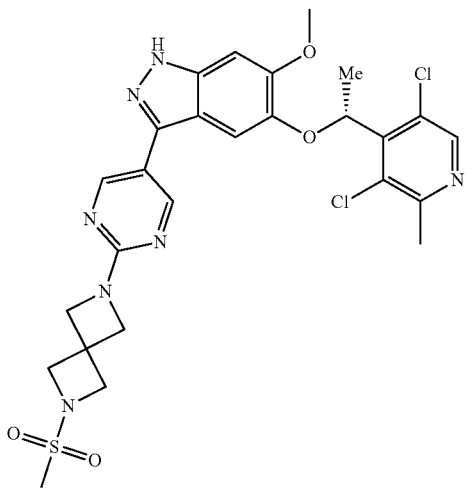 [SMILES: COc1cc2[nH]nc(-c3cnc(N4CC5(C4)CN(S(C)(=O)=O)C5)nc3)c2cc1O[C@H](C)c1c(Cl)cnc(C)c1Cl] | LCMS: m/z = 604 (M + H); 1H NMR (400 MHz, DMSO-d6) δ = 12.92 (s, 1H), 8.63 (s, 2H), 8.43 (s, 1H), 7.00 (s, 1H), 6.97 (s, 1H), 5.97 (q, J = 6.7 Hz, 1H), 4.31 - 4.23 (m, 4H), 4.12 (s, 4H), 3.86 (s, 3H), 3.02 (s, 3H), 2.60 (s, 3H), 1.75 (d, J = 6.7 Hz, 3H) |
| Example 241<br>[(2S)-1-[5-[5-[(1R)-1-(3,5-dichloro-2-methyl-4-pyridyl)ethoxy]-1H-indazol-3-yl]-2-pyridyl]pyrrolidin-2-yl]methanol | 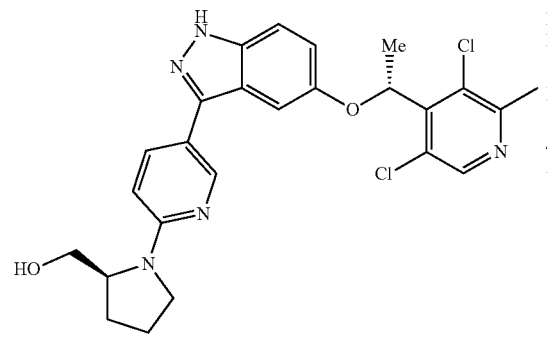 | LCMS: m/z = 498.1 (M + H); 1H NMR (400 MHz, DMSO-d6) δ = 12.92 (s, 1H), 8.44 (s, 1H), 8.35 (d, J = 2.1 Hz, 1H), 7.83 (dd, J = 2.4, 8.7 Hz, 1H), 7.44 (d, J = 9.2 Hz, 1H), 7.08 (d, J = 9.4 Hz, 1H), 7.05 (s, 1H), 6.62 (d, J = 8.7 Hz, 1H), 6.08 (q, J = 6.6 Hz, 1H), 4.90 (t, J = 5.6 Hz, 1H), 4.15 - 4.05 (m, 1H), 3.69 - 3.61 (m, 1H), 3.52 (br t, J = 7.3 Hz, 1H), 3.41 - 3.31 (m, 2H), 2.60 (s, 3H), 2.07 - 1.88 (m, 4H), 1.76 (d, J = 6.7 Hz, 3H). |
| Example 242<br>5-[(1R)-1-(3,5-dichloro-4-pyridyl)ethoxy]-3-[5-fluoro-6-(2-methylsulfonyl-2,6-diazaspiro[3.3]heptan-6-yl)-3-pyridyl]-6-methoxy-1H-indazole | 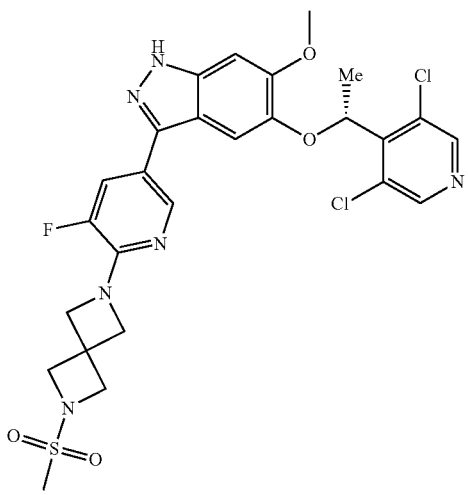 [SMILES: COc1cc2[nH]nc(-c3cnc(N4CC5(C4)CN(S(C)(=O)=O)C5)c(F)c3)c2cc1O[C@H](C)c1c(Cl)cncc1Cl] | LCMS: m/z = 607.1 (M + H); 1H NMR (400 MHz, DMSO-d6) δ 12.92 (s, 1 H) 8.58 (s, 2 H) 8.31 (t, J = 1.65 Hz, 1 H) 7.67 (dd, J = 13.08, 1.71 Hz, 1 H) 7.08 (s, 1 H) 7.00 (s, 1 H) 5.95 - 6.01 (m, 1 H) 4.30 (d, J = 1.83 Hz, 4 H) 4.12 (s, 4 H) 3.86 (s, 3 H) 3.02 (s, 3 H) 1.76 (d, J = 6.60 Hz, 3 H) |

-continued

| | | |
|---|---|---|
| Example 243<br>5-[(1R)-1-(3,5-dichloro-2-methyl-4-pyridyl)ethoxy]-3-[5-fluoro-6-(2-methylsulfonyl-2,6-diazaspiro[3.3]heptan-6-yl)-3-pyridyl]-6-methoxy-1H-indazole | 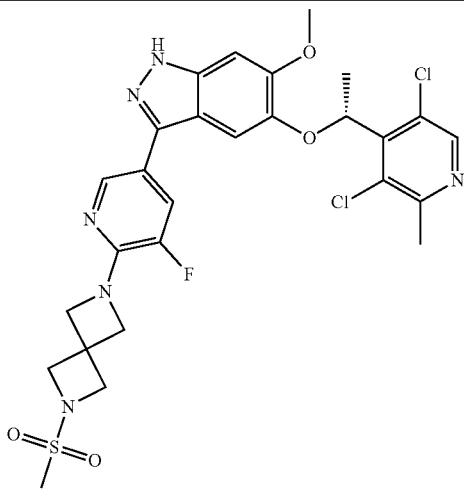 | LCMS: m/z = 621.1 (M + H); 1H NMR (400 MHz, DMSO-d6) δ = 12.91 (s, 1H), 8.43 (s, 1H), 8.19 (s, 1H), 7.65 (dd, J = 1.8, 13.0 Hz, 1H), 7.00 (s, 1H), 6.95 (s, 1H), 6.01 - 5.95 (m, 1H), 4.30 (d, J = 1.7 Hz, 4H), 4.12 (s, 4H), 3.87 (s, 3H), 3.02 (s, 3H), 2.61 (s, 3H), 1.76 (d, J = 6.7 Hz, 3H). |
| Example 244<br>5-[(1R)-1-(3,5-dichloro-2-methyl-4-pyridyl)ethoxy]-3-[5-fluoro-6-(2-methylsulfonyl-2,6-diazaspiro[3.3]heptan-6-yl)-3-pyridyl]-1H-indazole | 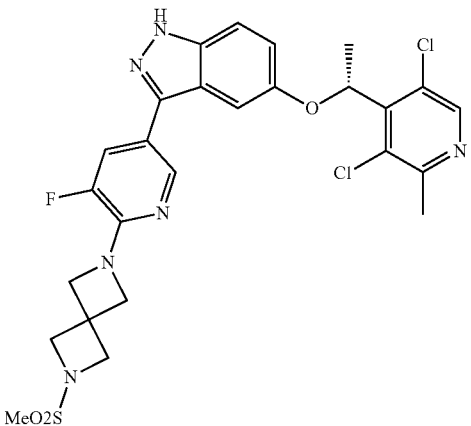 [SMILES: Cc1ncc(Cl)c([C@@H](C)Oc2ccc3[nH]nc(-c4cnc(N5CC6(C5)CN(S(C)(=O)=O)C6)c(F)c4)c3c2)c1Cl] | LCMS: m/z = 591 (M + H); 1H NMR (400 MHz, DMSO-d6) δ = 13.11 (s, 1H), 8.42 (s, 1H), 8.27 (s, 1H), 7.70 (dd, J = 1.8, 13.1 Hz, 1H), 7.48 (d, J = 8.9 Hz, 1H), 7.10 (dd, J = 2.3, 9.0 Hz, 1H), 7.07 (s, 1H), 6.14 - 6.08 (m, 1H), 4.31 (d, J = 1.7 Hz, 4H), 4.12 (s, 4H), 3.02 (s, 3H), 2.58 (s, 3H), 1.76 (d, J = 6.7 Hz, 3H) |
| Example 245<br>1-[6-[5-[(1R)-1-(3,5-dichloro-4-pyridyl)ethoxy]-1H-indazol-3-yl]-2-pyridyl]-2,6-diazaspiro[3.3]heptan-2-yl]-2,2,2-trifluoro-ethanone | 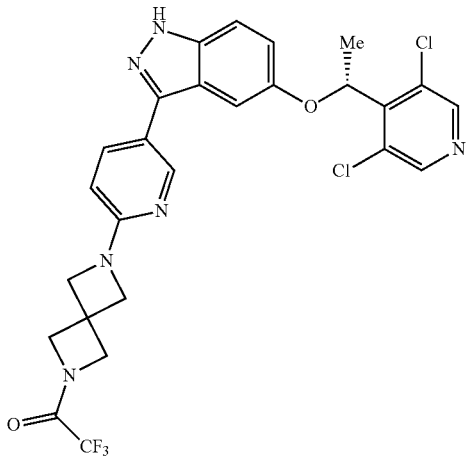 [SMILES: C[C@@H](Oc1ccc2[nH]nc(-c3ccc(N4CC5(CN(C(=O)C(F)(F)F)C5)C4)nc3)c2c1)c1c(Cl)cncc1Cl] | LCMS: m/z = 577 (M + H); 1H NMR (400 MHz, DMSO-d6) δ = 12.99 (s, 1H), 8.59 (s, 2H), 8.52 (d, J = 1.7 Hz, 1H), 7.87 (dd, J = 2.3, 8.6 Hz, 1H), 7.45 (d, J = 8.9 Hz, 1H), 7.17 (d, J = 2.0 Hz, 1H), 7.09 (dd, J = 2.3, 9.0 Hz, 1H), 6.54 (d, J = 8.7 Hz, 1H), 6.11 (q, J = 6.7 Hz, 1H), 4.66 (s, 2H), 4.33 (s, 2H), 4.20 (s, 4H), 1.76 (d, J = 6.6 Hz, 3H) |

-continued

| | | |
|---|---|---|
| Example 246<br>(R)-5-(1-(3,5-dichloropyridazin-4-yl)ethoxy)-3-(6-(6-(methylsulfonyl)-2,6-diazaspiro[3.3]heptan-2-yl)pyridin-3-yl)-1H-indazole | 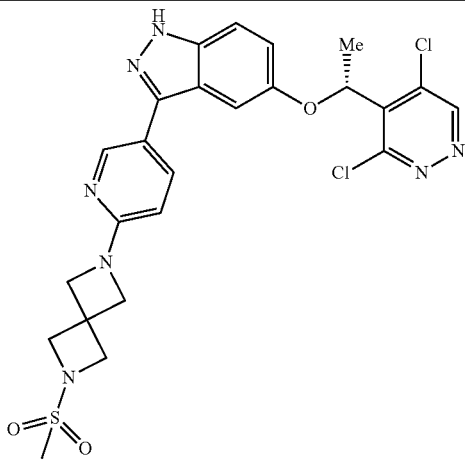 | LCMS: m/z = 560.2 (M + H); 1H NMR (400 MHz, DMSO-d6) δ 13.03 (s, 1H), 9.36 (s, 1H), 8.55 (d, J = 2.4 Hz, 1H), 7.93 (dd, J = 8.8 Hz, 2.4 Hz, 1H), 7.48 (d, J = 8.8 Hz, 1H), 7.24 (d, J = 1.6 Hz, 1H), 7.11 (dd, J = 8.8 Hz, 2.4 Hz, 1H), 6.55 (d, J = 9.2 Hz, 1H), 6.13 (q, J = 6.8 Hz, 1H), 4.18 (s, 4H), 4.12 (s, 4H), 3.03 (s, 3H), 1.78 (d, J = 6.4 Hz, 3H). |
| Example 247<br>2-[5-[5-[(1R)-1-(3,5-dichloro-2-methyl-4-pyridyl)ethoxy]-1H-indazol-3-yl]-2-pyridyl]-2-azaspiro[3.4]octan-6-ol | 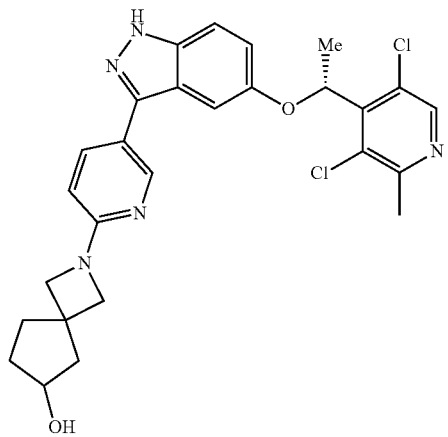 [SMILES: Cc1ncc(Cl)c([C@@H](C)Oc2ccc3[nH]nc(-c4ccc(N5CC6(CCC(O)C6)C5)nc4)c3c2)c1Cl] | LCMS: m/z = 524.2 (M + H); 1H NMR (400 MHz, DMSO-d6) δ = 12.96 (s, 1H), 8.43 (s, 1H), 8.38 (d, J = 2.0 Hz, 1H), 7.83 (dd, J = 2.3, 8.6 Hz, 1H), 7.45 (d, J = 9.2 Hz, 1H), 7.08 (d, J = 8.8 Hz, 1H), 7.06 (s, 1H), 6.46 (d, J = 8.7 Hz, 1H), 6.08 (q, J = 6.7 Hz, 1H), 4.53 (d, J = 3.5 Hz, 1H), 4.21 - 4.14 (m, 1H), 3.97 (d, J = 7.9 Hz, 1H), 3.90 - 3.83 (m, 3H), 2.59 - 2.52 (m, 3H), 2.09 - 1.98 (m, 2H), 1.90 - 1.70 (m, 6H), 1.66 - 1.44 (m, 1H) |
| Example 248<br>5-[(1R)-1-(3,5-dichloro-4-pyridyl)ethoxy]-3-[5-methyl-6-(2-methylsulfonyl-2,6-diazaspiro[3.3]heptan-6-yl)-3-pyridyl]-1H-indazole | 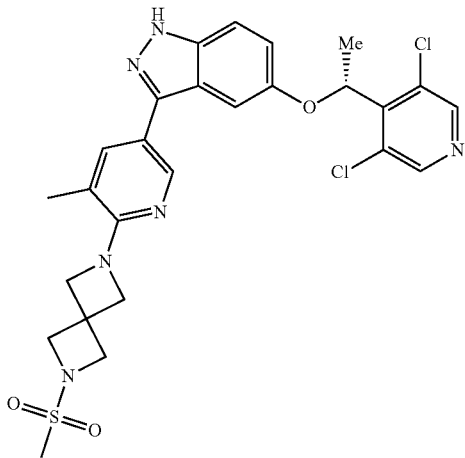 [SMILES: Cc1cc(-c2n[nH]c3ccc(O[C@H](C)c4c(Cl)cncc4Cl)cc23)cnc1N1CC2(C1)CN(S(C)(=O)=O)C2] | LCMS: m/z = 573.2 (M + H); 1H NMR (400 MHz, DMSO-d6) δ = 13.02 (br s, 1H), 8.58 (s, 2H), 8.40 (d, J = 1.8 Hz, 1H), 7.68 - 7.63 (m, 1H), 7.46 (d, J = 8.9 Hz, 1H), 7.14 (d, J = 2.0 Hz, 1H), 7.09 (dd, J = 2.3, 9.0 Hz, 1H), 6.11 (q, J = 6.7 Hz, 1H), 4.28 (s, 4H), 4.10 (s, 4H), 3.02 (s, 3H), 2.26 (s, 3H), 1.76 (d, J = 6.7 Hz, 3H) |

| Example 249 (R)-5-(1-(3,5-dichloropyridin-4-yl)ethoxy)-3-(6-(3-(trifluoromethyl)azetidin-1-yl)pyridin-3-yl)-1H-indazole | 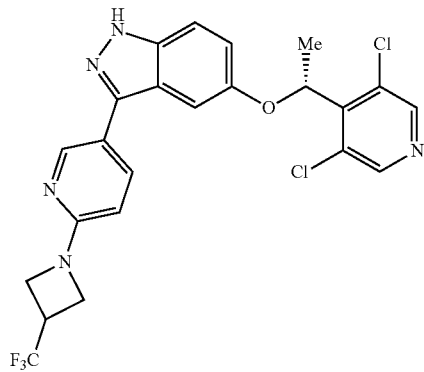 [SMILES: C[C@@H](Oc1ccc2[nH]nc(-c3ccc(N4CC(C(F)(F)F)C4)nc3)c2c1)c1c(Cl)cncc1Cl] | LCMS: m/z = 508.2 (M + H); 1H NMR (400 MHz, DMSO-d6) δ 13.04 (s, 1H), 8.59 (s, 2H), 8.55 (d, J = 1.6 Hz, 1H), 7.90 (dd, J = 8.8 Hz, 2.4 Hz, 1H), 7.46 (d, J = 8.8 Hz, 1H), 7.17 (d, J = 2.0 Hz, 1H), 7.09 (dd, J = 9.2 Hz, 2.0 Hz, 1H), 6.63 (d, J = 8.4 Hz, 1H), 6.11 (q, J = 6.4 Hz, 1H), 4.27 (t, J = 8.8 Hz, 2H), 4.06-4.02 (m, 2H), 3.81-3.73 (m, 1H), 1.76 (d, J = 6.8 Hz, 3H). |
|---|---|---|
| Example 250 5-[(1R)-1-(3,5-dichloro-4-pyridyl)ethoxy]-6-methoxy-3-[5-methyl-6-(2-methylsulfonyl-2,6-diazaspiro[3.3]heptan-6-yl)-3-pyridyl]-1H-indazole | 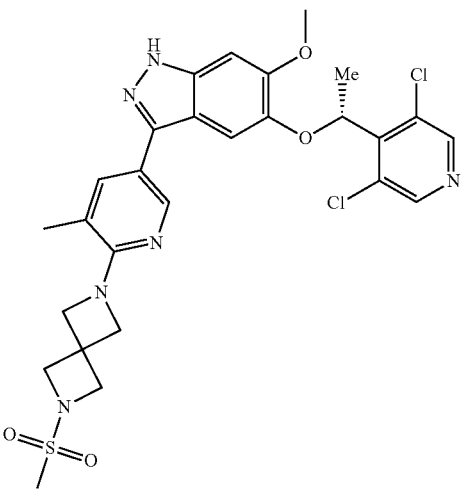 [SMILES: COc1cc2[nH]nc(-c3cnc(N4CC5(C4)CN(S(C)(=O)=O)C5)c(C)c3)c2cc1O[C@H](C)c1c(Cl)cncc1Cl] | LCMS: m/z = 603.2 (M + H); 1H NMR (400 MHz, DMSO-d6) δ = 12.84 - 12.78 (m, 1H), 8.60 (s, 2H), 8.33 (d, J = 2.0 Hz, 1H), 7.61 - 7.55 (m, 1H), 7.03 (s, 1H), 6.99 (s, 1H), 6.00 - 5.93 (m, 1H), 4.27 (s, 4H), 4.10 (s, 4H), 3.86 (s, 3H), 3.02 (s, 3H), 2.24 (s, 3H), 1.75 (d, J = 6.7 Hz, 3H) |
| Example 251 (R)-5-(1-(3,5-dichloropyridin-4-yl)ethoxy)-6-methyl-3-(6-(6-(methylsulfonyl)-2,6-diazaspiro[3.3]heptan-2-yl)pyridin-3-yl)-1H-indazole | 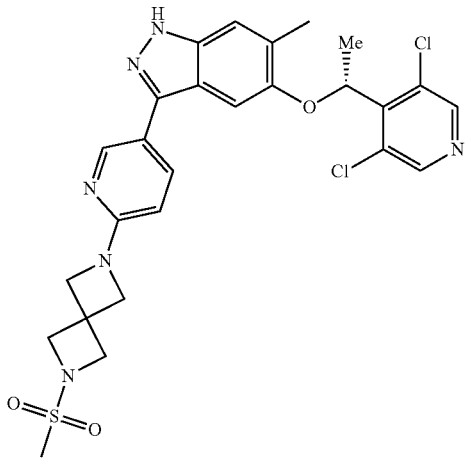 [SMILES: Cc1cc2[nH]nc(-c3ccc(N4CC5(C4)CN(S(C)(=O)=O)C5)nc3)c2cc1O[C@H](C)c1c(Cl)cncc1Cl] | LCMS: m/z = 573.2.2 (M + H) 1H NMR (400 MHz, DMSO-d6) δ 12.85 (s, 1H), 8.63 (s, 2H), 8.45 (d, J = 7.2 Hz, 1H), 7.77 (dd, J = 8.8 Hz, 1.6 Hz, 1H), 7.35 (s, 1H), 6.87 (s, 1H), 6.54 (d, J = 8.4 Hz, 1H), 6.03 (q, J = 6.8 Hz, 1H), 4.17 (s, 4H), 4.12 (s, 4H), 3.03 (s, 3H), 2.41 (s, 3H), 1.78 (d, J = 6.8 Hz, 3H).; |

| Example 252 (R)-5-(1-(3,5-dichloropyridin-4-yl)ethoxy)-3-(6-(3-(difluoromethyl)azetidin-1-yl)pyridin-3-yl)-1H-indazole | 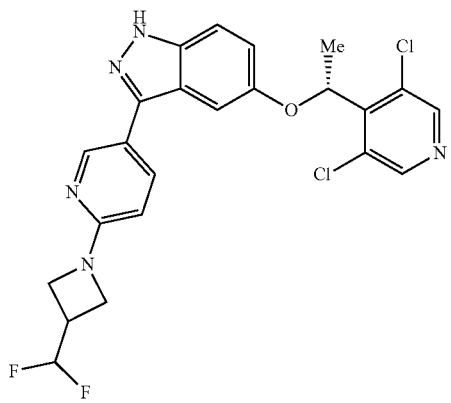 [SMILES: C[C@@H](Oc1ccc2[nH]nc(-c3ccc(N4CC(C(F)F)C4)nc3)c2c1)c1c(Cl)cncc1Cl] | LCMS: m/z = 490.2 (M + H); 1H NMR (400 MHz, DMSO-d6) δ 13.01 (s, 1H), 8.60 (s, 2H), 8.53 (d, J = 2.0 Hz, 1H), 7.87 (dd, J = 8.4 Hz, 2.4 Hz, 1H), 7.46 (d, J = 9.2 Hz, 1H), 7.17 (d, J = 2.0 Hz, 1H), 7.09 (dd, J = 8.8 Hz, 2.4 Hz, 1H), 6.59 (d, J = 8.4 Hz, 1H), 6.42 (td, J = 56.8 Hz, 4.8 Hz, 1H), 6.11 (q, J = 6.8 Hz, 1H), 4.13 (t, J = 8.4 Hz, 2H), 3.98-3.95 (m, 2H), 3.29-3.25 (m, 1H), 1.76 (d, J = 6.8 Hz, 3H). |
|---|---|---|
| Example 253 (R)-1-(5-(5-(1-(3,5-dichloropyridin-4-yl)ethoxy)-1H-indazol-3-yl)pyridin-2-yl)azetidine-3-carbonitrile | 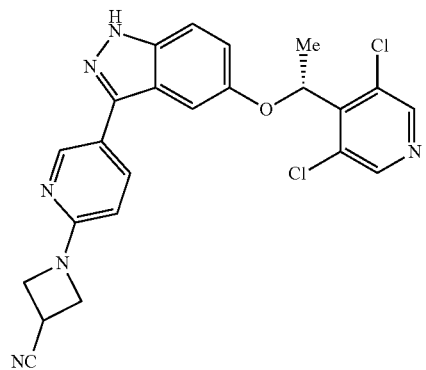 [SMILES: C[C@@H](Oc1ccc2[nH]nc(-c3ccc(N4CC(C#N)C4)nc3)c2c1)c1c(Cl)cncc1Cl] | LCMS: m/z = 465.2 (M + H); 1H NMR (400 MHz, CDCl3) δ 9.98 (brs, 1H), 8.66 (d, J = 2.2 Hz, 1H), 8.43 (s, 2H), 7.95 (d, J = 8.0 Hz, 1H), 7.36 (d, J = 8.8 Hz, 1H), 7.20 (d, J = 2.0 Hz, 1H), 7.13 (dd, J = 8.8 Hz, 2.4 Hz, 1H), 6.46 (d, J = 8.4 Hz, 1H), 6.08 (q, J = 6.8 Hz, 1H), 4.45-4.41 (m, 2H), 4.36-4.33 (m, 2H), 3.70-3.62 (m, 1H), 1.82 (d, J = 6.6 Hz, 3H). |
| Example 254 (S)-5-(1-(3,5-dichloropyridazin-4-yl)ethoxy)-3-(5-fluoro-6-(6-(methylsulfonyl)-2,6-diazaspiro[3.3]heptan-2-yl)pyridin-3-yl)-6-methyl-1H-indazole | 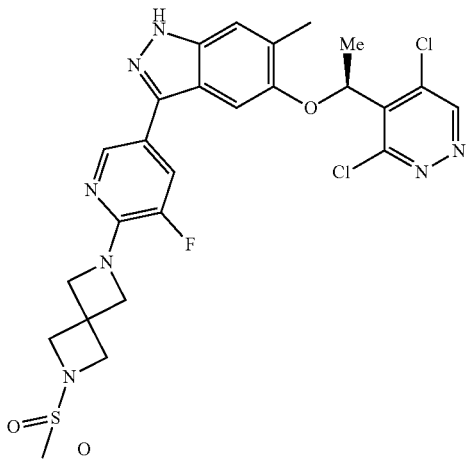 | LCMS: m/z = 592.2 (M + H); 1H NMR (400 MHz,DMSO-d6) δ 13.00 (s, 1H), 9.36 (s, 1H), 8.35 (t, J = 1.6 Hz, 1H), 7.72 (dd, J = 13.2 Hz, 1.6 Hz, 1H), 7.38 (s, 1H), 6.95 (s, 1H), 6.09 (q, J = 6.8 Hz, 1H), 4.31 (d, J = 1.6 Hz, 4H), 4.12 (s, 4H), 3.02 (s, 3H), 2.41 (s, 3H), 1.80 (d, J = 6.8 Hz, 3H). |

-continued

Example 255
(R)-5-(1-(3,5-dichloropyridin-4-yl)ethoxy)-6-fluoro-3-(6-(6-(methylsulfonyl)-2,6-diazaspiro[3.3]heptan-2-yl)pyridin-3-yl)-1H-indazole

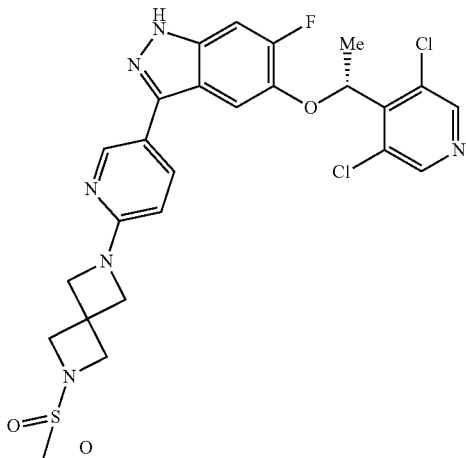

LCMS: m/z = 577.2 (M + H); 1H NMR (400 MHz, DMSO-d6) δ 13.07 (s, 1H), 8.62 (s, 2H), 8.49 (d, J = 2.0 Hz, 1H), 7.83 (dd, J = 8.4 Hz, 2.0 Hz, 1H), 7.43 (d, J = 10.8 Hz, 1H), 7.23 (d, J = 7.6 Hz, 1H), 6.54 (d, J = 8.8 Hz, 1H), 6.12 (q, J = 6.8 Hz, 1H), 4.18 (s, 4H), 4.12 (s, 4H), 3.03 (s, 3H), 1.80 (d, J = 6.8 Hz, 3H).

Example 256
5-[(1R)-1-(3,5-dichloro-4-pyridyl)ethoxy]-6-fluoro-3-[5-fluoro-6-(2-methylsulfonyl-2,6-diazaspiro[3.3]heptan-6-yl)-3-pyridyl]-1H-indazole

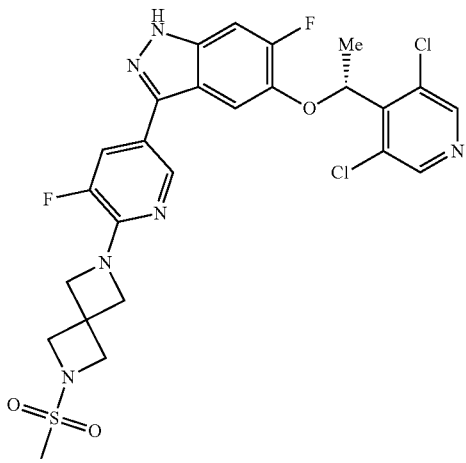 [SMILES: C[C@@H](Oc1cc2c(-c3cnc(N4CC5(C4)CN(S(C)(=O)=O)C5)c(F)c3)n[nH]c2cc1F)c1c(Cl)cncc1Cl]

LCMS: m/z = 595.1 (M + H); 1H NMR (400 MHz, DMSO-d6) δ = 13.19 (s, 1H), 8.60 (s, 2H), 8.36 (s, 1H), 7.71 (dd, J = 1.7, 13.1 Hz, 1H), 7.46 (d, J = 10.9 Hz, 1H), 7.27 (d, J = 7.8 Hz, 1H), 6.16 (q, J = 6.6 Hz, 1H), 4.36 - 4.29 (m, 4H), 4.13 (s, 4H), 3.04 (s, 3H), 1.80 (d, J = 6.7 Hz, 3H)

Example 257
(R)-1-(5-(5-(1-(3,5-dichloropyridin-4-yl)ethoxy)-1H-indazol-3-yl)pyridin-2-yl)-3-methylazetidin-3-amine

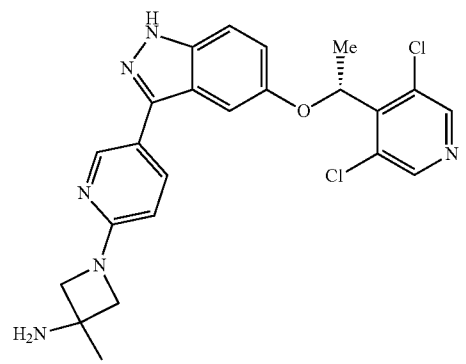 [SMILES: C[C@@H](Oc1ccc2[nH]nc(-c3ccc(N4CC(C)(N)C4)nc3)c2c1)c1c(Cl)cncc1Cl]

LCMS: m/z = 469.2 (M + H); 1H-NMR (400 MHz, DMSO-d6) δ 13.00 (brs, 1H), 8.61 (s, 2H), 8.51 (s, 1H), 7.84 (dd, J = 8.4 Hz, 1.2 Hz, 1H), 7.47 (d, J = 9.2 Hz, 1H), 7.18 (s, 1H), 7.10 (dd, J = 9.2 Hz, 1.6 Hz, 1H), 6.52 (d, J = 8.8 Hz, 1H), 6.12 (q, J = 6.4 Hz, 1H), 3.84 (d, J = 7.2 Hz, 2H), 3.74 (d, J = 7.6 Hz, 2H), 1.77 (d, J = 6.4 Hz, 3H), 1.43 (s, 3H).

-continued

| | | |
|---|---|---|
| Example 258<br>(R)-5-(1-(3,5-dichloropyridazin-4-yl)ethoxy)-6-fluoro-3-(5-fluoro-6-(6-(methylsulfonyl)-2,6-diazaspiro[3.3]heptan-2-yl)pyridin-3-yl)-1H-indazole | 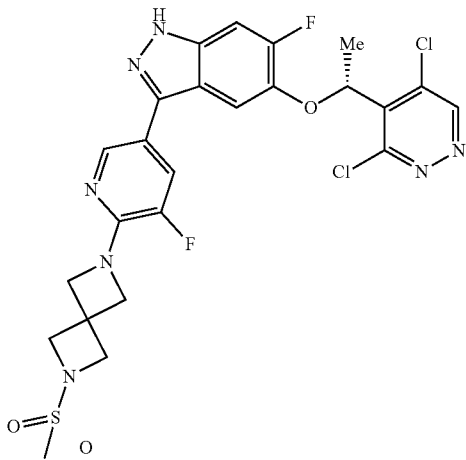 | LCMS: m/z = 596.2 (M + H); 1H NMR (400 MHz,DMSO-d6) δ 9.38 (s, 1H), 8.41 (t, J = 1.2 Hz, 1H), 7.79 (dd, J = 13.2 Hz, 1.6 Hz, 1H), 7.46 (d, J = 11.2 Hz, 1H), 7.42 (d, J = 7.6 Hz, 1H), 6.16 (q, J = 6.8 Hz, 1H), 4.31 (d, J = 1.6 Hz, 4H), 4.12 (s, 4H), 3.03 (s, 3H), 1.81 (d, J = 6.8 Hz, 3H). |
| Example 259<br>(R)-5-(1-(3,5-dichloropyridazin-4-yl)ethoxy)-3-(5-fluoro-6-(6-(methylsulfonyl)-2,6-diazaspiro[3.3]heptan-2-yl)pyridin-3-yl)-6-methyl-1H-indazole | 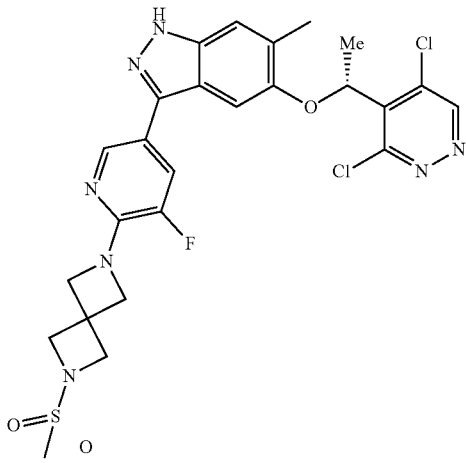 | LCMS: m/z = 592.2 (M + H); 1H NMR (400 MHz,DMSO-d6) δ 13.00 (s, 1H), 9.36 (s, 1H), 8.35 (s, 1H), 7.72 (d, J = 13.2 Hz, 1H), 7.38 (s, 1H), 6.95 (s, 1H), 6.09 (q, J = 6.4 Hz, 1H), 4.31 (s, 4H), 4.12 (s, 4H), 3.03 (s, 3H), 2.41 (s, 3H), 1.80 (d, J = 6.4 Hz, 3H). |
| Example 260<br>(R)-6-chloro-5-(1-(3,5-dichloropyridin-4-yl)ethoxy)-3-(6-(6-(methylsulfonyl)-2,6-diazaspiro[3.3]heptan-2-yl)pyridin-3-yl)-1H-indazole | 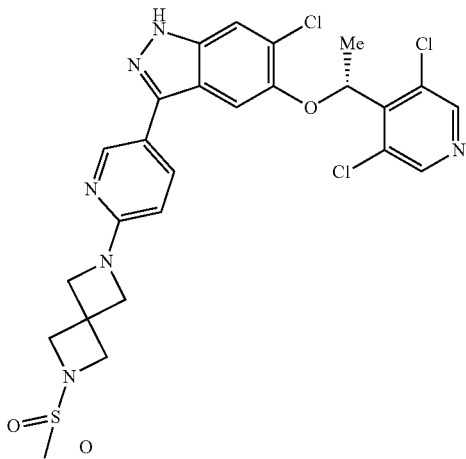 | LCMS: m/z = 593.2 (M + H); 1H NMR (400 MHz, DMSO-d6) δ 13.07 (brs, 1H), 8.63 (s, 2H), 8.45 (dd, J = 2.0 Hz, 0.4 Hz, 1H), 7.78 (dd, J = 8.8 Hz, 2.8 Hz, 1H), 7.70 (s, 1H), 7.11 (s, 1H), 6.55 (d, J = 8.4 Hz, 1H), 6.11 (q, J = 6.8 Hz, 1H), 4.18 (s, 4H), 4.12 (s, 4H), 3.03 (s, 3H), 1.81 (d, J = 6.8 Hz, 3H). |

| | | |
|---|---|---|
| Example 261<br>(R)-5-(1-(3,5-dichloropyridazin-4-yl)ethoxy)-6-methoxy-3-(6-(6-(methylsulfonyl)-2,6-diazaspiro[3.3]heptan-2-yl)pyridin-3-yl)-1H-indazole | 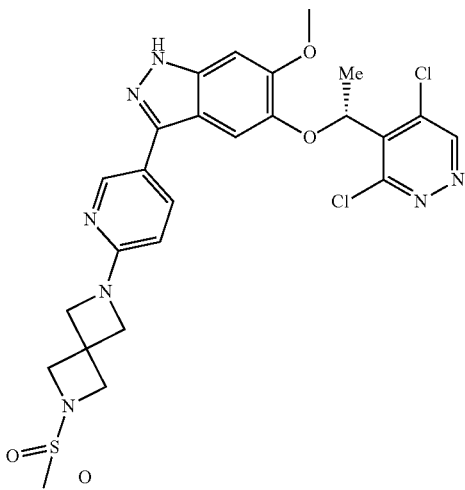 | LCMS: m/z = 590.2 (M + H); 1H NMR (400 MHz, DMSO-d6) δ 12.85 (s, 1H), 9.38 (s, 1H), 8.51 (s, 1H), 7.89 (d, J = 8.4 Hz, 1H), 7.21 (s, 1H), 6.99 (s, 1H), 6.52 (d, J = 8.8 Hz, 1H), 5.91 (q, J = 6.4 Hz, 1H), 4.17 (s, 4H), 4.11 (s, 4H), 3.82 (s, 3H), 3.03 (s, 3H), 1.78 (d, J = 6.4 Hz, 3H). |
| Example 262<br>(R)-5-(1-(3,5-dichloropyridazin-4-yl)ethoxy)-6-fluoro-3-(6-(6-(methylsulfonyl)-2,6-diazaspiro[3.3]heptan-2-yl)pyridin-3-yl)-1H-indazole | 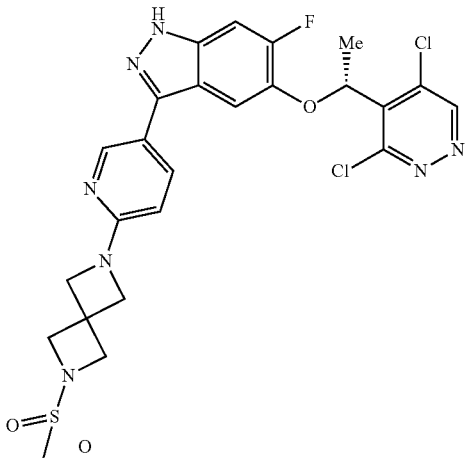 | LCMS: m/z = 578.1 (M + H); 1H NMR (400 MHz, DMSO-d6) δ 13.10 (brs, 1H), 9.40 (s, 1H), 8.54 (s, 1H), 7.90 (d, J = 8.4 Hz,1H), 7.45 (d, J = 10.4 Hz, 1H), 7.36 (d, J = 8.0 Hz, 1H), 6.54 (d, J = 8.8 Hz, 1H), 6.13 (q, J = 6.4 Hz, 1H), 4.18 (s, 4H), 4.12 (s, 4H), 3.03 (s, 3H), 1.82 (d, J = 6.8 Hz, 3H). |
| Example 263<br>(R)-6-chloro-5-(1-(3,5-dichloropyridazin-4-yl)ethoxy)-3-(6-(6-(methylsulfonyl)-2,6-diazaspiro[3.3]heptan-2-yl)pyridin-3-yl)-1H-indazole | 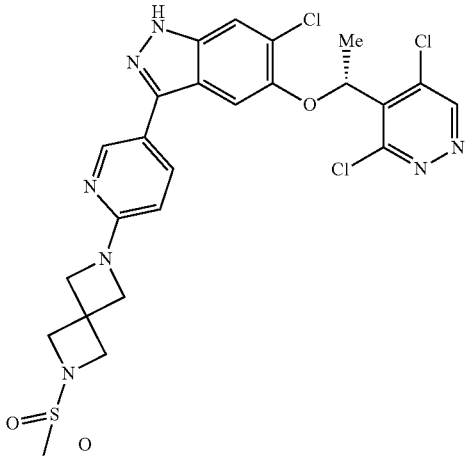 | LCMS: m/z = 594.1 (M + H); 1H-NMR (400 MHz, DMSO-d6) δ 9.41 (s, 1H), 8.53 (d, J = 2.0 Hz, 1H), 7.88 (dd, J = 8.8 Hz, 2.4 Hz, 1H), 7.72 (s, 1H), 7.23 (s, 1H), 6.54 (d, J = 8.4 Hz, 1H), 6.14 (q, J = 6.4 Hz, 1H), 4.19 (s, 4H), 4.13 (s, 4H), 3.04 (s, 3H), 1.83 (d, J = 6.8 Hz, 3H). |

-continued

| Example 264 (R)-6-chloro-5-(1-(3,5-dichloropyridazin-4-yl)ethoxy)-3-(5-fluoro-6-(6-(methylsulfonyl)-2,6-diazaspiro[3.3]heptan-2-yl)pyridin-3-yl)-1H-indazole | 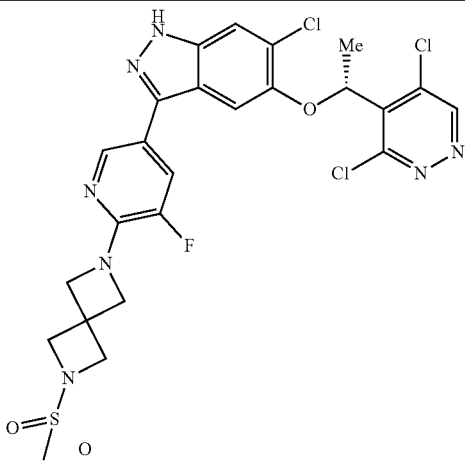 | LCMS: m/z = 612 (M + H); 1H-NMR (400 MHz, DMSO-d6) δ 13.25 (s, 1H), 9.37 (s, 1H), 8.39 (s, 1H), 7.77 (d, J = 12.8 Hz, 1H), 7.73 (s, 1H), 7.27 (s, 1H), 6.16 (q, J = 6.4 Hz, 1H), 4.32 (s, 4H), 4.12 (s, 4H), 3.03 (s, 3H), 1.83 (d, J = 6.4 Hz, 3H). |
|---|---|---|
| Example 265 (R)-1-(5-(5-(1-(3,5-dichloropyridin-4-yl)ethoxy)-1H-indazol-3-yl)-3-fluoropyridin-2-yl)-3-methylazetidin-3-amine | 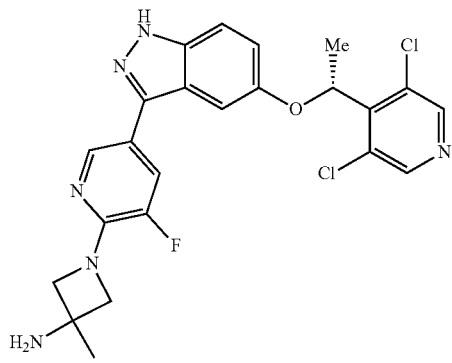 [SMILES: C[C@@H](Oc1ccc2[nH]nc(-c3cnc(N4CC(C)(N)C4)c(F)c3)c2c1)c1c(Cl)cncc1Cl] | LCMS: m/z = 487.2 (M + H); 1H-NMR (400 MHz, DMSO-d6) δ 13.11 (brs, 1H), 8.57 (s, 2H), 8.37 (d, J = 1.2 Hz, 1H), 7.69 (dd, J = 13.2 Hz, 2.0 Hz, 1H), 7.47 (d, J = 8.8 Hz, 1H), 7.20 (s, 1H), 7.10 (dd, J = 9.2 Hz, 2.0 Hz, 1H), 6.14 (q, J = 6.4 Hz, 1H), 3.91 (t, J = 9.6 Hz, 4H), 1.76 (d, J = 6.4 Hz, 3H), 1.44 (s, 3H). |
| Example 266 5-[(1R)-1-(3,5-dichloro-2-methyl-4-pyridyl)ethoxy]-6-fluoro-3-[6-(2-methylsulfonyl-2,6-diazaspiro[3.3]heptan-6-yl)-3-pyridyl]-1H-indazole | 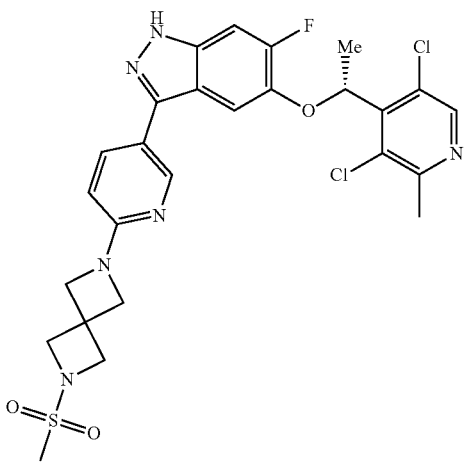 [SMILES: Cc1ncc(Cl)c([C@@H](C)Oc2cc3c(-c4ccc(N5CC6(C5)CN(S(C)(=O)=O)C6)nc4)n[nH]c3cc2F)c1Cl] | LCMS: m/z = 591.1 (M + H); 1H NMR (400 MHz, DMSO-d6) δ = 13.19 (br s, 1H), 8.47 (s, 1H), 8.35 (d, J = 1.8 Hz, 1H), 8.00 (br d, J = 8.8 Hz, 1H), 7.46 (d, J = 10.9 Hz, 1H), 7.17 (d, J = 7.8 Hz, 1H), 6.71 (br d, J = 8.7 Hz, 1H), 6.13 (q, J = 6.7 Hz, 1H), 4.47 (br s, 1H), 4.29 (s, 5H), 4.13 (s, 4H), 2.58 (s, 3H), 1.80 (d, J = 6.6 Hz, 3H) |
| Example 267 5-((R)-1-(3,5-dichloropyridin-4-yl)ethoxy)-3-(5-fluoro-6-((R)-2-methylazetidin-1-yl)pyridin-3-yl)-6-methoxy-1H-indazole | 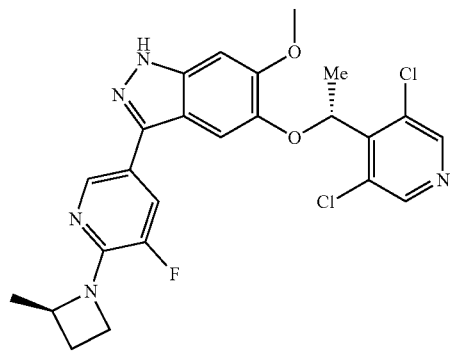 [SMILES: COc1cc2[nH]nc(-c3cnc(N4CC[C@H]4C)c(F)c3)c2cc1O[C@H](C)c1c(Cl)cncc1Cl] | LCMS: m/z = 502.2 (M + H); 1H-NMR (400 MHz, DMSO-d6) δ 12.91 (s, 1H), 8.58 (s, 2H), 8.30 (s, 1H), 7.62 (d, J = 13.2 Hz, 1H), 7.08 (s, 1H), 7.00 (s, 1H), 5.98 (q, J = 6.8 Hz, 1H), 4.59-4.52 (m, 1H), 4.14-4.08 (m, 1H), 4.01-3.94 (m, 1H), 3.85 (s, 3H), 2.48-2.43 (m, 1H), 2.06-1.97 (m, 1H), 1.76 (d, J = 6.8 Hz, 3H), 1.46 (d, J = 6.4 Hz, 3H). |

-continued

Example 268
(R)-3-(6-(azetidin-1-yl)-5-fluoropyridin-3-yl)-5-(1-(3,5-dichloropyridin-4-yl)ethoxy)-6-methoxy-1H-indazole

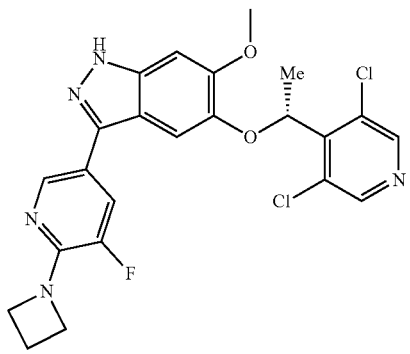 [SMILES: COc1cc2[nH]nc(-c3cnc(N4CCC4)c(F)c3)c2cc1O[C@H](C)c1c(Cl)cncc1Cl]

LCMS: m/z = 488.1 (M + H); 1H-NMR (400 MHz, DMSO-d6) δ 12.93 (s, 1H), 8.59 (s, 2H), 8.29 (s, 1H), 7.62 (d, J = 13.6 Hz, 1H), 7.08 (s, 1H), 7.00 (s, 1H), 5.98 (q, J = 6.4 Hz, 1H), 4.14 (t, J = 6.8 Hz, 4H), 3.85 (s, 3H), 2.41-2.30 (m, 2H), 1.75 (d, J = 6.0 Hz, 3H).

Example 269
5-[(1R)-1-(3,5-dichloro-2-methyl-4-pyridyl)ethoxy]-6-fluoro-3-[5-fluoro-6-(2-methylsulfonyl-2,6-diazaspiro[3.3]heptan-6-yl)-3-pyridyl]-1H-indazole

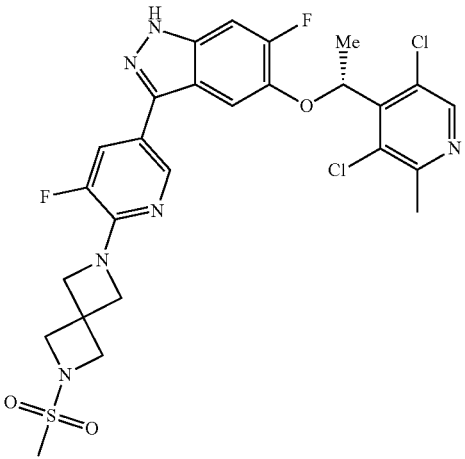 [SMILES: Cc1ncc(Cl)c([C@@H](C)Oc2cc3c(-c4cnc(N5CC6(C5)CN(S(C)(=O)=O)C6)c(F)c4)n[nH]c3cc2F)c1Cl]

LCMS: m/z = 609.1 (M + H); 1H NMR (400 MHz, DMSO-d6) δ = 13.19 (br s, 1H), 8.44 (s, 1H), 8.22 (t, J = 1.5 Hz, 1H), 7.68 (dd, J = 1.8, 13.0 Hz, 1H), 7.46 (d, J = 10.9 Hz, 1H), 7.13 (d, J = 7.9 Hz, 1H), 6.17 - 6.11 (m, 1H), 4.32 (d, J = 1.7 Hz, 4H), 4.12 (s, 4H), 3.02 (s, 3H), 2.60 (s, 3H), 1.80 (d, J = 6.7 Hz, 3H)

Example 270
6-chloro-5-[(1R)-1-(3,5-dichloro-2-methyl-4-pyridyl)ethoxy]-3-[5-fluoro-6-(2-methylsulfonyl-2,6-diazaspiro[3.3]heptan-6-yl)-3-pyridyl]-1H-indazole

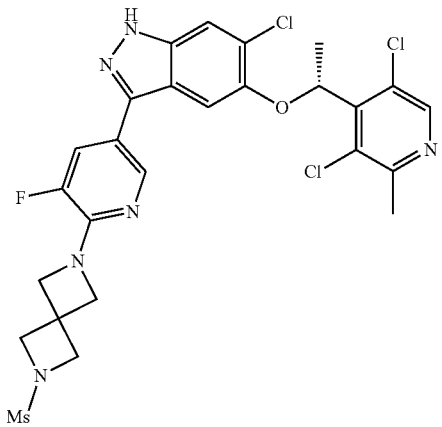 [SMILES: Cc1ncc(Cl)c([C@@H](C)Oc2cc3c(-c4cnc(N5CC6(C5)CN(S(C)(=O)=O)C6)c(F)c4)n[nH]c3cc2Cl)c1Cl]

LCMS: m/z = 625.1 (M + H); 1H NMR (400 MHz, DMSO-d6) δ = 13.21 (s, 1H), 8.44 (s, 1H), 8.20 - 8.16 (m, 1H), 7.72 (s, 1H), 7.66 (dd, J = 1.8, 13.0 Hz, 1H), 7.02 (s, 1H), 6.13 (q, J = 6.7 Hz, 1H), 4.32 (d, J = 1.7 Hz, 4H), 4.12 (s, 4H), 3.02 (s, 3H), 2.61 (s, 3H), 1.81 (d, J = 6.6 Hz, 3H)

Example 271
5-((R)-1-(3,5-dichloropyridin-4-yl)ethoxy)-3-(5-fluoro-6-((S)-2-methylazetidin-1-yl)pyridin-3-yl)-6-methoxy-1H-indazole

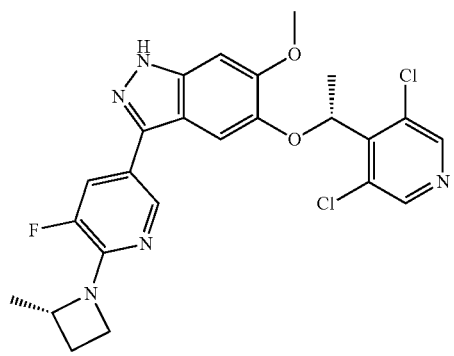 [SMILES: COc1cc2[nH]nc(-c3cnc(N4CC[C@@H]4C)c(F)c3)c2cc1O[C@H](C)c1c(Cl)cncc1Cl]

LCMS: m/z = 502.2 (M + H); 1H NMR (400 MHz, DMSO-d6) δ 12.91 (s, 1H), 8.59 (s, 2H), 8.29 (s, 1H), 7.63 (dd, J = 13.2 Hz, 1.6 Hz, 1H), 7.08 (s, 1H), 7.00 (s, 1H), 5.98 (q, J = 6.4 Hz, 1H), 4.59-4.51 (m, 1H), 4.15-4.09 (m, 1H), 4.01-3.96 (m, 1H), 3.86 (s, 3H), 2.47-2.44 (m, 1H), 2.07-1.98 (m, 1H), 1.76 (d, J = 6.4 Hz, 3H), 1.47 (d, J = 6.4 Hz, 3H).

-continued

| Example 272<br>6-chloro-5-((R)-1-(3,5-dichloropyridin-4-yl)ethoxy)-3-(5-fluoro-6-((R)-2-methylazetidin-1-yl)pyridin-3-yl)-1H-indazole | 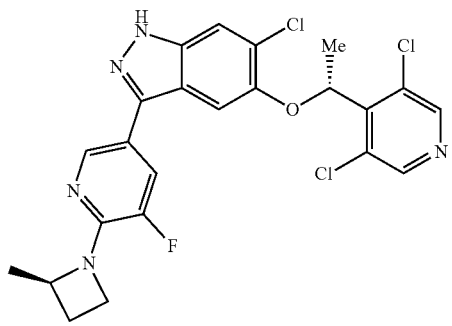 [SMILES: C[C@@H]1CCN1c1ncc(-c2n[nH]c3cc(Cl)c(O[C@H](C)c4c(Cl)cncc4Cl)cc23)cc1F] | LCMS: m/z = 506.1 (M + H); 1H-NMR (400 MHz, DMSO-d6) δ 13.24 (brs, 1H), 8.60 (s, 2H), 8.32 (s, 1H), 7.72 (s, 1H), 7.63 (dd, J = 13.2 Hz, 1.6 Hz, 1H), 7.14 (s, 1H), 6.16 (q, J = 6.4 Hz, 1H), 4.59-4.50 (m, 1H), 4.17-4.09 (m, 1H), 4.04-3.95 (m, 1H), 2.49-2.44 (m, 1H), 2.09-1.95 (m, 1H), 1.81 (d, J = 6.4 Hz, 3H), 1.48 (d, J = 6.4 Hz, 3H). |
| --- | --- | --- |
| Example 273<br>5-[(1R)-1-(3,5-dichloro-2-methyl-4-pyridyl)ethoxy]-3-[5-fluoro-6-(2-methylsulfonyl-2,6-diazaspiro[3.3]heptan-6-yl)-3-pyridyl]-6-methyl-1H-indazole | 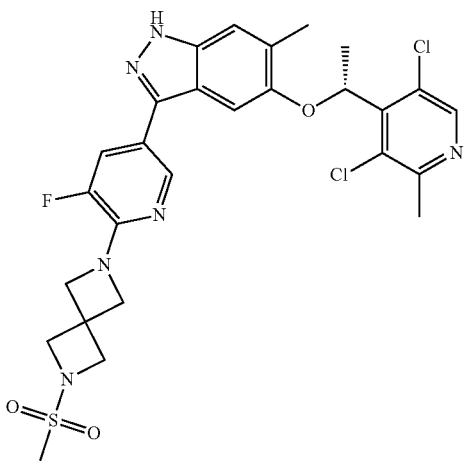 [SMILES: Cc1cc2[nH]nc(-c3cnc(N4CC5(C4)CN(S(C)(=O)=O)C5)c(F)c3)c2cc1O[C@H](C)c1c(Cl)cnc(C)c1Cl] | LCMS: m/z = 605.1 (M + H); 1H NMR (400 MHz, DMSO-d6) δ = 12.96 (s, 1H), 8.43 (s, 1H), 8.18 (s, 1H), 7.64 (dd, J = 1.8, 13.1 Hz, 1H), 7.36 (s, 1H), 6.79 (s, 1H), 6.04 (q, J = 6.7 Hz, 1H), 4.31 (d, J = 1.7 Hz, 4H), 4.12 (s, 4H), 3.02 (s, 3H), 2.67 - 2.60 (m, 3H), 2.41 (s, 3H), 1.79 (d, J = 6.6 Hz, 3H) |
| Example 274<br>3-[6-(azetidin-1-yl)-5-fluoro-3-pyridyl]-6-chloro-5-[(1R)-1-(3,5-dichloro-2-methyl-4-pyridyl)ethoxy]-1H-indazole | 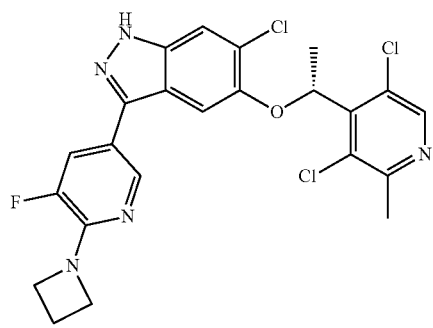 [SMILES: Cc1ncc(Cl)c([C@@H](C)Oc2cc3c(-c4cnc(N5CCC5)c(F)c4)n[nH]c3cc2Cl)c1Cl] | LCMS: m/z = 507.1 (M + H); 1H NMR (400 MHz, DMSO-d6) δ = 13.18 (s, 1H), 8.43 (s, 1H), 8.17 (s, 1H), 7.71 (s, 1H), 7.61 (dd, J = 1.8, 13.1 Hz, 1H), 7.00 (s, 1H), 6.11 (q, J = 6.7 Hz, 1H), 4.20 - 4.11 (m, 4H), 2.60 (s, 3H), 2.48 - 2.34 (m, 2H), 1.80 (d, J = 6.7 Hz, 3H) |
| Example 275<br>1-[5-[6-chloro-5-[(1R)-1-(3,5-dichloro-2-methyl-4-pyridyl)ethoxy]-1H-indazol-3-yl]-3-fluoro-2-pyridyl]-N,3-dimethyl-azetidin-3-amine | 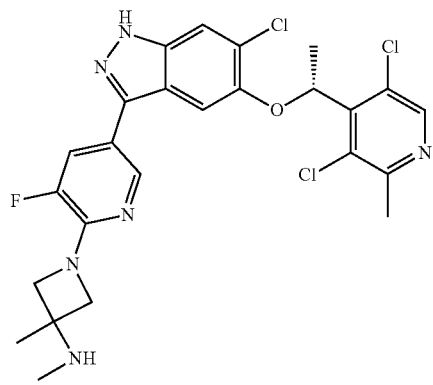 [SMILES: CNC1(C)CN(c2ncc(-c3n[nH]c4cc(Cl)c(O[C@H](C)c5c(Cl)cnc(C)c5Cl)cc34)cc2F)C1] | LCMS: m/z = 549.1 (M + H); 1H NMR (400 MHz, DMSO-d6) δ = 13.31 (br s, 1H), 9.38 (br s, 2H), 8.48 - 8.43 (m, 1H), 8.24 (s, 1H), 7.78 - 7.70 (m, 2H), 7.02 (s, 1H), 6.13 (q, J = 6.6 Hz, 1H), 4.33 (br d, J = 9.7 Hz, 2H), 4.12 (br d, J = 9.5 Hz, 2H), 2.66 (s, 3H), 2.61 (s, 3H), 1.85 - 1.75 (m, 3H), 1.65 (s, 3H) |

| | | |
|---|---|---|
| Example 276<br>(R)-5-(1-(3,5-dichloropyridin-4-yl)ethoxy)-3-(6-(3,3-dimethylazetidin-1-yl)-5-fluoropyridin-3-yl)-6-methoxy-1H-indazole | 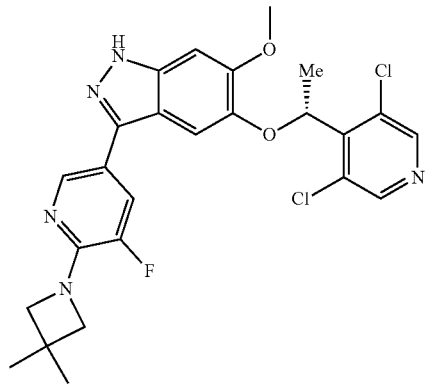 [SMILES: COc1cc2[nH]nc(-c3cnc(N4CC(C)(C)C4)c(F)c3)c2cc1O[C@H](C)c1c(Cl)cncc1Cl] | LCMS: m/z = 516.3 (M + H); 1H-NMR (400 MHz, DMSO-d6) δ 12.93 (brs, 1H), 8.59 (s, 2H), 8.29 (s, 1H), 7.62 (dd, J = 13.2 Hz, 0.8 Hz, 1H), 7.08 (s, 1H), 7.00 (s, 1H), 5.99 (q, J = 6.4 Hz, 1H), 3.86-3.83 (m, 7H), 1.75 (d, J = 6.4 Hz, 3H), 1.32 (s, 6H). |
| Example 277<br>6-chloro-5-((R)-1-(3,5-dichloropyridin-4-yl)ethoxy)-3-(5-fluoro-6-((S)-2-methylazetidin-1-yl)pyridin-3-yl)-1H-indazole | 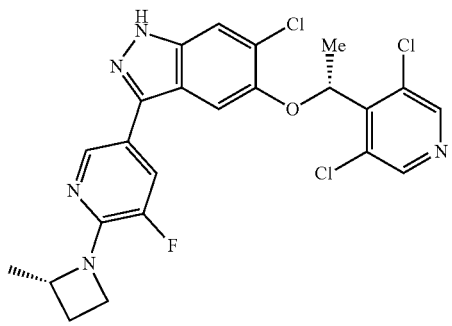 [SMILES: C[C@@H](Oc1cc2c(-c3cnc(N4CC[C@@H]4C)c(F)c3)n[nH]c2cc1Cl)c1c(Cl)cncc1Cl] | LCMS: m/z = 506.2 (M + H); 1H NMR (400 MHz, DMSO-d6) δ 13.21 (brs, 1H), 8.61 (s, 2H), 8.29 (s, 1H), 7.72 (s, 1H), 7.65 (dd, J = 13.2 Hz, 1.6 Hz, 1H), 7.13 (s, 1H) , 6.15 (q, J = 6.4 Hz, 1H), 4.60-4.53 (m, 1H), 4.14-4.12 (m, 1H), 4.01-3.99 (m, 1H), 2.46-2.44 (m, 1H), 2.07-1.98 (m, 1H), 1.81 (d, J = 6.4 Hz, 3H), 1.48 (d, J = 6.0 Hz ,3H). |
| Example 278<br>(R)-3-(6-(azetidin-1-yl)-5-fluoropyridin-3-yl)-6-chloro-5-(1-(3,5-dichloropyridin-4-yl)ethoxy)-1H-indazole | 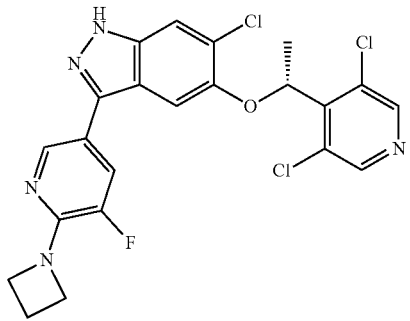 [SMILES: C[C@@H](Oc1cc2c(-c3cnc(N4CCC4)c(F)c3)n[nH]c2cc1Cl)c1c(Cl)cncc1Cl] | LCMS: m/z = 492.1 (M + H); 1H NMR (400 MHz, DMSO-d6) δ13.21 (s, 1H), 8.60 (s, 2H), 8.30 (s, 1H), 7.71 (s, 1H), 7.62 (dd, J = 13.2 Hz, 1.6 Hz, 1H), 7.12 (s, 1H), 6.14 (q, J = 6.4 Hz, 1H), 4.15 (t, J = 6.8 Hz, 4H), 2.41-2.34 (m, 2H), 1.80 (d, J = 6.4 Hz, 3H). |
| Example 279<br>(R)-5-(1-(3,5-dichloropyridin-4-yl)ethoxy)-3-(3,5-difluoro-4-(6-(methylsulfonyl)-2,6-diazaspiro[3.3]heptan-2-yl)phenyl)-6-methoxy-1H-indazole | 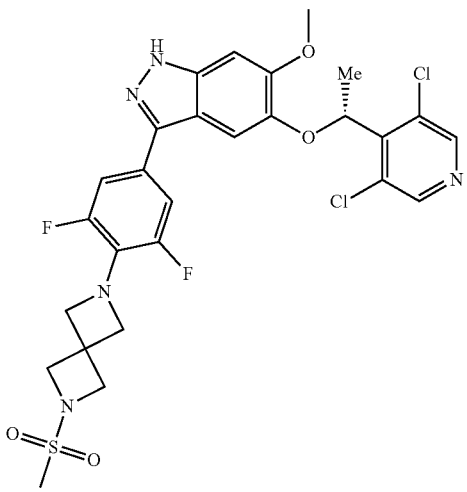 [SMILES: COc1cc2[nH]nc(-c3cc(F)c(N4CC5(C4)CN(S(C)(=O)=O)C5)c(F)c3)c2cc1O[C@H](C)c1c(Cl)cncc1Cl] | LCMS: m/z = 624.2 (M + H); 1H-NMR (400 MHz, DMSO-d6) δ 8.59 (s, 2H), 7.19 (dd, J = 8.8 Hz, 2.4 Hz, 2H), 6.99 (s, 1H), 6.95 (s, 1H), 5.99 (q, J = 6.4 Hz, 1H), 4.34 (s, 4H), 4.10 (s, 4H), 3.87 (s, 3H), 3.02 (s, 3H), 1.76 (d, J = 6.4 Hz, 3H). |

| | | |
|---|---|---|
| Example 280<br>(R)-3-(4-(azetidin-1-yl)-3,5-difluorophenyl)-5-(1-(3,5-dichloropyridin-4-yl)ethoxy)-6-methoxy-1H-indazole | 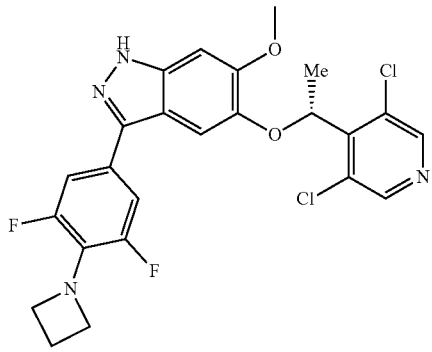 [SMILES: COc1cc2[nH]nc(-c3cc(F)c(N4CCC4)c(F)c3)c2cc1O[C@H](C)c1c(Cl)cncc1Cl] | LCMS: m/z = 505.2 (M + H); 1H NMR (400 MHz, DMSO-d6) δ 12.91 (s, 1H), 8.59 (s, 2H), 7.18 (d, J = 2.8 Hz, 1H), 7.15 (d, J = 2.8 Hz, 1H), 6.99 (s, 1H), 6.96 (s, 1H), 5.98 (q, J = 6.4 Hz, 1H), 4.20-4.16 (m, 4H), 3.87 (s, 3H), 2.33-2.26 (m, 2H), 1.76 (d, J = 6.4 Hz, 3H). |
| Example 281<br>(R)-1-(5-(5-(1-(3,5-dichloropyridin-4-yl)ethoxy)-6-methoxy-1H-indazol-3-yl)-3-fluoropyridin-2-yl)-N,N,3-trimethylazetidin-3-amine | 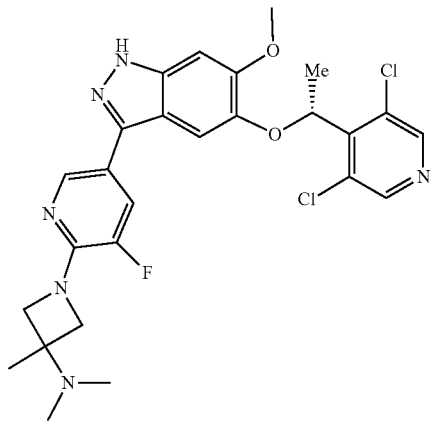 [SMILES: COc1cc2[nH]nc(-c3cnc(N4CC(C)(N(C)C)C4)c(F)c3)c2cc1O[C@H](C)c1c(Cl)cncc1Cl] | LCMS: m/z = 545.3 (M + H); 1H NMR (400 MHz, DMSO-d6) δ 12.94 (brs, 1H), 8.59 (s, 2H), 8.29 (s, 1H), 7.65 (dd, J = 12.8 Hz, 1.2 Hz, 1H), 7.08 (s, 1H), 7.00 (s, 1H), 6.00 (q, J = 6.8 Hz, 1H), 3.93 (d, J = 7.6 Hz, 2H), 3.86 (s, 3H), 3.80 (d, J = 8.0 Hz, 2H), 2.11 (s, 6H), 1.76 (d, J = 6.8 Hz, 3H), 1.31 (s, 3H). |
| Example 282<br>(R)-N-(1-(5-(5-(1-(3,5-dichloropyridin-4-yl)ethoxy)-6-methoxy-1H-indazol-3-yl)-3-fluoropyridin-2-yl)-3-methylazetidin-3-yl)-N-methylmethanesulfonamide | 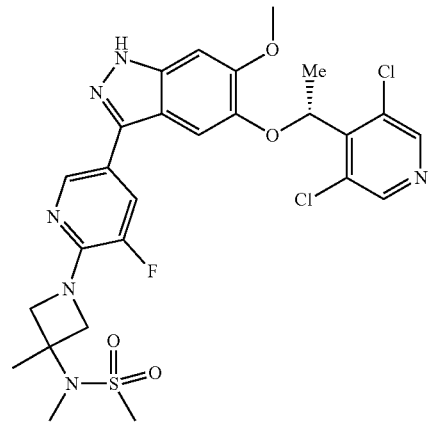 [SMILES: COc1cc2[nH]nc(-c3cnc(N4CC(C)(N(C)S(C)(=O)=O)C4)c(F)c3)c2cc1O[C@H](C)c1c(Cl)cncc1Cl] | LCMS: m/z = 609.2 (M + H); 1H NMR (400 MHz, DMSO-d6) δ 12.98 (s, 1H), 8.59 (s, 2H), 8.33 (s, 1H), 7.70 (dd, J = 13.2 Hz, 1.6 Hz, 1H), 7.08 (s, 1H), 7.00 (s, 1H), 6.00 (q, J = 6.4 Hz, 1H), 4.24-4.22 (m, 2H), 3.89-3.87 (m, 2H), 3.86 (s, 3H), 3.04 (s, 3H), 2.70 (s, 3H), 1.76 (d, J = 6.4 Hz, 3H), 1.70 (s, 3H). |
| Example 283<br>(S)-2-(azetidin-1-yl)-5-(5-(1-(3,5-dichloro-2-fluoropyridin-4-yl)ethoxy)-1H-indazol-3-yl)nicotinonitrile | 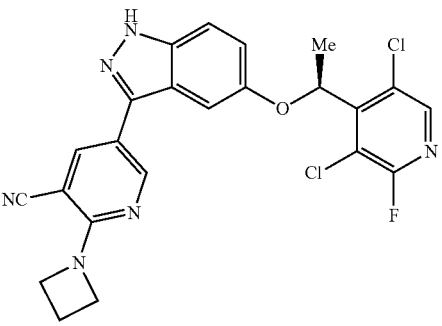 [SMILES: C[C@H](Oc1ccc2[nH]nc(-c3cnc(N4CCC4)c(C#N)c3)c2c1)c1c(Cl)cnc(F)c1Cl] | LCMS: m/z = 483.2 (M + H); 1H-NMR (400 MHz, DMSO-d6) δ 13.17 (brs, 1H), 8.79-8.77 (m, 1H), 8.34-8.31 (m, 1H), 8.24-8.20 (m, 1H), 7.53-7.48 (m, 1H), 7.24-7.10 (m, 2H), 6.25-6.15 (m, 1H), 4.36-4.33 (m, 4H), 2.42-2.33 (m, 2H), 1.81-1.76 (m, 3H). |

-continued

| Example 284 5-(5-((R)-1-(3,5-dichloro-2-fluoropyridin-4-yl)ethoxy)-1H-indazol-3-yl)-2-((R)-3-hydroxypyrrolidin-1-yl)nicotinonitrile | 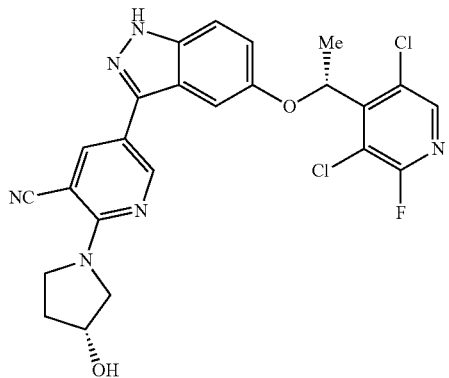 [SMILES: C[C@@H](Oc1ccc2[nH]nc(-c3cnc(N4CC[C@@H](O)C4)c(C#N)c3)c2c1)c1c(Cl)cnc(F)c1Cl] | LCMS: m/z = 513.2 (M + H); 1H-NMR (400 MHz, DMSO-d6) δ 13.16 (s, 1H), 8.78 (d, J = 2.8 Hz, 1H), 8.32 (s, 1H), 8.20 (d, J = 2.8 Hz, 1H), 7.49 (d, J = 9.2 Hz, 1H), 7.21 (d, J = 2.0 Hz, 1H), 7.11 (dd, J = 9.2 Hz, 2.4 Hz, 1H), 6.17 (q, J = 6.4 Hz, 1H), 5.10 (d, J = 3.6 Hz, 1H), 4.47-4.40 (m, 1H), 3.89-3.79 (m, 3H), 3.71-3.64 (m, 1H), 2.12-1.88 (m, 2H), 1.77 (d, J = 6.8 Hz, 3H). |
|---|---|---|
| Example 285 5-[5-[(1R)-1-(3,5-dichloro-4-pyridyl)ethoxy]-1H-indazol-3-yl]-2-pyrrolidin-1-yl-pyridine-3-carbonitrile | 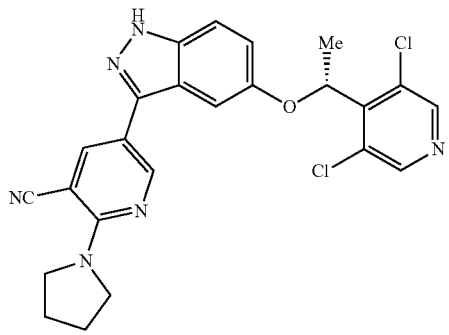 [SMILES: C[C@@H](Oc1ccc2[nH]nc(-c3cnc(N4CCCC4)c(C#N)c3)c2c1)c1c(Cl)cncc1Cl] | LCMS: m/z = 479.1 (M + H); 1H NMR (400 MHz, DMSO-d6) δ = 13.13 (br s, 1H), 8.76 (d, J = 2.4 Hz, 1H), 8.58 (s, 2H), 8.11 (d, J = 2.3 Hz, 1H), 7.48 (d, J = 9.2 Hz, 1H), 7.15 (d, J = 2.1 Hz, 1H), 7.10 (dd, J = 2.3, 8.9 Hz, 1H), 6.14 (q, J = 6.6 Hz, 1H), 3.78 - 3.72 (m, 4H), 2.01 - 1.95 (m, 4H), 1.76 (d, J = 6.7 Hz, 3H) |
| Example 286 (R)-2-(azetidin-1-yl)-5-(5-(1-(3,5-dichloro-2-fluoropyridin-4-yl)ethoxy)-1H-indazol-3-yl)nicotinonitrile | 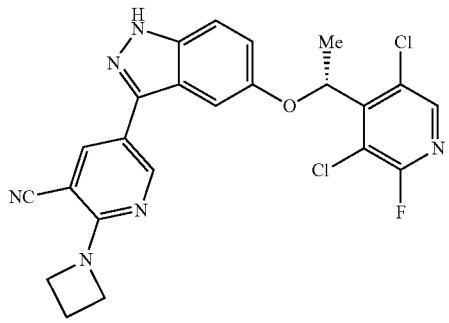 [SMILES: C[C@@H](Oc1ccc2[nH]nc(-c3cnc(N4CCC4)c(C#N)c3)c2c1)c1c(Cl)cnc(F)c1Cl] | LCMS: m/z = 483.1 (M + H); 1H-NMR (400 MHz, DMSO-d6) δ 13.18 (s, 1H), 8.77 (d, J = 2.8 Hz, 1H), 8.31 (d, J = 0.8 Hz, 1H), 8.21 (d, J = 2.0 Hz, 1H), 7.49 (d, J = 8.8 Hz, 1H), 7.21 (d, J = 2.0 Hz, 1H), 7.11 (dd, J = 9.2, 2.4 Hz, 1H), 6.17 (q, J = 6.8 Hz, 1H), 4.32 (t, J = 7.6 Hz, 4H), 2.43-2.35 (m, 2H), 1.77 (d, J = 6.8 Hz, 3H). |
| Example 287 (R)-5-(5-(1-(3,5-dichloro-2-fluoropyridin-4-yl)ethoxy)-1H-indazol-3-yl)-2-(3-hydroxyazetidin-1-yl)nicotinonitrile | 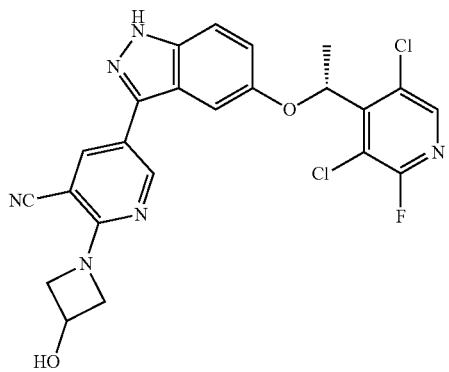 [SMILES: C[C@@H](Oc1ccc2[nH]nc(-c3cnc(N4CC(O)C4)c(C#N)c3)c2c1)c1c(Cl)cnc(F)c1Cl] | LCMS: m/z = 499.1 (M + H); 1H NMR (400 MHz, DMSO-d6) δ 13.17 (s, 1H), 8.77 (d, J = 2.4 Hz, 1H), 8.31 (d, J = 1.2 Hz, 1H), 8.22 (d, J = 2.0 Hz, 1H), 7.49 (d, J = 8.8 Hz, 1H), 7.22 (d, J = 2.0 Hz, 1H), 7.10 (dd, J = 9.2 Hz, 2.4 Hz, 1H), 6.16 (q, J = 6.8 Hz, 1H), 5.79 (d, J = 6.0 Hz, 1H), 4.63-4.61 (m, 1H), 4.54-4.50 (m, 2H), 4.05-4.02 (m, 2H), 1.77 (d, J = 6.4 Hz, 3H). |

-continued

| Example 288 5-(5-((R)-1-(3,5-dichloro-2-fluoropyridin-4-yl)ethoxy)-1H-indazol-3-yl)-2-((S)-3-hydroxypyrrolidin-1-yl)nicotinonitrile | 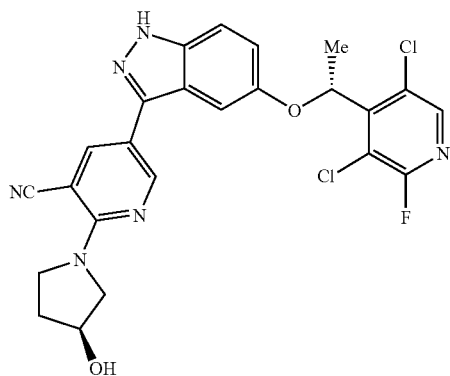 [SMILES: C[C@@H](Oc1ccc2[nH]nc(-c3cnc(N4CC[C@H](O)C4)c(C#N)c3)c2c1)c1c(Cl)cnc(F)c1Cl] | LCMS: m/z = 513.2 (M + H); 1H NMR (400 MHz, DMSO-d6) δ 13.16 (s, 1H), 8.77 (d, J = 2.4 Hz, 1H), 8.32 (s, 1H), 8.20 (d, J = 2.4 Hz, 1H) ), 7.49 (d, J = 8.8 Hz, 1H), 7.23-7.20 (m, 1H), 7.10 (dd, J = 9.2 Hz, 2.0 Hz, 1H), 6.17 (q, J = 6.4 Hz, 1H), 5.09 (d, J = 3.6 Hz, 1H), 4.47-4.40 (m, 1H), 3.86-3.81 (m, 3H), 3.68-3.65 (m, 1H), 2.07-1.94 (m, 2H), 1.77 (d, J = 6.4 Hz, 3H). |
|---|---|---|
| Example 289 2-(azetidin-1-yl)-5-[5-[(1R)-1-(3,5-dichloro-2-methyl-4-pyridyl)ethoxy]-1H-indazol-3-yl]pyridine-3-carbonitrile | 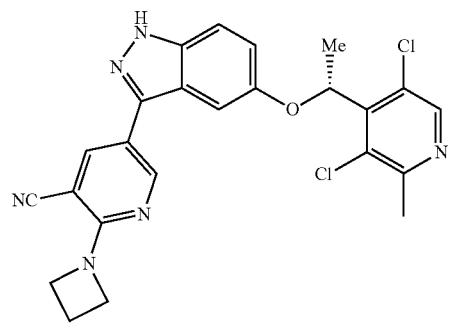 [SMILES: Cc1ncc(Cl)c([C@@H](C)Oc2ccc3[nH]nc(-c4cnc(N5CCC5)c(C#N)c4)c3c2)c1Cl] | LCMS: m/z = 479.2 (M + H); 1H NMR (400 MHz, DMSO-d6) δ = 13.15 (s, 1H), 8.68 (d, J = 2.3 Hz, 1H), 8.42 (s, 1H), 8.15 (d, J = 2.3 Hz, 1H), 7.51 - 7.45 (m, 1H), 7.12 - 7.07 (m, 2H), 6.13 (q, J = 6.7 Hz, 1H), 4.32 (t, J = 7.6 Hz, 4H), 2.56 (s, 3H), 2.39 (quin, J = 7.6 Hz, 2H), 1.75 (d, J = 6.7 Hz, 3H) |
| Example 290 5-[5-[(1R)-1-(3,5-dichloro-4-pyridyl)ethoxy]-1H-indazol-3-yl]-2-[(3S)-3-(1-hydroxy-1-methyl-ethyl)pyrrolidin-1-yl]pyridine-3-carbonitrile | 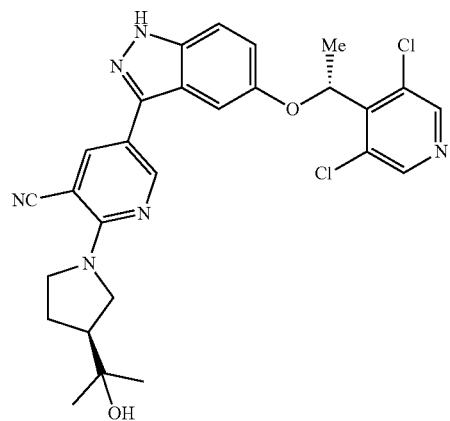 [SMILES: C[C@@H](Oc1ccc2[nH]nc(-c3cnc(N4CC[C@H](C(C)(C)O)C4)c(C#N)c3)c2c1)c1c(Cl)cncc1Cl] | LCMS: m/z = 537.2 (M + H); 1H NMR (400 MHz, DMSO-d6) δ = 13.12 (s, 1H), 8.77 (d, J = 2.4 Hz, 1H), 8.58 (s, 2H), 8.10 (d, J = 2.3 Hz, 1H), 7.48 (d, J = 8.9 Hz, 1H), 7.15 (d, J = 1.8 Hz, 1H), 7.10 (dd, J = 2.3, 9.0 Hz, 1H), 6.14 (q, J = 6.6 Hz, 1H), 4.45 (s, 1H), 3.95 (br t, J = 8.9 Hz, 1H), 3.85 - 3.78 (m, 1H), 3.71 - 3.62 (m, 2H), 2.36 - 2.26 (m, 1H), 1.99 - 1.82 (m, 2H), 1.76 (d, J = 6.7 Hz, 3H), 1.19 - 1.16 (m, 6H) |
| Example 291 (S)-5-(5-(1-(3,5-dichloro-2-fluoropyridin-4-yl)ethoxy)-1H-indazol-3-yl)-2-(3-hydroxyazetidin-1-yl)nicotinonitrile | 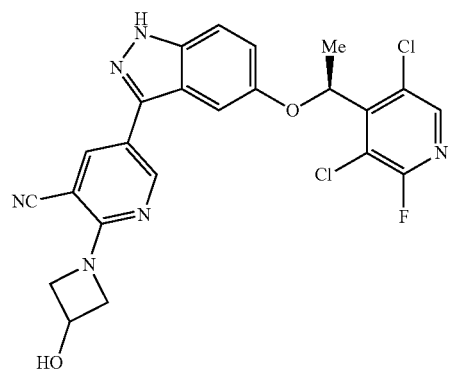 [SMILES: C[C@H](Oc1ccc2[nH]nc(-c3cnc(N4CC(O)C4)c(C#N)c3)c2c1)c1c(Cl)cnc(F)c1Cl] | LCMS: m/z = 499.1 (M + H); 1H NMR (400 MHz, DMSO-d6) δ 13.18 (s, 1H), 8.77 (d, J = 2.0 Hz, 1H), 8.31 (d, J = 0.8 Hz, 1H), 8.22 (d, J = 2.0 Hz, 1H), 7.49 (d, J = 9.2 Hz, 1H), 7.22 (d, J = 2.0 Hz, 1H), 7.10 (dd, J = 9.2 Hz, 2.4 Hz, 1H), 6.17 (q, J = 6.8 Hz, 1H), 5.80 (d, J = 6.0 Hz, 1H), 4.65-4.58 (m, 1H), 4.54-4.50 (m, 2H), 4.05-4.01 (m, 2H), 1.77 (d, J = 6.8 Hz, 3H). |

-continued

| Example 292 (R)-5-(5-(1-(3,5-dichloro-2-fluoropyridin-4-yl)ethoxy)-1H-indazol-3-yl)-2-(pyrrolidin-1-yl)nicotinonitrile | 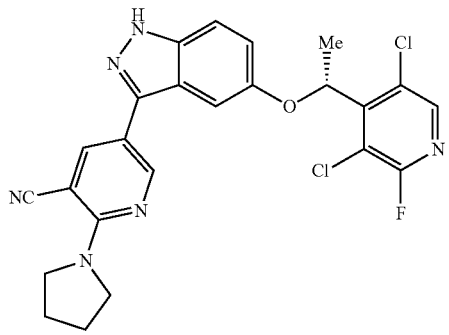 [SMILES: C[C@@H](Oc1ccc2[nH]nc(-c3cnc(N4CCCC4)c(C#N)c3)c2c1)c1c(Cl)cnc(F)c1Cl] | LCMS: m/z = 497.1 (M + H); 1H-NMR (400 MHz, DMSO-d6) δ 13.16 (s, 1H), 8.78 (d, J = 2.8 Hz, 1H), 8.32 (d, J = 0.8 Hz, 1H), 8.20 (d, J = 2.0 Hz, 1H), 7.49 (d, J = 9.2 Hz, 1H), 7.21 (d, J = 2.0 Hz, 1H), 7.11 (dd, J = 9.2 Hz, 2.4 Hz, 1H), 6.17 (q, J = 6.8 Hz, 1H), 3.75 (t, J = 6.4 Hz, 4H), 2.00-1.97 (m, 4H), 1.77 (d, J = 6.8 Hz, 3H) |
| --- | --- | --- |
| Example 293 5-[5-[(1R)-1-(3,5-dichloro-4-pyridyl)ethoxy]-1H-indazol-3-yl]-2-[(3S)-3-hydroxypyrrolidin-1-yl]pyridine-3-carbonitrile | 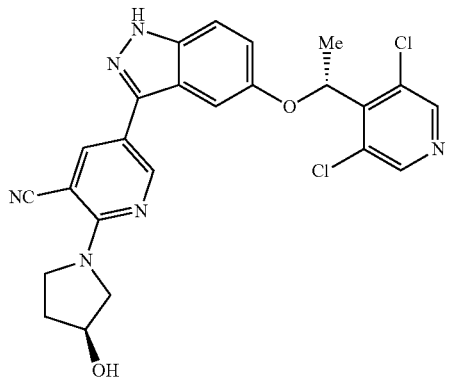 [SMILES: C[C@@H](Oc1ccc2[nH]nc(-c3cnc(N4CC[C@H](O)C4)c(C#N)c3)c2c1)c1c(Cl)cncc1Cl] | LCMS: m/z = 495.2 (M + H); 1H NMR (400 MHz, DMSO-d6) δ = 13.13 (s, 1H), 8.77 (d, J = 2.3 Hz, 1H), 8.58 (s, 2H), 8.12 (d, J = 2.3 Hz, 1H), 7.48 (d, J = 9.0 Hz, 1H), 7.16 (d, J = 2.0 Hz, 1H), 7.10 (dd, J = 2.3, 9.0 Hz, 1H), 6.14 (q, J = 6.7 Hz, 1H), 5.08 (d, J = 3.5 Hz, 1H), 4.43 (br s, 1H), 3.88 - 3.81 (m, 3H), 3.67 (br d, J = 11.6 Hz, 1H), 2.04 (tdd, J = 4.5, 8.7, 13.0 Hz, 1H), 1.98 - 1.90 (m, 1H), 1.76 (d, J = 6.6 Hz, 3H) |
| Example 294 5-[5-[(1R)-1-(3,5-dichloro-4-pyridyl)ethoxy]-1H-indazol-3-yl]-2-[(3R)-3-(1-hydroxy-1-methyl-ethyl)pyrrolidin-1-yl]pyridine-3-carbonitrile | 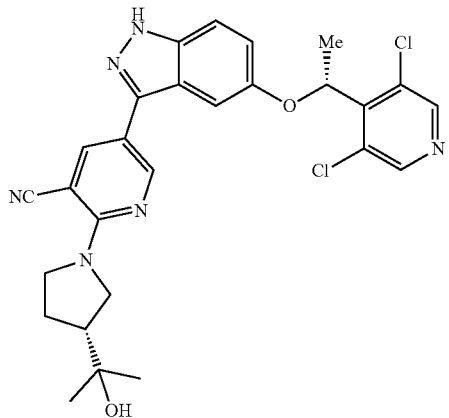 [SMILES: C[C@@H](Oc1ccc2[nH]nc(-c3cnc(N4CC[C@@H](C(C)(C)O)C4)c(C#N)c3)c2c1)c1c(Cl)cncc1Cl] | LCMS: m/z = 537.2 (M + H); 1H NMR (400 MHz, DMSO-d6) δ = 13.12 (br s, 1H), 8.77 (d, J = 2.3 Hz, 1H), 8.58 (s, 2H), 8.10 (d, J = 2.3 Hz, 1H), 7.49 (d, J = 8.8 Hz, 1H), 7.15 (d, J = 1.8 Hz, 1H), 7.10 (dd, J = 2.3, 9.0 Hz, 1H), 6.14 (q, J = 6.3 Hz, 1H), 4.46 (br s, 1H), 3.94 (br t, J = 9.1 Hz, 1H), 3.84 - 3.78 (m, 1H), 3.72 - 3.64 (m, 2H), 2.36 - 2.29 (m, 1H), 2.02 - 1.95 (m, 1H), 1.93 - 1.86 (m, 1H), 1.76 (d, J = 6.7 Hz, 3H), 1.18 (d, J = 3.5 Hz, 6H) |
| Example 295 5-[5-[(1R)-1-(3,5-dichloro-2-methyl-4-pyridyl)ethoxy]-1H-indazol-3-yl]-2-[3-(2,2,2-trifluoroethyl)azetidin-1-yl]pyridine-3-carbonitrile | 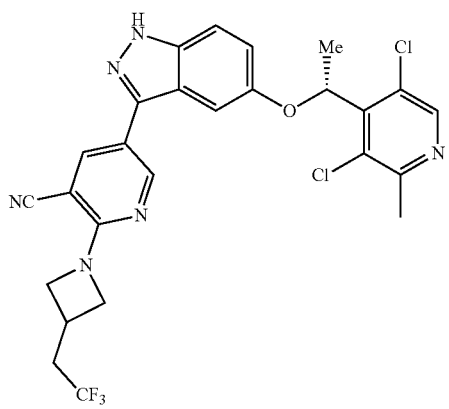 [SMILES: Cc1ncc(Cl)c([C@@H](C)Oc2ccc3[nH]nc(-c4cnc(N5CC(CC(F)(F)F)C5)c(C#N)c4)c3c2)c1Cl] | LCMS: m/z = 561 (M + H); 1H NMR (400 MHz, DMSO-d6) δ = 13.17 (br s, 1H), 8.70 (d, J = 2.3 Hz, 1H), 8.43 (s, 1H), 8.18 (d, J = 2.3 Hz, 1H), 7.50 - 7.46 (m, 1H), 7.10 (d, J = 9.4 Hz, 2H), 7.09 (s, 1H), 6.13 (q, J = 6.7 Hz, 1H), 4.47 (t, J = 8.6 Hz, 2H), 4.12 (br t, J = 7.3 Hz, 2H), 3.14 - 3.03 (m, 1H), 2.78 (dq, J = 7.6, 11.5 Hz, 2H), 2.56 (s, 3H), 1.75 (d, J = 6.7 Hz, 3H) |

| Example 296
5-[5-[(1R)-1-(3,5-dichloro-4-pyridyl)ethoxy]-1H-indazol-3-yl]-2-[3-(2,2,2-trifluoroethyl)azetidin-1-yl]pyridine-3-carbonitrile | 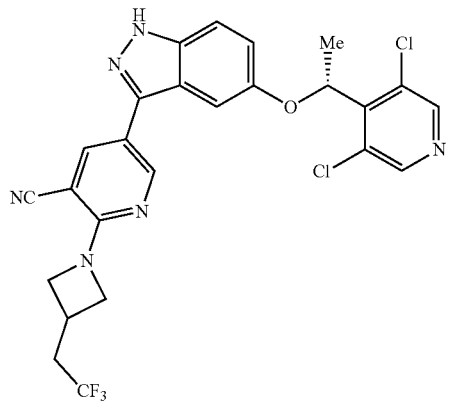 [SMILES: C[C@@H](Oc1ccc2[nH]nc(-c3cnc(N4CC(CC(F)(F)F)C4)c(C#N)c3)c2c1)c1c(Cl)cncc1Cl] | LCMS: m/z = 547.1 (M + H); 1H NMR (400 MHz, DMSO-d6) δ = 13.16 (br s, 1H), 8.77 (d, J = 2.3 Hz, 1H), 8.57 (s, 2H), 8.16 (d, J = 2.3 Hz, 1H), 7.49 (d, J = 8.9 Hz, 1H), 7.16 (d, J = 2.1 Hz, 1H), 7.10 (dd, J = 2.3, 9.0 Hz, 1H), 6.14 (q, J = 6.7 Hz, 1H), 4.47 (t, J = 8.5 Hz, 2H), 4.12 (dd, J = 6.4, 8.4 Hz, 2H), 3.14 - 3.03 (m, 1H), 2.78 (dq, J = 7.7, 11.4 Hz, 2H), 1.76 (d, J = 6.6 Hz, 3H) |
|---|---|---|
| Example 297
5-[5-[(1R)-1-(3,5-dichloro-4-pyridyl)ethoxy]-1H-indazol-3-yl]-2-[(3R)-3-hydroxypyrrolidin-1-yl]pyridine-3-carbonitrile | 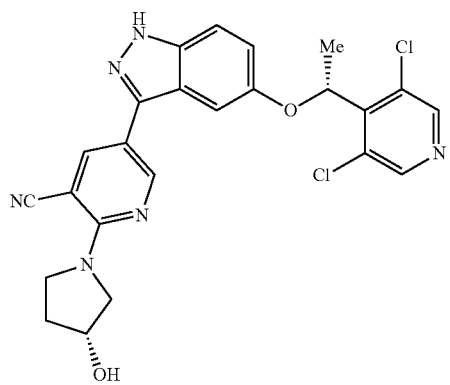 [SMILES: C[C@@H](Oc1ccc2[nH]nc(-c3cnc(N4CC[C@@H](O)C4)c(C#N)c3)c2c1)c1c(Cl)cncc1Cl] | LCMS: m/z = 495.1 (M + H); 1H NMR (400 MHz, DMSO-d6) δ = 13.13 (s, 1H), 8.77 (d, J = 2.4 Hz, 1H), 8.58 (s, 2H), 8.12 (d, J = 2.4 Hz, 1H), 7.48 (d, J = 9.0 Hz, 1H), 7.15 (d, J = 2.0 Hz, 1H), 7.10 (dd, J = 2.3, 8.9 Hz, 1H), 6.14 (q, J = 6.6 Hz, 1H), 5.09 (d, J = 3.5 Hz, 1H), 4.43 (br s, 1H), 3.88 - 3.80 (m, 3H), 3.68 (br d, J = 11.5 Hz, 1H), 2.09 - 2.00 (m, 1H), 1.98 - 1.90 (m, 1H), 1.76 (d, J = 6.6 Hz, 3H) |
| Example 298
5-[5-[(1R)-1-(3,5-dichloro-4-pyridyl)ethoxy]-1H-indazol-3-yl]-2-(4-hydroxy-1-piperidyl)pyridine-3-carbonitrile | 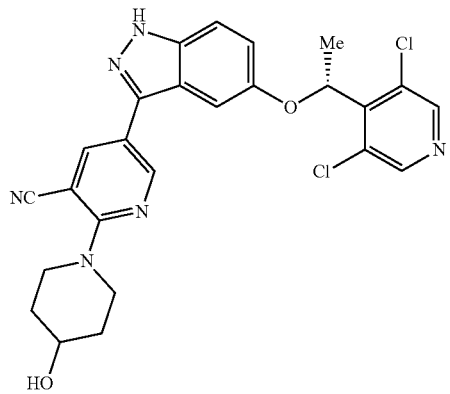 [SMILES: C[C@@H](Oc1ccc2[nH]nc(-c3cnc(N4CCC(O)CC4)c(C#N)c3)c2c1)c1c(Cl)cncc1Cl] | LCMS: m/z = 509.2 (M + H); 1H NMR (400 MHz, DMSO-d6) δ = 13.21 (s, 1H), 8.82 (d, J = 2.4 Hz, 1H), 8.57 (s, 2H), 8.22 (d, J = 2.3 Hz, 1H), 7.49 (dd, J = 0.4, 9.0 Hz, 1H), 7.19 (d, J = 2.1 Hz, 1H), 7.11 (dd, J = 2.3, 9.0 Hz, 1H), 6.15 (q, J = 6.8 Hz, 1H), 4.79 (d, J = 4.4 Hz, 1H), 4.12 - 4.05 (m, 2H), 3.79 (qt, J = 4.1, 8.4 Hz, 1H), 3.39 (br t, J = 11.1 Hz, 2H), 1.94 - 1.87 (m, 2H), 1.76 (d, J = 6.6 Hz, 3H), 1.53 (ddt, J = 3.5, 9.0, 12.6 Hz, 2H) |
| Example 299
2-(3,6-diazabicyclo[3.1.1]heptan-3-yl)-5-(5-((R)-1-(3,5-dimethylpyridazin-4-yl)ethoxy)-1H-indazol-3-yl)nicotinonitrile | 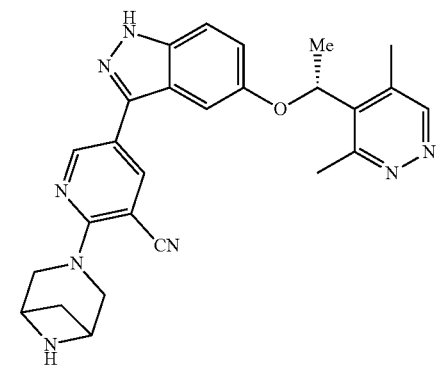 [SMILES: Cc1cnnc(C)c1[C@@H](C)Oc1ccc2[nH]nc(-c3cnc(N4CC5CC(C4)N5)c(C#N)c3)c2c1] | LCMS: m/z = 467.3 (M + H); 1H-NMR (400 MHz, DMSO-d6) δ 13.17 (s, 1H), 8.83-8.82 (m, 2H), 8.23 (d, J = 2.4 Hz, 1H), 7.49 (d, J = 9.2 Hz, 1H), 7.10 (dd, J = 8.8 Hz, 2.4 Hz, 1H), 7.02 (d, J = 2.0 Hz, 1H), 5.92 (q, J = 6.8 Hz, 1H), 4.13-4.01 (m, 4H), 3.88-3.79 (m, 2H), 2.80 (s, 3H), 2.60-2.54 (m, 1H), 2.47 (s, 3H), 1.67 (d, J = 6.8 Hz, 3H), 1.59 (d, J = 8.8 Hz, 1H). |

| Example | Structure | Data |
|---|---|---|
| Example 300<br>3-(5-(5-((R)-1-(3,5-dimethylpyridazin-4-yl)ethoxy)-1H-indazol-3-yl)-3-methoxypyridin-2-yl)-3,6-diazabicyclo[3.1.1]heptane | 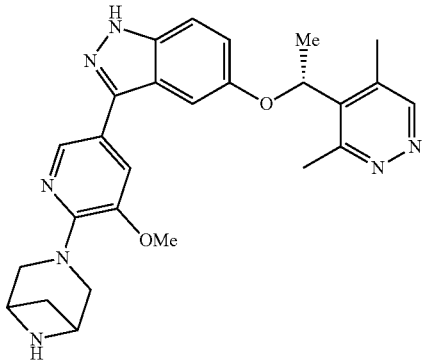 [SMILES: COc1cc(-c2n[nH]c3ccc(O[C@H](C)c4c(C)cnnc4C)cc23)cnc1N1CC2CC(C1)N2] | LCMS: m/z = 472.3 (M + H); 1H-NMR (400 MHz, DMSO-d6) δ 13.09 (s, 1H), 8.82 (s, 1H), 8.19 (d, J = 2.0 Hz, 1H), 7.56 (d, J = 1.6 Hz, 1H), 7.49 (d, J = 8.8 Hz, 1H), 7.11-7.07 (m, 2H), 5.90 (q, J = 6.8 Hz, 1H), 4.29-4.22 (m, 4H), 4.05-4.00 (m, 2H), 3.86 (s, 3H), 2.80 (s, 3H), 2.78-2.74 (m, 1H), 2.44 (s, 3H), 1.90 (d, J = 9.6 Hz, 1H), 1.67 (d, J = 6.8 Hz, 3H). |
| Example 301<br>5-(5-((R)-1-(3,5-dimethylpyridazin-4-yl)ethoxy)-1H-indazol-3-yl)-2-((S)-3-(2-hydroxypropan-2-yl)pyrrolidin-1-yl)nicotinonitrile | 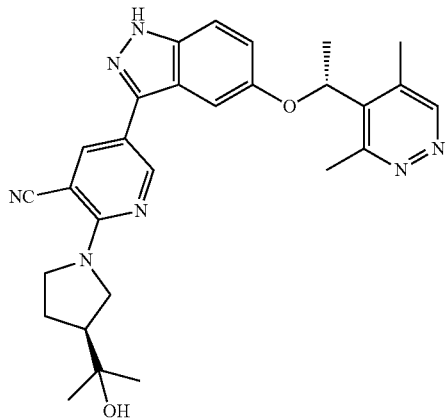 [SMILES: Cc1cnnc(C)c1[C@@H](C)Oc1ccc2[nH]nc(-c3cnc(N4CC[C@H](C(C)(C)O)C4)c(C#N)c3)c2c1] | LCMS: m/z = 498.3 (M + H); 1H NMR (400 MHz, DMSO-d6) δ 13.12 (s, 1H), 8.83 (s, 1H), 8.76 (d, J = 2.4 Hz, 1H), 8.15 (d, J = 2.4 Hz, 1H), 7.48 (d, J = 8.8 Hz, 1H), 7.09 (dd, J = 9.2 Hz, 2.0 Hz, 1H), 7.05-7.04 (m, 1H), 5.92 (q, J = 6.4 Hz, 1H), 4.47 (s, 1H), 3.94 (t, J = 9.2 Hz, 1H), 3.82-3.79 (m, 1H ), 3.68-3.63 (m, 2H), 2.79 (s, 3H), 2.47 (s, 3H), 2.33-2.28 (m, 1H), 1.95-1.98 (m, 2H), 1.67 (d, J = 6.4 Hz, 3H), 1.17 (d, J = 4.4 Hz, 6H). |
| Example 302<br>5-[5-[(1R)-1-(3,5-dichloro-4-pyridyl)ethoxy]-1H-indazol-3-yl]-2-(3-hydroxyazetidin-1-yl)pyridine-3-carbonitrile | 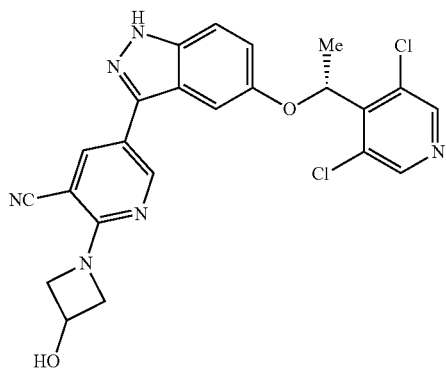 [SMILES: C[C@@H](Oc1ccc2[nH]nc(-c3cnc(N4CC(O)C4)c(C#N)c3)c2c1)c1c(Cl)cncc1Cl] | LCMS: m/z = 481.1 (M + H); 1H NMR (400 MHz, DMSO-d6) δ = 13.16 (s, 1H), 8.76 (d, J = 2.3 Hz, 1H), 8.57 (s, 2H), 8.14 (d, J = 2.3 Hz, 1H), 7.48 (d, J = 8.9 Hz, 1H), 7.16 (s, 1H), 7.10 (dd, J = 2.1, 9.0 Hz, 1H), 6.14 (q, J = 6.7 Hz, 1H), 5.79 (d, J = 6.2 Hz, 1H), 4.66 - 4.58 (m, 1H), 4.56 - 4.49 (m, 2H), 4.04 (dd, J = 4.0, 9.3 Hz, 2H), 1.76 (d, J = 6.6 Hz, 3H) |
| Example 303<br>5-[5-[(1R)-1-(3,5-dichloro-4-pyridyl)ethoxy]-1H-indazol-3-yl]-2-[4-(1-hydroxy-1-methyl-ethyl)-1-piperidyl]pyridine-3-carbonitrile | 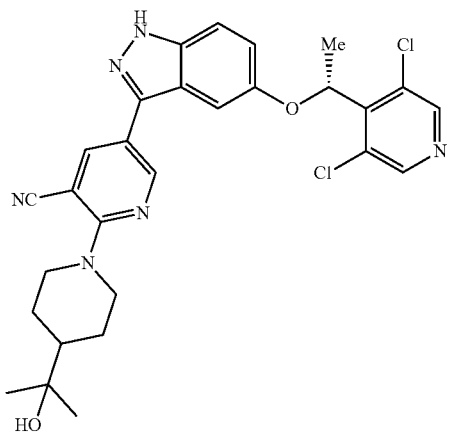 [SMILES: C[C@@H](Oc1ccc2[nH]nc(-c3cnc(N4CCC(C(C)(C)O)CC4)c(C#N)c3)c2c1)c1c(Cl)cncc1Cl] | LCMS: m/z = 551.2 (M + H); 1H NMR (400 MHz, DMSO-d6) δ = 13.20 (s, 1H), 8.82 (d, J = 2.3 Hz, 1H), 8.57 (s, 2H), 8.22 (d, J = 2.4 Hz, 1H), 7.49 (d, J = 9.0 Hz, 1H), 7.19 (d, J = 2.1 Hz, 1H), 7.11 (dd, J = 2.3, 9.0 Hz, 1H), 6.15 (q, J = 6.6 Hz, 1H), 4.46 (br d, J = 13.0 Hz, 2H), 4.18 (s, 1H), 2.99 (br t, J = 12.4 Hz, 2H), 1.86 (br d, J = 11.7 Hz, 2H), 1.76 (d, J = 6.6 Hz, 3H), 1.55 - 1.47 (m, 1H), 1.44 - 1.32 (m, 2H), 1.09 (s, 6H) |

-continued

| | | |
|---|---|---|
| Example 304<br>(R)-3-(6-(azetidin-1-yl)-5-methoxypyridin-3-yl)-5-(1-(3,5-dimethylpyridazin-4-yl)ethoxy)-1H-indazole | 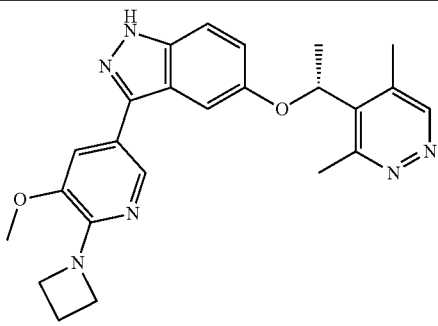 | LCMS: m/z = 431.3 (M + H); 1H-NMR (400 MHz, DMSO-d6) δ 12.99 (brs, 1H), 8.82 (s, 1H), 8.08 (d, J = 1.6 Hz, 1H), 7.46 (d, J = 9.2 Hz, 1H), 7.37 (d, J = 1.6 Hz, 1H), 7.09-7.06 (m, 2H), 5.89 (q, J = 6.8 Hz, 1H), 4.11 (t, J = 7.2 Hz, 4H), 3.80 (s, 3H), 2.78 (S, 3H), 2.44 (s, 3H), 2.31-2.25 (m, 2H), 1.66 (d, J = 6.8 Hz, 3H). |
| Example 305<br>(R)-5-(1-(3,5-dimethylpyridazin-4-yl)ethoxy)-3-(5-methoxy-6-(pyrrolidin-1-yl)pyridin-3-yl)-1H-indazole | 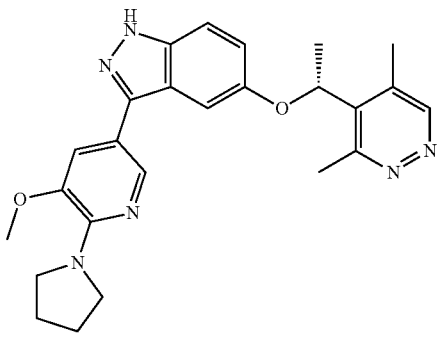 [SMILES: COc1cc(-c2n[nH]c3ccc(O[C@H](C)c4c(C)cnnc4C)cc23)cnc1N1CCCC1] | LCMS: m/z = 445.3 (M + H); 1H-NMR (400 MHz, DMSO-d6) δ 12.91 (s, 1H), 8.78 (s, 1H), 8.05 (d, J = 1.2 Hz, 1H), 7.42 (d, J = 8.8 Hz, 1H), 7.37 (d, J = 0.8 Hz, 1H), 7.06-7.02 (m, 2H), 5.86 (q, J = 6.8 Hz, 1H), 3.77 (s, 3H), 3.60-3.56 (m, 4H), 2.75 (s, 3H), 2.41 (s, 3H), 1.86-1.82 (m, 4H), 1.62 (d, J = 6.8 Hz, 3H). |
| Example 306<br>5-(5-((R)-1-(3,5-dimethylpyridazin-4-yl)ethoxy)-1H-indazol-3-yl)-2-((S)-3-hydroxypyrrolidin-1-yl)nicotinonitrile | 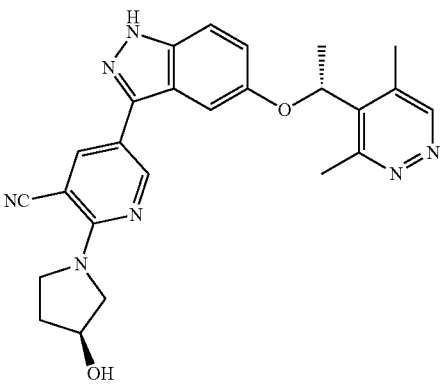 [SMILES: Cc1cnnc(C)c1[C@@H](C)Oc1ccc2[nH]nc(-c3cnc(N4CC[C@H](O)C4)c(C#N)c3)c2c1] | LCMS: m/z = 456.3 (M + H); 1H NMR (400 MHz, DMSO-d6) δ 13.13 (s, 1H), 8.82 (s, 1H), 8.76 (d, J = 2.8 Hz, 1H), 8.17 (d, J = 2.0 Hz, 1H), 7.48 (d, J = 8.8 Hz, 1H), 7.08 (dd, J = 8.8 Hz, 2.0 Hz, 1H), 7.05 (d, J = 2.0 Hz, 1H), 5.92 (q, J = 6.8 Hz, 1H), 5.10 (d, J = 3.6 Hz, 1H), 4.44-4.42 (m, 1H), 3.84-3.81 (m, 3H ), 3.68-3.65 (m, 1H), 2.79 (s, 3H), 2.47 (s, 3H), 2.07-2.02 (m, 1H), 1.97-1.94 (m, 1H), 1.67 (d, J = 6.8 Hz, 3H). |
| Example 307<br>5-(5-((R)-1-(3,5-dimethylpyridazin-4-yl)ethoxy)-1H-indazol-3-yl)-2-((R)-3-(2-hydroxypropan-2-yl)pyrrolidin-1-yl)nicotinonitrile | 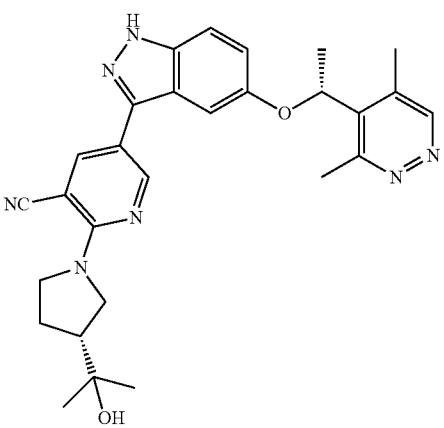 [SMILES: Cc1cnnc(C)c1[C@@H](C)Oc1ccc2[nH]nc(-c3cnc(N4CC[C@@H](C(C)(C)O)C4)c(C#N)c3)c2c1] | LCMS: m/z = 498.3 (M + H); 1H NMR (400 MHz, DMSO-d6) δ 13.11 (s, 1H), 8.83 (s, 1H), 8.76 (s, 1H), 8.16 (d, J = 2.4 Hz, 1H), 7.48 (dd, J = 9.2 Hz, 2.0 Hz, 1H), 7.10-7.05 (m, 2H), 5.92 (q, J = 7.2 Hz, 1H), 4.47 (d, J = 2.4 Hz, 1H), 3.94-3.92 (m, 1H), 3.81-3.79 (m, 1H), 3.69-3.66 (m, 2H), 2.79 (s, 3H), 2.47 (s, 3H), 2.34-2.29 (m, 1H), 1.98-1.90 (m, 2H), 1.68 (d, J = 6.4 Hz, 3H), 1.18 (s, 6H). |

-continued

| | | |
|---|---|---|
| Example 308<br>5-[5-[(1R)-1-(3,5-dichloro-2-methyl-4-pyridyl)ethoxy]-1H-indazol-3-yl]-2-(3-hydroxyazetidin-1-yl)pyridine-3-carbonitrile | 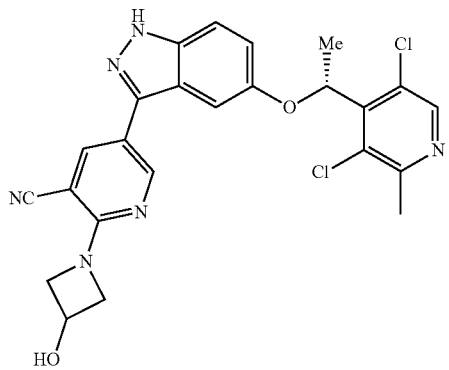 [SMILES: Cc1ncc(Cl)c([C@@H](C)Oc2ccc3[nH]nc(-c4cnc(N5CC(O)C5)c(C#N)c4)c3c2)c1Cl] | LCMS: m/z = 495.1 (M + H); 1H NMR (400 MHz, DMSO-d6) δ = 13.16 (s, 1H), 8.68 (d, J = 2.3 Hz, 1H), 8.42 (s, 1H), 8.17 (d, J = 2.4 Hz, 1H), 7.48 (d, J = 8.9 Hz, 1H), 7.12 - 7.07 (m, 2H), 6.16 - 6.10 (m, 1H), 5.79 (d, J = 6.2 Hz, 1H), 4.66 - 4.58 (m, 1H), 4.55 - 4.50 (m, 2H), 4.04 (dd, J = 4.3, 10.1 Hz, 2H), 2.56 (s, 3H), 1.75 (d, J = 6.6 Hz, 3H) |
| Example 309<br>2-(azetidin-1-yl)-5-[5-[(1R)-1-(3,5-dichloro-4-pyridyl)ethoxy]-1H-indazol-3-yl]pyridine-3-carbonitrile | 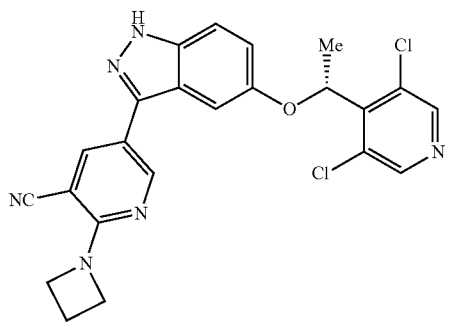 [SMILES: C[C@@H](Oc1ccc2[nH]nc(-c3cnc(N4CCC4)c(C#N)c3)c2c1)c1c(Cl)cncc1Cl] | LCMS: m/z = 465.1 (M + H); 1H NMR (400 MHz, DMSO-d6) δ = 13.15 (s, 1H), 8.76 (d, J = 2.3 Hz, 1H), 8.57 (s, 2H), 8.12 (d, J = 2.3 Hz, 1H), 7.48 (d, J = 9.0 Hz, 1H), 7.16 (d, J = 2.1 Hz, 1H), 7.10 (dd, J = 2.3, 9.0 Hz, 1H), 6.14 (q, J = 6.6 Hz, 1H), 4.32 (t, J = 7.6 Hz, 4H), 2.44 - 2.35 (m, 2H), 1.76 (d, J = 6.6 Hz, 3H). |
| Example 310<br>(R)-3-(6-(azetidin-1-yl)pyridin-3-yl)-5-(1-(3,5-dimethylpyridazin-4-yl)ethoxy)-6-methoxy-1H-indazole | 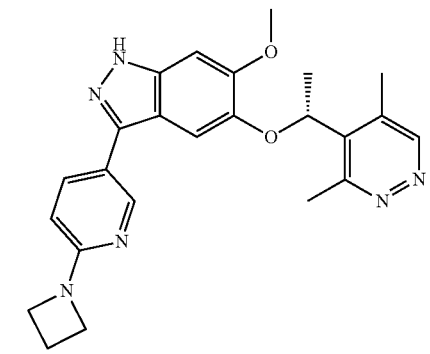 [SMILES: COc1cc2[nH]nc(-c3ccc(N4CCC4)nc3)c2cc1O[C@H](C)c1c(C)cnnc1C] | LCMS: m/z = 431.2 (M + H); 1H NMR (400 MHz, DMSO-d6) δ 12.77 (s, 1H), 8.85 (s, 1H), 8.47 (d, J = 2.0 Hz, 1H), 7.79 (dd, J = 8.8 Hz, 2.4 Hz, 1H), 7.01 (s, 1H), 6.99 (s, 1H), 6.45 (d, J = 8.8 Hz, 1H), 5.79 (q, J = 6.8 Hz, 1H), 4.01 (t, J = 7.2 Hz, 4H), 3.87 (s, 3H), 2.77 (s, 3H ), 2.44 (s, 3H), 2.39-2.32 (m, 2H), 1.65 (d, J = 6.8 Hz, 3H). |
| Example 311<br>5-(5-((R)-1-(3,5-dimethylpyridazin-4-yl)ethoxy)-6-methoxy-1H-indazol-3-yl)-2-((S)-3-hydroxypyrrolidin-1-yl)nicotinonitrile | 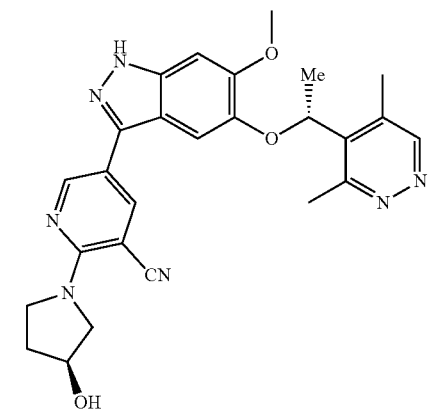 [SMILES: COc1cc2[nH]nc(-c3cnc(N4CC[C@H](O)C4)c(C#N)c3)c2cc1O[C@H](C)c1c(C)cnnc1C] | LCMS: m/z = 486.3 (M + H); 1H NMR (400 MHz, DMSO-d6) δ 12.92 (s, 1H), 8.83 (s, 1H), 8.75 (d, J = 2.8 Hz, 1H), 8.14 (d, J = 2.0 Hz, 1H), 7.03 (s, 1H), 7.00 (s, 1H), 5.85 (q, J = 6.8 Hz, 1H), 5.08 (d, J = 6.4 Hz, 1H), 4.46-4.40 (m, 1H), 3.88 (s, 3H), 3.86-3.81 (m, 3H), 3.68-3.65 (m, 1H), 2.78 (s, 3H), 2.46 (s, 3H), 2.08-2.00 (m, 1H), 1.97-1.93 (m, 1H), 1.66 (d, J = 6.8 Hz, 3H). |

| | | |
|---|---|---|
| Example 312<br>5-(5-((R)-1-(3,5-dimethylpyridazin-4-yl)ethoxy)-1H-indazol-3-yl)-2-(6-(2-hydroxy-2-methylpropyl)-3,6-diazabicyclo[3.1.1]heptan-3-yl)nicotinonitrile | 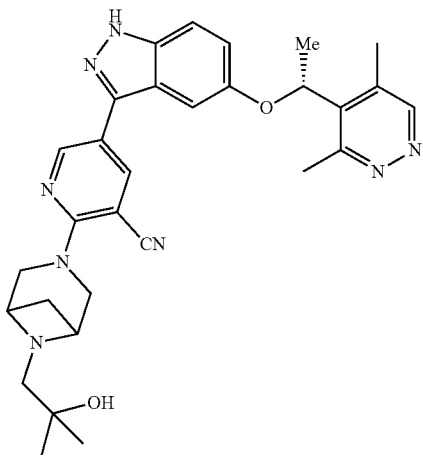 [SMILES: Cc1cnnc(C)c1[C@@H](C)Oc1ccc2[nH]nc(-c3cnc(N4CC5CC(C4)N5CC(C)(C)O)c(C#N)c3)c2c1] | LCMS: m/z = 539.4 (M + H); 1H-NMR (400 MHz, DMSO-d6) δ 13.17 (s, 1H), 8.83 (s, 2H), 8.21 (d, J = 2.0 Hz, 1H), 7.50 (d, J = 8.8 Hz, 1H), 7.12-7.04 (m, 2H), 5.92 (q, J = 6.4 Hz, 1H), 4.16-4.05 (m, 3H), 3.88-3.80 (m, 2H), 3.72 (d, J = 5.6 Hz, 2H), 2.80 (s, 3H), 2.57-2.52 (m, 1H), 2.48 (s, 3H), 2.28 (s, 2H), 1.67 (d, J = 6.8 Hz, 3H), 1.59 (d, J = 8.4 Hz, 1H), 1.10 (s, 6H). |
| Example 313<br>5-(5-((R)-1-(3,5-dimethylpyridazin-4-yl)ethoxy)-1H-indazol-3-yl)-2-((R)-3-hydroxypyrrolidin-1-yl)nicotinonitrile | 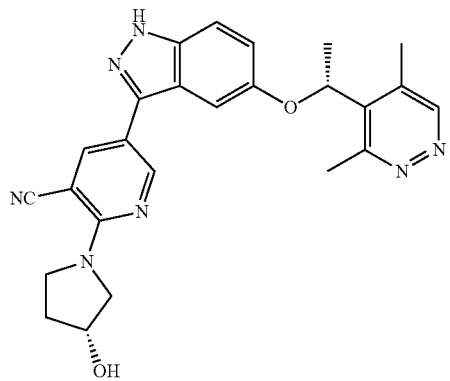 [SMILES: Cc1cnnc(C)c1[C@@H](C)Oc1ccc2[nH]nc(-c3cnc(N4CC[C@@H](O)C4)c(C#N)c3)c2c1] | LCMS: m/z = 456.2 (M + H); 1H NMR (400 MHz, DMSO-d6) δ 13.12 (s, 1H), 8.82 (s, 1H), 8.76 (d, J = 2.4 Hz, 1H), 8.17 (d, J = 2.4 Hz, 1H), 7.48 (d, J = 9.2 Hz, 1H), 7.10-7.05 (m, 2H), 5.91 (q, J = 6.8 Hz, 1H), 5.09 (d, J = 3.6 Hz, 1H), 4.45-4.40 (m, 1H), 3.85-3.81 (m, 3H), 3.68-3.65 (m, 1H), 2.79 (s, 3H), 2.47 (s, 3H), 2.03-1.96 (m, 2H), 1.67 (d, J = 6.4 Hz, 3H). |
| Example 314<br>3-(5-(5-((R)-1-(3,5-dimethylpyridazin-4-yl)ethoxy)-6-methoxy-1H-indazol-3-yl)pyridin-2-yl)-3,6-diazabicyclo[3.1.1]heptane | 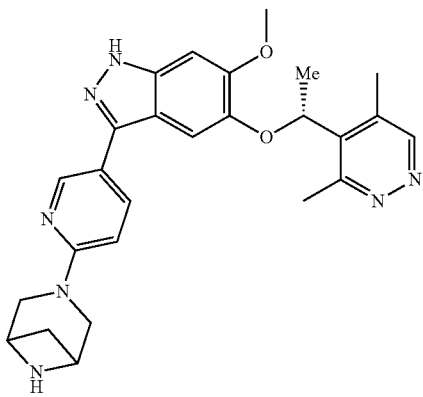 [SMILES: COc1cc2[nH]nc(-c3ccc(N4CC5CC(C4)N5)nc3)c2cc1O[C@H](C)c1c(C)cnnc1C] | LCMS: m/z = 472.3.2 (M + H); 1H-NMR (400 MHz, DMSO-d6) δ 12.75 (s, 1H), 8.85 (s, 1H), 8.54 (d, J = 2.0 Hz, 1H), 7.84 (dd, J = 8.8 Hz, 2.8 Hz, 1H), 7.01 (s, 1H), 6.99 (s, 1H), 6.70 (d, J = 8.8 Hz, 1H), 5.80 (q, J = 6.8 Hz, 1H), 3.87 (s, 3H), 3.73-3.63 (m, 6H), 2.78 (s, 3H), 2.55-2.51 (m, 1H), 2.44 (s, 3H), 1.66 (d, J = 6.8 Hz, 3H), 1.51 (d, J = 8.8 Hz, 1H). |
| Example 315<br>(R)-5-(1-(3,5-dimethylpyridazin-4-yl)ethoxy)-6-methoxy-3-(6-(pyrrolidin-1-yl)pyridin-3-yl)-1H-indazole | 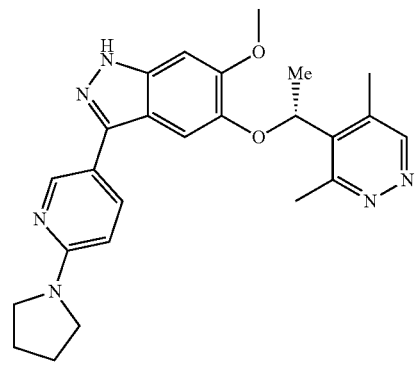 [SMILES: COc1cc2[nH]nc(-c3ccc(N4CCCC4)nc3)c2cc1O[C@H](C)c1c(C)cnnc1C] | LCMS: m/z = 445.3 (M + H); 1H NMR (400 MHz, DMSO-d6) δ 12.72 (s, 1H), 8.85 (s, 1H), 8.48 (d, J = 2.0 Hz, 1H), 7.78 (dd, J = 8.4 Hz, 2.0 Hz, 1H), 7.02 (s, 1H), 6.98 (s, 1H), 6.54 (d, J = 8.8 Hz, 1H), 5.79 (q, J = 6.8 Hz, 1H), 3.87 (s, 3H), 3.46 (t, J = 6.8 Hz, 4H), 2.77 (s, 3H), 2.44 (s, 3H), 2.00-1.97 (m, 4H), 1.65 (d, J = 6.4 Hz, 3H). |

-continued

Example 316
5-(5-((R)-1-(3,5-dimethylpyridazin-4-yl)ethoxy)-6-methoxy-1H-indazol-3-yl)-2-((S)-3-(2-hydroxypropan-2-yl)pyrrolidin-1-yl)nicotinonitrile

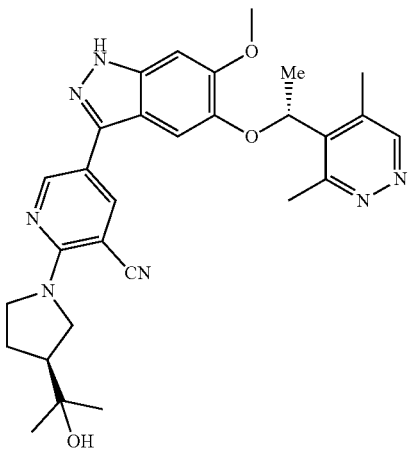 [SMILES: COc1cc2[nH]nc(-c3cnc(N4CC[C@H](C(C)(C)O)C4)c(C#N)c3)c2cc1O[C@H](C)c1c(C)cnnc1C]

LCMS: m/z = 528.3 (M + H); 1H NMR (400 MHz, DMSO-d6) δ 12.91 (s, 1H), 8.83 (s, 1H), 8.75 (d, J = 2.0 Hz, 1H), 8.12 (d, J = 2.4 Hz, 1H), 7.02 (s, 1H), 7.00 (s, 1H), 5.85 (q, J = 6.4 Hz, 1H), 4.46 (s, 1H), 3.96-3.92 (m, 1H), 3.88 (s, 3H), 3.83-3.79 (m, 1H), 3.70-3.63 (m, 2H), 2.78 (s, 3H), 2.46 (s, 3H), 2.33-2.32 (m, 1H), 1.98-1.87 (m, 2H), 1.66 (d, J = 6.4 Hz, 3H), 1.18 (d, J = 4.0 Hz, 6H).

Example 317
3-(5-(5-((R)-1-(3,5-dimethylpyridazin-4-yl)ethoxy)-6-methoxy-1H-indazol-3-yl)-3-methylpyridin-2-yl)-3,6-diazabicyclo[3.1.1]heptane

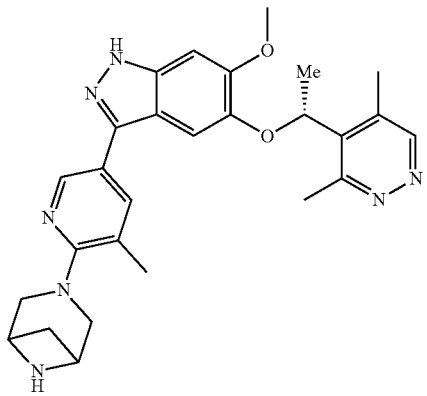 [SMILES: COc1cc2[nH]nc(-c3cnc(N4CC5CC(C4)N5)c(C)c3)c2cc1O[C@H](C)c1c(C)cnnc1C]

LCMS: m/z = 486.3 (M + H); 1H-NMR (400 MHz, DMSO-d6) δ 12.82 (s, 1H), 8.85 (s, 1H), 8.42 (d, J = 2.0 Hz, 1H), 7.63 (d, J = 1.6 Hz, 1H), 7.01 (s, 1H), 6.97 (s, 1H), 5.82 (q, J = 6.8 Hz, 1H), 3.99-3.86 (m, 5H), 3.85-3.77 (m, 2H), 3.65 (d, J = 5.6 Hz, 2H), 2.80 (s, 3H), 2.58-2.54 (m, 1H), 2.47 (s, 3H), 2.44 (s, 3H), 1.69-1.65 (m, 4H).

Example 318
(R)-5-(5-(1-(3,5-dimethylpyridazin-4-yl)ethoxy)-1H-indazol-3-yl)-2-(3-hydroxyazetidin-1-yl)nicotinonitrile

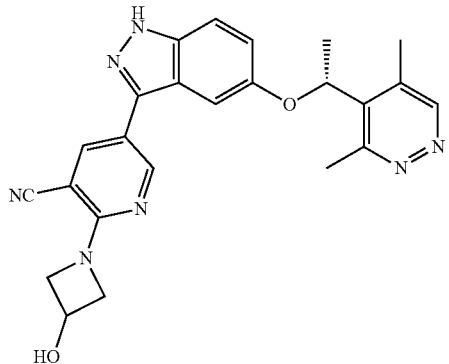 [SMILES: Cc1cnnc(C)c1[C@@H](C)Oc1ccc2[nH]nc(-c3cnc(N4CC(O)C4)c(C#N)c3)c2c1]

LCMS: m/z = 442.2 (M + H); 1H NMR (400 MHz, DMSO-d6) δ 13.15 (s, 1H), 8.82 (s, 1H), 8.76 (d, J = 2.4 Hz, 1H), 8.20 (d, J = 2.4 Hz, 1H), 7.48 (d, J = 9.2 Hz, 1H), 7.10-7.07 (m, 2H), 5.91 (q, J = 6.8 Hz, 1H), 5.80 (d, J = 6.4 Hz, 1H), 4.64-4.59 (m, 1H), 4.54-4.50 (m, 2H), 4.05-4.02 (m, 2H), 2.79 (s, 3H), 2.46 (s, 3H), 1.67 (d, J = 6.4 Hz, 3H).

| | | -continued | |
|---|---|---|---|

Example 319
5-(5-((R)-1-(3,5-dimethylpyridazin-4-yl)ethoxy)-6-methoxy-1H-indazol-3-yl)-2-((R)-3-hydroxypyrrolidin-1-yl)nicotinonitrile

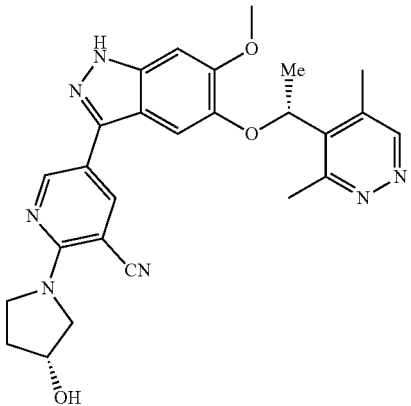 [SMILES: COc1cc2[nH]nc(-c3cnc(N4CC[C@@H](O)C4)c(C#N)c3)c2cc1O[C@H](C)c1c(C)cnnc1C]

LCMS: m/z = 486.2 (M + H); 1H NMR (400 MHz, DMSO-d6) δ 12.93 (s, 1H), 8.83 (s, 1H), 8.75 (d, J = 2.0 Hz, 1H), 8.14 (d, J = 2.4 Hz, 1H), 7.03-7.00 (m, 2H), 5.85 (q, J = 6.8 Hz, 1H), 5.10 (d, J = 3.6 Hz, 1H), 4.44-4.42 (m, 1H), 3.88 (s, 3H), 3.86-3.81 (m, 3H), 3.66 (d, J = 12.0 Hz, 1H), 2.78 (s, 3H), 2.46 (s, 3H), 2.06-2.02 (m, 1H), 1.96-1.95 (m, 1H), 1.66 (d, J = 6.4 Hz, 3H).

Example 320
(R)-5-(5-(1-(3,5-dimethylpyridazin-4-yl)ethoxy)-6-methoxy-1H-indazol-3-yl)-2-(3-hydroxyazetidin-1-yl)nicotinonitrile

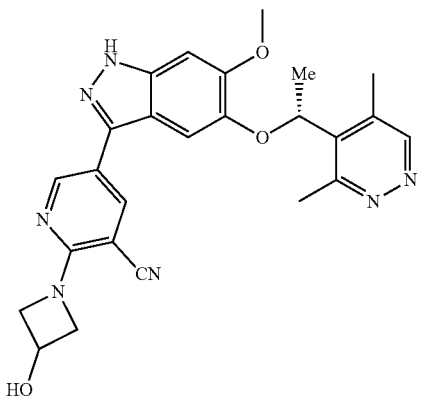 [SMILES: COc1cc2[nH]nc(-c3cnc(N4CC(O)C4)c(C#N)c3)c2cc1O[C@H](C)c1c(C)cnnc1C]

LCMS: m/z = 472.2 (M + H); 1H NMR (400 MHz, DMSO-d6) δ 12.95 (s, 1H), 8.82 (s, 1H), 8.75 (d, J = 2.4 Hz, 1H), 8.17 (d, J = 2.4 Hz, 1H), 7.04 (s, 1H), 7.00 (s, 1H), 5.85 (q, J = 6.4 Hz, 1H), 5.80 (d, J = 6.0 Hz, 1H), 4.65-4.58 (m, 1H), 4.54-4.50 (m, 2H), 4.05-4.01 (m, 2H), 3.87 (s, 3H), 2.78 (s, 3H), 2.46 (s, 3H), 1.65 (d, J = 6.4 Hz, 3H).

Example 321
5-(5-((R)-1-(3,5-dimethylpyridazin-4-yl)ethoxy)-6-methoxy-1H-indazol-3-yl)-2-((R)-3-(2-hydroxypropan-2-yl)pyrrolidin-1-yl)nicotinonitrile

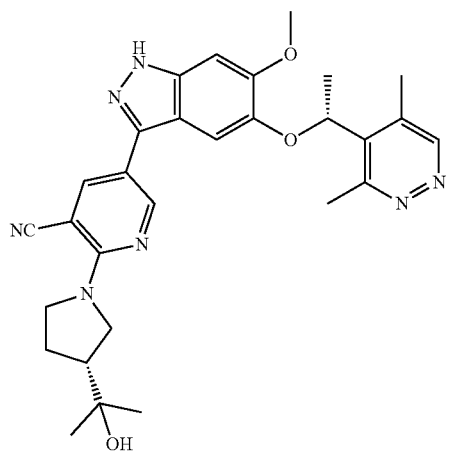 [SMILES: COc1cc2[nH]nc(-c3cnc(N4CC[C@@H](C(C)(C)O)C4)c(C#N)c3)c2cc1O[C@H](C)c1c(C)cnnc1C]

LCMS: m/z = 528.3 (M + H); 1H NMR (400 MHz, DMSO-d6) δ 12.91 (s, 1H), 8.83 (s, 1H), 8.74 (d, J = 2.0 Hz, 1H), 8.12 (d, J = 2.4 Hz, 1H), 7.02-7.00 (m, 2H), 5.85 (q, J = 6.4 Hz, 1H), 4.47 (s, 1H), 3.93-3.91 (m, 1H), 3.88 (s, 3H), 3.87-3.80 (m, 1H), 3.68-3.65 (m, 2H), 2.78 (s, 3H), 2.46 (s, 3H), 2.33-2.31 (m, 1H), 1.98-1.90 (m, 2H), 1.66 (d, J = 6.8 Hz, 3H), 1.17 (d, J = 2.8 Hz, 6H).

Example 322
(R)-2-(azetidin-1-yl)-5-(5-(1-(3,5-dimethylpyridazin-4-yl)ethoxy)-6-methoxy-1H-indazol-3-yl)nicotinonitrile

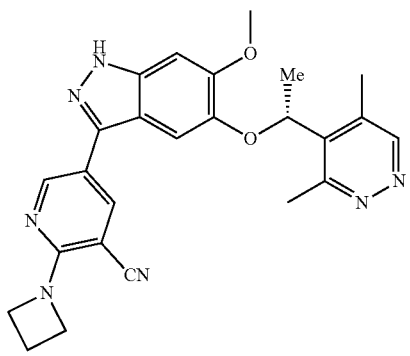 [SMILES: COc1cc2[nH]nc(-c3cnc(N4CCC4)c(C#N)c3)c2cc1O[C@H](C)c1c(C)cnnc1C]

LCMS: m/z = 456.2 (M + H); 1H NMR (400 MHz, DMSO-d6) δ 12.93 (s, 1H), 8.82 (s, 1H), 8.74 (d, J = 2.0 Hz, 1H), 8.15 (d, J = 2.0 Hz, 1H), 7.03 (s, 1H), 7.00 (s, 1H), 5.84 (q, J = 6.4 Hz, 1H), 4.32 (t, J = 7.6 Hz, 4H), 3.78 (s, 3H), 2.78 (s, 3H), 2.46 (s, 3H), 2.43-2.35 (m, 2H), 1.66 (d, J = 6.8 Hz, 3H).

-continued

Example 323
1-(3-(5-(5-((R)-1-(3,5-dimethylpyridazin-4-yl)ethoxy)-1H-indazol-3-yl)-3-methoxypyridin-2-yl)-3,6-diazabicyclo[3.1.1]heptan-6-yl)-2-methylpropan-2-ol

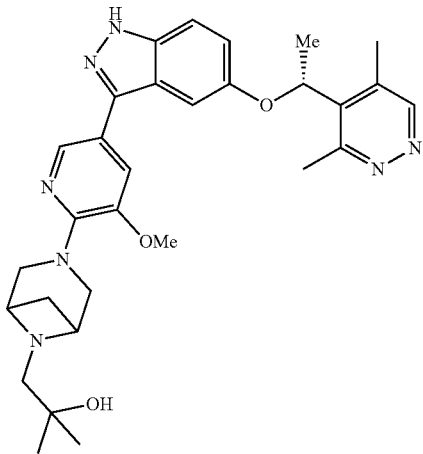 [SMILES: COc1cc(-c2n[nH]c3ccc(O[C@H](C)c4c(C)cnnc4C)cc23)cnc1N1CC2CC(C1)N2CC(C)(C)O]

LCMS: m/z = 544.4 (M + H); 1H-NMR (400 MHz, DMSO-d6) δ 13.00 (s, 1H), 8.83 (s, 1H), 8.15 (s, 1H), 7.49-7.46 (m, 2H), 7.16-7.03 (m, 2H), 5.90 (q, J = 6.8 Hz, 1H), 4.14-3.98 (m, 3H), 3.91-3.71 (m, 5H), 3.65-3.60 (m, 2H), 2.79 (s, 3H), 2.53-2.50 (m, 1H), 2.45 (s, 3H), 2.28 (s, 2H), 1.67 (d, J = 6.8 Hz, 3H), 1.61 (d, J = 8.0 Hz, 1H), 1.09 (s, 6H).

Example 324
(R)-5-(5-(1-(3,5-dimethylpyridazin-4-yl)ethoxy)-6-methoxy-1H-indazol-3-yl)-2-(2-oxa-6-azaspiro[3.3]heptan-6-yl)nicotinonitrile

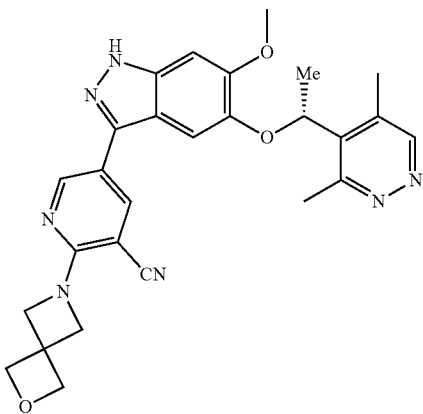

LCMS: m/z = 498.2 (M + H); 1H NMR (400 MHz, DMSO-d6) δ 12.96 (s, 1H), 8.82 (s, 1H), 8.75 (d, J = 2.4 Hz, 1H), 8.18 (d, J = 2.4 Hz, 1H), 7.01 (d, J = 6.0 Hz, 2H), 5.84 (q, J = 6.4 Hz, 1H), 4.76 (s, 4H), 4.48 (s, 4H), 3.87 (s, 3H), 2.78 (s, 3H), 2.45 (s, 3H), 1.66 (d, J = 6.8 Hz, 3H).

Example 325
5-(5-((R)-1-(3,5-dimethylpyridazin-4-yl)ethoxy)-1H-indazol-3-yl)-2-(3-oxohexahydroimidazo[1,5-a]pyrazin-7(1H)-yl)nicotinonitrile

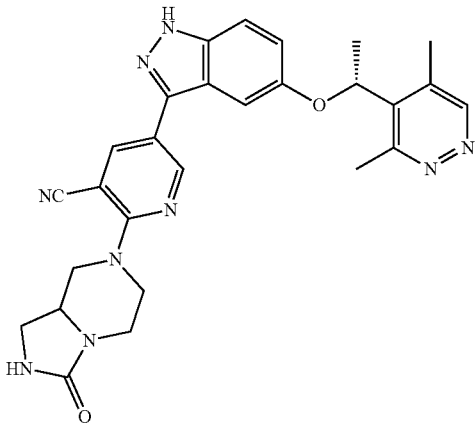 [SMILES: Cc1cnnc(C)c1[C@@H](C)Oc1ccc2[nH]nc(-c3cnc(N4CCN5C(=O)NCC5C4)c(C#N)c3)c2c1]

LCMS: m/z = 510.3 (M + H); 1H NMR (400 MHz, DMSO-d6) δ 13.26 (s, 1H), 8.86 (dd, J = 2.4 Hz, 1.6 Hz, 1H), 8.82 (s, 1H), 8.36 (dd, J = 2.0 Hz, 1.2 Hz, 1H), 7.50 (d, J = 9.2 Hz, 1H), 7.11-7.08 (m, 2H), 6.60 (s, 1H), 5.92 (q, J = 6.8 Hz, 1H), 4.31-4.22 (m, 2H), 3.86-3.81 (m, 1H), 3.76-3.74 (m, 1H), 3.50-3.43 (m, 1H), 3.08-2.95 (m, 4H), 2.79 (s, 3H), 2.47 (s, 3H), 1.67 (d, J = 6.8 Hz, 3H).

| | | |
|---|---|---|
| Example 326<br>5-[5-[(1R)-1-(3,5-dichloro-4-pyridyl)ethoxy]-6-methoxy-1H-indazol-3-yl]-2-(3-hydroxyazetidin-1-yl)pyridine-3-carbonitrile | 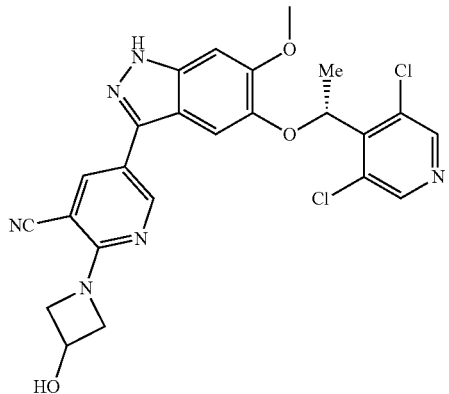 [SMILES: COc1cc2[nH]nc(-c3cnc(N4CC(O)C4)c(C#N)c3)c2cc1O[C@H](C)c1c(Cl)cncc1Cl] | LCMS: m/z = 511.1 (M + H); 1H NMR (400 MHz, DMSO-d6) δ = 12.96 (s, 1H), 8.72 (d, J = 2.3 Hz, 1H), 8.59 (s, 2H), 8.07 (d, J = 2.3 Hz, 1H), 7.05 (s, 1H), 7.00 (s, 1H), 6.02 - 5.96 (m, 1H), 5.79 (d, J = 6.2 Hz, 1H), 4.65 - 4.58 (m, 1H), 4.52 (dd, J = 6.8, 8.8 Hz, 2H), 4.03 (dd, J = 4.3, 9.3 Hz, 2H), 3.86 (s, 3H), 1.76 (d, J = 6.7 Hz, 3H) |
| Example 327<br>5-[5-[(1R)-1-(3,5-dichloro-4-pyridyl)ethoxy]-6-methoxy-1H-indazol-3-yl]-2-[(3S)-3-hydroxypyrrolidin-1-yl]pyridine-3-carbonitrile | 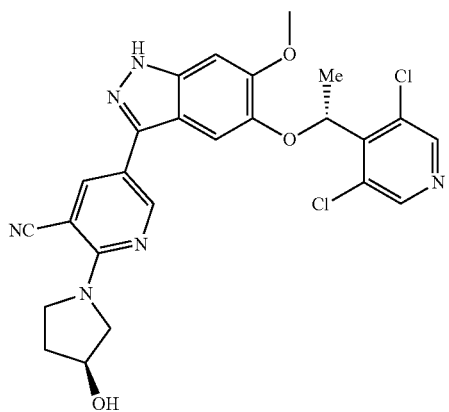 [SMILES: COc1cc2[nH]nc(-c3cnc(N4CC[C@H](O)C4)c(C#N)c3)c2cc1O[C@H](C)c1c(Cl)cncc1Cl] | LCMS: m/z = 525.1 (M + H); 1H NMR (400 MHz, DMSO-d6) δ = 12.94 (br s, 1H), 8.72 (d, J = 2.4 Hz, 1H), 8.63 - 8.54 (m, 2H), 8.04 (d, J = 2.3 Hz, 1H), 7.03 (s, 1H), 7.00 (s, 1H), 6.00 (q, J = 6.7 Hz, 1H), 5.08 (br d, J = 2.9 Hz, 1H), 4.43 (br s, 1H), 3.86 (s, 3H), 3.86 - 3.80 (m, 3H), 3.66 (br d, J = 11.5 Hz, 1H), 2.09 - 1.99 (m, 1H), 1.97 - 1.91 (m, 1H), 1.76 (d, J = 6.7 Hz, 3H) |
| Example 328<br>7-(5-(5-((R)-1-(3,5-dimethylpyridazin-4-yl)ethoxy)-1H-indazol-3-yl)-3-methoxypyridin-2-yl)hexahydroimidazo[1,5-a]pyrazin-3(2H)-one | 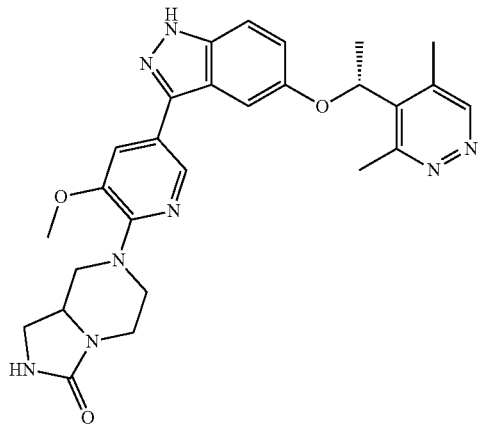 [SMILES: COc1cc(-c2n[nH]c3ccc(O[C@H](C)c4c(C)cnnc4C)cc23)cnc1N1CCN2C(=O)NCC2C1] | LCMS: m/z = 515.3 (M + H); 1H-NMR (400 MHz, DMSO-d6) δ 13.13 (brs, 1H), 8.82 (s, 1H), 8.20 (t, J = 2.0 Hz, 1H), 7.55 (d, J = 1.6 Hz, 1H), 7.49 (d, J = 9.2 Hz, 1H), 7.12 (s, 1H), 7.09 (dd, J = 9.2 Hz, 2.4 Hz, 1H), 6.49 (s, 1H), 5.90 (q, J = 6.8 Hz, 1H), 4.00-3.94 (m, 2H), 3.89 (s, 3H), 3.88-3.82 (m, 1H), 3.70-3.66 (m, 1H), 3.45-3.41 (m, 1H), 3.03-2.96 (m, 2H), 2.78 (s, 3H), 2.71-2.64 (m, 2H), 2.44 (s, 3H), 1.66 (d, J = 6.8 Hz, 3H). |

-continued

| Example 329 (R)-5-(5-(1-(3,5-dichloropyridin-4-yl)ethoxy)-1H-indazol-3-yl)-2-(6-(2,2,2-trifluoroethyl)-2,6-diazaspiro[3.3]heptan-2-yl)nicotinonitrile | 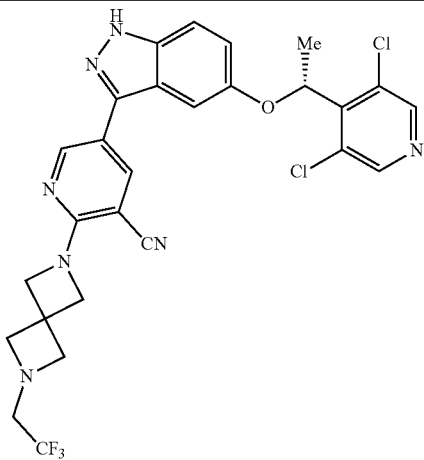 | LCMS: m/z = 588.3 (M + H); 1H NMR (400 MHz, DMSO-d6) δ 13.17 (s, 1H), 8.76 (d, J = 2.4 Hz, 1H), 8.57 (s, 2H), 8.14 (d, J = 2.4 Hz, 1H), 7.48 (d, J = 9.2 Hz, 1H), 7.16 (d, J = 2.0 Hz, 1H), 7.10 (dd, J = 8.8 Hz, 2.0 Hz, 1H), 6.14 (q, J = 6.4 Hz, 1H), 4.41 (s, 4H), 3.58 (s, 4H), 3.20 (q, J = 10.4 Hz, 2H), 1.76 (d, J = 6.4 Hz, 3H). |
|---|---|---|
| Example 330 (R)-5-(5-(1-(3,5-dichloropyridin-4-yl)ethoxy)-1H-indazol-3-yl)-2-(6-(2,2-difluoroethyl)-2,6-diazaspiro[3.3]heptan-2-yl)nicotinonitrile | 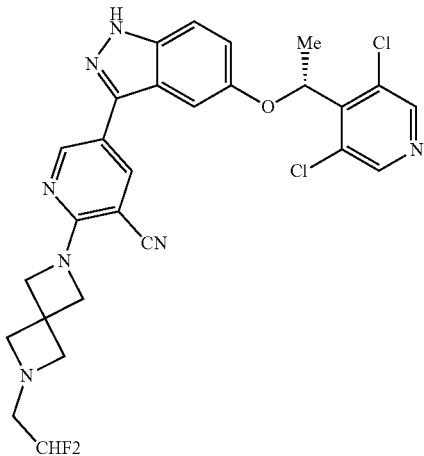 [SMILES: C[C@@H](Oc1ccc2[nH]nc(-c3cnc(N4CC5(CN(CC(F)F)C5)C4)c(C#N)c3)c2c1)c1c(Cl)cncc1Cl] | LCMS: m/z = 570.2 (M + H); 1H NMR (400 MHz, DMSO-d6) δ 13.17 (s, 1H), 8.76 (d, J = 2.4 Hz, 1H), 8.57 (s, 2H), 8.14 (d, J = 2.4 Hz, 1H), 7.47 (d, J = 9.2 Hz, 1H), 7.16 (d, J = 2.4 Hz, 1H), 7.11 (dd, J = 9.2 Hz, 2.4 Hz, 1H), 6.16 (q, J = 6.4 Hz, 1H), 6.10-5.81 (m, 1H), 4.40 (s, 4H), 3.49 (s, 4H), 2.85-2.76 (m, 2H), 1.77 (d, J = 6.8 Hz, 3H). |
| Example 331 5-(5-((R)-1-(3,5-dichloropyridin-4-yl)ethoxy)-1H-indazol-3-yl)-2-(6-hydroxy-3-azabicyclo[3.1.0]hexan-3-yl)nicotinonitrile | 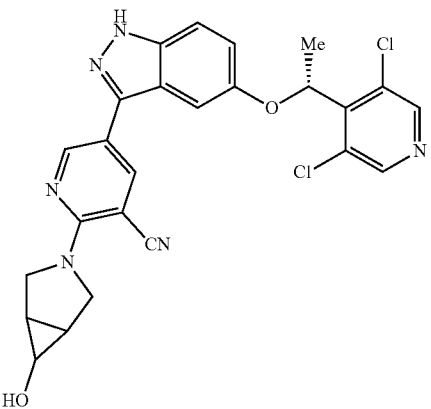 [SMILES: C[C@@H](Oc1ccc2[nH]nc(-c3cnc(N4CC5C(O)C5C4)c(C#N)c3)c2c1)c1c(Cl)cncc1Cl] | LCMS: m/z = 507.2 (M + H); 1H NMR (400 MHz, DMSO-d6) δ 13.16 (s, 1H), 8.76 (d, J = 2.8 Hz, 1H), 8.58 (s, 2H), 8.11 (d, J = 2.4 Hz, 1H), 7.47 (d, J = 9.2 Hz, 1H), 7.14 (s, 1H), 7.11 (dd, J = 9.2 Hz, 2.4 Hz, 1H), 6.16 (q, J = 6.4 Hz, 1H), 5.54 (d, J = 2.0 Hz, 1H), 4.04-4.00 (m, 2H), 3.83-3.80 (m, 2H), 3.04 (d, J = 1.6 Hz, 1H), 1.81 (t, J = 2.4 Hz, 2H), 1.77 (d, J = 6.8 Hz, 3H). |

-continued

Example 332
5-(5-((R)-1-(3,5-dichloropyridin-4-yl)ethoxy)-1H-indazol-3-yl)-2-((R)-2-(hydroxymethyl)pyrrolidin-1-yl)nicotinonitrile

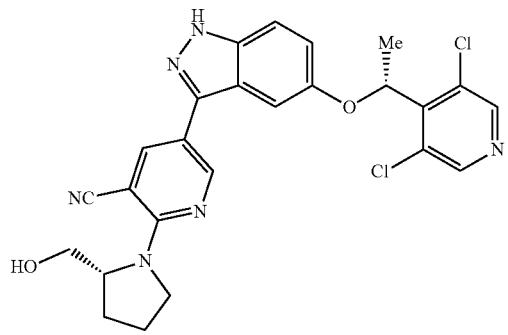 [SMILES: C[C@@H](Oc1ccc2[nH]nc(-c3cnc(N4CCC[C@@H]4CO)c(C#N)c3)c2c1)c1c(Cl)cncc1Cl]

LCMS: m/z = 509.2 (M + H); 1H-NMR (400 MHz, DMSO-d6) δ 13.16 (brs, 1H), 8.75 (d, J = 2.4 Hz, 1H), 8.60 (s, 2H), 8.11 (d, J = 2.8 Hz, 1H), 7.50 (d, J = 8.8 Hz, 1H), 7.16-7.09 (m, 2H), 6.14 (q, J = 6.8 Hz, 1H), 4.82 (brs, 1H), 4.59-4.49 (m, 1H), 4.01-3.90 (m, 1H), 3.80-3.71 (m, 1H), 3.70-3.62 (m, 1H), 3.56-3.45 (m, 1H), 2.17-1.89 (m, 4H), 1.77 (d, J = 6.8 Hz, 3H).

Example 333
5-[5-[(1R)-1-(3,5-dichloro-4-pyridyl)ethoxy]-6-methoxy-1H-indazol-3-yl]-2-pyrrolidin-1-yl-pyridine-3-carbonitrile

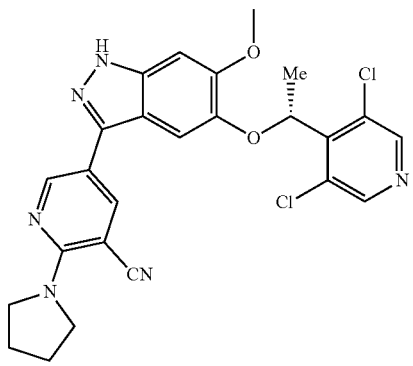 [SMILES: COc1cc2[nH]nc(-c3cnc(N4CCCC4)c(C#N)c3)c2cc1O[C@H](C)c1c(Cl)cncc1Cl]

LCMS: m/z = 509.1 (M + H); 1H NMR (400 MHz, DMSO-d6) δ = 12.93 (br s, 1H), 8.72 (d, J = 2.4 Hz, 1H), 8.59 (s, 2H), 8.04 (d, J = 2.4 Hz, 1H), 7.02 (d, J = 9.5 Hz, 2H), 5.99 (q, J = 6.7 Hz, 1H), 3.86 (s, 3H), 3.78 - 3.71 (m, 4H), 2.01 - 1.93 (m, 4H), 1.76 (d, J = 6.7 Hz, 3H)

Example 334
5-(5-((R)-1-(3,5-dichloropyridin-4-yl)ethoxy)-1H-indazol-3-yl)-2-((S)-2-(hydroxymethyl)pyrrolidin-1-yl)nicotinonitrile

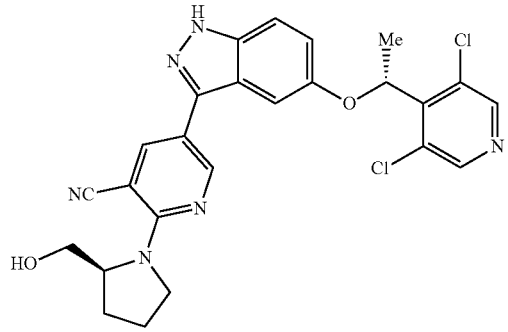 [SMILES: C[C@@H](Oc1ccc2[nH]nc(-c3cnc(N4CCC[C@H]4CO)c(C#N)c3)c2c1)c1c(Cl)cncc1Cl]

LCMS: m/z = 509.2 (M + H); 1H-NMR (400 MHz, DMSO-d6) δ 13.14 (brs, 1H), 8.76 (d, J = 2.4 Hz, 1H), 8.57 (s, 2H), 8.11 (d, J = 2.4 Hz, 1H), 7.49 (d, J = 8.8 Hz, 1H), 7.13-7.09 (m, 2H), 6.14 (q, J = 6.4 Hz, 1H), 4.81 (s, 1H), 4.55-4.50 (m, 1H), 3.95-3.92 (m, 1H), 3.77-3.71 (m, 1H), 3.66-3.64 (m, 1H), 3.52-3.47 (m, 1H), 2.11-1.95 (m, 4H), 1.76 (d, J = 6.8 Hz, 3H).

Example 335
5-(5-((R)-1-(3,5-dimethylpyridazin-4-yl)ethoxy)-1H-indazol-3-yl)-2-((R)-2-(hydroxymethyl)pyrrolidin-1-yl)nicotinonitrile

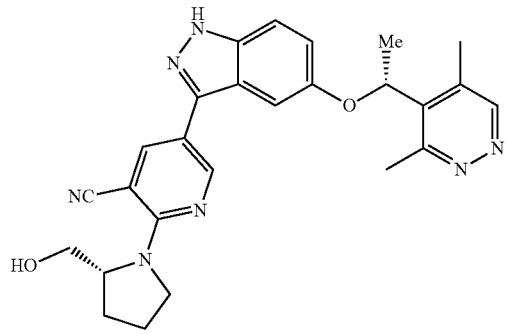 [SMILES: Cc1cnnc(C)c1[C@@H](C)Oc1ccc2[nH]nc(-c3cnc(N4CCC[C@@H]4CO)c(C#N)c3)c2c1]

LCMS: m/z = 470.3 (M + H); 1H-NMR (400 MHz, DMSO-d6) δ 13.14 (s, 1H), 8.84 (s, 1H), 8.74 (d, J = 2.0 Hz, 1H), 8.15 (d, J = 2.0 Hz, 1H), 7.49 (d, J = 8.8 Hz, 1H), 7.09 (dd, J = 8.8 Hz, 2.0 Hz, 1H), 7.03 (d, J = 1.6 Hz, 1H), 5.91 (q, J = 6.8 Hz, 1H), 4.82 (t, J = 5.6 Hz, 1H), 4.57-4.49 (m, 1H), 4.02-3.90 (m, 1H), 3.78-3.70 (m, 1H), 3.68-3.60 (m, 1H), 3.55-3.46 (m, 1H), 2.80 (s, 3H), 2.48 (s, 3H), 2.16-1.89 (m, 4H), 1.68 (d, J = 6.8 Hz, 3H).

-continued

| | | |
|---|---|---|
| Example 336<br>5-(5-((R)-1-(3,5-dimethylpyridazin-4-yl)ethoxy)-1H-indazol-3-yl)-2-((S)-2-(hydroxymethyl)pyrrolidin-1-yl)nicotinonitrile | 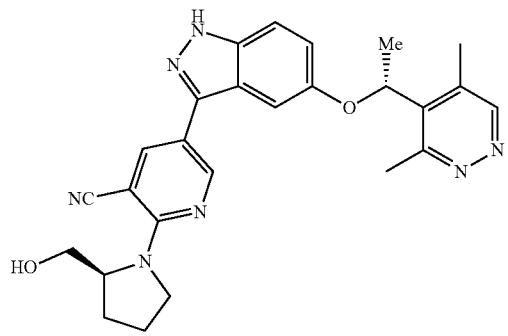 [SMILES: Cc1cnnc(C)c1[C@@H](C)Oc1ccc2[nH]nc(-c3cnc(N4CCC[C@H]4CO)c(C#N)c3)c2c1] | LCMS: m/z = 470.3 (M + H); 1H-NMR (400 MHz, DMSO-d6) δ 13.13 (s, 1H), 8.82 (s, 1H), 8.76 (d, J = 2.4 Hz, 1H), 8.15 (d, J = 2.4 Hz, 1H), 7.48 (d, J = 8.8 Hz, 1H), 7.09 (dd, J = 8.8 Hz, 2.0 Hz, 1H), 7.02 (s, 1H), 5.91 (q, J = 6.4 Hz, 1H), 4.82 (t, J = 5.2 Hz, 1H), 4.60-4.50 (m, 1H), 3.97-3.90 (m, 1H), 3.78-3.71 (m, 1H), 3.68-3.60 (m, 1H), 3.54-3.45 (m, 1H), 2.79 (s, 3H), 2.47 (s, 3H), 2.16-1.87 (m, 4H), 1.67 (d, J = 6.4 Hz, 3H). |
| Example 337<br>(R)-5-(5-(1-(3,5-dichloropyridin-4-yl)ethoxy)-1H-indazol-3-yl)-2-(6-(methylsulfonyl)-2,6-diazaspiro[3.3]heptan-2-yl)nicotinonitrile | 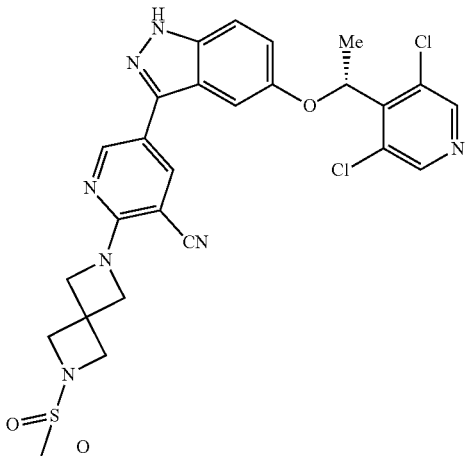 | LCMS: m/z = 584.2 (M + H); 1H-NMR (400 MHz, DMSO-d6) δ 13.19 (s, 1H), 8.77 (d, J = 2.4 Hz, 1H), 8.57 (s, 2H), 8.16 (d, J = 2.0 Hz, 1H), 7.49 (d, J = 8.8 Hz, 1H), 7.16 (d, J = 2.0 Hz, 1H), 7.10 (dd, J = 9.2 Hz, 2.4 Hz, 1H), 6.14 (q, J = 6.4 Hz, 1H), 4.49 (s, 4H), 4.14 (s, 4H), 3.03 (s, 3H), 1.76 (d, J = 6.8 Hz, 3H). |
| Example 338<br>(R)-5-(5-(1-(3,5-dichloropyridin-4-yl)ethoxy)-1H-indazol-3-yl)-2-(6-(methylsulfonyl)-2,6-diazaspiro[3.5]nonan-2-yl)nicotinonitrile | 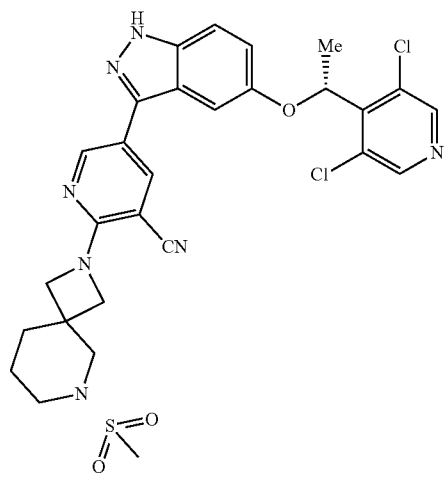 | LCMS: m/z = 612.3 (M + H); 1H NMR (400 MHz, DMSO-d6) δ 13.17 (s, 1H), 8.77 (d, J = 2.4 Hz, 1H), 8.57 (s, 2H), 8.15 (d, J = 2.4 Hz, 1H), 7.49 (d, J = 8.8 Hz, 1H), 7.16 (d, J = 1.6 Hz, 1H), 7.10 (dd, J = 8.8 Hz, 2.0 Hz, 1H), 6.14 (q, J = 6.4 Hz, 1H), 4.06-4.02 (m, 4H), 3.28 (s, 2H), 3.09 (t, J = 5.2 Hz, 2H), 2.90 (s, 3H), 1.82-1.79 (m, 2H), 1.76 (d, J = 6.8 Hz, 3H), 1.64-1.59 (m, 2H). |

| Example 339 (R)-5-(5-(1-(3,5-dichloropyridin-4-yl)ethoxy)-6-methoxy-1H-indazol-3-yl)-2-(6,6-dioxido-6-thia-2-azaspiro[3.4]octan-2-yl)nicotinonitrile | 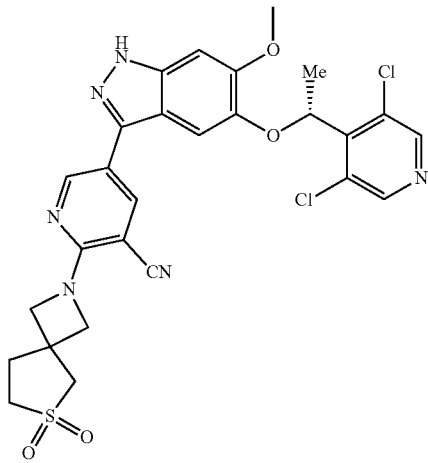 [SMILES: COc1cc2[nH]nc(-c3cnc(N4CC5(CCS(=O)(=O)C5)C4)c(C#N)c3)c2cc1O[C@H](C)c1c(Cl)cncc1Cl] | LCMS: m/z = 599.2 (M + H); 1H NMR (400 MHz, DMSO-d6) δ 12.99 (s, 1H), 8.73 (d, J = 2.4 Hz, 1H), 8.59 (s, 2H), 8.10 (d, J = 2.4 Hz, 1H), 7.03 (s, 1H), 7.01 (s, 1H) 6.00 (q, J = 6.4 Hz, 1H), 4.37 (d, J = 8.8 Hz, 2H), 4.28 (d, J = 9.2 Hz, 2H), 3.86 (s, 3H), 3.53 (s, 2H), 3.27 (t, J = 7.6 Hz, 2H), 2.53 - 2.51 (m, 2H), 1.76 (d, J = 6.4 Hz, 3H). |
|---|---|---|
| Example 340 (R)-5-(5-(1-(3,5-dichloropyridin-4-yl)ethoxy)-1H-indazol-3-yl)-2-(6,6-dioxido-6-thia-2-azaspiro[3.5]nonan-2-yl)nicotinonitrile | 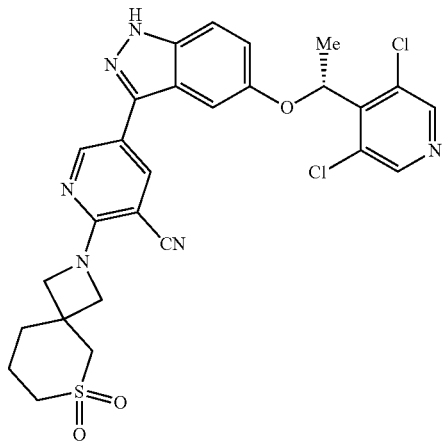 [SMILES: C[C@@H](Oc1ccc2[nH]nc(-c3cnc(N4CC5(CCCS(=O)(=O)C5)C4)c(C#N)c3)c2c1)c1c(Cl)cncc1Cl] | LCMS: m/z = 583.2 (M + H); 1H NMR (400 MHz, DMSO-d6) δ 13.18 (s, 1H), 8.77 (d, J = 2.4 Hz, 1H), 8.58 (s, 2H), 8.16 (d, J = 2.0 Hz, 1H), 7.48 (d, J = 8.8 Hz, 1H), 7.14 (s, 1H), 7.11 (dd, J = 8.8 Hz, 2.0 Hz, 1H), 6.14 (q, J = 6.8 Hz, 1H), 4.28 (d, J = 8.8 Hz, 2H), 4.07 (d, J = 8.8 Hz, 2H), 3.51 (s, 2H), 3.09-3.02 (m, 2H), 2.07-1.93 (m, 4H), 1.76 (d, J = 6.8 Hz, 3H). |
| Example 341 5-[5-[(1R)-1-(3,5-dichloro-2-methyl-4-pyridyl)ethoxy]-6-methoxy-1H-indazol-3-yl]-2-(2-methylsulfonyl-2,6-diazaspiro[3.3]heptan-6-yl)pyridine-3-carbonitrile | 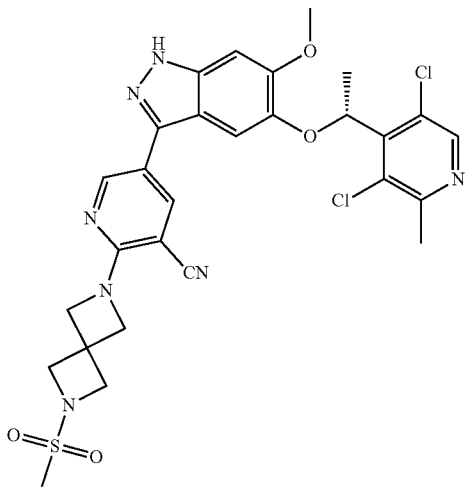 [SMILES: COc1cc2[nH]nc(-c3cnc(N4CC5(C4)CN(S(C)(=O)=O)C5)c(C#N)c3)c2cc1O[C@H](C)c1c(Cl)cnc(C)c1Cl] | LCMS: m/z = 628.2 (M + H); 1H NMR (400 MHz, DMSO-d6) δ = 12.96 (s, 1H), 8.63 (d, J = 2.2 Hz, 1H), 8.43 (s, 1H), 8.12 (d, J = 2.2 Hz, 1H), 7.00 (s, 1H), 6.95 (s, 1H), 6.00 (q, J = 6.7 Hz, 1H), 4.48 (s, 4H), 4.14 (s, 4H), 3.86 (s, 3H), 3.03 (s, 3H), 2.58 (s, 3H), 1.75 (d, J = 6.7 Hz, 3H) |

| Example 342 5-[5-[(1R)-1-(3,5-dichloro-4-pyridyl)ethoxy]-6-methoxy-1H-indazol-3-yl]-2-(2-methylsulfonyl-2,6-diazaspiro[3.3]heptan-6-yl)pyridine-3-carbonitrile | 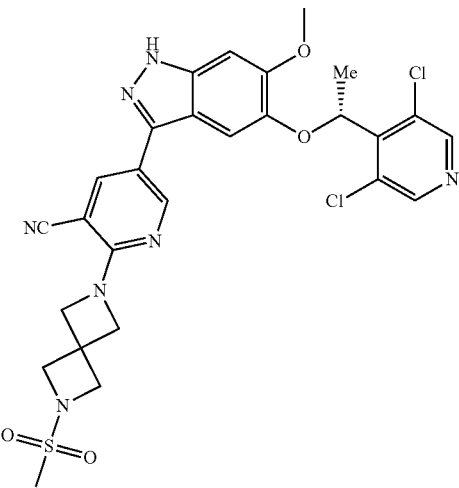 [SMILES: COc1cc2[nH]nc(-c3cnc(N4CC5(C4)CN(S(C)(=O)=O)C5)c(C#N)c3)c2cc1O[C@H](C)c1c(Cl)cncc1Cl] | LCMS: m/z = 614.1 (M + H); 1H NMR (400 MHz, DMSO-d6) δ ppm 12.97 (s, 1 H) 8.71 - 8.75 (m, 1 H) 8.59 (s, 2 H) 8.09 (d, J = 2.32 Hz, 1 H) 7.03 - 7.06 (m, 1 H) 7.01 (s, 1 H) 5.96 - 6.03 (m, 1 H) 4.48 (s, 4 H) 4.14 (s, 4 H) 3.86 (s, 3 H) 3.03 (s, 3 H) 1.76 (d, J = 6.72 Hz, 3 H) |
|---|---|---|
| Example 343 (R)-5-(5-(1-(3,5-dichloropyridin-4-yl)ethoxy)-1H-indazol-3-yl)-2-(6,6-dioxido-6-thia-2-azaspiro[3.4]octan-2-yl)nicotinonitrile | 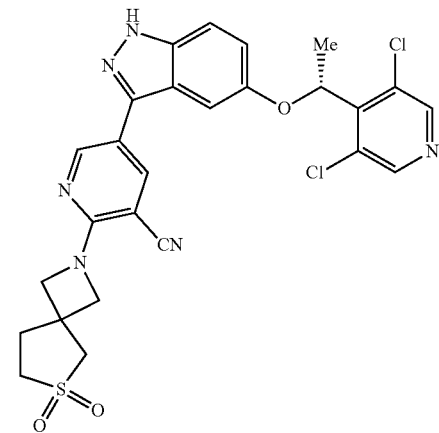 [SMILES: C[C@@H](Oc1ccc2[nH]nc(-c3cnc(N4CC5(CCS(=O)(=O)C5)C4)c(C#N)c3)c2c1)c1c(Cl)cncc1Cl] | LCMS: m/z = 569.2 (M + H); 1H NMR (400 MHz, DMSO-d6) δ 13.19 (s, 1H), 8.79 (d, J = 2.0 Hz, 1H), 8.58 (s, 2H), 8.18 (d, J = 2.4 Hz, 1H), 7.49 (d, J = 9.2 Hz, 1H), 7.16 (s, 1H), 7.11 (dd, J = 8.8 Hz, 2.0 Hz 1H), 6.15 (q, J = 6.8 Hz, 1H), 4.38 (d, J = 8.8 Hz, 2H), 4.29 (d, J = 9.2 Hz, 2H), 3.54 (s, 2H), 3.28 (t, J = 7.6 Hz, 2H), 2.52 (t, J = 7.6 Hz, 2H), 1.77 (d, J = 6.4 Hz, 3H). |
| Example 344 (R)-5-(5-(1-(3,5-dichloropyridin-4-yl)ethoxy)-3-(5-methoxy-6-(6-(methylsulfonyl)-2,6-diazaspiro[3.3]heptan-2-yl)pyridin-3-yl)-1H-indazole | 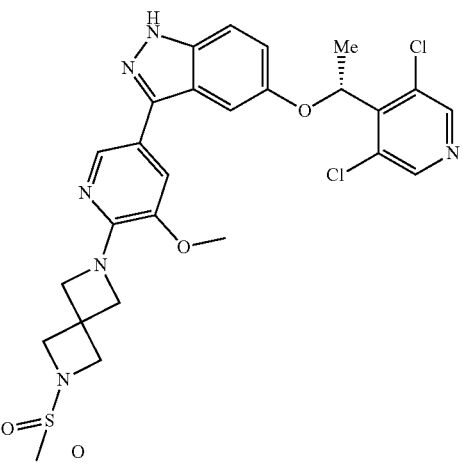 | LCMS: m/z = 589.2 (M + H); 1H-NMR (400 MHz, DMSO-d6) δ 13.04 (s, 1H), 8.57 (s, 2H), 8.10 (d, J = 1.6 Hz, 1H), 7.50-7.43 (m, 2H), 7.23 (d, J = 1.6 Hz, 1H), 7.11 (dd, J = 9.2 Hz, 2.0 Hz, 1H), 6.14 (q, J = 6.4 Hz, 1H), 4.24 (s, 4H), 4.10 (s, 4H), 3.83 (s, 3H), 3.02 (s, 3H), 1.75 (d, J = 6.8 Hz, 3H). |

| | | |
|---|---|---|
| Example 345<br>(R)-5-(5-(1-(3,5-dichloropyridin-4-yl)ethoxy)-1H-indazol-3-yl)-2-(3-(difluoromethyl)azetidin-1-yl)nicotinonitrile | 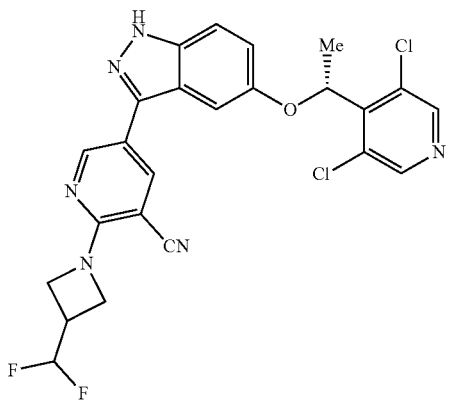 [SMILES: C[C@@H](Oc1ccc2[nH]nc(-c3cnc(N4CC(C(F)F)C4)c(C#N)c3)c2c1)c1c(Cl)cncc1Cl] | LCMS: m/z = 515.2 (M + H); 1H-NMR (400 MHz, DMSO-d6) δ 13.20 (s, 1H), 8.80 (d, J = 2.0 Hz, 1H), 8.58 (s, 2H), 8.20 (d, J = 2.4 Hz, 1H), 7.49 (d, J = 9.2 Hz, 1H), 7.18 (d, J = 2.0 Hz, 1H), 7.11 (dd, J = 8.8 Hz, 2.0 Hz, 1H), 6.45 (td, J = 56.4 Hz, 4.4 Hz, 1H), 6.15 (q, J = 6.8 Hz, 1H), 4.44 (t, J = 8.8 Hz, 2H), 4.25 (dd, J = 9.6 Hz, 5.6 Hz, 2H), 3.32-3.22 (m, 1H), 1.76 (d, J = 6.4 Hz, 3H). |
| Example 346<br>(R)-5-(5-(1-(3,5-dichloropyridin-4-yl)ethoxy)-6-methoxy-1H-indazol-3-yl)-2-(6,6-dioxido-6-thia-2-azaspiro[3.5]nonan-2-yl)nicotinonitrile | 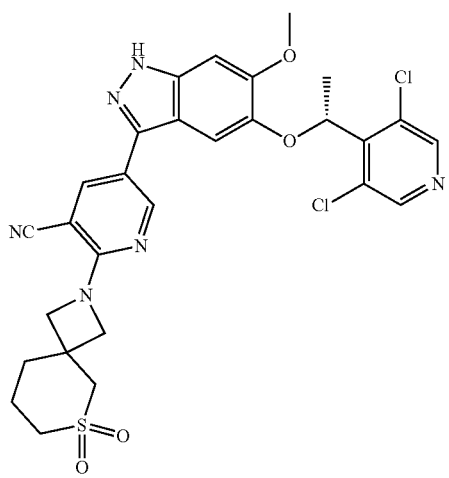 [SMILES: COc1cc2[nH]nc(-c3cnc(N4CC5(CCCS(=O)(=O)C5)C4)c(C#N)c3)c2cc1O[C@H](C)c1c(Cl)cncc1Cl] | LCMS: m/z = 613.1 (M + H); 1H NMR (400 MHz, CDCl3) δ 8.68 (d, J = 2.0 Hz, 1H), 8.48 (s, 2H), 7.96 (d, J = 2.0 Hz, 1H), 6.98 (s, 1H), 6.90 (s, 1H), 5.98 (q, J = 6.8 Hz, 1H), 4.39 (d, J = 9.2 Hz, 2H), 4.22 (dd, J = 9.6 Hz, 3.8 Hz, 2H), 3.93 (s, 3H), 3.29 (s, 2H), 3.01 (t, J = 5.4 Hz, 2H), 2.25-2.21 (m, 2H), 2.05-2.00 (m, 2H), 1.85 (d, J = 6.9 Hz, 3H) |
| Example 347<br>(R)-5-(5-(1-(3,5-dichloropyridin-4-yl)ethoxy)-1H-indazol-3-yl)-2-(3-(trifluoromethyl)azetidin-1-yl)nicotinonitrile | 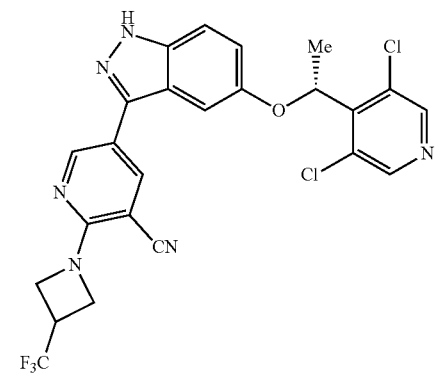 [SMILES: C[C@@H](Oc1ccc2[nH]nc(-c3cnc(N4CC(C(F)(F)F)C4)c(C#N)c3)c2c1)c1c(Cl)cncc1Cl] | LCMS: m/z = 533.2 (M + H); 1H-NMR (400 MHz, DMSO-d6) δ 13.25 (brs, 1H), 8.82 (d, J = 2.0 Hz, 1H), 8.58 (s, 2H), 8.24 (d, J = 2.4 Hz, 1H), 7.50 (d, J = 9.2 Hz, 1H), 7.18 (d, J = 1.6 Hz, 1H), 7.11 (dd, J = 9.2 Hz, 2.4 Hz, 1H), 6.15 (q, J = 6.4 Hz, 1H), 4.59 (t, J = 8.8 Hz, 2H), 4.30 (dd, J = 9.2 Hz, 5.2 Hz, 2H), 3.87-3.72 (m, 1H), 1.76 (d, J = 6.8 Hz, 3H). |
| Example 348<br>(R)-2-(3-cyanoazetidin-1-yl)-5-(5-(1-(3,5-dichloropyridin-4-yl)ethoxy)-1H-indazol-3-yl)nicotinonitrile | 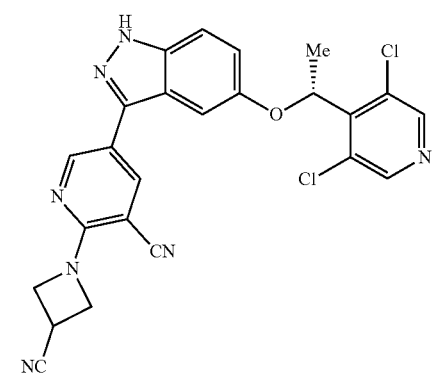 [SMILES: C[C@@H](Oc1ccc2[nH]nc(-c3cnc(N4CC(C#N)C4)c(C#N)c3)c2c1)c1c(Cl)cncc1Cl] | LCMS: m/z = 490.2 (M + H); 1H-NMR (400 MHz, DMSO-d6) δ 13.24 (s, 1H), 8.81 (d, J = 2.0 Hz, 1H), 8.57 (s, 2H), 8.23 (d, J = 2.4 Hz, 1H), 7.49 (d, J = 9.2 Hz, 1H), 7.18 (d, J = 2.4 Hz, 1H), 7.10 (dd, J = 8.8 Hz, 2.0 Hz, 1H), 6.14 (q, J = 6.8 Hz, 1H), 4.59 (t, J = 8.8 Hz, 2H), 4.50-4.43 (m, 2H), 3.99-3.90 (m, 1H), 1.76 (d, J = 6.8 Hz, 3H). |

| Example 349
5-[5-[(1R)-1-(3,5-dichloro-2-methyl-4-pyridyl)ethoxy]-1H-indazol-3-yl]-2-(6,6-dioxo-6λ⁶-thia-2-azaspiro[3.5]nonan-2-yl)pyridine-3-carbonitrile | 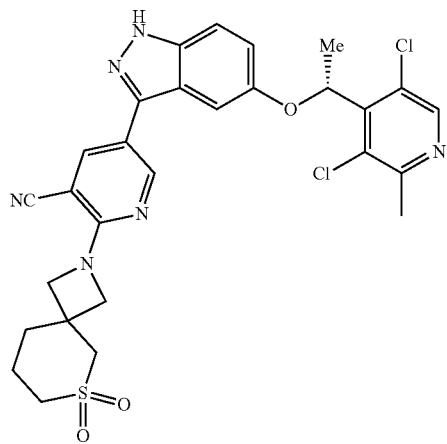 [SMILES: Cc1ncc(Cl)c([C@@H](C)Oc2ccc3[nH]nc(-c4cnc(N5CC6(CCCS(=O)(=O)C6)C5)c(C#N)c4)c3c2)c1Cl] | LCMS: m/z = 597.2 (M + H); 1H NMR (400 MHz, DMSO-d6) δ = 13.17 (s, 1H), 8.70 (d, J = 2.3 Hz, 1H), 8.43 (s, 1H), 8.18 (d, J = 2.3 Hz, 1H), 7.49 (d, J = 9.4 Hz, 1H), 7.13 - 7.06 (m, 2H), 6.13 (q, J = 6.7 Hz, 1H), 4.28 (d, J = 8.9 Hz, 2H), 4.07 (d, J = 8.8 Hz, 2H), 3.51 (s, 2H), 3.06 (br s, 2H), 2.56 (s, 3H), 2.01 (br s, 4H), 1.76 (d, J = 6.6 Hz, 3H) |
|---|---|---|
| Example 350
5-[5-[(1R)-1-(3,5-dichloro-2-methyl-4-pyridyl)ethoxy]-1H-indazol-3-yl]-2-(8-methylsulfonyl-2,8-diazaspiro[3.5]nonan-2-yl)pyridine-3-carbonitrile | 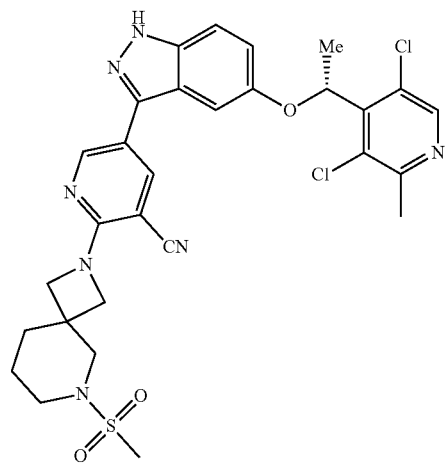 [SMILES: Cc1ncc(Cl)c([C@@H](C)Oc2ccc3[nH]nc(-c4cnc(N5CC6(CCCN(S(C)(=O)=O)C6)C5)c(C#N)c4)c3c2)c1Cl] | LCMS: m/z = 626.2 (M + H); 1H NMR (400 MHz, DMSO-d6) δ = 13.16 (br s, 1H), 8.69 (d, J = 2.2 Hz, 1H), 8.43 (s, 1H), 8.18 (d, J = 2.3 Hz, 1H), 7.48 (d, J = 8.4 Hz, 1H), 7.10 (d, J = 8.3 Hz, 2H), 7.09 (s, 1H), 6.16 - 6.10 (m, 1H), 4.08 - 4.00 (m, 4H), 3.28 - 3.04 (m, 3H), 2.91 (s, 3H), 2.58 - 2.52 (m, 3H), 1.84 - 1.78 (m, 2H), 1.76 (d, J = 6.6 Hz, 3H), 1.63 (br s, 2H) |
| Example 351
5-(5-((R)-1-(3,5-dichloropyridin-4-yl)ethoxy)-1H-indazol-3-yl)-2-((R)-2-(hydroxymethyl)azetidin-1-yl)nicotinonitrile | 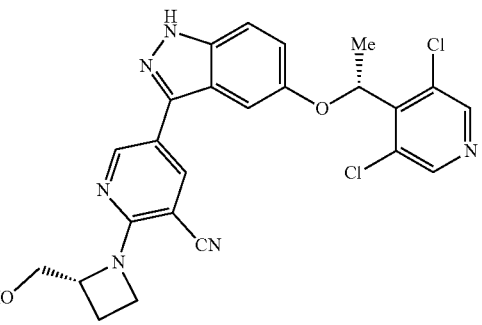 | LCMS: m/z = 495.2 (M + H); 1H-NMR (400 MHz, DMSO-d6) δ 13.18 (brs, 1H), 8.71 (d, J = 2.0 Hz, 1H), 8.58 (s, 2H), 8.13 (s, 1H), 7.48 (d, J = 9.2 Hz, 1H), 7.14 (d, J = 2.0 Hz, 1H), 7.10 (dd, J = 8.8 Hz, 2.4 Hz, 1H), 6.14 (q, J = 6.8 Hz, 1H), 4.96 (brs, 1H), 4.67-4.63 (m, 1H), 4.38-4.32 (m, 1H), 4.25-4.18 (m, 1H), 3.88-3.82 (m, 1H), 3.73-3.67 (m, 1H), 2.43-2.32 (m, 2H), 1.76 (d, J = 6.8 Hz, 3H). |

| | | |
|---|---|---|
| Example 352<br>(R)-5-(5-(1-(3,5-dichloropyridin-4-yl)ethoxy)-6-methyl-1H-indazol-3-yl)-2-(6-(methylsulfonyl)-2,6-diazaspiro[3.3]heptan-2-yl)nicotinonitrile | 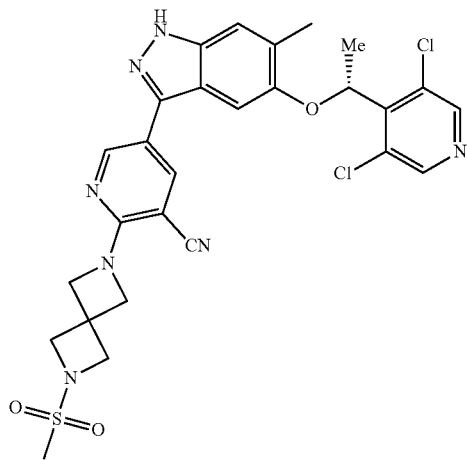 [SMILES: Cc1cc2[nH]nc(-c3cnc(N4CC5(C4)CN(S(C)(=O)=O)C5)c(C#N)c3)c2cc1O[C@H](C)c1c(Cl)cncc1Cl] | LCMS: m/z = 598.2 (M + H); 1H NMR (400 MHz, DMSO-d6) δ 13.03 (s, 1H), 8.73 (d, J = 2.0 Hz, 1H), 8.60 (s, 2H), 8.05 (d, J = 2.4 Hz, 1H), 7.38 (s, 1H), 6.86 (s, 1H), 6.08 (q, J = 6.8 Hz, 1H), 4.49 (s, 4H), 4.14 (s, 4H), 3.03 (s, 3H), 2.42 (s, 3H), 1.80 (d, J = 6.4 Hz, 3H). |
| Example 353<br>(R)-5-(5-(1-(3,5-dichloropyridin-4-yl)ethoxy)-1H-indazol-3-yl)-2-(3,3-difluoroazetidin-1-yl)nicotinonitrile | 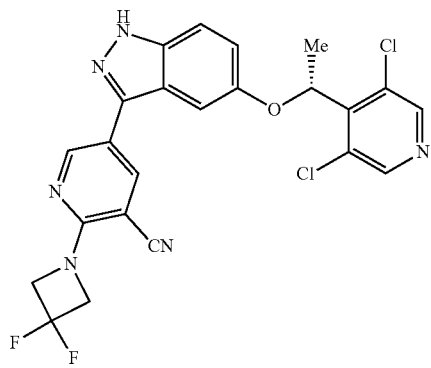 [SMILES: C[C@@H](Oc1ccc2[nH]nc(-c3cnc(N4CC(F)(F)C4)c(C#N)c3)c2c1)c1c(Cl)cncc1Cl] | LCMS: m/z = 501.1 (M + H); 1H-NMR (400 MHz, DMSO-d6) δ 13.26 (s, 1H), 8.84 (d, J = 2.4 Hz, 1H), 8.57 (s, 2H), 8.30 (d, J = 2.4 Hz, 1H), 7.50 (d, J = 8.8 Hz, 1H), 7.20 (d, J = 2.0 Hz, 1H), 7.11 (dd, J = 9.2 Hz, 2.4 Hz, 1H), 6.15 (q, J = 6.4 Hz, 1H), 4.74 (t, J = 12.4 Hz, 4H), 1.76 (d, J = 6.8 Hz, 3H). |
| Example 354<br>5-(5-((R)-1-(3,5-dichloropyridin-4-yl)ethoxy)-1H-indazol-3-yl)-2-((S)-2-(hydroxymethyl)azetidin-1-yl)nicotinonitrile | 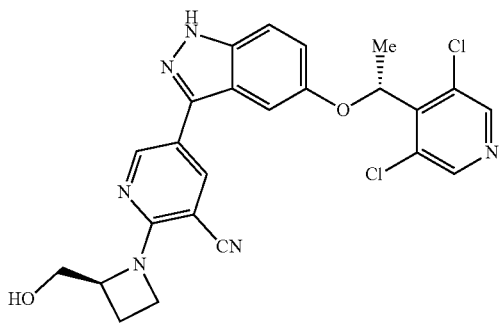 [SMILES: C[C@@H](Oc1ccc2[nH]nc(-c3cnc(N4CC[C@H]4CO)c(C#N)c3)c2c1)c1c(Cl)cncc1Cl] | LCMS: m/z = 495.1 (M + H); 1H NMR (400 MHz, DMSO-d6) δ 13.15 (s, 1H), 8.73 (d, J = 2.0 Hz, 1H), 8.57 (s, 2H), 8.13 (d, J = 2.4 Hz, 1H), 7.48 (d, J = 8.8 Hz, 1H), 7.14 (d, J = 1.6 Hz, 1H), 7.10 (dd, J = 8.8 Hz, 2.4 Hz, 1H), 6.13 (q, J = 7.2 Hz, 1H), 4.96 (t, J = 5.6 Hz, 1H), 4.69-4.63 (m, 1H), 4.38-4.33 (m, 1H), 4.25-4.19 (m, 1H), 3.89-3.83 (m, 1H), 3.73-3.67 (m, 1H), 2.44-2.34 (m, 2H), 1.76 (d, J = 6.4 Hz, 3H). |
| Example 355<br>(R)-5-(5-(1-(3,5-dichloropyridin-4-yl)ethoxy)-6-fluoro-1H-indazol-3-yl)-2-(6-(methylsulfonyl)-2,6-diazaspiro[3.3]heptan-2-yl)nicotinonitrile | 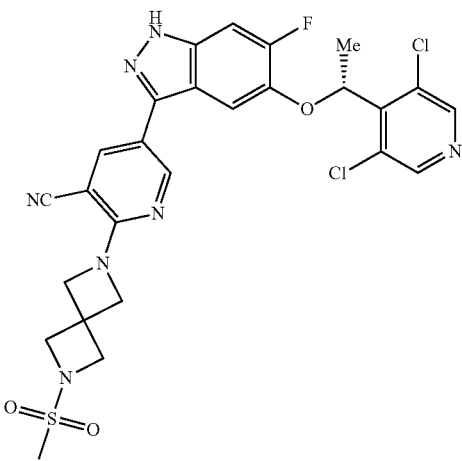 [SMILES: C[C@@H](Oc1cc2c(-c3cnc(N4CC5(C4)CN(S(C)(=O)=O)C5)c(C#N)c3)n[nH]c2cc1F)c1c(Cl)cncc1Cl] | LCMS: m/z = 602.2 (M + H); 1H NMR (400 MHz, DMSO-d6) δ 13.24 (s, 1H), 8.75 (d, J = 2.4 Hz, 1H), 8.59 (s, 2H), 8.14 (d, J = 2.0 Hz, 1H), 7.47 (d, J = 10.8 Hz, 1H), 7.24 (d, J = 8.0 Hz, 1H), 6.17 (q, J = 6.4 Hz, 1H), 4.49 (s, 4H), 4.14 (s, 4H), 3.03 (s, 3H), 1.80 (d, J = 6.4 Hz, 3H). |

| Example 356 (R)-1-(5-(5-(1-(3,5-dichloropyridin-4-yl)ethoxy)-1H-indazol-3-yl)-2-(6-(methylsulfonyl)-2,6-diazaspiro[3.3]heptan-2-yl)pyridin-3-yl)-N,N-dimethylmethanamine | 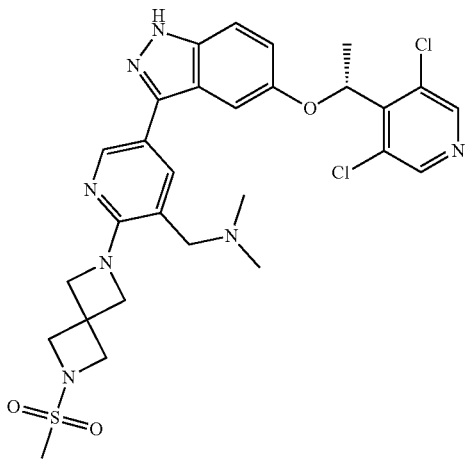 [SMILES: C[C@@H](Oc1ccc2[nH]nc(-c3cnc(N4CC5(C4)CN(S(C)(=O)=O)C5)c(CN(C)C)c3)c2c1)c1c(Cl)cncc1Cl] | LCMS: m/z = 616.3 (M + H); 1H NMR (400 MHz, DMSO- d6) δ 13.01 (s, 1H), 8.57 (s, 2H), 8.46 (d, J = 2.0 Hz, 1H), 7.80 (d, J = 2.0 Hz, 1H), 7.47 (d, J = 8.4 Hz, 1H), 7.20 (d, J = 1.6 Hz, 1H), 7.11 (dd, J = 9.2 Hz, 2.0 Hz, 1H), 6.12 (q, J = 6.4 Hz, 1H), 4.33 (s, 4H), 4.10 (s, 4H), 3.38-3.29 (m, 2H), 3.03 (s, 3H), 2.19 (s, 6H), 1.77 (d, J = 6.4 Hz, 3H) |
|---|---|---|
| Example 357 (R)-1-(5-(5-(1-(3,5-dichloropyridin-4-yl)ethoxy)-6-methoxy-1H-indazol-3-yl)-2-(6-(methylsulfonyl)-2,6-diazaspiro[3.3]heptan-2-yl)pyridin-3-yl)-N,N-dimethylmethanamine | 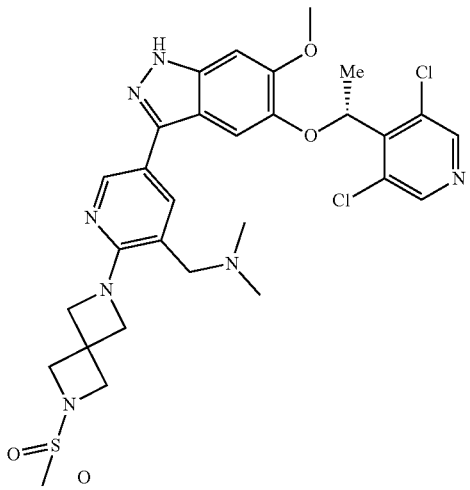 | LCMS: m/z = 646.3 (M + H); 1H NMR (400 MHz, DMSO- d6) δ 12.84 (s, 1H), 8.59 (s, 2H), 8.40 (d, J = 2.0 Hz, 1H), 7.73 (d, J = 2.0 Hz, 1H), 7.08 (s, 1H), 7.01 (s, 1H), 5.97 (q, J = 6.4 Hz, 1H), 4.32 (s, 4H), 4.09 (s, 4H), 3.87 (s, 3H), 3.31-3.28 (m, 2H), 3.03 (s, 3H), 2.18 (s, 6H), 1.76 (d, J = 6.4 Hz, 3H) |
| Example 358 (R)-2-(3-amino-3-methylazetidin-1-yl)-5-(5-(1-(3,5-dichloropyridin-4-yl)ethoxy)-1H-indazol-3-yl)nicotinonitrile | 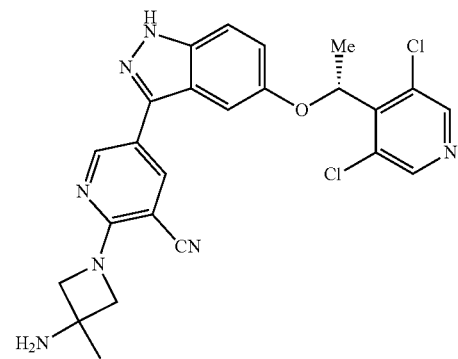 [SMILES: C[C@@H](Oc1ccc2[nH]nc(-c3cnc(N4CC(C)(N)C4)c(C#N)c3)c2c1)c1c(Cl)cncc1Cl] | LCMS: m/z = 494.2 (M + H); 1H-NMR (400 MHz, DMSO-d6) δ 13.15 (brs, 1H), 8.76 (d, J = 2.0 Hz, 1H), 8.57 (s, 2H), 8.12 (d, J = 2.4 Hz, 1H), 7.48 (d, J = 9.2 Hz, 1H), 7.16 (d, J = 2.4 Hz, 1H), 7.10 (dd, J = 8.8 Hz, 2.4 Hz, 1H), 6.14 (q, J = 7.2 Hz, 1H), 4.11 (d, J = 8.4 Hz, 2H), 4.04 (d, J = 8.8 Hz, 2H), 1.76 (d, J = 6.8 Hz, 3H), 1.42 (s, 3H). |

| Example | Structure | Data |
|---|---|---|
| Example 359<br>(R)-5-(6-chloro-5-(1-(3,5-dichloropyridin-4-yl)ethoxy)-1H-indazol-3-yl)-2-(6-(methylsulfonyl)-2,6-diazaspiro[3.3]heptan-2-yl)nicotinonitrile | 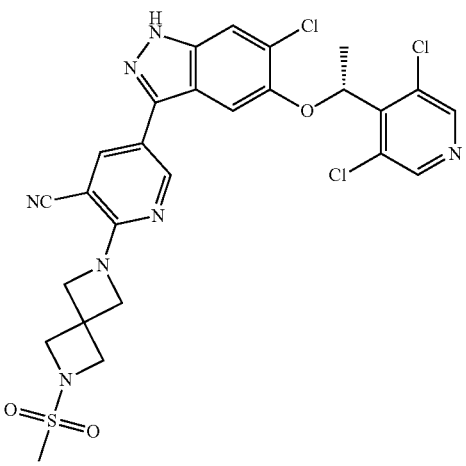 [SMILES: C[C@@H](Oc1cc2c(-c3cnc(N4CC5(C4)CN(S(C)(=O)=O)C5)c(C#N)c3)n[nH]c2cc1Cl)c1c(Cl)cncc1Cl] | LCMS: m/z = 618.2 (M + H); 1H NMR (400 MHz, DMSO-d6) δ 13.05 (brs, 1H), 8.73 (d, J = 2.4 Hz, 1H), 8.60 (s, 2H), 8.12 (d, J = 2.4 Hz, 1H), 7.73 (s, 1H) 7.11 (s, 1H), 6.17 (q, J = 6.8 Hz, 1H), 4.50 (s, 4H), 4.14 (s, 4H), 3.03 (s, 3H), 1.81 (d, J = 6.8 Hz, 3H). |
| Example 360<br>(R)-2-(azetidin-1-yl)-5-(5-(1-(3,5-dichloropyridazin-4-yl)ethoxy)-6-methoxy-1H-indazol-3-yl)nicotinonitrile | 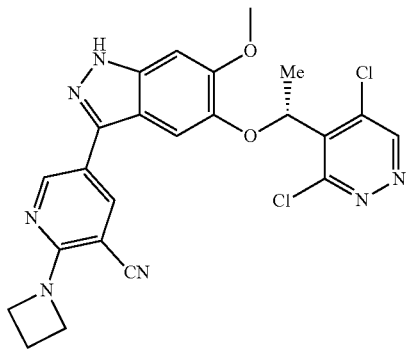 [SMILES: COc1cc2[nH]nc(-c3cnc(N4CCC4)c(C#N)c3)c2cc1O[C@H](C)c1c(Cl)cnnc1Cl] | LCMS: m/z = 496.2 (M + H); 1H-NMR (400 MHz, DMSO-d6) δ 13.00 (s, 1H), 9.36 (s, 1H), 8.76 (d, J = 2.0 Hz, 1H), 8.23 (d, J = 2.0 Hz, 1H), 7.26 (s, 1H), 7.00 (s, 1H), 5.95 (q, J = 6.4 Hz, 1H), 4.31 (t, J = 8.0 Hz, 4H), 3.81 (s, 3H), 2.44-2.33 (m, 2H), 1.78 (d, J = 6.8 Hz, 3H). |
| Example 361<br>(R)-2-(azetidin-1-yl)-5-(5-(1-(3,5-dichloropyridazin-4-yl)ethoxy)-1H-indazol-3-yl)nicotinonitrile | 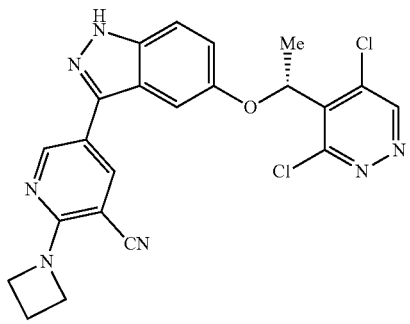 [SMILES: C[C@@H](Oc1ccc2[nH]nc(-c3cnc(N4CCC4)c(C#N)c3)c2c1)c1c(Cl)cnnc1Cl] | LCMS: m/z = 466 (M + H); 1H-NMR (400 MHz, DMSO-d6) δ 13.18 (brs, 1H), 9.33 (s, 1H), 8.78 (d, J = 2.4 Hz, 1H), 8.26 (d, J = 2.8 Hz, 1H), 7.49 (d, J = 8.8 Hz, 1H), 7.28 (d, J = 2.0 Hz, 1H), 7.11 (dd, J = 9.2 Hz, 2.4 Hz, 1H), 6.17 (q, J = 6.8 Hz, 1H), 4.32 (t, J = 7.6 Hz, 4H), 2.44-2.34 (m, 2H), 1.78 (d, J = 6.8 Hz, 3H). |
| Example 362<br>5-[5-[(1R)-1-(3,5-dichloro-4-pyridyl)ethoxy]-6-fluoro-1H-indazol-3-yl]-2-(6,6-dioxo-6λ$^6$-thia-2-azaspiro[3.5]nonan-2-yl)pyridine-3-carbonitrile | 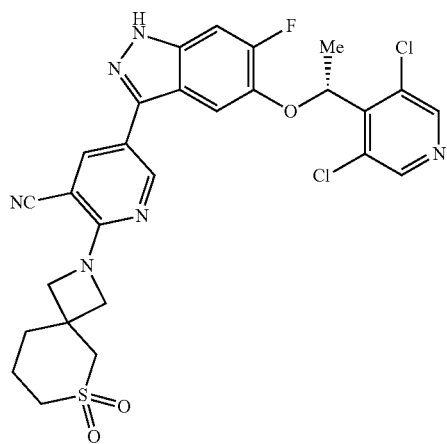 [SMILES: C[C@@H](Oc1cc2c(-c3cnc(N4CC5(CCCS(=O)(=O)C5)C4)c(C#N)c3)n[nH]c2cc1F)c1c(Cl)cncc1Cl] | LCMS: m/z = 601.1 (M + H); 1H NMR (400 MHz, DMSO-d6) δ = 13.23 (s, 1H), 8.75 (d, J = 2.3 Hz, 1H), 8.60 (s, 2H), 8.14 (d, J = 2.3 Hz, 1H), 7.47 (d, J = 10.9 Hz, 1H), 7.24 (d, J = 7.9 Hz, 1H), 6.18 (q, J = 6.6 Hz, 1H), 4.29 (d, J = 9.0 Hz, 2H), 4.07 (d, J = 8.9 Hz, 2H), 3.51 (s, 2H), 3.11 - 3.00 (m, 2H), 1.99 (br s, 4H), 1.81 (d, J = 6.6 Hz, 3H) |

| | | |
|---|---|---|
| Example 363<br>5-(5-((R)-1-(3,5-dichloropyridin-4-yl)ethoxy)-1H-indazol-3-yl)-2-(2-((dimethylamino)methyl)azetidin-1-yl)nicotinonitrile | 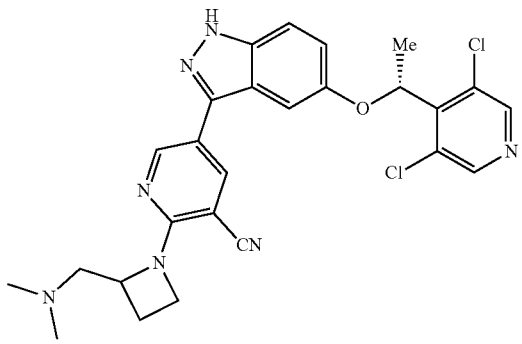 [SMILES: C[C@@H](Oc1ccc2[nH]nc(-c3cnc(N4CCC4CN(C)C)c(C#N)c3)c2c1)c1c(Cl)cncc1Cl] | LCMS: m/z = 522.2 (M + H); 1H-NMR (400 MHz, DMSO-d6) δ 12.99 (s, 1H), 8.59 (s, 2H), 8.07 (s, 1H), 7.89 (dd, J = 4.8 Hz, 2.0 Hz, 1H), 7.43 (d, J = 8.8 Hz, 1H), 7.08-7.04 (m, 2H), 6.11 (q, J = 6.8 Hz, 1H), 4.34-4.26 (m, 1H), 4.17-4.11 (m, 1H), 3.91-3.82 (m, 1H), 2.67-2.55 (m, 1H), 2.41-2.35 (m, 1H), 2.33-2.26 (m, 1H), 2.16 (s, 6H), 1.76 (d, J = 6.8 Hz, 3H), 1.72-1.62 (m, 1H). |
| Example 364<br>(R)-5-(6-chloro-5-(1-(3,5-dichloropyridin-4-yl)ethoxy)-1H-indazol-3-yl)-2-(3,3-dimethylazetidin-1-yl)nicotinonitrile | 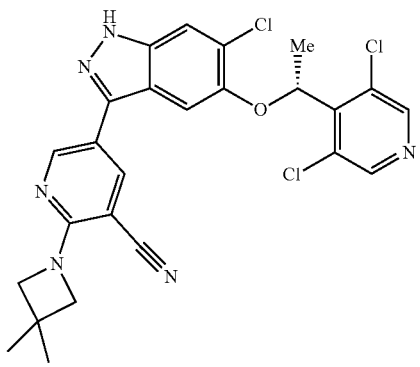 [SMILES: C[C@@H](Oc1cc2c(-c3cnc(N4CC(C)(C)C4)c(C#N)c3)n[nH]c2cc1Cl)c1c(Cl)cncc1Cl] | LCMS: m/z = 527.2 (M + H); 1H NMR (400 MHz, DMSO-d6) δ 13.25 (brs, 1H), 8.70 (d, J = 1.6 Hz, 1H), 8.60 (s, 2H), 8.07 (d, J = 2.0 Hz, 1H), 7.72 (s, 1H), 7.10 (s, 1H), 6.16 (q, J = 6.8 Hz, 1H), 4.02 (s, 4H), 1.80 (d, J = 6.8 Hz, 3H), 1.33 (s, 6H). |
| Example 365<br>5-(6-chloro-5-((R)-1-(3,5-dichloropyridin-4-yl)ethoxy)-1H-indazol-3-yl)-2-((S)-2-methylazetidin-1-yl)nicotinonitrile | 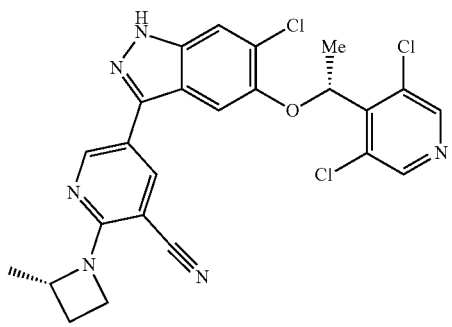 [SMILES: C[C@@H](Oc1cc2c(-c3cnc(N4CC[C@@H]4C)c(C#N)c3)n[nH]c2cc1Cl)c1c(Cl)cncc1Cl] | LCMS: m/z = 513.2 (M + H); 1H NMR (400 MHz, DMSO-d6) δ 13.26 (s, 1H), 8.69 (d, J = 2.4 Hz, 1H), 8.60 (s, 2H), 8.09 (d, J = 2.0 Hz, 1H), 7.73 (s, 1H), 7.11 (s, 1H), 6.17 (q, J = 6.0 Hz, 1H), 4.72-4.67 (m, 1H), 4.44-4.39 (m, 1H), 4.22-4.16 (m, 1H), 2.58-2.53 (m, 1H), 2.07-2.00 (m, 1H), 1.81 (d, J = 6.8 Hz, 3H), 1.51 (d, J = 6.0 Hz, 3H). |
| Example 366<br>(R)-1-(2-(azetidin-1-yl)-5-(6-chloro-5-(1-(3,5-dichloropyridin-4-yl)ethoxy)-1H-indazol-3-yl)pyridin-3-yl)-N,N-dimethylmethanamine | 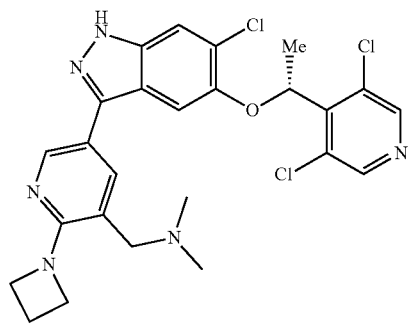 [SMILES: C[C@@H](Oc1cc2c(-c3cnc(N4CCC4)c(CN(C)C)c3)n[nH]c2cc1Cl)c1c(Cl)cncc1Cl] | LCMS: m/z = 531.2 (M + H); 1H-NMR (400 MHz, DMSO- d6) δ 13.11 (s, 1H), 8.62 (s, 2H), 8.39 (s, 1H), 7.71-7.66 (m, 2H), 7.15 (s, 1H), 6.11 (q, J = 6.4 Hz, 1H), 4.19 (t, J = 7.2 Hz, 4H), 3.33-3.27 (m, 2H), 2.31-2.24 (m, 2H), 2.15 (s, 6H), 1.81 (d, J = 6.8 Hz, 3H) |

| | | |
|---|---|---|
| Example 367<br>(R)-3-(6-(azetidin-1-yl)-5-(methylsulfonyl)pyridin-3-yl)-5-(1-(3,5-dichloropyridin-4-yl)ethoxy)-6-methoxy-1H-indazole | 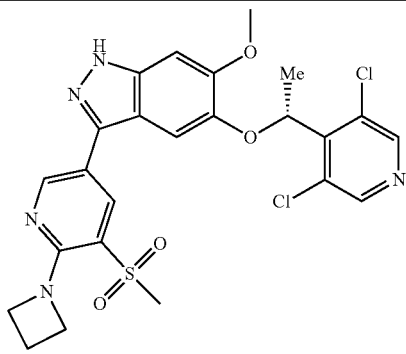 | LCMS: m/z = 548.2 (M + H); 1H NMR (400 MHz, DMSO-d6) δ 8.73 (d, J = 2.4 Hz, 1H), 8.60 (s, 2H), 8.36 (d, J = 2.0 Hz, 1H), 7.16 (s, 1H) 7.02 (s, 1H), 5.98 (q, J = 6.8 Hz, 1H), 4.34 (t, J = 7.6 Hz, 4H), 3.86 (s, 3H), 3.34 (s, 3H), 2.34-2.30 (m, 2H), 1.75 (d, J = 6.8 Hz, 3H). |
| Example 368<br>(R)-1-(5-(5-(1-(3,5-dichloropyridin-4-yl)ethoxy)-1H-indazol-3-yl)-2-(6-(methylsulfonyl)-2,6-diazaspiro[3.3]heptan-2-yl)pyridin-3-yl)-N-methylmethanamine | 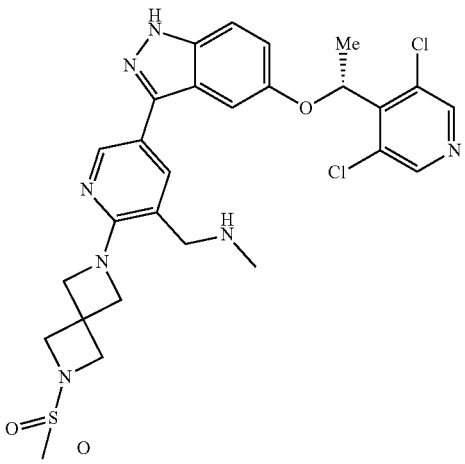 | LCMS: m/z = 602.3 (M + H); 1H NMR (400 MHz, DMSO-d6) δ 13.03 (s, 1H), 8.57 (s, 2H), 8.45 (s, 1H), 7.93 (s, 1H), 7.46 (d, J = 8.8 Hz, 1H), 7.23 (s, 1H), 7.09 (d, J = 8.8 Hz, 1H), 6.13 (q, J = 6.4 Hz, 1H), 4.31 (s, 4H), 4.10 (s, 4H), 3.65 (s, 2H), 3.03 (s, 3H), 2.37 (s, 3H), 1.76 (d, J = 6.8 Hz, 3H). |
| Example 369<br>(R)-1-(5-(5-(1-(3,5-dichloropyridin-4-yl)ethoxy)-6-methoxy-1H-indazol-3-yl)-2-(6-(methylsulfonyl)-2,6-diazaspiro[3.3]heptan-2-yl)pyridin-3-yl)-N-methylmethanamine | 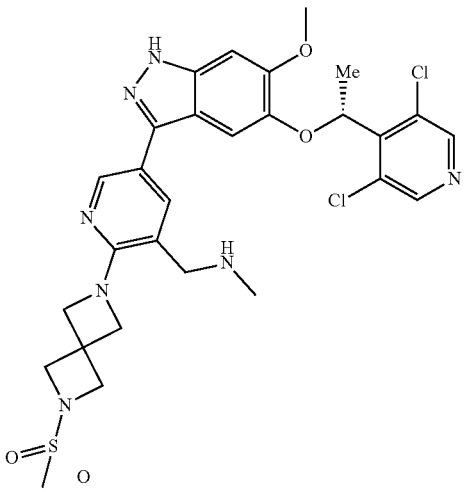 | LCMS: m/z = 632.2 (M + H); 1H NMR (400 MHz, DMSO-d6) δ 12.84 (s, 1H), 8.59 (s, 2H), 8.38 (s, 1H), 7.87 (s, 1H), 7.12 (s, 1H), 7.00 (s, 1H), 5.97 (q, J = 6.4 Hz, 1H), 4.29 (s, 4H), 4.10 (s, 4H), 3.86 (s, 3H), 3.61 (s, 2H), 3.02 (d, J = 1.2 Hz, 3H), 2.36 (s, 3H), 1.75 (d, J = 6.8 Hz, 3H). |
| Example 370<br>(R)-3-(6-(azetidin-1-yl)-5-(methylsulfonyl)pyridin-3-yl)-6-chloro-5-(1-(3,5-dichloropyridin-4-yl)ethoxy)-1H-indazole | 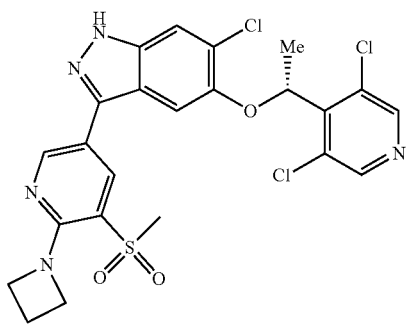 [SMILES: C[C@@H](Oc1cc2c(-c3cnc(N4CCC4)c(S(C)(=O)=O)c3)n[nH]c2cc1Cl)c1c(Cl)cncc1Cl] | LCMS: m/z = 552.1 (M + H); 1H NMR (400 MHz, DMSO-d6) δ 13.30 (s, 1H), 8.74 (d, J = 2.4 Hz, 1H), 8.60 (s, 2H), 8.35 (d, J = 2.4 Hz, 1H), 7.75 (s, 1H), 7.21 (s, 1H), 6.14 (q, J = 6.8 Hz, 1H), 4.36 (t, J = 7.6 Hz, 4H), 3.37 (s, 3H), 2.37-2.29 (m, 2H), 1.81 (d, J = 6.4 Hz, 3H). |

| Example | Structure | Data |
|---|---|---|
| Example 371<br>(R)-1-(5-(6-chloro-5-(1-(3,5-dichloropyridin-4-yl)ethoxy)-1H-indazol-3-yl)-2-(3,3-dimethylazetidin-1-yl)pyridin-3-yl)-N,N-dimethylmethanamine | 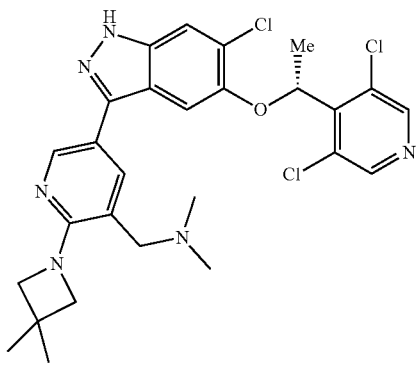 [SMILES: C[C@@H](Oc1cc2c(-c3cnc(N4CC(C)(C)C4)c(CN(C)C)c3)n[nH]c2cc1Cl)c1c(Cl)cncc1Cl] | LCMS: m/z = 559.3 (M + H); 1H-NMR (400 MHz, DMSO-d6) δ 13.11 (s, 1H), 8.62 (s, 2H), 8.39 (s, 1H), 7.71 (s, 2H), 7.16 (s, 1H), 6.11 (q, J = 6.8 Hz, 1H), 3.90 (s, 4H), 3.41-3.37 (s, 2H), 2.18 (s, 6H), 1.81 (d, J = 6.8 Hz, 3H), 1.30 (s, 6H) |
| Example 372<br>5-((R)-1-(3,5-dichloropyridin-4-yl)ethoxy)-6-methoxy-3-(6-((R)-2-methylazetidin-1-yl)-5-(methylsulfonyl)pyridin-3-yl)-1H-indazole | 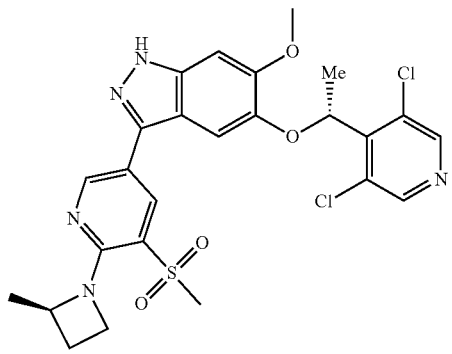 [SMILES: COc1cc2[nH]nc(-c3cnc(N4CC[C@H]4C)c(S(C)(=O)=O)c3)c2cc1O[C@H](C)c1c(Cl)cncc1Cl] | LCMS: m/z = 562.2 (M + H); 1H NMR (400 MHz, DMSO-d6) δ 13.01 (s, 1H), 8.75 (d, J = 0.8 Hz, 1H), 8.56 (s, 2H), 8.40 (d, J = 0.8 Hz, 1H), 7.15 (s, 1H), 7.02 (s, 1H), 5.98 (q, J = 6.4 Hz, 1H), 4.85-4.80 (m, 1H), 4.51-4.50 (m, 1H), 4.18-4.12 (m, 1H), 3.87 (s, 3H), 3.34 (s, 3H), 2.46-2.40 (m, 1H), 2.02-1.98 (m, 1H), 1.76 (d, J = 6.8 Hz, 3H), 1.45 (d, J = 6.0 Hz, 3H). |
| Example 373<br>5-[5-[(1R)-1-(3,5-dichloro-4-pyridyl)ethoxy]-6-fluoro-1H-indazol-3-yl]-2-(2-methylsulfonyl-2,6-diazaspiro[3.3]heptan-6-yl)pyridine-3-carbonitrile | 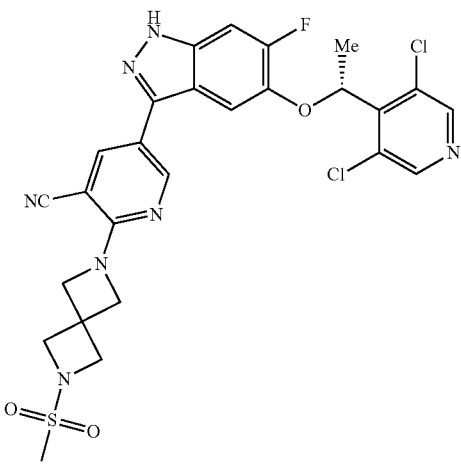 [SMILES: C[C@@H](Oc1cc2c(-c3cnc(N4CC5(C4)CN(S(C)(=O)=O)C5)c(C#N)c3)n[nH]c2cc1F)c1c(Cl)cncc1Cl] | LCMS: m/z = 602.1 (M + H); 1H NMR (400 MHz, DMSO-d6) δ = 13.24 (s, 1H), 8.75 (d, J = 2.3 Hz, 1H), 8.60 (s, 2H), 8.15 (d, J = 2.3 Hz, 1H), 7.47 (d, J = 10.8 Hz, 1H), 7.24 (d, J = 7.8 Hz, 1H), 6.18 (q, J = 6.7 Hz, 1H), 4.50 (s, 4H), 4.14 (s, 4H), 3.03 (s, 3H), 1.80 (d, J = 6.6 Hz, 3H) |
| Example 374<br>5-(6-chloro-5-((R)-1-(3,5-dichloropyridin-4-yl)ethoxy)-1H-indazol-3-yl)-2-((R)-2-methylazetidin-1-yl)nicotinonitrile | 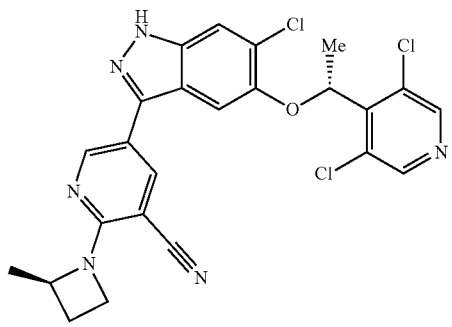 [SMILES: C[C@@H]1CCN1c1ncc(-c2n[nH]c3cc(Cl)c(O[C@H](C)c4c(Cl)cncc4Cl)cc23)cc1C#N] | LCMS: m/z = 513 (M + H); 1H NMR (400 MHz, DMSO-d6) δ 13.26 (s, 1H), 8.72 (d, J = 2.0 Hz, 1H), 8.59 (s, 2H), 8.08 (s, 1H), 7.73 (s, 1H), 7.10 (s, 1H), 6.16 (q, J = 6.0 Hz, 1H), 4.72-4.67 (m, 1H), 4.44-4.38 (m, 1H), 4.22-4.16 (m, 1H), 2.58-2.53 (m, 1H), 2.07-1.99 (m, 1H), 1.81 (d, J = 6.8 Hz, 3H), 1.51 (d, J = 6.0 Hz, 3H) |

| | | |
|---|---|---|
| Example 375<br>5-((R)-1-(3,5-dichloropyridin-4-yl)ethoxy)-6-methoxy-3-(6-((S)-2-methylazetidin-1-yl)-5-(methylsulfonyl)pyridin-3-yl)-1H-indazole | 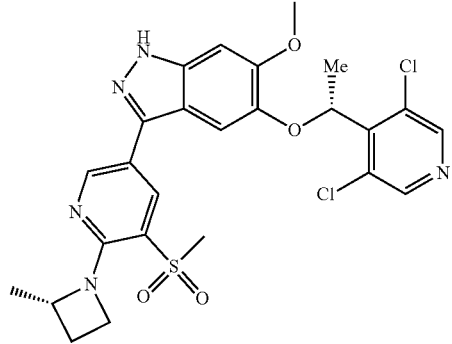 [SMILES: COc1cc2[nH]nc(-c3cnc(N4CC[C@@H]4C)c(S(C)(=O)=O)c3)c2cc1O[C@H](C)c1c(Cl)cncc1Cl] | LCMS: m/z = 562.2 (M + H); 1H NMR (400 MHz, DMSO-d6) δ 13.02 (s, 1H), 8.72 (d, J = 2.0 Hz, 1H), 8.59 (s, 2H), 8.36 (d, J = 2.0 Hz, 1H), 7.12 (s, 1H), 7.02 (s, 1H), 5.97 (q, J = 6.4 Hz, 1H), 4.87-4.79 (m, 1H), 4.51-4.56 (m, 1H), 4.18-4.11 (m, 1H), 3.87 (s, 3H), 3.35 (s, 3H), 2.45-2.38 (m, 1H), 2.04-1.96 (m, 1H), 1.76 (d, J = 6.4 Hz, 3H), 1.45 (d, J = 6.0 Hz, 3H). |
| Example 376<br>(R)-5-(1-(3,5-dichloropyridin-4-yl)ethoxy)-3-(6-(3,3-dimethylazetidin-1-yl)-5-(methylsulfonyl)pyridin-3-yl)-6-methoxy-1H-indazole | 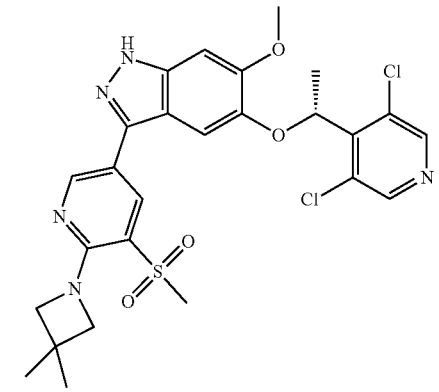 [SMILES: COc1cc2[nH]nc(-c3cnc(N4CC(C)(C)C4)c(S(C)(=O)=O)c3)c2cc1O[C@H](C)c1c(Cl)cncc1Cl] | LCMS: m/z = 576.2 (M + H); 1H NMR (400 MHz, DMSO-d6) δ 13.01 (s, 1H), 8.73 (d, J = 2.0 Hz, 1H), 8.58 (s, 2H), 8.36 (d, J = 2.0 Hz, 1H), 7.15 (s, 1H), 7.02 (s, 1H), 5.98 (q, J = 7.2 Hz, 1H), 4.03 (s, 4H), 3.87 (s, 3H), 3.34 (s, 3H), 1.75 (d, J = 6.4 Hz, 3H), 1.32 (s, 6H). |
| Example 377<br>2-(azetidin-1-yl)-5-[6-chloro-5-[(1R)-1-(3,5-dichloro-4-pyridyl)ethoxy]-1H-indazol-3-yl]pyridine-3-carbonitrile | 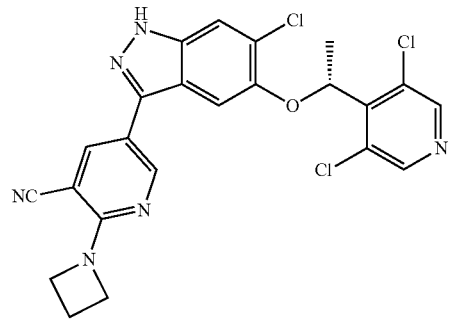 [SMILES: C[C@@H](Oc1cc2c(-c3cnc(N4CCC4)c(C#N)c3)n[nH]c2cc1Cl)c1c(Cl)cncc1Cl] | LCMS: m/z = 499.1 (M + H); 1H NMR (400 MHz, DMSO-d6) δ = 13.24 (s, 1H), 8.72 (d, J = 2.3 Hz, 1H), 8.60 (s, 2H), 8.08 (d, J = 2.3 Hz, 1H), 7.72 (s, 1H), 7.11 (s, 1H), 6.17 (q, J = 6.7 Hz, 1H), 4.33 (t, J = 7.6 Hz, 4H), 2.40 (quin, J = 7.6 Hz, 2H), 1.81 (d, J = 6.7 Hz, 3H. |
| Example 378<br>5-[5-[(1R)-1-(3,5-dichloro-4-pyridyl)ethoxy]-6-fluoro-1H-indazol-3-yl]-2-(6,6-dioxo-6λ$^6$-thia-2-azaspiro[3.4]octan-2-yl)pyridine-3-carbonitrile | 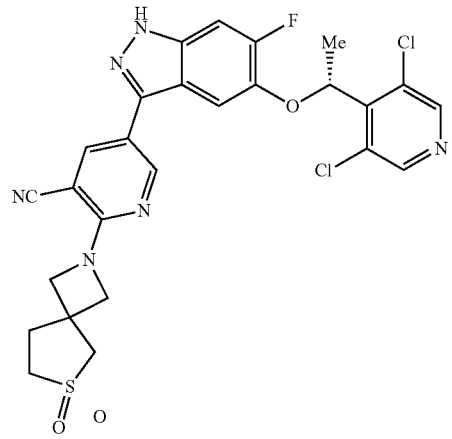 | LCMS: m/z = 587 (M + H); 1H NMR (400 MHz, DMSO-d6) δ = 13.24 (s, 1H), 8.76 (d, J = 2.2 Hz, 1H), 8.60 (s, 2H), 8.17 (d, J = 2.3 Hz, 1H), 7.47 (d, J = 10.9 Hz, 1H), 7.24 (d, J = 7.8 Hz, 1H), 6.18 (q, J = 6.5 Hz, 1H), 4.38 (d, J = 9.0 Hz, 2H), 4.29 (d, J = 8.9 Hz, 2H), 3.54 (s, 2H), 3.30 - 3.25 (m, 3H), 2.59 - 2.52 (m, 2H), 1.81 (d, J = 6.6 Hz, 3H) |

-continued

| | | |
|---|---|---|
| Example 379<br>5-[5-[(1R)-1-(3,5-dichloro-2-methyl-4-pyridyl)ethoxy]-6-fluoro-1H-indazol-3-yl]-2-(2-methylsulfonyl-2,6-diazaspiro[3.3]heptan-6-yl)pyridine-3-carbonitrile | 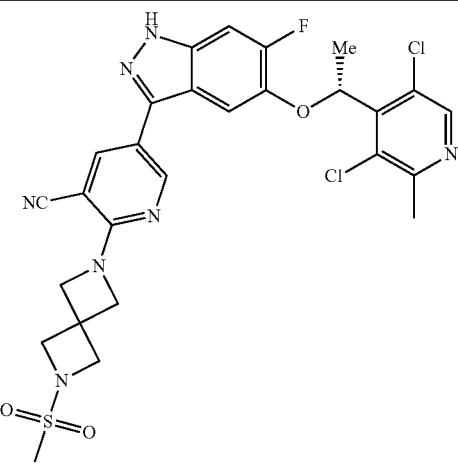 | LCMS: m/z = 616.1 (M + H); 1H NMR (400 MHz, DMSO-d6) δ = 13.24 (s, 1H), 8.66 (d, J = 2.3 Hz, 1H), 8.45 (s, 1H), 8.20 - 8.16 (m, 1H), 7.47 (d, J = 10.9 Hz, 1H), 7.16 (d, J = 7.8 Hz, 1H), 6.17 (q, J = 6.6 Hz, 1H), 4.49 (s, 4H), 4.16 - 4.09 (m, 4H), 3.03 (s, 3H), 2.58 (s, 3H), 1.80 (d, J = 6.6 Hz, 3H) |
| Example 380<br>5-[5-[(1R)-1-(3,5-dichloro-4-pyridyl)ethoxy]-6-fluoro-1H-indazol-3-yl]-2-(8-methylsulfonyl-2,8-diazaspiro[3.5]nonan-2-yl)pyridine-3-carbonitrile | 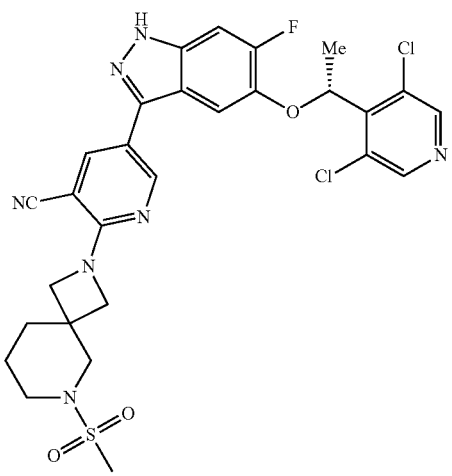 [SMILES: C[C@@H](Oc1cc2c(-c3cnc(N4CC5(CCCN(S(C)(=O)=O)C5)C4)c(C#N)c3)n[nH]c2cc1F)c1c(Cl)cncc1Cl] | LCMS: m/z = 630.2 (M + H); 1H NMR (400 MHz, DMSO-d6) δ = 13.23 (s, 1H), 8.75 (d, J = 2.3 Hz, 1H), 8.60 (s, 2H), 8.14 (d, J = 2.3 Hz, 1H), 7.47 (d, J = 10.9 Hz, 1H), 7.25 (d, J = 7.8 Hz, 1H), 6.18 (q, J = 6.7 Hz, 1H), 4.10 - 3.99 (m, 4H), 3.09 (br t, J = 5.4 Hz, 2H), 2.91 (s, 3H), 1.80 (d, J = 6.6 Hz, 5H), 1.63 (br s, 2H) |
| Example 381<br>(R)-6-chloro-5-(1-(3,5-dichloropyridin-4-yl)ethoxy)-3-(6-(3,3-dimethylazetidin-1-yl)-5-(methylsulfonyl)pyridin-3-yl)-1H-indazole | 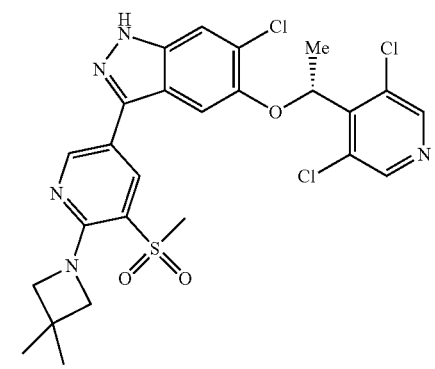 [SMILES: C[C@@H](Oc1cc2c(-c3cnc(N4CC(C)(C)C4)c(S(C)(=O)=O)c3)n[nH]c2cc1Cl)c1c(Cl)cncc1Cl] | LCMS: m/z = 580.2 (M + H); 1H-NMR (400 MHz, DMSO-d6) δ 13.30 (brs, 1H), 8.73 (d, J = 2.4 Hz, 1H), 8.60 (s, 2H), 8.36 (d, J = 2.4 Hz, 1H), 7.75 (s, 1H), 7.20 (s, 1H), 6.13 (q, J = 6.4 Hz, 1H), 4.04 (s, 4H), 3.34 (s, 3H), 1.81 (d, J = 6.4 Hz, 3H), 1.32 (s, 6H). |
| Example 382<br>(R)-1-(2-(azetidin-1-yl)-5-(6-chloro-5-(1-(3,5-dichloropyridin-4-yl)ethoxy)-1H-indazol-3-yl)pyridin-3-yl)-N-methylmethanamine | 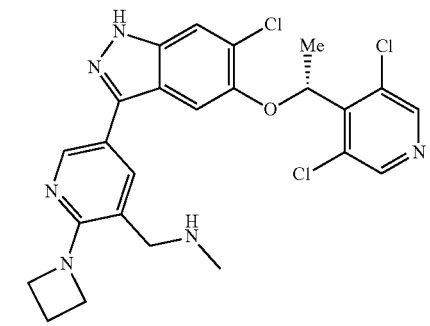 [SMILES: CNCc1cc(-c2n[nH]c3cc(Cl)c(O[C@H](C)c4c(Cl)cncc4Cl)cc23)cnc1N1CCC1] | LCMS: m/z = 517.2 (M + H); 1H NMR (400 MHz, DMSO-d6) δ 13.12 (brs, 1H), 8.61 (s, 2H), 8.36 (d, J = 2.0 Hz, 1H), 7.80 (d, J = 2.0 Hz, 1H), 7.71 (s, 1H), 7.17 (s, 1H), 6.12 (q, J = 6.8 Hz, 1H), 4.15 (t, J = 7.2 Hz, 4H), 3.58 (s, 2H), 2.31 (s, 3H), 2.30-2.24 (m, 2H), 1.80 (d, J = 6.4 Hz, 3H). |

-continued

| | | |
|---|---|---|
| Example 383<br>(R)-3-(6-(azetidin-1-yl)-5-(trifluoromethyl)pyridin-3-yl)-6-chloro-5-(1-(3,5-dichloropyridin-4-yl)ethoxy)-1H-indazole | 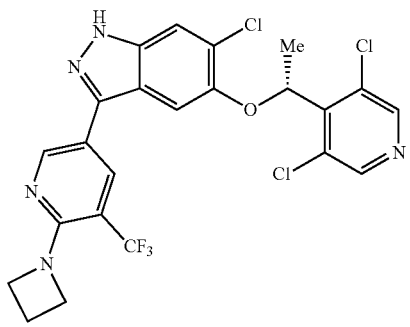 [SMILES: C[C@@H](Oc1cc2c(-c3cnc(N4CCC4)c(C(F)(F)F)c3)n[nH]c2cc1Cl)c1c(Cl)cncc1Cl] | LCMS: m/z = 542.2 (M + H); 1H NMR (400 MHz, DMSO-d6) δ13.25 (s, 1H), 8.71 (d, J = 1.6 Hz, 1H), 8.58 (s, 2H), 7.87 (d, J = 2.4 Hz, 1H), 7.74 (s, 1H), 7.12 (s, 1H), 6.14 (q, J = 6.8 Hz, 1H), 4.22 (t, J = 7.6 Hz, 4H), 2.39-2.31 (m, 2H), 1.80 (d, J = 6.4 Hz, 3H). |
| Example 384<br>6-chloro-5-((R)-1-(3,5-dichloropyridin-4-yl)ethoxy)-3-(6-((S)-2-methylazetidin-1-yl)-5-(trifluoromethyl)pyridin-3-yl)-1H-indazole | 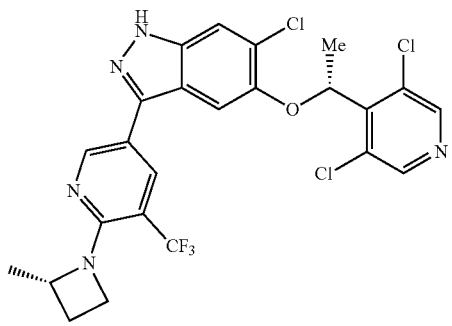 [SMILES: C[C@@H](Oc1cc2c(-c3cnc(N4CC[C@@H]4C)c(C(F)(F)F)c3)n[nH]c2cc1Cl)c1c(Cl)cncc1Cl] | LCMS: m/z = 556.8 (M + H); 1H NMR (400 MHz, DMSO-d6) δ13.22 (brs, 1H), 8.66 (d, J = 2.0 Hz, 1H), 8.59 (s, 2H), 8.02 (d, J = 2.0 Hz, 1H), 7.74 (s, 1H), 7.09 (s, 1H), 6.13 (q, J = 7.2 Hz, 1H), 4.78-4.69 (m, 1H), 4.25-4.20 (m, 1H), 4.07-3.98 (m, 1H), 2.47-2.41 (m, 1H), 2.05-2.00 (m, 1H), 1.79 (d, J = 6.8 Hz, 3H), 1.48 (d, J = 6.0 Hz, 3H). |
| Example 385<br>(R)-1-(5-(6-chloro-5-(1-(3,5-dichloropyridin-4-yl)ethoxy)-1H-indazol-3-yl)-3-(trifluoromethyl)pyridin-2-yl)-N,N,3-trimethylazetidin-3-amine | 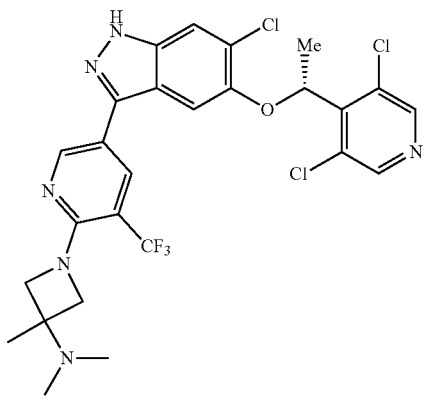 [SMILES: C[C@@H](Oc1cc2c(-c3cnc(N4CC(C)(N(C)C)C4)c(C(F)(F)F)c3)n[nH]c2cc1Cl)c1c(Cl)cncc1Cl] | LCMS: m/z = 599.2 (M + H); 1H NMR (400 MHz, DMSO-d6) δ 13.28 (s, 1H), 8.72 (d, J = 2.0 Hz, 1H), 8.60 (s, 2H), 8.08 (d, J = 2.0 Hz, 1H), 7.75 (s, 1H), 7.14 (s, 1H), 6.15 (q, J = 6.4 Hz, 1H), 4.00 (d, J = 8.4 Hz, 2H), 3.86 (d, J = 8.4 Hz, 2H), 2.15 (s, 6H), 1.81 (d, J = 6.4 Hz, 3H), 1.30 (s, 3H). |
| Example 386<br>6-chloro-5-((R)-1-(3,5-dichloropyridin-4-yl)ethoxy)-3-(6-((R)-2-methylazetidin-1-yl)-5-(trifluoromethyl)pyridin-3-yl)-1H-indazole | 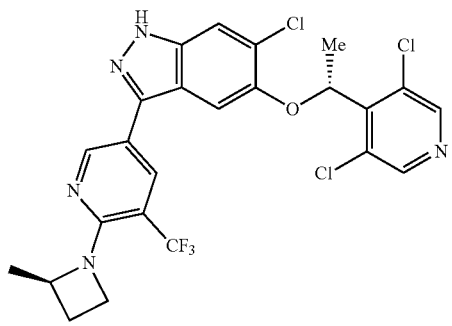 [SMILES: C[C@@H]1CCN1c1ncc(-c2n[nH]c3cc(Cl)c(O[C@H](C)c4c(Cl)cncc4Cl)cc23)cc1C(F)(F)F] | LCMS: m/z = 556.1 (M + H); 1H NMR (400 MHz,DMSO-d6) δ 13.26 (brs, 1H), 8.72 (d, J = 2.0 Hz, 1H), 8.56 (s, 2H), 8.10 (d, J = 2.0 Hz, 1H), 7.74 (s, 1H), 7.12 (s, 1H), 6.15 (q, J = 6.8 Hz, 1H), 4.78-4.70 (m, 1H), 4.25-4.20 (m, 1H), 4.07-4.01 (m, 1H), 2.47-2.41 (m, 1H), 2.06-1.97 (m, 1H), 1.80 (d, J = 6.8 Hz, 3H), 1.48 (d, J = 6.4 Hz, 3H). |

| | | | | |
|---|---|---|---|---|
| Example 387 (R)-1-(5-(6-chloro-5-(1-(3,5-dichloropyridin-4-yl)ethoxy)-1H-indazol-3-yl)-3-(methylsulfonyl)pyridin-2-yl)-N,N,3-trimethylazetidin-3-amine | 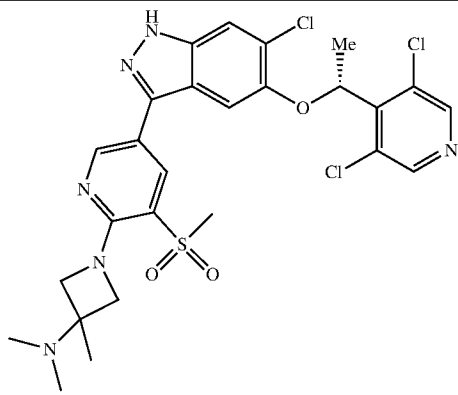 | | | LCMS: m/z = 609.2 (M + H); 1H NMR (400 MHz, DMSO-d6) δ 13.32 (brs, 1H), 8.74 (d, J = 2.4 Hz, 1H), 8.61 (s, 2H), 8.37 (d, J = 2.0 Hz, 1H), 7.76 (s, 1H), 7.21 (s, 1H), 6.14 (q, J = 6.8 Hz, 1H), 4.13 (d, J = 8.8 Hz, 2H), 3.99 (dd, J = 8.8 Hz, 3.2 Hz, 2H), 3.36 (s, 3H), 2.14 (s, 6H), 1.81 (d, J = 6.4 Hz, 3H), 1.31 (s, 3H). |

Kinase Assays

Kinase-tagged T7 phage strains were prepared in an *E. coli* host derived from the BL21 strain. *E. coli* were grown to log-phase and infected with T7 phage and incubated with shaking at 32° C. until lysis. The lysates were centrifuged and filtered to remove cell debris. Streptavidin-coated magnetic beads were treated with biotinylated small molecule ligands for 30 minutes at room temperature to generate affinity resins for kinase assays. The liganded beads were blocked with excess biotin and washed with blocking buffer SeaBlock (Pierce), 100 BSA, 0.0500 Tween 20, 1 mM DTT to remove unbound ligand and to reduce non-specific binding. Binding reactions were assembled by combining kinases, liganded affinity beads, and test compounds in 1× binding buffer (2000 SeaBlock, 0.17×PBS, 0.0500 Tween 20, 6 mM DTT).

Test compounds were prepared as 111λ stocks in 10000 DMSO. Kds were determined using an 11-point 3-fold compound dilution series with three DMSO control points. All compounds for Kd measurements are distributed by acoustic transfer (non-contact dispensing) in 100% DMSO. The compounds were then diluted directly into the assays such that the final concentration of DMSO was 0.9%. All reactions performed in polypropylene 384-well plate. Each was a final volume of 0.02 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 M non-biotinylated affinity ligand) and incubated at room temperature with shaking for 30 minutes. The kinase concentration in the eluates was measured by qPCR.

Binding Constants (Kds)

Binding constants were calculated with a standard dose-response curve using the Hill equation:

$$\text{Response} = \text{Background} + \frac{\text{Signal} - \text{Background}}{1 + \left(\frac{Kd^{Hill\,Slope}}{\text{Dose}^{Hill\,Slope}}\right)}$$

The Hill Slope was set to −1. Curves were fitted using a non-linear least square fit with the Levenberg-Marquardt algorithm.

TABLE 4

| Example | FGFR1 ($K_d$ nM) | FGFR2 ($K_d$ nM) | FGFR3 ($K_d$ nM) | FGFR3 (V555M) ($K_d$ nM) | FGFR4 ($K_d$ nM) |
|---|---|---|---|---|---|
| 1. | A | A | A | A | A |
| 2. | A | A | A | A | A |
| 3. | A | A | A | A | A |
| 4. | A | A | A | A | A |
| 5. | A | A | A | A | A |
| 6. | A | B | A | A | A |
| 7. | A | B | A | A | A |
| 8. | B | B | A | A | A |
| 9. | A | A | A | A | A |
| 10. | A | A | A | A | A |
| 11. | A | A | A | A | A |
| 12. | A | A | A | A | A |
| 13. | A | A | A | A | A |
| 14. | A | B | A | A | A |
| 15. | A | A | A | A | A |
| 16. | A | A | A | A | A |
| 17. | B | D | A | A | A |
| 18. | B | B | A | A | A |
| 19. | A | C | A | A | A |
| 20. | B | B | A | A | A |
| 21. | A | A | A | A | A |
| 22. | B | B | A | A | A |
| 23. | D | D | C | B | D |
| 24. | A | A | A | A | A |
| 25. | B | B | A | A | B |
| 26. | B | B | A | A | A |
| 27. | B | A | A | A | A |
| 28. | B | B | A | A | A |
| 29. | A | A | A | A | A |
| 30. | A | A | A | A | A |
| 31. | A | A | A | A | A |
| 32. | A | A | A | A | A |
| 33. | A | A | A | A | A |
| 34. | A | A | A | A | A |
| 35. | B | B | A | A | A |
| 36. | A | A | A | A | A |
| 37. | B | B | A | A | A |
| 38. | B | B | A | A | A |
| 39. | B | B | A | A | A |
| 40. | A | A | A | A | A |
| 41. | A | A | A | A | A |
| 42. | A | B | A | A | A |
| 43. | A | A | A | A | A |
| 44. | A | A | A | A | A |
| 45. | A | A | A | A | A |
| 46. | A | A | A | A | A |
| 47. | A | A | A | A | A |
| 48. | B | B | A | A | A |
| 49. | B | B | A | A | A |
| 50. | B | B | A | A | A |
| 51. | B | B | A | A | A |
| 52. | A | B | A | A | A |

TABLE 4-continued

| Example | FGFR1 (K$_d$ nM) | FGFR2 (K$_d$ nM) | FGFR3 (K$_d$ nM) | FGFR3 (V555M) (K$_d$ nM) | FGFR4 (K$_d$ nM) |
|---|---|---|---|---|---|
| 53. | B | B | A | A | A |
| 54. | A | A | A | A | A |
| 55. | B | B | A | A | A |
| 56. | A | B | A | A | A |
| 57. | B | B | A | A | A |
| 58. | B | B | A | A | A |
| 59. | B | C | B | B | B |
| 60. | A | A | A | A | A |
| 61. | A | B | A | A | A |
| 62. | B | B | A | A | A |
| 63. | B | B | A | A | A |
| 64. | A | A | A | A | A |
| 65. | A | A | A | A | A |
| 66. | A | A | A | A | A |
| 67. | A | A | A | A | A |
| 68. | A | A | A | A | A |
| 69. | A | A | A | A | A |
| 70. | A | A | A | A | A |
| 71. | A | A | A | A | A |
| 72. | A | A | A | A | A |
| 73. | A | B | A | A | A |
| 74. | A | A | A | A | A |
| 75. | A | A | A | A | A |
| 76. | B | B | A | A | A |
| 77. | A | B | A | A | A |
| 78. | A | A | A | A | A |
| 79. | A | A | A | A | A |
| 80. | A | A | A | A | C |
| 81. | A | A | A | A | A |
| 82. | A | A | A | A | B |
| 83. | A | A | A | A | B |
| 84. | A | A | A | A | B |
| 85. | A | A | A | A | A |
| 86. | A | A | A | A | A |
| 87. | A | A | A | A | B |
| 88. | A | A | A | A | B |
| 89. | A | A | A | A | B |
| 90. | A | A | A | A | B |
| 91. | A | A | A | A | B |
| 92. | A | A | A | A | B |
| 93. | A | A | A | A | B |
| 94. | B | A | A | A | B |
| 95. | A | A | A | A | B |
| 96. | A | A | A | A | A |
| 97. | A | A | A | A | A |
| 98. | A | A | A | A | A |
| 99. | A | A | A | A | A |
| 100. | A | A | A | A | A |
| 101. | B | B | A | A | A |
| 102. | B | B | A | A | A |
| 103. | A | B | A | A | A |
| 104. | B | A | A | A | B |
| 105. | D | D | C | C | B |
| 106. | A | A | A | A | A |
| 107. | B | B | A | A | A |
| 108. | B | A | A | A | B |
| 109. | B | A | A | A | A |
| 110. | A | A | A | A | A |
| 111. | B | B | A | A | A |
| 112. | A | B | A | A | A |
| 113. | A | A | A | A | A |
| 114. | A | A | A | A | B |
| 115. | A | A | A | A | A |
| 116. | B | B | A | A | B |
| 117. | A | A | A | A | A |
| 118. | A | B | A | A | A |
| 119. | B | B | A | A | A |
| 120. | B | B | A | A | A |
| 121. | B | B | A | A | A |
| 122. | A | B | A | A | A |
| 123. | A | A | A | A | A |
| 124. | B | B | A | A | A |
| 125. | B | B | A | A | A |
| 126. | C | C | A | A | A |
| 127. | B | B | A | A | A |
| 128. | B | B | A | A | A |
| 129. | B | B | A | A | A |
| 130. | B | B | A | A | A |
| 131. | C | C | A | A | A |
| 132. | A | A | A | A | A |
| 133. | A | A | A | A | A |
| 134. | B | B | A | A | A |
| 135. | D | D | B | A | A |
| 136. | B | A | A | A | A |
| 137. | B | B | A | A | A |
| 138. | B | B | A | A | A |
| 139. | B | A | A | A | A |
| 140. | D | D | B | A | D |
| 141. | B | B | A | A | A |
| 142. | B | A | A | A | A |
| 143. | C | B | A | A | A |
| 144. | A | A | A | A | A |
| 145. | D | B | B | A | C |
| 146. | C | B | A | A | A |
| 147. | D | D | D | D | D |
| 148. | A | A | A | A | A |
| 149. | D | C | B | B | C |
| 150. | A | A | A | A | A |
| 151. | D | C | B | A | C |
| 152. | B | A | A | A | A |
| 153. | D | C | B | A | C |
| 154. | D | D | C | B | C |
| 155. | D | D | D | D | C |
| 156. | C | B | A | A | A |
| 157. | B | B | A | A | A |
| 158. | B | B | A | A | A |
| 159. | A | A | A | A | A |
| 160. | D | C | B | A | C |
| 161. | A | A | A | A | A |
| 162. | B | A | A | A | A |
| 163. | A | A | A | A | A |
| 164. | A | A | A | A | A |
| 165. | B | A | A | A | A |
| 166. | B | A | A | A | D |
| 167. | B | B | B | A | D |
| 168. | C | B | A | A | D |
| 169. | B | B | A | A | B |
| 170. | C | B | A | A | C |
| 171. | C | B | B | A | D |
| 172. | C | B | A | A | B |
| 173. | C | D | B | B | A |
| 174. | A | A | A | A | A |
| 175. | A | A | A | A | A |
| 176. | A | A | A | A | A |
| 177. | A | B | A | A | A |
| 178. | A | A | A | A | A |
| 179. | B | B | A | A | A |
| 180. | B | B | A | A | B |
| 181. | C | D | A | A | A |
| 182. | B | A | A | A | A |
| 183. | A | A | A | A | A |
| 184. | A | A | A | A | A |
| 185. | D | C | B | A | A |
| 186. | C | B | A | A | B |
| 187. | A | A | A | A | A |
| 188. | B | A | A | A | A |
| 189. | B | A | A | A | A |
| 190. | C | C | A | A | B |
| 191. | A | A | A | A | A |
| 192. | C | B | A | A | C |
| 193. | D | D | D | C | D |
| 194. | A | A | A | A | A |
| 195. | C | B | A | A | B |
| 196. | C | C | A | A | B |
| 197. | B | B | A | A | A |
| 198. | D | D | C | B | D |
| 199. | D | D | C | B | D |
| 200. | D | D | D | C | D |
| 201. | B | A | A | A | A |
| 202. | A | A | A | A | A |
| 203. | B | A | A | A | A |
| 204. | B | A | A | A | B |

TABLE 4-continued

| Example | FGFR1 (K$_d$ nM) | FGFR2 (K$_d$ nM) | FGFR3 (K$_d$ nM) | FGFR3 (V555M) (K$_d$ nM) | FGFR4 (K$_d$ nM) |
|---|---|---|---|---|---|
| 205. | A | A | A | A | A |
| 206. | A | A | A | A | A |
| 207. | A | A | A | A | A |
| 208. | B | A | A | A | A |
| 209. | A | A | A | A | A |
| 210. | B | A | A | A | A |
| 211. | A | A | A | A | A |
| 212. | D | C | B | A | C |
| 213. | A | | A | A | A |
| 214. | A | A | A | A | A |
| 215. | | | | | |
| 216. | B | A | A | A | A |
| 217. | C | B | A | A | A |
| 218. | B | B | B | B | A |
| 219. | B | A | A | A | A |
| 220. | B | B | A | A | A |
| 221. | A | A | A | A | A |
| 222. | B | B | A | A | A |
| 223. | D | C | B | B | D |
| 224. | A | B | A | A | A |
| 225. | B | A | A | A | A |
| 226. | B | B | A | A | B |
| 227. | B | A | A | A | A |
| 228. | A | A | A | A | A |
| 229. | D | C | B | B | D |
| 230. | A | A | A | A | A |
| 231. | B | A | A | A | A |
| 232. | B | B | A | A | A |
| 233. | D | C | B | B | D |
| 234. | C | C | A | A | A |
| 235. | C | C | A | A | A |
| 236. | B | A | A | A | A |
| 237. | A | A | A | A | A |
| 238. | B | B | A | A | A |
| 239. | A | A | A | A | A |
| 240. | A | A | A | A | A |
| 241. | A | B | A | A | A |
| 242. | A | A | A | A | A |
| 243. | A | A | A | A | A |
| 244. | B | B | A | A | A |
| 245. | A | A | A | A | A |
| 246. | A | A | A | A | A |
| 247. | B | B | A | A | A |
| 248. | B | B | A | A | A |
| 249. | B | B | A | A | A |
| 250. | A | A | A | A | A |
| 251. | A | A | A | A | A |
| 252. | B | B | A | A | A |
| 253. | A | A | A | A | A |
| 254. | D | C | B | A | D |
| 255. | A | A | A | A | A |
| 256. | A | A | A | A | A |
| 257. | A | A | A | A | A |
| 258. | A | A | A | A | A |
| 259. | A | A | A | A | A |
| 260. | A | A | A | A | A |
| 261. | A | A | A | A | A |
| 262. | A | A | A | A | A |
| 263. | A | A | A | A | A |
| 264. | A | A | A | A | A |
| 265. | A | A | A | A | A |
| 266. | A | A | A | A | A |
| 267. | B | B | A | A | A |
| 268. | B | B | A | A | A |
| 269. | B | B | A | A | A |
| 270. | B | B | A | A | A |
| 271. | B | B | A | A | A |
| 272. | D | D | B | B | B |
| 273. | B | B | A | 1.8 | A |
| 274. | C | C | B | A | B |
| 275. | A | B | A | A | A |
| 276. | | | | | |
| 277. | | | | | |
| 278. | | | | | |
| 279. | | | | | |
| 280. | | | | | |
| 281. | | | | | |
| 282. | | | | | |
| 283. | D | D | D | D | D |
| 284. | D | D | C | B | B |
| 285. | D | D | C | B | A |
| 286. | D | D | D | D | C |
| 287. | D | D | C | C | B |
| 288. | D | D | B | B | A |
| 289. | | | | | |
| 290. | | | | | |
| 291. | D | D | D | D | D |
| 292. | D | D | D | D | C |
| 293. | B | B | A | A | A |
| 294. | D | D | C | B | B |
| 295. | D | D | D | C | B |
| 296. | D | D | D | C | B |
| 297. | B | C | A | A | A |
| 298. | B | B | A | A | A |
| 299. | B | B | A | A | A |
| 300. | C | C | B | B | B |
| 301. | C | C | B | A | A |
| 302. | C | C | B | A | A |
| 303. | B | B | A | A | A |
| 304. | D | D | C | B | A |
| 305. | D | D | D | C | B |
| 306. | C | B | B | A | A |
| 307. | C | B | B | A | A |
| 308. | D | D | C | B | A |
| 309. | D | D | C | B | A |
| 310. | A | A | A | A | A |
| 311. | B | B | B | A | A |
| 312. | A | A | A | A | A |
| 313. | C | B | B | A | A |
| 314. | A | A | A | A | A |
| 315. | A | A | A | A | A |
| 316. | B | B | A | A | A |
| 317. | A | A | A | A | A |
| 318. | C | C | B | A | A |
| 319. | B | B | A | A | A |
| 320. | B | B | B | A | A |
| 321. | B | A | A | A | A |
| 322. | C | B | B | A | A |
| 323. | D | D | D | B | A |
| 324. | B | B | B | A | A |
| 325. | B | A | A | A | A |
| 326. | B | B | A | A | A |
| 327. | A | A | A | A | A |
| 328. | C | C | C | B | A |
| 329. | C | D | B | A | A |
| 330. | C | C | B | A | A |
| 331. | C | C | A | A | A |
| 332. | B | B | A | A | A |
| 333. | C | C | B | A | A |
| 334. | B | B | A | A | A |
| 335. | A | B | A | A | A |
| 336. | B | B | B | A | A |
| 337. | B | C | B | A | A |
| 338. | C | D | B | A | A |
| 339. | A | A | A | A | A |
| 340. | C | C | A | C | A |
| 341. | B | B | A | A | A |
| 342. | B | A | A | A | A |
| 343. | B | B | A | A | A |
| 344. | D | D | C | B | A |
| 345. | D | D | B | B | A |
| 346. | A | A | A | A | A |
| 347. | D | D | B | B | A |
| 348. | B | D | A | A | A |
| 349. | C | C | B | A | A |
| 350. | D | C | 90 | B | A |
| 351. | B | C | A | A | A |
| 352. | B | C | A | A | A |
| 353. | D | D | B | B | A |
| 354. | B | B | A | A | A |
| 355. | A | B | A | A | A |
| 356. | D | D | D | C | B |

TABLE 4-continued

| Example | FGFR1 ($K_d$ nM) | FGFR2 ($K_d$ nM) | FGFR3 ($K_d$ nM) | FGFR3 (V555M) ($K_d$ nM) | FGFR4 ($K_d$ nM) |
|---|---|---|---|---|---|
| 357. | D | D | C | B | A |
| 358. | B | C | A | A | A |
| 359. | B | B | A | D | A |
| 360. | C | B | B | D | A |
| 361. | D | C | C | C | A |
| 362. | B | C | A | A | A |
| 363. | D | D | D | D | D |
| 364. | B | A | A | A | B |
| 365. | D | D | C | C | B |
| 366. | C | D | B | B | A |
| 367. | D | D | C | B | B |
| 368. | D | D | D | C | C |
| 369. | D | D | B | B | B |
| 370. | D | D | B | B | B |
| 371. | D | D | D | D | C |
| 372. | C | C | B | A | A |
| 373. |   |   |   |   |   |
| 374. | D | D | C | B | B |
| 375. | D | D | C | B | A |
| 376. | D | C | B | B | A |
| 377. | D | D | C | B | A |
| 378. | C | B | A | A | A |
| 379. | C | C | B | A | A |
| 380. | C | D | B | B | A |

A = 1-20 nM
B = >20 to 100 nM
C = >100 to 300 nM
D = >300 nM

Cell Viability Assays

Cell Lines Used for Cell Viability Assays

| Cell line | Mutation or Fusion | Source |
|---|---|---|
| Ba/F3 FGFR1-BCR | FGFR1-fusion | Advanced Cellular Dynamics, (Seattle, WA) |
| Ba/F3 FGFR3-BAIAP2L1 | FGFR3-fusion | Advanced Cellular Dynamics, (Seattle, WA) |
| RT112/84 | FGFR3-fusion | American Type Culture Collection (Manassas, VA) |
| UM-UC-14 | FGFR3(S249C) | Sigma, (St. Louis, MO) |
| KG-1 | FGFR1-fusion | American Type Culture Collection (Manassas, VA) |

Ba/F3 Cell Viability Assays

Experimental Purpose: Recombinant kinase fusions are transduced into parental Ba/F3, which becomes dependent upon this constitutive kinase activity for IL3-independent survival. Inhibition of kinase activity leads to cell death, which is monitored using CellTiter-Glo® 2.0 (Promega) which measures intracellular ATP concentration that in turn serves as a marker for viability. FGFR1-BCR Ba/F3 and FGFR3-BAIAP2L1 Ba/F3 were obtained from Advanced Cellular Dynamics (Seattle, WA)

Cell Viability Assay Procedure: Cell Titer-Glo® 2.0 Luminescent cell viability assay reagent was purchased from Promega (Madison, WI). FGFR1-BCR Ba/F3 and FGFR3-BAIAP2L1 Ba/F3 cells were cultured in RPMI1640 media supplemented with 10% fetal bovine serum. Cultures were maintained at 37° C. in a humidified atmosphere of 5% $C_{O2}$ and 95% air.

Cells were plated in 96-well clear bottom/white plates (Corning #3903) at 10,000 cells/well in 100 µl of media, incubated overnight. The next day, test compound DMSO stock solutions were made at 10 mM and 2 µM final concentration. Compounds were then added to cells in a 9-dose, 10-fold dilution series starting at 30 µM with an HP 300e Digital Dispenser (each dose was applied in triplicate). DMSO was backfilled to each well up to 301 nL total volume of test compound+DMSO, and a total of 301 nL DMSO was added to a control/no test compound well in triplicate. The cells in cell culture plates were incubated with the compounds at 37° C. and 5% $C_{O2}$ for 48 hours. Then 50 µl of Cell Titer Glo 2.0 reagent was added to each well of the cell culture plates. The contents were covered from light and mixed on an orbital shaker at room temperature for 10 min. Luminescence was recorded by a Synergy H1 Microplate Reader (Biotek, Winooski, VT). Cells were assessed as a percentage of DMSO only treated control cells. Curves were plotted and $IC_{50}$ values were calculated using the GraphPad Prism 8 program based on a sigmoidal dose-response equation (4 parameter).

RT112/84, UM-UC-14 and KG-1 Cancer Cell Line Cell Viability Assays

Experimental Purpose: To detect the change of intracellular ATP by Cell Titer-Glo® and to evaluate the inhibitory effect of the compounds on cancer cell lines by determining the in vitro $IC_{50}$ value of the compounds.

Cell Titer-Glo® 2.0 Luminescent cell viability assay reagent was purchased from Promega (Madison, WI). RT112/84 and KG-1 cell lines were purchased from American Type Culture Collection (Manassas, VA). UM-UC-14 cell line was purchased from Sigma (St. Louis, MO). RT112/84, UM-UC-14, and KG-1 cells were cultured in RPMI1640 media supplemented with 10% fetal bovine serum. Cultures were maintained at 37° C. in a humidified atmosphere of 5% $C_{O2}$ and 95% air.

Cell Viability Assay Procedure: Cells were plated in 96-well clear bottom/white plates (Corning #3903) at 10,000 cells/well in 100 µl of media, incubated overnight. The next day, test compound DMSO stock solutions were made at 10 mM and 2 µM final concentration. Compounds were then added to cells in a 9-dose, 10-fold dilution series starting at 30 µM with an HP 300e Digital Dispenser (each dose was applied in triplicate). DMSO was backfilled to each well up to 301 nL total volume of test compound+DMSO, and a total of 301 nL DMSO was added to a control/no test compound well in triplicate. The cells in cell culture plates were incubated with the compounds at 37° C. and 5% $C_{O2}$ for 72 hours. Then 50 µl of Cell Titer Glo 2.0 reagent was added to each well of the cell culture plates. The contents were covered from light and mixed on an orbital shaker at room temperature for 10 min. Luminescence was recorded by a Synergy H1 Microplate Reader (Biotek, Winooski, VT). Cells were assessed as a percentage of DMSO only treated control cells. Curves were plotted and $IC_{50}$ values were calculated using the GraphPad Prism 8 program based on a sigmoidal dose-response equation (4 parameter). Results are shown in Table 5.

TABLE 5

FGFR3 Selectivity in Cell Based Assays

| | Ba/F3 Cells | | Cancer Cell Viability Assays | | |
|---|---|---|---|---|---|
| | | | RT112/84 | UM-UC-14 | KG-1 |
| Example | FGFR3 (IC50 nM) | FGFR1 (IC50 nM) | FGFR3 (IC50 nM) | FGFR3 (IC50 nM) | FGFR1 (IC50 nM) |
| 1 | A | C | A | A | C |
| 2 | A | C | | A | |

TABLE 5-continued

FGFR3 Selectivity in Cell Based Assays

| | Ba/F3 Cells | | Cancer Cell Viability Assays | | |
| --- | --- | --- | --- | --- | --- |
| | | | RT112/84 | UM-UC-14 | KG-1 |
| Example | FGFR3 (IC50 nM) | FGFR1 (IC50 nM) | FGFR3 (IC50 nM) | FGFR3 (IC50 nM) | FGFR1 (IC50 nM) |
| 3 | A | B | A | A | B |
| 4 | A | C | A | A | B |
| 5 | A | C | A | A | B |
| 6 | A | B | A | A | B |
| 7 | B | D | | | |
| 8 | A | C | A | A | C |
| 9 | A | C | A | A | B |
| 10 | A | B | A | A | B |
| 11 | A | C | A | B | B |
| 12 | A | C | A | A | B |
| 13 | B | C | A | B | B |
| 14 | A | D | A | B | C |
| 15 | B | D | A | A | B |
| 16 | B | D | A | A | B |
| 17 | B | | B | B | D |
| 18 | B | D | | | |
| 19 | A | C | A | A | C |
| 20 | B | D | B | B | C |
| 21 | A | C | A | A | B |
| 22 | A | C | A | A | B |
| 23 | A | C | A | A | C |
| 24 | A | B | A | A | B |
| 25 | B | D | | | |
| 26 | B | D | B | B | D |
| 27 | A | C | A | A | C |
| 28 | A | D | A | A | C |
| 29 | A | C | A | | B |
| 30 | A | C | A | | B |
| 31 | | | A | | B |
| 32 | A | C | A | A | B |
| 33 | A | B | A | A | B |
| 34 | A | B | A | A | B |
| 35 | B | D | | | |
| 36 | A | B | | | |
| 37 | A | C | | | |
| 38 | A | C | | | |
| 39 | A | C | | | |
| 40 | A | B | | | |
| 42 | A | C | A | | B |
| 43 | A | B | | | |
| 44 | A | B | | | |
| 46 | A | B | A | A | B |
| 47 | A | C | A | A | C |
| 48 | B | C | B | B | C |
| 49 | A | C | B | B | C |
| 50 | A | C | B | | C |
| 51 | B | C | B | B | C |
| 52 | B | C | B | B | B |
| 53 | B | C | | | |
| 54 | A | C | A | A | C |
| 55 | B | D | | | |
| 56 | B | D | | | |
| 57 | A | C | | | |
| 58 | B | C | | | |
| 60 | A | C | B | B | C |
| 62 | B | D | | | |
| 63 | B | D | | | |
| 64 | A | C | | | |
| 65 | A | B | A | | B |
| 67 | A | B | | | |
| 68 | A | C | | | |
| 70 | A | B | | | |
| 71 | A | B | | | |
| 72 | A | B | | | |
| 73 | B | C | | | |
| 74 | B | C | | | |
| 75 | A | C | | | |
| 77 | A | C | A | | C |
| 78 | A | B | | | |
| 79 | A | B | | | |
| 80 | A | C | | | |
| 82 | A | C | | | |
| 87 | A | B | A | | B |
| 88 | A | C | B | | C |
| 90 | A | B | | | |
| 91 | A | C | | | |
| 92 | B | C | | | |
| 93 | B | C | A | | C |
| 94 | 15 | C | A | | C |
| 95 | B | D | B | | C |
| 96 | A | B | A | | B |
| 97 | A | B | A | | B |
| 98 | A | B | A | | B |
| 100 | A | D | | | |
| 104 | B | D | | | |
| 106 | A | C | A | | C |
| 107 | A | C | B | | C |
| 108 | A | C | | | |
| 109 | A | C | B | | C |
| 111 | A | C | A | | |
| 112 | A | C | A | | |
| 113 | A | B | A | | |
| 114 | B | C | | | |
| 115 | A | B | A | | C |
| 116 | A | C | | | |
| 117 | A | B | A | | B |
| 119 | A | B | B | | C |
| 120 | B | C | B | | D |
| 121 | A | C | A | | C |
| 122 | A | B | A | | C |
| 123 | A | B | A | | C |
| 124 | A | C | A | | C |
| 125 | A | C | A | | C |
| 127 | A | C | B | | C |
| 128 | B | D | | | |
| 129 | B | C | | | |
| 130 | B | D | | | |
| 131 | C | D | | | |
| 135 | C | D | | | |
| 139 | B | C | A | A | C |
| 136 | B | D | | | |
| 140 | C | D | | | |
| 137 | A | C | | | |
| 138 | B | D | | | |
| 141 | D | D | | | |
| 142 | A | C | B | A | C |
| 143 | C | D | | | |
| 144 | B | D | | | |
| 145 | D | D | | | |
| 146 | C | D | | | |
| 148 | B | D | | | |
| 157 | A | C | B | C | |
| 159 | A | B | A | B | A |
| 160 | C | D | | | |
| 162 | A | C | | | |
| 163 | A | B | | | |
| 165 | A | C | | | |
| 166 | C | D | | | |
| 168 | B | D | | | |
| 170 | B | D | | | |

A = 1-20 nM
B = >20 to 100 nM
C = >100 to 300 nM
D = >300 nM

TABLE 6

FGFR3 > FGFR1 Selectivity Ratio
in Ba/F3 FGFR Fusion Cell Based Assays

| Example | Ba/F3 FGFR1/FGFR3 Selectivity |
|---|---|
| 1 | 33 |
| 2 | 15 |
| 3 | 18 |
| 4 | 29 |
| 5 | 22 |
| 6 | 13 |
| 7 | 15 |
| 8 | 16 |
| 9 | 19 |
| 10 | 9 |
| 11 | 9 |
| 12 | 19 |
| 13 | 11 |
| 14 | 18 |
| 15 | 10 |
| 16 | 14 |
| 18 | 21 |
| 19 | 15 |
| 20 | 15 |
| 21 | 13 |
| 22 | 11 |
| 23 | 16 |
| 24 | 18 |
| 25 | 22 |
| 26 | 28 |
| 27 | 24 |
| 28 | 22 |
| 29 | 19 |
| 30 | 18 |
| 32 | 12 |
| 33 | 16 |
| 34 | 28 |
| 35 | 6 |
| 36 | 23 |
| 37 | 12 |
| 38 | 21 |
| 39 | 16 |
| 40 | 30 |
| 42 | 17 |
| 43 | 10 |
| 46 | 14 |
| 47 | 21 |
| 48 | 8 |
| 49 | 10 |
| 50 | 16 |
| 51 | 7 |
| 52 | 7 |
| 53 | 11 |
| 54 | 13 |
| 55 | 16 |
| 56 | 5 |
| 57 | 15 |
| 58 | 11 |
| 60 | 13 |
| 62 | 8 |
| 63 | 16 |
| 64 | 16 |
| 67 | 12 |
| 70 | 20 |
| 71 | 15 |
| 72 | 15 |
| 73 | 11 |
| 74 | 6 |
| 75 | 14 |
| 77 | 14 |
| 78 | 13 |
| 79 | 14 |
| 80 | 17 |
| 82 | 11 |
| 87 | 17 |
| 88 | 20 |
| 90 | 10 |
| 91 | 8 |

TABLE 6-continued

FGFR3 > FGFR1 Selectivity Ratio
in Ba/F3 FGFR Fusion Cell Based Assays

| Example | Ba/F3 FGFR1/FGFR3 Selectivity |
|---|---|
| 92 | 18 |
| 93 | 11 |
| 94 | 11 |
| 95 | 14 |
| 96 | 13 |
| 97 | 15 |
| 98 | 24 |
| 100 | 22 |
| 104 | 10 |
| 106 | 11 |
| 107 | 16 |
| 108 | 14 |
| 109 | 12 |
| 111 | 15 |
| 112 | 12 |
| 113 | 11 |
| 114 | 12 |
| 115 | 14 |
| 116 | 12 |
| 117 | 15 |
| 119 | 9 |
| 120 | 7 |
| 121 | 14 |
| 122 | 7 |
| 123 | 15 |
| 124 | 17 |
| 125 | 16 |
| 127 | 11 |
| 128 | 8 |
| 129 | 6 |
| 130 | 12 |
| 131 | 5 |
| 135 | 9 |
| 139 | 14 |
| 136 | 6 |
| 140 | 19 |
| 137 | 11 |
| 138 | 8 |
| 141 | 3 |
| 142 | 25 |
| 143 | 14 |
| 144 | 33 |
| 145 | 2 |
| 146 | 15 |
| 148 | 16 |
| 157 | 7 |
| 159 | 16 |
| 160 | 17 |
| 162 | 12 |
| 163 | 17 |
| 165 | 16 |
| 166 | 6 |
| 168 | 8 |
| 170 | 14 |

The disclosure is also directed to the following aspects:

Aspect 1. A compound of formula (I)

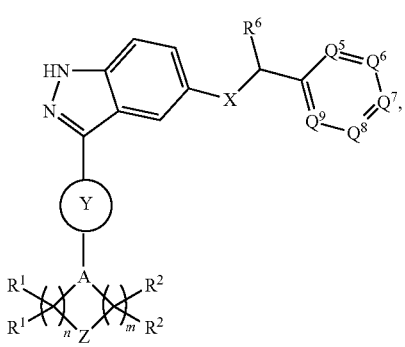

(I)

or a pharmaceutically acceptable salt thereof,
wherein n=1, 2, or 3;
m=1, 2, or 3;
each $R^1$ is independently H or optionally substituted $C_1$-$C_6$alkyl;
each $R^2$ is independently H or optionally substituted $C_1$-$C_6$alkyl;
or two $R^1$ groups attached to the same carbon atom, together with the carbon atom to which they are both attached form an optionally substituted 3-7 membered spirocycloalkyl ring or an optionally substituted 3-7 membered spiroheterocycloalkyl ring;
or two $R^1$ groups attached to the same carbon atom, together with that carbon atom, represent a carbonyl group (C=O);
or two $R^2$ groups attached to the same carbon atom, together with the carbon atom to which they are both attached form an optionally substituted 3-7 membered spirocycloalkyl ring or an optionally substituted 3-7 membered spiroheterocycloalkyl ring;
or two $R^2$ groups attached to the same carbon atom, together with that carbon atom, represent a carbonyl group (C=O);
or two $R^1$ groups attached to different carbon atoms, together with the carbon atoms to which they are attached, form a 3-7 membered cycloalkyl ring;
or two $R^2$ groups attached to different carbon atoms, together with the carbon atoms to which they are attached, form a 3-7 membered cycloalkyl ring;
or an $R^1$ group and an $R^2$ group are attached to form a 6-9 membered bridged bicyclic ring;
A=N or CH;
Z=S(O)$_2$; S(O); O, NR$^3$ or CR$^4$R$^{4'}$;
$R^3$ is H; optionally substituted $C_1$-$C_6$alkyl, 3-5 membered heterocycloalkyl, —C(O)NR$^a$R$^b$; —C(O)OR$^c$; —C(O)R$^c$; —S(O)$_2$R$^c$; or —S(O)$_2$NR$^a$R$^b$;
$R^a$ is H or $C_1$-$C_6$alkyl;
$R^b$ is H or $C_1$-$C_6$alkyl;
or $R^a$ and $R^b$ together with the N atom to which they are both attached, form an optionally substituted 3 to 7 membered heterocycloalkyl ring;
$R^c$ is optionally substituted $C_1$-$C_6$alkyl, or cycloalkyl;
$R^4$ is H or optionally substituted $C_1$-$C_6$alkyl;
$R^{4'}$ is H, —OH, or optionally substituted $C_1$-$C_6$alkyl;
or $R^4$ and $R^{4'}$ together with the C atom to which they are both attached, form an optionally substituted 3 to 7 membered heterocycloalkyl ring;
Y is a 5- or 6-membered heteroaryl ring;

$Q_5$, $Q^6$, $Q^7$, $Q^8$, and $Q^9$, are each independently N or CR$^5$, wherein one or two of $Q^5$, $Q^6$, $Q^7$, $Q^8$, and $Q^9$ is N and the remainder are CR$^5$;
$R^5$ is H, halogen, $C_1$-$C_3$alkyl; $C_1$-$C_3$ alkoxyl, or cycloalkyl;
X=O, S, or NR wherein R is H or $C_1$-$C_3$alkyl; and
$R^6$ is $C_1$-$C_6$alkyl.

Aspect 2. The compound according to aspect 1, wherein Y is a 6-membered heteroaryl ring.

Aspect 3. The compound according to aspect 2, wherein the compound of formula (I) is a compound of formula (IA):

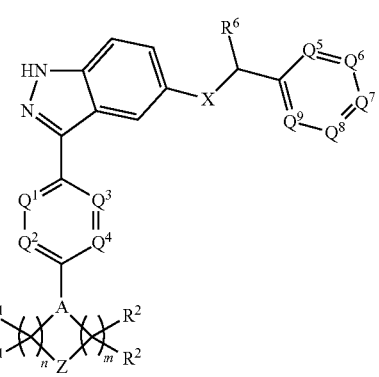

(IA)

wherein one or two of $Q^1$, $Q^2$, $Q^3$, $Q^4$ is N and the others are each independently CR$^{5a}$ wherein R$^{5a}$ is H, halogen, or $C_1$-$C_3$alkyl.

Aspect 4. The compound according to any one of aspects 1-3, wherein X is O.

Aspect 5. The compound according to any one of aspects 3-4, wherein the compound of formula (IA) is a compound of formula (IA-1):

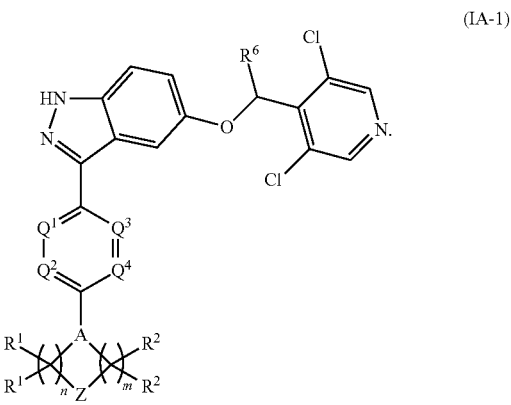

(IA-1)

Aspect 6. The compound according to any one of the preceding aspects, wherein $R^6$ is —CH$_3$.

Aspect 7. The compound according to any one of aspects 3-6, wherein $Q^3$ is CR$^{5a}$.

Aspect 8. The compound according to aspect 7, wherein R$^{5a}$ is halogen.

Aspect 9. The compound according to aspect 8, wherein the halogen is —F.

Aspect 10. The compound according to aspect 5, wherein the compound of formula (IA-1) is a compound of formula (IA-2):

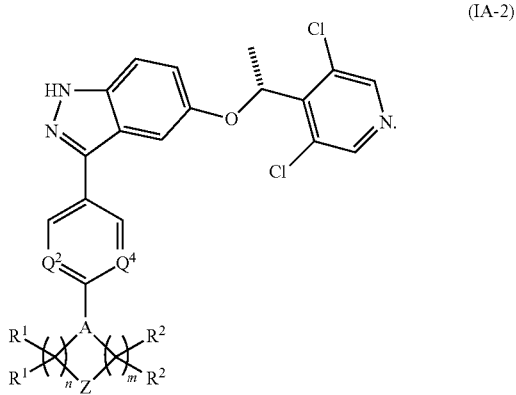

(IA-2)

Aspect 11. The compound according to any one of aspects 1-10, wherein n=2 and m=2.

Aspect 12. The compound according to any one of aspects 1-10, wherein n=1 and m=1.

Aspect 13. The compound according to any one of aspects 1-10, wherein n=1 and m=2.

Aspect 14. The compound according to any one of aspects 1-10, wherein n=3 and m=2.

Aspect 15. The compound according to aspect 10, wherein the compound of formula (IA-2) is a compound of formula (IA-3):

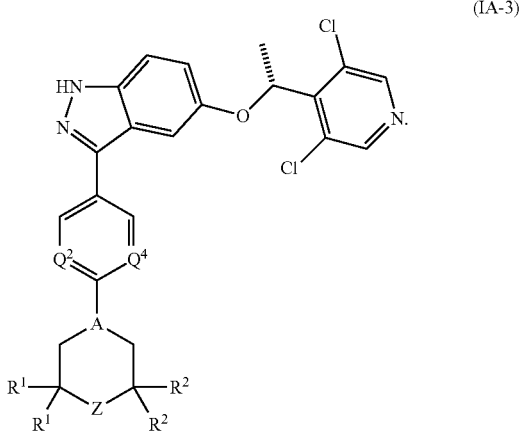

(IA-3)

Aspect 16. The compound according to aspect 15, wherein each $R^1$ and each $R^2$ is independently H or optionally substituted $C_1$-$C_6$alkyl.

Aspect 17. The compound according to aspect 15, wherein each $R^1$ and each $R^2$ is H.

Aspect 18. The compound according to aspect 15, wherein each $R^1$ is H, and two $R^2$ groups attached to the same carbon atom, together with the carbon atom to which they are both attached form a 3-7 membered spirocycloalkyl ring.

Aspect 19. The compound according to aspect 18, wherein said 3-7 membered spirocycloalkyl ring is a 3-membered spirocycloalkyl ring.

Aspect 20. The compound according to aspect 15, wherein one $R_1$ group and one $R^2$ group are attached to form 6-9 membered bridged bicyclic ring, the other $R^1$ is H, and the other $R^2$ is H.

Aspect 21. The compound according to aspect 20, wherein said 6-9 membered bridged bicyclic ring is a 7-membered bridged bicyclic ring.

Aspect 22. The compound according to aspect 20, wherein each $R^1$ is H, and two $R^2$ groups attached to the same carbon atom represent a carbonyl group (C=O).

Aspect 23. The compound according to aspect 10, wherein the compound of formula (IA-2) is a compound of formula (IA-4):

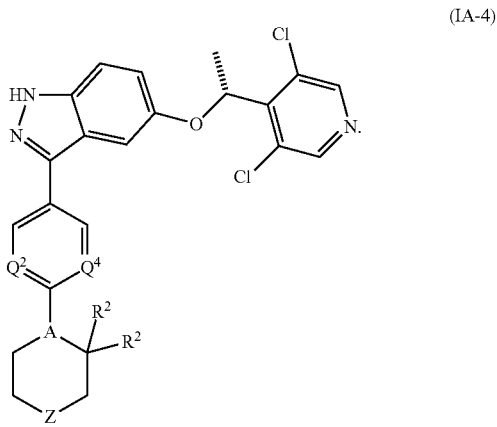

(IA-4)

Aspect 24. The compound according to aspect 23, wherein the two $R^2$ groups attached to the same carbon atom represent a carbonyl group (C=O).

Aspect 25. The compound according to aspect 10, wherein the compound of formula (IA-2) is a compound of formula (IA-5):

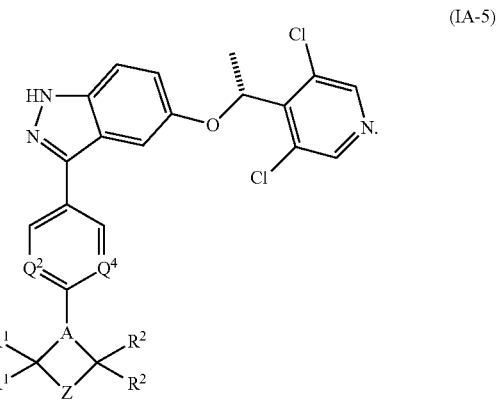

(IA-5)

Aspect 26. The compound according to aspect 25, wherein each $R^1$ and each $R^2$ is independently H or optionally substituted $C_1$-$C_6$alkyl.

Aspect 27. The compound according to aspect 25, wherein each $R^1$ and each $R^2$ is H.

Aspect 28. The compound according to 25, wherein each $R^1$ is H, and two $R^2$ groups attached to the same carbon atom, together with the carbon atom to which they are both attached form a 3-7 membered spirocycloalkyl ring.

Aspect 29. The compound according to aspect 28, wherein said 3-7 membered spirocycloalkyl ring is a 3-membered spirocycloalkyl ring.

Aspect 30. The compound according to aspect 25, wherein one $R^1$ group and one $R^2$ group are attached to form 6-9 membered bridged bicyclic ring, the other $R^1$ is H, and the other $R^2$ is H.

Aspect 31. The compound according to aspect 30, wherein said 6-9 membered bridged bicyclic ring is a 7-membered bridged bicyclic ring.

Aspect 32. The compound according to aspect 10, wherein the compound of formula (IA-2) is a compound of formula (IA-6):

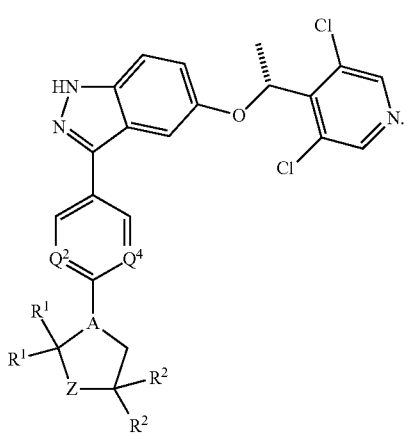

(IA-6)

Aspect 33. The compound according to aspect 32, wherein the two $R^1$ groups attached to the same carbon atom represent a carbonyl group (C=O).

Aspect 34. The compound according to aspect 32 or aspect 33, wherein the two $R^2$ groups attached to the same carbon atom, together with the carbon atom to which they are both attached form an optionally substituted 3-7 membered spirocycloalkyl ring or an optionally substituted 3-7 membered spiroheterocycloalkyl ring.

Aspect 35. The compound of aspect 34 wherein the two $R^2$ groups attached to the same carbon atom, together with the carbon atom to which they are both attached form an optionally substituted 3-7 membered spiroheterocycloalkyl ring.

Aspect 36. The compound according to aspect 35, wherein said optionally substituted 3-7 membered spiroheterocycloalkyl ring is an optionally substituted azetinyl ring, an optionally substituted pyrrolidinyl ring, or an optionally substituted piperidinyl ring.

Aspect 37. The compound according to aspect 36, wherein said optionally substituted 3-7 membered spiroheterocycloalkyl ring is an azetinyl ring, a pyrrolidinyl ring, a piperidinyl ring, an N-methylpiperidinyl ring, or an N-(methylsulfonyl)piperidinyl ring.

Aspect 38. The compound according to aspect 10, wherein the compound of formula (IA-2) is a compound of formula (IA-7):

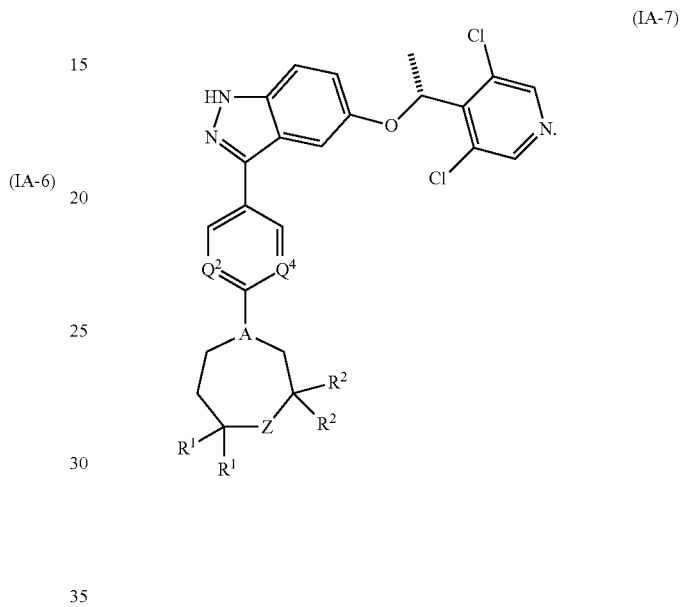

(IA-7)

Aspect 39. The compound according to aspect 38, wherein each $R^1$ is H.

Aspect 40. The compound according to aspect 38, wherein the two $R^1$ groups attached to the same carbon atom represent a carbonyl group (C=O).

Aspect 41. The compound according to any one of aspects 38-40, wherein each $R^2$ is H.

Aspect 42. The compound according to any one of aspects 38-40, wherein the two $R^2$ groups attached to the same carbon atom represent a carbonyl group (C=O).

Aspect 43. The compound according to and one of aspects 3-42, wherein $Q^2$ is N.

Aspect 44. The compound according to any one of aspects 3-43, wherein $Q^4$ is N.

Aspect 45. The compound according to any one of aspects 3-43, wherein $Q^4$ is $CR^5$, Aspect 46. The compound according to aspect 45, wherein $R^{5a}$ is H.

Aspect 47. The compound according to aspect 45, wherein $R^{5a}$ is halogen.

Aspect 48. The compound according to aspect 47, wherein the halogen is —F.

Aspect 49. The compound according to aspect 1, wherein Y is a 5-membered heteroaryl ring.

Aspect 50. The compound according to aspect 49, wherein the compound of formula (I) is a compound of formula IB:

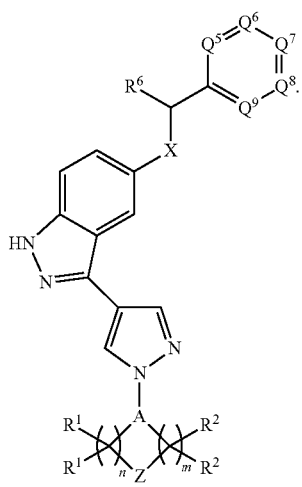

(IB)

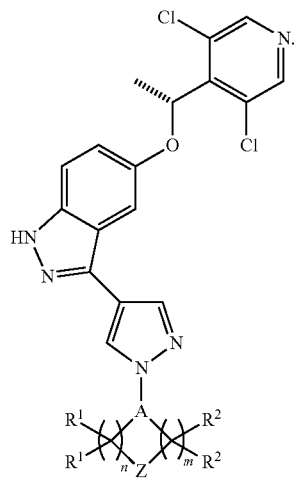

(IB-2)

Aspect 51. The compound according to aspect 50, wherein the compound of formula (IB) is a compound of formula IB-1:

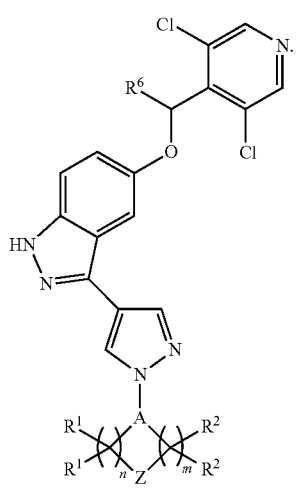

(IB-1)

Aspect 52. The compound according to aspect 51, wherein the compound of formula (IB-1) is a compound of formula IB-2:

Aspect 53. The compound according to any one of aspects 49-52, wherein n=2 and m=2.

Aspect 54. The compound according to any one of aspects 49-52, wherein n=1 and m=1.

Aspect 55. The compound according to any one of aspects 49-52, wherein n=1 and m=2.

Aspect 56. The compound according to any one of aspects 49-52, wherein n=3 and m=2.

Aspect 57. The compound according any one of aspects 49-56, wherein each $R^1$ is H, and each $R^2$ is H.

Aspect 58. The compound according to any one of the preceding aspects, wherein A is N.

Aspect 59. The compound according to any one of the preceding aspects, wherein A is CH.

Aspect 60. The compound according to any one of the preceding aspects, wherein Z is $S(O)_2$.

Aspect 61. The compound according to any one of aspects 1-59, wherein Z is S(O).

Aspect 62. The compound according to any one of aspects 1-59, wherein Z is O.

Aspect 63. The compound according to any one of aspects 1-59, wherein Z is $NR^3$.

Aspect 64. The compound according to aspect 63, wherein $R^3$ is H.

Aspect 65. The compound according to aspect 63, wherein $R^3$ is —$C(O)NR^aR^b$.

Aspect 66. The compound according to aspect 63, wherein $R^3$ is —$S(O)_2NR^aR^b$.

Aspect 67. The compound according to any one of aspects 65 or 66, wherein $R^a$ is H and $R^b$ is H.

Aspect 68. The compound according to any one of aspects 65 or 66, wherein $R^a$ is H and $R^b$ is $C_1$-$C_6$alkyl.

Aspect 69. The compound according to any one of aspects 65 or 66, wherein $R^a$ is $C_1$-$C_6$alkyl and $R^b$ is $C_1$-$C_6$alkyl.

Aspect 70. The compound according to any one of aspects 65 or 66, wherein $R^a$ and $R^b$, together with the N atom to which they are both attached, form an optionally substituted 3 to 7 membered heterocycloalkyl ring.

Aspect 71. The compound according to aspect 70, wherein said optionally substituted 3 to 7 membered heterocycloalkyl ring is an optionally substituted piperidinyl, optionally substituted piperazinyl, or optionally substituted morpholinyl ring.

Aspect 72. The compound according to aspect 71, wherein said optionally substituted 3 to 7 membered heterocycloalkyl ring is a 4-methylpiperazin-1-yl, or a morpholinyl ring.

Aspect 73. The compound according to aspect 63, wherein $R^3$ is —C(O)OR$^c$.

Aspect 74. The compound according to aspect 63, wherein $R^3$ is —C(O)R$^c$.

Aspect 75. The compound according to aspect 63, wherein $R^3$ is —S(O)$_2$R$^c$.

Aspect 76. The compound according to any one of aspects 73 to 75, wherein said R$^c$ is —CH$_3$.

Aspect 77. The compound according to any one of aspects 73 to 75, wherein said R$^c$ is —CH$_2$CH$_3$.

Aspect 78. The compound according to aspect 63, wherein $R^3$ is C$_1$-C$_6$alkyl.

Aspect 79. The compound according to aspect 78, wherein said C$_1$-C$_6$alkyl is —CH$_3$.

Aspect 80. The compound according to aspect 63, wherein $R^3$ is a 3-5 membered heterocycloalkyl.

Aspect 81. The compound according to aspect 80, wherein said 3-5 membered heterocycloalkyl is oxetanyl.

Aspect 82. The compound according to any one of aspects 1-59, wherein Z is CR$^4$R$^{4'}$.

Aspect 83. The compound according to aspect 82, wherein R$^4$ and R$^{4'}$ are each H.

Aspect 84. The compound according to aspect 82, wherein R$^4$ and R$^{4'}$ are each optionally substituted C$_1$-C$_6$alkyl.

Aspect 85. The compound according to aspect 82, wherein R$^4$ is H and R$^{4'}$ is —OH.

Aspect 86. The compound according to aspect 82, wherein R$^4$ and R$^{4'}$ together with the C atom to which they are both attached, form an optionally substituted 3 to 7 membered heterocycloalkyl ring.

Aspect 87. The compound according to aspect 86, wherein the optionally substituted 3 to 7 membered heterocycloalkyl ring is an optionally substituted 4-membered heterocycloalkyl ring.

Aspect 88. The compound according to aspect 87, wherein the optionally substituted 4 membered heterocycloalkyl ring is an azetidinyl ring.

Aspect 89. The compound according to aspect 88, wherein the azetidinyl ring is not substituted.

Aspect 90. The compound according to aspect 88, wherein the azetidinyl ring is N-substituted.

Aspect 91. The compound according to aspect 90, wherein the N-substituent is C$_1$-C$_6$alkyl, —C(O)N(C$_1$-C$_6$alkyl)$_2$, or —SO$_2$—C$_1$-C$_6$alkyl.

Aspect 92. The compound according to aspect 91, wherein the N-substituent is —CH$_3$, —CH(CH$_3$)$_2$, —C(O)N(CH$_3$)$_2$, or —SO$_2$CH$_3$.

Aspect 93. The compound according to aspect 86, wherein the optionally substituted 3 to 7 membered heterocycloalkyl ring is an optionally substituted 5-membered heterocycloalkyl ring.

Aspect 94. The compound according to aspect 93, wherein the optionally substituted 5-membered heterocycloalkyl ring is an unsubstituted pyrrolidinyl ring, N-substituted pyrrolidinyl ring, unsubstituted pyrrolidinyl-2-one ring, N-substituted pyrrolidinyl-2-one ring, unsubstituted pyrrolo-2,5-dione ring, N-substituted pyrrolo-2,5-dione ring, unsubstituted imidazolidinyl-2-one ring, N-substituted imidazolidinyl-2-one ring, a tetrahydrofuranyl ring, or a tetrahydrothiophene-1,1-dioxide ring.

Aspect 95. The compound according to aspect 94, wherein said N-substituent is —CH$_3$.

Aspect 96. The compound according to aspect 86, wherein the optionally substituted 3 to 7 membered heterocycloalkyl ring is an optionally substituted 6-membered heterocycloalkyl ring.

Aspect 97. The compound according to aspect 96, wherein the optionally substituted 6-membered heterocycloalkyl ring is an unsubstituted piperizinyl-2-one ring or an N-substituted piperizinyl-2-one ring.

Aspect 98. The compound according to aspect 97, wherein the N-substituent is —CH$_3$.

Aspect 99. A pharmaceutical composition comprising a compound of any one of aspects 1-98, or a pharmaceutically acceptable salt thereof, and a pharmaceutically acceptable excipient.

Aspect 100. A method of treating cancer in a subject in need thereof comprising administering to the subject a compound of any one of aspects 1 to 98, or a pharmaceutically acceptable salt thereof.

Aspect 101. The method of aspect 100, wherein the cancer is urothelial carcinoma, breast carcinoma, endometrial adenocarcinoma, ovarian carcinoma, primary glioma, cholangiocarcinoma, gastric adenocarcinoma, non-small cell lung carcinoma, pancreatic exocrine carcinoma, oral, prostate, bladder, colorectal carcinoma, renal cell carcinoma, neuroendocrine carcinoma, myeloproliferative neoplasms, head and neck (squamous), melanoma, leiomyosarcoma, and/or sarcomas.

Aspect 102. The method of aspect 101, wherein the cancer is an intrahepatic cholangiocarcinoma.

Aspect 103. The method of any one of aspects 100 to 102, wherein the cancer is an FGFR-mutant cancer.

Aspect 104. A compound of formula (I)

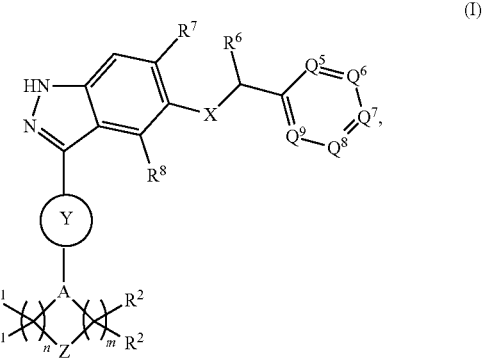

(I)

or a pharmaceutically acceptable salt thereof,
wherein n=1, 2, or 3;
  m=1, 2, or 3;
  each R$^1$ is independently H or optionally substituted C$_1$-C$_6$alkyl;
  each R$^2$ is independently H or optionally substituted C$_1$-C$_6$alkyl;
    or two R$^1$ groups attached to the same carbon atom, together with the carbon atom to which they are both attached form an optionally substituted 3-7 membered spirocycloalkyl ring or an optionally substituted 3-7 membered spiroheterocycloalkyl ring;
    or two R$^1$ groups attached to the same carbon atom, together with that carbon atom, represent a carbonyl group (C=O);
    or two R$^2$ groups attached to the same carbon atom, together with the carbon atom to which they are both attached form an optionally substituted 3-7 membered spirocycloalkyl ring or an optionally substituted 3-7 membered spiroheterocycloalkyl ring;

or two R² groups attached to the same carbon atom, together with that carbon atom, represent a carbonyl group (C=O);
or two R¹ groups attached to different carbon atoms, together with the carbon atoms to which they are attached, form a 3-7 membered cycloalkyl ring;
or two R² groups attached to different carbon atoms, together with the carbon atoms to which they are attached, form a 3-7 membered cycloalkyl ring;
or an R¹ group and an R² group are attached to form a 6-9 membered bridged bicyclic ring;

A=N or CH;
Z=S(O)₂; S(O); O, NR³ or CR⁴R⁴';
R³ is H; optionally substituted $C_1$-$C_6$alkyl, 3-5-membered cycloalkyl, 3-5 membered heterocycloalkyl, —C(O)NR$^a$R$^b$; —C(O)OR$^c$; —C(O)R$^c$; —S(O)₂R$^c$; or —S(O)₂NR$^a$R$^b$;
R$^a$ is H or $C_1$-$C_6$alkyl;
R$^b$ is H or $C_1$-$C_6$alkyl;
or R$^a$ and R$^b$ together with the N atom to which they are both attached, form an optionally substituted 3 to 7 membered heterocycloalkyl ring;
R$^c$ is optionally substituted $C_1$-$C_6$alkyl, or cycloalkyl;
R⁴ is H or optionally substituted $C_1$-$C_6$alkyl;
R⁴' is H, —OH, or optionally substituted $C_1$-$C_6$alkyl;
or R⁴ and R⁴' together with the C atom to which they are both attached, form an optionally substituted 3 to 7 membered heterocycloalkyl ring;
Y is a 5- or 6-membered heteroaryl ring;
Q⁵, Q⁶, Q⁷, Q⁸, and Q⁹, are each independently N or CR⁵, wherein one or two of Q⁵, Q⁶, Q⁷, Q⁸, and Q⁹ is N and the remainder are CR⁵;
R⁵ is H, halogen, $C_1$-$C_3$alkyl; $C_1$-$C_3$ alkoxyl, or cycloalkyl;
X=O, S, or NR wherein R is H or $C_1$-$C_3$alkyl;
R⁶ is $C_1$-$C_6$alkyl;
R⁷ is H, halogen, —$C_1$-$C_6$alkyl; —$C_1$-$C_6$ alkoxyl, or -cycloalkyl; and
R⁸ is H, halogen, —$C_1$-$C_6$alkyl; —$C_1$-$C_6$ alkoxyl, or -cycloalkyl.

Aspect 105. The compound according to aspect 104, wherein Y is a 6-membered heteroaryl ring.

Aspect 106. The compound according to aspect 105, wherein the compound of formula (I) is a compound of formula (IA):

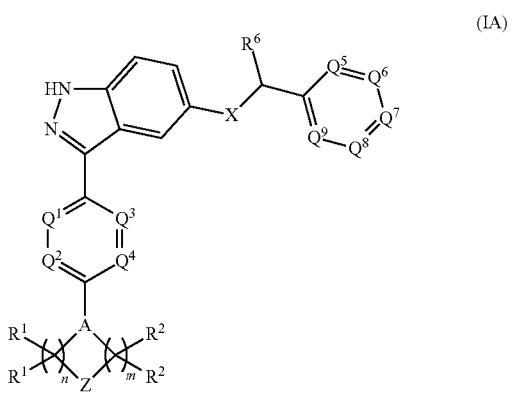

(IA)

wherein one or two of Q¹, Q², Q³, Q⁴ is N and the others are each independently CR$^{5a}$ wherein R$^{5a}$ is H, halogen, —CN, or $C_1$-$C_3$alkyl.

Aspect 107. The compound according to any one of aspects 104-106, wherein X is O.

Aspect 108. The compound according to any one of aspects 104-107, wherein Q⁵ and Q⁹ are each CR⁵ wherein each R⁵ is halogen; Q⁶ and Q⁸ are each CR⁵ wherein each R⁵ is H; and Q⁷ is N.

Aspect 109. The compound according to any one of aspects 104-107, wherein Q⁵ and Q⁹ are each CR⁵ wherein each R⁵ is halogen; Q⁶ is CR⁵ wherein R⁵ is H; Q⁸ is CR⁵ wherein R⁵ is $C_1$-$C_3$alkyl; and Q⁷ is N.

Aspect 110. The compound according to any one of aspects 104-107, wherein Q⁵ and Q⁹ are each CR⁵ wherein each R⁵ is —$C_1$; Q⁶ is CR⁵ wherein R⁵ is H; Q⁸ is CR⁵ wherein R⁵ is —CH₃; and Q⁷ is N.

Aspect 111. The compound according to any one of aspects 104-107, wherein Q⁵ and Q⁹ are each CR⁵ wherein each R⁵ is halogen; Q⁶ is CR⁵ wherein R⁵ is H; Q⁸ is N; and Q⁷ is CR⁵ wherein R⁵ is H.

Aspect 112. The compound according to any one of aspects 104-107, wherein Q⁵ and Q⁹ are each CR⁵ wherein each R⁵ is —$C_1$; Q⁶ is CR⁵ wherein R⁵ is H; Q⁸ is N; and Q⁷ is CR⁵ wherein R⁵ is H.

Aspect 113. The compound according to any one of aspects 104-107, wherein Q⁵ and Q⁹ are each CR⁵ wherein each R⁵ is halogen; Q⁶ is CR⁵ wherein R⁵ is H; Q⁶ is N; and Q⁷ is N.

Aspect 114. The compound according to any one of aspects 104-107, wherein Q⁵ and Q⁹ are each CR⁵ wherein each R⁵ is —$C_1$; Q⁶ is CR⁵ wherein R⁵ is H; Q⁸ is N; and Q⁷ is N.

Aspect 115. The compound according to any one of aspects 104-107, wherein Q⁵ and Q⁹ are each CR⁵ wherein each R⁵ is $C_1$-$C_3$alkyl; Q⁶ is CR⁵ wherein R⁵ is H; Q⁸ is N; and Q⁷ is N.

Aspect 116. The compound according to any one of aspects 104-107, wherein Q⁵ and Q⁹ are each CR⁵ wherein each R⁵ is —CH₃; Q⁶ is CR⁵ wherein R⁵ is H; Q⁶ is N; and Q⁷ is N.

Aspect 117. The compound according to any one of aspects 104-107, wherein Q⁵, Q⁸, and Q⁹ are each independently CR⁵ wherein each R⁵ is halogen; Q⁶ is CR⁵ wherein R⁵ is H; and Q⁷ is N.

Aspect 118. The compound according to any one of aspects 104-107, wherein Q⁵ and Q⁹ are each independently CR⁵ wherein each R⁵ is —$C_1$; Q⁶ is CR⁵ wherein R⁵ is H; Q⁸ is CR⁵ wherein R⁵ is —F; and Q⁷ is N.

Aspect 119. The compound according to any one of aspects 106-108, wherein the compound of formula (IA) is a compound of formula (IA-1):

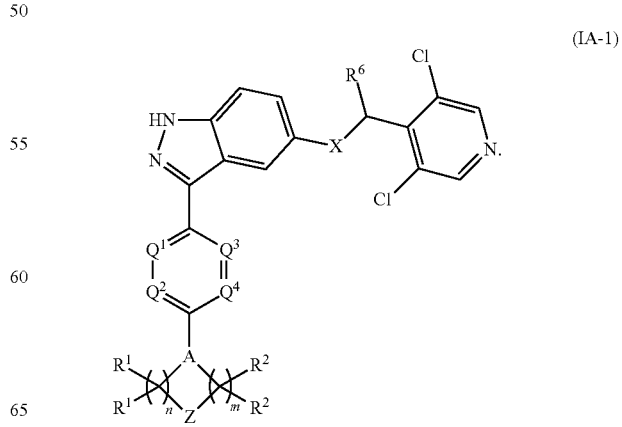

(IA-1)

Aspect 120. The compound according to any one of the preceding aspects, wherein $R^6$ is —$CH_3$.

Aspect 121. The compound according to any one of aspects 106-120, wherein $Q^3$ is $CR^{5a}$.

Aspect 122. The compound according to aspect 121, wherein $R^{5a}$ is halogen.

Aspect 123. The compound according to aspect 122, wherein the halogen is —F.

Aspect 124. The compound according to aspect 119, wherein the compound of formula (IA-1) is a compound of formula (IA-2):

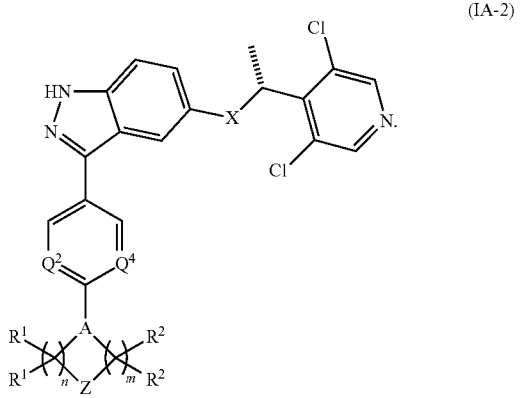

(IA-2)

Aspect 125. The compound according to any one of aspects 104-124, wherein n=2 and m=2.

Aspect 126. The compound according to any one of aspects 104-124, wherein n=1 and m=1.

Aspect 127. The compound according to any one of aspects 104-124, wherein n=1 and m=2.

Aspect 128. The compound according to any one of aspects 104-124, wherein n=3 and m=2.

Aspect 129. The compound according to aspect 124, wherein the compound of formula (IA-2) is a compound of formula (IA-3):

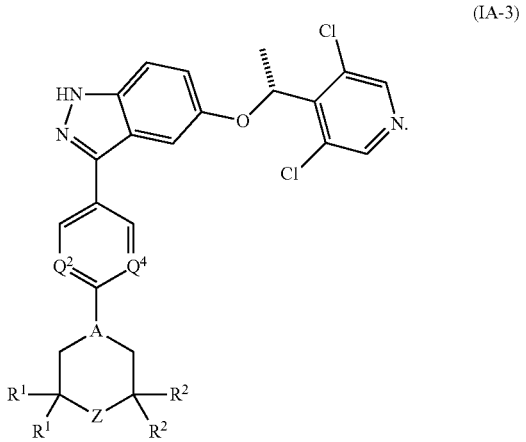

(IA-3)

Aspect 130. The compound according to aspect 129, wherein each $R^1$ and each $R^2$ is independently H or optionally substituted $C_1$-$C_6$alkyl.

Aspect 131. The compound according to aspect 129, wherein each $R^1$ and each $R^2$ is H.

Aspect 132. The compound according to aspect 129, wherein each $R^1$ is H, and two $R^2$ groups attached to the same carbon atom, together with the carbon atom to which they are both attached form a 3-7 membered spirocycloalkyl ring.

Aspect 133. The compound according to aspect 132, wherein said 3-7 membered spirocycloalkyl ring is a 3-membered spirocycloalkyl ring.

Aspect 134. The compound according to aspect 129, wherein one $R^1$ group and one $R^2$ group are attached to form 6-9 membered bridged bicyclic ring, the other $R^1$ is H, and the other $R^2$ is H.

Aspect 135. The compound according to aspect 134, wherein said 6-9 membered bridged bicyclic ring is a 7-membered bridged bicyclic ring.

Aspect 136. The compound according to aspect 129, wherein each $R^1$ is H, and two $R^2$ groups attached to the same carbon atom represent a carbonyl group (C=O).

Aspect 137. The compound according to aspect 124, wherein the compound of formula (IA-2) is a compound of formula (IA-4):

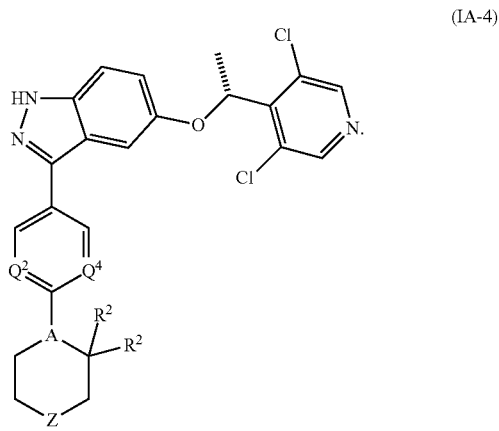

(IA-4)

Aspect 138. The compound according to aspect 137, wherein the two $R^2$ groups attached to the same carbon atom represent a carbonyl group (C=O).

Aspect 139. The compound according to aspect 124, wherein the compound of formula (IA-2) is a compound of formula (IA-5):

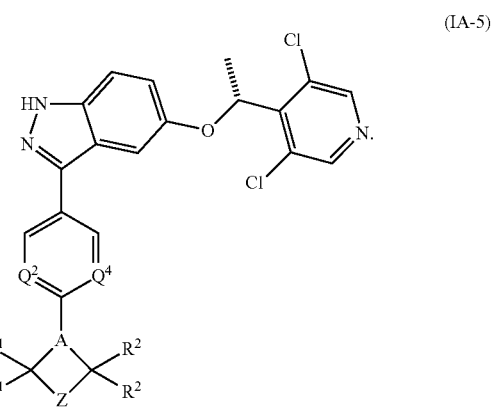

(IA-5)

Aspect 140. The compound according to aspect 139, wherein each $R^1$ and each $R^2$ is independently H or optionally substituted $C_1$-$C_6$alkyl.

Aspect 141. The compound according to aspect 139, wherein each $R^1$ and each $R^2$ is H.

Aspect 142. The compound according to 139, wherein each $R^1$ is H, and two $R^2$ groups attached to the same carbon atom, together with the carbon atom to which they are both attached form a 3-7 membered spirocycloalkyl ring.

Aspect 143. The compound according to aspect 142, wherein said 3-7 membered spirocycloalkyl ring is a 3-membered spirocycloalkyl ring.

Aspect 144. The compound according to aspect 139, wherein one $R^1$ group and one $R^2$ group are attached to form 6-9 membered bridged bicyclic ring, the other $R^1$ is H, and the other $R^2$ is H.

Aspect 145. The compound according to aspect 144, wherein said 6-9 membered bridged bicyclic ring is a 7-membered bridged bicyclic ring.

Aspect 146. The compound according to aspect 124, wherein the compound of formula (IA-2) is a compound of formula (IA-6):

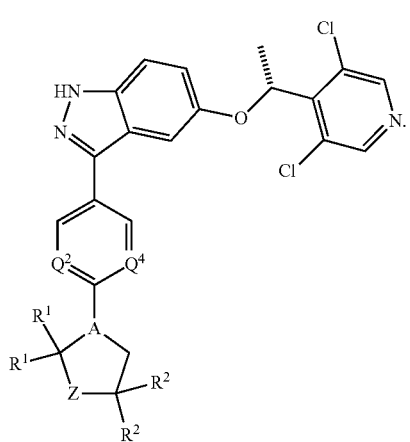

(IA-6)

Aspect 147. The compound according to aspect 146, wherein the two $R^1$ groups attached to the same carbon atom represent a carbonyl group (C=O).

Aspect 148. The compound according to aspect 146 or aspect 147, wherein the two $R^2$ groups attached to the same carbon atom, together with the carbon atom to which they are both attached form an optionally substituted 3-7 membered spirocycloalkyl ring or an optionally substituted 3-7 membered spiroheterocycloalkyl ring.

Aspect 149. The compound of aspect 148 wherein the two $R^2$ groups attached to the same carbon atom, together with the carbon atom to which they are both attached form an optionally substituted 3-7 membered spiroheterocycloalkyl ring.

Aspect 150. The compound according to aspect 149, wherein said optionally substituted 3-7 membered spiroheterocycloalkyl ring is an optionally substituted azetinyl ring, an optionally substituted pyrrolidinyl ring, or an optionally substituted piperidinyl ring.

Aspect 151. The compound according to aspect 150, wherein said optionally substituted 3-7 membered spiroheterocycloalkyl ring is an azetinyl ring, a pyrrolidinyl ring, a piperidinyl ring, an N-methylpiperidinyl ring, or an N-(methylsulfonyl)piperidinyl ring.

Aspect 152. The compound according to aspect 124, wherein the compound of formula (IA-2) is a compound of formula (IA-7):

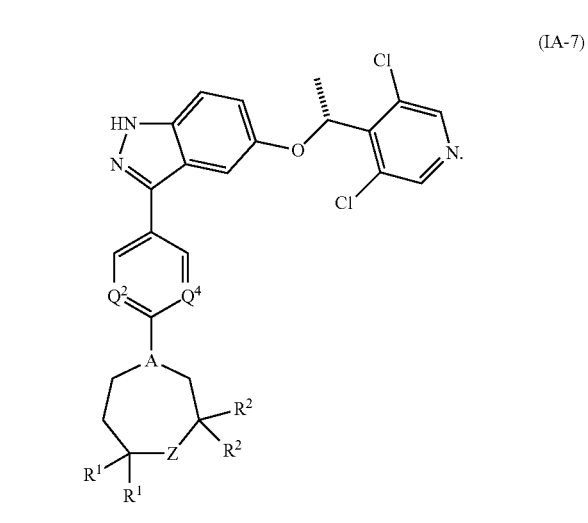

(IA-7)

Aspect 153. The compound according to aspect 152, wherein each $R^1$ is H.

Aspect 154. The compound according to aspect 152, wherein the two $R^1$ groups attached to the same carbon atom represent a carbonyl group (C=O).

Aspect 155. The compound according to any one of aspects 152-154, wherein each $R^2$ is H.

Aspect 156. The compound according to any one of aspects 152-154, wherein the two R groups attached to the same carbon atom represent a carbonyl group (C=O).

Aspect 157. The compound according to and one of aspects 117-156, wherein $Q^2$ is N.

Aspect 158. The compound according to any one of aspects 117-157, wherein $Q^4$ is N.

Aspect 159. The compound according to any one of aspects 117-157, wherein $Q^4$ is $CR^{5a}$.

Aspect 160. The compound according to aspect 159, wherein $R^{5a}$ is H.

Aspect 161. The compound according to aspect 159, wherein $R^{5a}$ is halogen.

Aspect 162. The compound according to aspect 159, wherein the halogen is —F.

Aspect 163. The compound according to aspect 104, wherein Y is a 5-membered heteroaryl ring.

Aspect 164. The compound according to aspect 163, wherein the compound of formula (I) is a compound of formula IB:

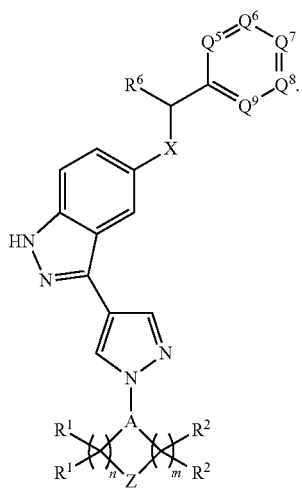

(IB)

Aspect 165. The compound according to any one of aspects 163-164, wherein X is O.

Aspect 166. The compound according to any one of aspects 163-165, wherein $Q^5$ and $Q^9$ are each independently $CR^5$ wherein each $R^5$ is halogen; $Q^6$ and $Q^8$ are $CR^5$ wherein $R^5$ is H; and $Q^7$ is N.

Aspect 167. The compound according to any one of aspects 163-165, wherein $Q^5$ and $Q^9$ are each independently $CR^5$ wherein each $R^5$ is halogen; $Q^6$ is $CR^5$ wherein $R^5$ is H; $Q^8$ is $CR^5$ wherein $R^5$ is $C_1$-$C_3$alkyl; and $Q^7$ is N.

Aspect 168. The compound according to any one of aspects 163-165, wherein $Q^5$ and $Q^9$ are each independently $CR^5$ wherein each $R^5$ is —$C_1$; $Q^6$ is $CR^5$ wherein $R^5$ is H; $Q^8$ is $CR^5$ wherein $R^5$ is —$CH_3$; and $Q^7$ is N.

Aspect 169. The compound according to any one of aspects 163-165, wherein $Q^5$ and $Q^9$ are each independently $CR^5$ wherein each $R^5$ is halogen; $Q^6$ is $CR^5$ wherein $R^5$ is H; $Q^8$ is N; and $Q^7$ is $CR^5$ wherein $R^5$ is H.

Aspect 170. The compound according to any one of aspects 163-165, wherein $Q^5$ and $Q^9$ are each independently $CR^5$ wherein each $R^5$ is —$C_1$; $Q^6$ is $CR^5$ wherein $R^5$ is H; $Q^6$ is N; and $Q^7$ is $CR^5$ wherein $R^5$ is H.

Aspect 171. The compound according to any one of aspects 163-165, wherein $Q^5$ and $Q^9$ are each independently $CR^5$ wherein each $R^5$ is halogen; $Q^6$ is $CR^5$ wherein $R^5$ is H; $Q^8$ is N; and $Q^7$ is N.

Aspect 172. The compound according to any one of aspects 163-165, wherein $Q^5$ and $Q^9$ are each independently $CR^5$ wherein each $R^5$ is —$C_1$; $Q^6$ is $CR^5$ wherein $R^5$ is H; $Q^8$ is N; and $Q^7$ is N.

Aspect 173. The compound according to any one of aspects 163-165, wherein $Q^5$ and $Q^9$ are each independently $CR^5$ wherein each $R^5$ is $C_1$-$C_3$alkyl; $Q^6$ is $CR^5$ wherein $R^5$ is H; $Q^8$ is N; and $Q^7$ is N.

Aspect 174. The compound according to any one of aspects 163-165, wherein $Q^5$ and $Q^9$ are each independently $CR^5$ wherein each $R^5$ is —$CH_3$; $Q^6$ is $CR^5$ wherein $R^5$ is H; $Q^6$ is N; and $Q^7$ is N.

Aspect 175. The compound according to any one of aspects 163-165, wherein $Q^5$, $Q^8$, and $Q^9$ are each independently $CR^5$ wherein each $R^5$ is halogen; $Q^6$ is $CR^5$ wherein $R^5$ is H; and $Q^7$ is N.

Aspect 176. The compound according to any one of aspects 163-165, wherein $Q^5$ and $Q^9$ are each independently $CR^5$ wherein each $R^5$ is —$C_1$; $Q^6$ is $CR^5$ wherein $R^5$ is H; $Q^8$ is $CR^5$ wherein $R^5$ is —F; and $Q^7$ is N.

Aspect 177. The compound according to aspect 164, wherein the compound of formula (IB) is a compound of formula IB-1:

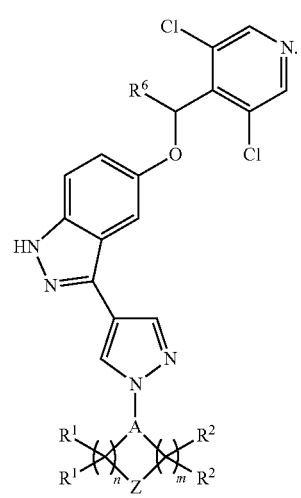

(IB-1)

Aspect 178. The compound according to aspect 177, wherein the compound of formula (IB-1) is a compound of formula IB-2:

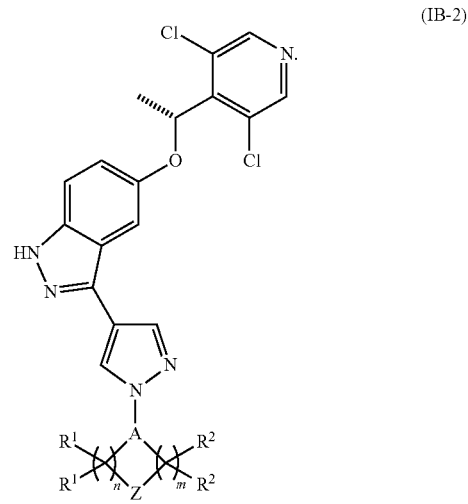

(IB-2)

Aspect 179. The compound according to any one of aspects 164-178, wherein n=2 and m=2.

Aspect 180. The compound according to any one of aspects 164-178, wherein n=1 and m=1.

Aspect 181. The compound according to any one of aspects 164-178, wherein n=1 and m=2.

Aspect 182. The compound according to any one of aspects 164-178, wherein n=3 and m=2.

Aspect 183. The compound according any one of aspects 164-178, wherein each $R^1$ is H, and each $R^2$ is H.

Aspect 184. The compound according to any one of the aspects 104-183, wherein A is N.

Aspect 185. The compound according to any one of the aspects 104-183, wherein A is CH.

Aspect 186. The compound according to any one of the aspects 104-185, wherein Z is $S(O)_2$.

Aspect 187. The compound according to any one of aspects 104-185, wherein Z is S(O).

Aspect 188. The compound according to any one of aspects 104-185, wherein Z is O.

Aspect 189. The compound according to any one of aspects 104-185, wherein Z is $NR^3$.

Aspect 190. The compound according to aspect 189, wherein $R^3$ is H.

Aspect 191. The compound according to aspect 189, wherein $R^3$ is —$C(O)NR^aR^b$.

Aspect 192. The compound according to aspect 189, wherein $R^3$ is —$S(O)_2NR^aR^b$.

Aspect 193. The compound according to any one of aspects 191 or 192, wherein $R^a$ is H and $R^b$ is H.

Aspect 194. The compound according to any one of aspects 191 or 192, wherein $R^a$ is H and $R^b$ is $C_1$-$C_6$alkyl.

Aspect 195. The compound according to any one of aspects 191 or 192, wherein $R^a$ is $C_1$-$C_6$alkyl and $R^b$ is $C_1$-$C_6$alkyl.

Aspect 196. The compound according to any one of aspects 191 or 192, wherein $R^a$ and $R^b$, together with the N atom to which they are both attached, form an optionally substituted 3 to 7 membered heterocycloalkyl ring.

Aspect 197. The compound according to aspect 196, wherein said optionally substituted 3 to 7 membered heterocycloalkyl ring is an optionally substituted piperidinyl, optionally substituted piperazinyl, or optionally substituted morpholinyl ring.

Aspect 198. The compound according to aspect 197, wherein said optionally substituted 3 to 7 membered heterocycloalkyl ring is a 4-methylpiperazin-1-yl, or a morpholinyl ring.

Aspect 199. The compound according to aspect 189, wherein $R^3$ is —$C(O)OR^c$.

Aspect 200. The compound according to aspect 186, wherein $R^3$ is —$C(O)R^c$.

Aspect 201. The compound according to aspect 186, wherein $R^3$ is —$S(O)_2R^c$.

Aspect 202. The compound according to any one of aspects 199 to 201, wherein said $R^c$ is —$CH_3$.

Aspect 203. The compound according to any one of aspects 199 to 201, wherein said $R^c$ is —$CH_2CH_3$.

Aspect 204. The compound according to aspect 189, wherein $R^3$ is $C_1$-$C_6$alkyl.

Aspect 205. The compound according to aspect 204, wherein said $C_1$-$C_6$alkyl is —$CH_3$.

Aspect 206. The compound according to aspect 189, wherein $R^3$ is a 3-5 membered heterocycloalkyl.

Aspect 207. The compound according to aspect 206, wherein said 3-5 membered heterocycloalkyl is oxetanyl.

Aspect 208. The compound according to any one of aspects 104-185, wherein Z is $CR^4R^{4'}$.

Aspect 209. The compound according to aspect 208, wherein $R^4$ and $R^{4'}$ are each H.

Aspect 210. The compound according to aspect 208, wherein $R^4$ and $R^{4'}$ are each optionally substituted $C_1$-$C_6$alkyl.

Aspect 211. The compound according to aspect 208, wherein $R^4$ is H and $R^{4'}$ is —OH.

Aspect 212. The compound according to aspect 208, wherein $R^4$ and $R^{4'}$ together with the C atom to which they are both attached, form an optionally substituted 3 to 7 membered heterocycloalkyl ring.

Aspect 213. The compound according to aspect 212, wherein the optionally substituted 3 to 7 membered heterocycloalkyl ring is an optionally substituted 4-membered heterocycloalkyl ring.

Aspect 214. The compound according to aspect 213, wherein the optionally substituted 4 membered heterocycloalkyl ring is an azetidinyl ring.

Aspect 215. The compound according to aspect 214, wherein the azetidinyl ring is not substituted.

Aspect 216. The compound according to aspect 214, wherein the azetidinyl ring is N-substituted.

Aspect 217. The compound according to aspect 216, wherein the N-substituent is $C_1$-$C_6$alkyl, —$C(O)OC_1$-$C_6$alkyl, —$C(O)C_1$-$C_6$alkyl, —$C(O)N(C_1$-$C_6$alkyl$)_2$, or —$SO_2$—$C_1$-$C_6$alkyl.

Aspect 218. The compound according to aspect 217, wherein the N-substituent is —$CH_3$, —$CH(CH_3)_2$, —$C(O)OCH_2CH_3$, —$C(O)N(CH_3)_2$, —$SO_2CH_3$, —$SO_2CH(CH_3)_2$, or —$SO_2CH_2CH_3$.

Aspect 219. The compound according to aspect 213, wherein the optionally substituted 4 membered heterocycloalkyl ring is an optionally substituted thietane 1,1-dioxide ring.

Aspect 220. The compound according to aspect 213, wherein the optionally substituted 3 to 7 membered heterocycloalkyl ring is an optionally substituted 5-membered heterocycloalkyl ring.

Aspect 221. The compound according to aspect 220, wherein the optionally substituted 5-membered heterocycloalkyl ring is an unsubstituted pyrrolidinyl ring, N-substituted pyrrolidinyl ring, unsubstituted pyrrolidinyl-2-one ring, N-substituted pyrrolidinyl-2-one ring, unsubstituted pyrrolo-2,5-dione ring, N-substituted pyrrolo-2,5-dione ring, unsubstituted imidazolidinyl-2-one ring, N-substituted imidazolidinyl-2-one ring, a tetrahydrofuranyl ring, or a tetrahydrothiophene-1,1-dioxide ring.

Aspect 222. The compound according to aspect 221, wherein said N-substituent is —$C_1$-$C_6$alkyl, —$C(O)OC_1$-$C_6$alkyl, —$C(O)C_1$-$C_6$alkyl, or —$SO_2C_1$-$C_6$alkyl.

Aspect 223. The compound according to aspect 222, wherein said N-substituent is —$CH_3$, —$C(O)OCH_3$, —$C(O)OCH_2CH_3$, —$C(O)OCH(CH_3)_2$, or —$SO_2CH_3$.

Aspect 224. The compound according to aspect 212, wherein the optionally substituted 3 to 7 membered heterocycloalkyl ring is an optionally substituted 6-membered heterocycloalkyl ring.

Aspect 225. The compound according to aspect 224, wherein the optionally substituted 6-membered heterocycloalkyl ring is an unsubstituted piperizinyl-2-one ring, an N-substituted piperizinyl-2-one ring, an N-substituted or unsubstituted piperidine ring, or a tetrahydro-2H-thiopyran 1,1-dioxide ring.

Aspect 226. The compound according to aspect 225, wherein the N-substituent is —$C_1$-$C_6$alkyl, —$C(O)OC_1$-$C_6$alkyl, —$C(O)C_1$-$C_6$alkyl, or —$SO_2C_1$-$C_6$alkyl.

Aspect 227. The compound according to aspect 226, wherein the N-substituent is —$CH_3$, —$C(O)OCH_3$, —$C(O)OCH_2CH_3$, —$C(O)OCH(CH_3)_2$, or —$SO_2CH_3$.

Aspect 228. A pharmaceutical composition comprising a compound of any one of aspects 104-227, or a pharmaceutically acceptable salt thereof, and a pharmaceutically acceptable excipient.

Aspect 229. A method of treating cancer in a subject in need thereof comprising administering to the subject a compound of any one of aspects 104 to 227, or a pharmaceutically acceptable salt thereof.

Aspect 230. The method of aspect 229, wherein the cancer is urothelial carcinoma, breast carcinoma, endometrial adenocarcinoma, ovarian carcinoma, primary glioma, cholangiocarcinoma, gastric adenocarcinoma, non-small cell lung carcinoma, pancreatic exocrine carcinoma, oral, prostate, bladder, colorectal carcinoma, renal cell carcinoma, neuroendocrine carcinoma, myeloproliferative neoplasms, head and neck (squamous), melanoma, leiomyosarcoma, and/or sarcomas.

Aspect 231. The method of aspect 230, wherein the cancer is an intrahepatic cholangiocarcinoma.

Aspect 232. The method of any one of aspects 229 to 231, wherein the cancer is an FGFR-mutant cancer.

What is claimed:
1. A compound of formula (I):

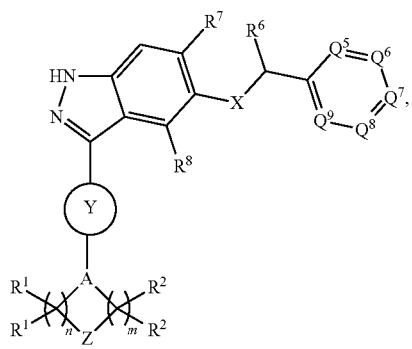

(I)

or a pharmaceutically acceptable salt thereof,
wherein n=1, 2, or 3;
m=0, 1, 2, or 3;
each $R^1$ is independently H, CN, or optionally substituted $C_1$-$C_6$alkyl;
each $R^2$ is independently H, CN, or optionally substituted $C_1$-$C_6$alkyl;
or two $R^1$ groups attached to the same carbon atom, together with the carbon atom to which they are both attached form an optionally substituted 3-7 membered spirocycloalkyl ring or an optionally substituted 3-7 membered spiroheterocycloalkyl ring;
or two $R^1$ groups attached to the same carbon atom, together with that carbon atom, represent a carbonyl group (C=O);
or two $R^2$ groups attached to the same carbon atom, together with the carbon atom to which they are both attached form an optionally substituted 3-7 membered spirocycloalkyl ring or an optionally substituted 3-7 membered spiroheterocycloalkyl ring;
or two $R^2$ groups attached to the same carbon atom, together with that carbon atom, represent a carbonyl group (C=O);
or two $R^1$ groups attached to different carbon atoms, together with the carbon atoms to which they are attached, form a 3-7 membered cycloalkyl ring;
or two $R^2$ groups attached to different carbon atoms, together with the carbon atoms to which they are attached, form a 3-7 membered cycloalkyl ring;
or an $R^1$ group and an $R^2$ group are attached to form a 6-9 membered bridged bicyclic ring;
A=N or CH;
Z=S(O)$_2$; S(O); O, NR$^3$ or CR$^4$R$^{4'}$;
$R^3$ is H; optionally substituted $C_1$-$C_6$alkyl, 3-5 membered cycloalkyl, 3-5 membered heterocycloalkyl, —C(O)NR$^a$R$^b$; —C(O)OR$^c$; —C(O)R$^c$; —S(O)$_2$R$^c$; or —S(O)$_2$NR$^a$R$^b$;
or $R^3$ together with an $R^1$ or an $R^2$ form an optionally substituted 3- to 7-membered heterocycloalkyl ring;
$R^a$ is H or $C_1$-$C_6$alkyl;
$R^b$ is H or $C_1$-$C_6$alkyl;
or $R^a$ and $R^b$ together with the N atom to which they are both attached, form an optionally substituted 3 to 7 membered heterocycloalkyl ring;
$R^c$ is optionally substituted $C_1$-$C_6$alkyl, or cycloalkyl;
$R^4$ is H, —F, or optionally substituted $C_1$-$C_6$alkyl;
$R^{4'}$ is H, —F, —OH, —CN, —NH$_2$, —NH(C$_1$-C$_3$alkyl), —N(C$_1$-C$_3$alkyl)$_2$, —N(C$_1$-C$_3$alkyl)-SO$_2$(C$_1$-C$_3$alkyl), —C$_1$-C$_6$haloalkyl, optionally substituted $C_1$-$C_6$alkyl, or optionally substituted $C_1$-$C_6$alkoxyl;
or $R^4$ and $R^{4'}$ together with the C atom to which they are both attached, form an optionally substituted 3 to 7 membered heterocycloalkyl ring or an optionally substituted 3 to 7 membered cycloalkyl ring;
or $R^4$ and $R^{4'}$, together with the carbon atom to which they are both attached, form an oxo group;
or $R^4$ together with an $R^1$ or an $R^2$ form an optionally substituted 3- to 7-membered heterocycloalkyl ring or an optionally substituted 3- to 7-membered cycloalkyl ring;
Y is an optionally substituted 5- or 6-membered heteroaryl ring, or an optionally substituted 6-membered aryl ring;
$Q^5$, $Q^6$, $Q^7$, $Q^8$, and $Q^9$, are each independently N or CR$^5$, wherein one or two of $Q^5$, $Q^6$, $Q^7$, $Q^8$, and $Q^9$ is N and the remainder are CR$^5$;
$R^5$ is H, halogen, $C_1$-$C_3$alkyl; $C_1$-$C_3$alkoxyl, or cycloalkyl;
X=O, S, or NR wherein R is H or $C_1$-$C_3$alkyl;
$R^6$ is $C_1$-$C_6$alkyl;
$R^7$is H, halogen, —$C_1$-$C_6$alkyl; —$C_1$-$C_6$ alkoxyl, or -cycloalkyl; and
$R^8$ is H, halogen, —$C_1$-$C_6$alkyl; —$C_1$-$C_6$ alkoxyl, or -cycloalkyl;
wherein groups that are identified as "optionally substituted" are either unsubstituted, or substituted with one or more of: —F, —Cl, —Br, —I, cyano, —OH, —$C_1$-$C_6$alkyl, $C_3$-$C_6$cycloalkyl, 3-7 membered heterocycloalkyl, —$C_3$-$C_6$spirocycloalkyl, 3-7 membered spiroheterocycloalkyl, bridged cycloalkyl, bridged heterocycloalkyl, $C_2$-$C_6$alkenyl, $C_2$-$C_6$ alkynyl, $C_1$-$C_6$haloalkyl, —$C_1$-C6alkoxy, —$C_1$-$C_6$ haloalkoxy, —$C_1$-$C_6$alkylthio, —$C_1$-$C_6$ alkylamino, —NH$_2$, —NH(C$_1$-C$_6$ alkyl), —N(C$_1$-C$_6$ alkyl)$_2$, —NH(C$_1$-C$_6$ alkoxy), —C(O)NHC$_1$-C$_6$alkyl, —C(O)N(C$_1$-C$_6$ alkyl)$_2$, —COOH, —C$_1$-C$_6$alkylCOOH, —C$_3$-C$_6$cycloalkylCOOH, —C(O)NH$_2$, —C$_1$-C$_6$alkylCONH$_2$, —C$_3$-C$_6$cycloalkylCONH$_2$, —C$_1$-C$_6$alkylCONHC$_1$-C$_6$alkyl, —C$_1$-C$_6$alkylCON(C$_1$-C$_6$alkyl)$_2$, —C(O)C$_1$-C$_6$ alkyl, —C(O)OC$_1$-C$_6$ alkyl, —NHCO(C$_1$-C$_6$ alkyl), —N(C$_1$-C$_6$ alkyl)C(O)(C$_1$-C$_6$ alkyl), —S(O)C$_1$-C$_6$ alkyl, —S(O)$_2$C$_1$-C$_6$ alkyl, oxo, 6-12 membered aryl, 5 to 12 membered heteroaryl groups, —C(O)(C$_1$-C$_6$haloalkyl), —NHSO$_2$(C$_1$-C$_6$alkyl), —N(C$_1$-C$_6$alkyl)SO$_2$(C$_1$-C$_6$alkyl), and —P(O)(C$_1$-C$_6$alkyl)$_2$.

2. The compound of claim 1,
wherein n=1, 2, or 3;
m=1, 2, or 3;
each $R^1$ is independently H or optionally substituted $C_1$-$C_6$alkyl;
each $R^2$ is independently H or optionally substituted $C_1$-$C_6$alkyl;
or two $R^1$ groups attached to the same carbon atom, together with the carbon atom to which they are both attached form an optionally substituted 3-7 membered spirocycloalkyl ring or an optionally substituted 3-7 membered spiroheterocycloalkyl ring;
or two $R^1$ groups attached to the same carbon atom, together with that carbon atom, represent a carbonyl group (C=O);
or two $R^2$ groups attached to the same carbon atom, together with the carbon atom to which they are both attached form an optionally substituted 3-7 membered spirocycloalkyl ring or an optionally substituted 3-7 membered spiroheterocycloalkyl ring;
or two $R^2$ groups attached to the same carbon atom, together with that carbon atom, represent a carbonyl group (C=O);
or two $R^1$ groups attached to different carbon atoms, together with the carbon atoms to which they are attached, form a 3-7 membered cycloalkyl ring;
or two $R^2$ groups attached to different carbon atoms, together with the carbon atoms to which they are attached, form a 3-7 membered cycloalkyl ring;
or an $R^1$ group and an $R^2$ group are attached to form a 6-9 membered bridged bicyclic ring;
A=N or CH;
Z=S(O)$_2$; S(O); O, NR$^3$ or CR$^4$R$^{4'}$, R$^3$ is H; optionally substituted $C_1$-$C_6$alkyl, 3-5-membered cycloalkyl, 3-5 membered heterocycloalkyl, —C(O)NR$^a$R$_b$; —C(O)OR$^c$; —C(O)R$^c$; —S(O)$_2$R$^c$; or —S(O)$_2$NR$^a$R$^b$;
$R^a$ is H or $C_1$-$C_6$alkyl;
$R^b$ is H or $C_1$-$C_6$alkyl;
or $R^a$ and $R^b$ together with the N atom to which they are both attached, form an optionally substituted 3 to 7 membered heterocycloalkyl ring;
$R^c$ is optionally substituted $C_1$-$C_6$alkyl, or cycloalkyl;
$R^4$ is H or optionally substituted $C_1$-$C_6$alkyl;
$R^{4'}$ is H, —OH, or optionally substituted $C_1$-$C_6$alkyl;
or $R^4$ and $R^{4'}$ together with the C atom to which they are both attached, form an optionally substituted 3 to 7 membered heterocycloalkyl ring;
Y is an optionally substituted 5- or 6-membered heteroaryl ring;
$Q^5$, $Q^6$, $Q^7$, $Q^8$, and $Q^9$, are each independently N or $CR^5$, wherein one or two of $Q^5$, $Q^6$, $Q^7$, $Q^8$, and $Q^9$ is N and the remainder are $CR^5$;
$R^5$ is H, halogen, $C_1$-$C_3$alkyl; $C_1$-$C_3$ alkoxyl, or cycloalkyl;
X=O, S, or NR wherein R is H or $C_1$-$C_3$alkyl;
$R^6$ is $C_1$-$C_6$alkyl;
$R^7$ is H, halogen, —$C_1$-$C_6$alkyl; —$C_1$-$C_6$ alkoxyl, or -cycloalkyl; and
$R^8$ is H, halogen, —$C_1$-$C_6$alkyl; —$C_1$-$C_6$ alkoxyl, or -cycloalkyl.

3. The compound according to claim 1, wherein Y is an optionally substituted 6-membered heteroaryl ring.

4. The compound according to claim 3, wherein the compound of formula (I) is a compound of formula (IA):

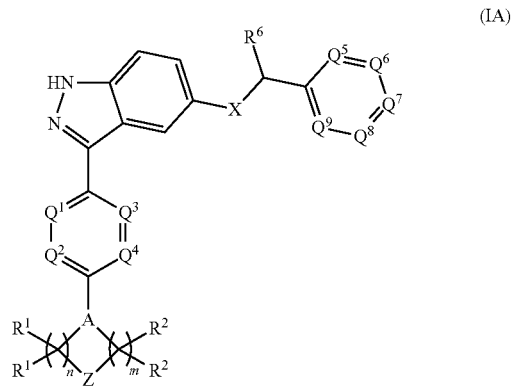

(IA)

wherein one or two of $Q^1$, $Q^2$, $Q^3$, $Q^4$ is N and the others are each independently $CR^{5a}$ wherein $R^{5a}$ is H, halogen, —CN, or $C_1$-$C_3$alkyl.

5. The compound according to claim 1, wherein X is O.

6. The compound according to claim 1, wherein $Q^5$ and $Q^9$ are each $CR^5$ wherein each $R^5$ is halogen; $Q^6$ and $Q^8$ are each $CR^5$ wherein each $R^5$ is H; and $Q^7$ is N.

7. The compound according to claim 4, wherein the compound of formula (IA) is a compound of formula (IA-1):

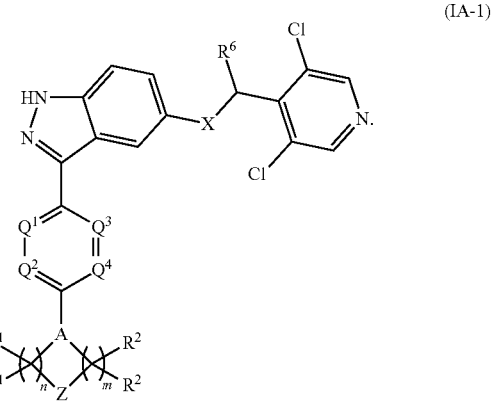

(IA-1)

8. The compound according to claim 1, wherein $R^6$ is —CH$_3$.

9. The compound according to claim 1, wherein the compound of formula (I) is a compound of formula (IA-8):

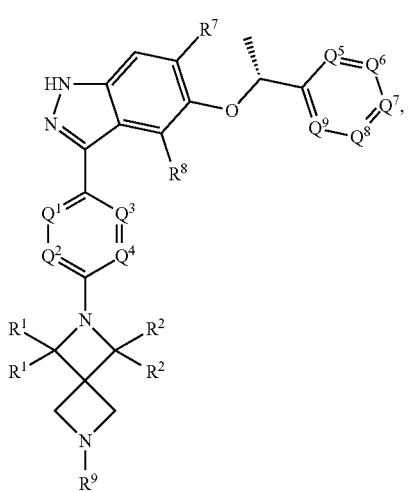

(IA-8)

wherein $R^9$ is $-C_1$-$C_6$alkyl, $-C_1$-$C_6$haloalkyl, $-C(O)C_1$-$C_6$haloalkyl, $-C(O)OC_1$-$C_6$alkyl, $-C(O)C_1$-$C_6$alkyl, $-C(O)N(C_1$-$C_6$alkyl$)_2$, or $-SO_2$—$C_1$-$C_6$alkyl; wherein one or two of $Q^1$, $Q^2$, $Q^3$, $Q^4$ is N and the others are each independently $CR^{5a}$ wherein $R^{5a}$ is H, halogen, —CN, or $C_1$-$C_3$alkyl.

10. The compound of claim 9, wherein $R^9$ is $-CH_2CF_3$, $-CH_2CHF_2$, $-C(O)CF_3$, $-C(O)OCH_3$, $-C(O)OCH_2CH_3$, $-SO_2CH_2CH_3$, or $-SO_2CH(CH_3)_2$.

11. The compound according to claim 9, wherein $Q^2$ is N.

12. The compound according to claim 9, wherein $Q^4$ is N.

13. The compound according to claim 9, wherein $Q^4$ is $CR^5a$, preferably wherein $R^{5a}$ is H or halogen, wherein the halogen is preferably —F.

14. The compound according to claim 1, wherein Z is $CR^4R^{4'}$.

15. The compound according to claim 14, wherein $R^4$ and $R^{4'}$ together with the C atom to which they are both attached, form an optionally substituted 3 to 7 membered heterocycloalkyl ring.

16. A pharmaceutical composition comprising a compound of claim 1, or a pharmaceutically acceptable salt thereof, and a pharmaceutically acceptable excipient.

17. A method of treating cancer in a subject in need thereof comprising administering to the subject a compound of claim 1, or a pharmaceutically acceptable salt thereof, wherein the cancer is urothelial carcinoma, breast carcinoma, endometrial adenocarcinoma, ovarian carcinoma, primary glioma, cholangiocarcinoma, gastric adenocarcinoma, non-small cell lung carcinoma, pancreatic exocrine carcinoma, oral, prostate, bladder, colorectal carcinoma, renal cell carcinoma, neuroendocrine carcinoma, myeloproliferative neoplasms, head and neck (squamous), melanoma, leiomyosarcoma, and/or sarcomas.

18. The method of claim 17, wherein the cancer is an intrahepatic cholangiocarcinoma.

19. The method of claim 17, wherein the cancer is an FGFR-mutant cancer.

20. A compound, or a pharmaceutically acceptable salt thereof, wherein the compound is
4-[5-[5-[(1R)-1-(3,5-dichloro-4-pyridyl)ethoxy]-1H-indazol-3-yl]-2-pyridyl]-1,4-thiazinane 1,1-dioxide;
(R)-5-(1-(3,5-Dichloropyridin-4-yl)ethoxy)-3-(6-(piperazin-1-yl)pyridin-3-yl)-1H-indazole dihydrochloride;
[4-[5-[5-[(1R)-1-(3,5-dichloro-4-pyridyl)ethoxy]-1H-indazol-3-yl]-2-pyridyl]piperazin-1-yl]-morpholino-methanone;
[4-[5-[5-[(1R)-1-(3,5-dichloro-4-pyridyl)ethoxy]-1H-indazol-3-yl]-2-pyridyl]piperazin-1-yl]-(4-methylpiperazin-1-yl)methanone;
4-[5-[5-[(1R)-1-(3,5-dichloro-4-pyridyl)ethoxy]-1H-indazol-3-yl]-2-pyridyl]-N,N-dimethyl-piperazine-1-carboxamide;
5-[(1R)-1-(3,5-dichloro-4-pyridyl)ethoxy]-3-[6-(4-methylsulfonylpiperazin-1-yl)-3-pyridyl]-1H-indazole;
Methyl 4-[5-[5-[(1R)-1-(3,5-dichloro-4-pyridyl)ethoxy]-1H-indazol-3-yl]-2-pyridyl]piperazine-1-carboxylate;
5-[(1R)-1-(3,5-dichloro-4-pyridyl)ethoxy]-3-[6-[4-(4-methylpiperazin-1-yl)sulfonylpiperazin-1-yl]-3-pyridyl]-1H-indazole;
1-[4-[5-[5-[(1R)-1-(3,5-dichloro-4-pyridyl)ethoxy]-1H-indazol-3-yl]-2-pyridyl]piperazin-1-yl]propan-1-one;
5-[(1R)-1-(3,5-Dichloro-4-pyridyl)ethoxy]-3-(5-fluoro-6-piperazin-1-yl-3-pyridyl)-1H-indazole;
5-[(1R)-1-(3,5-dichloro-4-pyridyl)ethoxy]-3-(2-piperazin-1-ylpyrimidin-5-yl)-1H-indazole;
4-[5-[5-[(1R)-1-(3,5-dichloro-4-pyridyl)ethoxy]-1H-indazol-3-yl]-2-pyridyl]piperazine-1-carboxamide;
[4-[5-[5-[(1R)-1-(3,5-Dichloro-4-pyridyl)ethoxy]-1H-indazol-3-yl]-3-fluoro-2-pyridyl]piperazin-1-yl]-(4-methylpiperazin-1-yl)methanone;
5-[(1R)-1-(3,5-Dichloro-4-pyridyl)ethoxy]-3-[2-(4-methylsulfonylpiperazin-1-yl)pyrimidin-5-yl]-1H-indazole;
[4-[5-[5-[(1R)-1-(3,5-dichloro-4-pyridyl)ethoxy]-1H-indazol-3-yl]pyrimidin-2-yl]piperazin-1-yl]-(4-methylpiperazin-1-yl)methanone;
3-[6-(3,6-Diazabicyclo[3.1.1]heptan-3-yl)-3-pyridyl]-5-[(1R)-1-(3,5-dichloro-4-pyridyl)ethoxy]-1H-indazole;
5-[(1R)-1-(3,5-Dichloro-4-pyridyl)ethoxy]-3-[5-fluoro-6-(4-methylsulfonyl-piperazin-1-yl)-3-pyridyl]-1H-indazole;
3-(6-Chloro-3-pyridyl)-5-[(1R)-1-(3,5-dichloro-4-pyridyl)ethoxy]-1H-indazole;
4-[5-[5-[(1R)-1-(3,5-Dichloro-4-pyridyl)ethoxy]-1H-indazol-3-yl]pyrimidin-2-yl]-N,N-dimethyl-piperazine-1-carboxamide;
5-[(1R)-1-(3,5-dichloro-4-pyridyl)ethoxy]-3-[6-(6-methylsulfonyl-3,6-diazabicyclo[3.1.1]heptan-3-yl)-3-pyridyl]-1H-indazole;
3-[6-(4,7-diazaspiro[2.5]octan-7-yl)-3-pyridyl]-5-[(1R)-1-(3,5-dichloro-4-pyridyl)ethoxy]-1H-indazole;
5-[(1R)-1-(3,5-dichloro-4-pyridyl)ethoxy]-3-[6-(4-methylsulfonyl-4,7-diazaspiro[2.5]octan-7-yl)-3-pyridyl]-1H-indazole;
(R)-7-(5-(5-(1-(3,5-dichloropyridin-4-yl)ethoxy)-1H-indazol-3-yl)pyridin-2-yl)-N,N-dimethyl-4, 7-diazaspiro[2.5]octane-4-carboxamide;
7-[5-[5-[(1R)-1-(3,5-dichloro-4-pyridyl)ethoxy]-1H-indazol-3-yl]-2-pyridyl]-4,7-diazaspiro[2.5]octane-4-carboxamide;
5-[(1R)-1-(3,5-Dichloro-4-pyridyl)ethoxy]-3-(6-fluoro-3-pyridyl)-1H-indazole;
8-[5-[5-[(1R)-1-(3,5-dichloro-4-pyridyl)ethoxy]-1H-indazol-3-yl]-2-pyridyl]-1-oxa-8-azaspiro[4.5]decane;
8-[5-[5-[(1R)-1-(3,5-dichloro-4-pyridyl)ethoxy]-1H-indazol-3-yl]-2-pyridyl]-2,8-diazaspiro[4.5]decan-1-one;
8-[5-[5-[(1R)-1-(3,5-dichloro-4-pyridyl)ethoxy]-1H-indazol-3-yl]-2-pyridyl]-2-oxa-8-azaspiro[4.5]decane;

8-[5-[5-[(1R)-1-(3,5-dichloro-4-pyridyl)ethoxy]-1H-indazol-3-yl]-2-pyridyl]-1,8-diazaspiro[4.5]decan-2-one;

1-[5-[5-[(1R)-1-(3,5-dichloro-4-pyridyl)ethoxy]-1H-indazol-3-yl]-2-pyridyl]-1,4-diazepan-5-one;

5-[(1R)-1-(3,5-dichloro-4-pyridyl)ethoxy]-3-[6-(2-isopropyl-2,6-diazaspiro[3.3]heptan-6-yl)-3-pyridyl]-1H-indazole;

8-[5-[5-[(1R)-1-(3,5-dichloro-4-pyridyl)ethoxy]-1H-indazol-3-yl]-2-pyridyl]-2-methyl-2,8-diazaspiro[4.5]decane;

8-[5-[5-[(1R)-1-(3,5-dichloro-4-pyridyl)ethoxy]-1H-indazol-3-yl]-2-pyridyl]-1-methyl-1,8-diazaspiro[4.5]decane;

9-[5-[5-[(1R)-1-(3,5-dichloro-4-pyridyl)ethoxy]-1H-indazol-3-yl]-2-pyridyl]-1-methyl-1,4,9-triazaspiro[5.5]undecan-5-one;

4-[5-[5-[(1R)-1-(3,5-dichloro-4-pyridyl)ethoxy]-1H-indazol-3-yl]-2-pyridyl]-1,4-diazepan-2-one;

4-[5-[5-[(1R)-1-(3,5-dichloro-4-pyridyl)ethoxy]-1H-indazol-3-yl]-2-pyridyl]piperazin-2-one;

1-[5-[5-[(1R)-1-(3,5-dichloro-4-pyridyl)ethoxy]-1H-indazol-3-yl]-2-pyridyl]piperazin-2-one;

1-[5-[5-[(1R)-1-(3,5-dichloro-4-pyridyl)ethoxy]-1H-indazol-3-yl]-2-pyridyl]-4-methyl-piperazin-2-one;

1-[5-[5-[(1R)-1-(3,5-dichloro-4-pyridyl)ethoxy]-1H-indazol-3-yl]-2-pyridyl]-4-methylsulfonyl-piperazin-2-one;

8-[5-[5-[(1R)-1-(3,5-dichloro-4-pyridyl)ethoxy]-1H-indazol-3-yl]-2-pyridyl]-1-methyl-1,8-diazaspiro[4.5]decan-2-one;

8-[5-[5-[(1R)-1-(3,5-dichloro-4-pyridyl)ethoxy]-1H-indazol-3-yl]-3-fluoro-2-pyridyl]-1,8-diazaspiro[4.5]decan-2-one;

8-[5-[5-[(1R)-1-(3,5-dichloro-4-pyridyl)ethoxy]-1H-indazol-3-yl]-3-fluoro-2-pyridyl]-1,8-diazaspiro[4.5]decan-2-one;

8-[5-[5-[(1R)-1-(3,5-dichloro-4-pyridyl)ethoxy]-1H-indazol-3-yl]-3-fluoro-2-pyridyl]-1-methyl-1,8-diazaspiro[4.5]decan-2-one;

9-[5-[5-[(1R)-1-(3,5-dichloro-4-pyridyl)ethoxy]-1H-indazol-3-yl]-3-fluoro-2-pyridyl]-1-methyl-1,4,9-triazaspiro[5.5]undecan-5-one;

3-[6-(2,6-diazaspiro[3.3]heptan-2-yl)-3-pyridyl]-5-[(1R)-1-(3,5-dichloro-4-pyridyl)ethoxy]-1H-indazole;

5-[(1R)-1-(3,5-dichloro-4-pyridyl)ethoxy]-3-[6-(2-methylsulfonyl-2,6-diazaspiro[3.3]heptan-6-yl)-3-pyridyl]-1H-indazole;

6-[5-[5-[(1R)-1-(3,5-dichloro-4-pyridyl)ethoxy]-1H-indazol-3-yl]-2-pyridyl]-N,N-dimethyl-2,6-diazaspiro[3.3]heptane-2-carboxamide;

8-[5-[5-[(1R)-1-(3,5-dichloro-4-pyridyl)ethoxy]-1H-indazol-3-yl]pyrimidin-2-yl]-1,8-diazaspiro[4.5]decan-2-one;

8-[5-[5-[(1R)-1-(3,5-dichloro-4-pyridyl)ethoxy]-1H-indazol-3-yl]pyrimidin-2-yl]-2,8-diazaspiro[4.5]decan-3-one;

8-[5-[5-[(1R)-1-(3,5-dichloro-4-pyridyl)ethoxy]-1H-indazol-3-yl]pyrimidin-2-yl]-2,8-diazaspiro-[4.5]decane-1,3-dione;

8-[5-[5-[(1R)-1-(3,5-dichloro-4-pyridyl)ethoxy]-1H-indazol-3-yl]pyrimidin-2-yl]-2-methyl-2,8-diazaspiro[4.5]decan-1-one;

8-[5-[5-[(1R)-1-(3,5-dichloro-4-pyridyl)ethoxy]-1H-indazol-3-yl]pyrimidin-2-yl]-1-methyl-1,8-diazaspiro[4.5]decane;

8-[5-[5-[(1R)-1-(3,5-dichloro-4-pyridyl)ethoxy]-1H-indazol-3-yl]pyrimidin-2-yl]-1,3,8-triazaspiro-[4.5]decan-2-one;

8-[5-[5-[(1R)-1-(3,5-dichloro-4-pyridyl)ethoxy]-1H-indazol-3-yl]pyrimidin-2-yl]-1-methyl-1,8-diazaspiro[4.5]decan-2-one;

8-[5-[5-[(1R)-1-(3,5-dichloro-4-pyridyl)ethoxy]-1H-indazol-3-yl]pyrimidin-2-yl]-2,8-diazaspiro-[4.5]decan-1-one;

8-[5-[5-[(1R)-1-(3,5-dichloro-4-pyridyl)ethoxy]-1H-indazol-3-yl]pyrimidin-2-yl]-1,8-diazaspiro[4.5]decane;

8-[5-[5-[(1R)-1-(3,5-dichloro-4-pyridyl)ethoxy]-1H-indazol-3-yl]pyrimidin-2-yl]-2$\lambda^6$-thia-8-azaspiro[4.5]decane 2,2-dioxide;

9-[5-[5-[(1R)-1-(3,5-dichloro-4-pyridyl)ethoxy]-1H-indazol-3-yl]pyrimidin-2-yl]-1-methyl-1,4,9-triazaspiro[5.5]undecan-5-one;

5-[(1R)-1-(3,5-Dichloro-4-pyridyl)ethoxy]-3-[2-[4-(oxetan-3-yl)-1,4-diazepan-1-yl]pyrimidin-5-yl]-1H-indazole;

3-[2-(1,4-Diazepan-1-yl)pyrimidin-5-yl]-5-[(1R)-1-(3,5-dichloro-4-pyridyl)ethoxy]-1H-indazole;

4-[5-[5-[(1R)-1-(3,5-Dichloro-4-pyridyl)ethoxy]-1H-indazol-3-yl]pyrimidin-2-yl]-1,4-diazepane-1-carboxamide;

5-[(1R)-1-(3,5-Dichloro-4-pyridyl)ethoxy]-3-[2-(4-methylsulfonyl-1,4-diazepan-1-yl)pyrimidin-5-yl]-1H-indazole;

5-[(1R)-1-(3,5-dichloro-4-pyridyl)ethoxy]-3-[1-(4-piperidyl)pyrazol-4-yl]-1H-indazole;

5-[(1R)-1-(3,5-dichloro-4-pyridyl)ethoxy]-3-[1-(1-methyl-4-piperidyl)pyrazol-4-yl]-1H-indazole;

5-[(1R)-1-(3,5-dichloro-4-pyridyl)ethoxy]-3-[1-(1-methylsulfonyl-4-piperidyl)pyrazol-4-yl]-1H-indazole;

4-[4-[5-[(1R)-1-(3,5-dichloro-4-pyridyl)ethoxy]-1H-indazol-3-yl]pyrazol-1-yl]-N,N-dimethyl-piperidine-1-carboxamide;

4-[4-[5-[(1R)-1-(3,5-dichloro-4-pyridyl)ethoxy]-1H-indazol-3-yl]pyrazol-1-yl]piperidine-1-carboxamide;

5-[(1R)-1-(3,5-dichloro-4-pyridyl)ethoxy]-3-[6-(4-piperidyl)-3-pyridyl]-1H-indazole;

5-[(1R)-1-(3,5-dichloro-4-pyridyl)ethoxy]-3-[6-(1-methylsulfonyl-4-piperidyl)-3-pyridyl]-1H-indazole;

4-[5-[5-[(1R)-1-(3,5-dichloro-4-pyridyl)ethoxy]-1H-indazol-3-yl]-2-pyridyl]-N,N-dimethyl-piperidine-1-carboxamide;

4-[5-[5-[(1R)-1-(3,5-dichloro-4-pyridyl)ethoxy]-1H-indazol-3-yl]-2-pyridyl]piperidine-1-carboxamide;

7-[5-[5-[(1R)-1-(3,5-dichloro-4-pyridyl)ethoxy]-1H-indazol-3-yl]-2-pyridyl]-5-oxa-2,7-diazaspiro[3.4]octan-6-one;

3-[5-[5-[(1R)-1-(3,5-dichloro-4-pyridyl)ethoxy]-1H-indazol-3-yl]-2-pyridyl]-1-oxa-3,8-diazaspiro[4.5]decan-2-one;

3-[5-[5-[(1R)-1-(3,5-dichloro-4-pyridyl)ethoxy]-1H-indazol-3-yl]-2-pyridyl]-8-methyl-1-oxa-3,8-diazaspiro[4.5]decan-2-one;

3-[5-[5-[(1R)-1-(3,5-dichloro-4-pyridyl)ethoxy]-1H-indazol-3-yl]-2-pyridyl]-8-methylsulfonyl-1-oxa-3,8-diazaspiro[4.5]decan-2-one;

8-[5-[5-[(1R)-1-(3,5-dichloro-4-pyridyl)ethoxy]-1H-indazol-3-yl]-3-fluoro-2-pyridyl]-2$\lambda^6$-thia-8-azaspiro[4.5]decane 2,2-dioxide;

8-[5-[5-[(1R)-1-(3,5-dichloro-4-pyridyl)ethoxy]-1H-indazol-3-yl]--2-pyridyl]-2$\lambda^6$-thia-8-azaspiro[4.5]decane 2,2-dioxide;

2-[4-[4-[5-[(1R)-1-(3,5-dichloro-4-pyridyl)ethoxy]-1H-indazol-3-yl]pyrazol-1-yl]-1-piperidyl]ethanol;
5-[(1R)-1-(3,5-dichloro-2-methyl-4-pyridyl)ethoxy]-3-[1-(1-methyl-4-piperidyl)pyrazol-4-yl]-1H-indazole;
1-[4-[4-[5-[(1R)-1-(3,5-dichloro-4-pyridyl)ethoxy]-1H-indazol-3-yl]pyrazol-1-yl]-1-piperidyl]-2-(dimethylamino)ethanone;
1-[4-[4-[5-[(1R)-1-(3,5-dichloro-4-pyridyl)ethoxy]-1H-indazol-3-yl]pyrazol-1-yl]-1-piperidyl]-3-(dimethylamino)propan-1-one;
5-[(1R)-1-(3,5-dichloro-4-pyridyl)ethoxy]-3-[1-(1-isopropyl-4-piperidyl)pyrazol-4-yl]-1H-indazole;
5-[(1R)-1-(3,5-dichloro-4-pyridyl)ethoxy]-3-[(1R)-1-(1-isopropylpyrrolidin-3-yl)pyrazol-4-yl]-1H-indazole;
3-[1-(azetidin-3-yl)pyrazol-4-yl]-5-[(1R)-1-(3,5-dichloro-4-pyridyl)ethoxy]-1H-indazole;
5-[(1R)-1-(3,5-dichloro-4-pyridyl)ethoxy]-3-[1-(1-isopropylazetidin-3-yl)pyrazol-4-yl]-1H-indazole;
5-[(1R)-1-(3,5-dichloro-4-pyridyl)ethoxy]-3-[1-[1-(oxetan-3-yl)-4-piperidyl]pyrazol-4-yl]-1H-indazole;
5-[(1R)-1-(3,5-dichloro-4-pyridyl)ethoxy]-3-[1-[(3S)-pyrrolidin-3-yl]pyrazol-4-yl]-1H-indazole;
5-[(1R)-1-(3,5-dichloro-4-pyridyl)ethoxy]-3-[1-[(3S)-1-ethylpyrrolidin-3-yl]pyrazol-4-yl]-1H-indazole;
3-[1-(1-cyclobutyl-4-piperidyl)pyrazol-4-yl]-5-[(1R)-1-(3,5-dichloro-4-pyridyl)ethoxy]-1H-indazole;
5-[(1R)-1-(3,5-dichloro-4-pyridyl)ethoxy]-3-[1-[(3R)-1-ethylpyrrolidin-3-yl]pyrazol-4-yl]-1H-indazole;
5-[(1R)-1-(3,5-dichloro-2-methyl-4-pyridyl)ethoxy]-3-[1-(4-piperidyl)pyrazol-4-yl]-1H-indazole;
5-[(1R)-1-(3,5-dichloro-2-methyl-4-pyridyl)ethoxy]-3-[1-(1-isopropyl-4-piperidyl)pyrazol-4-yl]-1H-indazole;
5-[(1R)-1-(3,5-dichloro-2-methyl-4-pyridyl)ethoxy]-3-[1-[1-(oxetan-3-yl)-4-piperidyl]pyrazol-4-yl]-1H-indazole;
3-[1-(1-cyclobutyl-4-piperidyl)pyrazol-4-yl]-5-[(1R)-1-(3,5-dichloro-2-methyl-4-pyridyl)ethoxy]-1H-indazole;
5-[(1R)-1-(3,5-dichloro-4-pyridyl)ethoxy]-3-[6-(1-methyl-1,6-diazaspiro[3.3]heptan-6-yl)-3-pyridyl]-1H-indazole;
9-[5-[5-[(1R)-1-(3,5-dichloro-4-pyridyl)ethoxy]-1H-indazol-3-yl]-2-pyridyl]-4-methyl-1,4,9-triazaspiro[5.5]undecan-2-one;
9-[5-[5-[(1R)-1-(3,5-dichloro-4-pyridyl)ethoxy]-1H-indazol-3-yl]-2-pyridyl]-1,4-dimethyl-1,4,9-triazaspiro[5.5]undecan-2-one;
3-[6-(1,6-diazaspiro[3.3]heptan-6-yl)-3-pyridyl]-5-[(1R)-1-(3,5-dichloro-4-pyridyl)ethoxy]-1H-indazole;
5-[(1R)-1-(3,5-dichloro-4-pyridyl)ethoxy]-3-[6-(1-methylsulfonyl-1,6-diazaspiro[3.3]heptan-6-yl)-3-pyridyl]-1H-indazole;
4-[5-[5-[(1R)-1-(3,5-dichloro-4-pyridyl)ethoxy]-1H-indazol-3-yl]-3-methyl-2-pyridyl]morpholine;
5-[5-[(1R)-1-(3,5-dichloro-4-pyridyl)ethoxy]-1H-indazol-3-yl]-2-morpholino-pyridine-3-carbonitrile;
4-[6-[5-[(1R)-1-(3,5-dichloro-4-pyridyl)ethoxy]-1H-indazol-3-yl]-3-pyridyl]morpholine;
5-[(1R)-1-(3,5-dichloro-2-methyl-4-pyridyl)ethoxy]-3-(1-tetrahydropyran-4-ylpyrazol-4-yl)-1H-indazole;
4-[5-[5-[(1R)-1-(3,5-dichloro-4-pyridyl)ethoxy]-1H-indazol-3-yl]-3-methoxy-2-pyridyl]morpholine;
5-[(1R)-1-(3,5-dichloro-4-pyridyl)ethoxy]-3-(1-tetrahydropyran-4-ylpyrazol-4-yl)-1H-indazole;
5-[(1R)-1-(3,5-dichloro-2-methyl-4-pyridyl)ethoxy]-3-[6-(2-methylsulfonyl-2,6-diazaspiro[3.3]heptan-6-yl)-3-pyridyl]-1H-indazole;
5-[1-(2,4-dichloro-3-pyridyl)ethoxy]-3-[1-[1-(oxetan-3-yl)-4-piperidyl]pyrazol-4-yl]-1H-indazole;
5-[1-(2,4-dichloro-3-pyridyl)ethoxy]-3-[6-(2-methylsulfonyl-2,6-diazaspiro[3.3]heptan-6-yl)-3-pyridyl]-1H-indazole;
3-[6-(2,7-diazaspiro[3.5]nonan-2-yl)-3-pyridyl]-5-[(1R)-1-(3,5-dichloro-4-pyridyl)ethoxy]-1H-indazole;
5-[(1R)-1-(3,5-dichloro-4-pyridyl)ethoxy]-3-[6-(7-methylsulfonyl-2,7-diazaspiro[3.5]nonan-2-yl)-3-pyridyl]-1H-indazole;
6-[5-[5-[(1R)-1-(3,5-dichloro-4-pyridyl)ethoxy]-1H-indazol-3-yl]-2-pyridyl]-2$\lambda^6$-thia-6-azaspiro[3.3]heptane 2,2-dioxide;
2-[5-[5-[(1R)-1-(3,5-dichloro-4-pyridyl)ethoxy]-1H-indazol-3-yl]-2-pyridyl]-7$\lambda^6$-thia-2-azaspiro[3.5]nonane 7,7-dioxide;
4-[4-[5-[(1R)-1-(3,5-dichloro-4-pyridyl)ethoxy]-1H-indazol-3-yl]pyrazol-1-yl]thiane 1,1-dioxide;
5-[(1R)-1-(3,5-dichloro-4-pyridyl)ethoxy]-3-[6-(7-methylsulfonyl-2,7-diazaspiro[3.4]octan-2-yl)-3-pyridyl]-1H-indazole;
4-[4-[5-[(1R)-1-(3,5-dichloro-2-methyl-4-pyridyl)ethoxy]-1H-indazol-3-yl]pyrazol-1-yl]thiane 1,1-dioxide;
2-[5-[5-[(1R)-1-(3,5-dichloro-4-pyridyl)ethoxy]-1H-indazol-3-yl]-2-pyridyl]-6$\lambda^6$-thia-2-azaspiro[3.4]octane 6,6-dioxide;
3-[2-(2,6-diazaspiro[3.3]heptan-2-yl)pyrimidin-5-yl]-5-[(1R)-1-(3,5-dichloro-4-pyridyl)ethoxy]-1H-indazole;
5-[(1R)-1-(3,5-dichloro-4-pyridyl)ethoxy]-3-[2-(2-methylsulfonyl-2,6-diazaspiro[3.3]heptan-6-yl)pyrimidin-5-yl]-1H-indazole;
5-[(1R)-1-(3,5-dichloro-4-pyridyl)ethoxy]-3-[2-(2-isopropylsulfonyl-2,6-diazaspiro[3.3]heptan-6-yl)pyrimidin-5-yl]-1H-indazole;
ethyl 6-[5-[5-[(1R)-1-(3,5-dichloro-4-pyridyl)ethoxy]-1H-indazol-3-yl]-2-pyridyl]-2,6-diazaspiro[3.3]heptane-2-carboxylate;
2-[5-[5-[(1R)-1-(3,5-dichloro-4-pyridyl)ethoxy]-1H-indazol-3-yl]pyrimidin-2-yl]-6$\lambda^6$-thia-2-azaspiro[3.4]octane 6,6-dioxide;
methyl 6-[5-[5-[(1R)-1-(3,5-dichloro-4-pyridyl)ethoxy]-1H-indazol-3-yl]-2-pyridyl]-2,6-diazaspiro[3.3]heptane-2-carboxylate;
5-[(1R)-1-(3,5-dichloro-4-pyridyl)ethoxy]-3-[6-(2-ethylsulfonyl-2,6-diazaspiro[3.3]heptan-6-yl)-3-pyridyl]-1H-indazole;
methyl 2-[5-[5-[(1R)-1-(3,5-dichloro-4-pyridyl)ethoxy]-1H-indazol-3-yl]-2-pyridyl]-2,7-diazaspiro[3.5]nonane-7-carboxylate;
ethyl 2-[5-[5-[(1R)-1-(3,5-dichloro-4-pyridyl)ethoxy]-1H-indazol-3-yl]pyrimidin-2-yl]-2,7-diazaspiro[3.5]nonane-7-carboxylate;
7-[5-[5-[(1R)-1-(3,5-dichloro-4-pyridyl)ethoxy]-1H-indazol-3-yl]pyrimidin-2-yl]-2$\lambda^6$-thia-7-azaspiro[4.4]nonane 2,2-dioxide;
5-[(1R)-1-(3,5-dichloro-4-pyridyl)ethoxy]-3-[2-(2-ethylsulfonyl-2,6-diazaspiro[3.3]heptan-6-yl)pyrimidin-5-yl]-1H-indazole;
2-[5-[5-[(1R)-1-(3,5-dichloro-4-pyridyl)ethoxy]-1H-indazol-3-yl]pyrimidin-2-yl]-6$\lambda^6$-thia-2-azaspiro[3.5]nonane 6,6-dioxide;

ethyl 2-[5-[5-[(1R)-1-(3,5-dichloro-4-pyridyl)ethoxy]-1H-indazol-3-yl]-2-pyridyl]-2,7-diazaspiro[3.5]nonane-7-carboxylate;
ethyl 2-[5-[5-[(1R)-1-(3,5-dichloro-4-pyridyl)ethoxy]-1H-indazol-3-yl]pyrimidin-2-yl]-2,8-diazaspiro[3.5]nonane-8-carboxylate;
3-[2-(2,8-diazaspiro[3.5]nonan-2-yl)pyrimidin-5-yl]-5-[(1R)-1-(3,5-dichloro-4-pyridyl)ethoxy]-1H-indazole;
3-[2-(2,7-diazaspiro[3.5]nonan-2-yl)pyrimidin-5-yl]-5-[(1R)-1-(3,5-dichloro-4-pyridyl)ethoxy]-1H-indazole;
5-[(1R)-1-(3,5-dichloro-4-pyridyl)ethoxy]-3-[2-(8-methylsulfonyl-2,8-diazaspiro[3.5]nonan-2-yl)pyrimidin-5-yl]-1H-indazole;
isopropyl 2-[5-[5-[(1R)-1-(3,5-dichloro-4-pyridyl)ethoxy]-1H-indazol-3-yl]pyrimidin-2-yl]-2,8-diazaspiro[3.5]nonane-8-carboxylate;
methyl 2-[5-[5-[(1R)-1-(3,5-dichloro-4-pyridyl)ethoxy]-1H-indazol-3-yl]pyrimidin-2-yl]-2,7-diazaspiro[3.5]nonane-7-carboxylate;
5-[(1R)-1-(3,5-dichloro-4-pyridyl)ethoxy]-3-[2-(7-methylsulfonyl-2,7-diazaspiro[3.5]nonan-2-yl)pyrimidin-5-yl]-1H-indazole;
methyl 2-[5-[5-[(1R)-1-(3,5-dichloro-4-pyridyl)ethoxy]-1H-indazol-3-yl]pyrimidin-2-yl]-2,8-diazaspiro[3.5]nonane-8-carboxylate;
5-[(1R)-1-(3,5-dimethyl-4-pyridyl)ethoxy]-3-[6-(2-methylsulfonyl-2,6-diazaspiro[3.3]heptan-6-yl)-3-pyridyl]-1H-indazole;
5-[(1S)-1-(3,5-dimethyl-4-pyridyl)ethoxy]-3-[6-(2-methylsulfonyl-2,6-diazaspiro[3.3]heptan-6-yl)-3-pyridyl]-1H-indazole;
2-[5-[5-[(1R)-1-(3,5-Dimethylpyridazin-4-yl)ethoxy]-1H-indazol-3-yl]-2-pyridyl]-6$\lambda^6$-thia-2-azaspiro[3.4]octane 6,6-dioxide;
2-[5-[5-[(1S)-1-(3,5-Dimethylpyridazin-4-yl)ethoxy]-1H-indazol-3-yl]-2-pyridyl]-6$\lambda^6$-thia-2-azaspiro[3.4]octane 6,6-dioxide;
2-[5-[5-[(1R)-1-(3,5-dimethylpyridazin-4-yl)ethoxy]-1H-indazol-3-yl]pyrimidin-2-yl]-6$\lambda^6$-thia-2-azaspiro[3.4]octane 6,6-dioxide;
ethyl 6-[5-[5-[(1R)-1-(3,5-dimethylpyridazin-4-yl)ethoxy]-1H-indazol-3-yl]-2-pyridyl]-2,6-diazaspiro[3.3]heptane-2-carboxylate;
methyl 6-[5-[5-[(1R)-1-(3,5-dimethylpyridazin-4-yl)ethoxy]-1H-indazol-3-yl]pyrimidin-2-yl]-2,6-diazaspiro[3.3]heptane-2-carboxylate;
2-[5-[5-[(1R)-1-(3,5-dimethylpyridazin-4-yl)ethoxy]-1H-indazol-3-yl]-2-pyridyl]-6$\lambda^6$-thia-2-azaspiro[3.4]octane 6,6-dioxide;
2-[5-[5-[(1S)-1-(3,5-dimethylpyridazin-4-yl)ethoxy]-1H-indazol-3-yl]-2-pyridyl]-6$\lambda^6$-thia-2-azaspiro[3.4]octane 6,6-dioxide;
ethyl 6-[5-[5-[(1R)-1-(3,5-dimethylpyridazin-4-yl)ethoxy]-1H-indazol-3-yl]pyrimidin-2-yl]-2,6-diazaspiro[3.3]heptane-2-carboxylate;
2-[5-[5-[(1S)-1-(3,5-dimethylpyridazin-4-yl)ethoxy]-1H-indazol-3-yl]pyrimidin-2-yl]-6$\lambda^6$-thia-2-azaspiro[3.4]octane 6,6-dioxide;
5-[(1R)-1-(3,5-dimethylpyridazin-4-yl)ethoxy]-3-[6-(2-methylsulfonyl-2,6-diazaspiro[3.3]heptan-6-yl)-3-pyridyl]-1H-indazole;
5-[(1S)-1-(3,5-dimethylpyridazin-4-yl)ethoxy]-3-[6-(2-methylsulfonyl-2,6-diazaspiro[3.3]heptan-6-yl)-3-pyridyl]-1H-indazole;
methyl 6-[5-[5-[(1R)-1-(3,5-dimethylpyridazin-4-yl)ethoxy]-1H-indazol-3-yl]-2-pyridyl]-2,6-diazaspiro[3.3]heptane-2-carboxylate;
ethyl 6-[5-[5-[(1S)-1-(3,5-dimethylpyridazin-4-yl)ethoxy]-1H-indazol-3-yl]-2-pyridyl]-2,6-diazaspiro[3.3]heptane-2-carboxylate;
8-[5-[5-[(1R)-1-(3,5-dimethylpyridazin-4-yl)ethoxy]-1H-indazol-3-yl]pyrimidin-2-yl]-2$\lambda^6$-thia-8-azaspiro[4.5]decane 2,2-dioxide;
methyl 6-[5-[5-[(1S)-1-(3,5-dimethylpyridazin-4-yl)ethoxy]-1H-indazol-3-yl]-2-pyridyl]-2,6-diazaspiro[3.3]heptane-2-carboxylate;
8-[5-[5-[(1S)-1-(3,5-dimethylpyridazin-4-yl)ethoxy]-1H-indazol-3-yl]pyrimidin-2-yl]-2$\lambda^6$-thia-8-azaspiro[4.5]decane 2,2-dioxide;
5-[(1S)-1-(3,5-dimethylpyridazin-4-yl)ethoxy]-3-[2-(2-methylsulfonyl-2,6-diazaspiro[3.3]heptan-6-yl)pyrimidin-5-yl]-1H-indazole;
5-[(1R)-1-(3,5-dimethylpyridazin-4-yl)ethoxy]-3-[2-(2-methylsulfonyl-2,6-diazaspiro[3.3]heptan-6-yl)pyrimidin-5-yl]-1H-indazole;
5-[(1R)-1-(3,5-dichloro-4-pyridyl)ethoxy]-3-[2-(7-methylsulfonyl-2,7-diazaspiro[3.4]octan-2-yl)pyrimidin-5-yl]-1H-indazole;
3-[2-(2,7-diazaspiro[3.4]octan-2-yl)pyrimidin-5-yl]-5-[(1R)-1-(3,5-dichloro-4-pyridyl)ethoxy]-1H-indazole;
2-[5-[5-[(1R)-1-(3,5-dichloro-4-pyridyl)ethoxy]-1H-indazol-3-yl]-2-pyridyl]-6$\lambda^6$-thia-2-azaspiro[3.5]nonane 6,6-dioxide;
5-[(1S)-1-(3,5-dichloro-4-pyridyl)ethoxy]-3-[6-(2-methylsulfonyl-2,6-diazaspiro[3.3]heptan-6-yl)-3-pyridyl]-1H-indazole;
3-[6-(2,8-diazaspiro[3.5]nonan-2-yl)-3-pyridyl]-5-[(1R)-1-(3,5-dichloro-4-pyridyl)ethoxy]-1H-indazole;
5-[(1R)-1-(3,5-dichloro-4-pyridyl)ethoxy]-3-[6-(8-methylsulfonyl-2,8-diazaspiro[3.5]nonan-2-yl)-3-pyridyl]-1H-indazole;
5-[(1R)-1-(3,5-dichloro-4-pyridyl)ethoxy]-3-[6-(7-methylsulfonyl-2,7-diazaspiro[3.4]octan-2-yl)-3-pyridyl]-1H-indazole;
3-[6-(2,7-diazaspiro[3.4]octan-2-yl)-3-pyridyl]-5-[(1R)-1-(3,5-dichloro-4-pyridyl)ethoxy]-1H-indazole;
methyl 2-[5-[5-[(1R)-1-(3,5-dichloro-4-pyridyl)ethoxy]-1H-indazol-3-yl]-2-pyridyl]-2,8-diazaspiro[3.5]nonane-8-carboxylate;
5-[(1R)-1-(3,5-difluorophenyl)ethoxy]-3-[1-(4-piperidyl)pyrazol-4-yl]-1H-indazole;
3-[1-(1-cyclobutyl-4-piperidyl)pyrazol-4-yl]-5-[(1R)-1-(3,5-difluorophenyl)ethoxy]-1H-indazole;
5-[(1R)-1-(3,5-difluorophenyl)ethoxy]-3-[1-[1-(oxetan-3-yl)-4-piperidyl]pyrazol-4-yl]-1H-indazole;
3-[6-(2,6-diazaspiro[3.3]heptan-2-yl)-3-pyridyl]-5-[(1R)-1-(3,5-difluorophenyl)ethoxy]-1H-indazole;
5-[(1R)-1-(2,6-dichlorophenyl)ethoxy]-3-[6-(2-methylsulfonyl-2,6-diazaspiro[3.3]heptan-6-yl)-3-pyridyl]-1H-indazole;
4-[4-[5-[(1R)-1-(3,5-difluorophenyl)ethoxy]-1H-indazol-3-yl]pyrazol-1-yl]thiane 1,1-dioxide;
5-[(1R)-1-(3,5-difluorophenyl)ethoxy]-3-[6-(2-methylsulfonyl-2,6-diazaspiro[3.3]heptan-6-yl)-3-pyridyl]-1H-indazole;
5-[5-[(1R)-1-(3,5-dimethylpyridazin-4-yl)ethoxy]-1H-indazol-3-yl]-2-pyrrolidin-1-yl-pyridine-3-carbonitrile;
5-[(1R)-1-(3,5-dichloro-4-pyridyl)ethoxy]-6-methoxy-3-[6-(2-methylsulfonyl-2,6-diazaspiro[3.3]heptan-6-yl)-3-pyridyl]-1H-indazole;
5-[(1S)-1-(3,5-dimethylpyridazin-4-yl)ethoxy]-6-methoxy-3-[6-(2-methylsulfonyl-2,6-diazaspiro[3.3]heptan-6-yl)-3-pyridyl]-1H-indazole;

Ethyl 6-[5-[5-[(1S)-1-(3,5-dichloro-2-fluoro-4-pyridyl)ethoxy]-1H-indazol-3-yl]-2-pyridyl]-2,6-diazaspiro[3.3]heptane-2-carboxylate;
5-[(1R)-1-(3,5-dimethylpyridazin-4-yl)ethoxy]-6-methoxy-3-[6-(2-methylsulfonyl-2,6-diazaspiro[3.3]heptan-6-yl)-3-pyridyl]-1H-indazole;
5-[(1R)-1-(3,5-dimethylpyridazin-4-yl)ethoxy]-4-methoxy-3-[6-(2-methylsulfonyl-2,6-diazaspiro[3.3]heptan-6-yl)-3-pyridyl]-1H-indazole;
(R)-5-(5-(1-(3,5-dimethylpyridazin-4-yl)ethoxy)-6-methoxy-1H-indazol-3-yl)-2-(2-oxa-6-azaspiro[3.3]heptan-6-yl)nicotinonitrile;
(R)-5-(1-(3,5-dichloropyridin-4-yl)ethoxy)-3-(3,5-difluoro-4-(6-(methylsulfonyl)-2,6-diazaspiro[3.3]heptan-2-yl)phenyl)-6-methoxy-1H-indazole;
5-[5-[(1R)-1-(3,5-dichloro-4-pyridyl)ethoxy]-6-fluoro-1H-indazol-3-yl]-2-(6,6-dioxo-6λ⁶-thia-2-azaspiro[3.5]nonan-2-yl)pyridine-3-carbonitrile;
3-[6-[(8aS)-3,4,6,7,8,8a-hexahydro-1H-pyrrolo[1,2-a]pyrazin-2-yl]-3-pyridyl]-5-[(1R)-1-(3,5-dimethylpyridazin-4-yl)ethoxy]-1H-indazole;
Example 175;
3-[6-[(8aR)-3,4,6,7,8,8a-hexahydro-1H-pyrrolo[1,2-a]pyrazin-2-yl]-3-pyridyl]-5-[(1R)-1-(3,5-dimethylpyridazin-4-yl)ethoxy]-1H-indazole;
(7R,8aS)-2-[5-[5-[(1R)-1-(3,5-dimethylpyridazin-4-yl)ethoxy]-1H-indazol-3-yl]-2-pyridyl]-3,4,6,7,8,8a-hexahydro-1H-pyrrolo[1,2-a]pyrazin-7-ol;
3-[6-(2,6-diazaspiro[3.3]heptan-2-yl)-3-pyridyl]-5-[(1R)-1-(3,5-dichloro-2-methyl-4-pyridyl)ethoxy]-1H-indazole;
(7R,8aS)-2-[5-[5-[(1R)-1-(3,5-dichloro-4-pyridyl)ethoxy]-1H-indazol-3-yl]-2-pyridyl]-3,4,6,7,8,8a-hexahydro-1H-pyrrolo[1,2-a]pyrazin-7-ol;
3-[2-(2,6-diazaspiro[3.3]heptan-2-yl)pyrimidin-5-yl]-5-[(1R)-1-(3,5-dichloro-2-methyl-4-pyridyl)ethoxy]-1H-indazole;
5-[(1R)-1-(3,5-dichloro-2-methyl-4-pyridyl)ethoxy]-3-[6-(2-ethylsulfonyl-2,6-diazaspiro[3.3]heptan-6-yl)-3-pyridyl]-1H-indazole;
5-[(1R)-1-(3,5-dichloro-2-methyl-4-pyridyl)ethoxy]-3-[2-(2-ethylsulfonyl-2,6-diazaspiro[3.3]heptan-6-yl)pyrimidin-5-yl]-1H-indazole;
ethyl 2-[5-[5-[(1R)-1-(3,5-dimethylpyridazin-4-yl)ethoxy]-1H-indazol-3-yl]-2-pyridyl]-2,8-diazaspiro[3.5]nonane-8-carboxylate;
3-[6-[(8aS)-3,4,6,7,8,8a-hexahydro-1H-pyrrolo[1,2-a]pyrazin-2-yl]-3-pyridyl]-5-[(1R)-1-(3,5-dichloro-4-pyridyl)ethoxy]-1H-indazole;
3-[6-[(8aR)-3,4,6,7,8,8a-hexahydro-1H-pyrrolo[1,2-a]pyrazin-2-yl]-3-pyridyl]-5-[(1R)-1-(3,5-dichloro-4-pyridyl)ethoxy]-1H-indazole;
ethyl 6-[5-[5-[(1R)-1-(3,5-dichloro-2-methyl-4-pyridyl)ethoxy]-1H-indazol-3-yl]pyrimidin-2-yl]-2,6-diazaspiro[3.3]heptane-2-carboxylate;
5-[(1R)-1-(3,5-dimethylpyridazin-4-yl)ethoxy]-3-[6-(8-ethylsulfonyl-2,8-diazaspiro[3.5]nonan-2-yl)-3-pyridyl]-1H-indazole;
methyl 2-[5-[5-[(1R)-1-(3,5-dimethylpyridazin-4-yl)ethoxy]-1H-indazol-3-yl]-2-pyridyl]-2,8-diazaspiro[3.5]nonane-8-carboxylate;
5-[(1R)-1-(3,5-dimethylpyridazin-4-yl)ethoxy]-3-[6-(8-methylsulfonyl-2,8-diazaspiro[3.5]nonan-2-yl)-3-pyridyl]-1H-indazole;
isopropyl 2-[5-[5-[(1R)-1-(3,5-dimethylpyridazin-4-yl)ethoxy]-1H-indazol-3-yl]-2-pyridyl]-2,8-diazaspiro[3.5]nonane-8-carboxylate;
ethyl 6-[5-[5-[(1R)-1-(3,5-dichloro-2-methyl-4-pyridyl)ethoxy]-1H-indazol-3-yl]-2-pyridyl]-2,6-diazaspiro[3.3]heptane-2-carboxylate;
5-[(1R)-1-(3,5-dichloro-4-pyridyl)ethoxy]-6-methoxy-3-[6-(2-methylsulfonyl-2,6-diazaspiro[3.3]heptan-6-yl)-3-pyridyl]-1H-indazole;
5-[(1S)-1-(3,5-dimethylpyridazin-4-yl)ethoxy]-6-methoxy-3-[6-(2-methylsulfonyl-2,6-diazaspiro[3.3]heptan-6-yl)-3-pyridyl]-1H-indazole;
ethyl 6-[5-[5-[(1S)-1-(3,5-dichloro-2-fluoro-4-pyridyl)ethoxy]-1H-indazol-3-yl]-2-pyridyl]-2,6-diazaspiro[3.3]heptane-2-carboxylate;
5-[(1R)-1-(3,5-dimethylpyridazin-4-yl)ethoxy]-6-methoxy-3-[6-(2-methylsulfonyl-2,6-diazaspiro[3.3]heptan-6-yl)-3-pyridyl]-1H-indazole;
methyl 6-[5-[5-[(1R)-1-(3,5-dichloro-2-fluoro-4-pyridyl)ethoxy]-1H-indazol-3-yl]-2-pyridyl]-2,6-diazaspiro[3.3]heptane-2-carboxylate;
ethyl 6-[5-[5-[(1R)-1-(3,5-dichloro-2-fluoro-4-pyridyl)ethoxy]-1H-indazol-3-yl]-2-pyridyl]-2,6-diazaspiro[3.3]heptane-2-carboxylate;
5-[(1R)-1-(3,5-dichloro-2-fluoro-4-pyridyl)ethoxy]-3-[6-(2-methylsulfonyl-2,6-diazaspiro[3.3]heptan-6-yl)-3-pyridyl]-1H-indazole;
methyl 6-[5-[5-[(1S)-1-(3,5-dichloro-2-fluoro-4-pyridyl)ethoxy]-1H-indazol-3-yl]-2-pyridyl]-2,6-diazaspiro[3.3]heptane-2-carboxylate;
5-[(1S)-1-(3,5-dichloro-2-fluoro-4-pyridyl)ethoxy]-3-[6-(2-methylsulfonyl-2,6-diazaspiro[3.3]heptan-6-yl)-3-pyridyl]-1H-indazole;
5-[(1R)-1-(3,5-dimethylpyridazin-4-yl)ethoxy]-4-methoxy-3-[6-(2-methylsulfonyl-2,6-diazaspiro[3.3]heptan-6-yl)-3-pyridyl]-1H-indazole;
6-[5-[5-[(1R)-1-(3,5-dichloro-2-methyl-4-pyridyl)ethoxy]-1H-indazol-3-yl]-2-pyridyl]-2-oxa-6-azaspiro[3.3]heptane;
6-[5-[5-[(1R)-1-(3,5-dimethylpyridazin-4-yl)ethoxy]-6-methoxy-1H-indazol-3-yl]-2-pyridyl]-2-oxa-6-azaspiro[3.3]heptane;
6-[5-[5-[(1R)-1-(3,5-dichloro-2-fluoro-4-pyridyl)ethoxy]-1H-indazol-3-yl]-2-pyridyl]-2-oxa-6-azaspiro[3.3]heptane;
(R)-2-(5-(5-(1-(3,5-dichloro-2-fluoropyridin-4-yl)ethoxy)-1H-indazol-3-yl)pyridin-2-yl)-6-oxa-2-azaspiro[3.4]octane;
6-[5-[5-[(1R)-1-(3,5-dimethylpyridazin-4-yl)ethoxy]-1H-indazol-3-yl]-2-pyridyl]-2-oxa-6-azaspiro[3.3]heptane;
(R)-2-(5-(5-(1-(3,5-dimethylpyridazin-4-yl)ethoxy)-1H-indazol-3-yl)pyridin-2-yl)-6-oxa-2-azaspiro[3.4]octane;
5-[(1R)-1-(3,5-dichloro-2-methyl-4-pyridyl)ethoxy]-6-methoxy-3-[6-(2-methylsulfonyl-2,6-diazaspiro[3.3]heptan-6-yl)-3-pyridyl]-1H-indazole;
1-[5-[5-[(1R)-1-(3,5-dichloro-2-methyl-4-pyridyl)ethoxy]-6-methoxy-1H-indazol-3-yl]-2-pyridyl]azetidin-3-ol;
(3R)-1-[5-[5-[(1R)-1-(3,5-dichloro-2-methyl-4-pyridyl)ethoxy]-6-methoxy-1H-indazol-3-yl]-2-pyridyl]pyrrolidin-3-ol;
5-[(1R)-1-(3,5-dichloro-2-methyl-4-pyridyl)ethoxy]-3-[6-(3-methoxy-3-methyl-azetidin-1-yl)-3-pyridyl]-1H-indazole;
6-[5-[5-[(1R)-1-(3,5-dichloro-2-methyl-4-pyridyl)ethoxy]-6-methoxy-1H-indazol-3-yl]-2-pyridyl]-2-oxa-6-azaspiro[3.3]heptane;

3-[6-(2-azaspiro[3.3]-heptan-2-yl)-3-pyridyl]-5-[(1R)-1-(3,5-dichloro-2-methyl-4-pyridyl)ethoxy]-1H-indazole;

3-(5-(5-((R)-1-(3,5-dimethylpyridazin-4-yl)ethoxy)-6-methoxy-1H-indazol-3-yl)pyridin-2-yl)-6-ethyl-3,6-diazabicyclo[3.1.1]heptane;

1-(3-(5-(5-((R)-1-(3,5-dimethylpyridazin-4-yl)ethoxy)-6-methoxy-1H-indazol-3-yl)-3-methylpyridin-2-yl)-3,6-diazabicyclo[3.1.1]heptan-6-yl)-2-methylpropan-2-ol;

2-[5-[5-[(1R)-1-(3,5-dichloro-2-methyl-4-pyridyl)ethoxy]-6-methoxy-1H-indazol-3-yl]-2-pyridyl]-1,3,4,7,8,8a-hexahydropyrrolo[1,2-a]pyrazin-6-one;

2-[5-[5-[(1R)-1-(3,5-dichloro-2-methyl-4-pyridyl)ethoxy]-1H-indazol-3-yl]-2-pyridyl]-6-oxa-2-azaspiro[3.4]octane;

2-[5-[5-[(1R)-1-(3,5-dichloro-2-methyl-4-pyridyl)ethoxy]-1H-indazol-3-yl]-3-methyl-2-pyridyl]-6-oxa-2-azaspiro[3.4]octane;

(R)-5-(5-(1-(3,5-dimethylpyridazin-4-yl)ethoxy)-6-methoxy-1H-indazol-3-yl)-2-(2-oxa-6-azaspiro[3.3]heptan-6-yl)nicotinonitrile;

(R)-6-(5-(5-(1-(3,5-dimethylpyridazin-4-yl)ethoxy)-6-methoxy-1H-indazol-3-yl)-3-methylpyridin-2-yl)-2-oxa-6-azaspiro[3.3]heptane;

5-[(1R)-1-(3,5-dichloro-2-methyl-4-pyridyl)ethoxy]-6-methoxy-3-(6-pyrrolidin-1-yl-3-pyridyl)-1H-indazole;

(3S)-1-[5-[5-[(1R)-1-(3,5-dichloro-2-methyl-4-pyridyl)ethoxy]-6-methoxy-1H-indazol-3-yl]-2-pyridyl]pyrrolidin-3-ol;

1-[5-[5-[(1R)-1-(3,5-dichloro-2-methyl-4-pyridyl)ethoxy]-1H-indazol-3-yl]-2-pyridyl]-3-methyl-azetidin-3-ol;

(R)-2-(5-(5-(1-(3,5-dichloropyridazin-4-yl)ethoxy)-1H-indazol-3-yl)pyridin-2-yl)-6-oxa-2-azaspiro[3.4]octane;

(R)-5-(1-(3,5-dichloropyridin-4-yl)ethoxy)-3-(6-(6-(2,2,2-trifluoroethyl)-2,6-diazaspiro[3.3]heptan-2-yl)pyridin-3-yl)-1H-indazole;

2-[5-[5-[(1R)-1-(3,5-dichloro-2-methyl-4-pyridyl)ethoxy]-1H-indazol-3-yl]-2-pyridyl]-1,3,4,7,8,8a-hexahydropyrrolo[1,2-a]pyrazin-6-one;

2-[5-[5-[(1R)-1-(3,5-dichloro-2-methyl-4-pyridyl)ethoxy]-1H-indazol-3-yl]-2-pyridyl]-5-oxa-2-azaspiro[3.4]octane;

2-[5-[5-[(1R)-1-(3,5-dichloro-2-methyl-4-pyridyl)ethoxy]-1H-indazol-3-yl]-2-pyridyl]-2-azaspiro[3.3]heptan-6-ol;

7-(5-(5-((R)-1-(3,5-dimethylpyridazin-4-yl)ethoxy)-6-methoxy-1H-indazol-3-yl)pyridin-2-yl)hexahydroimidazo[1,5-a]pyrazin-3(2H)-one;

(R)-6-(5-(5-(1-(3,5-dichloropyridazin-4-yl)ethoxy)-1H-indazol-3-yl)pyridin-2-yl)-2-oxa-6-azaspiro[3.3]heptane;

(R)-5-(1-(3,5-dichloropyridin-4-yl)ethoxy)-3-(6-(6-(2,2-difluoroethyl)-2,6-diazaspiro[3.3]heptan-2-yl)pyridin-3-yl)-1H-indazole;

7-(5-(5-((R)-1-(3,5-dimethylpyridazin-4-yl)ethoxy)-1H-indazol-3-yl)-3-methylpyridin-2-yl)hexahydroimidazo[1,5-a]pyrazin-3(2H)-one;

[(2R)-1-[5-[5-[(1R)-1-(3,5-dichloro-2-methyl-4-pyridyl)ethoxy]-1H-indazol-3-yl]-2-pyridyl]pyrrolidin-2-yl]methanol;

(R)-5-(1-(3,5-dichloropyridazin-4-yl)ethoxy)-3-(6-(6-(methylsulfonyl)-2,6-diazaspiro[3.3]heptan-2-yl)pyridin-3-yl)-1H-indazole;

[1-[5-[5-[(1R)-1-(3,5-dichloro-2-methyl-4-pyridyl)ethoxy]-1H-indazol-3-yl]-3-methyl-2-pyridyl]-3-(hydroxymethyl)azetidin-3-yl]methanol;

5-[(1R)-1-(3,5-dichloro-2-methyl-4-pyridyl)ethoxy]-3-[5-methyl-6-(2-methylsulfonyl-2,6-diazaspiro[3.3]heptan-6-yl)-3-pyridyl]-1H-indazole;

((R)-1-(5-(5-((R)-1-(3,5-dichloropyridin-4-yl)ethoxy)-1H-indazol-3-yl)pyridin-2-yl) pyrrolidin-2-yl) methanol;

((S)-1-(5-(5-((R)-1-(3,5-dichloropyridin-4-yl)ethoxy)-1H-indazol-3-yl)pyridin-2-yl) pyrrolidin-2-yl) methanol;

5-[(1R)-1-(3,5-dichloro-2-methyl-4-pyridyl)ethoxy]-3-[6-(6-methoxy-2-azaspiro[3.3]heptan-2-yl)-3-pyridyl]-1H-indazole;

5-[(1R)-1-(3,5-dichloro-4-pyridyl)ethoxy]-6-methoxy-3-[2-(2-methylsulfonyl-2,6-diazaspiro[3.3]heptan-6-yl)pyrimidin-5-yl]-1H-indazole;

5-[(1R)-1-(3,5-dichloro-2-methyl-4-pyridyl)ethoxy]-6-methoxy-3-[2-(2-methylsulfonyl-2,6-diazaspiro[3.3]heptan-6-yl)pyrimidin-5-yl]-1H-indazole;

[(2S)-1-[5-[5-[(1R)-1-(3,5-dichloro-2-methyl-4-pyridyl)ethoxy]-1H-indazol-3-yl]-2-pyridyl]pyrrolidin-2-yl]methanol;

5-[(1R)-1-(3,5-dichloro-4-pyridyl)ethoxy]-3-[5-fluoro-6-(2-methylsulfonyl-2,6-diazaspiro[3.3]heptan-6-yl)-3-pyridyl]-6-methoxy-1H-indazole;

5-[(1R)-1-(3,5-dichloro-2-methyl-4-pyridyl)ethoxy]-3-[5-fluoro-6-(2-methylsulfonyl-2,6-diazaspiro[3.3]heptan-6-yl)-3-pyridyl]-6-methoxy-1H-indazole;

5-[(1R)-1-(3,5-dichloro-2-methyl-4-pyridyl)ethoxy]-3-[5-fluoro-6-(2-methylsulfonyl-2,6-diazaspiro[3.3]heptan-6-yl)-3-pyridyl]-1H-indazole;

1-[6-[5-[(1R)-1-(3,5-dichloro-4-pyridyl)ethoxy]-1H-indazol-3-yl]-2-pyridyl]-2,6-diazaspiro[3.3]heptan-2-yl]-2,2,2-trifluoro-ethanone;

(R)-5-(1-(3,5-dichloropyridazin-4-yl)ethoxy)-3-(6-(6-(methylsulfonyl)-2,6-diazaspiro[3.3]heptan-2-yl)pyridin-3-yl)-1H-indazole;

2-[5-[5-[(1R)-1-(3,5-dichloro-2-methyl-4-pyridyl)ethoxy]-1H-indazol-3-yl]-2-pyridyl]-2-azaspiro[3.4]octan-6-ol;

5-[(1R)-1-(3,5-dichloro-4-pyridyl)ethoxy]-3-[5-methyl-6-(2-methylsulfonyl-2,6-diazaspiro[3.3]heptan-6-yl)-3-pyridyl]-1H-indazole;

(R)-5-(1-(3,5-dichloropyridin-4-yl)ethoxy)-3-(6-(3-(trifluoromethyl)azetidin-1-yl)pyridin-3-yl)-1H-indazole;

5-[(1R)-1-(3,5-dichloro-4-pyridyl)ethoxy]-6-methoxy-3-[5-methyl-6-(2-methylsulfonyl-2,6-diazaspiro[3.3]heptan-6-yl)-3-pyridyl]-1H-indazole;

(R)-5-(1-(3,5-dichloropyridin-4-yl)ethoxy)-6-methyl-3-(6-(6-(methylsulfonyl)-2,6-diazaspiro[3.3]heptan-2-yl)pyridin-3-yl)-1H-indazole;

(R)-5-(1-(3,5-dichloropyridin-4-yl)ethoxy)-3-(6-(3-(difluoromethyl)azetidin-1-yl)pyridin-3-yl)-1H-indazole;

(R)-1-(5-(5-(1-(3,5-dichloropyridin-4-yl)ethoxy)-1H-indazol-3-yl)pyridin-2-yl) azetidine-3-carbonitrile;

(S)-5-(1-(3,5-dichloropyridazin-4-yl)ethoxy)-3-(5-fluoro-6-(6-(methylsulfonyl)-2,6-diazaspiro[3.3]heptan-2-yl)pyridin-3-yl)-6-methyl-1H-indazole;

(R)-5-(1-(3,5-dichloropyridin-4-yl)ethoxy)-6-fluoro-3-(6-(6-(methylsulfonyl)-2,6-diazaspiro[3.3]heptan-2-yl)pyridin-3-yl)-1H-indazole;

5-[(1R)-1-(3,5-dichloro-4-pyridyl)ethoxy]-6-fluoro-3-[5-fluoro-6-(2-methylsulfonyl-2,6-diazaspiro[3.3]heptan-6-yl)-3-pyridyl]-1H-indazole;

(R)-1-(5-(5-(1-(3,5-dichloropyridin-4-yl)ethoxy)-1H-indazol-3-yl)pyridin-2-yl)-3-methylazetidin-3-amine;
(R)-5-(1-(3,5-dichloropyridazin-4-yl)ethoxy)-6-fluoro-3-(5-fluoro-6-(6-(methylsulfonyl)-2,6-diazaspiro[3.3]heptan-2-yl)pyridin-3-yl)-1H-indazole;
(R)-5-(1-(3,5-dichloropyridazin-4-yl)ethoxy)-3-(5-fluoro-6-(6-(methylsulfonyl)-2,6-diazaspiro[3.3]heptan-2-yl)pyridin-3-yl)-6-methyl-1H-indazole;
(R)-6-chloro-5-(1-(3,5-dichloropyridin-4-yl)ethoxy)-3-(6-(6-(methylsulfonyl)-2,6-diazaspiro[3.3]heptan-2-yl)pyridin-3-yl)-1H-indazole;
(R)-5-(1-(3,5-dichloropyridazin-4-yl)ethoxy)-6-methoxy-3-(6-(6-(methylsulfonyl)-2,6-diazaspiro[3.3]heptan-2-yl)pyridin-3-yl)-1H-indazole;
(R)-5-(1-(3,5-dichloropyridazin-4-yl)ethoxy)-6-fluoro-3-(6-(6-(methylsulfonyl)-2,6-diazaspiro[3.3]heptan-2-yl)pyridin-3-yl)-1H-indazole;
(R)-6-chloro-5-(1-(3,5-dichloropyridazin-4-yl)ethoxy)-3-(6-(6-(methylsulfonyl)-2,6-diazaspiro[3.3]heptan-2-yl)pyridin-3-yl)-1H-indazole;
(R)-6-chloro-5-(1-(3,5-dichloropyridazin-4-yl)ethoxy)-3-(5-fluoro-6-(6-(methylsulfonyl)-2,6-diazaspiro[3.3]heptan-2-yl)pyridin-3-yl)-1H-indazole;
(R)-1-(5-(5-(1-(3,5-dichloropyridin-4-yl)ethoxy)-1H-indazol-3-yl)-3-fluoropyridin-2-yl)-3-methylazetidin-3-amine;
5-[(1R)-1-(3,5-dichloro-2-methyl-4-pyridyl)ethoxy]-6-fluoro-3-[6-(2-methylsulfonyl-2,6-diazaspiro[3.3]heptan-6-yl)-3-pyridyl]-1H-indazole;
5-((R)-1-(3,5-dichloropyridin-4-yl)ethoxy)-3-(5-fluoro-6-((R)-2-methylazetidin-1-yl)pyridin-3-yl)-6-methoxy-1H-indazole;
(R)-3-(6-(azetidin-1-yl)-5-fluoropyridin-3-yl)-5-(1-(3,5-dichloropyridin-4-yl)ethoxy)-6-methoxy-1H-indazole;
5-[(1R)-1-(3,5-dichloro-2-methyl-4-pyridyl)ethoxy]-6-fluoro-3-[5-fluoro-6-(2-methylsulfonyl-2,6-diazaspiro[3.3]heptan-6-yl)-3-pyridyl]-1H-indazole;
6-chloro-5-[(1R)-1-(3,5-dichloro-2-methyl-4-pyridyl)ethoxy]-3-[5-fluoro-6-(2-methylsulfonyl-2,6-diazaspiro[3.3]heptan-6-yl)-3-pyridyl]-1H-indazole;
5-((R)-1-(3,5-dichloropyridin-4-yl)ethoxy)-3-(5-fluoro-6-((S)-2-methylazetidin-1-yl)pyridin-3-yl)-6-methoxy-1H-indazole;
6-chloro-5-((R)-1-(3,5-dichloropyridin-4-yl)ethoxy)-3-(5-fluoro-6-((R)-2-methylazetidin-1-yl)pyridin-3-yl)-1H-indazole;
5-[(1R)-1-(3,5-dichloro-2-methyl-4-pyridyl)ethoxy]-3-[5-fluoro-6-(2-methylsulfonyl-2,6-diazaspiro[3.3]heptan-6-yl)-3-pyridyl]-6-methyl-1H-indazole;
3-[6-(azetidin-1-yl)-5-fluoro-3-pyridyl]-6-chloro-5-[(1R)-1-(3,5-dichloro-2-methyl-4-pyridyl)ethoxy]-1H-indazole;
1-[5-[6-chloro-5-[(1R)-1-(3,5-dichloro-2-methyl-4-pyridyl)ethoxy]-1H-indazol-3-yl]-3-fluoro-2-pyridyl]-N,3-dimethyl-azetidin-3-amine;
(R)-5-(1-(3,5-dichloropyridin-4-yl)ethoxy)-3-(6-(3,3-dimethylazetidin-1-yl)-5-fluoropyridin-3-yl)-6-methoxy-1H-indazole;
6-chloro-5-((R)-1-(3,5-dichloropyridin-4-yl)ethoxy)-3-(5-fluoro-6-((S)-2-methylazetidin-1-yl)pyridin-3-yl)-1H-indazole;
(R)-3-(6-(azetidin-1-yl)-5-fluoropyridin-3-yl)-6-chloro-5-(1-(3,5-dichloropyridin-4-yl)ethoxy)-1H-indazole;
(R)-5-(1-(3,5-dichloropyridin-4-yl)ethoxy)-3-(3,5-difluoro-4-(6-(methylsulfonyl)-2,6-diazaspiro[3.3]heptan-2-yl)phenyl)-6-methoxy-1H-indazole;
(R)-3-(4-(azetidin-1-yl)-3,5-difluorophenyl)-5-(1-(3,5-dichloropyridin-4-yl)ethoxy)-6-methoxy-1H-indazole;
(R)-1-(5-(5-(1-(3,5-dichloropyridin-4-yl)ethoxy)-6-methoxy-1H-indazol-3-yl)-3-fluoropyridin-2-yl)-N,N,3-trimethylazetidin-3-amine;
(R)—N-(1-(5-(5-(1-(3,5-dichloropyridin-4-yl)ethoxy)-6-methoxy-1H-indazol-3-yl)-3-fluoropyridin-2-yl)-3-methylazetidin-3-yl)-N-methylmethanesulfonamide;
(S)-2-(azetidin-1-yl)-5-(5-(1-(3,5-dichloro-2-fluoropyridin-4-yl)ethoxy)-1H-indazol-3-yl)nicotinonitrile;
5-(5-((R)-1-(3,5-dichloro-2-fluoropyridin-4-yl)ethoxy)-1H-indazol-3-yl)-2-((R)-3-hydroxypyrrolidin-1-yl)nicotinonitrile;
5-[5-[(1R)-1-(3,5-dichloro-4-pyridyl)ethoxy]-1H-indazol-3-yl]-2-pyrrolidin-1-yl-pyridine-3-carbonitrile;
(R)-2-(azetidin-1-yl)-5-(5-(1-(3,5-dichloro-2-fluoropyridin-4-yl)ethoxy)-1H-indazol-3-yl)nicotinonitrile;
(R)-5-(5-(1-(3,5-dichloro-2-fluoropyridin-4-yl)ethoxy)-1H-indazol-3-yl)-2-(3-hydroxyazetidin-1-yl)nicotinonitrile;
5-(5-((R)-1-(3,5-dichloro-2-fluoropyridin-4-yl)ethoxy)-1H-indazol-3-yl)-2-((S)-3-hydroxypyrrolidin-1-yl)nicotinonitrile;
2-(azetidin-1-yl)-5-[5-[(1R)-1-(3,5-dichloro-2-methyl-4-pyridyl)ethoxy]-1H-indazol-3-yl]pyridine-3-carbonitrile;
5-[5-[(1R)-1-(3,5-dichloro-4-pyridyl)ethoxy]-1H-indazol-3-yl]-2-[(3 S)-3-(1-hydroxy-1-methyl-ethyl) pyrrolidin-1-yl]pyridine-3-carbonitrile;
(S)-5-(5-(1-(3,5-dichloro-2-fluoropyridin-4-yl)ethoxy)-1H-indazol-3-yl)-2-(3-hydroxyazetidin-1-yl)nicotinonitrile;
(R)-5-(5-(1-(3,5-dichloro-2-fluoropyridin-4-yl)ethoxy)-1H-indazol-3-yl)-2-(pyrrolidin-1-yl)nicotinonitrile;
5-[5-[(1R)-1-(3,5-dichloro-4-pyridyl)ethoxy]-1H-indazol-3-yl]-2-[(3 S)-3-hydroxypyrrolidin-1-yl]pyridine-3-carbonitrile;
5-[5-[(1R)-1-(3,5-dichloro-4-pyridyl)ethoxy]-1H-indazol-3-yl]-2-[(3R)-3-(1-hydroxy-1-methyl-ethyl) pyrrolidin-1-yl]pyridine-3-carbonitrile;
5-[5-[(1R)-1-(3,5-dichloro-2-methyl-4-pyridyl)ethoxy]-1H-indazol-3-yl]-2-[3-(2,2,2-trifluoroethyl)azetidin-1-yl]pyridine-3-carbonitrile;
5-[5-[(1R)-1-(3,5-dichloro-4-pyridyl)ethoxy]-1H-indazol-3-yl]-2-[3-(2,2,2-trifluoroethyl)azetidin-1-yl]pyridine-3-carbonitrile;
5-[5-[(1R)-1-(3,5-dichloro-4-pyridyl)ethoxy]-1H-indazol-3-yl]-2-[(3R)-3-hydroxypyrrolidin-1-yl]pyridine-3-carbonitrile;
5-[5-[(1R)-1-(3,5-dichloro-4-pyridyl)ethoxy]-1H-indazol-3-yl]-2-(4-hydroxy-1-piperidyl)pyridine-3-carbonitrile;
2-(3,6-diazabicyclo[3.1.1]heptan-3-yl)-5-(5-((R)-1-(3,5-dimethylpyridazin-4-yl)ethoxy)-1H-indazol-3-yl)nicotinonitrile;
3-(5-(5-((R)-1-(3,5-dimethylpyridazin-4-yl)ethoxy)-1H-indazol-3-yl)-3-methoxypyridin-2-yl)-3,6-diazabicyclo[3.1.1]heptane;
5-(5-((R)-1-(3,5-dimethylpyridazin-4-yl)ethoxy)-1H-indazol-3-yl)-2-((S)-3-(2-hydroxypropan-2-yl) pyrrolidin-1-yl)nicotinonitrile;
5-[5-[(1R)-1-(3,5-dichloro-4-pyridyl)ethoxy]-1H-indazol-3-yl]-2-(3-hydroxyazetidin-1-yl)pyridine-3-carbonitrile;
5-[5-[(1R)-1-(3,5-dichloro-4-pyridyl)ethoxy]-1H-indazol-3-yl]-2-[4-(1-hydroxy-1-methyl-ethyl)-1-piperidyl]pyridine-3-carbonitrile;

(R)-3-(6-(azetidin-1-yl)-5-methoxypyridin-3-yl)-5-(1-(3,5-dimethylpyridazin-4-yl)ethoxy)-1H-indazole;

(R)-5-(1-(3,5-dimethylpyridazin-4-yl)ethoxy)-3-(5-methoxy-6-(pyrrolidin-1-yl)pyridin-3-yl)-1H-indazole;

5-(5-((R)-1-(3,5-dimethylpyridazin-4-yl)ethoxy)-1H-indazol-3-yl)-2-((S)-3-hydroxypyrrolidin-1-yl)nicotinonitrile;

5-(5-((R)-1-(3,5-dimethylpyridazin-4-yl)ethoxy)-1H-indazol-3-yl)-2-((R)-3-(2-hydroxypropan-2-yl) pyrrolidin-1-yl)nicotinonitrile;

5-[5-[(1R)-1-(3,5-dichloro-2-methyl-4-pyridyl)ethoxy]-1H-indazol-3-yl]-2-(3-hydroxyazetidin-1-yl)pyridine-3-carbonitrile;

2-(azetidin-1-yl)-5-[5-[(1R)-1-(3,5-dichloro-4-pyridyl)ethoxy]-1H-indazol-3-yl]pyridine-3-carbonitrile;

(R)-3-(6-(azetidin-1-yl)pyridin-3-yl)-5-(1-(3,5-dimethylpyridazin-4-yl)ethoxy)-6-methoxy-1H-indazole;

5-(5-((R)-1-(3,5-dimethylpyridazin-4-yl)ethoxy)-6-methoxy-1H-indazol-3-yl)-2-((S)-3-hydroxypyrrolidin-1-yl)nicotinonitrile;

5-(5-((R)-1-(3,5-dimethylpyridazin-4-yl)ethoxy)-1H-indazol-3-yl)-2-(6-(2-hydroxy-2-methylpropyl)-3,6-diazabicyclo[3.1.1]heptan-3-yl)nicotinonitrile;

5-(5-((R)-1-(3,5-dimethylpyridazin-4-yl)ethoxy)-1H-indazol-3-yl)-2-((R)-3-hydroxypyrrolidin-1-yl)nicotinonitrile;

3-(5-(5-((R)-1-(3,5-dimethylpyridazin-4-yl)ethoxy)-6-methoxy-1H-indazol-3-yl)pyridin-2-yl)-3,6-diazabicyclo[3.1.1]heptane;

(R)-5-(1-(3,5-dimethylpyridazin-4-yl)ethoxy)-6-methoxy-3-(6-(pyrrolidin-1-yl)pyridin-3-yl)-1H-indazole;

5-(5-((R)-1-(3,5-dimethylpyridazin-4-yl)ethoxy)-6-methoxy-1H-indazol-3-yl)-2-((S)-3-(2-hydroxypropan-2-yl) pyrrolidin-1-yl)nicotinonitrile;

3-(5-(5-((R)-1-(3,5-dimethylpyridazin-4-yl)ethoxy)-6-methoxy-1H-indazol-3-yl)-3-methylpyridin-2-yl)-3,6-diazabicyclo[3.1.1]heptane;

(R)-5-(5-(1-(3,5-dimethylpyridazin-4-yl)ethoxy)-1H-indazol-3-yl)-2-(3-hydroxyazetidin-1-yl)nicotinonitrile;

5-(5-((R)-1-(3,5-dimethylpyridazin-4-yl)ethoxy)-6-methoxy-1H-indazol-3-yl)-2-((R)-3-hydroxypyrrolidin-1-yl)nicotinonitrile;

(R)-5-(5-(1-(3,5-dimethylpyridazin-4-yl)ethoxy)-6-methoxy-1H-indazol-3-yl)-2-(3-hydroxyazetidin-1-yl)nicotinonitrile;

5-(5-((R)-1-(3,5-dimethylpyridazin-4-yl)ethoxy)-6-methoxy-1H-indazol-3-yl)-2-((R)-3-(2-hydroxypropan-2-yl) pyrrolidin-1-yl)nicotinonitrile;

(R)-2-(azetidin-1-yl)-5-(5-(1-(3,5-dimethylpyridazin-4-yl)ethoxy)-6-methoxy-1H-indazol-3-yl)nicotinonitrile;

1-(3-(5-(5-((R)-1-(3,5-dimethylpyridazin-4-yl)ethoxy)-1H-indazol-3-yl)-3-methoxypyridin-2-yl)-3,6-diazabicyclo[3.1.1]heptan-6-yl)-2-methylpropan-2-ol;

(R)-5-(5-(1-(3,5-dimethylpyridazin-4-yl)ethoxy)-6-methoxy-1H-indazol-3-yl)-2-(2-oxa-6-azaspiro[3.3]heptan-6-yl)nicotinonitrile;

5-(5-((R)-1-(3,5-dimethylpyridazin-4-yl)ethoxy)-1H-indazol-3-yl)-2-(3-oxohexahydroimidazo[1,5-a]pyrazin-7(1H)-yl)nicotinonitrile;

5-[5-[(1R)-1-(3,5-dichloro-4-pyridyl)ethoxy]-6-methoxy-1H-indazol-3-yl]-2-(3-hydroxyazetidin-1-yl)pyridine-3-carbonitrile;

5-[5-[(1R)-1-(3,5-dichloro-4-pyridyl)ethoxy]-6-methoxy-1H-indazol-3-yl]-2-[(3S)-3-hydroxypyrrolidin-1-yl]pyridine-3-carbonitrile;

7-(5-(5-((R)-1-(3,5-dimethylpyridazin-4-yl)ethoxy)-1H-indazol-3-yl)-3-methoxypyridin-2-yl)hexahydroimidazo[1,5-a]pyrazin-3(2H)-one;

(R)-5-(5-(1-(3,5-dichloropyridin-4-yl)ethoxy)-1H-indazol-3-yl)-2-(6-(2,2,2-trifluoroethyl)-2,6-diazaspiro[3.3]heptan-2-yl)nicotinonitrile;

(R)-5-(5-(1-(3,5-dichloropyridin-4-yl)ethoxy)-1H-indazol-3-yl)-2-(6-(2,2-difluoroethyl)-2,6-diazaspiro[3.3]heptan-2-yl)nicotinonitrile;

5-(5-((R)-1-(3,5-dichloropyridin-4-yl)ethoxy)-1H-indazol-3-yl)-2-(6-hydroxy-3-azabicyclo[3.1.0]hexan-3-yl)nicotinonitrile;

5-(5-((R)-1-(3,5-dichloropyridin-4-yl)ethoxy)-1H-indazol-3-yl)-2-((R)-2-(hydroxymethyl) pyrrolidin-1-yl)nicotinonitrile;

5-[5-[(1R)-1-(3,5-dichloro-4-pyridyl)ethoxy]-6-methoxy-1H-indazol-3-yl]-2-pyrrolidin-1-yl-pyridine-3-carbonitrile;

5-(5-((R)-1-(3,5-dichloropyridin-4-yl)ethoxy)-1H-indazol-3-yl)-2-((S)-2-(hydroxymethyl) pyrrolidin-1-yl)nicotinonitrile;

5-(5-((R)-1-(3,5-dimethylpyridazin-4-yl)ethoxy)-1H-indazol-3-yl)-2-((R)-2-(hydroxymethyl) pyrrolidin-1-yl)nicotinonitrile;

5-(5-((R)-1-(3,5-dimethylpyridazin-4-yl)ethoxy)-1H-indazol-3-yl)-2-((S)-2-(hydroxymethyl) pyrrolidin-1-yl)nicotinonitrile;

(R)-5-(5-(1-(3,5-dichloropyridin-4-yl)ethoxy)-1H-indazol-3-yl)-2-(6-(methylsulfonyl)-2,6-diazaspiro[3.3]heptan-2-yl)nicotinonitrile;

(R)-5-(5-(1-(3,5-dichloropyridin-4-yl)ethoxy)-1H-indazol-3-yl)-2-(6-(methylsulfonyl)-2,6-diazaspiro[3.5]nonan-2-yl)nicotinonitrile;

(R)-5-(5-(1-(3,5-dichloropyridin-4-yl)ethoxy)-6-methoxy-1H-indazol-3-yl)-2-(6,6-dioxido-6-thia-2-azaspiro[3.4]octan-2-yl)nicotinonitrile;

(R)-5-(5-(1-(3,5-dichloropyridin-4-yl)ethoxy)-1H-indazol-3-yl)-2-(6,6-dioxido-6-thia-2-azaspiro[3.5]nonan-2-yl)nicotinonitrile;

5-[5-[(1R)-1-(3,5-dichloro-2-methyl-4-pyridyl)ethoxy]-6-methoxy-1H-indazol-3-yl]-2-(2-methylsulfonyl-2,6-diazaspiro[3.3]heptan-6-yl)pyridine-3-carbonitrile;

5-[5-[(1R)-1-(3,5-dichloro-4-pyridyl)ethoxy]-6-methoxy-1H-indazol-3-yl]-2-(2-methylsulfonyl-2,6-diazaspiro[3.3]heptan-6-yl)pyridine-3-carbonitrile;

(R)-5-(5-(1-(3,5-dichloropyridin-4-yl)ethoxy)-1H-indazol-3-yl)-2-(6,6-dioxido-6-thia-2-azaspiro[3.4]octan-2-yl)nicotinonitrile;

(R)-5-(1-(3,5-dichloropyridin-4-yl)ethoxy)-3-(5-methoxy-6-(6-(methylsulfonyl)-2,6-diazaspiro[3.3]heptan-2-yl)pyridin-3-yl)-1H-indazole;

(R)-5-(5-(1-(3,5-dichloropyridin-4-yl)ethoxy)-1H-indazol-3-yl)-2-(3-(difluoromethyl)azetidin-1-yl)nicotinonitrile;

(R)-5-(5-(1-(3,5-dichloropyridin-4-yl)ethoxy)-6-methoxy-1H-indazol-3-yl)-2-(6,6-dioxido-6-thia-2-azaspiro[3.5]nonan-2-yl)nicotinonitrile;

(R)-5-(5-(1-(3,5-dichloropyridin-4-yl)ethoxy)-1H-indazol-3-yl)-2-(3-(trifluoromethyl)azetidin-1-yl)nicotinonitrile;

(R)-2-(3-cyanoazetidin-1-yl)-5-(5-(1-(3,5-dichloropyridin-4-yl)ethoxy)-1H-indazol-3-yl)nicotinonitrile;

5-[5-[(1R)-1-(3,5-dichloro-2-methyl-4-pyridyl)ethoxy]-1H-indazol-3-yl]-2-(6,6-dioxo-6$\lambda^6$-thia-2-azaspiro[3.5]nonan-2-yl)pyridine-3-carbonitrile;

5-[5-[(1R)-1-(3,5-dichloro-2-methyl-4-pyridyl)ethoxy]-1H-indazol-3-yl]-2-(8-methylsulfonyl-2,8-diazaspiro[3.5]nonan-2-yl)pyridine-3-carbonitrile;

5-(5-((R)-1-(3,5-dichloropyridin-4-yl)ethoxy)-1H-indazol-3-yl)-2-((R)-2-(hydroxymethyl)azetidin-1-yl)nicotinonitrile;

(R)-5-(5-(1-(3,5-dichloropyridin-4-yl)ethoxy)-6-methyl-1H-indazol-3-yl)-2-(6-(methylsulfonyl)-2,6-diazaspiro[3.3]heptan-2-yl)nicotinonitrile;

(R)-5-(5-(1-(3,5-dichloropyridin-4-yl)ethoxy)-1H-indazol-3-yl)-2-(3,3-difluoroazetidin-1-yl)nicotinonitrile;

5-(5-((R)-1-(3,5-dichloropyridin-4-yl)ethoxy)-1H-indazol-3-yl)-2-((S)-2-(hydroxymethyl)azetidin-1-yl)nicotinonitrile;

(R)-5-(5-(1-(3,5-dichloropyridin-4-yl)ethoxy)-6-fluoro-1H-indazol-3-yl)-2-(6-(methylsulfonyl)-2,6-diazaspiro[3.3]heptan-2-yl)nicotinonitrile;

(R)-1-(5-(5-(1-(3,5-dichloropyridin-4-yl)ethoxy)-1H-indazol-3-yl)-2-(6-(methylsulfonyl)-2,6-diazaspiro[3.3]heptan-2-yl)pyridin-3-yl)-N,N-dimethylmethanamine;

(R)-1-(5-(5-(1-(3,5-dichloropyridin-4-yl)ethoxy)-6-methoxy-1H-indazol-3-yl)-2-(6-(methylsulfonyl)-2,6-diazaspiro[3.3]heptan-2-yl)pyridin-3-yl)-N,N-dimethylmethanamine;

(R)-2-(3-amino-3-methylazetidin-1-yl)-5-(5-(1-(3,5-dichloropyridin-4-yl)ethoxy)-1H-indazol-3-yl)nicotinonitrile;

(R)-5-(6-chloro-5-(1-(3,5-dichloropyridin-4-yl)ethoxy)-1H-indazol-3-yl)-2-(6-(methylsulfonyl)-2,6-diazaspiro[3.3]heptan-2-yl)nicotinonitrile;

(R)-2-(azetidin-1-yl)-5-(5-(1-(3,5-dichloropyridazin-4-yl)ethoxy)-6-methoxy-1H-indazol-3-yl)nicotinonitrile;

(R)-2-(azetidin-1-yl)-5-(5-(1-(3,5-dichloropyridazin-4-yl)ethoxy)-1H-indazol-3-yl)nicotinonitrile;

5-[5-[(1R)-1-(3,5-dichloro-4-pyridyl)ethoxy]-6-fluoro-1H-indazol-3-yl]-2-(6,6-dioxo-6λ$^6$-thia-2-azaspiro[3.5]nonan-2-yl)pyridine-3-carbonitrile;

5-(5-((R)-1-(3,5-dichloropyridin-4-yl)ethoxy)-1H-indazol-3-yl)-2-(2-((dimethylamino)methyl)azetidin-1-yl)nicotinonitrile;

(R)-5-(6-chloro-5-(1-(3,5-dichloropyridin-4-yl)ethoxy)-1H-indazol-3-yl)-2-(3,3-dimethylazetidin-1-yl)nicotinonitrile;

5-(6-chloro-5-((R)-1-(3,5-dichloropyridin-4-yl)ethoxy)-1H-indazol-3-yl)-2-((S)-2-methylazetidin-1-yl)nicotinonitrile;

(R)-1-(2-(azetidin-1-yl)-5-(6-chloro-5-(1-(3,5-dichloropyridin-4-yl)ethoxy)-1H-indazol-3-yl)pyridin-3-yl)-N,N-dimethylmethanamine;

(R)-3-(6-(azetidin-1-yl)-5-(methylsulfonyl)pyridin-3-yl)-5-(1-(3,5-dichloropyridin-4-yl)ethoxy)-6-methoxy-1H-indazole;

(R)-1-(5-(5-(1-(3,5-dichloropyridin-4-yl)ethoxy)-1H-indazol-3-yl)-2-(6-(methylsulfonyl)-2,6-diazaspiro[3.3]heptan-2-yl)pyridin-3-yl)-N-methylmethanamine;

(R)-1-(5-(5-(1-(3,5-dichloropyridin-4-yl)ethoxy)-6-methoxy-1H-indazol-3-yl)-2-(6-(methylsulfonyl)-2,6-diazaspiro[3.3]heptan-2-yl)pyridin-3-yl)-N-methylmethanamine;

(R)-3-(6-(azetidin-1-yl)-5-(methylsulfonyl)pyridin-3-yl)-6-chloro-5-(1-(3,5-dichloropyridin-4-yl)ethoxy)-1H-indazole;

(R)-1-(5-(6-chloro-5-(1-(3,5-dichloropyridin-4-yl)ethoxy)-1H-indazol-3-yl)-2-(3,3-dimethylazetidin-1-yl)pyridin-3-yl)-N,N-dimethylmethanamine;

5-((R)-1-(3,5-dichloropyridin-4-yl)ethoxy)-6-methoxy-3-(6-((R)-2-methylazetidin-1-yl)-5-(methylsulfonyl)pyridin-3-yl)-1H-indazole;

5-[5-[(1R)-1-(3,5-dichloro-4-pyridyl)ethoxy]-6-fluoro-1H-indazol-3-yl]-2-(2-methylsulfonyl-2,6-diazaspiro[3.3]heptan-6-yl)pyridine-3-carbonitrile;

5-(6-chloro-5-((R)-1-(3,5-dichloropyridin-4-yl)ethoxy)-1H-indazol-3-yl)-2-((R)-2-methylazetidin-1-yl)nicotinonitrile;

5-((R)-1-(3,5-dichloropyridin-4-yl)ethoxy)-6-methoxy-3-(6-((S)-2-methylazetidin-1-yl)-5-(methylsulfonyl)pyridin-3-yl)-1H-indazole;

(R)-5-(1-(3,5-dichloropyridin-4-yl)ethoxy)-3-(6-(3,3-dimethylazetidin-1-yl)-5-(methylsulfonyl)pyridin-3-yl)-6-methoxy-1H-indazole;

2-(azetidin-1-yl)-5-[6-chloro-5-[(1R)-1-(3,5-dichloro-4-pyridyl)ethoxy]-1H-indazol-3-yl]pyridine-3-carbonitrile;

5-[5-[(1R)-1-(3,5-dichloro-4-pyridyl)ethoxy]-6-fluoro-1H-indazol-3-yl]-2-(6,6-dioxo-6λ$^6$-thia-2-azaspiro[3.4]octan-2-yl)pyridine-3-carbonitrile;

5-[5-[(1R)-1-(3,5-dichloro-2-methyl-4-pyridyl)ethoxy]-6-fluoro-1H-indazol-3-yl]-2-(2-methylsulfonyl-2,6-diazaspiro[3.3]heptan-6-yl)pyridine-3-carbonitrile;

5-[5-[(1R)-1-(3,5-dichloro-4-pyridyl)ethoxy]-6-fluoro-1H-indazol-3-yl]-2-(8-methylsulfonyl-2,8-diazaspiro[3.5]nonan-2-yl)pyridine-3-carbonitrile;

(R)-6-chloro-5-(1-(3,5-dichloropyridin-4-yl)ethoxy)-3-(6-(3,3-dimethylazetidin-1-yl)-5-(methylsulfonyl)pyridin-3-yl)-1H-indazole;

(R)-1-(2-(azetidin-1-yl)-5-(6-chloro-5-(1-(3,5-dichloropyridin-4-yl)ethoxy)-1H-indazol-3-yl)pyridin-3-yl)-N-methylmethanamine;

(R)-3-(6-(azetidin-1-yl)-5-(trifluoromethyl)pyridin-3-yl)-6-chloro-5-(1-(3,5-dichloropyridin-4-yl)ethoxy)-1H-indazole;

6-chloro-5-((R)-1-(3,5-dichloropyridin-4-yl)ethoxy)-3-(6-((S)-2-methylazetidin-1-yl)-5-(trifluoromethyl)pyridin-3-yl)-1H-indazole;

(R)-1-(5-(6-chloro-5-(1-(3,5-dichloropyridin-4-yl)ethoxy)-1H-indazol-3-yl)-3-(trifluoromethyl)pyridin-2-yl)-N,N,3-trimethylazetidin-3-amine;

6-chloro-5-((R)-1-(3,5-dichloropyridin-4-yl)ethoxy)-3-(6-((R)-2-methylazetidin-1-yl)-5-(trifluoromethyl)pyridin-3-yl)-1H-indazole; or (R)-1-(5-(6-chloro-5-(1-(3,5-dichloropyridin-4-yl)ethoxy)-1H-indazol-3-yl)-3-(methylsulfonyl)pyridin-2-yl)-N,N,3-trimethylazetidin-3-amine.

21. A method of treating achondroplasia, chondrodysplasia syndromes, hypochondroplasia (Hch), severe achondroplasia with developmental delay and acanthosis nigricans (SADDAN), or thanatophoric dysplasia (TD) in a subject in need thereof comprising administering to the subject a compound of claim 1, or a pharmaceutically acceptable salt thereof.

* * * * *